US012617865B2

(12) United States Patent
Campbell et al.

(10) Patent No.: US 12,617,865 B2
(45) **Date of Patent: *May 5, 2026**

(54) ACTIVATED ANTIBODIES TARGETING PSMA AND EFFECTOR CELL ANTIGENS

(71) Applicant: Janux Therapeutics, Inc., San Diego, CA (US)

(72) Inventors: David Campbell, San Diego, CA (US); Thomas R. DiRaimondo, San Diego, CA (US)

(73) Assignee: JANUX THERAPEUTICS, INC., San Diego, CA (US)

( * ) Notice: Subject to any disclaimer, the term of this patent is extended or adjusted under 35 U.S.C. 154(b) by 754 days.

This patent is subject to a terminal disclaimer.

(21) Appl. No.: 18/055,932

(22) Filed: Nov. 16, 2022

(65) Prior Publication Data

US 2023/0348618 A1     Nov. 2, 2023

Related U.S. Application Data

(63) Continuation of application No. 17/544,539, filed on Dec. 7, 2021, now Pat. No. 11,555,078.

(60) Provisional application No. 63/187,699, filed on May 12, 2021, provisional application No. 63/123,329, filed on Dec. 9, 2020.

(51) Int. Cl.
| | |
|---|---|
| *A61P 35/00* | (2006.01) |
| *C07K 14/765* | (2006.01) |
| *C07K 16/28* | (2006.01) |
| *C07K 16/30* | (2006.01) |

(52) U.S. Cl.
CPC ........ *C07K 16/3069* (2013.01); *C07K 14/765* (2013.01); *C07K 16/2809* (2013.01); *C07K 2317/565* (2013.01); *C07K 2317/569* (2013.01); *C07K 2317/622* (2013.01); *C07K 2317/92* (2013.01); *C07K 2319/30* (2013.01); *C07K 2319/31* (2013.01)

(58) Field of Classification Search
None
See application file for complete search history.

(56) References Cited

U.S. PATENT DOCUMENTS

| | | | |
|---|---|---|---|
| 5,747,654 | A | 5/1998 | Pastan et al. |
| 7,850,971 | B2 | 12/2010 | Maddon et al. |
| 8,114,965 | B2 | 2/2012 | Maddon et al. |
| 8,470,330 | B2 | 6/2013 | Maddon et al. |
| 8,784,821 | B1 | 7/2014 | Kufer et al. |
| 9,249,211 | B2 | 2/2016 | Schellenberger et al. |
| 9,453,078 | B2 | 9/2016 | Stagliano et al. |
| 9,562,073 | B2 | 2/2017 | Moore et al. |
| 9,650,445 | B2 | 5/2017 | Cobbold et al. |
| 9,695,248 | B2 | 7/2017 | Maddon et al. |
| 9,708,412 | B2 | 7/2017 | Baeuerle et al. |
| 9,822,180 | B2 | 11/2017 | Cobbold et al. |
| 9,856,314 | B2 | 1/2018 | Lowman et al. |
| 9,889,211 | B2 | 2/2018 | Lowman et al. |
| 9,976,166 | B2 | 5/2018 | Schellenberger et al. |
| 10,066,016 | B2 | 9/2018 | Dubridge et al. |
| 10,106,621 | B2 | 10/2018 | Cobbold et al. |
| 10,118,961 | B2 | 11/2018 | Stagliano et al. |
| 10,138,272 | B2 | 11/2018 | Moore et al. |
| 10,544,221 | B2 | 1/2020 | Dubridge et al. |
| 11,028,126 | B2 | 6/2021 | Moore et al. |
| 11,512,113 | B2 | 11/2022 | Campbell et al. |
| 11,555,078 | B2 | 1/2023 | Campbell et al. |
| 12,060,654 | B2 | 8/2024 | Igawa et al. |
| 2001/0031264 | A1 | 10/2001 | Segal |
| 2004/0175756 | A1 | 9/2004 | Kolkman et al. |
| 2010/0150918 | A1 | 6/2010 | Kufer et al. |
| 2010/0189718 | A1 | 7/2010 | Dall'Acqua et al. |
| 2011/0293619 | A1 | 12/2011 | Kufer et al. |
| 2014/0154253 | A1 | 6/2014 | Ng et al. |
| 2015/0335706 | A1 | 11/2015 | Olbrich et al. |
| 2016/0122436 | A1 | 5/2016 | Kufer et al. |
| 2016/0193332 | A1 | 7/2016 | Lowman et al. |
| 2016/0194399 | A1 | 7/2016 | Irving et al. |
| 2016/0264671 | A1 | 9/2016 | Kufer et al. |
| 2016/0355599 | A1 | 12/2016 | Sagert et al. |
| 2017/0051074 | A1 | 2/2017 | Kirshner et al. |
| 2017/0196996 | A1 | 7/2017 | Lowman et al. |
| 2017/0247476 | A1 | 8/2017 | Yan et al. |
| 2017/0349668 | A1 | 12/2017 | Rattel et al. |
| 2017/0369563 | A1 | 12/2017 | Dubridge et al. |
| 2018/0125988 | A1 | 5/2018 | Yang et al. |
| 2018/0162949 | A1 | 6/2018 | Baeuerle et al. |

(Continued)

FOREIGN PATENT DOCUMENTS

| | | |
|---|---|---|
| EP | 2155783 A2 | 2/2010 |
| EP | 3197916 A2 | 8/2017 |

(Continued)

OTHER PUBLICATIONS

Iizuka, Akira et al. A T-cell-engaging B7-H4/CD3-bispecific Fab-scFv Antibody Targets Human Breast Cancer. Clin Cancer Res. 25(9):2925-2934 (2019).
Chemical Abstracts Service. CAS Registry No. 914157-12-3. Protein (Methanosarcina barkeri strain Fusaro 155-amino acid) (ACI) . STN Entry Date Nov. 28, 2006.
Maeder, Dennis L. et al. The Methanosarcina barkeri genome: comparative analysis with Methanosarcina acetivorans and Methanosarcina mazei reveals extensive rearrangement within methanosarcinal genomes. Journal of bacteriology 188(22): 7922-7931 (2006).
UniProtKB Accession No. A0A1H0WWF1. Lipoprotein. Record Created Nov. 22, 2017. pp. 1-3. Retrieved Jul. 25, 2024 at URL: https://www.uniprot.org/uniprotkb/A0A1H0WWF1/entry.
U.S. Appl. No. 17/972,348 Office Action dated May 15, 2024.
PCT/IB2023/000223 International Search Report and Written Opinion dated Apr. 1, 2024.

(Continued)

*Primary Examiner* — Zachary S Skelding
(74) *Attorney, Agent, or Firm* — WILSON SONSINI GOODRICH & ROSATI

(57) ABSTRACT

Provided herein are multispecific antibodies that selectively bind to PSMA and effector cell antigens such as CD3, pharmaceutical compositions thereof, as well as nucleic acids, and methods for making and discovering the same.

31 Claims, 46 Drawing Sheets

Specification includes a Sequence Listing.

(56)                    References Cited

U.S. PATENT DOCUMENTS

| | | |
|---|---|---|
| 2019/0040133 A1 | 2/2019 | Kufer et al. |
| 2019/0070248 A1 | 3/2019 | Sahin et al. |
| 2019/0153115 A1 | 5/2019 | Schellenberger et al. |
| 2019/0169295 A1 | 6/2019 | Kufer et al. |
| 2019/0169310 A1 | 6/2019 | Kufer et al. |
| 2019/0315863 A1 | 10/2019 | Kim et al. |
| 2019/0359714 A1 | 11/2019 | Tipton et al. |
| 2019/0381183 A1 | 12/2019 | Ward Ober et al. |
| 2020/0040099 A1 | 2/2020 | Kufer et al. |
| 2020/0181249 A1 | 6/2020 | Curtis et al. |
| 2021/0002343 A1 | 1/2021 | Karow et al. |
| 2021/0020264 A1 | 1/2021 | Stroh et al. |
| 2021/0040212 A1 | 2/2021 | Liu et al. |
| 2021/0054077 A1 | 2/2021 | Schellenberger et al. |
| 2021/0403595 A1 | 12/2021 | Kirshner et al. |
| 2023/0147782 A1 | 5/2023 | Campbell et al. |
| 2023/0220105 A1 | 7/2023 | Campbell et al. |
| 2023/0220109 A1 | 7/2023 | Campbell et al. |
| 2024/0034814 A1 | 2/2024 | Campbell et al. |
| 2024/0043536 A1 | 2/2024 | Campbell et al. |
| 2024/0043565 A1 | 2/2024 | Campbell et al. |
| 2024/0059790 A1 | 2/2024 | Campbell et al. |
| 2024/0376226 A1 | 11/2024 | Campbell et al. |
| 2025/0019403 A1 | 1/2025 | Campbell et al. |

FOREIGN PATENT DOCUMENTS

| | | | |
|---|---|---|---|
| EP | 2820047 B1 | 4/2018 | |
| EP | 2819701 B1 | 7/2018 | |
| EP | 3174901 B1 | 6/2019 | |
| EP | 2970449 B1 | 9/2019 | |
| WO | WO-2007147001 A2 | 12/2007 | |
| WO | WO-2008119567 A1 | 10/2008 | |
| WO | WO-2009026303 A1 | 2/2009 | |
| WO | WO-2009040134 A1 | 4/2009 | |
| WO | WO-2009068649 A2 | 6/2009 | |
| WO | WO-2010037836 A2 | 4/2010 | |
| WO | WO-2010037837 A2 | 4/2010 | |
| WO | WO-2011121110 A1 | 10/2011 | |
| WO | WO-2013128194 A1 | 9/2013 | |
| WO | WO-2014079000 A1 | 5/2014 | |
| WO | WO-2016014974 A2 | 1/2016 | |
| WO | WO-2016046778 A2 | 3/2016 | |
| WO | WO-2016077505 A2 | 5/2016 | |
| WO | WO-2016118629 A1 | 7/2016 | |
| WO | WO-2017023761 A1 | 2/2017 | |
| WO | WO-2017040344 A2 | 3/2017 | |
| WO | WO-2017134158 A1 | 8/2017 | |
| WO | WO-2017156178 A1 | 9/2017 | |
| WO | WO-2017184619 A2 | 10/2017 | |
| WO | WO-2018209304 A1 | 11/2018 | |
| WO | WO-2019051102 A2 | 3/2019 | |
| WO | WO-2019075405 A1 | 4/2019 | |
| WO | WO-2019096121 A1 | 5/2019 | |
| WO | WO-2019126576 A1 | 6/2019 | |
| WO | WO-2019183218 A1 | 9/2019 | |
| WO | WO-2019222278 A1 | 11/2019 | |
| WO | WO-2019222282 A1 | 11/2019 | |
| WO | WO-2019222283 A1 | 11/2019 | |
| WO | WO-2020033837 A1 | 2/2020 | |
| WO | WO-2020048525 A1 | 3/2020 | |
| WO | WO-2020058762 A1 | 3/2020 | |
| WO | WO-2020069398 A1 | 4/2020 | |
| WO | WO-2020118109 A2 | 6/2020 | |
| WO | WO-2020150702 A1 | 7/2020 | |
| WO | WO-2020181140 A1 | 9/2020 | |
| WO | WO-2020181145 A1 | 9/2020 | |
| WO | WO-2020225805 A2 | 11/2020 | |
| WO | WO-2020247867 A2 | 12/2020 | |
| WO | WO-2020247871 A2 | 12/2020 | |
| WO | WO-2022035866 A1 | 2/2022 | |
| WO | WO-2022060878 A1 * | 3/2022 | ......... C07K 16/3069 |
| WO | WO-2022067224 A1 | 3/2022 | |
| WO | WO-2022081822 A1 | 4/2022 | |
| WO | WO-2022098909 A1 | 5/2022 | |
| WO | WO-2022125562 A1 | 6/2022 | |
| WO | WO-2022125566 A1 | 6/2022 | |
| WO | WO-2022125576 A1 | 6/2022 | |
| WO | WO-2023194807 A2 | 10/2023 | |

OTHER PUBLICATIONS

Altschul et al. Basic Local Alignment Search Tool. J. Mol. Biol. 215:403-410 (1990).

Altschul, et al. Gapped BLAST and PSI-BLAST: a new generation of protein database search programs. Nucleic Acids Res 25:3389-3402 (1997).

Bedouelle et al. Diversity and junction residues as hotspots of binding energy in an antibody neutralizing the dengue virus. FEBS J 273(1):34-46 (2006).

Bird et al. Single-chain antigen-binding proteins. Science 242:423-442 (1988).

Blumberg et al. Structure of the T-cell antigen receptor: evidence for two CD3 epsilon subunits in the T-cell receptor-CD3 complex. PNAS USA 87(18):7220-4 (1990).

Brown et al. Tolerance of single, but not multiple, amino acid replacements in antibody VH CDR 2: a means of minimizing B cell wastage from somatic hypermutation? J Immunol 156(9):3285-3291 (1996).

Chatalic et al. A Novel 111 In-labeled Anti-PSMA Nanobody for Targeted SPECT/CT Imaging of Prostate Cancer. J Nucl Med 56(7):1094-1099 and Supplemental Data (2015).

Clackson et al. Making antibody fragments using phage display libraries. Nature 352(6336):624-628 (1991).

Colberre-Garapin et al. A new dominant hybrid selective marker for higher eukaryotic cells. J Mol Biol 150:1-14 (1981).

Cole et al. The EBV-hybridoma technique and its application to human lung cancer. In, Monoclonal Antibodies and Cancer Therapy (vol. 27, UCLA Symposia on Molecular and Cellular Biology, New Series) (eds. R.A. Reisfeld and S.Sell), New York: Alan R. Liss, Inc. pgs. 77-96 (1985).

Colman et al. Effects of amino acid sequence changes on antibody-antigen interactions. Research in Immunology 145(1):33-36 (1994).

Courtenay-Luck. Genetic manipulation of monoclonal antibodies. Monoclonal Antibodies: Production, Engineering and Clinical Application pp. 166-179 (1995).

Crouse et al. Expression and amplification of engineered mouse dihydrofolate reductase minigenes. Mol Cell Biol 3(2):257-266 (1983).

Geiger et al. Protease-activation using anti-idiotypic masks enables tumor specificity of a folate receptor 1-T cell bispecific antibody. Nat Commun 11(1):3196 (2020).

Goldspiel et al. Human gene therapy. Clin Pharm 12:488-505 (1993).

Hanes et al. In vitro selection and evolution of functional proteins by using ribosome display. PNAS USA 94:4937-4942 (1997).

Huse et al. Generation of a large combinatorial library of the immunoglobulin repertoire in phage lambda. Science 246(4935):1275-1281 (1989).

Huston et al. Protein engineering of antibody binding sites: recovery of specific activity in an anti-digoxin single-chain Fv analogue produced in *Escherichia coli*. PNAS USA 85(16):5879-5883 (1988).

Karlin, et al. Applications and statistics for multiple high-scoring segments in molecular sequences. PNAS USA 90:5873-5877 (1993).

Karlin et al. Methods for assessing the statistical significance of molecular sequence features by using general scoring schemes. PNAS USA 87:2264-2268 (1990).

Kessenbrock et al. Matrix metalloproteinases: regulators of the tumor microenvironment. Cell 141(1):52-67 (2010).

Kinoshita et al. Expression of prostate- specific membrane antigen in normal and malignant human tissues. World J Surg 30:628-36 (2006).

Kohler et al. Continuous cultures of fused cells secreting antibody of predefined specificity. Nature 256:495-497 (1975).

Kozbor et al. The production of monoclonal antibodies from human lymphocytes. Immunology Today 4:72-79 (1983).

(56)                    References Cited

OTHER PUBLICATIONS

Kutmeier et al. Assembly of humanized antibody genes from synthetic oligonucleotides using a single-round PCR. BioTechniques 17:242 (1994).

Larrick et al. PCR amplification of antibody genes. Methods 2:106-110 (1991).

Liao et al. Activation of lymphocytes by anti-CD3 single-chain antibody dinners expressed on the plasma membrane of tumor cells. Gene Therapy. 7:339-347 (2000).

Lowy et al., Isolation of transforming DNA: Cloning the hamster aprt gene. Cell 22:817-823 (1980).

Morgan et al. Human gene therapy. Ann Rev Biochem 62:191-217 (1993).

Morrison et al. Chimeric human antibody molecules: mouse antigen-binding domains with human constant region domains. PNAS USA 81(21):6851-6855 (1984).

Mulligan et al. Selection for animal cells that express the *Escherichia coli* gene coding for xanthine-guanine phosphoribosyltransferase. PNAS USA 78(4):2072-2076 (1981).

Mulligan. The basic science of gene therapy. Science 260(5110):926-932 (1993).

Multispecies: sporulation protein [Methanosarcina]. NCBI WP 048120037.1. https://www.ncbi.nlm.nih.gov/protein/WP048120037. 1?report=genbank&log$=protalign . . . Jan. 22, 2022.

Neuberger et al. Recombinant antibodies possessing novel effector functions. Nature 312(5995):604-608 (1984).

O'Hare et al. Transformation of mouse fibroblasts to methotrexate resistance by a recombinant plasmid expressing a prokaryotic dihydrofolate reductase. PNAS USA 78:1527-1531 (1981).

Olson et al. In vivo characterization of activatable cell penetrating peptides for targeting protease activity in cancer. Integr Biol (Camb) 1(5-6):382-393 (2009).

Pan et al. Site-specific PEGylation of an anti-CEA/CD3 bispecific antibody improves its antitumor efficacy. Int. J. Nanomed 13:3189-3201 (2018).

PCT/US2020/036493 International Invitation to Pay Additional Fees dated Sep. 15, 2020.

PCT/US2020/036493 International Search Report and Written Opinion dated Dec. 21, 2020.

PCT/US2021/045395 International Search Report and Written Opinion dated Dec. 10, 2021.

PCT/US2021/054948 International Search Report and Written Opinion dated Feb. 25, 2022.

PCT/US2021/062233 International Search Report and Written Opinion dated Apr. 26, 2022.

PCT/US2021/062238 International Search Report and Written Opinion dated Apr. 26, 2022.

PCT/US2021/062249 International Search Report and Written Opinion dated May 17, 2022.

PCT/US2021/062249 Invitation to Pay Additional Fees dated Mar. 15, 2022.

Pessano et al. The T3/T cell receptor complex: antigenic distinction between the two 20-kd T3 (T3-delta and T3-epsilon) subunits. The EMBO Journal 4(2):337-344 (1985).

Robert W. Bahr Memorandum of Feb. 22, 2018, 2 pages. (2018).

Rudikoff et al. Single amino acid substitution altering antigen-binding Specificity. PNAS USA 79:1979-1983 (1982).

Santerre et al. Expression of prokaryotic genes for hygromycin B and G418 resistance as dominant-selection markers in mouse L cells. Gene 30(1-3):147-156 (1984).

Skerra et al. Assembly of a functional Immunoglobulin Fv fragment in *Escherichia coli*. Science 240(4855):1038-1041 (1988).

Szybalska et al. Genetics of human cell line. IV. DNA-mediated heritable transformation of a biochemical trait. PNAS USA 48:2026-2034 (1962).

Takeda et al. Construction of chimaeric processed immunoglobulin genes containing mouse variable and human constant region sequences. Nature 314(6010):452-454 (1985).

Tolstoshev. Gene Therapy, Concepts, Current Trials and Future Directions. Ann. Rev. Pharmacol. Toxicol. 32:573-596 (1993).

UniProt Accession No. A0A315V0J1 (A0A315V0J1_GAMAF) Gambusia affinis (Western mosquitofish) (Heterandria affinis) Phosphoinositide phospholipase C; retrieved from https://www.uniprot.org/uniprot/A0A315V0J1 (2018).

UniProtKB A0A1D2VVTX0. Sporulatioti protein [online] Dec. 11, 2019 [retrieved Nov. 2, 2021]. Available on the internet: httias://www.uniprot.org/uniprot/A0A1D2VVIX0.

UniProtKB Accession No. A0A101XTH3_ 9BACL, Acidibacillus ferrooxidans ATVV55 11625gene Uncharacterized protein. Apr. 13, 2016 [online]. [Retrieved on Mar. 4, 2022]. Retrieved from the internet: <url: <a=href=>https://www.uniprot.org/uniprot/A0A101XTH3.</url:>.

U.S. Appl. No. 17/398,500 Office Action dated Feb. 18, 2022.

U.S. Appl. No. 17/544,539 Office Action dated Jul. 1, 2022.

Vajdos et al. Comprehensive functional maps of the antigen-binding site of an anti-ErbB2 antibody obtained with shotgun scanning mutagenesis. J Mol Biol 320:415-428 (2002).

Ward et al. Binding activities of a repertoire of single immuno-globulin variable domains secreted from Escherichia coli. Nature 341(6242):544-546 (1989).

Ward et al. Genetic Manipulation and Expression of Antibodies. Monoclonal Antibodies: Principles and Applications, Wiley-Liss Inc., pp. 137-185 (1995).

Wigler et al. Transfer of purified herpes virus thymidine kinase gene to cultured mouse cells. Cell 11:223-232 (1977).

Wigler et al. Transformation of mammalian cells with an amplifi-able dominant-acting gene. PNAS USA 77:3567-3570 (1980).

Wootton et al. Statistics of local complexity in amino acid sequences and sequence databases. Computers & Chemistry 17(2):149-163 (Jun. 1993).

Wu et al. Delivery systems for gene therapy. Biotherapy 3:87-95 (1991).

Zhao et al. High-efficiency transfection of primary human and mouse T lymphocytes using RNA electroporation. Mol. Ther. 13:151-159 (2006).

Al-Lazikani, B, et al., Standard Conformations for the Canonical Structures of Immunoglobulins. Journal of Molecular Biology 273(4):927-948 (1997).

Harvey et al. Cancer, inflammation, and therapy: effects on cytochrome p450-mediated drug metabolism and implications for novel immunotherapeutic agents. Clin Pharmacol Ther. 96(4):449-457 (2014).

Honegger, A et al., Yet Another Numbering Scheme for Immuno-globulin Variable Domains: An Automatic Modeling and Analysis Tool. Journal of Molecular Biology 309(3):657-670 (2001).

Huang et al. Therapeutic protein-drug interactions and implications for drug development. Clin Pharmacol Ther. 87(4):497-503 (2010).

Huston et al., Protein engineering of single-chain Fv analogs and fusion proteins. Methods Enzymol. 203:46-96 (1991).

Kabat et al. Sequences of proteins of immunological interest. NIH Publ. No. 91-3242 1:647-669 (1991).

Lefranc, Marie-Paule, et al., IMGT Unique Numbering for Immu-noglobulin and T Cell Receptor Variable Domains and Ig Superfam-ily V-like Domains. Developmental & Comparative Immunology 27(1):55-77 (2003).

Maccallum, R M, et al., Antibody-Antigen Interactions: Contact Analysis and Binding Site Topography. Journal of Molecular Biol-ogy 262(5):732-745 (1996).

Morris et al. Diagnostic Performance of (18)F-DCFPyL-PET/CT in Men with Biochemically Recurrent Prostate Cancer: Results from the CONDOR Phase III, Multicenter Study. Clin Cancer Res. 27(13):3674-3682 (2021).

PCT/US2021/054948 International Invitation to Pay Additional Fees dated Dec. 16, 2021.

Sartor et al. Lutetium-177-PSMA-617 for Metastatic Castration-Resistant Prostate Cancer. N Engl J Med 385(12):1091-1103 (2021).

Sartor et al. Metastatic Prostate Cancer. N Engl J Med. 378(17):1653-1654 (2018).

Seitz et al. Pharmacokinetic drug-drug interaction potentials for therapeutic monoclonal antibodies: reality check. J Clin Pharmacol. 47(9):1104-1118 (2007).

(56) References Cited

OTHER PUBLICATIONS

Sheehan et al., Prostate-specific Membrane Antigen Biology in Lethal Prostate Cancer and its Therapeutic Implications. Eur Urol Focus. 8(5):1157-1168 (2022).

Silver et al. Prostate-specific membrane antigen expression in normal and malignant human tissues. Clin Cancer Res 3:81-5 (1997).

The Protein Atlas, 2022. Available online at www.proteinatlas.org.

Tran et al. Phase I study of AMG 160, a half-life extended bispecific T-cell engager (HLE BiTE immune therapy) targeting prostate-specific membrane antigen, in patients with metastatic castration-resistant prostate cancer (mCRPC). J Clin Oncol 38(15_suppl):TPS5590-TPS5590 (2020).

Wang et al. Monoclonal antibody pharmacokinetics and pharmacodynamics. Clin Pharmacol Ther. 84(5):548-558 (2008).

Whitelegg, N R, et al., WAM: An Improved Algorithm for Modelling Antibodies on the WEB. Protein Engineering 13(12):819-824 (2000).

Beirnaert, Els et al. Bivalent Llama Single-Domain Antibody Fragments against Tumor Necrosis Factor Have Picomolar Potencies due to Intramolecular Interactions. Frontiers in Immunology 8:867, 1-13 (2017).

Chen, Timothy T. et al. Conditionally active T cell engagers for the treatment of solid tumors: rationale and clinical development. Expert Opinion on Biological Therapy 22(8):955-963 (2022).

Co-pending U.S. Appl. No. 19/201,165, inventors Campbell; David et al., filed on May 7, 2025.

Co-pending U.S. Appl. No. 19/320,207, inventors Campbell; David et al., filed on Sep. 5, 2025.

Edwards, Bryan M. et al. The Remarkable Flexibility of the Human Antibody Repertoire; Isolation of Over One Thousand Different Antibodies to a Single Protein, BLyS. Journal of Molecular Biology 334(1):103-118 (2003).

Gizinski, Alison M. et al. Co-stimulation and T cells at therapeutic targets. Best Practice Research Clinical Rheumatology 24(4):463-477 (2010).

Hall, Brenda L. et al. A single amino acid mutation in CDR3 of the 3-14-9 L chain abolished expression of the IDA 10-defined idiotope and antigen binding. The Journal of Immunology 149(5): 1605-1612 (1992).

Janeway, Charles Alderson et al. Chapter 3: Structure of the antibody molecule and Immunoglobulin genes, Immunobiology: The Immune System in Health and Disease, 3rd Edition. Current Biology limited, Garland Publishing Inc pp. 3.1-3.11 (1997).

Janeway Jr., Charles A. et al. The generation of diversity in immunoglobulins. Immunobiology: The Immune System in Health and Disease. 5th Edition, Garland Science :1-15 (2001).

Liddy, Nathaniel et al. Monoclonal TCR-redirected tumor cell killing. Nature Medicine 18(6):980-988 (2012).

Liu, Longchao et al. Therapeutic antibodies for precise cancer immunotherapy: current and future perspectives. Medical Review 2(6):555-569 (2022).

Marhelava, Katsiaryna et al. Targeting negative and positive immune checkpoints with monoclonal antibodies in therapy of cancer. Cancers 11(11):1756, 1-21 (2019).

Nakakido, Makoto et al. Development of novel humanized VHH synthetic libraries based on physicochemical analyses. Scientific Report 14:19533, 1-13 (2024).

Rabia, Lilia A. et al. Understanding and overcoming trade-offs between antibody affinity, specificity, stability and solubility. Biochemical Engineering Journal 137:365-374 (2018).

Tanabe, Lauren M. et al. The role of type II transmembrane serine protease-mediated signaling in cancer. The FEBS Journal 284(10):1421-1436 (2017).

Townsend, Catherine L. et al. Significant differences in physicochemical properties of human immunoglobulin kappa and lambda CDR3 regions. Frontiers in immunology 7:388, 1-12 (2016).

U.S. Appl. No. 17/616,281 Office Action dated Oct. 21, 2025.

U.S. Appl. No. 18/031,724 Office Action dated Nov. 10, 2025.

U.S. Appl. No. 18/785,900 Office Action dated May 8, 2025.

Vignali, Dario A. A. et al. How regulatory T cells work. Nature Reviews Immunology 8(7):523-532 (2008).

* cited by examiner

Form Vh = normal

Form Vl = flipped

Binding Immobilized PSMA-biotin

PC3
PC3 + MTSP1
PC1

OD 450 nm

Log [nM ]

SEQUENCE LISTING

```
Sequence total quantity: 966
SEQ ID NO: 1          moltype = AA  length = 8
FEATURE               Location/Qualifiers
REGION                1..8
                      note = Description of Artificial Sequence: Synthetic peptide
source                1..8
```

-continued

```
                          mol_type = protein
                          organism = synthetic construct
SEQUENCE: 1
GFTFNKYA                                                          8

SEQ ID NO: 2               moltype = AA   length = 10
FEATURE                    Location/Qualifiers
REGION                     1..10
                          note = Description of Artificial Sequence: Synthetic peptide
source                     1..10
                          mol_type = protein
                          organism = synthetic construct
SEQUENCE: 2
IRSKYNNYAT                                                       10

SEQ ID NO: 3               moltype = AA   length = 16
FEATURE                    Location/Qualifiers
REGION                     1..16
                          note = Description of Artificial Sequence: Synthetic peptide
source                     1..16
                          mol_type = protein
                          organism = synthetic construct
SEQUENCE: 3
VRHGNFGNSY ISYWAY                                                16

SEQ ID NO: 4               moltype = AA   length = 9
FEATURE                    Location/Qualifiers
REGION                     1..9
                          note = Description of Artificial Sequence: Synthetic peptide
source                     1..9
                          mol_type = protein
                          organism = synthetic construct
SEQUENCE: 4
TGAVTSGNY                                                         9

SEQ ID NO: 5               moltype =    length =
SEQUENCE: 5
000

SEQ ID NO: 6               moltype = AA   length = 9
FEATURE                    Location/Qualifiers
REGION                     1..9
                          note = Description of Artificial Sequence: Synthetic peptide
source                     1..9
                          mol_type = protein
                          organism = synthetic construct
SEQUENCE: 6
VLWYSNRWV                                                         9

SEQ ID NO: 7               moltype = AA   length = 249
FEATURE                    Location/Qualifiers
REGION                     1..249
                          note = Description of Artificial Sequence: Synthetic
                           polypeptide
source                     1..249
                          mol_type = protein
                          organism = synthetic construct
SEQUENCE: 7
EVQLVESGGG LVQPGGSLKL SCAASGFTFN KYAMNWVRQA PGKGLEWVAR IRSKYNNYAT  60
YYADSVKDRF TISRDDSKNT AYLQMNNLKT EDTAVYYCVR HGNFGNSYIS YWAYWGQGTL  120
VTVSSGGGGS GGGGSGGGGS QTVVTQEPSL TVSPGGTVTL TCGSSTGAVT SGNYPNWVQQ  180
KPGQAPRGLI GGTKFLAPGT PARFSGSLLG GKAALTLSGV QPEDEAEYYC VLWYSNRWVF  240
GGGTKLTVL                                                         249

SEQ ID NO: 8               moltype = AA   length = 8
FEATURE                    Location/Qualifiers
REGION                     1..8
                          note = Description of Artificial Sequence: Synthetic peptide
source                     1..8
                          mol_type = protein
                          organism = synthetic construct
SEQUENCE: 8
GFAFSRYG                                                          8

SEQ ID NO: 9               moltype = AA   length = 8
FEATURE                    Location/Qualifiers
REGION                     1..8
                          note = Description of Artificial Sequence: Synthetic peptide
source                     1..8
```

```
                          mol_type = protein
                          organism = synthetic construct
SEQUENCE: 9
IWYDGSNK                                                                    8

SEQ ID NO: 10             moltype = AA  length = 16
FEATURE                   Location/Qualifiers
REGION                    1..16
                          note = Description of Artificial Sequence: Synthetic peptide
source                    1..16
                          mol_type = protein
                          organism = synthetic construct
SEQUENCE: 10
ARGGDFLYYY YYGMDV                                                          16

SEQ ID NO: 11             moltype = AA  length = 6
FEATURE                   Location/Qualifiers
REGION                    1..6
                          note = Description of Artificial Sequence: Synthetic peptide
source                    1..6
                          mol_type = protein
                          organism = synthetic construct
SEQUENCE: 11
QGISNY                                                                      6

SEQ ID NO: 12             moltype =   length =
SEQUENCE: 12
000

SEQ ID NO: 13             moltype = AA  length = 9
FEATURE                   Location/Qualifiers
REGION                    1..9
                          note = Description of Artificial Sequence: Synthetic peptide
source                    1..9
                          mol_type = protein
                          organism = synthetic construct
SEQUENCE: 13
QNYNSAPFT                                                                   9

SEQ ID NO: 14             moltype = AA  length = 214
FEATURE                   Location/Qualifiers
REGION                    1..214
                          note = Description of Artificial Sequence: Synthetic
                           polypeptide
source                    1..214
                          mol_type = protein
                          organism = synthetic construct
SEQUENCE: 14
DIQMTQSPSS LSASVGDRVT ITCRASQGIS NYLAWYQQKT GKVPKFLIYE ASTLQSGVPS  60
RFSGGGSGTD FTLTISSLQP EDVATYYCQN YNSAPFTFGP GTKVDIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 15             moltype = AA  length = 226
FEATURE                   Location/Qualifiers
REGION                    1..226
                          note = Description of Artificial Sequence: Synthetic
                           polypeptide
source                    1..226
                          mol_type = protein
                          organism = synthetic construct
SEQUENCE: 15
QVQLVESGGG VVQPGRSLRL SCAASGFAFS RYGMHWVRQA PGKGLEWVAV IWYDGSNKYY  60
ADSVKGRFTI SRDNSKNTQY LQMNSLRAED TAVYYCARGG DFLYYYYGM DVWGQGTTVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSC                226

SEQ ID NO: 16             moltype = AA  length = 16
FEATURE                   Location/Qualifiers
REGION                    1..16
                          note = Description of Artificial Sequence: Synthetic peptide
source                    1..16
                          mol_type = protein
                          organism = synthetic construct
SEQUENCE: 16
GGGSQCLGPE WEVCPY                                                          16

SEQ ID NO: 17             moltype = AA  length = 16
FEATURE                   Location/Qualifiers
```

```
REGION                     1..16
                           note = Description of Artificial Sequence: Synthetic peptide
source                     1..16
                           mol_type = protein
                           organism = synthetic construct
SEQUENCE: 17
GGVYCGPEFD ESVGCM                                                              16

SEQ ID NO: 18              moltype = AA  length = 14
FEATURE                    Location/Qualifiers
REGION                     1..14
                           note = Description of Artificial Sequence: Synthetic peptide
source                     1..14
                           mol_type = protein
                           organism = synthetic construct
SEQUENCE: 18
GSQCLGPEWE VCPY                                                                14

SEQ ID NO: 19              moltype = AA  length = 14
FEATURE                    Location/Qualifiers
REGION                     1..14
                           note = Description of Artificial Sequence: Synthetic peptide
source                     1..14
                           mol_type = protein
                           organism = synthetic construct
SEQUENCE: 19
VYCGPEFDES VGCM                                                                14

SEQ ID NO: 20              moltype = AA  length = 15
FEATURE                    Location/Qualifiers
REGION                     1..15
                           note = Description of Artificial Sequence: Synthetic peptide
source                     1..15
                           mol_type = protein
                           organism = synthetic construct
SEQUENCE: 20
GGGGSGGGGS GGGGS                                                               15

SEQ ID NO: 21              moltype = AA  length = 5
FEATURE                    Location/Qualifiers
REGION                     1..5
                           note = Description of Artificial Sequence: Synthetic peptide
source                     1..5
                           mol_type = protein
                           organism = synthetic construct
SEQUENCE: 21
GGGGS                                                                          5

SEQ ID NO: 22              moltype = AA  length = 9
FEATURE                    Location/Qualifiers
REGION                     1..9
                           note = Description of Artificial Sequence: Synthetic peptide
source                     1..9
                           mol_type = protein
                           organism = synthetic construct
SEQUENCE: 22
GGGGSGGGS                                                                      9

SEQ ID NO: 23              moltype = AA  length = 28
FEATURE                    Location/Qualifiers
REGION                     1..28
                           note = Description of Artificial Sequence: Synthetic peptide
source                     1..28
                           mol_type = protein
                           organism = synthetic construct
SEQUENCE: 23
GGGGSGGGLS GRSDAGSPLG LAGSGGGS                                                 28

SEQ ID NO: 24              moltype = AA  length = 18
FEATURE                    Location/Qualifiers
REGION                     1..18
                           note = Description of Artificial Sequence: Synthetic peptide
source                     1..18
                           mol_type = protein
                           organism = synthetic construct
SEQUENCE: 24
GGGGSLSGRS DNHGSSGT                                                            18

SEQ ID NO: 25              moltype = AA  length = 26
```

-continued

```
FEATURE               Location/Qualifiers
REGION                1..26
                      note = Description of Artificial Sequence: Synthetic peptide
source                1..26
                      mol_type = protein
                      organism = synthetic construct
SEQUENCE: 25
GGGGSSGGSG GSGLSGRSDN HGSSGT                                    26

SEQ ID NO: 26         moltype = AA   length = 8
FEATURE               Location/Qualifiers
REGION                1..8
                      note = Description of Artificial Sequence: Synthetic peptide
source                1..8
                      mol_type = protein
                      organism = synthetic construct
SEQUENCE: 26
ASGRSDNH                                                        8

SEQ ID NO: 27         moltype = AA   length = 8
FEATURE               Location/Qualifiers
REGION                1..8
                      note = Description of Artificial Sequence: Synthetic peptide
source                1..8
                      mol_type = protein
                      organism = synthetic construct
SEQUENCE: 27
LAGRSDNH                                                        8

SEQ ID NO: 28         moltype = AA   length = 13
FEATURE               Location/Qualifiers
REGION                1..13
                      note = Description of Artificial Sequence: Synthetic peptide
source                1..13
                      mol_type = protein
                      organism = synthetic construct
SEQUENCE: 28
ISSGLASGRS DNH                                                  13

SEQ ID NO: 29         moltype = AA   length = 13
FEATURE               Location/Qualifiers
REGION                1..13
                      note = Description of Artificial Sequence: Synthetic peptide
source                1..13
                      mol_type = protein
                      organism = synthetic construct
SEQUENCE: 29
ISSGLLAGRS DNH                                                  13

SEQ ID NO: 30         moltype = AA   length = 8
FEATURE               Location/Qualifiers
REGION                1..8
                      note = Description of Artificial Sequence: Synthetic peptide
source                1..8
                      mol_type = protein
                      organism = synthetic construct
SEQUENCE: 30
LSGRSDNH                                                        8

SEQ ID NO: 31         moltype = AA   length = 13
FEATURE               Location/Qualifiers
REGION                1..13
                      note = Description of Artificial Sequence: Synthetic peptide
source                1..13
                      mol_type = protein
                      organism = synthetic construct
SEQUENCE: 31
ISSGLLSGRS DNP                                                  13

SEQ ID NO: 32         moltype = AA   length = 13
FEATURE               Location/Qualifiers
REGION                1..13
                      note = Description of Artificial Sequence: Synthetic peptide
source                1..13
                      mol_type = protein
                      organism = synthetic construct
SEQUENCE: 32
ISSGLLSGRS DNH                                                  13
```

```
SEQ ID NO: 33          moltype = AA   length = 16
FEATURE                Location/Qualifiers
REGION                 1..16
                       note = Description of Artificial Sequence: Synthetic peptide
source                 1..16
                       mol_type = protein
                       organism = synthetic construct
SEQUENCE: 33
LSGRSDNHSP LGLAGS                                              16

SEQ ID NO: 34          moltype = AA   length = 16
FEATURE                Location/Qualifiers
REGION                 1..16
                       note = Description of Artificial Sequence: Synthetic peptide
source                 1..16
                       mol_type = protein
                       organism = synthetic construct
SEQUENCE: 34
SPLGLAGSLS GRSDNH                                              16

SEQ ID NO: 35          moltype = AA   length = 12
FEATURE                Location/Qualifiers
REGION                 1..12
                       note = Description of Artificial Sequence: Synthetic peptide
source                 1..12
                       mol_type = protein
                       organism = synthetic construct
SEQUENCE: 35
SPLGLSGRSD NH                                                  12

SEQ ID NO: 36          moltype = AA   length = 16
FEATURE                Location/Qualifiers
REGION                 1..16
                       note = Description of Artificial Sequence: Synthetic peptide
source                 1..16
                       mol_type = protein
                       organism = synthetic construct
SEQUENCE: 36
LAGRSDNHSP LGLAGS                                              16

SEQ ID NO: 37          moltype = AA   length = 16
FEATURE                Location/Qualifiers
REGION                 1..16
                       note = Description of Artificial Sequence: Synthetic peptide
source                 1..16
                       mol_type = protein
                       organism = synthetic construct
SEQUENCE: 37
LSGRSDNHVP LSLKMG                                              16

SEQ ID NO: 38          moltype = AA   length = 16
FEATURE                Location/Qualifiers
REGION                 1..16
                       note = Description of Artificial Sequence: Synthetic peptide
source                 1..16
                       mol_type = protein
                       organism = synthetic construct
SEQUENCE: 38
LSGRSDNHVP LSLSMG                                              16

SEQ ID NO: 39          moltype = AA   length = 31
FEATURE                Location/Qualifiers
REGION                 1..31
                       note = Description of Artificial Sequence: Synthetic
                        polypeptide
source                 1..31
                       mol_type = protein
                       organism = synthetic construct
SEQUENCE: 39
GSSGGSGGSG GSGISSGLLS GRSDNHGSSG T                             31

SEQ ID NO: 40          moltype = AA   length = 28
FEATURE                Location/Qualifiers
REGION                 1..28
                       note = Description of Artificial Sequence: Synthetic peptide
source                 1..28
                       mol_type = protein
                       organism = synthetic construct
SEQUENCE: 40
```

```
GSSGGSGGSG GISSGLLSGR SDNHGGGS                                                     28

SEQ ID NO: 41              moltype = AA   length = 8
FEATURE                    Location/Qualifiers
REGION                     1..8
                           note = Description of Artificial Sequence: Synthetic peptide
source                     1..8
                           mol_type = protein
                           organism = synthetic construct
SEQUENCE: 41
ASGRSDNH                                                                           8

SEQ ID NO: 42              moltype = AA   length = 8
FEATURE                    Location/Qualifiers
REGION                     1..8
                           note = Description of Artificial Sequence: Synthetic peptide
source                     1..8
                           mol_type = protein
                           organism = synthetic construct
SEQUENCE: 42
LAGRSDNH                                                                           8

SEQ ID NO: 43              moltype = AA   length = 13
FEATURE                    Location/Qualifiers
REGION                     1..13
                           note = Description of Artificial Sequence: Synthetic peptide
source                     1..13
                           mol_type = protein
                           organism = synthetic construct
SEQUENCE: 43
ISSGLASGRS DNH                                                                     13

SEQ ID NO: 44              moltype = AA   length = 8
FEATURE                    Location/Qualifiers
REGION                     1..8
                           note = Description of Artificial Sequence: Synthetic peptide
source                     1..8
                           mol_type = protein
                           organism = synthetic construct
SEQUENCE: 44
LSGRSDAG                                                                           8

SEQ ID NO: 45              moltype = AA   length = 13
FEATURE                    Location/Qualifiers
REGION                     1..13
                           note = Description of Artificial Sequence: Synthetic peptide
source                     1..13
                           mol_type = protein
                           organism = synthetic construct
SEQUENCE: 45
ISSGLLSGRS DAG                                                                     13

SEQ ID NO: 46              moltype = AA   length = 18
FEATURE                    Location/Qualifiers
REGION                     1..18
                           note = Description of Artificial Sequence: Synthetic peptide
source                     1..18
                           mol_type = protein
                           organism = synthetic construct
SEQUENCE: 46
AAGLLAPPGG LSGRSDAG                                                                18

SEQ ID NO: 47              moltype = AA   length = 12
FEATURE                    Location/Qualifiers
REGION                     1..12
                           note = Description of Artificial Sequence: Synthetic peptide
source                     1..12
                           mol_type = protein
                           organism = synthetic construct
SEQUENCE: 47
SPLGLSGRSD AG                                                                      12

SEQ ID NO: 48              moltype = AA   length = 15
FEATURE                    Location/Qualifiers
REGION                     1..15
                           note = Description of Artificial Sequence: Synthetic peptide
source                     1..15
                           mol_type = protein
                           organism = synthetic construct
```

-continued

```
SEQUENCE: 48
LSGRSDAGSP LGLAG                                                              15

SEQ ID NO: 49          moltype = AA  length = 28
FEATURE                Location/Qualifiers
REGION                 1..28
                       note = Description of Artificial Sequence: Synthetic peptide
source                 1..28
                       mol_type = protein
                       organism = synthetic construct
SEQUENCE: 49
GGGGSGGGSG GGGSGGASSG AGGSGGGS                                                28

SEQ ID NO: 50          moltype = AA  length = 5
FEATURE                Location/Qualifiers
REGION                 1..5
                       note = Description of Artificial Sequence: Synthetic peptide
source                 1..5
                       mol_type = protein
                       organism = synthetic construct
SEQUENCE: 50
GSGGS                                                                         5

SEQ ID NO: 51          moltype = AA  length = 4
FEATURE                Location/Qualifiers
REGION                 1..4
                       note = Description of Artificial Sequence: Synthetic peptide
source                 1..4
                       mol_type = protein
                       organism = synthetic construct
SEQUENCE: 51
GGGS                                                                          4

SEQ ID NO: 52          moltype = AA  length = 5
FEATURE                Location/Qualifiers
REGION                 1..5
                       note = Description of Artificial Sequence: Synthetic peptide
source                 1..5
                       mol_type = protein
                       organism = synthetic construct
SEQUENCE: 52
GGGGS                                                                         5

SEQ ID NO: 53          moltype = AA  length = 6
FEATURE                Location/Qualifiers
REGION                 1..6
                       note = Description of Artificial Sequence: Synthetic peptide
source                 1..6
                       mol_type = protein
                       organism = synthetic construct
SEQUENCE: 53
GSSGGS                                                                        6

SEQ ID NO: 54          moltype = AA  length = 8
FEATURE                Location/Qualifiers
REGION                 1..8
                       note = Description of Artificial Sequence: Synthetic peptide
source                 1..8
                       mol_type = protein
                       organism = synthetic construct
SEQUENCE: 54
GSTFYTAV                                                                      8

SEQ ID NO: 55          moltype = AA  length = 8
FEATURE                Location/Qualifiers
REGION                 1..8
                       note = Description of Artificial Sequence: Synthetic peptide
source                 1..8
                       mol_type = protein
                       organism = synthetic construct
SEQUENCE: 55
IRWTALTT                                                                      8

SEQ ID NO: 56          moltype = AA  length = 17
FEATURE                Location/Qualifiers
REGION                 1..17
                       note = Description of Artificial Sequence: Synthetic peptide
source                 1..17
                       mol_type = protein
```

```
                          organism = synthetic construct
SEQUENCE: 56
AARGTLGLFT TADSYDY                                                    17

SEQ ID NO: 57            moltype = AA   length = 124
FEATURE                  Location/Qualifiers
REGION                   1..124
                         note = Description of Artificial Sequence: Synthetic
                          polypeptide
source                   1..124
                         mol_type = protein
                         organism = synthetic construct
SEQUENCE: 57
EVQLVESGGG LVQPGGSLRL SCAASGSTFY TAVMGWVRQA PGKGLEWVAA IRWTALTTSY   60
ADSVKGRFTI SRDGAKTTLY LQMNSLRPED TAVYYCAARG TLGLFTTADS YDYWGQGTLV   120
TVSS                                                                 124

SEQ ID NO: 58            moltype = AA   length = 8
FEATURE                  Location/Qualifiers
REGION                   1..8
                         note = Description of Artificial Sequence: Synthetic peptide
source                   1..8
                         mol_type = protein
                         organism = synthetic construct
SEQUENCE: 58
GFTFSKFG                                                              8

SEQ ID NO: 59            moltype = AA   length = 8
FEATURE                  Location/Qualifiers
REGION                   1..8
                         note = Description of Artificial Sequence: Synthetic peptide
source                   1..8
                         mol_type = protein
                         organism = synthetic construct
SEQUENCE: 59
ISGSGRDT                                                              8

SEQ ID NO: 60            moltype = AA   length = 8
FEATURE                  Location/Qualifiers
REGION                   1..8
                         note = Description of Artificial Sequence: Synthetic peptide
source                   1..8
                         mol_type = protein
                         organism = synthetic construct
SEQUENCE: 60
TIGGSLSV                                                              8

SEQ ID NO: 61            moltype = AA   length = 115
FEATURE                  Location/Qualifiers
REGION                   1..115
                         note = Description of Artificial Sequence: Synthetic
                          polypeptide
source                   1..115
                         mol_type = protein
                         organism = synthetic construct
SEQUENCE: 61
EVQLVESGGG LVQPGNSLRL SCAASGFTFS KFGMSWVRQA PGKGLEWVSS ISGSGRDTLY   60
ADSVKGRFTI SRDNAKTTLY LQMNSLRPED TAVYYCTIGG SLSVSSQGTL VTVSS         115

SEQ ID NO: 62            moltype = AA   length = 214
FEATURE                  Location/Qualifiers
REGION                   1..214
                         note = Description of Artificial Sequence: Synthetic
                          polypeptide
source                   1..214
                         mol_type = protein
                         organism = synthetic construct
SEQUENCE: 62
DIQMTQSPSS LSASVGDRVT ITCRASQGIS NYLAWYQQKT GKVPKFLIYE ASTLQSGVPS   60
RFSGGGSGTD FTLTISSLQP EDVATYYCQN YNSAPFTFGP GTKVDIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                                214

SEQ ID NO: 63            moltype = AA   length = 480
FEATURE                  Location/Qualifiers
REGION                   1..480
                         note = Description of Artificial Sequence: Synthetic
                          polypeptide
source                   1..480
```

-continued

```
                        mol_type = protein
                        organism = synthetic construct
SEQUENCE: 63
EVQLVESGGG LVQPGGSLKL SCAASGFTFN KYAMNWVRQA PGKGLEWVAR IRSKYNNYAT   60
YYADSVKDRF TISRDDSKNT AYLQMNNLKT EDTAVYYCVR HGNFGNSYIS YWAYWGQGTL  120
VTVSSGGGGS GGGGSGGGGS QTVVTQEPSL TVSPGGTVTL TCGSSTGAVT SGNYPNWVQQ  180
KPGQAPRGLI GGTKFLAPGT PARFSGSLLG GKAALTLSGV QPEDEAEYYC VLWYSNRWVF  240
GGGTKLTVLG GGGSQVQLVE SGGGVVQPGR SLRLSCAASG FAFSRYGMHW VRQAPGKGLE  300
WVAVIWYDGS NKYYADSVKG RFTISRDNSK NTQYLQMNSL RAEDTAVYYC ARGGDFLYYY  360
YYGMDVWGQG TTVTVSSAST KGPSVFPLAP SSKSTSGGTA ALGCLVKDYF PEPVTVSWNS  420
GALTSGVHTF PAVLQSSGLY SLSSVVTVPS SSLGTQTYIC NVNHKPSNTK VDKKVEPKSC  480

SEQ ID NO: 64          moltype = AA  length = 468
FEATURE                Location/Qualifiers
REGION                 1..468
                       note = Description of Artificial Sequence: Synthetic
                        polypeptide
source                 1..468
                       mol_type = protein
                       organism = synthetic construct
SEQUENCE: 64
EVQLVESGGG LVQPGGSLKL SCAASGFTFN KYAMNWVRQA PGKGLEWVAR IRSKYNNYAT   60
YYADSVKDRF TISRDDSKNT AYLQMNNLKT EDTAVYYCVR HGNFGNSYIS YWAYWGQGTL  120
VTVSSGGGGS GGGGSGGGGS QTVVTQEPSL TVSPGGTVTL TCGSSTGAVT SGNYPNWVQQ  180
KPGQAPRGLI GGTKFLAPGT PARFSGSLLG GKAALTLSGV QPEDEAEYYC VLWYSNRWVF  240
GGGTKLTVLG GGGSDIQMTQ SPSSLSASVG DRVTITCRAS QGISNYLAWY QQKTGKVPKF  300
LIYEASTLQS GVPSRFSGGG SGTDFTLTIS SLQPEDVATY YCQNYNSAPF TFGPGTKVDI  360
KRTVAAPSVF IFPPSDEQLK SGTASVVCLL NNFYPREAKV QWKVDNALQS GNSQESVTEQ  420
DSKDSTYSLS STLTLSKADY EKHKVYACEV THQGLSSPVT KSFNRGEC              468

SEQ ID NO: 65          moltype = AA  length = 226
FEATURE                Location/Qualifiers
REGION                 1..226
                       note = Description of Artificial Sequence: Synthetic
                        polypeptide
source                 1..226
                       mol_type = protein
                       organism = synthetic construct
SEQUENCE: 65
QVQLVESGGG VVQPGRSLRL SCAASGFAFS RYGMHWVRQA PGKGLEWVAV IWYDGSNKYY   60
ADSVKGRFTI SRDNSKNTQY LQMNSLRAED TAVYYCARGG DFLYYYYGM DVWGQGTTVT   120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSC              226

SEQ ID NO: 66          moltype = AA  length = 214
FEATURE                Location/Qualifiers
REGION                 1..214
                       note = Description of Artificial Sequence: Synthetic
                        polypeptide
source                 1..214
                       mol_type = protein
                       organism = synthetic construct
SEQUENCE: 66
DIQMTQSPSS LSASVGDRVT ITCRASQGIS NYLAWYQQKT GKVPKFLIYE ASTLQSGVPS   60
RFSGGGSGTD FTLTISSLQP EDVATYYCQN YNSAPFTFGP GTKVDIKRTV AAPSVFIFPP  120
SDEQLKSGTA SVVCLLNNFY PREAKVQWKV DNALQSGNSP ESVTEQDSKD STYSLSSTLT  180
LSKADYEKHK VYACEVTHQG LSSPVTKSFN RGEC                          214

SEQ ID NO: 67          moltype = AA  length = 657
FEATURE                Location/Qualifiers
REGION                 1..657
                       note = Description of Artificial Sequence: Synthetic
                        polypeptide
source                 1..657
                       mol_type = protein
                       organism = synthetic construct
SEQUENCE: 67
EVQLVESGGG LVQPGGSLRL SCAASGSTFY TAVMGWVRQA PGKGLEWVAA IRWTALTTSY   60
ADSVKGRFTI SRDGAKTTLY LQMNSLRPED TAVYYCAARG TLGLFTTADS YDYWGQGTLV  120
TVSSGGGGSG GGSGGGGSQCL GPEWEVCPYG GGGSGGGLSG RSDAGSPLGL AGSGGGGSEVQ 180
LVESGGGLVQ PGGSLKLSCA ASGFTFNKYA MNWVRQAPGK GLEWVARIRS KYNNYATYYA  240
DSVKDRFTIS RDDSKNTAYL QMNNLKTEDT AVYYCVRHGN FGNSYISYWA YWGQGTLVTV  300
SSGGGGSGGG GSGGGGSQTV VTQEPSLTVS PGGTVTLTCG SSTGAVTSGN YPNWVQQKPG  360
QAPRGLIGGT KFLAPGTPAR FSGSLLGGKA ALTLSGVQPE DEAEYYCVLW YSNRWVFGGG  420
TKLTVLGGGG SQVQLVESGG GVVQPGRSLR LSCAASGFAF SRYGMHWVRQ APGKGLEWVA  480
VIWYDGSNKY YADSVKGRFT ISRDNSKNTQ YLQMNSLRAE DTAVYYCARG GDFLYYYYYG  540
MDVWGQGTTV TVSSASTKGP SVFPLAPSSK STSGGTAALG CLVKDYFPEP VTVSWNSGAL  600
TSGVHTFPAV LQSSGLYSLS SVVTVPSSSL GTQTYICNVN HKPSNTKVDK KVEPKSC     657
```

-continued

```
SEQ ID NO: 68              moltype = AA   length = 645
FEATURE                    Location/Qualifiers
REGION                     1..645
                           note = Description of Artificial Sequence: Synthetic
                            polypeptide
source                     1..645
                           mol_type = protein
                           organism = synthetic construct
SEQUENCE: 68
EVQLVESGGG LVQPGGSLRL SCAASGSTFY TAVMGWVRQA PGKGLEWVAA IRWTALTTSY  60
ADSVKGRFTI SRDGAKTTLY LQMNSLRPED TAVYYCAARG TLGLFTTADS YDYWGQGTLV  120
TVSSGGGGSG GGSGGGGSQCL GPEWEVCPYG GGGSGGGLSG RSDAGSPLGL AGSGGGSEVQ  180
LVESGGGLVQ PGGSLKLSCA ASGFTFNKYA MNWVRQAPGK GLEWVARIRS KYNNYATYYA  240
DSVKDRFTIS RDDSKNTAYL QMNNLKTEDT AVYYCVRHGN FGNSYISYWA YWGQGTLVTV  300
SSGGGGSGGG GSGGGGSQTV VTQEPSLTVS PGGTVTLTCG SSTGAVTSGN YPNWVQQKPG  360
QAPRGLIGGT KFLAPGTPAR FSGSLLGGKA ALTLSGVQPE DEAEYYCVLW YSNRWVFGGG  420
TKLTVLGGGG SDIQMTQSPS SLSASVGDRV TITCRASQGI SNYLAWYQQK TGKVPKFLIY  480
EASTLQSGVP SRFSGGGSGT DFTLTISSLQ PEDVATYYCQ NYNSAPFTFG PGTKVDIKRT  540
VAAPSVFIFP PSDEQLKSGT ASVVCLLNNF YPREAKVQWK VDNALQSGNS QESVTEQDSK  600
DSTYSLSSTL TLSKADYEKH KVYACEVTHQ GLSSPVTKSF NRGEC              645

SEQ ID NO: 69              moltype = AA   length = 226
FEATURE                    Location/Qualifiers
REGION                     1..226
                           note = Description of Artificial Sequence: Synthetic
                            polypeptide
source                     1..226
                           mol_type = protein
                           organism = synthetic construct
SEQUENCE: 69
QVQLVESGGG VVQPGRSLRL SCAASGFAFS RYGMHWVRQA PGKGLEWVAV IWYDGSNKYY  60
ADSVKGRFTI SRDNSKNTQY LQMNSLRAED TAVYYCARGG DFLYYYYGM DVWGQGTTVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSC              226

SEQ ID NO: 70              moltype = AA   length = 214
FEATURE                    Location/Qualifiers
REGION                     1..214
                           note = Description of Artificial Sequence: Synthetic
                            polypeptide
source                     1..214
                           mol_type = protein
                           organism = synthetic construct
SEQUENCE: 70
DIQMTQSPSS LSASVGDRVT ITCRASQGIS NYLAWYQQKT GKVPKFLIYE ASTLQSGVPS  60
RFSGGGSGTD FTLTISSLQP EDVATYYCQN YNSAPFTFGP GTKVDIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                          214

SEQ ID NO: 71              moltype = AA   length = 657
FEATURE                    Location/Qualifiers
REGION                     1..657
                           note = Description of Artificial Sequence: Synthetic
                            polypeptide
source                     1..657
                           mol_type = protein
                           organism = synthetic construct
SEQUENCE: 71
EVQLVESGGG LVQPGGSLRL SCAASGSTFY TAVMGWVRQA PGKGLEWVAA IRWTALTTSY  60
ADSVKGRFTI SRDGAKTTLY LQMNSLRPED TAVYYCAARG TLGLFTTADS YDYWGQGTLV  120
TVSSGGGGSG GGSGGVYCGP EFDESVGCMG GGGSGGGLSG RSDAGSPLGL AGSGGGSEVQ  180
LVESGGGLVQ PGGSLKLSCA ASGFTFNKYA MNWVRQAPGK GLEWVARIRS KYNNYATYYA  240
DSVKDRFTIS RDDSKNTAYL QMNNLKTEDT AVYYCVRHGN FGNSYISYWA YWGQGTLVTV  300
SSGGGGSGGG GSGGGGSQTV VTQEPSLTVS PGGTVTLTCG SSTGAVTSGN YPNWVQQKPG  360
QAPRGLIGGT KFLAPGTPAR FSGSLLGGKA ALTLSGVQPE DEAEYYCVLW YSNRWVFGGG  420
TKLTVLGGGG SQVQLVESGG GVVQPGRSLR LSCAASGFAF SRYGMHWVRQ APGKGLEWVA  480
VIWYDGSNKY YADSVKGRFT ISRDNSKNTQ YLQMNSLRAE DTAVYYCARG GDFLYYYYG  540
MDVWGQGTTV TVSSASTKGP SVFPLAPSSK STSGGTAALG CLVKDYFPEP VTVSWNSGAL  600
TSGVHTFPAV LQSSGLYSLS SVVTVPSSSL GTQTYICNVN HKPSNTKVDK KVEPKSC     657

SEQ ID NO: 72              moltype = AA   length = 645
FEATURE                    Location/Qualifiers
REGION                     1..645
                           note = Description of Artificial Sequence: Synthetic
                            polypeptide
source                     1..645
                           mol_type = protein
                           organism = synthetic construct
SEQUENCE: 72
```

```
EVQLVESGGG LVQPGGSLRL SCAASGSTFY TAVMGWVRQA PGKGLEWVAA IRWTALTTSY   60
ADSVKGRFTI SRDGAKTTLY LQMNSLRPED TAVYYCAARG TLGLFTTADS YDYWGQGTLV  120
TVSSGGGGSG GGSGGVYCGP EFDESVGCMG GGGSGGGLSG RSDAGSPLGL AGSGGGSEVQ  180
LVESGGGLVQ PGGSLKLSCA ASGFTFNKYA MNWVRQAPGK GLEWVARIRS KYNNYATYYA  240
DSVKDRFTIS RDDSKNTAYL QMNNLKTEDT AVYYCVRHGN FGNSYISYWA YWGQGTLVTV  300
SSGGGGSGGG GSGGGGSQTV VTQEPSLTVS PGGTVTLTCG SSTGAVTSGN YPNWVQQKPG  360
QAPRGLIGGT KFLAPGTPAR FSGSLLGGKA ALTLSGVQPE DEAEYYCVLW YSNRWVFGGG  420
TKLTVLGGGS DIQMTQSPS SLSASVGDRV TITCRASQGI SNYLAWYQQK TGKVPKFLIY  480
EASTLQSGVP SRFSGGGSGT DFTLTISSLQ PEDVATYYCQ NYNSAPFTFG PGTKVDIKRT  540
VAAPSVFIFP PSDEQLKSGT ASVVCLLNNF YPREAKVQWK VDNALQSGNS QESVTEQDSK  600
DSTYSLSSTL TLSKADYEKH KVYACEVTHQ GLSSPVTKSF NRGEC              645

SEQ ID NO: 73            moltype = AA  length = 226
FEATURE                  Location/Qualifiers
REGION                   1..226
                         note = Description of Artificial Sequence: Synthetic
                          polypeptide
source                   1..226
                         mol_type = protein
                         organism = synthetic construct
SEQUENCE: 73
QVQLVESGGG VVQPGRSLRL SCAASGFAFS RYGMHWVRQA PGKGLEWVAV IWYDGSNKYY   60
ADSVKGRFTI SRDNSKNTQY LQMNSLRAED TAVYYCARGG DFLYYYYGM DVWGQGTTVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSC              226

SEQ ID NO: 74            moltype = AA  length = 636
FEATURE                  Location/Qualifiers
REGION                   1..636
                         note = Description of Artificial Sequence: Synthetic
                          polypeptide
source                   1..636
                         mol_type = protein
                         organism = synthetic construct
SEQUENCE: 74
EVQLVESGGG LVQPGNSLRL SCAASGFTFS KFGMSWVRQA PGKGLEWVSS ISGSGRDTLY   60
ADSVKGRFTI SRDNAKTTLY LQMNSLRPED TAVYYCTIGG SLSVSSQGTL VTVSSGGGGS  120
GGGSGGVYCG PEFDESVGCM GGGGSGGGLS GRSDAGSPLG LAGSGGGSEV QLVESGGGLV  180
QPGGSLKLSC AASGFTFNKY AMNWVRQAPG KGLEWVARIR SKYNNYATYY ADSVKDRFTI  240
SRDDSKNTAY LQMNNLKTED TAVYYCVRHG NFGNSYISYW AYWGQGTLVT VSSGGGGSGG  300
GGSGGGGSQT VVTQEPSLTV SPGGTVTLTC GSSTGAVTSG NYPNWVQQKP GQAPRGLIGG  360
TKFLAPGTPA RFSGSLLGGK AALTLSGVQP EDEAEYYCVL WYSNRWVFGG GTKLTVLGGG  420
GSDIQMTQSP SSLSASVGDR VTITCRASQG ISNYLAWYQQ KTGKVPKFLI YEASTLQSGV  480
PSRFSGGGSG TDFTLTISSL QPEDVATYYC QNYNSAPFTF GPGTKVDIKR TVAAPSVFIF  540
PPSDEQLKSG TASVVCLLNN FYPREAKVQW KVDNALQSGN SQESVTEQDS KDSTYSLSST  600
LTLSKADYEK HKVYACEVTH QGLSSPVTKS FNRGEC                       636

SEQ ID NO: 75            moltype = AA  length = 226
FEATURE                  Location/Qualifiers
REGION                   1..226
                         note = Description of Artificial Sequence: Synthetic
                          polypeptide
source                   1..226
                         mol_type = protein
                         organism = synthetic construct
SEQUENCE: 75
QVQLVESGGG VVQPGRSLRL SCAASGFAFS RYGMHWVRQA PGKGLEWVAV IWYDGSNKYY   60
ADSVKGRFTI SRDNSKNTQY LQMNSLRAED TAVYYCARGG DFLYYYYGM DVWGQGTTVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSC              226

SEQ ID NO: 76            moltype = AA  length = 636
FEATURE                  Location/Qualifiers
REGION                   1..636
                         note = Description of Artificial Sequence: Synthetic
                          polypeptide
source                   1..636
                         mol_type = protein
                         organism = synthetic construct
SEQUENCE: 76
EVQLVESGGG LVQPGNSLRL SCAASGFTFS KFGMSWVRQA PGKGLEWVSS ISGSGRDTLY   60
ADSVKGRFTI SRDNAKTTLY LQMNSLRPED TAVYYCTIGG SLSVSSQGTL VTVSSGGGGS  120
GGGSGGVYCG PEFDESVGCM GGGGSGGGSG GGGSGGGSEV AGGSGGGSEV QLVESGGGLV  180
QPGGSLKLSC AASGFTFNKY AMNWVRQAPG KGLEWVARIR SKYNNYATYY ADSVKDRFTI  240
SRDDSKNTAY LQMNNLKTED TAVYYCVRHG NFGNSYISYW AYWGQGTLVT VSSGGGGSGG  300
GGSGGGGSQT VVTQEPSLTV SPGGTVTLTC GSSTGAVTSG NYPNWVQQKP GQAPRGLIGG  360
TKFLAPGTPA RFSGSLLGGK AALTLSGVQP EDEAEYYCVL WYSNRWVFGG GTKLTVLGGG  420
GSDIQMTQSP SSLSASVGDR VTITCRASQG ISNYLAWYQQ KTGKVPKFLI YEASTLQSGV  480
PSRFSGGGSG TDFTLTISSL QPEDVATYYC QNYNSAPFTF GPGTKVDIKR TVAAPSVFIF  540
```

```
PPSDEQLKSG TASVVCLLNN FYPREAKVQW KVDNALQSGN SQESVTEQDS KDSTYSLSST  600
LTLSKADYEK HKVYACEVTH QGLSSPVTKS FNRGEC                             636

SEQ ID NO: 77          moltype = AA  length = 226
FEATURE                Location/Qualifiers
REGION                 1..226
                       note = Description of Artificial Sequence: Synthetic
                        polypeptide
source                 1..226
                       mol_type = protein
                       organism = synthetic construct
SEQUENCE: 77
QVQLVESGGG VVQPGRSLRL SCAASGFAFS RYGMHWVRQA PGKGLEWVAV IWYDGSNKYY  60
ADSVKGRFTI SRDNSKNTQY LQMNSLRAED TAVYYCARGG DFLYYYYGM DVWGQGTTVT   120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSC                 226

SEQ ID NO: 78          moltype = AA  length = 14
FEATURE                Location/Qualifiers
REGION                 1..14
                       note = Description of Artificial Sequence: Synthetic peptide
source                 1..14
                       mol_type = protein
                       organism = synthetic construct
SEQUENCE: 78
YLWGCEWNCA GITT                                                     14

SEQ ID NO: 79          moltype = AA  length = 14
FEATURE                Location/Qualifiers
REGION                 1..14
                       note = Description of Artificial Sequence: Synthetic peptide
source                 1..14
                       mol_type = protein
                       organism = synthetic construct
SEQUENCE: 79
GSQCLGPEWE VCPY                                                     14

SEQ ID NO: 80          moltype = AA  length = 14
FEATURE                Location/Qualifiers
REGION                 1..14
                       note = Description of Artificial Sequence: Synthetic peptide
source                 1..14
                       mol_type = protein
                       organism = synthetic construct
SEQUENCE: 80
ASQCLGPEWE VCPY                                                     14

SEQ ID NO: 81          moltype = AA  length = 14
FEATURE                Location/Qualifiers
REGION                 1..14
                       note = Description of Artificial Sequence: Synthetic peptide
source                 1..14
                       mol_type = protein
                       organism = synthetic construct
SEQUENCE: 81
GAQCLGPEWE VCPY                                                     14

SEQ ID NO: 82          moltype = AA  length = 14
FEATURE                Location/Qualifiers
REGION                 1..14
                       note = Description of Artificial Sequence: Synthetic peptide
source                 1..14
                       mol_type = protein
                       organism = synthetic construct
SEQUENCE: 82
GSACLGPEWE VCPY                                                     14

SEQ ID NO: 83          moltype = AA  length = 14
FEATURE                Location/Qualifiers
REGION                 1..14
                       note = Description of Artificial Sequence: Synthetic peptide
source                 1..14
                       mol_type = protein
                       organism = synthetic construct
SEQUENCE: 83
GSQCAGPEWE VCPY                                                     14

SEQ ID NO: 84          moltype = AA  length = 14
FEATURE                Location/Qualifiers
```

-continued

```
REGION                    1..14
                          note = Description of Artificial Sequence: Synthetic peptide
source                    1..14
                          mol_type = protein
                          organism = synthetic construct
SEQUENCE: 84
GSQCLAPEWE VCPY                                                                    14

SEQ ID NO: 85             moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 85
GSQCLGAEWE VCPY                                                                    14

SEQ ID NO: 86             moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 86
GSQCLGPAWE VCPY                                                                    14

SEQ ID NO: 87             moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 87
GSQCLGPEAE VCPY                                                                    14

SEQ ID NO: 88             moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 88
GSQCLGPEWA VCPY                                                                    14

SEQ ID NO: 89             moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 89
GSQCLGPEWE ACPY                                                                    14

SEQ ID NO: 90             moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 90
GSQCLGPEWE VCAY                                                                    14

SEQ ID NO: 91             moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 91
GSQCLGPEWE VCPA                                                                    14

SEQ ID NO: 92             moltype = AA  length = 14
```

```
FEATURE                Location/Qualifiers
REGION                 1..14
                       note = Description of Artificial Sequence: Synthetic peptide
source                 1..14
                       mol_type = protein
                       organism = synthetic construct
SEQUENCE: 92
GSQCLGPEWE VCPY                                                            14

SEQ ID NO: 93          moltype = AA  length = 14
FEATURE                Location/Qualifiers
REGION                 1..14
                       note = Description of Artificial Sequence: Synthetic peptide
source                 1..14
                       mol_type = protein
                       organism = synthetic construct
SEQUENCE: 93
VYCGPEFDES VGCM                                                            14

SEQ ID NO: 94          moltype = AA  length = 14
FEATURE                Location/Qualifiers
REGION                 1..14
                       note = Description of Artificial Sequence: Synthetic peptide
source                 1..14
                       mol_type = protein
                       organism = synthetic construct
SEQUENCE: 94
AYCGPEFDES VGCM                                                            14

SEQ ID NO: 95          moltype = AA  length = 14
FEATURE                Location/Qualifiers
REGION                 1..14
                       note = Description of Artificial Sequence: Synthetic peptide
source                 1..14
                       mol_type = protein
                       organism = synthetic construct
SEQUENCE: 95
VACGPEFDES VGCM                                                            14

SEQ ID NO: 96          moltype = AA  length = 14
FEATURE                Location/Qualifiers
REGION                 1..14
                       note = Description of Artificial Sequence: Synthetic peptide
source                 1..14
                       mol_type = protein
                       organism = synthetic construct
SEQUENCE: 96
VYCAPEFDES VGCM                                                            14

SEQ ID NO: 97          moltype = AA  length = 14
FEATURE                Location/Qualifiers
REGION                 1..14
                       note = Description of Artificial Sequence: Synthetic peptide
source                 1..14
                       mol_type = protein
                       organism = synthetic construct
SEQUENCE: 97
VYCGAEFDES VGCM                                                            14

SEQ ID NO: 98          moltype = AA  length = 14
FEATURE                Location/Qualifiers
REGION                 1..14
                       note = Description of Artificial Sequence: Synthetic peptide
source                 1..14
                       mol_type = protein
                       organism = synthetic construct
SEQUENCE: 98
VYCGPAFDES VGCM                                                            14

SEQ ID NO: 99          moltype = AA  length = 14
FEATURE                Location/Qualifiers
REGION                 1..14
                       note = Description of Artificial Sequence: Synthetic peptide
source                 1..14
                       mol_type = protein
                       organism = synthetic construct
SEQUENCE: 99
VYCGPEADES VGCM                                                            14
```

```
SEQ ID NO: 100          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 100
VYCGPEFAES VGCM                                                             14

SEQ ID NO: 101          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 101
VYCGPEFDAS VGCM                                                             14

SEQ ID NO: 102          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 102
VYCGPEFDEA VGCM                                                             14

SEQ ID NO: 103          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 103
VYCGPEFDES AGCM                                                             14

SEQ ID NO: 104          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 104
VYCGPEFDES VACM                                                             14

SEQ ID NO: 105          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 105
VYCGPEFDES VGCA                                                             14

SEQ ID NO: 106          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 106
DDCWPDWEFD FACA                                                             14

SEQ ID NO: 107          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 107
YICGLDFPDF LYCD                                                             14
```

-continued

```
SEQ ID NO: 108        moltype = AA   length = 14
FEATURE               Location/Qualifiers
REGION                1..14
                      note = Description of Artificial Sequence: Synthetic peptide
source                1..14
                      mol_type = protein
                      organism = synthetic construct
SEQUENCE: 108
FDCWPDWEEY FVCD                                                        14

SEQ ID NO: 109        moltype = AA   length = 14
FEATURE               Location/Qualifiers
REGION                1..14
                      note = Description of Artificial Sequence: Synthetic peptide
source                1..14
                      mol_type = protein
                      organism = synthetic construct
SEQUENCE: 109
YICWPDWEEY FDCD                                                        14

SEQ ID NO: 110        moltype = AA   length = 14
FEATURE               Location/Qualifiers
REGION                1..14
                      note = Description of Artificial Sequence: Synthetic peptide
source                1..14
                      mol_type = protein
                      organism = synthetic construct
SEQUENCE: 110
NICWPDWEDD YFCF                                                        14

SEQ ID NO: 111        moltype = AA   length = 14
FEATURE               Location/Qualifiers
REGION                1..14
                      note = Description of Artificial Sequence: Synthetic peptide
source                1..14
                      mol_type = protein
                      organism = synthetic construct
SEQUENCE: 111
NFCWPDWEYI YPCI                                                        14

SEQ ID NO: 112        moltype = AA   length = 14
FEATURE               Location/Qualifiers
REGION                1..14
                      note = Description of Artificial Sequence: Synthetic peptide
source                1..14
                      mol_type = protein
                      organism = synthetic construct
SEQUENCE: 112
VDCWPDWEED FLCI                                                        14

SEQ ID NO: 113        moltype = AA   length = 14
FEATURE               Location/Qualifiers
REGION                1..14
                      note = Description of Artificial Sequence: Synthetic peptide
source                1..14
                      mol_type = protein
                      organism = synthetic construct
SEQUENCE: 113
HACWPDWEEY FPCN                                                        14

SEQ ID NO: 114        moltype = AA   length = 14
FEATURE               Location/Qualifiers
REGION                1..14
                      note = Description of Artificial Sequence: Synthetic peptide
source                1..14
                      mol_type = protein
                      organism = synthetic construct
SEQUENCE: 114
YDCGPDVDES YVCV                                                        14

SEQ ID NO: 115        moltype = AA   length = 14
FEATURE               Location/Qualifiers
REGION                1..14
                      note = Description of Artificial Sequence: Synthetic peptide
source                1..14
                      mol_type = protein
                      organism = synthetic construct
SEQUENCE: 115
```

-continued

```
IDCWPDWEDD TFCY                                                    14

SEQ ID NO: 116        moltype = AA   length = 14
FEATURE               Location/Qualifiers
REGION                1..14
                      note = Description of Artificial Sequence: Synthetic peptide
source                1..14
                      mol_type = protein
                      organism = synthetic construct
SEQUENCE: 116
YLCGPDGDET LACY                                                    14

SEQ ID NO: 117        moltype = AA   length = 14
FEATURE               Location/Qualifiers
REGION                1..14
                      note = Description of Artificial Sequence: Synthetic peptide
source                1..14
                      mol_type = protein
                      organism = synthetic construct
SEQUENCE: 117
VDCGPDGDES ILCY                                                    14

SEQ ID NO: 118        moltype = AA   length = 9
FEATURE               Location/Qualifiers
REGION                1..9
                      note = Description of Artificial Sequence: Synthetic peptide
SITE                  1..9
                      note = This sequence may encompass 1-3 "Gly Gly Ser"
                       repeating units
source                1..9
                      mol_type = protein
                      organism = synthetic construct
SEQUENCE: 118
GGSGGSGGS                                                         9

SEQ ID NO: 119        moltype = AA   length = 14
FEATURE               Location/Qualifiers
REGION                1..14
                      note = Description of Artificial Sequence: Synthetic peptide
source                1..14
                      mol_type = protein
                      organism = synthetic construct
SEQUENCE: 119
FICWPDWEED YFCA                                                    14

SEQ ID NO: 120        moltype = AA   length = 14
FEATURE               Location/Qualifiers
REGION                1..14
                      note = Description of Artificial Sequence: Synthetic peptide
source                1..14
                      mol_type = protein
                      organism = synthetic construct
SEQUENCE: 120
GDCWPDWEWD FYCD                                                    14

SEQ ID NO: 121        moltype = AA   length = 14
FEATURE               Location/Qualifiers
REGION                1..14
                      note = Description of Artificial Sequence: Synthetic peptide
source                1..14
                      mol_type = protein
                      organism = synthetic construct
SEQUENCE: 121
YLCWPDWEYI DLCD                                                    14

SEQ ID NO: 122        moltype = AA   length = 14
FEATURE               Location/Qualifiers
REGION                1..14
                      note = Description of Artificial Sequence: Synthetic peptide
source                1..14
                      mol_type = protein
                      organism = synthetic construct
SEQUENCE: 122
SFCWPDWEEY FDCD                                                    14

SEQ ID NO: 123        moltype = AA   length = 14
FEATURE               Location/Qualifiers
REGION                1..14
                      note = Description of Artificial Sequence: Synthetic peptide
```

```
source                     1..14
                           mol_type = protein
                           organism = synthetic construct
SEQUENCE: 123
DDCWPDWEEY ASCD                                                                    14

SEQ ID NO: 124             moltype = AA  length = 14
FEATURE                    Location/Qualifiers
REGION                     1..14
                           note = Description of Artificial Sequence: Synthetic peptide
source                     1..14
                           mol_type = protein
                           organism = synthetic construct
SEQUENCE: 124
NLCWPDWEYP FFCD                                                                    14

SEQ ID NO: 125             moltype = AA  length = 14
FEATURE                    Location/Qualifiers
REGION                     1..14
                           note = Description of Artificial Sequence: Synthetic peptide
source                     1..14
                           mol_type = protein
                           organism = synthetic construct
SEQUENCE: 125
FDCWPDWEES FVCD                                                                    14

SEQ ID NO: 126             moltype = AA  length = 14
FEATURE                    Location/Qualifiers
REGION                     1..14
                           note = Description of Artificial Sequence: Synthetic peptide
source                     1..14
                           mol_type = protein
                           organism = synthetic construct
SEQUENCE: 126
DICGPDGDET IICD                                                                    14

SEQ ID NO: 127             moltype = AA  length = 14
FEATURE                    Location/Qualifiers
REGION                     1..14
                           note = Description of Artificial Sequence: Synthetic peptide
source                     1..14
                           mol_type = protein
                           organism = synthetic construct
SEQUENCE: 127
DDCWPDWEYY AVCD                                                                    14

SEQ ID NO: 128             moltype = AA  length = 14
FEATURE                    Location/Qualifiers
REGION                     1..14
                           note = Description of Artificial Sequence: Synthetic peptide
source                     1..14
                           mol_type = protein
                           organism = synthetic construct
SEQUENCE: 128
YDCWPDWEEY SNCD                                                                    14

SEQ ID NO: 129             moltype = AA  length = 14
FEATURE                    Location/Qualifiers
REGION                     1..14
                           note = Description of Artificial Sequence: Synthetic peptide
source                     1..14
                           mol_type = protein
                           organism = synthetic construct
SEQUENCE: 129
INCWPDWEDY FFCD                                                                    14

SEQ ID NO: 130             moltype = AA  length = 14
FEATURE                    Location/Qualifiers
REGION                     1..14
                           note = Description of Artificial Sequence: Synthetic peptide
source                     1..14
                           mol_type = protein
                           organism = synthetic construct
SEQUENCE: 130
NICWPDWEDD TFCF                                                                    14

SEQ ID NO: 131             moltype = AA  length = 14
FEATURE                    Location/Qualifiers
REGION                     1..14
```

```
                          note = Description of Artificial Sequence: Synthetic peptide
source                    1..14
                          mol_type = protein
                          organism = synthetic construct
SEQUENCE: 131
NICWPDWEPN SFCF                                                            14

SEQ ID NO: 132            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 132
YDCGPEMDES IDCF                                                            14

SEQ ID NO: 133            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 133
DFCWPDWEFP FICH                                                            14

SEQ ID NO: 134            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 134
DFCGPEMDES ITCI                                                            14

SEQ ID NO: 135            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 135
YDCGPEFDES TVCI                                                            14

SEQ ID NO: 136            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 136
HDCWPDWEWD IFCI                                                            14

SEQ ID NO: 137            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 137
HACWPDWEEY NPCN                                                            14

SEQ ID NO: 138            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 138
DVCWPDWEWD FFCN                                                            14

SEQ ID NO: 139            moltype = AA  length = 14
FEATURE                   Location/Qualifiers
```

-continued

```
REGION                    1..14
                          note = Description of Artificial Sequence: Synthetic peptide
source                    1..14
                          mol_type = protein
                          organism = synthetic construct
SEQUENCE: 139
NYCWPDWEYY IPCN                                                          14

SEQ ID NO: 140            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 140
IICWPDWEFI DYCN                                                          14

SEQ ID NO: 141            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 141
SLCWPDWEYD IACP                                                          14

SEQ ID NO: 142            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 142
DLCGPELDES IFCP                                                          14

SEQ ID NO: 143            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 143
TNCWPDWEWV LPCP                                                          14

SEQ ID NO: 144            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 144
IECWPDWEPN YFCP                                                          14

SEQ ID NO: 145            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 145
IFCWPDWEDY VDCP                                                          14

SEQ ID NO: 146            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 146
IDCWPDWEYD FFCP                                                          14

SEQ ID NO: 147            moltype = AA  length = 14
```

-continued

| FEATURE | Location/Qualifiers |
| --- | --- |
| REGION | 1..14 |
| | note = Description of Artificial Sequence: Synthetic peptide |
| source | 1..14 |
| | mol_type = protein |
| | organism = synthetic construct |

SEQUENCE: 147
LFCWPDWEDS FFCP                                                    14

| SEQ ID NO: 148 | moltype = AA  length = 14 |
| --- | --- |
| FEATURE | Location/Qualifiers |
| REGION | 1..14 |
| | note = Description of Artificial Sequence: Synthetic peptide |
| source | 1..14 |
| | mol_type = protein |
| | organism = synthetic construct |

SEQUENCE: 148
VDCWPDWEDY ADCT                                                    14

| SEQ ID NO: 149 | moltype = AA  length = 14 |
| --- | --- |
| FEATURE | Location/Qualifiers |
| REGION | 1..14 |
| | note = Description of Artificial Sequence: Synthetic peptide |
| source | 1..14 |
| | mol_type = protein |
| | organism = synthetic construct |

SEQUENCE: 149
VICWPDWEQY FPCV                                                    14

| SEQ ID NO: 150 | moltype = AA  length = 14 |
| --- | --- |
| FEATURE | Location/Qualifiers |
| REGION | 1..14 |
| | note = Description of Artificial Sequence: Synthetic peptide |
| source | 1..14 |
| | mol_type = protein |
| | organism = synthetic construct |

SEQUENCE: 150
IECWPDWEPI YPCY                                                    14

| SEQ ID NO: 151 | moltype = AA  length = 14 |
| --- | --- |
| FEATURE | Location/Qualifiers |
| REGION | 1..14 |
| | note = Description of Artificial Sequence: Synthetic peptide |
| source | 1..14 |
| | mol_type = protein |
| | organism = synthetic construct |

SEQUENCE: 151
ITCWPDWEVY FPCY                                                    14

| SEQ ID NO: 152 | moltype = AA  length = 14 |
| --- | --- |
| FEATURE | Location/Qualifiers |
| REGION | 1..14 |
| | note = Description of Artificial Sequence: Synthetic peptide |
| source | 1..14 |
| | mol_type = protein |
| | organism = synthetic construct |

SEQUENCE: 152
IDCWPDWEYI HPCY                                                    14

| SEQ ID NO: 153 | moltype = AA  length = 14 |
| --- | --- |
| FEATURE | Location/Qualifiers |
| REGION | 1..14 |
| | note = Description of Artificial Sequence: Synthetic peptide |
| source | 1..14 |
| | mol_type = protein |
| | organism = synthetic construct |

SEQUENCE: 153
IDCWPDWEYI NPCY                                                    14

| SEQ ID NO: 154 | moltype = AA  length = 14 |
| --- | --- |
| FEATURE | Location/Qualifiers |
| REGION | 1..14 |
| | note = Description of Artificial Sequence: Synthetic peptide |
| source | 1..14 |
| | mol_type = protein |
| | organism = synthetic construct |

SEQUENCE: 154
ADCWPDWEEA FPCY                                                    14

-continued

```
SEQ ID NO: 155          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 155
IDCWPDWEYI YPCY                                                    14

SEQ ID NO: 156          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 156
NICWPDWEDD NFCF                                                    14

SEQ ID NO: 157          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 157
YDCWPDWEYV DACY                                                    14

SEQ ID NO: 158          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 158
FYCGPDGDES YVCD                                                    14

SEQ ID NO: 159          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 159
DICWPDWEYI NICS                                                    14

SEQ ID NO: 160          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 160
FVCWPDWEDF NFCD                                                    14

SEQ ID NO: 161          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 161
FACWPDWEDY VACD                                                    14

SEQ ID NO: 162          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 162
DNCWPDWEYD FFCV                                                    14
```

-continued

```
SEQ ID NO: 163            moltype = AA   length = 14
FEATURE                   Location/Qualifiers
REGION                    1..14
                          note = Description of Artificial Sequence: Synthetic peptide
source                    1..14
                          mol_type = protein
                          organism = synthetic construct SEQUENCE: 163
YDCWPDWEEY NDCA                                                             14

SEQ ID NO: 164            moltype = AA   length = 14
FEATURE                   Location/Qualifiers
REGION                    1..14
                          note = Description of Artificial Sequence: Synthetic peptide
source                    1..14
                          mol_type = protein
                          organism = synthetic construct SEQUENCE: 164
DDCGPDGDET IICV                                                             14

SEQ ID NO: 165            moltype = AA   length = 14
FEATURE                   Location/Qualifiers
REGION                    1..14
                          note = Description of Artificial Sequence: Synthetic peptide
source                    1..14
                          mol_type = protein
                          organism = synthetic construct SEQUENCE: 165
FPCWPDWEEY AICD                                                             14

SEQ ID NO: 166            moltype = AA   length = 14
FEATURE                   Location/Qualifiers
REGION                    1..14
                          note = Description of Artificial Sequence: Synthetic peptide
source                    1..14
                          mol_type = protein
                          organism = synthetic construct SEQUENCE: 166
PDCGPDGDES LFCT                                                             14

SEQ ID NO: 167            moltype = AA   length = 14
FEATURE                   Location/Qualifiers
REGION                    1..14
                          note = Description of Artificial Sequence: Synthetic peptide
source                    1..14
                          mol_type = protein
                          organism = synthetic construct SEQUENCE: 167
DNCWPDWEYD YFCV                                                             14

SEQ ID NO: 168            moltype = AA   length = 14
FEATURE                   Location/Qualifiers
REGION                    1..14
                          note = Description of Artificial Sequence: Synthetic peptide
source                    1..14
                          mol_type = protein
                          organism = synthetic construct SEQUENCE: 168
IFCWPDWEEF YDCY                                                             14

SEQ ID NO: 169            moltype = AA   length = 14
FEATURE                   Location/Qualifiers
REGION                    1..14
                          note = Description of Artificial Sequence: Synthetic peptide
source                    1..14
                          mol_type = protein
                          organism = synthetic construct SEQUENCE: 169
ADCWPDWEEY FPCN                                                             14

SEQ ID NO: 170            moltype = AA   length = 14
FEATURE                   Location/Qualifiers
REGION                    1..14
                          note = Description of Artificial Sequence: Synthetic peptide
source                    1..14
                          mol_type = protein
                          organism = synthetic construct

SEQUENCE: 170
```

```
HTCWPDWEDD IFCN                                          14

SEQ ID NO: 171          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 171
FACWPDWEEA FLCL                                          14

SEQ ID NO: 172          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 172
YDCGPELDES IACD                                          14

SEQ ID NO: 173          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 173
NSCWPDWEYD IICD                                          14

SEQ ID NO: 174          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 174
FACWPDWEEV APCY                                          14

SEQ ID NO: 175          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 175
LDCGPDGDET LTCY                                          14

SEQ ID NO: 176          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 176
VLCWPDWEEF YDCP                                          14

SEQ ID NO: 177          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 177
HACWPVWEEY FPCN                                          14

SEQ ID NO: 178          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
```

```
SEQUENCE: 178
NECWPNGEPT FPCT                                                            14

SEQ ID NO: 179          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 179
LTCGPDGDET LYCD                                                            14

SEQ ID NO: 180          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 180
YDCGPEYDES VPCI                                                            14

SEQ ID NO: 181          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 181
IECWPDWEPN SFCD                                                            14

SEQ ID NO: 182          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 182
YDCGPELDES IHCY                                                            14

SEQ ID NO: 183          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 183
IYCGPEFDES TICN                                                            14

SEQ ID NO: 184          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 184
IYCGPEVEEA YLCY                                                            14

SEQ ID NO: 185          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 185
FDCGPDGDET VYCD                                                            14

SEQ ID NO: 186          moltype = AA   length = 14
FEATURE                 Location/Qualifiers
REGION                  1..14
                        note = Description of Artificial Sequence: Synthetic peptide
source                  1..14
                        mol_type = protein
```

```
                                        organism = synthetic construct
SEQUENCE: 186
IDCGPDGDET ISCY                                                              14

SEQ ID NO: 187         moltype = AA   length = 14
FEATURE                Location/Qualifiers
REGION                 1..14
                       note = Description of Artificial Sequence: Synthetic peptide
source                 1..14
                       mol_type = protein
                       organism = synthetic construct
SEQUENCE: 187
NYCGPEFDES STCL                                                              14

SEQ ID NO: 188         moltype = AA   length = 14
FEATURE                Location/Qualifiers
REGION                 1..14
                       note = Description of Artificial Sequence: Synthetic peptide
source                 1..14
                       mol_type = protein
                       organism = synthetic construct
SEQUENCE: 188
YDCGPDGDES YFCD                                                              14

SEQ ID NO: 189         moltype = AA   length = 14
FEATURE                Location/Qualifiers
REGION                 1..14
                       note = Description of Artificial Sequence: Synthetic peptide
source                 1..14
                       mol_type = protein
                       organism = synthetic construct
SEQUENCE: 189
NFCWPDWEYF NDCN                                                              14

SEQ ID NO: 190         moltype = AA   length = 14
FEATURE                Location/Qualifiers
REGION                 1..14
                       note = Description of Artificial Sequence: Synthetic peptide
source                 1..14
                       mol_type = protein
                       organism = synthetic construct
SEQUENCE: 190
VLCWPDWEAF FDCD                                                              14

SEQ ID NO: 191         moltype = AA   length = 14
FEATURE                Location/Qualifiers
REGION                 1..14
                       note = Description of Artificial Sequence: Synthetic peptide
source                 1..14
                       mol_type = protein
                       organism = synthetic construct
SEQUENCE: 191
IYCGPEWEWP VACN                                                              14

SEQ ID NO: 192         moltype = AA   length = 14
FEATURE                Location/Qualifiers
REGION                 1..14
                       note = Description of Artificial Sequence: Synthetic peptide
source                 1..14
                       mol_type = protein
                       organism = synthetic construct
SEQUENCE: 192
VFCWPDWEDN FFCN                                                              14

SEQ ID NO: 193         moltype = AA   length = 14
FEATURE                Location/Qualifiers
REGION                 1..14
                       note = Description of Artificial Sequence: Synthetic peptide
source                 1..14
                       mol_type = protein
                       organism = synthetic construct
SEQUENCE: 193
VVCWPDWETF FPCD                                                              14

SEQ ID NO: 194         moltype = AA   length = 14
FEATURE                Location/Qualifiers
REGION                 1..14
                       note = Description of Artificial Sequence: Synthetic peptide
source                 1..14
```

```
                              mol_type = protein
                              organism = synthetic construct
SEQUENCE: 194
DNCGPDGDET YICN                                                        14

SEQ ID NO: 195      moltype = AA  length = 14
FEATURE             Location/Qualifiers
REGION              1..14
                    note = Description of Artificial Sequence: Synthetic peptide
source              1..14
                    mol_type = protein
                    organism = synthetic construct
SEQUENCE: 195
DNCWPDWEYN FFCV                                                        14

SEQ ID NO: 196      moltype = AA  length = 14
FEATURE             Location/Qualifiers
REGION              1..14
                    note = Description of Artificial Sequence: Synthetic peptide
source              1..14
                    mol_type = protein
                    organism = synthetic construct
SEQUENCE: 196
FYCGPEVEED YLCI                                                        14

SEQ ID NO: 197      moltype = AA  length = 14
FEATURE             Location/Qualifiers
REGION              1..14
                    note = Description of Artificial Sequence: Synthetic peptide
source              1..14
                    mol_type = protein
                    organism = synthetic construct
SEQUENCE: 197
DNCWPDWEYD IFCV                                                        14

SEQ ID NO: 198      moltype = AA  length = 14
FEATURE             Location/Qualifiers
REGION              1..14
                    note = Description of Artificial Sequence: Synthetic peptide
source              1..14
                    mol_type = protein
                    organism = synthetic construct
SEQUENCE: 198
IDCGPEFDES IACP                                                        14

SEQ ID NO: 199      moltype = AA  length = 14
FEATURE             Location/Qualifiers
REGION              1..14
                    note = Description of Artificial Sequence: Synthetic peptide
source              1..14
                    mol_type = protein
                    organism = synthetic construct
SEQUENCE: 199
YFCGPEVEEY TLCF                                                        14

SEQ ID NO: 200      moltype = AA  length = 14
FEATURE             Location/Qualifiers
REGION              1..14
                    note = Description of Artificial Sequence: Synthetic peptide
source              1..14
                    mol_type = protein
                    organism = synthetic construct
SEQUENCE: 200
FYCGPEFDES APCN                                                        14

SEQ ID NO: 201      moltype = AA  length = 14
FEATURE             Location/Qualifiers
REGION              1..14
                    note = Description of Artificial Sequence: Synthetic peptide
source              1..14
                    mol_type = protein
                    organism = synthetic construct
SEQUENCE: 201
FDCGPEVEEY FYCA                                                        14

SEQ ID NO: 202      moltype = AA  length = 14
FEATURE             Location/Qualifiers
REGION              1..14
                    note = Description of Artificial Sequence: Synthetic peptide
```

-continued

```
source                   1..14
                         mol_type = protein
                         organism = synthetic construct
SEQUENCE: 202
DFCWPDWEDF FFCA                                                       14

SEQ ID NO: 203           moltype = AA   length = 14
FEATURE                  Location/Qualifiers
REGION                   1..14
                         note = Description of Artificial Sequence: Synthetic peptide
source                   1..14
                         mol_type = protein
                         organism = synthetic construct
SEQUENCE: 203
FFCGPDGDET LSCN                                                       14

SEQ ID NO: 204           moltype = AA   length = 14
FEATURE                  Location/Qualifiers
REGION                   1..14
                         note = Description of Artificial Sequence: Synthetic peptide
source                   1..14
                         mol_type = protein
                         organism = synthetic construct
SEQUENCE: 204
FICGPEFDES VACL                                                       14

SEQ ID NO: 205           moltype = AA   length = 14
FEATURE                  Location/Qualifiers
REGION                   1..14
                         note = Description of Artificial Sequence: Synthetic peptide
source                   1..14
                         mol_type = protein
                         organism = synthetic construct
SEQUENCE: 205
YDCGPEFDEA IGCY                                                       14

SEQ ID NO: 206           moltype = AA   length = 14
FEATURE                  Location/Qualifiers
REGION                   1..14
                         note = Description of Artificial Sequence: Synthetic peptide
source                   1..14
                         mol_type = protein
                         organism = synthetic construct
SEQUENCE: 206
YICWPDWEEY LYCP                                                       14

SEQ ID NO: 207           moltype = AA   length = 14
FEATURE                  Location/Qualifiers
REGION                   1..14
                         note = Description of Artificial Sequence: Synthetic peptide
source                   1..14
                         mol_type = protein
                         organism = synthetic construct
SEQUENCE: 207
FDCWPDWEEP TTCH                                                       14

SEQ ID NO: 208           moltype = AA   length = 14
FEATURE                  Location/Qualifiers
REGION                   1..14
                         note = Description of Artificial Sequence: Synthetic peptide
source                   1..14
                         mol_type = protein
                         organism = synthetic construct
SEQUENCE: 208
YDCWPDWEDF PICD                                                       14

SEQ ID NO: 209           moltype = AA   length = 14
FEATURE                  Location/Qualifiers
REGION                   1..14
                         note = Description of Artificial Sequence: Synthetic peptide
source                   1..14
                         mol_type = protein
                         organism = synthetic construct
SEQUENCE: 209
VVCWPDWEYI DDCS                                                       14

SEQ ID NO: 210           moltype = AA   length = 14
FEATURE                  Location/Qualifiers
REGION                   1..14
```

-continued

```
                              note = Description of Artificial Sequence: Synthetic peptide
source                        1..14
                              mol_type = protein
                              organism = synthetic construct
SEQUENCE: 210
INCWPDWEVI SFCD                                                             14

SEQ ID NO: 211                moltype = AA  length = 14
FEATURE                       Location/Qualifiers
REGION                        1..14
                              note = Description of Artificial Sequence: Synthetic peptide
source                        1..14
                              mol_type = protein
                              organism = synthetic construct
SEQUENCE: 211
LSCWPDWEEV TPCL                                                             14

SEQ ID NO: 212                moltype = AA  length = 14
FEATURE                       Location/Qualifiers
REGION                        1..14
                              note = Description of Artificial Sequence: Synthetic peptide
source                        1..14
                              mol_type = protein
                              organism = synthetic construct
SEQUENCE: 212
FACWPDWEEV DICY                                                             14

SEQ ID NO: 213                moltype = AA  length = 14
FEATURE                       Location/Qualifiers
REGION                        1..14
                              note = Description of Artificial Sequence: Synthetic peptide
source                        1..14
                              mol_type = protein
                              organism = synthetic construct
SEQUENCE: 213
YDCGPEMDES IVCD                                                             14

SEQ ID NO: 214                moltype = AA  length = 14
FEATURE                       Location/Qualifiers
REGION                        1..14
                              note = Description of Artificial Sequence: Synthetic peptide
source                        1..14
                              mol_type = protein
                              organism = synthetic construct
SEQUENCE: 214
YDCWPDWEVF IVCD                                                             14

SEQ ID NO: 215                moltype = AA  length = 14
FEATURE                       Location/Qualifiers
REGION                        1..14
                              note = Description of Artificial Sequence: Synthetic peptide
source                        1..14
                              mol_type = protein
                              organism = synthetic construct
SEQUENCE: 215
DNCWPDWEHN FFCV                                                             14

SEQ ID NO: 216                moltype = AA  length = 14
FEATURE                       Location/Qualifiers
REGION                        1..14
                              note = Description of Artificial Sequence: Synthetic peptide
source                        1..14
                              mol_type = protein
                              organism = synthetic construct
SEQUENCE: 216
YDCGPDGDES IYCP                                                             14

SEQ ID NO: 217                moltype = AA  length = 14
FEATURE                       Location/Qualifiers
REGION                        1..14
                              note = Description of Artificial Sequence: Synthetic peptide
source                        1..14
                              mol_type = protein
                              organism = synthetic construct
SEQUENCE: 217
YDCGPEFEFP YYCF                                                             14

SEQ ID NO: 218                moltype = AA  length = 14
FEATURE                       Location/Qualifiers
```

-continued

```
REGION                    1..14
                          note = Description of Artificial Sequence: Synthetic peptide
source                    1..14
                          mol_type = protein
                          organism = synthetic construct
SEQUENCE: 218
ADCGPEYDES VPCV                                                              14

SEQ ID NO: 219            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 219
FLCGPEVEEV HYCS                                                              14

SEQ ID NO: 220            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 220
TDCWPDWEYI TSCS                                                              14

SEQ ID NO: 221            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 221
AFCGPELDES ITCD                                                              14

SEQ ID NO: 222            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 222
NDCWPDWEEY FSCY                                                              14

SEQ ID NO: 223            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 223
FDCGPEWEIV TDCY                                                              14

SEQ ID NO: 224            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 224
NLCGPEMDES IICP                                                              14

SEQ ID NO: 225            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 225
DLCGPEMDES IYCD                                                              14

SEQ ID NO: 226            moltype = AA  length = 14
```

-continued

| FEATURE | Location/Qualifiers |
|---|---|
| REGION | 1..14 |
| | note = Description of Artificial Sequence: Synthetic peptide |
| source | 1..14 |
| | mol_type = protein |
| | organism = synthetic construct |

SEQUENCE: 226
FDCGPDGVED YICD                                                          14

| SEQ ID NO: 227 | moltype = AA  length = 14 |
|---|---|
| FEATURE | Location/Qualifiers |
| REGION | 1..14 |
| | note = Description of Artificial Sequence: Synthetic peptide |
| source | 1..14 |
| | mol_type = protein |
| | organism = synthetic construct |

SEQUENCE: 227
YACWPDWEED FACY                                                          14

| SEQ ID NO: 228 | moltype = AA  length = 14 |
|---|---|
| FEATURE | Location/Qualifiers |
| REGION | 1..14 |
| | note = Description of Artificial Sequence: Synthetic peptide |
| source | 1..14 |
| | mol_type = protein |
| | organism = synthetic construct |

SEQUENCE: 228
HDCGPEMDES IVCV                                                          14

| SEQ ID NO: 229 | moltype = AA  length = 14 |
|---|---|
| FEATURE | Location/Qualifiers |
| REGION | 1..14 |
| | note = Description of Artificial Sequence: Synthetic peptide |
| source | 1..14 |
| | mol_type = protein |
| | organism = synthetic construct |

SEQUENCE: 229
VFCGPEFEFI FLCA                                                          14

| SEQ ID NO: 230 | moltype = AA  length = 14 |
|---|---|
| FEATURE | Location/Qualifiers |
| REGION | 1..14 |
| | note = Description of Artificial Sequence: Synthetic peptide |
| source | 1..14 |
| | mol_type = protein |
| | organism = synthetic construct |

SEQUENCE: 230
YDCGPELDES ILCD                                                          14

| SEQ ID NO: 231 | moltype = AA  length = 14 |
|---|---|
| FEATURE | Location/Qualifiers |
| REGION | 1..14 |
| | note = Description of Artificial Sequence: Synthetic peptide |
| source | 1..14 |
| | mol_type = protein |
| | organism = synthetic construct |

SEQUENCE: 231
SVCWPDWEEF YSCD                                                          14

| SEQ ID NO: 232 | moltype = AA  length = 14 |
|---|---|
| FEATURE | Location/Qualifiers |
| REGION | 1..14 |
| | note = Description of Artificial Sequence: Synthetic peptide |
| source | 1..14 |
| | mol_type = protein |
| | organism = synthetic construct |

SEQUENCE: 232
PYCGPDGDET AICT                                                          14

| SEQ ID NO: 233 | moltype = AA  length = 14 |
|---|---|
| FEATURE | Location/Qualifiers |
| REGION | 1..14 |
| | note = Description of Artificial Sequence: Synthetic peptide |
| source | 1..14 |
| | mol_type = protein |
| | organism = synthetic construct |

SEQUENCE: 233
DDCGPELEWY YPCY                                                          14

-continued

```
SEQ ID NO: 234          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct

SEQUENCE: 234
FICGPEFDES LPCN                                                 14

SEQ ID NO: 235          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct

SEQUENCE: 235
IDCGPEFDES LPCD                                                 14

SEQ ID NO: 236          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct

SEQUENCE: 236
FLCGPEFEED APCY                                                 14

SEQ ID NO: 237          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct

SEQUENCE: 237
IFCGPDGDET HICH                                                 14

SEQ ID NO: 238          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct

SEQUENCE: 238
VFCWPDWEYI DFCN                                                 14

SEQ ID NO: 239          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct

SEQUENCE: 239
IFCGPEYDES LHCI                                                 14

SEQ ID NO: 240          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct

SEQUENCE: 240
HLCWPDWEWY VDCP                                                 14

SEQ ID NO: 241          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct SEQUENCE: 241
FICGPEMDES IACN                                                 14
```

-continued

```
SEQ ID NO: 242            moltype = AA   length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 242
IFCGPEVEMI FLCN                                                          14

SEQ ID NO: 243            moltype = AA   length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 243
YDCGPEWEFP VDCI                                                          14

SEQ ID NO: 244            moltype = AA   length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 244
NLCGPELDES ITCF                                                          14

SEQ ID NO: 245            moltype = AA   length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 245
FYCGPEVEDF YFCY                                                          14

SEQ ID NO: 246            moltype = AA   length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 246
DYCGPEFDES LICN                                                          14

SEQ ID NO: 247            moltype = AA   length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 247
DYCGPEFDES LPCD                                                          14

SEQ ID NO: 248            moltype = AA   length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 248
AICGPELDES IACP                                                          14

SEQ ID NO: 249            moltype = AA   length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 249
```

```
VICGPEVEDY NLCY                                                            14

SEQ ID NO: 250          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 250
HTCWPDWEDY TVCP                                                            14

SEQ ID NO: 251          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 251
SDCWPDWEYF YDCN                                                            14

SEQ ID NO: 252          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 252
VFCGPDGDET VHCD                                                            14

SEQ ID NO: 253          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 253
DYCGPEYDES VHCI                                                            14

SEQ ID NO: 254          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 254
ADCGPDGDES IICH                                                            14

SEQ ID NO: 255          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 255
FYCGPELDES LTCV                                                            14

SEQ ID NO: 256          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 256
ILCGPEVEED YYCY                                                            14

SEQ ID NO: 257          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
```

```
SEQUENCE: 257
HLCWPDWEEY HSCD                                                              14

SEQ ID NO: 258       moltype = AA  length = 14
FEATURE              Location/Qualifiers
REGION               1..14
                     note = Description of Artificial Sequence: Synthetic peptide
source               1..14
                     mol_type = protein
                     organism = synthetic construct
SEQUENCE: 258
IFCWPDWEDY NFCT                                                              14

SEQ ID NO: 259       moltype = AA  length = 14
FEATURE              Location/Qualifiers
REGION               1..14
                     note = Description of Artificial Sequence: Synthetic peptide
source               1..14
                     mol_type = protein
                     organism = synthetic construct
SEQUENCE: 259
IVCGPDGDET LICH                                                              14

SEQ ID NO: 260       moltype = AA  length = 14
FEATURE              Location/Qualifiers
REGION               1..14
                     note = Description of Artificial Sequence: Synthetic peptide
source               1..14
                     mol_type = protein
                     organism = synthetic construct
SEQUENCE: 260
ADCWPDWEWD YTCD                                                              14

SEQ ID NO: 261       moltype = AA  length = 14
FEATURE              Location/Qualifiers
REGION               1..14
                     note = Description of Artificial Sequence: Synthetic peptide
source               1..14
                     mol_type = protein
                     organism = synthetic construct
SEQUENCE: 261
ITCGPEFDES TTCN                                                              14

SEQ ID NO: 262       moltype = AA  length = 14
FEATURE              Location/Qualifiers
REGION               1..14
                     note = Description of Artificial Sequence: Synthetic peptide
source               1..14
                     mol_type = protein
                     organism = synthetic construct
SEQUENCE: 262
YHCWPDWEEY TSCD                                                              14

SEQ ID NO: 263       moltype = AA  length = 14
FEATURE              Location/Qualifiers
REGION               1..14
                     note = Description of Artificial Sequence: Synthetic peptide
source               1..14
                     mol_type = protein
                     organism = synthetic construct
SEQUENCE: 263
NYCGPEVEEY ALCT                                                              14

SEQ ID NO: 264       moltype = AA  length = 14
FEATURE              Location/Qualifiers
REGION               1..14
                     note = Description of Artificial Sequence: Synthetic peptide
source               1..14
                     mol_type = protein
                     organism = synthetic construct
SEQUENCE: 264
FICGPEMDES IHCD                                                              14

SEQ ID NO: 265       moltype = AA  length = 14
FEATURE              Location/Qualifiers
REGION               1..14
                     note = Description of Artificial Sequence: Synthetic peptide
source               1..14
                     mol_type = protein
```

-continued

```
                        organism = synthetic construct
SEQUENCE: 265
DNCWPDWEEF AVCP                                                    14

SEQ ID NO: 266          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 266
YDCGPELDET VVCD                                                    14

SEQ ID NO: 267          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 267
YDCGPEFDES IACY                                                    14

SEQ ID NO: 268          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 268
IDCWPDWEYT VHCD                                                    14

SEQ ID NO: 269          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 269
DDCGPELDES IICI                                                    14

SEQ ID NO: 270          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 270
VYCGPEYDES SFCF                                                    14

SEQ ID NO: 271          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 271
FNCWPDWEDP YFCV                                                    14

SEQ ID NO: 272          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 272
YDCGPEYDES SYCS                                                    14

SEQ ID NO: 273          moltype = AA  length = 14
FEATURE                 Location/Qualifiers
REGION                  1..14
                        note = Description of Artificial Sequence: Synthetic peptide
source                  1..14
```

```
                          mol_type = protein
                          organism = synthetic construct
SEQUENCE: 273
VACWPDWEYT DSCF                                                          14

SEQ ID NO: 274            moltype = AA   length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 274
TDCGPEFDES VACY                                                          14

SEQ ID NO: 275            moltype = AA   length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 275
TDCWPDWEFY ADCD                                                          14

SEQ ID NO: 276            moltype = AA   length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 276
YDCGPELDES VICH                                                          14

SEQ ID NO: 277            moltype = AA   length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 277
SDCGPDGDES IICT                                                          14

SEQ ID NO: 278            moltype = AA   length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 278
YYCGPEFDES IDCD                                                          14

SEQ ID NO: 279            moltype = AA   length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 279
FFCGPEIDES IACV                                                          14

SEQ ID NO: 280            moltype = AA   length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 280
DYCGPEFDES TFCD                                                          14

SEQ ID NO: 281            moltype = AA   length = 14
FEATURE                   Location/Qualifiers
REGION                    1..14
                          note = Description of Artificial Sequence: Synthetic peptide
```

-continued

```
source                    1..14
                          mol_type = protein
                          organism = synthetic construct
SEQUENCE: 281
YDCGPEWEWP IDCV                                                     14

SEQ ID NO: 282            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 282
FYCGPEIELF SFCY                                                     14

SEQ ID NO: 283            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 283
YYCGPEVDES ITCP                                                     14

SEQ ID NO: 284            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 284
ILCGPEFDES INCN                                                     14

SEQ ID NO: 285            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 285
VVCGPAMGQH YLCD                                                     14

SEQ ID NO: 286            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 286
VVCGTKMGEH YLCS                                                     14

SEQ ID NO: 287            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 287
YDCWPDWEYV YACY                                                     14

SEQ ID NO: 288            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 288
DLCGPELDES VNCD                                                     14

SEQ ID NO: 289            moltype = AA  length = 14
FEATURE                   Location/Qualifiers
REGION                    1..14
```

-continued

```
                             note = Description of Artificial Sequence: Synthetic peptide
source                       1..14
                             mol_type = protein
                             organism = synthetic construct
SEQUENCE: 289
YYCGPEFDES TVCY                                                              14

SEQ ID NO: 290               moltype = AA   length = 14
FEATURE                      Location/Qualifiers
REGION                       1..14
                             note = Description of Artificial Sequence: Synthetic peptide
source                       1..14
                             mol_type = protein
                             organism = synthetic construct
SEQUENCE: 290
LDCWPDWEWP YSCN                                                              14

SEQ ID NO: 291               moltype = AA   length = 14
FEATURE                      Location/Qualifiers
REGION                       1..14
                             note = Description of Artificial Sequence: Synthetic peptide
source                       1..14
                             mol_type = protein
                             organism = synthetic construct
SEQUENCE: 291
FICWPDWEDD FFCY                                                              14

SEQ ID NO: 292               moltype = AA   length = 14
FEATURE                      Location/Qualifiers
REGION                       1..14
                             note = Description of Artificial Sequence: Synthetic peptide
source                       1..14
                             mol_type = protein
                             organism = synthetic construct
SEQUENCE: 292
DLCGPEVEWY FFCN                                                              14

SEQ ID NO: 293               moltype = AA   length = 14
FEATURE                      Location/Qualifiers
REGION                       1..14
                             note = Description of Artificial Sequence: Synthetic peptide
source                       1..14
                             mol_type = protein
                             organism = synthetic construct
SEQUENCE: 293
YDCGPELDES IVCF                                                              14

SEQ ID NO: 294               moltype = AA   length = 14
FEATURE                      Location/Qualifiers
REGION                       1..14
                             note = Description of Artificial Sequence: Synthetic peptide
source                       1..14
                             mol_type = protein
                             organism = synthetic construct
SEQUENCE: 294
LNCWPVWEDD VFCY                                                              14

SEQ ID NO: 295               moltype = AA   length = 14
FEATURE                      Location/Qualifiers
REGION                       1..14
                             note = Description of Artificial Sequence: Synthetic peptide
source                       1..14
                             mol_type = protein
                             organism = synthetic construct
SEQUENCE: 295
FNCWPDWEDP NFCV                                                              14

SEQ ID NO: 296               moltype = AA   length = 14
FEATURE                      Location/Qualifiers
REGION                       1..14
                             note = Description of Artificial Sequence: Synthetic peptide
source                       1..14
                             mol_type = protein
                             organism = synthetic construct
SEQUENCE: 296
VICWPDWEDD YFCP                                                              14

SEQ ID NO: 297               moltype = AA   length = 14
FEATURE                      Location/Qualifiers
```

```
REGION                    1..14
                          note = Description of Artificial Sequence: Synthetic peptide
source                    1..14
                          mol_type = protein
                          organism = synthetic construct
SEQUENCE: 297
FLCGPEFDES SVCY                                                          14

SEQ ID NO: 298            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 298
YDCGPELDES IFCY                                                          14

SEQ ID NO: 299            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 299
HLCGPDGDES FTCF                                                          14

SEQ ID NO: 300            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 300
YFCGPEMDES LYCI                                                          14

SEQ ID NO: 301            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 301
YYCGPEVEEY ANCY                                                          14

SEQ ID NO: 302            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 302
NTCGPEFDES TACY                                                          14

SEQ ID NO: 303            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 303
IDCWPDWEEA FNCY                                                          14

SEQ ID NO: 304            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 304
AYCGPELEEF FLCT                                                          14

SEQ ID NO: 305            moltype = AA  length = 14
```

```
FEATURE            Location/Qualifiers
REGION             1..14
                   note = Description of Artificial Sequence: Synthetic peptide
source             1..14
                   mol_type = protein
                   organism = synthetic construct
SEQUENCE: 305
IYCGPEVEEV HHCY                                                            14

SEQ ID NO: 306     moltype = AA  length = 14
FEATURE            Location/Qualifiers
REGION             1..14
                   note = Description of Artificial Sequence: Synthetic peptide
source             1..14
                   mol_type = protein
                   organism = synthetic construct
SEQUENCE: 306
FFCGPEFDES VACD                                                            14

SEQ ID NO: 307     moltype = AA  length = 14
FEATURE            Location/Qualifiers
REGION             1..14
                   note = Description of Artificial Sequence: Synthetic peptide
source             1..14
                   mol_type = protein
                   organism = synthetic construct
SEQUENCE: 307
YDCGPELDET IICA                                                            14

SEQ ID NO: 308     moltype = AA  length = 14
FEATURE            Location/Qualifiers
REGION             1..14
                   note = Description of Artificial Sequence: Synthetic peptide
source             1..14
                   mol_type = protein
                   organism = synthetic construct
SEQUENCE: 308
ILCGPEWEYP LDCS                                                            14

SEQ ID NO: 309     moltype = AA  length = 14
FEATURE            Location/Qualifiers
REGION             1..14
                   note = Description of Artificial Sequence: Synthetic peptide
source             1..14
                   mol_type = protein
                   organism = synthetic construct
SEQUENCE: 309
FICGPEFDES TTCN                                                            14

SEQ ID NO: 310     moltype = AA  length = 14
FEATURE            Location/Qualifiers
REGION             1..14
                   note = Description of Artificial Sequence: Synthetic peptide
source             1..14
                   mol_type = protein
                   organism = synthetic construct
SEQUENCE: 310
FYCGPELDES VSCD                                                            14

SEQ ID NO: 311     moltype = AA  length = 14
FEATURE            Location/Qualifiers
REGION             1..14
                   note = Description of Artificial Sequence: Synthetic peptide
source             1..14
                   mol_type = protein
                   organism = synthetic construct
SEQUENCE: 311
HLCGPELDES VTCF                                                            14

SEQ ID NO: 312     moltype = AA  length = 14
FEATURE            Location/Qualifiers
REGION             1..14
                   note = Description of Artificial Sequence: Synthetic peptide
source             1..14
                   mol_type = protein
                   organism = synthetic construct
SEQUENCE: 312
LICGPEVEDY SLCH                                                            14
```

```
SEQ ID NO: 313          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 313
YFCGPEMDES VYCD                                                             14

SEQ ID NO: 314          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 314
HYCGPEMDES IYCI                                                             14

SEQ ID NO: 315          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 315
FDCGPELDES INCD                                                             14

SEQ ID NO: 316          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 316
YYCGPEVEEY IYCT                                                             14

SEQ ID NO: 317          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 317
LACWPVREEI NACI                                                            14

SEQ ID NO: 318          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 318
IDCWPDWEDI TFCD                                                             14

SEQ ID NO: 319          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 319
IVCGPELDES ITCP                                                             14

SEQ ID NO: 320          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 320
FYCGPEFELP ADCD                                                             14
```

-continued

```
SEQ ID NO: 321          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 321
FDCGPEFDES NPCF                                                          14

SEQ ID NO: 322          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 322
DACWPDWEEY SSCD                                                          14

SEQ ID NO: 323          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 323
DHCWPDWEPN YFCV                                                          14

SEQ ID NO: 324          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 324
DYCWPDWEIN YICF                                                          14

SEQ ID NO: 325          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 325
IYCWPDWEYV YACN                                                          14

SEQ ID NO: 326          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 326
DFCGPEVEED YLCD                                                          14

SEQ ID NO: 327          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 327
HDCGPDGRED YDCA                                                          14

SEQ ID NO: 328          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 328
```

```
LACWPDWEDD YFCV                                                       14

SEQ ID NO: 329            moltype = AA   length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 329
DICWPDWEDY LPCV                                                       14

SEQ ID NO: 330            moltype = AA   length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 330
ILCGPEIEVY ALCP                                                       14

SEQ ID NO: 331            moltype = AA   length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 331
IFCGPEWEFS VLCN                                                       14

SEQ ID NO: 332            moltype = AA   length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 332
TYCGPEVEDF SLCV                                                       14

SEQ ID NO: 333            moltype = AA   length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 333
FICGPEWEFV DACF                                                       14

SEQ ID NO: 334            moltype = AA   length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 334
FACWPDWEED SPCD                                                       14

SEQ ID NO: 335            moltype = AA   length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 335
ILCGPEVEEL IFCP                                                       14

SEQ ID NO: 336            moltype = AA   length = 14
FEATURE                   Location/Qualifiers
REGION                    1..14
                          note = Description of Artificial Sequence: Synthetic peptide
source                    1..14
                          mol_type = protein
                          organism = synthetic construct
```

```
SEQUENCE: 336
FYCGPEVEEY IYCY                                                      14

SEQ ID NO: 337        moltype = AA  length = 14
FEATURE               Location/Qualifiers
REGION                1..14
                      note = Description of Artificial Sequence: Synthetic peptide
source                1..14
                      mol_type = protein
                      organism = synthetic construct
SEQUENCE: 337
DSCGPELDES IICD                                                      14

SEQ ID NO: 338        moltype = AA  length = 14
FEATURE               Location/Qualifiers
REGION                1..14
                      note = Description of Artificial Sequence: Synthetic peptide
source                1..14
                      mol_type = protein
                      organism = synthetic construct
SEQUENCE: 338
FLCGPDGDET SVCD                                                      14

SEQ ID NO: 339        moltype = AA  length = 14
FEATURE               Location/Qualifiers
REGION                1..14
                      note = Description of Artificial Sequence: Synthetic peptide
source                1..14
                      mol_type = protein
                      organism = synthetic construct
SEQUENCE: 339
FNCWPNGEPT YFCV                                                      14

SEQ ID NO: 340        moltype = AA  length = 14
FEATURE               Location/Qualifiers
REGION                1..14
                      note = Description of Artificial Sequence: Synthetic peptide
source                1..14
                      mol_type = protein
                      organism = synthetic construct
SEQUENCE: 340
LACWPVWEYP VTCI                                                      14

SEQ ID NO: 341        moltype = AA  length = 14
FEATURE               Location/Qualifiers
REGION                1..14
                      note = Description of Artificial Sequence: Synthetic peptide
source                1..14
                      mol_type = protein
                      organism = synthetic construct
SEQUENCE: 341
DYCGPEVEED VYCY                                                      14

SEQ ID NO: 342        moltype = AA  length = 14
FEATURE               Location/Qualifiers
REGION                1..14
                      note = Description of Artificial Sequence: Synthetic peptide
source                1..14
                      mol_type = protein
                      organism = synthetic construct
SEQUENCE: 342
ITCWPDWEEY ANCT                                                      14

SEQ ID NO: 343        moltype = AA  length = 14
FEATURE               Location/Qualifiers
REGION                1..14
                      note = Description of Artificial Sequence: Synthetic peptide
source                1..14
                      mol_type = protein
                      organism = synthetic construct
SEQUENCE: 343
FFCGPDGDET YSCI                                                      14

SEQ ID NO: 344        moltype = AA  length = 14
FEATURE               Location/Qualifiers
REGION                1..14
                      note = Description of Artificial Sequence: Synthetic peptide
source                1..14
                      mol_type = protein
```

```
                              organism = synthetic construct
SEQUENCE: 344
TDCWPDWEYA TSCD                                                       14

SEQ ID NO: 345                moltype = AA   length = 14
FEATURE                       Location/Qualifiers
REGION                        1..14
                              note = Description of Artificial Sequence: Synthetic peptide
source                        1..14
                              mol_type = protein
                              organism = synthetic construct
SEQUENCE: 345
FNCGPDGYED YLCD                                                       14

SEQ ID NO: 346                moltype = AA   length = 14
FEATURE                       Location/Qualifiers
REGION                        1..14
                              note = Description of Artificial Sequence: Synthetic peptide
source                        1..14
                              mol_type = protein
                              organism = synthetic construct
SEQUENCE: 346
YDCWPDWEVD FHCP                                                       14

SEQ ID NO: 347                moltype = AA   length = 14
FEATURE                       Location/Qualifiers
REGION                        1..14
                              note = Description of Artificial Sequence: Synthetic peptide
source                        1..14
                              mol_type = protein
                              organism = synthetic construct
SEQUENCE: 347
NICWPDWEDD SFCF                                                       14

SEQ ID NO: 348                moltype = AA   length = 14
FEATURE                       Location/Qualifiers
REGION                        1..14
                              note = Description of Artificial Sequence: Synthetic peptide
source                        1..14
                              mol_type = protein
                              organism = synthetic construct
SEQUENCE: 348
ATCGPEFDES IGCS                                                       14

SEQ ID NO: 349                moltype = AA   length = 14
FEATURE                       Location/Qualifiers
REGION                        1..14
                              note = Description of Artificial Sequence: Synthetic peptide
source                        1..14
                              mol_type = protein
                              organism = synthetic construct
SEQUENCE: 349
SYCGPEFDES TFCD                                                       14

SEQ ID NO: 350                moltype = AA   length = 14
FEATURE                       Location/Qualifiers
REGION                        1..14
                              note = Description of Artificial Sequence: Synthetic peptide
source                        1..14
                              mol_type = protein
                              organism = synthetic construct
SEQUENCE: 350
PICGPEYDES DVCA                                                       14

SEQ ID NO: 351                moltype = AA   length = 14
FEATURE                       Location/Qualifiers
REGION                        1..14
                              note = Description of Artificial Sequence: Synthetic peptide
source                        1..14
                              mol_type = protein
                              organism = synthetic construct
SEQUENCE: 351
YYCGPDGDEY NSCI                                                       14

SEQ ID NO: 352                moltype = AA   length = 14
FEATURE                       Location/Qualifiers
REGION                        1..14
                              note = Description of Artificial Sequence: Synthetic peptide
source                        1..14
```

-continued

```
                              mol_type = protein
                              organism = synthetic construct
SEQUENCE: 352
VDCWPDWEVF IACD                                                              14

SEQ ID NO: 353                moltype = AA  length = 14
FEATURE                       Location/Qualifiers
REGION                        1..14
                              note = Description of Artificial Sequence: Synthetic peptide
source                        1..14
                              mol_type = protein
                              organism = synthetic construct
SEQUENCE: 353
DLCGPEVEEV NLCL                                                              14

SEQ ID NO: 354                moltype = AA  length = 14
FEATURE                       Location/Qualifiers
REGION                        1..14
                              note = Description of Artificial Sequence: Synthetic peptide
source                        1..14
                              mol_type = protein
                              organism = synthetic construct
SEQUENCE: 354
FDCGPEMDES TTCF                                                              14

SEQ ID NO: 355                moltype = AA  length = 14
FEATURE                       Location/Qualifiers
REGION                        1..14
                              note = Description of Artificial Sequence: Synthetic peptide
source                        1..14
                              mol_type = protein
                              organism = synthetic construct
SEQUENCE: 355
NFCWPDWEPI YFCT                                                              14

SEQ ID NO: 356                moltype = AA  length = 14
FEATURE                       Location/Qualifiers
REGION                        1..14
                              note = Description of Artificial Sequence: Synthetic peptide
source                        1..14
                              mol_type = protein
                              organism = synthetic construct
SEQUENCE: 356
VDCGPDGDES FFCL                                                              14

SEQ ID NO: 357                moltype = AA  length = 14
FEATURE                       Location/Qualifiers
REGION                        1..14
                              note = Description of Artificial Sequence: Synthetic peptide
source                        1..14
                              mol_type = protein
                              organism = synthetic construct
SEQUENCE: 357
VDCGPDGDET AFCI                                                              14

SEQ ID NO: 358                moltype = AA  length = 14
FEATURE                       Location/Qualifiers
REGION                        1..14
                              note = Description of Artificial Sequence: Synthetic peptide
source                        1..14
                              mol_type = protein
                              organism = synthetic construct
SEQUENCE: 358
NICGPEMDES LVCI                                                              14

SEQ ID NO: 359                moltype = AA  length = 14
FEATURE                       Location/Qualifiers
REGION                        1..14
                              note = Description of Artificial Sequence: Synthetic peptide
source                        1..14
                              mol_type = protein
                              organism = synthetic construct
SEQUENCE: 359
IICGPEFDES FFCF                                                              14

SEQ ID NO: 360                moltype = AA  length = 14
FEATURE                       Location/Qualifiers
REGION                        1..14
                              note = Description of Artificial Sequence: Synthetic peptide
```

-continued

```
source                    1..14
                          mol_type = protein
                          organism = synthetic construct
SEQUENCE: 360
NFCGPEYDES ISCI                                                        14

SEQ ID NO: 361            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 361
HLCGPEIEEA DICN                                                        14

SEQ ID NO: 362            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 362
DYCGPEVEED YLCD                                                        14

SEQ ID NO: 363            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 363
DYCGPELDES INCD                                                        14

SEQ ID NO: 364            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 364
FYCGPELDES LFCV                                                        14

SEQ ID NO: 365            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 365
PDCGPEWEFY VTCN                                                        14

SEQ ID NO: 366            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 366
FDCGPEFEYI YACT                                                        14

SEQ ID NO: 367            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 367
DYCGPEFDES SICN                                                        14

SEQ ID NO: 368            moltype = AA  length = 14
FEATURE                   Location/Qualifiers
REGION                    1..14
```

```
                          note = Description of Artificial Sequence: Synthetic peptide
source                    1..14
                          mol_type = protein
                          organism = synthetic construct
SEQUENCE: 368
DFCGPEVEEY IFCF                                                              14

SEQ ID NO: 369            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 369
PVCWPDWEYV SSCD                                                              14

SEQ ID NO: 370            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 370
YICGPERDES NLCL                                                              14

SEQ ID NO: 371            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 371
YDCGPELDES IVCD                                                              14

SEQ ID NO: 372            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 372
HDCWPDWEDF YFCV                                                              14

SEQ ID NO: 373            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 373
HYCGPEYDES IDCY                                                              14

SEQ ID NO: 374            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 374
LFCGPEMPED IFCN                                                              14

SEQ ID NO: 375            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 375
HDCGPELEFH YACY                                                              14

SEQ ID NO: 376            moltype = AA  length = 14
FEATURE                   Location/Qualifiers
```

-continued

```
REGION                    1..14
                          note = Description of Artificial Sequence: Synthetic peptide
source                    1..14
                          mol_type = protein
                          organism = synthetic construct
SEQUENCE: 376
DFCGPELDES INCF                                                          14

SEQ ID NO: 377            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 377
YFCGPELDES IACN                                                          14

SEQ ID NO: 378            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 378
TDCWPDWEDD IICD                                                          14

SEQ ID NO: 379            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 379
YDCGPELDES IYCF                                                          14

SEQ ID NO: 380            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 380
YYCWPDWWEY VTCD                                                          14

SEQ ID NO: 381            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 381
PICGPELEES YLCN                                                          14

SEQ ID NO: 382            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 382
FDCGPEFDES IVCY                                                          14

SEQ ID NO: 383            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 383
VLCGPDGIEF FDCP                                                          14

SEQ ID NO: 384            moltype = AA  length = 14
```

-continued

| FEATURE | Location/Qualifiers |
| --- | --- |
| REGION | 1..14 |
|  | note = Description of Artificial Sequence: Synthetic peptide |
| source | 1..14 |
|  | mol_type = protein |
|  | organism = synthetic construct |

SEQUENCE: 384
AYCGPEYDES LTCV                                                                            14

| SEQ ID NO: 385 | moltype = AA  length = 14 |
| --- | --- |
| FEATURE | Location/Qualifiers |
| REGION | 1..14 |
|  | note = Description of Artificial Sequence: Synthetic peptide |
| source | 1..14 |
|  | mol_type = protein |
|  | organism = synthetic construct |

SEQUENCE: 385
DFCGPELDES IICA                                                                            14

| SEQ ID NO: 386 | moltype = AA  length = 14 |
| --- | --- |
| FEATURE | Location/Qualifiers |
| REGION | 1..14 |
|  | note = Description of Artificial Sequence: Synthetic peptide |
| source | 1..14 |
|  | mol_type = protein |
|  | organism = synthetic construct |

SEQUENCE: 386
YDCGPEFDES LDCN                                                                            14

| SEQ ID NO: 387 | moltype = AA  length = 14 |
| --- | --- |
| FEATURE | Location/Qualifiers |
| REGION | 1..14 |
|  | note = Description of Artificial Sequence: Synthetic peptide |
| source | 1..14 |
|  | mol_type = protein |
|  | organism = synthetic construct |

SEQUENCE: 387
AICGPEFDES VACD                                                                            14

| SEQ ID NO: 388 | moltype = AA  length = 14 |
| --- | --- |
| FEATURE | Location/Qualifiers |
| REGION | 1..14 |
|  | note = Description of Artificial Sequence: Synthetic peptide |
| source | 1..14 |
|  | mol_type = protein |
|  | organism = synthetic construct |

SEQUENCE: 388
LLCGPDGVED FFCD                                                                            14

| SEQ ID NO: 389 | moltype = AA  length = 14 |
| --- | --- |
| FEATURE | Location/Qualifiers |
| REGION | 1..14 |
|  | note = Description of Artificial Sequence: Synthetic peptide |
| source | 1..14 |
|  | mol_type = protein |
|  | organism = synthetic construct |

SEQUENCE: 389
NFCGPELPED IFCF                                                                            14

| SEQ ID NO: 390 | moltype = AA  length = 14 |
| --- | --- |
| FEATURE | Location/Qualifiers |
| REGION | 1..14 |
|  | note = Description of Artificial Sequence: Synthetic peptide |
| source | 1..14 |
|  | mol_type = protein |
|  | organism = synthetic construct |

SEQUENCE: 390
FYCGPEVEEV SLCN                                                                            14

| SEQ ID NO: 391 | moltype = AA  length = 14 |
| --- | --- |
| FEATURE | Location/Qualifiers |
| REGION | 1..14 |
|  | note = Description of Artificial Sequence: Synthetic peptide |
| source | 1..14 |
|  | mol_type = protein |
|  | organism = synthetic construct |

SEQUENCE: 391
YDCGPDGYEA FYCH                                                                            14

-continued

```
SEQ ID NO: 392            moltype = AA   length = 14
FEATURE                   Location/Qualifiers
REGION                    1..14
                          note = Description of Artificial Sequence: Synthetic peptide
source                    1..14
                          mol_type = protein
                          organism = synthetic construct

SEQUENCE: 392
NFCGPEIEFD YLCD                                              14

SEQ ID NO: 393            moltype = AA   length = 14
FEATURE                   Location/Qualifiers
REGION                    1..14
                          note = Description of Artificial Sequence: Synthetic peptide
source                    1..14
                          mol_type = protein
                          organism = synthetic construct

SEQUENCE: 393
DYCGPDGVED FICN                                              14

SEQ ID NO: 394            moltype = AA   length = 14
FEATURE                   Location/Qualifiers
REGION                    1..14
                          note = Description of Artificial Sequence: Synthetic peptide
source                    1..14
                          mol_type = protein
                          organism = synthetic construct

SEQUENCE: 394
TDCWPDWEYI YSCS                                              14

SEQ ID NO: 395            moltype = AA   length = 14
FEATURE                   Location/Qualifiers
REGION                    1..14
                          note = Description of Artificial Sequence: Synthetic peptide
source                    1..14
                          mol_type = protein
                          organism = synthetic construct

SEQUENCE: 395
FYCGPEFEEI TNCI                                              14

SEQ ID NO: 396            moltype = AA   length = 14
FEATURE                   Location/Qualifiers
REGION                    1..14
                          note = Description of Artificial Sequence: Synthetic peptide
source                    1..14
                          mol_type = protein
                          organism = synthetic construct

SEQUENCE: 396
FDCWPDWEES FFCH                                              14

SEQ ID NO: 397            moltype = AA   length = 14
FEATURE                   Location/Qualifiers
REGION                    1..14
                          note = Description of Artificial Sequence: Synthetic peptide
source                    1..14
                          mol_type = protein
                          organism = synthetic construct

SEQUENCE: 397
DFCGPDGDES VFCP                                              14

SEQ ID NO: 398            moltype = AA   length = 14
FEATURE                   Location/Qualifiers
REGION                    1..14
                          note = Description of Artificial Sequence: Synthetic peptide
source                    1..14
                          mol_type = protein
                          organism = synthetic construct

SEQUENCE: 398
HNCGPELDES LVCD                                              14

SEQ ID NO: 399            moltype = AA   length = 14
FEATURE                   Location/Qualifiers
REGION                    1..14
                          note = Description of Artificial Sequence: Synthetic peptide
source                    1..14
                          mol_type = protein
                          organism = synthetic construct SEQUENCE: 399
IYCGPDGAED YTCD                                              14
```

-continued

```
SEQ ID NO: 400          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 400
FDCGPEFEFP VICF                                                              14

SEQ ID NO: 401          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 401
YNCGPELDES VTCD                                                              14

SEQ ID NO: 402          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 402
FDCGPELDES IHCA                                                              14

SEQ ID NO: 403          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 403
DICGPEVEEY FLCF                                                              14

SEQ ID NO: 404          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 404
FDCGPEVDES LTCF                                                              14

SEQ ID NO: 405          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 405
FDCGPEIEEF HLCF                                                              14

SEQ ID NO: 406          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 406
AYCGPELDES IICD                                                              14

SEQ ID NO: 407          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 407
```

```
YNCGPELDES ITCN                                                    14

SEQ ID NO: 408          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 408
FDCWPDWEEP VDCL                                                    14

SEQ ID NO: 409          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 409
DVCGPELDES VLCP                                                    14

SEQ ID NO: 410          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 410
NYCGPELDES LPCP                                                    14

SEQ ID NO: 411          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 411
YYCWPDWEYD IFCS                                                    14

SEQ ID NO: 412          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 412
DDCGPEFDES TYCN                                                    14

SEQ ID NO: 413          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 413
FYCGPEFEEV FHCY                                                    14

SEQ ID NO: 414          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 414
TDCWPDWEEY FLCD                                                    14

SEQ ID NO: 415          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
```

SEQUENCE: 415
VYCGPEWEES YLCP                                                                          14

SEQ ID NO: 416          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 416
DDCGPNGYAT FICY                                                                          14

SEQ ID NO: 417          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 417
FLCGPEIEDD THCY                                                                          14

SEQ ID NO: 418          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 418
FACWPDWEET IPCH                                                                          14

SEQ ID NO: 419          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 419
VLCGPEFDES YNCY                                                                          14

SEQ ID NO: 420          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 420
YDCGPEFDES ISCI                                                                          14

SEQ ID NO: 421          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 421
YDCGPEFDES VNCY                                                                          14

SEQ ID NO: 422          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 422
AICWPDWEEF VDCY                                                                          14

SEQ ID NO: 423          moltype = AA  length = 14
FEATURE                 Location/Qualifiers
REGION                  1..14
                        note = Description of Artificial Sequence: Synthetic peptide
source                  1..14
                        mol_type = protein

```
SEQUENCE: 423
LTCWPVREEI FACD                                                    14

SEQ ID NO: 424        moltype = AA   length = 14
FEATURE               Location/Qualifiers
REGION                1..14
                      note = Description of Artificial Sequence: Synthetic peptide
source                1..14
                      mol_type = protein
                      organism = synthetic construct
SEQUENCE: 424
VLCGPEFDES YYCN                                                    14

SEQ ID NO: 425        moltype = AA   length = 14
FEATURE               Location/Qualifiers
REGION                1..14
                      note = Description of Artificial Sequence: Synthetic peptide
source                1..14
                      mol_type = protein
                      organism = synthetic construct
SEQUENCE: 425
NVCGPEYDES APCN                                                    14

SEQ ID NO: 426        moltype = AA   length = 14
FEATURE               Location/Qualifiers
REGION                1..14
                      note = Description of Artificial Sequence: Synthetic peptide
source                1..14
                      mol_type = protein
                      organism = synthetic construct
SEQUENCE: 426
HDCGPEFDES ISCV                                                    14

SEQ ID NO: 427        moltype = AA   length = 14
FEATURE               Location/Qualifiers
REGION                1..14
                      note = Description of Artificial Sequence: Synthetic peptide
source                1..14
                      mol_type = protein
                      organism = synthetic construct
SEQUENCE: 427
FDCGPELDET VDCN                                                    14

SEQ ID NO: 428        moltype = AA   length = 14
FEATURE               Location/Qualifiers
REGION                1..14
                      note = Description of Artificial Sequence: Synthetic peptide
source                1..14
                      mol_type = protein
                      organism = synthetic construct
SEQUENCE: 428
YFCGPEVEEH FYCY                                                    14

SEQ ID NO: 429        moltype = AA   length = 14
FEATURE               Location/Qualifiers
REGION                1..14
                      note = Description of Artificial Sequence: Synthetic peptide
source                1..14
                      mol_type = protein
                      organism = synthetic construct
SEQUENCE: 429
DYCGPELDES IICH                                                    14

SEQ ID NO: 430        moltype = AA   length = 14
FEATURE               Location/Qualifiers
REGION                1..14
                      note = Description of Artificial Sequence: Synthetic peptide
source                1..14
                      mol_type = protein
                      organism = synthetic construct
SEQUENCE: 430
DDCGPEVPED ITCY                                                    14

SEQ ID NO: 431        moltype = AA   length = 14
FEATURE               Location/Qualifiers
REGION                1..14
                      note = Description of Artificial Sequence: Synthetic peptide
source                1..14
```

```
                            mol_type = protein
                            organism = synthetic construct
SEQUENCE: 431
DNCGPELDES VVCD                                                   14

SEQ ID NO: 432              moltype = AA  length = 14
FEATURE                     Location/Qualifiers
REGION                      1..14
                            note = Description of Artificial Sequence: Synthetic peptide
source                      1..14
                            mol_type = protein
                            organism = synthetic construct
SEQUENCE: 432
VHCWPDWEPN YVCD                                                   14

SEQ ID NO: 433              moltype = AA  length = 14
FEATURE                     Location/Qualifiers
REGION                      1..14
                            note = Description of Artificial Sequence: Synthetic peptide
source                      1..14
                            mol_type = protein
                            organism = synthetic construct
SEQUENCE: 433
DYCGPELDES LFCL                                                   14

SEQ ID NO: 434              moltype = AA  length = 14
FEATURE                     Location/Qualifiers
REGION                      1..14
                            note = Description of Artificial Sequence: Synthetic peptide
source                      1..14
                            mol_type = protein
                            organism = synthetic construct
SEQUENCE: 434
DDCGPELDES VVCA                                                   14

SEQ ID NO: 435              moltype = AA  length = 14
FEATURE                     Location/Qualifiers
REGION                      1..14
                            note = Description of Artificial Sequence: Synthetic peptide
source                      1..14
                            mol_type = protein
                            organism = synthetic construct
SEQUENCE: 435
AACGPELDES IVCD                                                   14

SEQ ID NO: 436              moltype = AA  length = 14
FEATURE                     Location/Qualifiers
REGION                      1..14
                            note = Description of Artificial Sequence: Synthetic peptide
source                      1..14
                            mol_type = protein
                            organism = synthetic construct
SEQUENCE: 436
DFCGPEFEEI NNCF                                                   14

SEQ ID NO: 437              moltype = AA  length = 14
FEATURE                     Location/Qualifiers
REGION                      1..14
                            note = Description of Artificial Sequence: Synthetic peptide
source                      1..14
                            mol_type = protein
                            organism = synthetic construct
SEQUENCE: 437
YYCGPEFDES NACY                                                   14

SEQ ID NO: 438              moltype = AA  length = 14
FEATURE                     Location/Qualifiers
REGION                      1..14
                            note = Description of Artificial Sequence: Synthetic peptide
source                      1..14
                            mol_type = protein
                            organism = synthetic construct
SEQUENCE: 438
VLCGPEFDES NSCY                                                   14

SEQ ID NO: 439              moltype = AA  length = 14
FEATURE                     Location/Qualifiers
REGION                      1..14
                            note = Description of Artificial Sequence: Synthetic peptide
```

-continued

```
source                    1..14
                          mol_type = protein
                          organism = synthetic construct
SEQUENCE: 439
YDCGPEFDES IDCD                                                          14

SEQ ID NO: 440            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 440
DSCGPEFEFY YVCF                                                          14

SEQ ID NO: 441            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 441
YICGPELDES LICH                                                          14

SEQ ID NO: 442            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 442
FDCGPEVEED YFCY                                                          14

SEQ ID NO: 443            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 443
FDCGPEYDES LYCF                                                          14

SEQ ID NO: 444            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 444
VLCGPDGDEY SFCH                                                          14

SEQ ID NO: 445            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 445
IPCGPEMDES VVCN                                                          14

SEQ ID NO: 446            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 446
IICGPDGYED FTCD                                                          14

SEQ ID NO: 447            moltype = AA  length = 14
FEATURE                   Location/Qualifiers
REGION                    1..14
```

```
                            note = Description of Artificial Sequence: Synthetic peptide
source                      1..14
                            mol_type = protein
                            organism = synthetic construct
SEQUENCE: 447
IFCGPELDES IICY                                                          14

SEQ ID NO: 448              moltype = AA  length = 14
FEATURE                     Location/Qualifiers
REGION                      1..14
                            note = Description of Artificial Sequence: Synthetic peptide
source                      1..14
                            mol_type = protein
                            organism = synthetic construct
SEQUENCE: 448
VDCGPEFDES YDCY                                                          14

SEQ ID NO: 449              moltype = AA  length = 14
FEATURE                     Location/Qualifiers
REGION                      1..14
                            note = Description of Artificial Sequence: Synthetic peptide
source                      1..14
                            mol_type = protein
                            organism = synthetic construct
SEQUENCE: 449
LSCGPEMDES LYCD                                                          14

SEQ ID NO: 450              moltype = AA  length = 14
FEATURE                     Location/Qualifiers
REGION                      1..14
                            note = Description of Artificial Sequence: Synthetic peptide
source                      1..14
                            mol_type = protein
                            organism = synthetic construct
SEQUENCE: 450
YDCWPDWEYN IDCT                                                          14

SEQ ID NO: 451              moltype = AA  length = 14
FEATURE                     Location/Qualifiers
REGION                      1..14
                            note = Description of Artificial Sequence: Synthetic peptide
source                      1..14
                            mol_type = protein
                            organism = synthetic construct
SEQUENCE: 451
NHCGPDGDET IVCF                                                          14

SEQ ID NO: 452              moltype = AA  length = 14
FEATURE                     Location/Qualifiers
REGION                      1..14
                            note = Description of Artificial Sequence: Synthetic peptide
source                      1..14
                            mol_type = protein
                            organism = synthetic construct
SEQUENCE: 452
NFCGPELDES IPCH                                                          14

SEQ ID NO: 453              moltype = AA  length = 14
FEATURE                     Location/Qualifiers
REGION                      1..14
                            note = Description of Artificial Sequence: Synthetic peptide
source                      1..14
                            mol_type = protein
                            organism = synthetic construct
SEQUENCE: 453
FHCGPEIEEY ALCD                                                          14

SEQ ID NO: 454              moltype = AA  length = 14
FEATURE                     Location/Qualifiers
REGION                      1..14
                            note = Description of Artificial Sequence: Synthetic peptide
source                      1..14
                            mol_type = protein
                            organism = synthetic construct
SEQUENCE: 454
VYCGPEVEDY NLCY                                                          14

SEQ ID NO: 455              moltype = AA  length = 14
FEATURE                     Location/Qualifiers
```

-continued

```
REGION                     1..14
                           note = Description of Artificial Sequence: Synthetic peptide
source                     1..14
                           mol_type = protein
                           organism = synthetic construct
SEQUENCE: 455
VYCGPDGDEL ANCY                                                                    14

SEQ ID NO: 456             moltype = AA  length = 14
FEATURE                    Location/Qualifiers
REGION                     1..14
                           note = Description of Artificial Sequence: Synthetic peptide
source                     1..14
                           mol_type = protein
                           organism = synthetic construct
SEQUENCE: 456
LICGPVIAED LPCN                                                                    14

SEQ ID NO: 457             moltype = AA  length = 14
FEATURE                    Location/Qualifiers
REGION                     1..14
                           note = Description of Artificial Sequence: Synthetic peptide
source                     1..14
                           mol_type = protein
                           organism = synthetic construct
SEQUENCE: 457
DICGPEIPED VSCD                                                                    14

SEQ ID NO: 458             moltype = AA  length = 14
FEATURE                    Location/Qualifiers
REGION                     1..14
                           note = Description of Artificial Sequence: Synthetic peptide
source                     1..14
                           mol_type = protein
                           organism = synthetic construct
SEQUENCE: 458
IYCGPEWEEA DYCD                                                                    14

SEQ ID NO: 459             moltype = AA  length = 14
FEATURE                    Location/Qualifiers
REGION                     1..14
                           note = Description of Artificial Sequence: Synthetic peptide
source                     1..14
                           mol_type = protein
                           organism = synthetic construct
SEQUENCE: 459
IDCWPDWEDD SICY                                                                    14

SEQ ID NO: 460             moltype = AA  length = 14
FEATURE                    Location/Qualifiers
REGION                     1..14
                           note = Description of Artificial Sequence: Synthetic peptide
source                     1..14
                           mol_type = protein
                           organism = synthetic construct
SEQUENCE: 460
VLCGPEVEDF TLCD                                                                    14

SEQ ID NO: 461             moltype = AA  length = 14
FEATURE                    Location/Qualifiers
REGION                     1..14
                           note = Description of Artificial Sequence: Synthetic peptide
source                     1..14
                           mol_type = protein
                           organism = synthetic construct
SEQUENCE: 461
LYCGPVIEEI YYCY                                                                    14

SEQ ID NO: 462             moltype = AA  length = 14
FEATURE                    Location/Qualifiers
REGION                     1..14
                           note = Description of Artificial Sequence: Synthetic peptide
source                     1..14
                           mol_type = protein
                           organism = synthetic construct
SEQUENCE: 462
FFCGPEFEVH SDCN                                                                    14

SEQ ID NO: 463             moltype = AA  length = 14
```

-continued

| FEATURE | Location/Qualifiers |
|---|---|
| REGION | 1..14 |
| | note = Description of Artificial Sequence: Synthetic peptide |
| source | 1..14 |
| | mol_type = protein |
| | organism = synthetic construct |

SEQUENCE: 463
NDCGPEVELV SDCN                                                          14

| SEQ ID NO: 464 | moltype = AA  length = 14 |
|---|---|
| FEATURE | Location/Qualifiers |
| REGION | 1..14 |
| | note = Description of Artificial Sequence: Synthetic peptide |
| source | 1..14 |
| | mol_type = protein |
| | organism = synthetic construct |

SEQUENCE: 464
DLCGPELDES TVCD                                                          14

| SEQ ID NO: 465 | moltype = AA  length = 14 |
|---|---|
| FEATURE | Location/Qualifiers |
| REGION | 1..14 |
| | note = Description of Artificial Sequence: Synthetic peptide |
| source | 1..14 |
| | mol_type = protein |
| | organism = synthetic construct |

SEQUENCE: 465
IPCGPEVEDY NLCN                                                          14

| SEQ ID NO: 466 | moltype = AA  length = 14 |
|---|---|
| FEATURE | Location/Qualifiers |
| REGION | 1..14 |
| | note = Description of Artificial Sequence: Synthetic peptide |
| source | 1..14 |
| | mol_type = protein |
| | organism = synthetic construct |

SEQUENCE: 466
YYCGPELEWP VVCN                                                          14

| SEQ ID NO: 467 | moltype = AA  length = 14 |
|---|---|
| FEATURE | Location/Qualifiers |
| REGION | 1..14 |
| | note = Description of Artificial Sequence: Synthetic peptide |
| source | 1..14 |
| | mol_type = protein |
| | organism = synthetic construct |

SEQUENCE: 467
YDCGPELDES VICN                                                          14

| SEQ ID NO: 468 | moltype = AA  length = 14 |
|---|---|
| FEATURE | Location/Qualifiers |
| REGION | 1..14 |
| | note = Description of Artificial Sequence: Synthetic peptide |
| source | 1..14 |
| | mol_type = protein |
| | organism = synthetic construct |

SEQUENCE: 468
VYCGPDGDES FDCA                                                          14

| SEQ ID NO: 469 | moltype = AA  length = 14 |
|---|---|
| FEATURE | Location/Qualifiers |
| REGION | 1..14 |
| | note = Description of Artificial Sequence: Synthetic peptide |
| source | 1..14 |
| | mol_type = protein |
| | organism = synthetic construct |

SEQUENCE: 469
NDCGPEWEDT YFCL                                                          14

| SEQ ID NO: 470 | moltype = AA  length = 14 |
|---|---|
| FEATURE | Location/Qualifiers |
| REGION | 1..14 |
| | note = Description of Artificial Sequence: Synthetic peptide |
| source | 1..14 |
| | mol_type = protein |
| | organism = synthetic construct |

SEQUENCE: 470
PYCGPEMEEL SNCS                                                          14

SEQ ID NO: 471          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 471
DDCGPEFEVI SDCY                                                                    14

SEQ ID NO: 472          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 472
DLCGPEFPED VPCD                                                                    14

SEQ ID NO: 473          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 473
IYCGPEFDES FVCY                                                                    14

SEQ ID NO: 474          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 474
AYCGPEYEVF ADCN                                                                    14

SEQ ID NO: 475          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 475
IDCGPEYDES VDCL                                                                    14

SEQ ID NO: 476          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 476
HICWPDWEEF HDCN                                                                    14

SEQ ID NO: 477          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 477
YDCGPELDET ITCL                                                                    14

SEQ ID NO: 478          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 478
YLCGPELDET ILCN                                                                    14

-continued

```
SEQ ID NO: 479          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 479
FFCGPEFEEA FLCF                                                          14

SEQ ID NO: 480          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 480
ILCGPELDES FTCA                                                          14

SEQ ID NO: 481          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 481
FHCGPEVELY TDCN                                                          14

SEQ ID NO: 482          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 482
NLCGPEVEEY NFCY                                                          14

SEQ ID NO: 483          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 483
FDCGPEVEET YYCF                                                          14

SEQ ID NO: 484          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 484
VFCGPEFEED HYCY                                                          14

SEQ ID NO: 485          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 485
AICGPEWEVV ADCN                                                          14

SEQ ID NO: 486          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 486
```

```
FICWPDWEED NYCN                                                    14

SEQ ID NO: 487        moltype = AA  length = 14
FEATURE               Location/Qualifiers
REGION                1..14
                      note = Description of Artificial Sequence: Synthetic peptide
source                1..14
                      mol_type = protein
                      organism = synthetic construct
SEQUENCE: 487
IYCGPEFDES FICD                                                    14

SEQ ID NO: 488        moltype = AA  length = 14
FEATURE               Location/Qualifiers
REGION                1..14
                      note = Description of Artificial Sequence: Synthetic peptide
source                1..14
                      mol_type = protein
                      organism = synthetic construct SEQUENCE: 488
NLCGPEVEDV YDCH                                                    14

SEQ ID NO: 489        moltype = AA  length = 14
FEATURE               Location/Qualifiers
REGION                1..14
                      note = Description of Artificial Sequence: Synthetic peptide
source                1..14
                      mol_type = protein
                      organism = synthetic construct SEQUENCE: 489
HYCGPEVEEY HNCN                                                    14

SEQ ID NO: 490        moltype = AA  length = 14
FEATURE               Location/Qualifiers
REGION                1..14
                      note = Description of Artificial Sequence: Synthetic peptide
source                1..14
                      mol_type = protein
                      organism = synthetic construct SEQUENCE: 490
DICGPEYDES YSCT                                                    14

SEQ ID NO: 491        moltype = AA  length = 14
FEATURE               Location/Qualifiers
REGION                1..14
                      note = Description of Artificial Sequence: Synthetic peptide
source                1..14
                      mol_type = protein
                      organism = synthetic construct SEQUENCE: 491
DYCGPELDET LICA                                                    14

SEQ ID NO: 492        moltype = AA  length = 14
FEATURE               Location/Qualifiers
REGION                1..14
                      note = Description of Artificial Sequence: Synthetic peptide
source                1..14
                      mol_type = protein
                      organism = synthetic construct SEQUENCE: 492
IACGPEMPED IDCY                                                    14

SEQ ID NO: 493        moltype = AA  length = 14
FEATURE               Location/Qualifiers
REGION                1..14
                      note = Description of Artificial Sequence: Synthetic peptide
source                1..14
                      mol_type = protein
                      organism = synthetic construct SEQUENCE: 493
IDCGPELDES IFCD                                                    14

SEQ ID NO: 494        moltype = AA  length = 14
FEATURE               Location/Qualifiers
REGION                1..14
                      note = Description of Artificial Sequence: Synthetic peptide
source                1..14
                      mol_type = protein
                      organism = synthetic construct
```

-continued

```
SEQUENCE: 494
YFCGPDVEED FACD                                                          14

SEQ ID NO: 495           moltype = AA  length = 14
FEATURE                  Location/Qualifiers
REGION                   1..14
                         note = Description of Artificial Sequence: Synthetic peptide
source                   1..14
                         mol_type = protein
                         organism = synthetic construct
SEQUENCE: 495
YNCGPEWEYA ILCD                                                          14

SEQ ID NO: 496           moltype = AA  length = 14
FEATURE                  Location/Qualifiers
REGION                   1..14
                         note = Description of Artificial Sequence: Synthetic peptide
source                   1..14
                         mol_type = protein
                         organism = synthetic construct
SEQUENCE: 496
IYCGPEVEDY IVCN                                                          14

SEQ ID NO: 497           moltype = AA  length = 14
FEATURE                  Location/Qualifiers
REGION                   1..14
                         note = Description of Artificial Sequence: Synthetic peptide
source                   1..14
                         mol_type = protein
                         organism = synthetic construct
SEQUENCE: 497
YDCGPEIDES TPCA                                                          14

SEQ ID NO: 498           moltype = AA  length = 14
FEATURE                  Location/Qualifiers
REGION                   1..14
                         note = Description of Artificial Sequence: Synthetic peptide
source                   1..14
                         mol_type = protein
                         organism = synthetic construct
SEQUENCE: 498
DTCWPDWEHI YACD                                                          14

SEQ ID NO: 499           moltype = AA  length = 14
FEATURE                  Location/Qualifiers
REGION                   1..14
                         note = Description of Artificial Sequence: Synthetic peptide
source                   1..14
                         mol_type = protein
                         organism = synthetic construct
SEQUENCE: 499
DICGPEMDES VTCN                                                          14

SEQ ID NO: 500           moltype = AA  length = 14
FEATURE                  Location/Qualifiers
REGION                   1..14
                         note = Description of Artificial Sequence: Synthetic peptide
source                   1..14
                         mol_type = protein
                         organism = synthetic construct
SEQUENCE: 500
YDCWPDWERY FPCI                                                          14

SEQ ID NO: 501           moltype = AA  length = 14
FEATURE                  Location/Qualifiers
REGION                   1..14
                         note = Description of Artificial Sequence: Synthetic peptide
source                   1..14
                         mol_type = protein
                         organism = synthetic construct
SEQUENCE: 501
HLCGPELDES VACS                                                          14

SEQ ID NO: 502           moltype = AA  length = 14
FEATURE                  Location/Qualifiers
REGION                   1..14
                         note = Description of Artificial Sequence: Synthetic peptide
source                   1..14
                         mol_type = protein
```

```
                              organism = synthetic construct
SEQUENCE: 502
YDCGPDGDET TICA                                                          14

SEQ ID NO: 503                moltype = AA   length = 14
FEATURE                       Location/Qualifiers
REGION                        1..14
                              note = Description of Artificial Sequence: Synthetic peptide
source                        1..14
                              mol_type = protein
                              organism = synthetic construct
SEQUENCE: 503
YYCGPEYEDV LDCF                                                          14

SEQ ID NO: 504                moltype = AA   length = 14
FEATURE                       Location/Qualifiers
REGION                        1..14
                              note = Description of Artificial Sequence: Synthetic peptide
source                        1..14
                              mol_type = protein
                              organism = synthetic construct
SEQUENCE: 504
DFCGPEMDET ISCD                                                          14

SEQ ID NO: 505                moltype = AA   length = 14
FEATURE                       Location/Qualifiers
REGION                        1..14
                              note = Description of Artificial Sequence: Synthetic peptide
source                        1..14
                              mol_type = protein
                              organism = synthetic construct
SEQUENCE: 505
ILCGPELDES LVCD                                                          14

SEQ ID NO: 506                moltype = AA   length = 14
FEATURE                       Location/Qualifiers
REGION                        1..14
                              note = Description of Artificial Sequence: Synthetic peptide
source                        1..14
                              mol_type = protein
                              organism = synthetic construct
SEQUENCE: 506
LICGPEWEVI TNCD                                                          14

SEQ ID NO: 507                moltype = AA   length = 14
FEATURE                       Location/Qualifiers
REGION                        1..14
                              note = Description of Artificial Sequence: Synthetic peptide
source                        1..14
                              mol_type = protein
                              organism = synthetic construct
SEQUENCE: 507
YDCGPEFDEY FGCP                                                          14

SEQ ID NO: 508                moltype = AA   length = 14
FEATURE                       Location/Qualifiers
REGION                        1..14
                              note = Description of Artificial Sequence: Synthetic peptide
source                        1..14
                              mol_type = protein
                              organism = synthetic construct
SEQUENCE: 508
ALCGPEVEVY DVCV                                                          14

SEQ ID NO: 509                moltype = AA   length = 14
FEATURE                       Location/Qualifiers
REGION                        1..14
                              note = Description of Artificial Sequence: Synthetic peptide
source                        1..14
                              mol_type = protein
                              organism = synthetic construct
SEQUENCE: 509
YHCWPDWEDV NFCY                                                          14

SEQ ID NO: 510                moltype = AA   length = 14
FEATURE                       Location/Qualifiers
REGION                        1..14
                              note = Description of Artificial Sequence: Synthetic peptide
source                        1..14
```

```
                        mol_type = protein
                        organism = synthetic construct
SEQUENCE: 510
FLCGPMGGLT FYCY                                                14

SEQ ID NO: 511          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 511
IICGPEFDEY VGCF                                                14

SEQ ID NO: 512          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 512
FFCGPEMDES VHCF                                                14

SEQ ID NO: 513          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 513
AFCGPEFDES LFCA                                                14

SEQ ID NO: 514          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 514
NYCGPDGDET NICD                                                14

SEQ ID NO: 515          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 515
YLCGPEWEWV HNCL                                                14

SEQ ID NO: 516          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 516
ATCGPDGDES HICA                                                14

SEQ ID NO: 517          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 517
VYCGPEVEVL DYCD                                                14

SEQ ID NO: 518          moltype = AA  length = 14
FEATURE                 Location/Qualifiers
REGION                  1..14
                        note = Description of Artificial Sequence: Synthetic peptide
```

-continued

```
source                       1..14
                             mol_type = protein
                             organism = synthetic construct
SEQUENCE: 518
IHCGPEWEFY TDCD                                                              14

SEQ ID NO: 519               moltype = AA  length = 14
FEATURE                      Location/Qualifiers
REGION                       1..14
                             note = Description of Artificial Sequence: Synthetic peptide
source                       1..14
                             mol_type = protein
                             organism = synthetic construct
SEQUENCE: 519
DDCGPELDET VACD                                                              14

SEQ ID NO: 520               moltype = AA  length = 14
FEATURE                      Location/Qualifiers
REGION                       1..14
                             note = Description of Artificial Sequence: Synthetic peptide
source                       1..14
                             mol_type = protein
                             organism = synthetic construct
SEQUENCE: 520
YLCGPEFDES IDCN                                                              14

SEQ ID NO: 521               moltype = AA  length = 14
FEATURE                      Location/Qualifiers
REGION                       1..14
                             note = Description of Artificial Sequence: Synthetic peptide
source                       1..14
                             mol_type = protein
                             organism = synthetic construct
SEQUENCE: 521
LLCGPEVEDV FACY                                                              14

SEQ ID NO: 522               moltype = AA  length = 14
FEATURE                      Location/Qualifiers
REGION                       1..14
                             note = Description of Artificial Sequence: Synthetic peptide
source                       1..14
                             mol_type = protein
                             organism = synthetic construct
SEQUENCE: 522
YDCGPELDES LTCD                                                              14

SEQ ID NO: 523               moltype = AA  length = 14
FEATURE                      Location/Qualifiers
REGION                       1..14
                             note = Description of Artificial Sequence: Synthetic peptide
source                       1..14
                             mol_type = protein
                             organism = synthetic construct
SEQUENCE: 523
FDCGPELDET VNCY                                                              14

SEQ ID NO: 524               moltype = AA  length = 14
FEATURE                      Location/Qualifiers
REGION                       1..14
                             note = Description of Artificial Sequence: Synthetic peptide
source                       1..14
                             mol_type = protein
                             organism = synthetic construct
SEQUENCE: 524
FACWPDWEEI NDCH                                                              14

SEQ ID NO: 525               moltype = AA  length = 14
FEATURE                      Location/Qualifiers
REGION                       1..14
                             note = Description of Artificial Sequence: Synthetic peptide
source                       1..14
                             mol_type = protein
                             organism = synthetic construct
SEQUENCE: 525
YYCGPEYEED IYCN                                                              14

SEQ ID NO: 526               moltype = AA  length = 14
FEATURE                      Location/Qualifiers
REGION                       1..14
```

-continued

```
                          note = Description of Artificial Sequence: Synthetic peptide
source                    1..14
                          mol_type = protein
                          organism = synthetic construct
SEQUENCE: 526
NVCGPEVEDY TFCY                                                          14

SEQ ID NO: 527            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 527
AYCGPELEEY DFCT                                                          14

SEQ ID NO: 528            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 528
FDCGPEIDES TICT                                                          14

SEQ ID NO: 529            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 529
NLCGPELDET LVCA                                                          14

SEQ ID NO: 530            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 530
YSCWPDWEEY LACN                                                          14

SEQ ID NO: 531            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 531
GICGPEVEDY NYCD                                                          14

SEQ ID NO: 532            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 532
FFCGPELDES VNCH                                                          14

SEQ ID NO: 533            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 533
YYCGPEYEED FYCF                                                          14

SEQ ID NO: 534            moltype = AA  length = 14
FEATURE                   Location/Qualifiers
```

-continued

```
REGION                   1..14
                         note = Description of Artificial Sequence: Synthetic peptide
source                   1..14
                         mol_type = protein
                         organism = synthetic construct
SEQUENCE: 534
LYCGPEYDES TDCY                                                             14

SEQ ID NO: 535           moltype = AA  length = 14
FEATURE                  Location/Qualifiers
REGION                   1..14
                         note = Description of Artificial Sequence: Synthetic peptide
source                   1..14
                         mol_type = protein
                         organism = synthetic construct
SEQUENCE: 535
DYCGPEVEED FLCY                                                             14

SEQ ID NO: 536           moltype = AA  length = 14
FEATURE                  Location/Qualifiers
REGION                   1..14
                         note = Description of Artificial Sequence: Synthetic peptide
source                   1..14
                         mol_type = protein
                         organism = synthetic construct
SEQUENCE: 536
TLCGPEVELY IFCD                                                             14

SEQ ID NO: 537           moltype = AA  length = 14
FEATURE                  Location/Qualifiers
REGION                   1..14
                         note = Description of Artificial Sequence: Synthetic peptide
source                   1..14
                         mol_type = protein
                         organism = synthetic construct
SEQUENCE: 537
FYCGPEFEQI ADCY                                                             14

SEQ ID NO: 538           moltype = AA  length = 14
FEATURE                  Location/Qualifiers
REGION                   1..14
                         note = Description of Artificial Sequence: Synthetic peptide
source                   1..14
                         mol_type = protein
                         organism = synthetic construct
SEQUENCE: 538
DDCGPEVEEY HLCD                                                             14

SEQ ID NO: 539           moltype = AA  length = 14
FEATURE                  Location/Qualifiers
REGION                   1..14
                         note = Description of Artificial Sequence: Synthetic peptide
source                   1..14
                         mol_type = protein
                         organism = synthetic construct
SEQUENCE: 539
DYCGPELEDV TLCH                                                             14

SEQ ID NO: 540           moltype = AA  length = 14
FEATURE                  Location/Qualifiers
REGION                   1..14
                         note = Description of Artificial Sequence: Synthetic peptide
source                   1..14
                         mol_type = protein
                         organism = synthetic construct
SEQUENCE: 540
VLCGPEVEDV NLCY                                                             14

SEQ ID NO: 541           moltype = AA  length = 14
FEATURE                  Location/Qualifiers
REGION                   1..14
                         note = Description of Artificial Sequence: Synthetic peptide
source                   1..14
                         mol_type = protein
                         organism = synthetic construct
SEQUENCE: 541
DICGPELDET IDCY                                                             14

SEQ ID NO: 542           moltype = AA  length = 14
```

-continued

```
FEATURE               Location/Qualifiers
REGION                1..14
                      note = Description of Artificial Sequence: Synthetic peptide
source                1..14
                      mol_type = protein
                      organism = synthetic construct
SEQUENCE: 542
TYCGPEVEED INCY                                                        14

SEQ ID NO: 543        moltype = AA  length = 14
FEATURE               Location/Qualifiers
REGION                1..14
                      note = Description of Artificial Sequence: Synthetic peptide
source                1..14
                      mol_type = protein
                      organism = synthetic construct
SEQUENCE: 543
IVCWPDWEEY PNCD                                                        14

SEQ ID NO: 544        moltype = AA  length = 14
FEATURE               Location/Qualifiers
REGION                1..14
                      note = Description of Artificial Sequence: Synthetic peptide
source                1..14
                      mol_type = protein
                      organism = synthetic construct
SEQUENCE: 544
SDCGPELDES IICT                                                        14

SEQ ID NO: 545        moltype = AA  length = 14
FEATURE               Location/Qualifiers
REGION                1..14
                      note = Description of Artificial Sequence: Synthetic peptide
source                1..14
                      mol_type = protein
                      organism = synthetic construct
SEQUENCE: 545
YDCGPELPED YDCN                                                        14

SEQ ID NO: 546        moltype = AA  length = 14
FEATURE               Location/Qualifiers
REGION                1..14
                      note = Description of Artificial Sequence: Synthetic peptide
source                1..14
                      mol_type = protein
                      organism = synthetic construct
SEQUENCE: 546
NLCWPDWEEY YACD                                                        14

SEQ ID NO: 547        moltype = AA  length = 14
FEATURE               Location/Qualifiers
REGION                1..14
                      note = Description of Artificial Sequence: Synthetic peptide
source                1..14
                      mol_type = protein
                      organism = synthetic construct
SEQUENCE: 547
DDCGPELDES LPCH                                                        14

SEQ ID NO: 548        moltype = AA  length = 14
FEATURE               Location/Qualifiers
REGION                1..14
                      note = Description of Artificial Sequence: Synthetic peptide
source                1..14
                      mol_type = protein
                      organism = synthetic construct
SEQUENCE: 548
SLCGPDGQED YTCF                                                        14

SEQ ID NO: 549        moltype = AA  length = 14
FEATURE               Location/Qualifiers
REGION                1..14
                      note = Description of Artificial Sequence: Synthetic peptide
source                1..14
                      mol_type = protein
                      organism = synthetic construct
SEQUENCE: 549
LICWPDWEEY NFCT                                                        14
```

```
SEQ ID NO: 550          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 550
FHCGPDGDET VPCI                                                       14

SEQ ID NO: 551          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 551
FDCGPEWEWI YDCF                                                       14

SEQ ID NO: 552          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 552
IYCGPEWDES LDCD                                                       14

SEQ ID NO: 553          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 553
LICGPEIDES ASCN                                                       14

SEQ ID NO: 554          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 554
TSCWVDWEEF SDCI                                                       14

SEQ ID NO: 555          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 555
YYCGPEVEED YVCD                                                       14

SEQ ID NO: 556          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 556
DDCGPEQEFI YACI                                                       14

SEQ ID NO: 557          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 557
ADCWPDWEEY ADCY                                                       14
```

-continued

```
SEQ ID NO: 558          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 558
YYCGPEFDES IHCI                                                          14

SEQ ID NO: 559          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 559
SECWPDWEPF FDCN                                                          14

SEQ ID NO: 560          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 560
YHCGPEMDES LICT                                                          14

SEQ ID NO: 561          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 561
SDCWPDWEDA YFCI                                                          14

SEQ ID NO: 562          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 562
VDCGPEVEEY YHCD                                                          14

SEQ ID NO: 563          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 563
DNCGPEYDES IACN                                                          14

SEQ ID NO: 564          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 564
LYCGPVFEFY DYCY                                                          14

SEQ ID NO: 565          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 565
```

-continued

```
YTCGPEMDES VTCI                                                          14

SEQ ID NO: 566          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 566
NFCWPDWEVN SFCD                                                          14

SEQ ID NO: 567          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 567
NACWPDWEYI DFCN                                                          14

SEQ ID NO: 568          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 568
YNCGPEMDES IFCS                                                          14

SEQ ID NO: 569          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 569
LDCGPELDES ITCY                                                          14

SEQ ID NO: 570          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 570
HYCGPEFDES INCD                                                          14

SEQ ID NO: 571          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 571
IICGPELPED YVCT                                                          14

SEQ ID NO: 572          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 572
DICGPEFDES IDCS                                                          14

SEQ ID NO: 573          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
```

```
SEQUENCE: 573
PYCGPEFDES VLCF                                                    14

SEQ ID NO: 574         moltype = AA  length = 14
FEATURE                Location/Qualifiers
REGION                 1..14
                       note = Description of Artificial Sequence: Synthetic peptide
source                 1..14
                       mol_type = protein
                       organism = synthetic construct
SEQUENCE: 574
VFCGPEFDES VDCY                                                    14

SEQ ID NO: 575         moltype = AA  length = 14
FEATURE                Location/Qualifiers
REGION                 1..14
                       note = Description of Artificial Sequence: Synthetic peptide
source                 1..14
                       mol_type = protein
                       organism = synthetic construct
SEQUENCE: 575
YDCWPDWEEA LPCA                                                    14

SEQ ID NO: 576         moltype = AA  length = 14
FEATURE                Location/Qualifiers
REGION                 1..14
                       note = Description of Artificial Sequence: Synthetic peptide
source                 1..14
                       mol_type = protein
                       organism = synthetic construct
SEQUENCE: 576
DDCWPDWEDY VFCF                                                    14

SEQ ID NO: 577         moltype = AA  length = 14
FEATURE                Location/Qualifiers
REGION                 1..14
                       note = Description of Artificial Sequence: Synthetic peptide
source                 1..14
                       mol_type = protein
                       organism = synthetic construct
SEQUENCE: 577
HFCGPEWELF SDCY                                                    14

SEQ ID NO: 578         moltype = AA  length = 14
FEATURE                Location/Qualifiers
REGION                 1..14
                       note = Description of Artificial Sequence: Synthetic peptide
source                 1..14
                       mol_type = protein
                       organism = synthetic construct
SEQUENCE: 578
ITCWPDWEVN FPCY                                                    14

SEQ ID NO: 579         moltype = AA  length = 14
FEATURE                Location/Qualifiers
REGION                 1..14
                       note = Description of Artificial Sequence: Synthetic peptide
source                 1..14
                       mol_type = protein
                       organism = synthetic construct
SEQUENCE: 579
PDCGPELDES ITCN                                                    14

SEQ ID NO: 580         moltype = AA  length = 14
FEATURE                Location/Qualifiers
REGION                 1..14
                       note = Description of Artificial Sequence: Synthetic peptide
source                 1..14
                       mol_type = protein
                       organism = synthetic construct
SEQUENCE: 580
NLCWPDWEAF FPCY                                                    14

SEQ ID NO: 581         moltype = AA  length = 14
FEATURE                Location/Qualifiers
REGION                 1..14
                       note = Description of Artificial Sequence: Synthetic peptide
source                 1..14
                       mol_type = protein
```

-continued

```
                        organism = synthetic construct
SEQUENCE: 581
FYCGPEFEYI RDCY                                                        14

SEQ ID NO: 582          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 582
FFCGPEFDES IICD                                                        14

SEQ ID NO: 583          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 583
VLCGPKGGPT YNCS                                                        14

SEQ ID NO: 584          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 584
LACWPVWEEP GHCD                                                        14

SEQ ID NO: 585          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 585
DYCGPEVEDV NDCY                                                        14

SEQ ID NO: 586          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 586
DYCGPEFEEA HYCN                                                        14

SEQ ID NO: 587          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 587
VLCGPELDET LTCI                                                        14

SEQ ID NO: 588          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 588
YYCGPEIEDY NLCN                                                        14

SEQ ID NO: 589          moltype = AA   length = 14
FEATURE                 Location/Qualifiers
REGION                  1..14
                        note = Description of Artificial Sequence: Synthetic peptide
source                  1..14
```

```
                            mol_type = protein
                            organism = synthetic construct
SEQUENCE: 589
YICGPEVEEY YNCF                                                       14

SEQ ID NO: 590              moltype = AA  length = 14
FEATURE                    Location/Qualifiers
REGION                     1..14
                            note = Description of Artificial Sequence: Synthetic peptide
source                     1..14
                            mol_type = protein
                            organism = synthetic construct
SEQUENCE: 590
DICGPELDES IFCF                                                       14

SEQ ID NO: 591              moltype = AA  length = 14
FEATURE                    Location/Qualifiers
REGION                     1..14
                            note = Description of Artificial Sequence: Synthetic peptide
source                     1..14
                            mol_type = protein
                            organism = synthetic construct
SEQUENCE: 591
DICGPEVEED YLCY                                                       14

SEQ ID NO: 592              moltype = AA  length = 14
FEATURE                    Location/Qualifiers
REGION                     1..14
                            note = Description of Artificial Sequence: Synthetic peptide
source                     1..14
                            mol_type = protein
                            organism = synthetic construct
SEQUENCE: 592
TLCGPEFEED APCI                                                       14

SEQ ID NO: 593              moltype = AA  length = 14
FEATURE                    Location/Qualifiers
REGION                     1..14
                            note = Description of Artificial Sequence: Synthetic peptide
source                     1..14
                            mol_type = protein
                            organism = synthetic construct
SEQUENCE: 593
NYCWPDWEYI NSCV                                                       14

SEQ ID NO: 594              moltype = AA  length = 14
FEATURE                    Location/Qualifiers
REGION                     1..14
                            note = Description of Artificial Sequence: Synthetic peptide
source                     1..14
                            mol_type = protein
                            organism = synthetic construct
SEQUENCE: 594
NDCGPEVEEY YYCT                                                       14

SEQ ID NO: 595              moltype = AA  length = 14
FEATURE                    Location/Qualifiers
REGION                     1..14
                            note = Description of Artificial Sequence: Synthetic peptide
source                     1..14
                            mol_type = protein
                            organism = synthetic construct
SEQUENCE: 595
ITCGPEMDES IDCN                                                       14

SEQ ID NO: 596              moltype = AA  length = 14
FEATURE                    Location/Qualifiers
REGION                     1..14
                            note = Description of Artificial Sequence: Synthetic peptide
source                     1..14
                            mol_type = protein
                            organism = synthetic construct
SEQUENCE: 596
YYCGPEMAED LICD                                                       14

SEQ ID NO: 597              moltype = AA  length = 14
FEATURE                    Location/Qualifiers
REGION                     1..14
                            note = Description of Artificial Sequence: Synthetic peptide
```

-continued

```
source                    1..14
                          mol_type = protein
                          organism = synthetic construct
SEQUENCE: 597
IDCGPELDES IVCT                                                    14

SEQ ID NO: 598            moltype = AA   length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 598
HTCWPDWEWD VYCD                                                    14

SEQ ID NO: 599            moltype = AA   length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 599
IHCGPEWELI DDCL                                                    14

SEQ ID NO: 600            moltype = AA   length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 600
YTCGPELDES ITCT                                                    14

SEQ ID NO: 601            moltype = AA   length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 601
FHCGPEVEET VYCF                                                    14

SEQ ID NO: 602            moltype = AA   length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 602
DYCGPELDES LICN                                                    14

SEQ ID NO: 603            moltype = AA   length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 603
IYCGPEFDES DYCI                                                    14

SEQ ID NO: 604            moltype = AA   length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 604
DLCGPEIEED LVCT                                                    14

SEQ ID NO: 605            moltype = AA   length = 14
FEATURE                   Location/Qualifiers
REGION                    1..14
```

-continued

```
                       note = Description of Artificial Sequence: Synthetic peptide
source                 1..14
                       mol_type = protein
                       organism = synthetic construct
SEQUENCE: 605
NICGPELQED IVCP                                                          14

SEQ ID NO: 606         moltype = AA  length = 14
FEATURE                Location/Qualifiers
REGION                 1..14
                       note = Description of Artificial Sequence: Synthetic peptide
source                 1..14
                       mol_type = protein
                       organism = synthetic construct
SEQUENCE: 606
NNCGPEMDES ITCY                                                          14

SEQ ID NO: 607         moltype = AA  length = 14
FEATURE                Location/Qualifiers
REGION                 1..14
                       note = Description of Artificial Sequence: Synthetic peptide
source                 1..14
                       mol_type = protein
                       organism = synthetic construct
SEQUENCE: 607
HTCGPELDES IVCV                                                          14

SEQ ID NO: 608         moltype = AA  length = 14
FEATURE                Location/Qualifiers
REGION                 1..14
                       note = Description of Artificial Sequence: Synthetic peptide
source                 1..14
                       mol_type = protein
                       organism = synthetic construct
SEQUENCE: 608
YYCGPEIEDI LVCT                                                          14

SEQ ID NO: 609         moltype = AA  length = 14
FEATURE                Location/Qualifiers
REGION                 1..14
                       note = Description of Artificial Sequence: Synthetic peptide
source                 1..14
                       mol_type = protein
                       organism = synthetic construct
SEQUENCE: 609
NTCGPEFEFV HLCP                                                          14

SEQ ID NO: 610         moltype = AA  length = 14
FEATURE                Location/Qualifiers
REGION                 1..14
                       note = Description of Artificial Sequence: Synthetic peptide
source                 1..14
                       mol_type = protein
                       organism = synthetic construct
SEQUENCE: 610
DICGPEMDES TVCD                                                          14

SEQ ID NO: 611         moltype = AA  length = 14
FEATURE                Location/Qualifiers
REGION                 1..14
                       note = Description of Artificial Sequence: Synthetic peptide
source                 1..14
                       mol_type = protein
                       organism = synthetic construct
SEQUENCE: 611
AICGPEVEIV NYCY                                                          14

SEQ ID NO: 612         moltype = AA  length = 14
FEATURE                Location/Qualifiers
REGION                 1..14
                       note = Description of Artificial Sequence: Synthetic peptide
source                 1..14
                       mol_type = protein
                       organism = synthetic construct
SEQUENCE: 612
HLCGPEVEDP TACV                                                          14

SEQ ID NO: 613         moltype = AA  length = 14
FEATURE                Location/Qualifiers
```

```
REGION                    1..14
                          note = Description of Artificial Sequence: Synthetic peptide
source                    1..14
                          mol_type = protein
                          organism = synthetic construct
SEQUENCE: 613
ADCGPELDES ISCT                                                              14

SEQ ID NO: 614            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 614
FDCGPELDES VICD                                                              14

SEQ ID NO: 615            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 615
DVCGPEFDES IDCN                                                              14

SEQ ID NO: 616            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 616
YLCGPEVEEI SICF                                                             14

SEQ ID NO: 617            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 617
SACGPEFDES LHCV                                                             14

SEQ ID NO: 618            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 618
HLCWPDWEED SACN                                                             14

SEQ ID NO: 619            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 619
HTCWPDWEYD YDCF                                                             14

SEQ ID NO: 620            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 620
YDCGPEWEEV ALCN                                                             14

SEQ ID NO: 621            moltype = AA  length = 14
```

-continued

| FEATURE | Location/Qualifiers |
|---|---|
| REGION | 1..14 |
| | note = Description of Artificial Sequence: Synthetic peptide |
| source | 1..14 |
| | mol_type = protein |
| | organism = synthetic construct |

SEQUENCE: 621
TLCGPEIEEY IVCY                                                              14

| SEQ ID NO: 622 | moltype = AA  length = 14 |
|---|---|
| FEATURE | Location/Qualifiers |
| REGION | 1..14 |
| | note = Description of Artificial Sequence: Synthetic peptide |
| source | 1..14 |
| | mol_type = protein |
| | organism = synthetic construct |

SEQUENCE: 622
SYCGPEFDES IFCT                                                              14

| SEQ ID NO: 623 | moltype = AA  length = 14 |
|---|---|
| FEATURE | Location/Qualifiers |
| REGION | 1..14 |
| | note = Description of Artificial Sequence: Synthetic peptide |
| source | 1..14 |
| | mol_type = protein |
| | organism = synthetic construct |

SEQUENCE: 623
DICGPEFDES LHCY                                                              14

| SEQ ID NO: 624 | moltype = AA  length = 14 |
|---|---|
| FEATURE | Location/Qualifiers |
| REGION | 1..14 |
| | note = Description of Artificial Sequence: Synthetic peptide |
| source | 1..14 |
| | mol_type = protein |
| | organism = synthetic construct |

SEQUENCE: 624
LFCGPEFEEA YLCI                                                              14

| SEQ ID NO: 625 | moltype = AA  length = 14 |
|---|---|
| FEATURE | Location/Qualifiers |
| REGION | 1..14 |
| | note = Description of Artificial Sequence: Synthetic peptide |
| source | 1..14 |
| | mol_type = protein |
| | organism = synthetic construct |

SEQUENCE: 625
IFCGPEIEED FVCT                                                              14

| SEQ ID NO: 626 | moltype = AA  length = 14 |
|---|---|
| FEATURE | Location/Qualifiers |
| REGION | 1..14 |
| | note = Description of Artificial Sequence: Synthetic peptide |
| source | 1..14 |
| | mol_type = protein |
| | organism = synthetic construct |

SEQUENCE: 626
DDCGPEWEYY VACV                                                              14

| SEQ ID NO: 627 | moltype = AA  length = 14 |
|---|---|
| FEATURE | Location/Qualifiers |
| REGION | 1..14 |
| | note = Description of Artificial Sequence: Synthetic peptide |
| source | 1..14 |
| | mol_type = protein |
| | organism = synthetic construct |

SEQUENCE: 627
DDCGPELDET TICY                                                              14

| SEQ ID NO: 628 | moltype = AA  length = 14 |
|---|---|
| FEATURE | Location/Qualifiers |
| REGION | 1..14 |
| | note = Description of Artificial Sequence: Synthetic peptide |
| source | 1..14 |
| | mol_type = protein |
| | organism = synthetic construct |

SEQUENCE: 628
ASCGPELDES IACD                                                              14

```
SEQ ID NO: 629          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 629
YLCGPEVEDY DYCY                                                       14

SEQ ID NO: 630          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 630
DLCGPEWEET IFCA                                                       14

SEQ ID NO: 631          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 631
DFCGPDGEEF YICP                                                       14

SEQ ID NO: 632          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 632
VYCGPEVEEN ILCH                                                       14

SEQ ID NO: 633          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 633
DYCGPEVEEN YFCF                                                       14

SEQ ID NO: 634          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 634
NDCWPDWYEF LSCD                                                       14

SEQ ID NO: 635          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 635
RDCWPDWEVP YFCD                                                       14

SEQ ID NO: 636          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 636
NLCGPEVEEA VYCY                                                       14
```

-continued

```
SEQ ID NO: 637              moltype = AA   length = 14
FEATURE                     Location/Qualifiers
REGION                      1..14
                            note = Description of Artificial Sequence: Synthetic peptide
source                      1..14
                            mol_type = protein
                            organism = synthetic construct
SEQUENCE: 637
FDCWPDGELN YLCT                                                                    14

SEQ ID NO: 638              moltype = AA   length = 14
FEATURE                     Location/Qualifiers
REGION                      1..14
                            note = Description of Artificial Sequence: Synthetic peptide
source                      1..14
                            mol_type = protein
                            organism = synthetic construct
SEQUENCE: 638
YYCGPEVEDV NLCI                                                                    14

SEQ ID NO: 639              moltype = AA   length = 14
FEATURE                     Location/Qualifiers
REGION                      1..14
                            note = Description of Artificial Sequence: Synthetic peptide
source                      1..14
                            mol_type = protein
                            organism = synthetic construct
SEQUENCE: 639
DNCGPEYDES ITCL                                                                    14

SEQ ID NO: 640              moltype = AA   length = 14
FEATURE                     Location/Qualifiers
REGION                      1..14
                            note = Description of Artificial Sequence: Synthetic peptide
source                      1..14
                            mol_type = protein
                            organism = synthetic construct
SEQUENCE: 640
LNCWPDWEED YSCN                                                                    14

SEQ ID NO: 641              moltype = AA   length = 14
FEATURE                     Location/Qualifiers
REGION                      1..14
                            note = Description of Artificial Sequence: Synthetic peptide
source                      1..14
                            mol_type = protein
                            organism = synthetic construct
SEQUENCE: 641
PTCGPEVEEL LSCN                                                                    14

SEQ ID NO: 642              moltype = AA   length = 14
FEATURE                     Location/Qualifiers
REGION                      1..14
                            note = Description of Artificial Sequence: Synthetic peptide
source                      1..14
                            mol_type = protein
                            organism = synthetic construct
SEQUENCE: 642
DHCGPEVELI FYCH                                                                    14

SEQ ID NO: 643              moltype = AA   length = 14
FEATURE                     Location/Qualifiers
REGION                      1..14
                            note = Description of Artificial Sequence: Synthetic peptide
source                      1..14
                            mol_type = protein
                            organism = synthetic construct
SEQUENCE: 643
FHCGPELDES IFCY                                                                    14

SEQ ID NO: 644              moltype = AA   length = 14
FEATURE                     Location/Qualifiers
REGION                      1..14
                            note = Description of Artificial Sequence: Synthetic peptide
source                      1..14
                            mol_type = protein
                            organism = synthetic construct
SEQUENCE: 644
```

-continued

```
FDCGPELEET VVCP                                              14

SEQ ID NO: 645          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 645
DFCGPELDES LPCA                                              14

SEQ ID NO: 646          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 646
DSCGPELDES IYCD                                              14

SEQ ID NO: 647          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 647
ADCWPDWEEF LLCF                                              14

SEQ ID NO: 648          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 648
ILCGPEVEEL DFCN                                              14

SEQ ID NO: 649          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 649
FFCGPEFEEI FLCY                                              14

SEQ ID NO: 650          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 650
YNCGPDGDES YDCH                                              14

SEQ ID NO: 651          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 651
DNCGPELDET ITCF                                              14

SEQ ID NO: 652          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
```

-continued

```
SEQUENCE: 652
HNCGPDGDEA FICN                                                       14

SEQ ID NO: 653          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 653
DYCGPEVEED LVCP                                                       14

SEQ ID NO: 654          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 654
DYCGPELDES LNCF                                                       14

SEQ ID NO: 655          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 655
DYCGPEFQED FHCH                                                       14

SEQ ID NO: 656          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 656
YDCGPEWEFT DDCI                                                       14

SEQ ID NO: 657          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 657
DICGPEYEED IICY                                                       14

SEQ ID NO: 658          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 658
FDCGPELDET VPCP                                                       14

SEQ ID NO: 659          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 659
NYCGPELDET SVCD                                                       14

SEQ ID NO: 660          moltype = AA  length = 14
FEATURE                 Location/Qualifiers
REGION                  1..14
                        note = Description of Artificial Sequence: Synthetic peptide
source                  1..14
                        mol_type = protein
```

```
                              organism = synthetic construct
SEQUENCE: 660
YYCGPEWEFS FDCD                                                        14

SEQ ID NO: 661        moltype = AA  length = 14
FEATURE               Location/Qualifiers
REGION                1..14
                      note = Description of Artificial Sequence: Synthetic peptide
source                1..14
                      mol_type = protein
                      organism = synthetic construct
SEQUENCE: 661
YACGPELDES VTCD                                                        14

SEQ ID NO: 662        moltype = AA  length = 14
FEATURE               Location/Qualifiers
REGION                1..14
                      note = Description of Artificial Sequence: Synthetic peptide
source                1..14
                      mol_type = protein
                      organism = synthetic construct
SEQUENCE: 662
FLCGPEVEQD YFCV                                                        14

SEQ ID NO: 663        moltype = AA  length = 14
FEATURE               Location/Qualifiers
REGION                1..14
                      note = Description of Artificial Sequence: Synthetic peptide
source                1..14
                      mol_type = protein
                      organism = synthetic construct
SEQUENCE: 663
DNCGPEFDES VRCD                                                        14

SEQ ID NO: 664        moltype = AA  length = 14
FEATURE               Location/Qualifiers
REGION                1..14
                      note = Description of Artificial Sequence: Synthetic peptide
source                1..14
                      mol_type = protein
                      organism = synthetic construct
SEQUENCE: 664
NDCGPDGIET VDCY                                                        14

SEQ ID NO: 665        moltype = AA  length = 14
FEATURE               Location/Qualifiers
REGION                1..14
                      note = Description of Artificial Sequence: Synthetic peptide
source                1..14
                      mol_type = protein
                      organism = synthetic construct
SEQUENCE: 665
YFCGPEVEDY NDCF                                                        14

SEQ ID NO: 666        moltype = AA  length = 14
FEATURE               Location/Qualifiers
REGION                1..14
                      note = Description of Artificial Sequence: Synthetic peptide
source                1..14
                      mol_type = protein
                      organism = synthetic construct
SEQUENCE: 666
NLCGPEFDES IFCY                                                        14

SEQ ID NO: 667        moltype = AA  length = 14
FEATURE               Location/Qualifiers
REGION                1..14
                      note = Description of Artificial Sequence: Synthetic peptide
source                1..14
                      mol_type = protein
                      organism = synthetic construct
SEQUENCE: 667
IDCWPDWEEY IPCT                                                        14

SEQ ID NO: 668        moltype = AA  length = 14
FEATURE               Location/Qualifiers
REGION                1..14
                      note = Description of Artificial Sequence: Synthetic peptide
source                1..14
```

```
                          mol_type = protein
                          organism = synthetic construct
SEQUENCE: 668
IYCGPDGDES FICA                                                          14

SEQ ID NO: 669           moltype = AA  length = 14
FEATURE                  Location/Qualifiers
REGION                   1..14
                         note = Description of Artificial Sequence: Synthetic peptide
source                   1..14
                         mol_type = protein
                         organism = synthetic construct
SEQUENCE: 669
DYCGPEFDES VVCY                                                          14

SEQ ID NO: 670           moltype = AA  length = 14
FEATURE                  Location/Qualifiers
REGION                   1..14
                         note = Description of Artificial Sequence: Synthetic peptide
source                   1..14
                         mol_type = protein
                         organism = synthetic construct
SEQUENCE: 670
VFCGPEWEDI TDCD                                                          14

SEQ ID NO: 671           moltype = AA  length = 14
FEATURE                  Location/Qualifiers
REGION                   1..14
                         note = Description of Artificial Sequence: Synthetic peptide
source                   1..14
                         mol_type = protein
                         organism = synthetic construct
SEQUENCE: 671
LDCGPEVDET FTCH                                                          14

SEQ ID NO: 672           moltype = AA  length = 14
FEATURE                  Location/Qualifiers
REGION                   1..14
                         note = Description of Artificial Sequence: Synthetic peptide
source                   1..14
                         mol_type = protein
                         organism = synthetic construct
SEQUENCE: 672
DDCGPEYDES FACH                                                          14

SEQ ID NO: 673           moltype = AA  length = 14
FEATURE                  Location/Qualifiers
REGION                   1..14
                         note = Description of Artificial Sequence: Synthetic peptide
source                   1..14
                         mol_type = protein
                         organism = synthetic construct
SEQUENCE: 673
IYCGPEYQED LPCN                                                          14

SEQ ID NO: 674           moltype = AA  length = 14
FEATURE                  Location/Qualifiers
REGION                   1..14
                         note = Description of Artificial Sequence: Synthetic peptide
source                   1..14
                         mol_type = protein
                         organism = synthetic construct
SEQUENCE: 674
LDCGPEVEEY NYCV                                                          14

SEQ ID NO: 675           moltype = AA  length = 14
FEATURE                  Location/Qualifiers
REGION                   1..14
                         note = Description of Artificial Sequence: Synthetic peptide
source                   1..14
                         mol_type = protein
                         organism = synthetic construct
SEQUENCE: 675
YVCGPEFDES SACN                                                          14

SEQ ID NO: 676           moltype = AA  length = 14
FEATURE                  Location/Qualifiers
REGION                   1..14
                         note = Description of Artificial Sequence: Synthetic peptide
```

-continued

```
source                    1..14
                          mol_type = protein
                          organism = synthetic construct
SEQUENCE: 676
TPCGPELEEA IGCY                                                    14

SEQ ID NO: 677            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 677
YFCGPEFDES ADCN                                                    14

SEQ ID NO: 678            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 678
DDCGPEFEED IICD                                                    14

SEQ ID NO: 679            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 679
LYCGPVVEEL NHCN                                                    14

SEQ ID NO: 680            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 680
VICGPDGEEL IACA                                                    14

SEQ ID NO: 681            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 681
FACWPDWQET YVCN                                                    14

SEQ ID NO: 682            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 682
YICGPEVEFL FFCN                                                    14

SEQ ID NO: 683            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 683
TQCGPKGEPT YHCY                                                    14

SEQ ID NO: 684            moltype = AA  length = 14
FEATURE                   Location/Qualifiers
REGION                    1..14
```

-continued

```
                            note = Description of Artificial Sequence: Synthetic peptide
source                      1..14
                            mol_type = protein
                            organism = synthetic construct
SEQUENCE: 684
NYCGPEVEEY HNCD                                                             14

SEQ ID NO: 685              moltype = AA   length = 14
FEATURE                     Location/Qualifiers
REGION                      1..14
                            note = Description of Artificial Sequence: Synthetic peptide
source                      1..14
                            mol_type = protein
                            organism = synthetic construct
SEQUENCE: 685
VYCGPEWEFF SDCA                                                             14

SEQ ID NO: 686              moltype = AA   length = 14
FEATURE                     Location/Qualifiers
REGION                      1..14
                            note = Description of Artificial Sequence: Synthetic peptide
source                      1..14
                            mol_type = protein
                            organism = synthetic construct
SEQUENCE: 686
FYCGPELEES FFCY                                                             14

SEQ ID NO: 687              moltype = AA   length = 14
FEATURE                     Location/Qualifiers
REGION                      1..14
                            note = Description of Artificial Sequence: Synthetic peptide
source                      1..14
                            mol_type = protein
                            organism = synthetic construct
SEQUENCE: 687
DYCGPEIEEN FYCY                                                             14

SEQ ID NO: 688              moltype = AA   length = 14
FEATURE                     Location/Qualifiers
REGION                      1..14
                            note = Description of Artificial Sequence: Synthetic peptide
source                      1..14
                            mol_type = protein
                            organism = synthetic construct
SEQUENCE: 688
YACGPEVEEY VYCA                                                             14

SEQ ID NO: 689              moltype = AA   length = 14
FEATURE                     Location/Qualifiers
REGION                      1..14
                            note = Description of Artificial Sequence: Synthetic peptide
source                      1..14
                            mol_type = protein
                            organism = synthetic construct
SEQUENCE: 689
VDCGPELDES IICD                                                             14

SEQ ID NO: 690              moltype = AA   length = 14
FEATURE                     Location/Qualifiers
REGION                      1..14
                            note = Description of Artificial Sequence: Synthetic peptide
source                      1..14
                            mol_type = protein
                            organism = synthetic construct
SEQUENCE: 690
NDCGPEMDES IACY                                                             14

SEQ ID NO: 691              moltype = AA   length = 14
FEATURE                     Location/Qualifiers
REGION                      1..14
                            note = Description of Artificial Sequence: Synthetic peptide
source                      1..14
                            mol_type = protein
                            organism = synthetic construct
SEQUENCE: 691
VYCGPEFDEY LACA                                                             14

SEQ ID NO: 692              moltype = AA   length = 14
FEATURE                     Location/Qualifiers
```

```
REGION                  1..14
                        note = Description of Artificial Sequence: Synthetic peptide
source                  1..14
                        mol_type = protein
                        organism = synthetic construct
SEQUENCE: 692
VICGPEFDES ANCD                                                              14

SEQ ID NO: 693          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 693
LTCWPDWEED FFCN                                                              14

SEQ ID NO: 694          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 694
FYCGPEQEEI NYCY                                                              14

SEQ ID NO: 695          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 695
TYCGPELEEF FLCY                                                              14

SEQ ID NO: 696          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 696
PDCGPELDES VACH                                                              14

SEQ ID NO: 697          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 697
NDCGPEFEEI IFCV                                                              14

SEQ ID NO: 698          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 698
YICGPEFDES FYCN                                                              14

SEQ ID NO: 699          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 699
HACGPELDES LLCN                                                              14

SEQ ID NO: 700          moltype = AA  length = 14
```

-continued

| FEATURE | Location/Qualifiers |
| --- | --- |
| REGION | 1..14 |
| | note = Description of Artificial Sequence: Synthetic peptide |
| source | 1..14 |
| | mol_type = protein |
| | organism = synthetic construct |

SEQUENCE: 700
YYCGPEWEEA VLCA                                                       14

| SEQ ID NO: 701 | moltype = AA  length = 14 |
| --- | --- |
| FEATURE | Location/Qualifiers |
| REGION | 1..14 |
| | note = Description of Artificial Sequence: Synthetic peptide |
| source | 1..14 |
| | mol_type = protein |
| | organism = synthetic construct |

SEQUENCE: 701
AFCGPEVEEY DLCN                                                       14

| SEQ ID NO: 702 | moltype = AA  length = 14 |
| --- | --- |
| FEATURE | Location/Qualifiers |
| REGION | 1..14 |
| | note = Description of Artificial Sequence: Synthetic peptide |
| source | 1..14 |
| | mol_type = protein |
| | organism = synthetic construct |

SEQUENCE: 702
YNCGPEFDES VACS                                                       14

| SEQ ID NO: 703 | moltype = AA  length = 14 |
| --- | --- |
| FEATURE | Location/Qualifiers |
| REGION | 1..14 |
| | note = Description of Artificial Sequence: Synthetic peptide |
| source | 1..14 |
| | mol_type = protein |
| | organism = synthetic construct |

SEQUENCE: 703
YLCGPEVEDD TLCA                                                       14

| SEQ ID NO: 704 | moltype = AA  length = 14 |
| --- | --- |
| FEATURE | Location/Qualifiers |
| REGION | 1..14 |
| | note = Description of Artificial Sequence: Synthetic peptide |
| source | 1..14 |
| | mol_type = protein |
| | organism = synthetic construct |

SEQUENCE: 704
AVCGPEFDES VNCD                                                       14

| SEQ ID NO: 705 | moltype = AA  length = 14 |
| --- | --- |
| FEATURE | Location/Qualifiers |
| REGION | 1..14 |
| | note = Description of Artificial Sequence: Synthetic peptide |
| source | 1..14 |
| | mol_type = protein |
| | organism = synthetic construct |

SEQUENCE: 705
NYCGPEWEVY SLCP                                                       14

| SEQ ID NO: 706 | moltype = AA  length = 14 |
| --- | --- |
| FEATURE | Location/Qualifiers |
| REGION | 1..14 |
| | note = Description of Artificial Sequence: Synthetic peptide |
| source | 1..14 |
| | mol_type = protein |
| | organism = synthetic construct |

SEQUENCE: 706
DFCGPEVEED TYCH                                                       14

| SEQ ID NO: 707 | moltype = AA  length = 14 |
| --- | --- |
| FEATURE | Location/Qualifiers |
| REGION | 1..14 |
| | note = Description of Artificial Sequence: Synthetic peptide |
| source | 1..14 |
| | mol_type = protein |
| | organism = synthetic construct |

SEQUENCE: 707
ISCGPEYEWD YACN                                                       14

-continued

```
SEQ ID NO: 708         moltype = AA  length = 14
FEATURE                Location/Qualifiers
REGION                 1..14
                       note = Description of Artificial Sequence: Synthetic peptide
source                 1..14
                       mol_type = protein
                       organism = synthetic construct
SEQUENCE: 708
VNCGPELDES IICY                                              14

SEQ ID NO: 709         moltype = AA  length = 14
FEATURE                Location/Qualifiers
REGION                 1..14
                       note = Description of Artificial Sequence: Synthetic peptide
source                 1..14
                       mol_type = protein
                       organism = synthetic construct
SEQUENCE: 709
YDCGPEFDET APCY                                              14

SEQ ID NO: 710         moltype = AA  length = 14
FEATURE                Location/Qualifiers
REGION                 1..14
                       note = Description of Artificial Sequence: Synthetic peptide
source                 1..14
                       mol_type = protein
                       organism = synthetic construct
SEQUENCE: 710
YLCGPEFEEN FLCT                                              14

SEQ ID NO: 711         moltype = AA  length = 14
FEATURE                Location/Qualifiers
REGION                 1..14
                       note = Description of Artificial Sequence: Synthetic peptide
source                 1..14
                       mol_type = protein
                       organism = synthetic construct
SEQUENCE: 711
FDCGPEVDES VDCA                                              14

SEQ ID NO: 712         moltype = AA  length = 14
FEATURE                Location/Qualifiers
REGION                 1..14
                       note = Description of Artificial Sequence: Synthetic peptide
source                 1..14
                       mol_type = protein
                       organism = synthetic construct
SEQUENCE: 712
YDCGPEQEEI SFCN                                              14

SEQ ID NO: 713         moltype = AA  length = 14
FEATURE                Location/Qualifiers
REGION                 1..14
                       note = Description of Artificial Sequence: Synthetic peptide
source                 1..14
                       mol_type = protein
                       organism = synthetic construct
SEQUENCE: 713
IDCGPEIELY DDCF                                              14

SEQ ID NO: 714         moltype = AA  length = 14
FEATURE                Location/Qualifiers
REGION                 1..14
                       note = Description of Artificial Sequence: Synthetic peptide
source                 1..14
                       mol_type = protein
                       organism = synthetic construct
SEQUENCE: 714
TFCGPELDES VYCY                                              14

SEQ ID NO: 715         moltype = AA  length = 14
FEATURE                Location/Qualifiers
REGION                 1..14
                       note = Description of Artificial Sequence: Synthetic peptide
source                 1..14
                       mol_type = protein
                       organism = synthetic construct
SEQUENCE: 715
FFCGPEIDES NACV                                              14
```

```
SEQ ID NO: 716        moltype = AA   length = 14
FEATURE               Location/Qualifiers
REGION                1..14
                      note = Description of Artificial Sequence: Synthetic peptide
source                1..14
                      mol_type = protein
                      organism = synthetic construct
SEQUENCE: 716
YHCWPDWEPI YICI                                                        14

SEQ ID NO: 717        moltype = AA   length = 14
FEATURE               Location/Qualifiers
REGION                1..14
                      note = Description of Artificial Sequence: Synthetic peptide
source                1..14
                      mol_type = protein
                      organism = synthetic construct
SEQUENCE: 717
AICGPEYEED HYCY                                                        14

SEQ ID NO: 718        moltype = AA   length = 14
FEATURE               Location/Qualifiers
REGION                1..14
                      note = Description of Artificial Sequence: Synthetic peptide
source                1..14
                      mol_type = protein
                      organism = synthetic construct
SEQUENCE: 718
PLCGPDGFEN YNCF                                                        14

SEQ ID NO: 719        moltype = AA   length = 14
FEATURE               Location/Qualifiers
REGION                1..14
                      note = Description of Artificial Sequence: Synthetic peptide
source                1..14
                      mol_type = protein
                      organism = synthetic construct
SEQUENCE: 719
FPCWPDWEWD NNCH                                                        14

SEQ ID NO: 720        moltype = AA   length = 14
FEATURE               Location/Qualifiers
REGION                1..14
                      note = Description of Artificial Sequence: Synthetic peptide
source                1..14
                      mol_type = protein
                      organism = synthetic construct
SEQUENCE: 720
VDCGPDGDEL AACH                                                        14

SEQ ID NO: 721        moltype = AA   length = 14
FEATURE               Location/Qualifiers
REGION                1..14
                      note = Description of Artificial Sequence: Synthetic peptide
source                1..14
                      mol_type = protein
                      organism = synthetic construct
SEQUENCE: 721
VDCWPDWEEY YSCD                                                        14

SEQ ID NO: 722        moltype = AA   length = 14
FEATURE               Location/Qualifiers
REGION                1..14
                      note = Description of Artificial Sequence: Synthetic peptide
source                1..14
                      mol_type = protein
                      organism = synthetic construct
SEQUENCE: 722
VYCGPEYDES YDCT                                                        14

SEQ ID NO: 723        moltype = AA   length = 14
FEATURE               Location/Qualifiers
REGION                1..14
                      note = Description of Artificial Sequence: Synthetic peptide
source                1..14
                      mol_type = protein
                      organism = synthetic construct
SEQUENCE: 723
```

-continued

```
NLCGPEWENF ADCF                                                    14

SEQ ID NO: 724          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 724
YLCGPELEVF FVCD                                                    14

SEQ ID NO: 725          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 725
IFCGPELEDY SICF                                                    14

SEQ ID NO: 726          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 726
DYCGPELEQY DLCF                                                    14

SEQ ID NO: 727          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 727
LLCGPVNEDP LDCY                                                    14

SEQ ID NO: 728          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 728
IDCGPEFDES VFCY                                                    14

SEQ ID NO: 729          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 729
IICGPEVEEI DICS                                                    14

SEQ ID NO: 730          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 730
IACWPDWEDY SSCP                                                    14

SEQ ID NO: 731          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
```

-continued

```
SEQUENCE: 731
YYCGPEVEDI NDCI                                                              14

SEQ ID NO: 732           moltype = AA  length = 14
FEATURE                  Location/Qualifiers
REGION                   1..14
                         note = Description of Artificial Sequence: Synthetic peptide
source                   1..14
                         mol_type = protein
                         organism = synthetic construct
SEQUENCE: 732
NICGPEMDES IDCI                                                              14

SEQ ID NO: 733           moltype = AA  length = 14
FEATURE                  Location/Qualifiers
REGION                   1..14
                         note = Description of Artificial Sequence: Synthetic peptide
source                   1..14
                         mol_type = protein
                         organism = synthetic construct
SEQUENCE: 733
FDCWPDWEEL VSCY                                                              14

SEQ ID NO: 734           moltype = AA  length = 14
FEATURE                  Location/Qualifiers
REGION                   1..14
                         note = Description of Artificial Sequence: Synthetic peptide
source                   1..14
                         mol_type = protein
                         organism = synthetic construct
SEQUENCE: 734
YFCGPEWEDH FFCD                                                              14

SEQ ID NO: 735           moltype = AA  length = 14
FEATURE                  Location/Qualifiers
REGION                   1..14
                         note = Description of Artificial Sequence: Synthetic peptide
source                   1..14
                         mol_type = protein
                         organism = synthetic construct
SEQUENCE: 735
TYCGPEFEED SYCD                                                              14

SEQ ID NO: 736           moltype = AA  length = 14
FEATURE                  Location/Qualifiers
REGION                   1..14
                         note = Description of Artificial Sequence: Synthetic peptide
source                   1..14
                         mol_type = protein
                         organism = synthetic construct
SEQUENCE: 736
NLCGPEVELI DICS                                                             14

SEQ ID NO: 737           moltype = AA  length = 14
FEATURE                  Location/Qualifiers
REGION                   1..14
                         note = Description of Artificial Sequence: Synthetic peptide
source                   1..14
                         mol_type = protein
                         organism = synthetic construct
SEQUENCE: 737
DNCGPEWEEV YLCN                                                             14

SEQ ID NO: 738           moltype = AA  length = 14
FEATURE                  Location/Qualifiers
REGION                   1..14
                         note = Description of Artificial Sequence: Synthetic peptide
source                   1..14
                         mol_type = protein
                         organism = synthetic construct
SEQUENCE: 738
FLCGPEFDES DLCF                                                             14

SEQ ID NO: 739           moltype = AA  length = 14
FEATURE                  Location/Qualifiers
REGION                   1..14
                         note = Description of Artificial Sequence: Synthetic peptide
source                   1..14
                         mol_type = protein
```

```
                              organism = synthetic construct
SEQUENCE: 739
HICGPEQDES IGCT                                              14

SEQ ID NO: 740          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 740
FDCWPDWEDN SYCD                                              14

SEQ ID NO: 741          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 741
TACGPEWEFD FNCD                                              14

SEQ ID NO: 742          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 742
HHCWPDWEDY STCP                                              14

SEQ ID NO: 743          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 743
YYCGPEFDES VNCF                                              14

SEQ ID NO: 744          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 744
LHCWPDWEEI DICD                                              14

SEQ ID NO: 745          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 745
DICGPDGQED FVCS                                              14

SEQ ID NO: 746          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 746
DVCWPDWEVN YFCD                                              14

SEQ ID NO: 747          moltype = AA  length = 14
FEATURE                 Location/Qualifiers
REGION                  1..14
                        note = Description of Artificial Sequence: Synthetic peptide
source                  1..14
```

```
                          mol_type = protein
                          organism = synthetic construct
SEQUENCE: 747
VNCGPEMDES IDCA                                                    14

SEQ ID NO: 748           moltype = AA  length = 14
FEATURE                  Location/Qualifiers
REGION                   1..14
                         note = Description of Artificial Sequence: Synthetic peptide
source                   1..14
                         mol_type = protein
                         organism = synthetic construct
SEQUENCE: 748
DNCGPEFDEA TVCN                                                    14

SEQ ID NO: 749           moltype = AA  length = 14
FEATURE                  Location/Qualifiers
REGION                   1..14
                         note = Description of Artificial Sequence: Synthetic peptide
source                   1..14
                         mol_type = protein
                         organism = synthetic construct
SEQUENCE: 749
DLCGPEFEEV HNCN                                                    14

SEQ ID NO: 750           moltype = AA  length = 14
FEATURE                  Location/Qualifiers
REGION                   1..14
                         note = Description of Artificial Sequence: Synthetic peptide
source                   1..14
                         mol_type = protein
                         organism = synthetic construct
SEQUENCE: 750
VNCGPEFDES SYCF                                                    14

SEQ ID NO: 751           moltype = AA  length = 14
FEATURE                  Location/Qualifiers
REGION                   1..14
                         note = Description of Artificial Sequence: Synthetic peptide
source                   1..14
                         mol_type = protein
                         organism = synthetic construct
SEQUENCE: 751
NICWPDWEED NFCS                                                    14

SEQ ID NO: 752           moltype = AA  length = 14
FEATURE                  Location/Qualifiers
REGION                   1..14
                         note = Description of Artificial Sequence: Synthetic peptide
source                   1..14
                         mol_type = protein
                         organism = synthetic construct
SEQUENCE: 752
FVCGPEWEVY DDCD                                                    14

SEQ ID NO: 753           moltype = AA  length = 14
FEATURE                  Location/Qualifiers
REGION                   1..14
                         note = Description of Artificial Sequence: Synthetic peptide
source                   1..14
                         mol_type = protein
                         organism = synthetic construct
SEQUENCE: 753
AYCGPELEVV HLCV                                                    14

SEQ ID NO: 754           moltype = AA  length = 14
FEATURE                  Location/Qualifiers
REGION                   1..14
                         note = Description of Artificial Sequence: Synthetic peptide
source                   1..14
                         mol_type = protein
                         organism = synthetic construct
SEQUENCE: 754
PFCGPEMDET IDCY                                                    14

SEQ ID NO: 755           moltype = AA  length = 14
FEATURE                  Location/Qualifiers
REGION                   1..14
                         note = Description of Artificial Sequence: Synthetic peptide
```

-continued

```
source                    1..14
                          mol_type = protein
                          organism = synthetic construct
SEQUENCE: 755
LLCGPVMEDV FACY                                              14

SEQ ID NO: 756            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 756
DLCGPEFDES TNCY                                              14

SEQ ID NO: 757            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 757
HDCGPEMEEY YLCP                                              14

SEQ ID NO: 758            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 758
TDCGPEYDES IICP                                              14

SEQ ID NO: 759            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 759
VLCWPDWEDY ADCN                                              14

SEQ ID NO: 760            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 760
NDCGPELDES LTCD                                              14

SEQ ID NO: 761            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 761
IYCGPELDES IACY                                              14

SEQ ID NO: 762            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 762
NYCGPEVEEF NFCH                                              14

SEQ ID NO: 763            moltype = AA  length = 14
FEATURE                   Location/Qualifiers
REGION                    1..14
```

-continued

```
                        note = Description of Artificial Sequence: Synthetic peptide
source                  1..14
                        mol_type = protein
                        organism = synthetic construct
SEQUENCE: 763
DVCGPEIEEY SFCI                                                        14

SEQ ID NO: 764          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 764
DLCGPEVEEI TDCA                                                        14

SEQ ID NO: 765          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 765
HDCGPEFDES VFCI                                                        14

SEQ ID NO: 766          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 766
PLCGPVLEED IYCY                                                        14

SEQ ID NO: 767          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 767
DLCGPEFEDI IDCN                                                        14

SEQ ID NO: 768          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 768
DYCGPEVEVP SNCN                                                        14

SEQ ID NO: 769          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 769
IICGPELDES TACD                                                        14

SEQ ID NO: 770          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 770
DHCGPEFDES VNCD                                                        14

SEQ ID NO: 771          moltype = AA  length = 14
FEATURE                 Location/Qualifiers
```

```
REGION                    1..14
                          note = Description of Artificial Sequence: Synthetic peptide
source                    1..14
                          mol_type = protein
                          organism = synthetic construct
SEQUENCE: 771
FDCGPEFDES LYCS                                                                     14

SEQ ID NO: 772            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 772
FACWPDWEEV YICY                                                                     14

SEQ ID NO: 773            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 773
LYCGPEFDES LDCS                                                                     14

SEQ ID NO: 774            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 774
DLCGPELEEA FLCA                                                                     14

SEQ ID NO: 775            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 775
FACGPELDET LTCL                                                                     14

SEQ ID NO: 776            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 776
FDCGPEVEEI SNCD                                                                     14

SEQ ID NO: 777            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 777
VHCGPELEYP FDCN                                                                     14

SEQ ID NO: 778            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 778
AYCGPEFEEH TTCN                                                                     14

SEQ ID NO: 779            moltype = AA  length = 14
```

-continued

| FEATURE | Location/Qualifiers |
|---|---|
| REGION | 1..14 |
| | note = Description of Artificial Sequence: Synthetic peptide |
| source | 1..14 |
| | mol_type = protein |
| | organism = synthetic construct |

SEQUENCE: 779
LYCGPVSEQF TFCI                                                          14

| SEQ ID NO: 780 | moltype = AA  length = 14 |
|---|---|
| FEATURE | Location/Qualifiers |
| REGION | 1..14 |
| | note = Description of Artificial Sequence: Synthetic peptide |
| source | 1..14 |
| | mol_type = protein |
| | organism = synthetic construct |

SEQUENCE: 780
DYCGPELDES YDCN                                                          14

| SEQ ID NO: 781 | moltype = AA  length = 14 |
|---|---|
| FEATURE | Location/Qualifiers |
| REGION | 1..14 |
| | note = Description of Artificial Sequence: Synthetic peptide |
| source | 1..14 |
| | mol_type = protein |
| | organism = synthetic construct |

SEQUENCE: 781
FYCGPEWEEF DVCI                                                          14

| SEQ ID NO: 782 | moltype = AA  length = 14 |
|---|---|
| FEATURE | Location/Qualifiers |
| REGION | 1..14 |
| | note = Description of Artificial Sequence: Synthetic peptide |
| source | 1..14 |
| | mol_type = protein |
| | organism = synthetic construct |

SEQUENCE: 782
FTCGPEVEEY DHCI                                                          14

| SEQ ID NO: 783 | moltype = AA  length = 14 |
|---|---|
| FEATURE | Location/Qualifiers |
| REGION | 1..14 |
| | note = Description of Artificial Sequence: Synthetic peptide |
| source | 1..14 |
| | mol_type = protein |
| | organism = synthetic construct |

SEQUENCE: 783
YNCGPEFDES VTCF                                                          14

| SEQ ID NO: 784 | moltype = AA  length = 14 |
|---|---|
| FEATURE | Location/Qualifiers |
| REGION | 1..14 |
| | note = Description of Artificial Sequence: Synthetic peptide |
| source | 1..14 |
| | mol_type = protein |
| | organism = synthetic construct |

SEQUENCE: 784
AVCGPENDES NSCA                                                          14

| SEQ ID NO: 785 | moltype = AA  length = 14 |
|---|---|
| FEATURE | Location/Qualifiers |
| REGION | 1..14 |
| | note = Description of Artificial Sequence: Synthetic peptide |
| source | 1..14 |
| | mol_type = protein |
| | organism = synthetic construct |

SEQUENCE: 785
IYCWPDWEVP NDCA                                                          14

| SEQ ID NO: 786 | moltype = AA  length = 14 |
|---|---|
| FEATURE | Location/Qualifiers |
| REGION | 1..14 |
| | note = Description of Artificial Sequence: Synthetic peptide |
| source | 1..14 |
| | mol_type = protein |
| | organism = synthetic construct |

SEQUENCE: 786
YFCGPEFEEF FHCY                                                          14

-continued

```
SEQ ID NO: 787          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 787
YVCGPDGDES SFCD                                                    14

SEQ ID NO: 788          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 788
ISCGPEVEEF FYCY                                                    14

SEQ ID NO: 789          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 789
LICGPVFEED VYCD                                                    14

SEQ ID NO: 790          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 790
VYCGPEVEDH NYCA                                                    14

SEQ ID NO: 791          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 791
LDCGPEFEFV YICA                                                    14

SEQ ID NO: 792          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 792
YDCGPEFEED LPCI                                                    14

SEQ ID NO: 793          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 793
DVCGPEVEED YYCD                                                    14

SEQ ID NO: 794          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 794
NDCWPDWEYD NVCV                                                    14
```

```
SEQ ID NO: 795            moltype = AA   length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 795
DLCGPEFEVA NDCN                                                          14

SEQ ID NO: 796            moltype = AA   length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 796
HDCGPELDES ISCN                                                          14

SEQ ID NO: 797            moltype = AA   length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 797
LDCWPDWEET THCD                                                          14

SEQ ID NO: 798            moltype = AA   length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 798
IICGPEVEED DYCL                                                          14

SEQ ID NO: 799            moltype = AA   length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 799
YYCWPDWEEV IICD                                                          14

SEQ ID NO: 800            moltype = AA   length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 800
FDCGPEIDEY TNCN                                                          14

SEQ ID NO: 801            moltype = AA   length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 801
ITCGPELDET INCD                                                          14

SEQ ID NO: 802            moltype = AA   length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 802
```

-continued

```
DSCGPEVEED IYCI                                                   14

SEQ ID NO: 803          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 803
YLCGPEFDES GNCH                                                   14

SEQ ID NO: 804          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 804
DNCGPELPED YFCD                                                   14

SEQ ID NO: 805          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 805
VLCGPEFEEV SNCN                                                   14

SEQ ID NO: 806          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 806
VDCWPDWEED IVCD                                                   14

SEQ ID NO: 807          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 807
VYCWPDWEDN FPCY                                                   14

SEQ ID NO: 808          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 808
DYCGPEVEEH FNCH                                                   14

SEQ ID NO: 809          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 809
ADCGPEIEED AYCY                                                   14

SEQ ID NO: 810          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
```

```
SEQUENCE: 810
ILCWPDWEDA TFCY                                                          14

SEQ ID NO: 811             moltype = AA  length = 14
FEATURE                    Location/Qualifiers
REGION                     1..14
                           note = Description of Artificial Sequence: Synthetic peptide
source                     1..14
                           mol_type = protein
                           organism = synthetic construct
SEQUENCE: 811
IHCWPDWEDF NICP                                                          14

SEQ ID NO: 812             moltype = AA  length = 14
FEATURE                    Location/Qualifiers
REGION                     1..14
                           note = Description of Artificial Sequence: Synthetic peptide
source                     1..14
                           mol_type = protein
                           organism = synthetic construct
SEQUENCE: 812
TICGPEVEDY NDCI                                                          14

SEQ ID NO: 813             moltype = AA  length = 14
FEATURE                    Location/Qualifiers
REGION                     1..14
                           note = Description of Artificial Sequence: Synthetic peptide
source                     1..14
                           mol_type = protein
                           organism = synthetic construct
SEQUENCE: 813
DDCGPELDES VACI                                                          14

SEQ ID NO: 814             moltype = AA  length = 14
FEATURE                    Location/Qualifiers
REGION                     1..14
                           note = Description of Artificial Sequence: Synthetic peptide
source                     1..14
                           mol_type = protein
                           organism = synthetic construct
SEQUENCE: 814
DDCWPDWEDH IFCF                                                          14

SEQ ID NO: 815             moltype = AA  length = 14
FEATURE                    Location/Qualifiers
REGION                     1..14
                           note = Description of Artificial Sequence: Synthetic peptide
source                     1..14
                           mol_type = protein
                           organism = synthetic construct
SEQUENCE: 815
VNCGPEVEEI IFCD                                                          14

SEQ ID NO: 816             moltype = AA  length = 14
FEATURE                    Location/Qualifiers
REGION                     1..14
                           note = Description of Artificial Sequence: Synthetic peptide
source                     1..14
                           mol_type = protein
                           organism = synthetic construct
SEQUENCE: 816
IFCWPDWEDD TVCI                                                          14

SEQ ID NO: 817             moltype = AA  length = 14
FEATURE                    Location/Qualifiers
REGION                     1..14
                           note = Description of Artificial Sequence: Synthetic peptide
source                     1..14
                           mol_type = protein
                           organism = synthetic construct
SEQUENCE: 817
IICGPEFEEI SDCL                                                          14

SEQ ID NO: 818             moltype = AA  length = 14
FEATURE                    Location/Qualifiers
REGION                     1..14
                           note = Description of Artificial Sequence: Synthetic peptide
source                     1..14
                           mol_type = protein
```

-continued

```
                            organism = synthetic construct
SEQUENCE: 818
FDCGPEVEEY NDCD                                                    14

SEQ ID NO: 819           moltype = AA  length = 14
FEATURE                  Location/Qualifiers
REGION                   1..14
                         note = Description of Artificial Sequence: Synthetic peptide
source                   1..14
                         mol_type = protein
                         organism = synthetic construct
SEQUENCE: 819
NDCGPELDET LYCI                                                    14

SEQ ID NO: 820           moltype = AA  length = 14
FEATURE                  Location/Qualifiers
REGION                   1..14
                         note = Description of Artificial Sequence: Synthetic peptide
source                   1..14
                         mol_type = protein
                         organism = synthetic construct
SEQUENCE: 820
AICGPELEED ISCN                                                    14

SEQ ID NO: 821           moltype = AA  length = 14
FEATURE                  Location/Qualifiers
REGION                   1..14
                         note = Description of Artificial Sequence: Synthetic peptide
source                   1..14
                         mol_type = protein
                         organism = synthetic construct
SEQUENCE: 821
HLCGPEFDES TNCY                                                    14

SEQ ID NO: 822           moltype = AA  length = 14
FEATURE                  Location/Qualifiers
REGION                   1..14
                         note = Description of Artificial Sequence: Synthetic peptide
source                   1..14
                         mol_type = protein
                         organism = synthetic construct
SEQUENCE: 822
SYCGPELDES VACI                                                    14

SEQ ID NO: 823           moltype = AA  length = 14
FEATURE                  Location/Qualifiers
REGION                   1..14
                         note = Description of Artificial Sequence: Synthetic peptide
source                   1..14
                         mol_type = protein
                         organism = synthetic construct
SEQUENCE: 823
LYCGPEFEQL ADCT                                                    14

SEQ ID NO: 824           moltype = AA  length = 14
FEATURE                  Location/Qualifiers
REGION                   1..14
                         note = Description of Artificial Sequence: Synthetic peptide
source                   1..14
                         mol_type = protein
                         organism = synthetic construct
SEQUENCE: 824
IDCGPELDES IACN                                                    14

SEQ ID NO: 825           moltype = AA  length = 14
FEATURE                  Location/Qualifiers
REGION                   1..14
                         note = Description of Artificial Sequence: Synthetic peptide
source                   1..14
                         mol_type = protein
                         organism = synthetic construct
SEQUENCE: 825
FDCGPDGQED LVCN                                                    14

SEQ ID NO: 826           moltype = AA  length = 14
FEATURE                  Location/Qualifiers
REGION                   1..14
                         note = Description of Artificial Sequence: Synthetic peptide
source                   1..14
```

```
                            mol_type = protein
                            organism = synthetic construct
SEQUENCE: 826
NLCGPEFEEF FDCY                                                          14

SEQ ID NO: 827              moltype = AA   length = 14
FEATURE                     Location/Qualifiers
REGION                      1..14
                            note = Description of Artificial Sequence: Synthetic peptide
source                      1..14
                            mol_type = protein
                            organism = synthetic construct
SEQUENCE: 827
SICGPELQED IVCP                                                          14

SEQ ID NO: 828              moltype = AA   length = 14
FEATURE                     Location/Qualifiers
REGION                      1..14
                            note = Description of Artificial Sequence: Synthetic peptide
source                      1..14
                            mol_type = protein
                            organism = synthetic construct
SEQUENCE: 828
NPCGPEYDES AHCD                                                          14

SEQ ID NO: 829              moltype = AA   length = 14
FEATURE                     Location/Qualifiers
REGION                      1..14
                            note = Description of Artificial Sequence: Synthetic peptide
source                      1..14
                            mol_type = protein
                            organism = synthetic construct
SEQUENCE: 829
YDCGPELDEY YNCN                                                          14

SEQ ID NO: 830              moltype = AA   length = 14
FEATURE                     Location/Qualifiers
REGION                      1..14
                            note = Description of Artificial Sequence: Synthetic peptide
source                      1..14
                            mol_type = protein
                            organism = synthetic construct
SEQUENCE: 830
VDCGPELDET IFCD                                                          14

SEQ ID NO: 831              moltype = AA   length = 14
FEATURE                     Location/Qualifiers
REGION                      1..14
                            note = Description of Artificial Sequence: Synthetic peptide
source                      1..14
                            mol_type = protein
                            organism = synthetic construct
SEQUENCE: 831
DNCGPELDES VTCT                                                          14

SEQ ID NO: 832              moltype = AA   length = 14
FEATURE                     Location/Qualifiers
REGION                      1..14
                            note = Description of Artificial Sequence: Synthetic peptide
source                      1..14
                            mol_type = protein
                            organism = synthetic construct
SEQUENCE: 832
VDCGPELDES SYCD                                                          14

SEQ ID NO: 833              moltype = AA   length = 14
FEATURE                     Location/Qualifiers
REGION                      1..14
                            note = Description of Artificial Sequence: Synthetic peptide
source                      1..14
                            mol_type = protein
                            organism = synthetic construct
SEQUENCE: 833
YYCGPEFEFI DFCF                                                          14

SEQ ID NO: 834              moltype = AA   length = 14
FEATURE                     Location/Qualifiers
REGION                      1..14
                            note = Description of Artificial Sequence: Synthetic peptide
```

```
source                    1..14
                          mol_type = protein
                          organism = synthetic construct
SEQUENCE: 834
YDCWPDWEVI TYCN                                                       14

SEQ ID NO: 835            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 835
FDCGPEIEED FFCV                                                       14

SEQ ID NO: 836            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 836
IFCWPDWDDI NFCD                                                       14

SEQ ID NO: 837            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 837
NFCGPELPED ITCY                                                       14

SEQ ID NO: 838            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 838
SLCGPEFEEY YHCL                                                       14

SEQ ID NO: 839            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 839
ASCGPELDES LDCL                                                       14

SEQ ID NO: 840            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 840
SFCGPEREWD LACY                                                       14

SEQ ID NO: 841            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 841
HLCGPEFEDV LDCI                                                       14

SEQ ID NO: 842            moltype = AA  length = 14
FEATURE                   Location/Qualifiers
REGION                    1..14
```

-continued

```
                              note = Description of Artificial Sequence: Synthetic peptide
source                        1..14
                              mol_type = protein
                              organism = synthetic construct
SEQUENCE: 842
LDCGPDGDEF YYCL                                                                14

SEQ ID NO: 843                moltype = AA  length = 14
FEATURE                       Location/Qualifiers
REGION                        1..14
                              note = Description of Artificial Sequence: Synthetic peptide
source                        1..14
                              mol_type = protein
                              organism = synthetic construct
SEQUENCE: 843
DNCWPDWEED IACT                                                                14

SEQ ID NO: 844                moltype = AA  length = 14
FEATURE                       Location/Qualifiers
REGION                        1..14
                              note = Description of Artificial Sequence: Synthetic peptide
source                        1..14
                              mol_type = protein
                              organism = synthetic construct SEQUENCE: 844
SDCGPELDET IHCI                                                                14

SEQ ID NO: 845                moltype = AA  length = 14
FEATURE                       Location/Qualifiers
REGION                        1..14
                              note = Description of Artificial Sequence: Synthetic peptide
source                        1..14
                              mol_type = protein
                              organism = synthetic construct
SEQUENCE: 845
NSCGPDGDES VDCL                                                                14

SEQ ID NO: 846                moltype = AA  length = 14
FEATURE                       Location/Qualifiers
REGION                        1..14
                              note = Description of Artificial Sequence: Synthetic peptide
source                        1..14
                              mol_type = protein
                              organism = synthetic construct
SEQUENCE: 846
DLCGPELDES TLCI                                                                14

SEQ ID NO: 847                moltype = AA  length = 14
FEATURE                       Location/Qualifiers
REGION                        1..14
                              note = Description of Artificial Sequence: Synthetic peptide
source                        1..14
                              mol_type = protein
                              organism = synthetic construct
SEQUENCE: 847
FDCGPESDES FNCY                                                                14

SEQ ID NO: 848                moltype = AA  length = 14
FEATURE                       Location/Qualifiers
REGION                        1..14
                              note = Description of Artificial Sequence: Synthetic peptide
source                        1..14
                              mol_type = protein
                              organism = synthetic construct
SEQUENCE: 848
DLCGPEFEED DICY                                                                14

SEQ ID NO: 849                moltype = AA  length = 14
FEATURE                       Location/Qualifiers
REGION                        1..14
                              note = Description of Artificial Sequence: Synthetic peptide
source                        1..14
                              mol_type = protein
                              organism = synthetic construct
SEQUENCE: 849
HACGPEFEED TYCF                                                                14

SEQ ID NO: 850                moltype = AA  length = 14
FEATURE                       Location/Qualifiers
```

```
REGION                    1..14
                          note = Description of Artificial Sequence: Synthetic peptide
source                    1..14
                          mol_type = protein
                          organism = synthetic construct
SEQUENCE: 850
SDCGPELDES VACI                                                              14

SEQ ID NO: 851            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct SEQUENCE: 851
IVCGPELPED YNCY                                                              14

SEQ ID NO: 852            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct SEQUENCE: 852
DLCGPEFDES FICF                                                              14

SEQ ID NO: 853            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct SEQUENCE: 853
YDCGPEFDET LTCN                                                              14

SEQ ID NO: 854            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct SEQUENCE: 854
YDCGPEVEEI VNCD                                                              14

SEQ ID NO: 855            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 855
VFCGPEIEDD HVCI                                                              14

SEQ ID NO: 856            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct SEQUENCE: 856
FICGPEWEDD YACS                                                              14

SEQ ID NO: 857            moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 857
NFCGPEFDES VGCN                                                              14

SEQ ID NO: 858            moltype = AA  length = 14
```

-continued

| FEATURE | Location/Qualifiers |
|---|---|
| REGION | 1..14 |
| | note = Description of Artificial Sequence: Synthetic peptide |
| source | 1..14 |
| | mol_type = protein |
| | organism = synthetic construct |

SEQUENCE: 858
NLCGPEVEEI LICD                                                              14

| SEQ ID NO: 859 | moltype = AA  length = 14 |
|---|---|
| FEATURE | Location/Qualifiers |
| REGION | 1..14 |
| | note = Description of Artificial Sequence: Synthetic peptide |
| source | 1..14 |
| | mol_type = protein |
| | organism = synthetic construct |

SEQUENCE: 859
DSCGPEVEEY DLCN                                                              14

| SEQ ID NO: 860 | moltype = AA  length = 14 |
|---|---|
| FEATURE | Location/Qualifiers |
| REGION | 1..14 |
| | note = Description of Artificial Sequence: Synthetic peptide |
| source | 1..14 |
| | mol_type = protein |
| | organism = synthetic construct |

SEQUENCE: 860
TLCGPEFEEI TDCN                                                              14

| SEQ ID NO: 861 | moltype = AA  length = 14 |
|---|---|
| FEATURE | Location/Qualifiers |
| REGION | 1..14 |
| | note = Description of Artificial Sequence: Synthetic peptide |
| source | 1..14 |
| | mol_type = protein |
| | organism = synthetic construct |

SEQUENCE: 861
TVCGPKMEMN STCD                                                              14

| SEQ ID NO: 862 | moltype = AA  length = 14 |
|---|---|
| FEATURE | Location/Qualifiers |
| REGION | 1..14 |
| | note = Description of Artificial Sequence: Synthetic peptide |
| source | 1..14 |
| | mol_type = protein |
| | organism = synthetic construct |

SEQUENCE: 862
VHCWPDWEDA VSCN                                                              14

| SEQ ID NO: 863 | moltype = AA  length = 14 |
|---|---|
| FEATURE | Location/Qualifiers |
| REGION | 1..14 |
| | note = Description of Artificial Sequence: Synthetic peptide |
| source | 1..14 |
| | mol_type = protein |
| | organism = synthetic construct |

SEQUENCE: 863
DLCGPDGNEL DFCF                                                              14

| SEQ ID NO: 864 | moltype = AA  length = 14 |
|---|---|
| FEATURE | Location/Qualifiers |
| REGION | 1..14 |
| | note = Description of Artificial Sequence: Synthetic peptide |
| source | 1..14 |
| | mol_type = protein |
| | organism = synthetic construct |

SEQUENCE: 864
DLCGPDGEEH YYCD                                                              14

| SEQ ID NO: 865 | moltype = AA  length = 14 |
|---|---|
| FEATURE | Location/Qualifiers |
| REGION | 1..14 |
| | note = Description of Artificial Sequence: Synthetic peptide |
| source | 1..14 |
| | mol_type = protein |
| | organism = synthetic construct |

SEQUENCE: 865
FNCGPEVEEI LLCT                                                              14

-continued

---

SEQ ID NO: 866        moltype = AA   length = 14
FEATURE               Location/Qualifiers
REGION                1..14
                      note = Description of Artificial Sequence: Synthetic peptide
source                1..14
                      mol_type = protein
                      organism = synthetic construct
SEQUENCE: 866
HYCGPEVENI NDCI                                                    14

SEQ ID NO: 867        moltype = AA   length = 14
FEATURE               Location/Qualifiers
REGION                1..14
                      note = Description of Artificial Sequence: Synthetic peptide
source                1..14
                      mol_type = protein
                      organism = synthetic construct
SEQUENCE: 867
IDCGPELDES VICD                                                    14

SEQ ID NO: 868        moltype = AA   length = 14
FEATURE               Location/Qualifiers
REGION                1..14
                      note = Description of Artificial Sequence: Synthetic peptide
source                1..14
                      mol_type = protein
                      organism = synthetic construct
SEQUENCE: 868
IFCGPEIEQP ALCY                                                    14

SEQ ID NO: 869        moltype = AA   length = 14
FEATURE               Location/Qualifiers
REGION                1..14
                      note = Description of Artificial Sequence: Synthetic peptide
source                1..14
                      mol_type = protein
                      organism = synthetic construct
SEQUENCE: 869
YDCGPEFQED LVCP                                                    14

SEQ ID NO: 870        moltype = AA   length = 14
FEATURE               Location/Qualifiers
REGION                1..14
                      note = Description of Artificial Sequence: Synthetic peptide
source                1..14
                      mol_type = protein
                      organism = synthetic construct
SEQUENCE: 870
HACWPDWEEP NYCD                                                    14

SEQ ID NO: 871        moltype = AA   length = 14
FEATURE               Location/Qualifiers
REGION                1..14
                      note = Description of Artificial Sequence: Synthetic peptide
source                1..14
                      mol_type = protein
                      organism = synthetic construct
SEQUENCE: 871
NVCWPDWEED YNCY                                                    14

SEQ ID NO: 872        moltype = AA   length = 14
FEATURE               Location/Qualifiers
REGION                1..14
                      note = Description of Artificial Sequence: Synthetic peptide
source                1..14
                      mol_type = protein
                      organism = synthetic construct
SEQUENCE: 872
SFCGQELGDN YDCI                                                    14

SEQ ID NO: 873        moltype = AA   length = 14
FEATURE               Location/Qualifiers
REGION                1..14
                      note = Description of Artificial Sequence: Synthetic peptide
source                1..14
                      mol_type = protein
                      organism = synthetic construct
SEQUENCE: 873
DDCGPELDET TVCY                                                    14

-continued

```
SEQ ID NO: 874          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 874
NFCGPEWEVA TLCL                                                       14

SEQ ID NO: 875          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 875
DLCGPEVEED TYCN                                                       14

SEQ ID NO: 876          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 876
ALCGPEVEQV DLCT                                                       14

SEQ ID NO: 877          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 877
DDCGPELDES VNCN                                                       14

SEQ ID NO: 878          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 878
IFCGPEFEQI IYCD                                                       14

SEQ ID NO: 879          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 879
SDCWPDWEEV YYCS                                                       14

SEQ ID NO: 880          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 880
FFCGPDGDEV AICD                                                       14

SEQ ID NO: 881          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 881
```

-continued

```
DDCWPDWEDD VYCY                                                    14

SEQ ID NO: 882          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 882
YDCGPEFDET VVCP                                                    14

SEQ ID NO: 883          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 883
SYCGPELDES VNCV                                                    14

SEQ ID NO: 884          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 884
AFCVSFQQSL PHCD                                                    14

SEQ ID NO: 885          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 885
VNCGPEVEEY FVCF                                                    14

SEQ ID NO: 886          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 886
TNCWPDWEED FACV                                                    14

SEQ ID NO: 887          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 887
DDCGPEFEEI ILCF                                                    14

SEQ ID NO: 888          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 888
NSCGPELEDY HLCP                                                    14

SEQ ID NO: 889          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
```

```
SEQUENCE: 889
IHCGPDSDGF DFCD                                                          14

SEQ ID NO: 890          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 890
FDCGPELEED HLCF                                                          14

SEQ ID NO: 891          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 891
TVCWPDFEEY ADCD                                                          14

SEQ ID NO: 892          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 892
YFCWPDWEEA ADCL                                                          14

SEQ ID NO: 893          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 893
VSCGPEFDES VDCI                                                          14

SEQ ID NO: 894          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 894
AVCGPELPED IVCY                                                          14

SEQ ID NO: 895          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 895
VLCGPEVEEY HLCA                                                          14

SEQ ID NO: 896          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 896
SLCWPDWEEV DNCF                                                          14

SEQ ID NO: 897          moltype = AA  length = 14
FEATURE                 Location/Qualifiers
REGION                  1..14
                        note = Description of Artificial Sequence: Synthetic peptide
source                  1..14
                        mol_type = protein
```

-continued organism = synthetic construct

```
SEQUENCE: 897
TICGPDGQED YNCH                                                          14

SEQ ID NO: 898              moltype = AA   length = 14
FEATURE                    Location/Qualifiers
REGION                     1..14
                           note = Description of Artificial Sequence: Synthetic peptide
source                     1..14
                           mol_type = protein
                           organism = synthetic construct
SEQUENCE: 898
FLCGPEGEPT YLCT                                                          14

SEQ ID NO: 899              moltype = AA   length = 14
FEATURE                    Location/Qualifiers
REGION                     1..14
                           note = Description of Artificial Sequence: Synthetic peptide
source                     1..14
                           mol_type = protein
                           organism = synthetic construct
SEQUENCE: 899
DDCWLEQHDI YVCA                                                          14

SEQ ID NO: 900              moltype = AA   length = 14
FEATURE                    Location/Qualifiers
REGION                     1..14
                           note = Description of Artificial Sequence: Synthetic peptide
source                     1..14
                           mol_type = protein
                           organism = synthetic construct
SEQUENCE: 900
IFCGPEVEEV AFCF                                                          14

SEQ ID NO: 901              moltype = AA   length = 14
FEATURE                    Location/Qualifiers
REGION                     1..14
                           note = Description of Artificial Sequence: Synthetic peptide
source                     1..14
                           mol_type = protein
                           organism = synthetic construct
SEQUENCE: 901
ALCGPEVEDD YDCL                                                          14

SEQ ID NO: 902              moltype = AA   length = 14
FEATURE                    Location/Qualifiers
REGION                     1..14
                           note = Description of Artificial Sequence: Synthetic peptide
source                     1..14
                           mol_type = protein
                           organism = synthetic construct
SEQUENCE: 902
DDCGPEIELY LTCA                                                          14

SEQ ID NO: 903              moltype = AA   length = 14
FEATURE                    Location/Qualifiers
REGION                     1..14
                           note = Description of Artificial Sequence: Synthetic peptide
source                     1..14
                           mol_type = protein
                           organism = synthetic construct
SEQUENCE: 903
TDCWPDWEDD SICD                                                          14

SEQ ID NO: 904              moltype = AA   length = 14
FEATURE                    Location/Qualifiers
REGION                     1..14
                           note = Description of Artificial Sequence: Synthetic peptide
source                     1..14
                           mol_type = protein
                           organism = synthetic construct
SEQUENCE: 904
SICGPELEEI FLCN                                                          14

SEQ ID NO: 905              moltype = AA   length = 14
FEATURE                    Location/Qualifiers
REGION                     1..14
                           note = Description of Artificial Sequence: Synthetic peptide
source                     1..14
```

-continued

```
                            mol_type = protein
                            organism = synthetic construct
SEQUENCE: 905
NDCGPELEED ILCF                                                          14

SEQ ID NO: 906              moltype = AA  length = 14
FEATURE                     Location/Qualifiers
REGION                      1..14
                            note = Description of Artificial Sequence: Synthetic peptide
source                      1..14
                            mol_type = protein
                            organism = synthetic construct
SEQUENCE: 906
DDCGPELDET YSCY                                                          14

SEQ ID NO: 907              moltype = AA  length = 14
FEATURE                     Location/Qualifiers
REGION                      1..14
                            note = Description of Artificial Sequence: Synthetic peptide
source                      1..14
                            mol_type = protein
                            organism = synthetic construct
SEQUENCE: 907
FVCGPEWEEI DLCI                                                          14

SEQ ID NO: 908              moltype = AA  length = 14
FEATURE                     Location/Qualifiers
REGION                      1..14
                            note = Description of Artificial Sequence: Synthetic peptide
source                      1..14
                            mol_type = protein
                            organism = synthetic construct
SEQUENCE: 908
YDCGPELDES LSCP                                                          14

SEQ ID NO: 909              moltype = AA  length = 14
FEATURE                     Location/Qualifiers
REGION                      1..14
                            note = Description of Artificial Sequence: Synthetic peptide
source                      1..14
                            mol_type = protein
                            organism = synthetic construct
SEQUENCE: 909
NLCGPELDES IICP                                                          14

SEQ ID NO: 910              moltype = AA  length = 14
FEATURE                     Location/Qualifiers
REGION                      1..14
                            note = Description of Artificial Sequence: Synthetic peptide
source                      1..14
                            mol_type = protein
                            organism = synthetic construct
SEQUENCE: 910
IDCWPDWEEF NNCF                                                          14

SEQ ID NO: 911              moltype = AA  length = 14
FEATURE                     Location/Qualifiers
REGION                      1..14
                            note = Description of Artificial Sequence: Synthetic peptide
source                      1..14
                            mol_type = protein
                            organism = synthetic construct
SEQUENCE: 911
AYCGPELEEH DYCY                                                          14

SEQ ID NO: 912              moltype = AA  length = 14
FEATURE                     Location/Qualifiers
REGION                      1..14
                            note = Description of Artificial Sequence: Synthetic peptide
source                      1..14
                            mol_type = protein
                            organism = synthetic construct
SEQUENCE: 912
DDCSPQFDQI DLCD                                                          14

SEQ ID NO: 913              moltype = AA  length = 14
FEATURE                     Location/Qualifiers
REGION                      1..14
                            note = Description of Artificial Sequence: Synthetic peptide
```

```
source                  1..14
                        mol_type = protein
                        organism = synthetic construct
SEQUENCE: 913
SYCGPESDES IYCY                                                    14

SEQ ID NO: 914          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 914
SLCGPEFQED APCN                                                    14

SEQ ID NO: 915          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 915
DACGPELDET THCD                                                    14

SEQ ID NO: 916          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 916
NDCGPEVEEV ADCF                                                    14

SEQ ID NO: 917          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 917
YICGPEFEQD YFCF                                                    14

SEQ ID NO: 918          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 918
TDCGPDGDET NYCF                                                    14

SEQ ID NO: 919          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 919
YDCGPEVDES VLCP                                                    14

SEQ ID NO: 920          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 920
IDCGPEFDES AYCT                                                    14

SEQ ID NO: 921          moltype = AA  length = 14
FEATURE                 Location/Qualifiers
REGION                  1..14
```

-continued

```
                        note = Description of Artificial Sequence: Synthetic peptide
source                  1..14
                        mol_type = protein
                        organism = synthetic construct
SEQUENCE: 921
FDCGPEFEEF FHCY                                                              14

SEQ ID NO: 922          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 922
FPCGPEIEEY DYCV                                                              14

SEQ ID NO: 923          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 923
ADCGPIFESI DICV                                                              14

SEQ ID NO: 924          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 924
ISCGPDLWPT DICT                                                              14

SEQ ID NO: 925          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 925
DDCGPDGDEV HTCN                                                              14

SEQ ID NO: 926          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 926
IDCWPDWEGS FACN                                                              14

SEQ ID NO: 927          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 927
LNCGPDGDET FYCD                                                              14

SEQ ID NO: 928          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 928
IHCGPELGAY ISCS                                                              14

SEQ ID NO: 929          moltype = AA  length = 14
FEATURE                 Location/Qualifiers
```

-continued

```
REGION                  1..14
                        note = Description of Artificial Sequence: Synthetic peptide
source                  1..14
                        mol_type = protein
                        organism = synthetic construct
SEQUENCE: 929
TICWPDWEED YFCY                                                        14

SEQ ID NO: 930          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 930
HSCLAQFDQD LVCI                                                        14

SEQ ID NO: 931          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 931
NNCASDLSED NSCI                                                        14

SEQ ID NO: 932          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 932
VNCWPDWEED VACN                                                        14

SEQ ID NO: 933          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 933
VYCGPELDES FYCF                                                        14

SEQ ID NO: 934          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 934
LFCGTVLDEF FDCD                                                        14

SEQ ID NO: 935          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 935
FDCGPELDES VSCA                                                        14

SEQ ID NO: 936          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 936
YYCGPEVEEN VYCI                                                        14

SEQ ID NO: 937          moltype = AA  length = 14
```

-continued

```
FEATURE               Location/Qualifiers
REGION                1..14
                      note = Description of Artificial Sequence: Synthetic peptide
source                1..14
                      mol_type = protein
                      organism = synthetic construct
SEQUENCE: 937
DYCGPELDDS TICH                                                          14

SEQ ID NO: 938        moltype = AA  length = 14
FEATURE               Location/Qualifiers
REGION                1..14
                      note = Description of Artificial Sequence: Synthetic peptide
source                1..14
                      mol_type = protein
                      organism = synthetic construct
SEQUENCE: 938
VFCGPQWAEA NACF                                                          14

SEQ ID NO: 939        moltype = AA  length = 14
FEATURE               Location/Qualifiers
REGION                1..14
                      note = Description of Artificial Sequence: Synthetic peptide
source                1..14
                      mol_type = protein
                      organism = synthetic construct
SEQUENCE: 939
FTCGPEYDES ITCP                                                          14

SEQ ID NO: 940        moltype = AA  length = 14
FEATURE               Location/Qualifiers
REGION                1..14
                      note = Description of Artificial Sequence: Synthetic peptide
source                1..14
                      mol_type = protein
                      organism = synthetic construct
SEQUENCE: 940
LNCGPVNDES SVCI                                                          14

SEQ ID NO: 941        moltype = AA  length = 14
FEATURE               Location/Qualifiers
REGION                1..14
                      note = Description of Artificial Sequence: Synthetic peptide
source                1..14
                      mol_type = protein
                      organism = synthetic construct
SEQUENCE: 941
AICWPDWEEF SDCH                                                          14

SEQ ID NO: 942        moltype = AA  length = 14
FEATURE               Location/Qualifiers
REGION                1..14
                      note = Description of Artificial Sequence: Synthetic peptide
source                1..14
                      mol_type = protein
                      organism = synthetic construct
SEQUENCE: 942
YYCGVDLGAN VYCY                                                          14

SEQ ID NO: 943        moltype = AA  length = 14
FEATURE               Location/Qualifiers
REGION                1..14
                      note = Description of Artificial Sequence: Synthetic peptide
source                1..14
                      mol_type = protein
                      organism = synthetic construct
SEQUENCE: 943
HYCGPEVEED YHCD                                                          14

SEQ ID NO: 944        moltype = AA  length = 14
FEATURE               Location/Qualifiers
REGION                1..14
                      note = Description of Artificial Sequence: Synthetic peptide
source                1..14
                      mol_type = protein
                      organism = synthetic construct
SEQUENCE: 944
NDCGSLQYDI PTCV                                                          14
```

-continued

```
SEQ ID NO: 945            moltype = AA   length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 945
YVCRPQLDVY HYCN                                                     14

SEQ ID NO: 946            moltype = AA   length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 946
HDCGPDGDES IICS                                                     14

SEQ ID NO: 947            moltype = AA   length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 947
FDCGPELDET IICP                                                     14

SEQ ID NO: 948            moltype = AA   length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 948
VDCGSDRGEN AACH                                                     14

SEQ ID NO: 949            moltype = AA   length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 949
NICLAQFNED PTCN                                                     14

SEQ ID NO: 950            moltype = AA   length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 950
TNCGSKSQVS DHCI                                                     14

SEQ ID NO: 951            moltype = AA   length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 951
NHCHPQFWEL TNCN                                                     14

SEQ ID NO: 952            moltype = AA   length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 952
LLCHPQGDLY HLCH                                                     14
```

-continued

```
SEQ ID NO: 953           moltype = AA  length = 14
FEATURE                  Location/Qualifiers
REGION                   1..14
                         note = Description of Artificial Sequence: Synthetic peptide
source                   1..14
                         mol_type = protein
                         organism = synthetic construct
SEQUENCE: 953
TNCDSKLEGD DNCF                                                            14

SEQ ID NO: 954           moltype = AA  length = 14
FEATURE                  Location/Qualifiers
REGION                   1..14
                         note = Description of Artificial Sequence: Synthetic peptide
source                   1..14
                         mol_type = protein
                         organism = synthetic construct
SEQUENCE: 954
NDCGPEMDES LLCD                                                            14

SEQ ID NO: 955           moltype = AA  length = 14
FEATURE                  Location/Qualifiers
REGION                   1..14
                         note = Description of Artificial Sequence: Synthetic peptide
source                   1..14
                         mol_type = protein
                         organism = synthetic construct
SEQUENCE: 955
FHCGPEVDES INCN                                                            14

SEQ ID NO: 956           moltype = AA  length = 14
FEATURE                  Location/Qualifiers
REGION                   1..14
                         note = Description of Artificial Sequence: Synthetic peptide
source                   1..14
                         mol_type = protein
                         organism = synthetic construct
SEQUENCE: 956
DFCGPDGDET YVCS                                                            14

SEQ ID NO: 957           moltype = AA  length = 14
FEATURE                  Location/Qualifiers
REGION                   1..14
                         note = Description of Artificial Sequence: Synthetic peptide
source                   1..14
                         mol_type = protein
                         organism = synthetic construct
SEQUENCE: 957
VSCGPQFDEN NTCN                                                            14

SEQ ID NO: 958           moltype = AA  length = 14
FEATURE                  Location/Qualifiers
REGION                   1..14
                         note = Description of Artificial Sequence: Synthetic peptide
source                   1..14
                         mol_type = protein
                         organism = synthetic construct
SEQUENCE: 958
VYCHLESEQF DICI                                                            14

SEQ ID NO: 959           moltype = AA  length = 14
FEATURE                  Location/Qualifiers
REGION                   1..14
                         note = Description of Artificial Sequence: Synthetic peptide
source                   1..14
                         mol_type = protein
                         organism = synthetic construct
SEQUENCE: 959
DDCGPEWEFV FFCD                                                            14

SEQ ID NO: 960           moltype = AA  length = 14
FEATURE                  Location/Qualifiers
REGION                   1..14
                         note = Description of Artificial Sequence: Synthetic peptide
source                   1..14
                         mol_type = protein
                         organism = synthetic construct
SEQUENCE: 960
```

-continued

```
YNCEQQQDED PSCI                                                                14

SEQ ID NO: 961          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 961
NTCGTEQHEF NGCL                                                                14

SEQ ID NO: 962          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 962
HPCQPGFEEV DYCV                                                                14

SEQ ID NO: 963          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 963
VACSRQLGED AYCN                                                                14

SEQ ID NO: 964          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 964
DICGAQEVHV YTCP                                                                14

SEQ ID NO: 965          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 965
FFCEGNLDAY LLCL                                                                14

SEQ ID NO: 966          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 966
YYCGPDGEEN IVCD                                                                14
```

ACTIVATED ANTIBODIES TARGETING PSMA AND EFFECTOR CELL ANTIGENS

CROSS-REFERENCE

The present application is a continuation of U.S. patent application Ser. No. 17/544,539, filed Dec. 7, 2021, now U.S. Pat. No. 11,555,078, which claims the benefit of U.S. Provisional Application No. 63/187,699, filed May 12, 2021, and U.S. Provisional Application No. 63/123,329, filed Dec. 9, 2020, each of which is incorporated herein by reference in its entirety.

SEQUENCE LISTING

The instant application contains a Sequence Listing which has been submitted electronically in XML format and is hereby incorporated by reference in its entirety. Said XML copy, created on Nov. 11, 2022, is named 52426-730_301SL.xml and is 1,248,426 bytes in size.

SUMMARY

Disclosed herein, in certain embodiments, are isolated polypeptides or polypeptide complexes according to Formula I:

$$A_2\text{-}A_1\text{-}L_1\text{-}P_1\text{—}H_1 \qquad \text{(Formula I)}$$

wherein: $A_1$ comprises a first antigen recognizing molecule that binds to an effector cell antigen; $P_1$ comprises a peptide that binds to $A_1$; $L_1$ comprises a linking moiety that connects $A_1$ to $P_1$ and is a substrate for a tumor specific protease; $H_1$ comprises a half-life extending molecule; and $A_2$ comprises a second antigen recognizing molecule that binds to prostate-specific membrane antigen (PSMA). In some embodiments, the first antigen recognizing molecule comprises an antibody or antibody fragment. In some embodiments, first antigen recognizing molecule comprises an antibody or antibody fragment that is human or humanized. In some embodiments, $L_1$ is bound to a N-terminus of the first antigen recognizing molecule. In some embodiments, $A_2$ is bound to a C-terminus of the first antigen recognizing molecule. In some embodiments, $L_1$ is bound to a C-terminus of the first antigen recognizing molecule. In some embodiments, $A_2$ is bound to a N-terminus of the first antigen recognizing molecule. In some embodiments, the antibody or antibody fragment comprises a single chain variable fragment, a single domain antibody, or a Fab fragment. In some embodiments, $A_1$ is the single chain variable fragment (scFv). In some embodiments, the scFv comprises a scFv heavy chain polypeptide and a scFv light chain polypeptide. In some embodiments, $A_1$ is the single domain antibody, In some embodiments, the antibody or antibody fragment comprises a single chain variable fragment (scFv), a heavy chain variable domain (VH domain), a light chain variable domain (VL domain), or a variable domain (VHH) of a camelid derived single domain antibody. In some embodiments, $A_1$ comprises an anti-CD3e single chain variable fragment. In some embodiments, $A_1$ comprises an anti-CD3e single chain variable fragment that has a $K_D$ binding of 1 µM or less to CD3 on CD3 expressing cells. In some embodiments, the effector cell antigen comprises CD3. In some embodiments, $A_1$ comprises a variable light chain and variable heavy chain each of which is capable of specifically binding to human CD3. In some embodiments, $A_1$ comprises complementary determining regions (CDRs) selected from the group consisting of muromonab-CD3 (OKT3), otelixizumab (TRX4), teplizumab (MGA031), visilizumab (Nuvion), SP34, X35, VIT3, BMA030 (BW264/56), CLB-T3/3, CRIS7, YTH12.5, F111-409, CLB-T3.4.2, TR-66, WT32, SPv-T3b, 11D8, XIII-141, XIII-46, XIII-87, 12F6, T3/RW2-8C8, T3/RW2-4B6, OKT3D, M-T301, SMC2, F101.01, UCHT-1, WT-31, 15865, 15865v12, 15865v16, and 15865v19. In some embodiments, the polypeptide or polypeptide complex of Formula I binds to an effector cell when $L_1$ is cleaved by the tumor specific protease. In some embodiments, the polypeptide or polypeptide complex of Formula I binds to an effector cell when $L_1$ is cleaved by the tumor specific protease and $A_1$ binds to the effector cell. In some embodiments, the effector cell is a T cell. In some embodiments, $A_1$ binds to a polypeptide that is part of a TCR-CD3 complex on the effector cell. In some embodiments, the polypeptide that is part of the TCR-CD3 complex is human CD3E. In some embodiments, the effector cell antigen comprises CD3, wherein the scFv comprises complementarity determining regions (CDRs): HC-CDR1, HC-CDR2, and HC-CDR3, wherein the HC-CDR1, the HC-CDR2, and the HC-CDR3 of the scFv comprise: HC-CDR1: SEQ ID NO: 1, HC-CDR2: SEQ ID NO: 2, and HC-CDR3: SEQ ID NO: 3; and the scFv comprises CDRs: LC-CDR1, LC-CDR2, and LC-CDR3, wherein the LC-CDR1, the LC-CDR2, and the LC-CDR3 of the scFv comprises: LC-CDR1: SEQ ID NO: 4, LC-CDR2: SEQ ID NO:5, and LC-CDR3: SEQ ID NO: 6. In some embodiments, the effector cell antigen comprises CD3, and the scFv comprises an amino acid sequence according to SEQ ID NO: 7. In some embodiments, second antigen recognizing molecule comprises an antibody or antibody fragment. In some embodiments, the antibody or antibody fragment thereof comprises a single chain variable fragment, a single domain antibody, or a Fab. In some embodiments, the antibody or antibody fragment thereof comprises a single chain variable fragment (scFv), a heavy chain variable domain (VH domain), a light chain variable domain (VL domain), or a variable domain (VHH) of a camelid derived single domain antibody. In some embodiments, the antibody or antibody fragment thereof is humanized or human. In some embodiments, $A_2$ is the Fab. In some embodiments, the Fab comprises (a) a Fab light chain polypeptide and (b) a Fab heavy chain polypeptide. In some embodiments, the Fab comprises complementarity determining regions (CDRs): HC-CDR1, HC-CDR2, and HC-CDR3, wherein the HC-CDR1, the HC-CDR2, and the HC-CDR3 of the Fab comprise: HC-CDR1: SEQ ID NO: 8, HC-CDR2: SEQ ID NO: 9, and HC-CDR3: SEQ ID NO: 10; and the Fab comprises CDRs: LC-CDR1, LC-CDR2, and LC-CDR3, wherein the LC-CDR1, the LC-CDR2, and the LC-CDR3 of the Fab comprise LC-CDR1: SEQ ID NO: 11, LC-CDR2: SEQ ID NO:12, and LC-CDR3: SEQ ID NO: 13. In some embodiments, the Fab light chain polypeptide comprises an amino acid sequence according to SEQ ID NO: 14. In some embodiments, the Fab heavy chain polypeptide comprises an amino acid sequence according to SEQ ID NO: 15. In some embodiments, the Fab light chain polypeptide of $A_2$ is bound to a C-terminus of the single chain variable fragment (scFv) of $A_1$. In some embodiments, the Fab heavy chain polypeptide of $A_2$ is bound to a C-terminus of the single chain variable fragment (scFv) $A_1$. In some embodiments, the Fab light chain polypeptide of $A_2$ is bound to a N-terminus of the single chain variable fragment (scFv) of $A_1$. In some embodiments, the Fab heavy chain polypeptide of $A_2$ is bound to a N-terminus of the single chain variable fragment (scFv) $A_1$. In some embodiments, the Fab heavy chain polypeptide of $A_2$ is bound to the scFv heavy chain polypeptide of $A_1$. In some embodiments, the Fab light chain polypeptide of $A_2$ is bound to the scFv heavy chain polypeptide of $A_1$. In some embodiments, the Fab heavy chain polypeptide of $A_2$ is bound to the scFv light chain polypeptide of $A_1$. In some embodiments, the Fab light chain polypeptide of $A_2$ is bound to the scFv light chain polypeptide of $A_1$. In some embodiments, $A_2$ further comprises $P_2$ and $L_2$, wherein $P_2$ comprises a peptide that binds to $A_2$; and $L_2$ comprises a linking moiety that connects $A_2$ to $P_2$ and is a substrate for a tumor specific protease. In some embodiments, the polypeptide or polypeptide complex is according to Formula Ia:

$$P_2\text{-}L_2\text{-}A_2\text{-}A_1\text{-}L_1\text{-}P_1\text{—}H_1 \qquad \text{(Formula Ia)}$$

In some embodiments, the Fab heavy chain polypeptide of $A_2$ is bound to the scFv heavy chain polypeptide of $A_1$ and $L_2$ is bound to the Fab light chain polypeptide of $A_2$. In some embodiments, the Fab light chain polypeptide of $A_2$ is bound to the scFv heavy chain polypeptide of $A_1$ and $L_2$ is bound to the Fab heavy chain polypeptide of $A_2$. In some embodiments, the Fab heavy chain polypeptide of $A_2$ is bound to the scFv light chain polypeptide of $A_1$ and $L_2$ is bound to the Fab light chain polypeptide of $A_2$. In some embodiments, the Fab light chain polypeptide of $A_2$ is bound to the scFv light chain polypeptide of $A_1$ and $L_2$ is bound to the Fab heavy chain polypeptide of $A_2$. In some embodiments, $P_1$ impairs binding of $A_1$ to the effector cell antigen. In some embodiments, $P_1$ is bound to $A_1$ through ionic interactions, electrostatic interactions, hydrophobic interactions, Pi-stacking interactions, and H-bonding interactions, or a combination thereof. In some embodiments, $P_1$ has less than 70% sequence homology to the effector cell antigen. In some embodiments, $P_2$ impairs binding of $A_2$ to PSMA. In some embodiments, $P_2$ is bound to $A_2$ through ionic interactions, electrostatic interactions, hydrophobic interactions, Pi-stacking interactions, and H-bonding interactions, or a combination thereof. In some embodiments, $P_2$ is bound to $A_2$ at or near an antigen binding site. In some embodiments, $P_2$ has less than 70% sequence homology to PSMA. In some embodiments, $P_1$ or $P_2$ comprises a peptide sequence of at least 10 amino acids in length. In some embodiments, $P_1$ or $P_2$ comprises a peptide sequence of at least 10 amino acids in length and no more than 20 amino acids in length. In some embodiments, $P_1$ or $P_2$ comprises a peptide sequence of at least 16 amino acids in length. In some embodiments, $P_1$ or $P_2$ comprises a peptide sequence of no more than 40 amino acids in length. In some embodiments, $P_1$ or $P_2$ comprises at least two cysteine amino acid residues. In some embodiments, $P_1$ or $P_2$ comprises a cyclic peptide or a linear peptide. In some embodiments, $P_1$ or $P_2$ comprises a cyclic peptide. In some embodiments, $P_1$ or $P_2$ comprises a linear peptide In some embodiments, $P_1$ comprises at least two cysteine amino acid residues. In some embodiments, $P_1$ comprises an amino acid sequence according to any one of SEQ ID NOs: 16-19 or 78. In some embodiments, $L_1$ is bound to a N-terminus of $A_1$. In some embodiments, $L_1$ is bound to a C-terminus of $A_1$. In some embodiments, $L_2$ is bound to a N-terminus of $A_2$. In some embodiments, $L_2$ is bound to a C-terminus of $A_2$. In some embodiments, $L_1$ or $L_2$ is a peptide sequence having at least 5 to no more than 50 amino acids. In some embodiments, $L_1$ or $L_2$ is a peptide sequence having at least 10 to no more than 30 amino acids. In some embodiments, $L_1$ or $L_2$ is a peptide sequence having at least 10 amino acids. In some embodiments, $L_1$ or $L_2$ is a peptide sequence having at least 18 amino acids. In some embodiments, $L_1$ or $L_2$ is a peptide sequence having at least 26 amino acids. In some embodiments, $L_1$ or $L_2$ has a formula comprising $(G_2S)_n$, wherein n is an integer from 1 to 3 (SEQ ID NO: 118). In some embodiments, $L_1$ has a formula selected from the group consisting of $(G_2S)_n$, $(GS)_n$, $(GSGGS)_n$(SEQ ID NO: 50), $(GGGS)_n$(SEQ ID NO: 51), $(GGGGS)_n$(SEQ ID NO: 52), and $(GSSGGS)_n$(SEQ ID NO: 53), wherein n is an integer of at least 1. In some embodiments, $P_1$ becomes unbound from $A_1$ when $L_1$ is cleaved by the tumor specific protease thereby exposing $A_1$ to the effector cell antigen. In some embodiments, $P_2$ becomes unbound from $A_2$ when $L_2$ is cleaved by the tumor specific protease thereby exposing $A_2$ to PSMA. In some embodiments, the tumor specific protease is selected from the group consisting of a matrix metalloprotease (MMP), serine protease, cysteine protease, threonine protease, and aspartic protease. In some embodiments, the matrix metalloprotease comprises MMP2, MMP7, MMP9, MMP13, or MMP14. In some embodiments, the serine protease comprises matriptase (MTSP1), urokinase, or hepsin. In some embodiments, $L_1$ or $L_2$ comprises a urokinase cleavable amino acid sequence, a matriptase cleavable amino acid sequence, a matrix metalloprotease cleavable amino acid sequence, or a legumain cleavable amino acid sequence. In some embodiments, $L_1$ or $L_2$ comprises an amino acid sequence according to SEQ ID NO: 23. In some embodiments, $L_1$ or $L_2$ comprises an amino acid sequence according to any one of SEQ ID NOs: 20-49. In some embodiments, $L_1$ or $L_2$ comprises an amino acid sequence of Linker 25 (ISSGLLSGRSDAG) (SEQ ID NO: 45), Linker 26 (AAGLLAPPGGLSGRSDAG) (SEQ ID NO: 46), Linker 27 (SPLGLSGRSDAG) (SEQ ID NO: 47), or Linker 28 (LSGRSDAGSPLGLAG) (SEQ ID NO: 48), or an amino acid sequence that has 1, 2, or 3 amino acid substitutions, additions, or deletions relative to the amino acid sequence of Linker 25, Linker 26, Linker 27, or Linker 28. In some embodiments, $H_1$ comprises a polymer. In some embodiments, the polymer is polyethylene glycol (PEG). In some embodiments, $H_1$ comprises albumin. In some embodiments, $H_1$ comprises an Fc domain. In some embodiments, the albumin is serum albumin. In some embodiments, the albumin is human serum albumin. In some embodiments, $H_1$ comprises a polypeptide, a ligand, or a small molecule. In some embodiments, the polypeptide, the ligand or the small molecule binds serum protein or a fragment thereof, a circulating immunoglobulin or a fragment thereof, or CD35/CR1. In some embodiments, the serum protein comprises a thyroxine-binding protein, a transthyretin, a 1-acid glycoprotein, a transferrin, transferrin receptor or a transferrin-binding portion thereof, a fibrinogen, or an albumin. In some embodiments, the circulating immunoglobulin molecule comprises IgG1, IgG2, IgG3, IgG4, sIgA, IgM or IgD. In some embodiments, the serum protein is albumin. In some embodiments, the polypeptide is an antibody. In some embodiments, the antibody comprises a single domain antibody, a single chain variable fragment, or a Fab. In some embodiments, the single domain antibody comprises a single domain antibody that binds to albumin. In some embodiments, the single domain antibody is a human or humanized antibody. In some embodiments, the single domain antibody is 645gH1gL1. In some embodiments, the single domain antibody is 645dsgH5gL4. In some embodiments, the single domain antibody is 23-13-A01-sc02. In some embodiments, the single domain antibody is A10m3 or a fragment thereof. In some embodiments, the single domain antibody is DOM7r-31. In some embodiments, the single domain antibody is DOM7h-11-15. In some embodiments, the single domain antibody is Alb-1, Alb-8, or Alb-23. In some embodiments, the single domain antibody is 10E. In some embodiments, the single domain antibody comprises complementarity determining regions (CDRs): HC-CDR1, HC-CDR2, and HC-CDR3, wherein the HC-CDR1, the HC-CDR2, and the HC-CDR3 of the single domain antibody comprise: HC-CDR1: SEQ ID NO: 54, HC-CDR2: SEQ ID NO: 55, and HC-CDR3: SEQ ID NO: 56. In some embodiments, the single domain antibody comprises complementarity determining regions (CDRs): HC-CDR1, HC-CDR2, and HC-CDR3, wherein the HC-CDR1, the HC-CDR2, and the HC-CDR3 of the single domain antibody comprise: HC-CDR1: SEQ ID NO: 58, HC-CDR2: SEQ ID NO: 59, and HC-CDR3: SEQ ID NO: 60. In some embodiments, the single domain antibody is SA21. In some embodiments, the polypeptide or polypeptide complex comprises a modified amino acid, a non-natural amino acid, a modified non-natural amino acid, or a combination thereof. In some embodiments, the modified amino acid or modified non-natural amino acid comprises a post-translational modification. In some embodiments, $H_1$ comprises a linking moiety ($L_3$) that connects $H_1$ to P. In some embodiments, $L_3$ is a peptide sequence having at least 5 to no more than 50 amino acids. In some embodiments, $L_3$ is a peptide sequence having at least 10 to no more than 30 amino acids. In some embodiments, $L_3$ is a peptide sequence having at least 10 amino acids. In some embodiments, $L_3$ is a peptide sequence having at least 18 amino acids. In some embodiments, $L_3$ is a peptide sequence having at least 26 amino acids. In some embodiments, $L_3$ has a formula selected from the group consisting of $(G_2S)_n$, $(GS)_n$, $(GSGGS)_n$(SEQ ID NO: 50), $(GGGS)_n$(SEQ ID NO: 51), $(GGGGS)_n$(SEQ ID NO: 52), and $(GSSGGS)_n$(SEQ ID NO: 53), wherein n is an integer of at least 1. In some embodiments, $L_3$ comprises an amino acid sequence according to SEQ ID NO: 22. In some embodiments, the polypeptide or polypeptide complex comprises an amino acid sequence with at least 95% sequence identity to SEQ ID NOs: 62-77. In some embodiments, the polypeptide or polypeptide complex comprises an amino acid sequence with at least 95% sequence identity to SEQ ID NO: 72. In some embodiments, the polypeptide or polypeptide complex comprises an amino acid sequence with at least 95% sequence identity to SEQ ID NO: 73. In some embodiments, the polypeptide or polypeptide complex comprises an amino acid sequence with at least 95% sequence identity to SEQ ID NO: 62 and SEQ ID NO: 63. In some embodiments, the polypeptide or polypeptide complex comprises an amino acid sequence with at least 95% sequence identity to SEQ ID NO: 64 and SEQ ID NO: 65. In some embodiments, the polypeptide or polypeptide complex comprises an amino acid sequence with at least 95% sequence identity to SEQ ID NO: 66 and SEQ ID NO: 67. In some embodiments, the polypeptide or polypeptide complex comprises an amino acid sequence with at least 95% sequence identity to SEQ ID NO: 68 and SEQ ID NO: 69. In some embodiments, the polypeptide or polypeptide complex comprises an amino acid sequence with at least 95% sequence identity to SEQ ID NO: 70 and SEQ ID NO: 71. In some embodiments, the polypeptide or polypeptide complex comprises an amino acid sequence with at least 95% sequence identity to SEQ ID NO: 72 and SEQ ID NO: 73. In some embodiments, the polypeptide or polypeptide complex comprises an amino acid sequence with at least 95% sequence identity to SEQ ID NO: 74 and SEQ ID NO: 75. In some embodiments, the polypeptide or polypeptide complex comprises an amino acid sequence with at least 95% sequence identity to SEQ ID NO: 76 and SEQ ID NO: 77.

Disclosed herein, in certain embodiments, are pharmaceutical compositions comprising: (a) the polypeptide or polypeptide complex described herein; and (b) a pharmaceutically acceptable excipient.

Disclosed herein, in certain embodiments, are isolated recombinant nucleic acid molecules encoding the polypeptide or polypeptide complex described herein.

Disclosed herein, in certain embodiments, are isolated polypeptides or polypeptide complexes according to Formula II:

$$L_{1a}\text{-}P_{1a}\text{—}H_{1a} \qquad \text{(Formula II)}$$

wherein: $L_{1a}$ comprises a tumor specific protease-cleaved linking moiety that when uncleaved connects Pia to a first antigen recognizing molecule that binds to an effector cell antigen and the first antigen recognizing molecule is connected to a second antigen recognizing molecule that binds to PSMA; $P_{1a}$ comprises a peptide that binds to the first antigen recognizing molecule when $L_{1a}$ is uncleaved; and $H_{1a}$ comprises a half-life extending molecule. In some embodiments, $P_{1a}$ when $L_{1a}$ is uncleaved impairs binding of the first antigen recognizing molecule to the effector cell antigen. In some embodiments, the first antigen recognizing molecule comprises an antibody or antibody fragment. In some embodiments, the effector cell antigen is an anti-CD3 effector cell antigen. In some embodiments, $P_{1a}$ has less than 70% sequence homology to the effector cell antigen. In some embodiments, $P_{1a}$ comprises a peptide sequence of at least 10 amino acids in length. In some embodiments, $P_{1a}$ comprises a peptide sequence of at least 10 amino acids in length and no more than 20 amino acids in length. In some embodiments, $P_{1a}$ comprises a peptide sequence of at least 16 amino acids in length. In some embodiments, $P_{1a}$ comprises a peptide sequence of no more than 40 amino acids in length. In some embodiments, $P_{1a}$ comprises at least two cysteine amino acid residues. In some embodiments, $P_{1a}$ comprises a cyclic peptide or a linear peptide. In some embodiments, $P_{1a}$ comprises a cyclic peptide. In some embodiments, $P_{1a}$ comprises a linear peptide. In some embodiments, $P_{1a}$ comprises an amino acid sequence selected from the group consisting of any one of SEQ ID NOs: 16-19. In some embodiments, $H_{1a}$ comprises a polymer. In some embodiments, the polymer is polyethylene glycol (PEG). In some embodiments, $H_{1a}$ comprises albumin. In some embodiments, $H_{1a}$comprises an Fc domain. In some embodiments, the albumin is serum albumin. In some embodiments, the albumin is human serum albumin. In some embodiments, $H_{1a}$ comprises a polypeptide, a ligand, or a small molecule. In some embodiments, the polypeptide, the ligand or the small molecule binds a serum protein or a fragment thereof, a circulating immunoglobulin or a fragment thereof, or CD35/CR1. In some embodiments, the serum protein comprises a thyroxine-binding protein, a transthyretin, a 1-acid glycoprotein, a transferrin, transferrin receptor or a transferrin-binding portion thereof, a fibrinogen, or an albumin. In some embodiments, the circulating immunoglobulin molecule comprises IgG1, IgG2, IgG3, IgG4, sIgA, IgM or IgD. In some embodiments, the serum protein is albumin. In some embodiments, the polypeptide is an antibody. In some embodiments, the antibody comprises a single domain antibody, a single chain variable fragment or a Fab. In some embodiments, the antibody comprises a single domain antibody that binds to albumin. In some embodiments, the antibody is a human or humanized antibody. In some embodiments, the single domain antibody is 645gH1gL1. In some embodiments, the single domain antibody is 645dsgH5gL4. In some embodiments, the single domain antibody is 23-13-A01-sc02. In some embodiments, the single domain antibody is A10m3 or a fragment thereof. In some embodiments, the single domain antibody is DOM7r-31. In some embodiments, the single domain antibody is DOM7h-11-15. In some embodiments, the single domain antibody is Alb-1, Alb-8, or Alb-23. In some embodiments, the single domain antibody is 10E. In some embodiments, the single domain antibody comprises complementarity determining regions (CDRs): HC-CDR1, HC-CDR2, and HC-CDR3, wherein the HC-CDR1, the HC-CDR2, and the HC-CDR3 of the single domain antibody comprise: HC-CDR1: SEQ ID NO: 54, HC-CDR2: SEQ ID NO: 55, and HC-CDR3: SEQ ID NO: 56. In some embodiments, the single domain antibody comprises complementarity determining regions (CDRs): HC-CDR1, HC-CDR2, and HC-CDR3, wherein the HC-CDR1, the HC-CDR2, and the HC-CDR3 of the single domain antibody comprise: HC-CDR1: SEQ ID NO: 58, HC-CDR2: SEQ ID NO: 59, and HC-CDR3: SEQ ID NO: 60. In some embodiments, the single domain antibody is SA21. In some embodiments, $H_{1a}$ comprises a linking moiety ($L_{1a}$) that connects $H_{1a}$ to $P_{1a}$. In some embodiments, Lia is a peptide sequence having at least 5 to no more than 50 amino acids. In some embodiments, Lia is a peptide sequence having at least 10 to no more than 30 amino acids. In some embodiments, $L_{1a}$ is a peptide sequence having at least 10 amino acids. In some embodiments, Lia is a peptide sequence having at least 18 amino acids. In some embodiments, $L_{1a}$ is a peptide sequence having at least 26 amino acids. In some embodiments, Lia has a formula selected from the group consisting of $(G_2S)_n$, $(GS)_n$, $(GSGGS)_n$(SEQ ID NO: 50), $(GGGS)_n$(SEQ ID NO: 51), $(GGGGS)_n$(SEQ ID NO: 52), and $(GSSGGS)_n$(SEQ ID NO: 53), wherein n is an integer of at least 1. In some embodiments, $L_{1a}$ comprises an amino acid sequence according to SEQ ID NO: 23. Disclosed herein some embodiments are polypeptide complexes comprising a structural arrangement according to the configuration shown in FIG. 1C, wherein the polypeptide complex comprises a single chain variable fragment (scFv) comprising a light chain variable domain and a heavy chain variable domain, wherein the scFv further comprises a peptide that impairs binding of the scFv to an effector cell antigen and the peptide is linked to the heavy chain variable domain of the scFv with a linking moiety that is a substrate for a tumor specific protease, and the peptide further comprises a half-life extending molecule; and a Fab or a Fab' that binds to prostate-specific membrane antigen (PSMA), wherein the Fab or Fab' comprises a Fab light chain polypeptide chain and a Fab heavy chain polypeptide chain, and wherein the Fab heavy chain polypeptide chain is linked to a C terminus of the light chain variable domain of the scFv. Disclosed herein in some embodiments are polypeptide complexes comprising a structural arrangement according to the configuration shown in FIG. 1D, wherein the polypeptide complex comprises a single chain variable fragment (scFv) comprising a light chain variable domain and a heavy chain variable domain, wherein the scFv further comprises a peptide that impairs binding of the scFv to an effector cell antigen and the peptide is linked to a N-terminus of the heavy chain variable domain of the scFv with a linking moiety that is a substrate for a tumor specific protease, and the peptide further comprises a half-life extending molecule; and a Fab or Fab' that binds to prostate-specific membrane antigen (PSMA), wherein the Fab or Fab' comprises a Fab light chain polypeptide and a Fab heavy chain polypeptide, wherein the Fab light chain polypeptide is linked to a C terminus of the light chain variable domain of the scFv.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIGS. 8A-8B illustrates polypeptide complex mediated 22Rv1 tumor cell killing in the presence of CD8+ T cells.

FIGS. 12A-12F illustrate anti-CD3 scFv binding by alanine scanning peptides of anti-CD3 scFv Peptide-A and Peptide-B as measured by ELISA.

US 12,617,865 B2

9

Figure 14A:
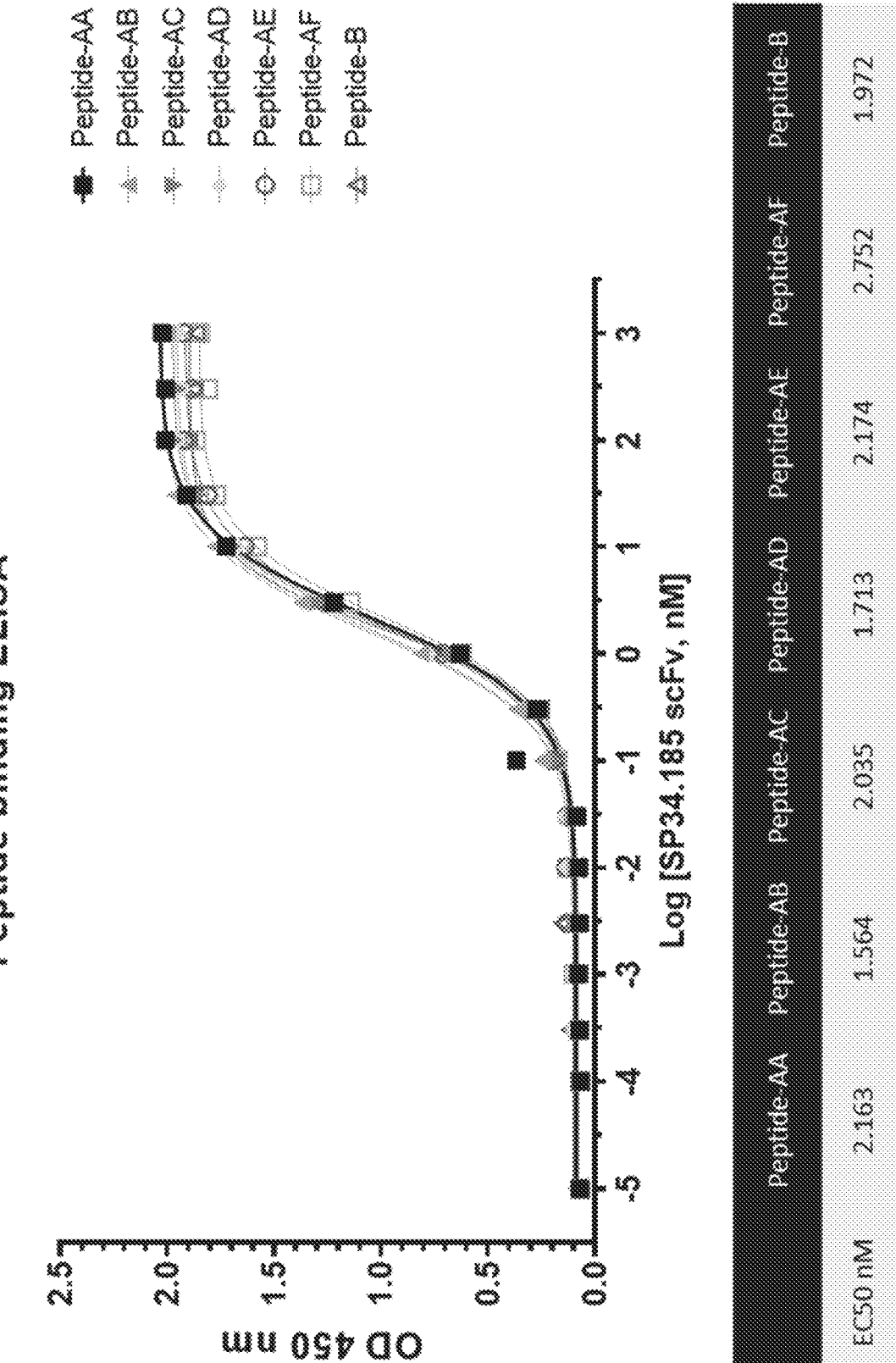
Figure 14B:
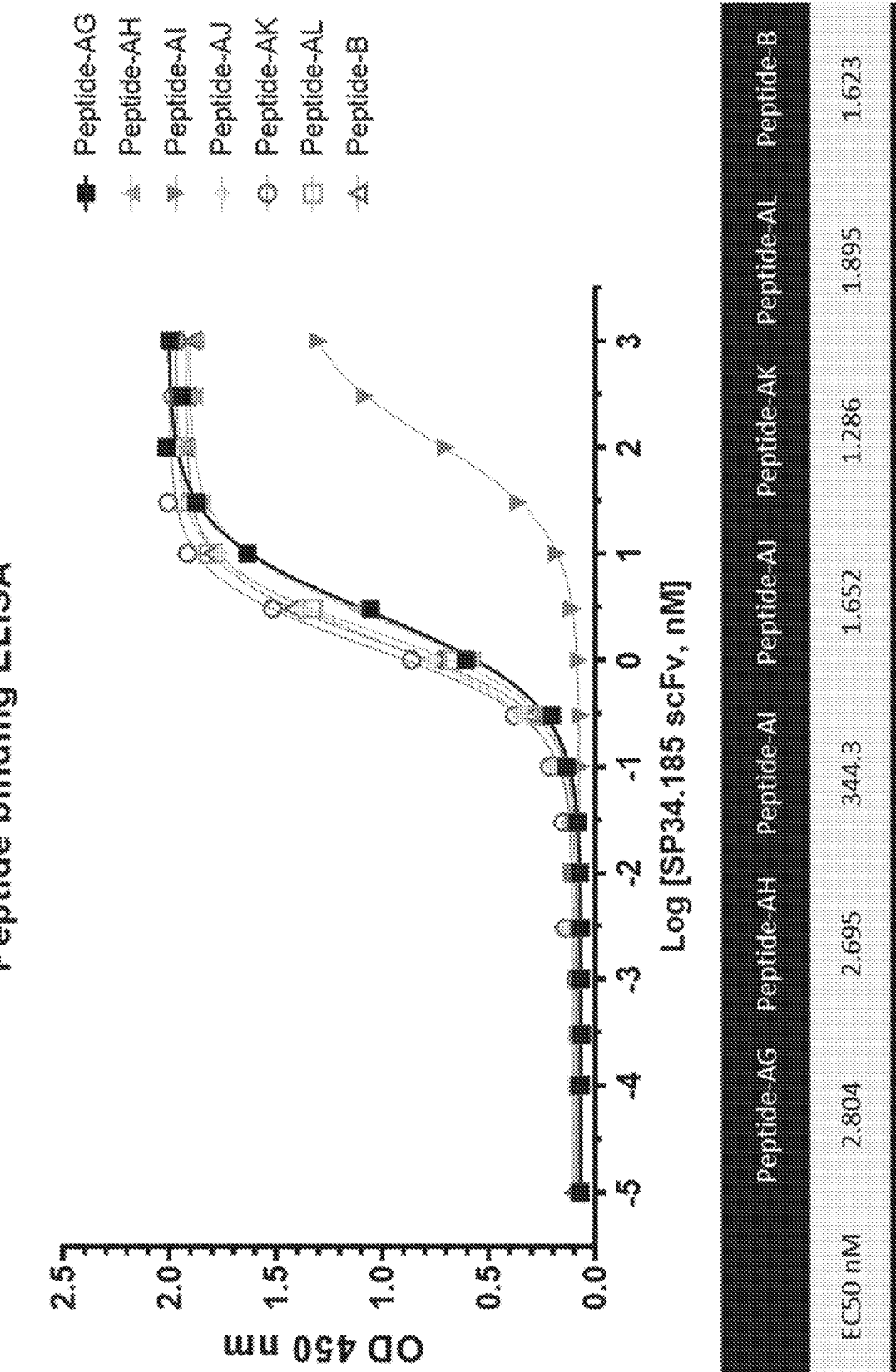

FIGS. 14A-14B illustrate anti-CD3 scFv binding by optimized anti-CD3 scFv Peptide-B sequences as measured by ELISA.

Figure 15A:
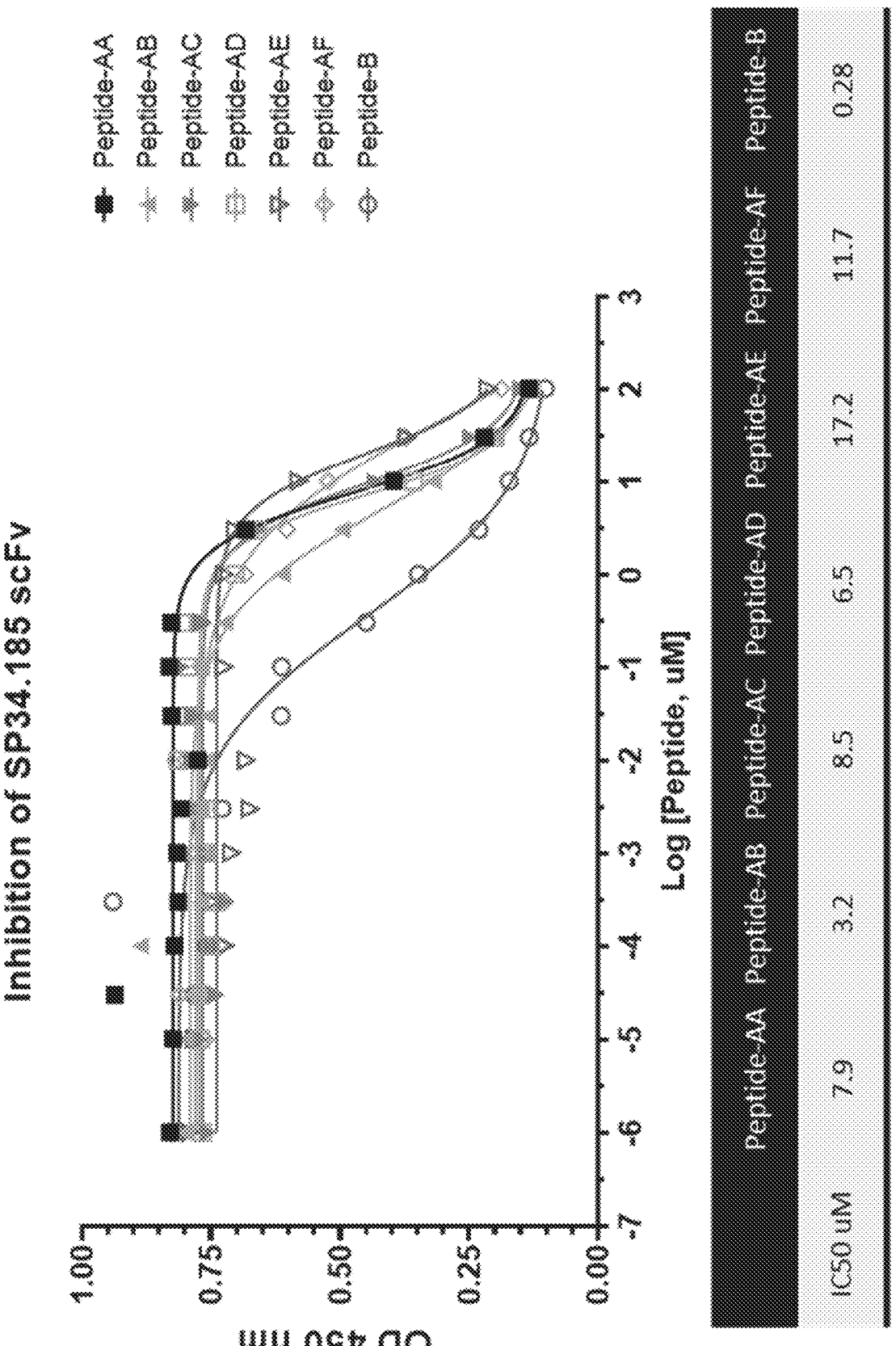
Figure 15B:

FIGS. 15A-15B illustrate inhibition of anti-CD3 scFv binding to CD3 by optimized anti-CD3 scFv Peptide-B sequences as measured by ELISA.

Figure 16:
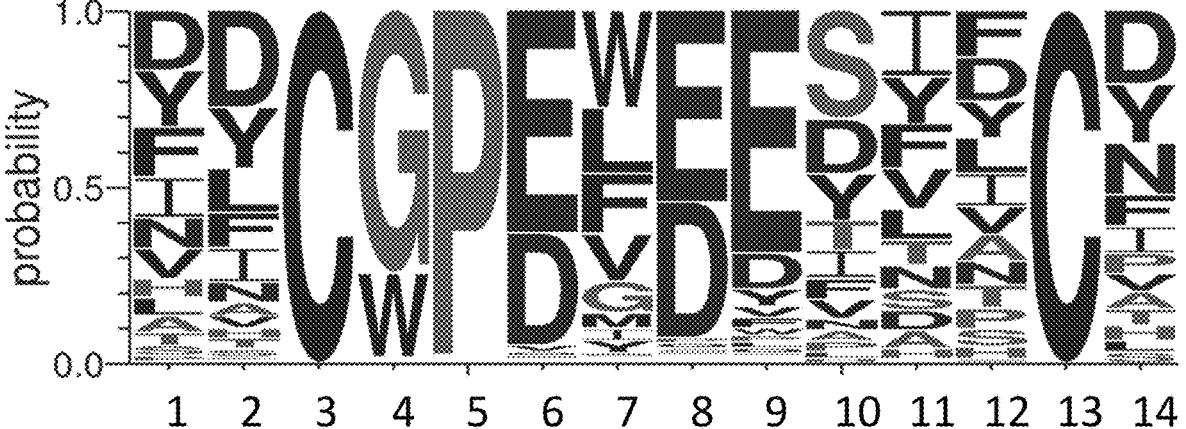

FIG. 16 illustrates the core sequence motif of optimized anti-CD3 scFv Peptide-B sequences generated using WebLogo 3.7.4.

DETAILED DESCRIPTION

Multispecific antibodies combine the benefits of different binding specificities derived from two or more antibodies into a single composition. Multispecific antibodies for redirecting T cells to cancers have shown promise in both pre-clinical and clinical studies. This approach relies on binding of one antigen interacting portion of the antibody to a tumor-associated antigen or marker, while a second antigen interacting portion can bind to an effector cell antigen on a T cell, such as CD3, which then triggers cytotoxic activity.

One such tumor-associated antigen is PSMA. Prostate-specific membrane antigen (PSMA), also known as glutamate carboxypeptidase II (GCPII), N-acetyl-L-aspartyl-L-glutamate peptidase I (NAALADase I), or NAAG peptidase is an enzyme that in humans is encoded by the FOLH1 (folate hydrolase 1) gene. PSMA is a zinc metalloenzyme that resides in membranes. Most of the enzyme resides in the extracellular space. Human PSMA is highly expressed in the prostate, roughly a hundred times greater than in most other tissues. In some prostate cancers, PSMA is the second-most upregulated gene product, with an 8- to 12-fold increase over levels in noncancerous prostate cells.

T cell engagers (TCEs) therapeutics have several benefits including they are not cell therapies and thus can be offered as off-the-shelf therapies as opposed to chimeric antigen receptor T cell (CAR T cell) therapies. While TCE therapeutics have displayed potent anti-tumor activity in hematological cancers, developing TCEs to treat solid tumors has faced challenges due to the limitations of prior TCE technologies, namely (i) overactivation of the immune system leading to cytokine release syndrome (CRS), (ii) on-target, healthy tissue toxicities and (iii) poor pharmacokinetics (PK) leading to short half-life. CRS arises from the systemic activation of T cells and can result in life-threatening elevations in inflammatory cytokines such as interleukin-6 (IL-6). Severe and acute CRS leading to dose limited toxicities and deaths have been observed upon the dosing of T cell engagers develop using other platforms to treat cancer patients in poor clinical studies. This toxicity restricts the maximum blood levels of T cell engagers that can be safely dosed. T cell engager effectiveness has also been limited because of on-target, healthy tissue toxicity. T cell engagers developed using a platform not designed for tumor-specification activation have resulted in clinicals holds and dose-limiting toxicities resulting from target expression in healthy tissues. T cell engagers have also been limited by short half-lives. T cell engagers quickly reach sub-therapeutic levels after being administered as they are quickly eliminated from the body due to their short exposure half-lives. For this reason, T cell engagers such as blinatumomab are typically administered by a low-dose, continuous infusion pump over a period of weeks to overcome the challenge of a short half-life and to maintain therapeutic levels of drug in the body. A continuous dosing regimen represents a significant burden for patients.

To overcome these challenges associated with the effectiveness of T cell engagers, described herein, are polypeptide or polypeptide complexes that comprise binding domains that selectively bind to an effector cell antigen and PSMA, in which one or more of the binding domains is selectively activated in the tumor microenvironment and the polypeptide or polypeptide complex comprises a half-life extending molecule. Such modifications reduce CRS and on-target healthy tissue toxicity risk, improves stability in the bloodstream and serum half-life prior to activation. The polypeptide or polypeptide complexes described herein have activity at low levels of target expression, and are easily manufactured.

In some embodiments, the polypeptides or polypeptide complexes described herein are used in a method of treating cancer. In some embodiments, the cancer has cells that express PSMA. In some embodiments, the polypeptides or polypeptide complexes described herein are used in a method of treating prostate cancer. In some embodiments, the prostate cancer is metastatic castrate resistant prostate cancer (mCRPC). Prostate cancer is the second most common cancer in men worldwide with over 3 million men living with prostate cancer in the United States alone. Early diagnoses and effective therapies mean that most prostate cancer patients have a prognosis with a mean five-year survival rate of approximately 98 percent. However, an estimated six percent of prostate cancer patients develop metastatic disease, which is associated with a five-year survival rate of approximately 30 percent. There were an estimated 33,000 deaths in the United States due to prostate cancer in 2020.

In some instances, the polypeptides or polypeptide complexes described herein are used to treat a solid tumor cancer. In some embodiments, the cancer is lung, breast (e.g. HER2+; ER/PR+; TNBC), cervical, ovarian, colorectal, pancreatic or gastric. In some embodiments, are methods of treating cancer comprising administering to a subject in need thereof an isolated polypeptide or polypeptide complex according to Formula I:

$$A_2\text{-}A_1\text{-}L_1\text{-}P_1—H_1 \qquad \text{(Formula I)}$$

wherein: $A_1$ comprises a first antigen recognizing molecule that binds to an effector cell antigen; $P_1$ comprises a peptide that binds to $A_1$; $L_1$ comprises a linking moiety that connects $A_1$ to $P_1$ and is a substrate for a tumor specific protease; $H_1$ comprises a half-life extending molecule; and $A_2$ comprises a second antigen recognizing molecule that binds to PSMA.

Disclosed herein, in some embodiments, are isolated polypeptides or polypeptide complexes according to Formula I:

$$A_2\text{-}A_1\text{-}L_1\text{-}P_1—H_1 \qquad \text{(Formula I)}$$

wherein: $A_1$ comprises a first antigen recognizing molecule that binds to an effector cell antigen; $P_1$ comprises a peptide that binds to $A_1$; $L_1$ comprises a linking moiety that connects $A_1$ to $P_1$ and is a substrate for a tumor specific protease; $H_1$ comprises a half-life extending molecule; and $A_2$ comprises a second antigen recognizing molecule that binds to prostate-specific membrane antigen (PSMA).

Disclosed herein, in some embodiments, are isolated polypeptides or polypeptide complexes according to Formula I:

$$A_2\text{-}A_1\text{-}L_1\text{-}P_1—H_1 \qquad \text{(Formula I)}$$

wherein: $A_1$ is a first antigen recognizing molecule that binds to an effector cell antigen; $P_1$ is a peptide that binds to $A_1$; $L_1$ is a linking moiety that connects $A_1$ to $P_1$ and is a substrate for a tumor specific protease; $H_1$ is a half-life extending molecule; and $A_2$ is a second antigen recognizing molecule that binds to prostate-specific membrane antigen (PSMA).

Disclosed herein, in some embodiments, are isolated polypeptides or polypeptide complexes comprising Formula I:

$$A_2\text{-}A_1\text{-}L_1\text{-}P_1\text{—}H_1 \tag{Formula I}$$

wherein: $A_1$ comprises a first antigen recognizing molecule that binds to an effector cell antigen; $P_1$ comprises a peptide that binds to $A_1$; $L_1$ comprises a linking moiety that connects $A_1$ to $P_1$ and is a substrate for a tumor specific protease; $H_1$ comprises a half-life extending molecule; and $A_2$ comprises a second antigen recognizing molecule that binds to prostate-specific membrane antigen (PSMA).

Disclosed herein, in some embodiments, are isolated polypeptides or polypeptide complexes comprising Formula I:

$$A_2\text{-}A_1\text{-}L_1\text{-}P_1\text{—}H_1 \tag{Formula I}$$

wherein: $A_1$ is a first antigen recognizing molecule that binds to an effector cell antigen; $P_1$ is a peptide that binds to $A_1$; $L_1$ is a linking moiety that connects $A_1$ to $P_1$ and is a substrate for a tumor specific protease; $H_1$ is a half-life extending molecule; and $A_2$ is a second antigen recognizing molecule that binds to prostate-specific membrane antigen (PSMA).

Disclosed herein, in some embodiments, are isolated polypeptides or polypeptide complexes according to Formula I:

$$A_2\text{-}A_1\text{-}L_1\text{-}P_1\text{—}H_1 \tag{Formula I}$$

wherein: $A_1$ comprises a first antigen recognizing molecule that binds to prostate-specific membrane antigen (PSMA); $P_1$ comprises a peptide that binds to $A_1$; $L_1$ comprises a linking moiety that connects $A_1$ to $P_1$ and is a substrate for a tumor specific protease; $H_1$ comprises a half-life extending molecule; and $A_2$ comprises a second antigen recognizing molecule that binds to an effector cell antigen.

Disclosed herein, in some embodiments, are isolated polypeptides or polypeptide complexes according to Formula I:

$$A_2\text{-}A_1\text{-}L_1\text{-}P_1\text{—}H_1 \tag{Formula I}$$

wherein: $A_1$ is a first antigen recognizing molecule that binds to prostate-specific membrane antigen (PSMA); $P_1$ is a peptide that binds to $A_1$; $L_1$ is a linking moiety that connects $A_1$ to $P_1$ and is a substrate for a tumor specific protease; $H_1$ is a half-life extending molecule; and $A_2$ is a second antigen recognizing molecule that binds to effector cell antigen.

Disclosed herein, in some embodiments, are isolated polypeptides or polypeptide complexes comprising Formula I:

$$A_2\text{-}A_1\text{-}L_1\text{-}P_1\text{—}H_1 \tag{Formula I}$$

wherein: $A_1$ comprises a first antigen recognizing molecule that binds to prostate-specific membrane antigen (PSMA); $P_1$ comprises a peptide that binds to $A_1$; $L_1$ comprises a linking moiety that connects $A_1$ to $P_1$ and is a substrate for a tumor specific protease; $H_1$ comprises a half-life extending molecule; and $A_2$ comprises a second antigen recognizing molecule that binds to an effector cell antigen.

Disclosed herein, in some embodiments, are isolated polypeptides or polypeptide complexes comprising Formula I:

$$A_2\text{-}A_1\text{-}L_1\text{-}P_1\text{—}H_1 \tag{Formula I}$$

12 wherein: $A_1$ is a first antigen recognizing molecule that binds to prostate-specific membrane antigen (PSMA); $P_1$ is a peptide that binds to $A_1$; $L_1$ is a linking moiety that connects $A_1$ to $P_1$ and is a substrate for a tumor specific protease; $H_1$ is a half-life extending molecule; and $A_2$ is a second antigen recognizing molecule that binds to an effector cell antigen.

Disclosed herein, in some embodiments, are isolated polypeptides or polypeptide complexes according to Formula Ia:

$$P_2\text{-}L_2\text{-}A_2\text{-}A_1\text{-}L_1\text{-}P_1\text{—}H_1 \tag{Formula Ia}$$

wherein $A_2$ further comprises $P_2$ and $L_2$, wherein $P_2$ comprises a peptide that binds to $A_2$; and $L_2$ comprises a linking moiety that connects $A_2$ to $P_2$ and is a substrate for a tumor specific protease.

Disclosed herein, in some embodiments, are isolated polypeptides or polypeptide complexes according to Formula Ia:

$$P_2\text{-}L_2\text{-}A_2\text{-}A_1\text{-}L_1\text{-}P_1\text{—}H_1 \tag{Formula Ia}$$

wherein $A_2$ further comprises $P_2$ and $L_2$, wherein $P_2$ is a peptide that binds to $A_2$; and $L_2$ is a linking moiety that connects $A_2$ to $P_2$ and is a substrate for a tumor specific protease.

Disclosed herein, in some embodiments, are isolated polypeptides or polypeptide complexes comprising Formula Ia:

$$P_2\text{-}L_2\text{-}A_2\text{-}A_1\text{-}L_1\text{-}P_1\text{—}H_1 \tag{Formula Ia}$$

wherein $A_2$ further comprises $P_2$ and $L_2$, wherein $P_2$ comprises a peptide that binds to $A_2$; and $L_2$ comprises a linking moiety that connects $A_2$ to $P_2$ and is a substrate for a tumor specific protease.

Disclosed herein, in some embodiments, are isolated polypeptides or polypeptide complexes comprising Formula Ia:

$$P_2\text{-}L_2\text{-}A_2\text{-}A_1\text{-}L_1\text{-}P_1\text{—}H_1 \tag{Formula Ia}$$

wherein $A_2$ further comprises $P_2$ and $L_2$, wherein $P_2$ is a peptide that binds to $A_2$; and $L_2$ is a linking moiety that connects $A_2$ to $P_2$ and is a substrate for a tumor specific protease.

Disclosed herein, in some embodiments, are isolated polypeptides or polypeptide complexes according to Formula TI:

$$L_{1a}\text{-}P_{1a}\text{—}H_{1a} \tag{Formula II}$$

wherein: $L_{1a}$ comprises a tumor specific protease-cleaved linking moiety that when uncleaved connects $P_{1a}$ to a first antigen recognizing molecule that binds to an effector cell antigen and the first antigen recognizing molecule is connected to a second antigen recognizing molecule that binds to prostate-specific membrane antigen (PSMA); $P_{1a}$ comprises a peptide that binds to the first antigen recognizing molecule when $L_{1a}$ is uncleaved; and $H_{1a}$ comprises a half-life extending molecule.

Disclosed herein, in some embodiments, are isolated polypeptides or polypeptide complexes comprising Formula II:

$$L_{1a}\text{-}P_{1a}\text{—}H_{1a} \tag{Formula II}$$

wherein: $L_{1a}$ comprises a tumor specific protease-cleaved linking moiety that when uncleaved connects $P_{1a}$ to a first antigen recognizing molecule that binds to an effector cell antigen and the first antigen recognizing molecule is connected to a second antigen recognizing molecule that binds to prostate-specific membrane antigen (PSMA); $P_{1a}$ comprises a peptide that binds to the first antigen recognizing molecule when $L_{1a}$ is uncleaved; and $H_{1a}$ comprises a half-life extending molecule.

Disclosed herein, in some embodiments, are isolated polypeptides or polypeptide complexes according to Formula II:

$$L_{1a}\text{-}P_{1a}\text{—}H_{1a} \qquad \text{(Formula II)}$$

wherein: $L_{1a}$ is a tumor specific protease-cleaved linking moiety that when uncleaved connects $P_{1a}$ to a first antigen recognizing molecule that binds to an effector cell antigen and the first antigen recognizing molecule is connected to a second antigen recognizing molecule that binds to prostate-specific membrane antigen (PSMA); $P_{1a}$ is a peptide that binds to the first antigen recognizing molecule when $L_{1a}$ is uncleaved; and $H_{1a}$ is a half-life extending molecule.

Disclosed herein, in some embodiments, are isolated polypeptides or polypeptide complexes comprising Formula II:

$$L_{1a}\text{-}P_{1a}\text{—}H_{1a} \qquad \text{(Formula II)}$$

wherein: $L_{1a}$ is a tumor specific protease-cleaved linking moiety that when uncleaved connects $P_{1a}$ to a first antigen recognizing molecule that binds to an effector cell antigen and the first antigen recognizing molecule is connected to a second antigen recognizing molecule that binds to prostate-specific membrane antigen (PSMA); $P_{1a}$ is a peptide that binds to the first antigen recognizing molecule when $L_{1a}$ is uncleaved; and $H_{1a}$ is a half-life extending molecule.

First Antigen Recognizing Molecule ($A_1$)

Disclosed herein, in some embodiments, are isolated polypeptides or polypeptide complexes, wherein the first antigen recognizing molecule binds to an effector cell antigen and the second antigen recognizing molecule binds to PSMA. In some embodiments, the effector cell antigen comprises CD3. In some embodiments, $A_1$ comprises a first antigen recognizing molecule that binds to an effector cell antigen.

In some embodiments, $A_1$ comprises an antibody or antibody fragment. In some embodiments, $A_1$ comprises an antibody or antibody fragment that is human or humanized. In some embodiments, $L_1$ is bound to a N-terminus of the antibody or antibody fragment. In some embodiments, $L_1$ is bound to a N-terminus of the antibody or antibody fragment and $A_2$ is bound to the other N-terminus of the antibody or antibody fragment. In some embodiments, $A_2$ is bound to a C-terminus of the antibody or antibody fragment. In some embodiments, $L_1$ is bound to a C-terminus of the antibody or antibody fragment. In some embodiments, $A_2$ is bound to a N-terminus of the antibody or antibody fragment. In some embodiments, the antibody or antibody fragment comprises a single chain variable fragment, a single domain antibody, or a Fab fragment. In some embodiments, $A_1$ is the single chain variable fragment (scFv). In some embodiments, the scFv comprises a scFv heavy chain polypeptide and a scFv light chain polypeptide. In some embodiments, $A_1$ is the single domain antibody. In some embodiments, $A_1$ comprises a variable light chain and variable heavy chain each of which is capable of specifically binding to human CD3. In some embodiments, the effector cell antigen comprises CD3. In some embodiments, $A_1$ comprises an anti-CD3e single chain variable fragment. In some embodiments, $A_1$ comprises an anti-CD3e single chain variable fragment that has a $K_D$ binding of 1 μM or less to CD3 on CD3 expressing cells. In some embodiments, $A_1$ comprises complementary determining regions (CDRs) selected from the group consisting of muromonab-CD3 (OKT3), otelixizumab (TRX4), teplizumab (MGA031), visilizumab (Nuvion), SP34, X35, VIT3, BMA030 (BW264/56), CLB-T3/3, CRIS7, YTH12.5, F111-409, CLB-T3.4.2, TR-66, WT32, SPv-T3b, 11D8, XIII-141, XIII-46, XIII-87, 12F6, T3/RW2-8C8, T3/RW2-4B6, OKT3D, M-T301, SMC2, F101.01, UCHT-1, WT-31, 15865, 15865v12, 15865v16, and 15865v19.

In some embodiments, $A_1$ comprises a first antigen recognizing molecule that binds PSMA. In some embodiments, $A_1$ comprises a variable light chain and variable heavy chain each of which is capable of specifically binding to human PSMA.

In some embodiments, the scFv that binds to CD3 comprises a scFv light chain variable domain and a scFv heavy chain variable domain. In some embodiments, the scFv heavy chain variable domain comprises at least one, two, or three complementarity determining regions (CDR)s disclosed in Table 1 or a sequence substantially identical thereto (e.g., a sequence that has at least 90%, 95%, 96%, 97%, 98%, or 99% sequence identity). In some embodiments, the scFv light chain variable domain comprises at least one, two, or three complementarity determining regions (CDR)s disclosed in Table 1 or a sequence substantially identical thereto (e.g., a sequence that has at least 90%, 95%, 96%, 97%, 98%, or 99% sequence identity).

In some embodiments, the scFv heavy chain variable domain comprises at least one, two, or three complementarity determining regions (CDR)s disclosed in Table 1 or a sequence substantially identical thereto (e.g., a sequence that has at least 90%, 95%, 96%, 97%, 98%, or 99% sequence identity); and the scFv light chain variable domain comprises at least one, two, or three complementarity determining regions (CDR)s disclosed in Table 1 or a sequence substantially identical thereto (e.g., a sequence that has at least 90%, 95%, 96%, 97%, 98%, or 99% sequence identity).

TABLE 1

| anti-CD3 amino acid sequences (CDRs as determined by IMGT numbering system) | | |
|---|---|---|
| Construct Description | Amino Acid Sequence (N to C) | SEQ ID NO: |
| SP34.185 CD3: HC: CDR1 | GFTFNKYA | 1 |
| SP34.185 CD3: HC: CDR2 | IRSKYNNYAT | 2 |
| SP34.185 CD3: HC: CDR3 | VRHGNFGNSYISYWAY | 3 |
| SP34.185 CD3: LC: CDR1 | TGAVTSGNY | 4 |
| SP34.185 CD3: LC: CDR2 | GT | 5 |
| SP34.185 CD3: LC: CDR3 | VLWYSNRWV | 6 |
| SP34.185 scFv (VH - linker 1 - VL) | EVQLVESGGGLVQPGGSLKLSCA ASGGFTFNKYAMNWVRQAPGKG LEWVARIRSKYNNYATYYADSV KDRFTISRDDSKNTAYLQMNNLK TEDTAVYYCVRHGNFGNSYISY WAYWGQGTLVTVSSGGGGSGGG GSGGGGSQTVVTQEPSLTVSPGG TVTLTCGSSTGAVTSGNYPNWV QQKPGQAPRGLIGTKFLAPGTP ARFSGSLLGGKAALTLSGVQPED EAEYYCVLWYSNRWVFGGGTKL TVL | 7 |

In some embodiments, the scFv heavy chain variable domain comprises complementarity determining regions (CDRs): HC-CDR1, HC-CDR2, and HC-CDR3, wherein the HC-CDR1, the HC-CDR2, and the HC-CDR3 of the scFv heavy chain variable domain comprise: HC-CDR1: SEQ ID NO: 1; HC-CDR2: SEQ ID NO: 2; HC-CDR3: SEQ ID NO: 3, and wherein the CDRs comprise from 0-2 amino acid modifications in at least one of the HC-CDR1, HC-CDR2, or HC-CDR3. In some embodiments, the scFv light chain variable domain comprises complementarity determining regions (CDRs): LC-CDR1, LC-CDR2, and LC-CDR3, wherein the LC-CDR1, the LC-CDR2, and the LC-CDR3 of the scFv light chain variable domain comprise: LC-CDR1: SEQ ID NO: 4; LC-CDR2: SEQ ID NO: 5; and LC-CDR3: SEQ ID NO: 6, and wherein the CDRs comprise from 0-2 amino acid modifications in at least one of the LC-CDR1, LC-CDR2, or LC-CDR3.

In some embodiments, the polypeptide or polypeptide complex of Formula I binds to an effector cell when $L_1$ is cleaved by the tumor specific protease. In some embodiments, the polypeptide or polypeptide complex of Formula I binds to an effector cell when $L_1$ is cleaved by the tumor specific protease and $A_1$ binds to the effector cell. In some embodiments, the effector cell is a T cell. In some embodiments, $A_1$ binds to a polypeptide that is part of a TCR-CD3 complex on the effector cell. In some embodiments, the polypeptide that is part of the TCR-CD3 complex is human CD3E. In some embodiments, the effector cell antigen comprises CD3, wherein the scFv comprises complementarity determining regions (CDRs): HC-CDR1, HC-CDR2, and HC-CDR3, wherein the HC-CDR1, the HC-CDR2, and the HC-CDR3 of the scFv comprise: HC-CDR1: SEQ ID NO: 1, HC-CDR2: SEQ ID NO: 2, and HC-CDR3: SEQ ID NO: 3; and the scFv comprises CDRs: LC-CDR1, LC-CDR2, and LC-CDR3, wherein the LC-CDR1, the LC-CDR2, and the LC-CDR3 of the scFv comprise: LC-CDR1: SEQ ID NO: 4, LC-CDR2: SEQ ID NO:5, and LC-CDR3: SEQ ID NO: 6. In some embodiments, the effector cell antigen comprises CD3, and the scFv comprises an amino acid sequence according to SEQ ID NO: 7.

In some embodiments, the effector cell antigen comprises CD3, and wherein $A_1$ comprises complementarity determining regions (CDRs): HC-CDR1, HC-CDR2, and HC-CDR3, wherein the HC-CDR1, the HC-CDR2, and the HC-CDR3 of $A_1$ comprises: HC-CDR1: SEQ ID NO: 1, HC-CDR2: SEQ ID NO: 2, and HC-CDR3: SEQ ID NO: 3; and $A_1$ comprises CDRs: LC-CDR1, LC-CDR2, and LC-CDR3, wherein the LC-CDR1, the LC-CDR2, and the LC-CDR3 of $A_1$ comprise: LC-CDR1: SEQ ID NO: 4, LC-CDR2: SEQ ID NO:5, and LC-CDR3: SEQ ID NO: 6. In some embodiments, the effector cell antigen comprises CD3, and $A_1$ comprises an amino acid sequence according to SEQ ID NO: 7.

In some embodiments, $A_1$ comprises an amino acid sequence according to SEQ ID NO: 7. In some embodiments, $A_1$ comprises an amino acid sequence that has at least 80% sequence identity to SEQ ID NO: 7. In some embodiments, $A_1$ comprises an amino acid sequence that has at least 85% sequence identity to SEQ ID NO: 7. In some embodiments, $A_1$ comprises an amino acid sequence that has at least 90% sequence identity to SEQ ID NO: 7. In some embodiments, $A_1$ comprises an amino acid sequence that has at least 95% sequence identity to SEQ ID NO: 7. In some embodiments, $A_1$ comprises an amino acid sequence that has at least 99% sequence identity to SEQ ID NO: 7.

In some embodiments, the polypeptide or polypeptide complex has weaker binding affinity for the tumor cell antigen as compared to the binding affinity for the tumor cell antigen of an isolated polypeptide or polypeptide complex that does not have $P_1$ or $L_1$. In some embodiments, the polypeptide or polypeptide complex has weaker binding affinity for the tumor cell antigen that is at least 5× higher than the binding affinity for the tumor cell antigen of a form of the polypeptide or polypeptide complex that does not have $P_1$ or $L_1$. In some embodiments, the polypeptide or polypeptide complex has weaker binding affinity for the tumor cell antigen that is at least 8×higher than the binding affinity for the tumor cell antigen of a form of the polypeptide or polypeptide complex that does not have $P_1$ or $L_1$. In some embodiments, the polypeptide or polypeptide complex has weaker binding affinity for the tumor cell antigen that is at least 10×higher than the binding affinity for the tumor cell antigen of a form of the polypeptide or polypeptide complex that does not have $P_1$ or $L_1$. In some embodiments, the polypeptide or polypeptide complex has weaker binding affinity for the tumor cell antigen that is at least 15× higher than the binding affinity for the tumor cell antigen of a form of the polypeptide or polypeptide complex that does not have $P_1$ or $L_1$. In some embodiments, the polypeptide or polypeptide complex has weaker binding affinity for the tumor cell antigen that is at least 20× higher than the binding affinity for the tumor cell antigen of a form of the polypeptide or polypeptide complex that does not have $P_1$ or $L_1$. In some embodiments, the polypeptide or polypeptide complex has weaker binding affinity for the tumor cell antigen that is at least 25× higher than the binding affinity for the tumor cell antigen of a form of the polypeptide or polypeptide complex that does not have $P_1$ or $L_1$. In some embodiments, the polypeptide or polypeptide complex has weaker binding affinity for the tumor cell antigen that is at least 30× higher than the binding affinity for the tumor cell antigen of a form of the polypeptide or polypeptide complex that does not have $P_1$ or $L_1$. In some embodiments, the polypeptide or polypeptide complex has weaker binding affinity for the tumor cell antigen that is at least 35× higher than the binding affinity for the tumor cell antigen of a form of the polypeptide or polypeptide complex that does not have $P_1$ or $L_1$. In some embodiments, the polypeptide or polypeptide complex has weaker binding affinity for the tumor cell antigen that is at least 40× higher than the binding affinity for the tumor cell antigen of a form of the polypeptide or polypeptide complex that does not have $P_1$ or $L_1$. In some embodiments, the polypeptide or polypeptide complex has weaker binding affinity for the tumor cell antigen that is at least 45× higher than the binding affinity for the tumor cell antigen of a form of the polypeptide or polypeptide complex that does not have $P_1$ or $L_1$. In some embodiments, the polypeptide or polypeptide complex has weaker binding affinity for the tumor cell antigen that is at least 50× higher than the binding affinity for the tumor cell antigen of a form of the polypeptide or polypeptide complex that does not have $P_1$ or $L_1$. In some embodiments, the polypeptide or polypeptide complex has weaker binding affinity for the tumor cell antigen that is at least 55× higher than the binding affinity for the tumor cell antigen of a form of the polypeptide or polypeptide complex that does not have $P_1$ or $L_1$. In some embodiments, the polypeptide or polypeptide complex has weaker binding affinity for the tumor cell antigen that is at least 60× higher than the binding affinity for the tumor cell antigen of a form of the polypeptide or polypeptide complex that does not have $P_1$ or $L_1$. In some embodiments, the polypeptide or polypeptide complex has weaker binding affinity for the tumor cell antigen that is at least 65× higher than the binding affinity for the tumor cell antigen of a form of the polypeptide or polypeptide complex that does not have $P_1$ or $L_1$. In some embodiments, the polypeptide or polypeptide complex has weaker binding affinity for the tumor cell antigen that is at least 70× higher than the binding affinity for the tumor cell antigen of a form of the polypeptide or polypeptide complex that does not have $P_1$ or $L_1$. In some embodiments, the polypeptide or polypeptide complex has weaker binding affinity for the tumor cell antigen that is at least 75× higher than the binding affinity for the tumor cell antigen of a form of the polypeptide or polypeptide complex that does not have $P_1$ or $L_1$. In some embodiments, the polypeptide or polypeptide complex has weaker binding affinity for the tumor cell antigen that is at least 80× higher than the binding affinity for the tumor cell antigen of a form of the polypeptide or polypeptide complex that does not have $P_1$ or $L_1$. In some embodiments, the polypeptide or polypeptide complex has weaker binding affinity for the tumor cell antigen that is at least 85× higher than the binding affinity for the tumor cell antigen of a form of the polypeptide or polypeptide complex that does not have $P_1$ or $L_1$. In some embodiments, the polypeptide or polypeptide complex has weaker binding affinity for the tumor cell antigen that is at least 90× higher than the binding affinity for the tumor cell antigen of a form of the polypeptide or polypeptide complex that does not have $P_1$ or $L_1$. In some embodiments, the polypeptide or polypeptide complex has weaker binding affinity for the tumor cell antigen that is at least 95× higher than the binding affinity for the tumor cell antigen of a form of the polypeptide or polypeptide complex that does not have $P_1$ or $L_1$. In some embodiments, the polypeptide or polypeptide complex has weaker binding affinity for the tumor cell antigen that is at least 100× higher than the binding affinity for the tumor cell antigen of a form of the polypeptide or polypeptide complex that does not have $P_1$ or $L_1$. In some embodiments, the polypeptide or polypeptide complex has weaker binding affinity for the tumor cell antigen that is at least 120× higher than the binding affinity for the tumor cell antigen of a form of the polypeptide or polypeptide complex that does not have $P_1$ or $L_1$. In some embodiments, the polypeptide or polypeptide complex has weaker binding affinity for the tumor cell antigen that is at least 1000× higher than the binding affinity for the tumor cell antigen of a form of the polypeptide or polypeptide complex that does not have $P_1$ or $L_1$.

In some embodiments, the polypeptide or polypeptide complex has weaker binding affinity for the tumor cell antigen as compared to the binding affinity for the tumor cell antigen of the polypeptide or polypeptide complex in which $L_1$ has been cleaved by the tumor specific protease. In some embodiments, the polypeptide or polypeptide complex has weaker binding affinity for the tumor cell antigen that is at least 5× higher than the binding affinity for the tumor cell antigen of the polypeptide or polypeptide complex in which $L_1$ has been cleaved by the tumor specific protease. In some embodiments, the polypeptide or polypeptide complex has weaker binding affinity for the tumor cell antigen that is at least 8× higher than the binding affinity for the tumor cell antigen of the polypeptide or polypeptide complex in which $L_1$ has been cleaved by the tumor specific protease. In some embodiments, the polypeptide or polypeptide complex has weaker binding affinity for the tumor cell antigen that is at least 10× higher than the binding affinity for the tumor cell antigen of the polypeptide or polypeptide complex in which $L_1$ has been cleaved by the tumor specific protease. In some embodiments, the polypeptide or polypeptide complex has weaker binding affinity for the tumor cell antigen that is at least 15× higher than the binding affinity for the tumor cell antigen of the polypeptide or polypeptide complex in which $L_1$ has been cleaved by the tumor specific protease. In some embodiments, the polypeptide or polypeptide complex has weaker binding affinity for the tumor cell antigen that is at least 20× higher than the binding affinity for the tumor cell antigen of the polypeptide or polypeptide complex in which $L_1$ has been cleaved by the tumor specific protease. In some embodiments, the polypeptide or polypeptide complex has weaker binding affinity for the tumor cell antigen that is at least 25× higher than the binding affinity for the tumor cell antigen of the polypeptide or polypeptide complex in which $L_1$ has been cleaved by the tumor specific protease. In some embodiments, the polypeptide or polypeptide complex has weaker binding affinity for the tumor cell antigen that is at least 30× higher than the binding affinity for the tumor cell antigen of the polypeptide or polypeptide complex in which $L_1$ has been cleaved by the tumor specific protease. In some embodiments, the polypeptide or polypeptide complex has weaker binding affinity for the tumor cell antigen that is at least 35× higher than the binding affinity for the tumor cell antigen of the polypeptide or polypeptide complex in which $L_1$ has been cleaved by the tumor specific protease. In some embodiments, the polypeptide or polypeptide complex has weaker binding affinity for the tumor cell antigen that is at least 40× higher than the binding affinity for the tumor cell antigen of the polypeptide or polypeptide complex in which $L_1$ has been cleaved by the tumor specific protease. In some embodiments, the polypeptide or polypeptide complex has weaker binding affinity for the tumor cell antigen that is at least 45× higher than the binding affinity for the tumor cell antigen of the polypeptide or polypeptide complex in which $L_1$ has been cleaved by the tumor specific protease. In some embodiments, the polypeptide or polypeptide complex has weaker binding affinity for the tumor cell antigen that is at least 50× higher than the binding affinity for the tumor cell antigen of the polypeptide or polypeptide complex in which $L_1$ has been cleaved by the tumor specific protease. In some embodiments, the polypeptide or polypeptide complex has weaker binding affinity for the tumor cell antigen that is at least 55× higher than the binding affinity for the tumor cell antigen of the polypeptide or polypeptide complex in which $L_1$ has been cleaved by the tumor specific protease. In some embodiments, the polypeptide or polypeptide complex has weaker binding affinity for the tumor cell antigen that is at least 60×higher than the binding affinity for the tumor cell antigen of the polypeptide or polypeptide complex in which $L_1$ has been cleaved by the tumor specific protease. In some embodiments, the polypeptide or polypeptide complex has weaker binding affinity for the tumor cell antigen that is at least 65×higher than the binding affinity for the tumor cell antigen of the polypeptide or polypeptide complex in which $L_1$ has been cleaved by the tumor specific protease. In some embodiments, the polypeptide or polypeptide complex has weaker binding affinity for the tumor cell antigen that is at least 70×higher than the binding affinity for the tumor cell antigen of the polypeptide or polypeptide complex in which $L_1$ has been cleaved by the tumor specific protease. In some embodiments, the polypeptide or polypeptide complex has weaker binding affinity for the tumor cell antigen that is at least 75×higher than the binding affinity for the tumor cell antigen of the polypeptide or polypeptide complex in which $L_1$ has been cleaved by the tumor specific protease. In some embodiments, the polypeptide or polypeptide complex has weaker binding affinity for the tumor cell antigen that is at least 80×higher than the binding affinity for the tumor cell antigen of the polypeptide or polypeptide complex in which $L_1$ has been cleaved by the tumor specific protease. In some embodiments, the polypeptide or polypeptide complex has weaker binding affinity for the tumor cell antigen that is at least 85×higher than the binding affinity for the tumor cell antigen of the polypeptide or polypeptide complex in which $L_1$ has been cleaved by the tumor specific protease. In some embodiments, the polypeptide or polypeptide complex has weaker binding affinity for the tumor cell antigen that is at least 90×higher than the binding affinity for the tumor cell antigen of the polypeptide or polypeptide complex in which $L_1$ has been cleaved by the tumor specific protease. In some embodiments, the polypeptide or polypeptide complex has weaker binding affinity for the tumor cell antigen that is at least 95×higher than the binding affinity for the tumor cell antigen of the polypeptide or polypeptide complex in which $L_1$ has been cleaved by the tumor specific protease. In some embodiments, the polypeptide or polypeptide complex has weaker binding affinity for the tumor cell antigen that is at least 100×higher than the binding affinity for the tumor cell antigen of the polypeptide or polypeptide complex in which $L_1$ has been cleaved by the tumor specific protease. In some embodiments, the polypeptide or polypeptide complex has weaker binding affinity for the tumor cell antigen that is at least 120×higher than the binding affinity for the tumor cell antigen of the polypeptide or polypeptide complex in which $L_1$ has been cleaved by the tumor specific protease. In some embodiments, the polypeptide or polypeptide complex has weaker binding affinity for the tumor cell antigen that is at least 1000×higher than the binding affinity for the tumor cell antigen of the polypeptide or polypeptide complex in which $L_1$ has been cleaved by the tumor specific protease.

In some embodiments, the polypeptide or polypeptide complex has an increased $EC_{50}$ in an IFNγ release T-cell activation assay as compared to the $EC_{50}$ in an IFNγ release T-cell activation assay of an isolated polypeptide or polypeptide complex that does not have $P_1$ or $L_1$. In some embodiments, the polypeptide or polypeptide complex has an increased $EC_{50}$ in an IFNγ release T-cell activation assay that is at least 10× higher than the $EC_{50}$ in an IFNγ release T-cell activation assay of a form of the polypeptide or polypeptide complex that does not have $P_1$ or $L_1$. In some embodiments, the polypeptide or polypeptide complex has an increased $EC_{50}$ in an IFNγ release T-cell activation assay that is at least 20×higher than the $EC_{50}$ in an IFNγ release T-cell activation assay of a form of the polypeptide or polypeptide complex that does not have $P_1$ or $L_1$. In some embodiments, the polypeptide or polypeptide complex has an increased $EC_{50}$ in an IFNγ release T-cell activation assay that is at least 30×higher than the $EC_{50}$ in an IFNγ release T-cell activation assay of a form of the polypeptide or polypeptide complex that does not have $P_1$ or $L_1$. In some embodiments, the polypeptide or polypeptide complex has an increased $EC_{50}$ in an IFNγ release T-cell activation assay that is at least 40×higher than the $EC_{50}$ in an IFNγ release T-cell activation assay of a form of the polypeptide or polypeptide complex that does not have $P_1$ or $L_1$. In some embodiments, the polypeptide or polypeptide complex has an increased $EC_{50}$ in an IFNγ release T-cell activation assay that is at least 50×higher than the $EC_{50}$ in an IFNγ release T-cell activation assay of a form of the polypeptide or polypeptide complex that does not have $P_1$ or $L_1$. In some embodiments, the polypeptide or polypeptide complex has an increased $EC_{50}$ in an IFNγ release T-cell activation assay that is at least 60×higher than the $EC_{50}$ in an IFNγ release T-cell activation assay of a form of the polypeptide or polypeptide complex that does not have $P_1$ or $L_1$. In some embodiments, the polypeptide or polypeptide complex has an increased $EC_{50}$ in an IFNγ release T-cell activation assay that is at least 70×higher than the $EC_{50}$ in an IFNγ release T-cell activation assay of a form of the polypeptide or polypeptide complex that does not have $P_1$ or $L_1$. In some embodiments, the polypeptide or polypeptide complex has an increased $EC_{50}$ in an IFNγ release T-cell activation assay that is at least 80×higher than the $EC_{50}$ in an IFNγ release T-cell activation assay of a form of the polypeptide or polypeptide complex that does not have $P_1$ or $L_1$. In some embodiments, the polypeptide or polypeptide complex has an increased $EC_{50}$ in an IFNγ release T-cell activation assay that is at least 90×higher than the $EC_{50}$ in an IFNγ release T-cell activation assay of a form of the polypeptide or polypeptide complex that does not have $P_1$ or $L_1$. In some embodiments, the polypeptide or polypeptide complex has an increased $EC_{50}$ in an IFNγ release T-cell activation assay that is at least 100× higher than the $EC_{50}$ in an IFNγ release T-cell activation assay of a form of the polypeptide or polypeptide complex that does not have $P_1$ or $L_1$. In some embodiments, the polypeptide or polypeptide complex has an increased $EC_{50}$ in an IFNγ release T-cell activation assay that is at least 1000× higher than the $EC_{50}$ in an IFNγ release T-cell activation assay of a form of the polypeptide or polypeptide complex that does not have $P_1$ or $L_1$.

In some embodiments, the polypeptide or polypeptide complex has an increased $EC_{50}$ in an IFNγ release T-cell activation assay as compared to the $EC_{50}$ in an IFNγ release T-cell activation assay of the polypeptide or polypeptide complex in which $L_1$ has been cleaved by the tumor specific protease. In some embodiments, the polypeptide or polypeptide complex has an increased $EC_{50}$ in an IFNγ release T-cell activation assay that is at least 10× higher than the $EC_{50}$ in an IFNγ release T-cell activation assay of the polypeptide or polypeptide complex in which $L_1$ has been cleaved by the tumor specific protease. In some embodiments, the polypeptide or polypeptide complex has an increased $EC_{50}$ in an IFNγ release T-cell activation assay that is at least 20×higher than the $EC_{50}$ in an IFNγ release T-cell activation assay of the polypeptide or polypeptide complex in which $L_1$ has been cleaved by the tumor specific protease. In some embodiments, the polypeptide or polypeptide complex has an increased $EC_{50}$ in an IFNγ release T-cell activation assay that is at least 30×higher than the $EC_{50}$ in an IFNγ release T-cell activation assay of the polypeptide or polypeptide complex in which $L_1$ has been cleaved by the tumor specific protease. In some embodiments, the polypeptide or polypeptide complex has an increased $EC_{50}$ in an IFNγ release T-cell activation assay that is at least 40×higher than the $EC_{50}$ in an IFNγ release T-cell activation assay of the polypeptide or polypeptide complex in which $L_1$ has been cleaved by the tumor specific protease. In some embodiments, the polypeptide or polypeptide complex has an increased $EC_{50}$ in an IFNγ release T-cell activation assay that is at least 50×higher than the $EC_{50}$ in an IFNγ release T-cell activation assay of the polypeptide or polypeptide complex in which $L_1$ has been cleaved by the tumor specific protease. In some embodiments, the polypeptide or polypeptide complex has an increased $EC_{50}$ in an IFNγ release T-cell activation assay that is at least 60×higher than the $EC_{50}$ in an IFNγ release T-cell activation assay of the polypeptide or polypeptide complex in which $L_1$ has been cleaved by the tumor specific protease. In some embodiments, the polypeptide or polypeptide complex has an increased $EC_{50}$ in an IFNγ release T-cell activation assay that is at least 70×higher than the $EC_{50}$ in an IFNγ release T-cell activation assay of the polypeptide or polypeptide complex in which $L_1$ has been cleaved by the tumor specific protease. In some embodiments, the polypeptide or polypeptide complex has an increased $EC_{50}$ in an IFNγ release T-cell activation assay that is at least 80×higher than the $EC_{50}$ in an IFNγ release T-cell activation assay of the polypeptide or polypeptide complex in which $L_1$ has been cleaved by the tumor specific protease. In some embodiments, the polypeptide or polypeptide complex has an increased $EC_{50}$ in an IFNγ release T-cell activation assay that is at least 90×higher than the $EC_{50}$ in an IFNγ release T-cell activation assay of the polypeptide or polypeptide complex in which $L_1$ has been cleaved by the tumor specific protease. In some embodiments, the polypeptide or polypeptide complex has an increased $EC_{50}$ in an IFNγ release T-cell activation assay that is at least 100× higher than the $EC_{50}$ in an IFNγ release T-cell activation assay of the polypeptide or polypeptide complex in which $L_1$ has been cleaved by the tumor specific protease. In some embodiments, the polypeptide or polypeptide complex has an increased $EC_{50}$ in an IFNγ release T-cell activation assay that is at least 1000× higher than the $EC_{50}$ in an IFNγ release T-cell activation assay of the polypeptide or polypeptide complex in which $L_1$ has been cleaved by the tumor specific protease.

In some embodiments, the polypeptide or polypeptide complex has an increased $EC_{50}$ in a T-cell cytolysis assay as compared to the $EC_{50}$ in a T-cell cytolysis assay of an isolated polypeptide or polypeptide complex that does not have $P_1$ or $L_1$. In some embodiments, the polypeptide or polypeptide complex has an increased $EC_{50}$ in a T-cell cytolysis assay that is at least 10× higher than the $EC_{50}$ in a T-cell cytolysis assay of a form of the polypeptide or polypeptide complex that does not have $P_1$ or $L_1$. In some embodiments, the polypeptide or polypeptide complex has an increased $EC_{50}$ in a T-cell cytolysis assay that is at least 20×higher than the $EC_{50}$ in a T-cell cytolysis assay of a form of the polypeptide or polypeptide complex that does not have $P_1$ or $L_1$. In some embodiments, the polypeptide or polypeptide complex has an increased $EC_{50}$ in a T-cell cytolysis assay that is at least 30×higher than the $EC_{50}$ in a T-cell cytolysis assay of a form of the polypeptide or polypeptide complex that does not have $P_1$ or $L_1$. In some embodiments, the polypeptide or polypeptide complex has an increased $EC_{50}$ in a T-cell cytolysis assay that is at least 40×higher than the $EC_{50}$ in a T-cell cytolysis assay of a form of the polypeptide or polypeptide complex that does not have $P_1$ or $L_1$. In some embodiments, the polypeptide or polypeptide complex has an increased $EC_{50}$ in a T-cell cytolysis assay that is at least 50×higher than the $EC_{50}$ in a T-cell cytolysis assay of a form of the polypeptide or polypeptide complex that does not have $P_1$ or $L_1$. In some embodiments, the polypeptide or polypeptide complex has an increased $EC_{50}$ in a T-cell cytolysis assay that is at least 60×higher than the $EC_{50}$ in a T-cell cytolysis assay of a form of the polypeptide or polypeptide complex that does not have $P_1$ or $L_1$. In some embodiments, the polypeptide or polypeptide complex has an increased $EC_{50}$ in a T-cell cytolysis assay that is at least 70×higher than the $EC_{50}$ in a T-cell cytolysis assay of a form of the polypeptide or polypeptide complex that does not have $P_1$ or $L_1$. In some embodiments, the polypeptide or polypeptide complex has an increased $EC_{50}$ in a T-cell cytolysis assay that is at least 80×higher than the $EC_{50}$ in a T-cell cytolysis assay of a form of the polypeptide or polypeptide complex that does not have $P_1$ or $L_1$. In some embodiments, the polypeptide or polypeptide complex has an increased $EC_{50}$ in a T-cell cytolysis assay that is at least 90×higher than the $EC_{50}$ in a T-cell cytolysis assay of a form of the polypeptide or polypeptide complex that does not have $P_1$ or $L_1$. In some embodiments, the polypeptide or polypeptide complex has an increased $EC_{50}$ in a T-cell cytolysis assay that is at least 100× higher than the $EC_{50}$ in a T-cell cytolysis assay of an isolated polypeptide or polypeptide complex that does not have $P_1$ or $L_1$. In some embodiments, the polypeptide or polypeptide complex has an increased $EC_{50}$ in a T-cell cytolysis assay that is at least 1000× higher than the $EC_{50}$ in a T-cell cytolysis assay of an isolated polypeptide or polypeptide complex that does not have $P_1$ or $L_1$.

In some embodiments, the polypeptide or polypeptide complex has an increased $EC_{50}$ in a T-cell cytolysis assay as compared to the $EC_{50}$ in a T-cell cytolysis assay of the polypeptide or polypeptide complex in which $L_1$ has been cleaved by the tumor specific protease. In some embodiments, the polypeptide or polypeptide complex has an increased $EC_{50}$ in a T-cell cytolysis assay that is at least 10× higher than the $EC_{50}$ in a T-cell cytolysis assay of the polypeptide or polypeptide complex in which $L_1$ has been cleaved by the tumor specific protease. In some embodiments, the polypeptide or polypeptide complex has an increased $EC_{50}$ in a T-cell cytolysis assay that is at least 20×higher than the $EC_{50}$ in a T-cell cytolysis assay of the polypeptide or polypeptide complex in which $L_1$ has been cleaved by the tumor specific protease. In some embodiments, the polypeptide or polypeptide complex has an increased $EC_{50}$ in a T-cell cytolysis assay that is at least 30×higher than the $EC_{50}$ in a T-cell cytolysis assay of the polypeptide or polypeptide complex in which $L_1$ has been cleaved by the tumor specific protease. In some embodiments, the polypeptide or polypeptide complex has an increased $EC_{50}$ in a T-cell cytolysis assay that is at least 40×higher than the $EC_{50}$ in a T-cell cytolysis assay of the polypeptide or polypeptide complex in which $L_1$ has been cleaved by the tumor specific protease. In some embodiments, the polypeptide or polypeptide complex has an increased $EC_0$ in a T-cell cytolysis assay that is at least 50×higher than the $EC_{50}$ in a T-cell cytolysis assay of the polypeptide or polypeptide complex in which $L_1$ has been cleaved by the tumor specific protease. In some embodiments, the polypeptide or polypeptide complex has an increased $EC_{50}$ in a T-cell cytolysis assay that is at least 60×higher than the $EC_{50}$ in a T-cell cytolysis assay of the polypeptide or polypeptide complex in which $L_1$ has been cleaved by the tumor specific protease. In some embodiments, the polypeptide or polypeptide complex has an increased $EC_{50}$ in a T-cell cytolysis assay that is at least 70×higher than the $EC_{50}$ in a T-cell cytolysis assay of the polypeptide or polypeptide complex in which $L_1$ has been cleaved by the tumor specific protease. In some embodiments, the polypeptide or polypeptide complex has an increased $EC_{50}$ in a T-cell cytolysis assay that is at least 80×higher than the $EC_{50}$ in a T-cell cytolysis assay of the polypeptide or polypeptide complex in which $L_1$ has been cleaved by the tumor specific protease. In some embodiments, the polypeptide or polypeptide complex has an increased $EC_{50}$ in a T-cell cytolysis assay that is at least 90×higher than the $EC_{50}$ in a T-cell cytolysis assay of the polypeptide or polypeptide complex in which $L_1$ has been cleaved by the tumor specific protease. In some embodiments, the polypeptide or polypeptide complex has an increased $EC_{50}$ in a T-cell cytolysis assay that is at least 100× higher than the $EC_{50}$ in a T-cell cytolysis assay of the polypeptide or polypeptide complex in which $L_1$ has been cleaved by the tumor specific protease. In some embodiments, the polypeptide or polypeptide complex has an increased $EC_{50}$ in a T-cell cytolysis assay that is at least 1,000×higher than the $EC_{50}$ in a T-cell cytolysis assay of the polypeptide or polypeptide complex in which $L_1$ has been cleaved by the tumor specific protease.

In some embodiments, the polypeptide or polypeptide complex $P_2$-$L_2$-$A_2$-$A_1$-$L_1$-$P_1$—$H_1$(Formula Ia) has weaker binding affinity for the tumor cell antigen as compared to the binding affinity for the tumor cell antigen of an isolated polypeptide or polypeptide complex of Formula Ia that does not have $P_1$, $L_1$, $P_2$, or $L_2$. In some embodiments, the polypeptide or polypeptide complex $P_2$-$L_2$-$A_2$-$A_1$-$L_1$-$P_1$—$H_1$ (Formula Ia) has weaker binding affinity for the tumor cell antigen that is at least 10× higher than the binding affinity for the tumor cell antigen of a form of the polypeptide or polypeptide complex of Formula Ia that does not have $P_1$, $L_1$, $P_2$, or $L_2$. In some embodiments, the polypeptide or polypeptide complex $P_2$-$L_2$-$A_2$-$A_1$-$L_1$-$P_1$—$H_1$(Formula Ta) has weaker binding affinity for the tumor cell antigen that is at least 50×higher than the binding affinity for the tumor cell antigen of a form of the polypeptide or polypeptide complex of Formula Ia that does not have $P_1$, $L_1$, $P_2$, or $L_2$. In some embodiments, the polypeptide or polypeptide complex $P_2$-$L_2$-$A_2$-$A_1$-$L_1$-$P_1$—$H_1$ (Formula Ia) has weaker binding affinity for the tumor cell antigen that is at least 75×higher than the binding affinity for the tumor cell antigen of a form of the polypeptide or polypeptide complex of Formula Ta that does not have $P_1$, $L_1$, $P_2$, or $L_2$. In some embodiments, the polypeptide or polypeptide complex $P_2$-$L_2$-$A_2$-$A_1$-$L_1$-$P_1$—$H_1$ (Formula Ia) has weaker binding affinity for the tumor cell antigen that is at least 100×higher than the binding affinity for the tumor cell antigen of a form of the polypeptide or polypeptide complex of Formula Ia that does not have $P_1$, $L_1$, $P_2$, or $L_2$. In some embodiments, the polypeptide or polypeptide complex $P_2$-$L_2$-$A_2$-$A_1$-$L_1$-$P_1$—$H_1$ (Formula Ia) has weaker binding affinity for the tumor cell antigen that is at least 120×higher than the binding affinity for the tumor cell antigen of a form of the polypeptide or polypeptide complex of Formula Ia that does not have $P_1$, $L_1$, $P_2$, or $L_2$. In some embodiments, the polypeptide or polypeptide complex $P_2$-$L_2$-$A_2$-$A_1$-$L_1$-$P_1$—$H_1$ (Formula Ia) has weaker binding affinity for the tumor cell antigen that is at least 200×higher than the binding affinity for the tumor cell antigen of a form of the polypeptide or polypeptide complex of Formula Ia that does not have $P_1$, $L_1$, $P_2$, or $L_2$. In some embodiments, the polypeptide or polypeptide complex $P_2$-$L_2$-$A_2$-$A_1$-$L_1$-$P_1$—$H_1$ (Formula Ia) has weaker binding affinity for the tumor cell antigen that is at least 300× higher than the binding affinity for the tumor cell antigen of a form of the polypeptide or polypeptide complex of Formula Ia that does not have $P_1$, $L_1$, $P_2$, or $L_2$. In some embodiments, the polypeptide or polypeptide complex $P_2$-$L_2$-$A_2$-$A_1$-$L_1$-$P_1$—$H_1$(Formula Ia) has weaker binding affinity for the tumor cell antigen that is at least 400×higher than the binding affinity for the tumor cell antigen of a form of the polypeptide or polypeptide complex of Formula Ia that does not have $P_1$, $L_1$, $P_2$, or $L_2$. In some embodiments, the polypeptide or polypeptide complex $P_2$-$L_2$-$A_2$-$A_1$-$L_1$-$P_1$—$H_1$ (Formula Ia) has weaker binding affinity for the tumor cell antigen that is at least 500×higher than the binding affinity for the tumor cell antigen of a form of the polypeptide or polypeptide complex of Formula Ia that does not have $P_1$, $L_1$, $P_2$, or $L_2$. In some embodiments, the polypeptide or polypeptide complex $P_2$-$L_2$-$A_2$-$A_1$-$L_1$-$P_1$—$H_1$ (Formula Ia) has weaker binding affinity for the tumor cell antigen that is at least 600×higher than the binding affinity for the tumor cell antigen of a form of the polypeptide or polypeptide complex of Formula Ia that does not have $P_1$, $L_1$, $P_2$, or $L_2$. In some embodiments, the polypeptide or polypeptide complex $P_2$-$L_2$-$A_2$-$A_1$-$L_1$-$P_1$—$H_1$ (Formula Ia) has weaker binding affinity for the tumor cell antigen that is at least 700×higher than the binding affinity for the tumor cell antigen of a form of the polypeptide or polypeptide complex of Formula Ia that does not have $P_1$, $L_1$, $P_2$, or $L_2$.

In some embodiments, the polypeptide or polypeptide complex $P_2$-$L_2$-$A_2$-$A_1$-$L_1$-$P_1$—$H_1$ (Formula Ia) has weaker binding affinity for the tumor cell antigen that is at least 800× higher than the binding affinity for the tumor cell antigen of a form of the polypeptide or polypeptide complex of Formula Ia that does not have $P_1$, $L_1$, $P_2$, or $L_2$. In some embodiments, the polypeptide or polypeptide complex $P_2$-$L_2$-$A_2$-$A_1$-$L_1$-$P_1$—$H_1$ (Formula Ia) has weaker binding affinity for the tumor cell antigen that is at least 900×higher than the binding affinity for the tumor cell antigen of a form of the polypeptide or polypeptide complex of Formula Ia that does not have $P_1$, $L_1$, $P_2$, or $L_2$. In some embodiments, the polypeptide or polypeptide complex $P_2$-$L_2$-$A_2$-$A_1$-$L_1$-$P_1$—$H_1$ (Formula Ia) has weaker binding affinity for the tumor cell antigen that is at least 1000×higher than the binding affinity for the tumor cell antigen of a form of the polypeptide or polypeptide complex of Formula Ta that does not have $P_1$, $L_1$, $P_2$, or $L_2$. In some embodiments, the polypeptide or polypeptide complex $P_2$-$L_2$-$A_2$-$A_1$-$L_1$-$P_1$—$H_1$ (Formula Ia) has weaker binding affinity for the tumor cell antigen that is at least 10,000×higher than the binding affinity for the tumor cell antigen of a form of the polypeptide or polypeptide complex of Formula Ia that does not have $P_1$, $L_1$, $P_2$, or $L_2$.

In some embodiments, the polypeptide or polypeptide complex $P_2$-$L_2$-$A_2$-$A_1$-$L_1$-$P_1$—$H_1$(Formula Ia) has weaker binding affinity for the tumor cell antigen as compared to the binding affinity for the tumor cell antigen of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-$L_1$-$P_1$—$H_1$ (Formula Ia) has weaker binding affinity for the tumor cell antigen that is at least 10× higher than the binding affinity for the tumor cell antigen of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-$L_1$-$P_1$—$H_1$ (Formula Ia) has weaker binding affinity for the tumor cell antigen that is at least 50×higher than the binding affinity for the tumor cell antigen of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-$L_1$-$P_1$—$H_1$ (Formula Ia) has weaker binding affinity for the tumor cell antigen that is at least 75×higher than the binding affinity for the tumor cell antigen of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-$L_1$-$P_1$—$H_1$ (Formula Ia) has weaker binding affinity for the tumor cell antigen that is at least 100×higher than the binding affinity for the tumor cell antigen of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-$L_1$-$P_1$—$H_1$ (Formula Ia) has weaker binding affinity for the tumor cell antigen that is at least 120×higher than the binding affinity for the tumor cell antigen of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-$L_1$-$P_1$—$H_1$ (Formula Ia) has weaker binding affinity for the tumor cell antigen that is at least 200×higher than the binding affinity for the tumor cell antigen of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-$L_1$-$P_1$—$H_1$ (Formula Ia) has weaker binding affinity for the tumor cell antigen that is at least 300×higher than the binding affinity for the tumor cell antigen of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-$L_1$-$P_1$—$H_1$ (Formula Ia) has weaker binding affinity for the tumor cell antigen that is at least 400× higher than the binding affinity for the tumor cell antigen of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-$L_1$-$P_1$—$H_1$ (Formula Ia) has weaker binding affinity for the tumor cell antigen that is at least 500×higher than the binding affinity for the tumor cell antigen of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-$L_1$-$P_1$—$H_1$ (Formula Ia) has weaker binding affinity for the tumor cell antigen that is at least 600×higher than the binding affinity for the tumor cell antigen of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-$L_1$-$P_1$—$H_1$ (Formula Ia) has weaker binding affinity for the tumor cell antigen that is at least 700×higher than the binding affinity for the tumor cell antigen of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-$L_1$-$P_1$—$H_1$ (Formula Ia) has weaker binding affinity for the tumor cell antigen that is at least 800×higher than the binding affinity for the tumor cell antigen of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-$L_1$-$P_1$—$H_1$ (Formula Ia) has weaker binding affinity for the tumor cell antigen that is at least 900×higher than the binding affinity for the tumor cell antigen of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-$L_1$-$P_1$—$H_1$ (Formula Ia) has weaker binding affinity for the tumor cell antigen that is at least 1000× higher than the binding affinity for the tumor cell antigen of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-$L_1$-$P_1$—$H_1$ (Formula Ia) has weaker binding affinity for the tumor cell antigen that is at least 10,000×higher than the binding affinity for the tumor cell antigen of the polypeptide or polypeptide complex of Formula Ia in which $L_1$ and $L_2$ have been cleaved by the tumor specific proteases.

In some embodiments, the polypeptide or polypeptide complex $P_2$-$L_2$-$A_2$-$A_1$-$L_1$-$P_1$—$H_1$(Formula Ia) has an increased $EC_{50}$ in an IFNγ release T-cell activation assay as compared to the $EC_{50}$ in an IFNγ release T-cell activation assay of an isolated polypeptide or polypeptide complex of Formula Ia that does not have $P_1$, $L_1$, $P_2$, or $L_2$. In some embodiments, the polypeptide or polypeptide complex $P_2$-$L_2$-$A_2$-$A_1$-$L_1$-$P_1$—$H_1$ (Formula Ia) has an increased $EC_{50}$ in an IFNγ release T-cell activation assay that is at least 10× higher than the $EC_{50}$ in an IFNγ release T-cell activation assay of a form of the polypeptide or polypeptide complex of Formula Ia that does not have $P_1$, $L_1$, $P_2$, or $L_2$. In some embodiments, the polypeptide or polypeptide complex $P_2$-$L_2$-$A_2$-$A_1$-$L_1$-$P_1$—$H_1$ (Formula Ia) has an increased $EC_{50}$ in an IFNγ release T-cell activation assay that is at least 50×higher than the $EC_{50}$ in an IFNγ release T-cell activation assay of a form of the polypeptide or polypeptide complex of Formula Ia that does not have $P_1$, $L_1$, $P_2$, or $L_2$. In some embodiments, the polypeptide or polypeptide complex $P_2$-$L_2$-$A_2$-$A_1$-$L_1$-$P_1$—$H_1$ (Formula Ia) has an increased $EC_{50}$ in an IFNγ release T-cell activation assay that is at least 75×higher than the $EC_{50}$ in an IFNγ release T-cell activation assay of a form of the polypeptide or polypeptide complex of Formula Ia that does not have $P_1$, $L_1$, $P_2$, or $L_2$. In some embodiments, the polypeptide or polypeptide complex $P_2$-$L_2$-$A_2$-$A_1$-$L_1$-$P_1$—$H_1$ (Formula Ia) has an increased $EC_{50}$ in an IFNγ release T-cell activation assay that is at least 100× higher than the $EC_{50}$ in an IFNγ release T-cell activation assay of a form of the polypeptide or polypeptide complex of Formula Ia that does not have $P_1$, $L_1$, $P_2$, or $L_2$. In some embodiments, the polypeptide or polypeptide complex $P_2$-$L_2$-$A_2$-$A_1$-$L_1$-$P_1$—$H_1$ (Formula Ia) has an increased $EC_{50}$ in an IFNγ release T-cell activation assay that is at least 200×higher than the $EC_{50}$ in an IFNγ release T-cell activation assay of a form of the polypeptide or polypeptide complex of Formula Ia that does not have $P_1$, $L_1$, $P_2$, or $L_2$. In some embodiments, the polypeptide or polypeptide complex $P_2$-$L_2$-$A_2$-$A_1$-$L_1$-$P_1$—$H_1$ (Formula Ia) has an increased $EC_{50}$ in an IFNγ release T-cell activation assay that is at least 300×higher than the $EC_{50}$ in an IFNγ release T-cell activation assay of a form of the polypeptide or polypeptide complex of Formula Ia that does not have $P_1$, $L_1$, $P_2$, or $L_2$. In some embodiments, the polypeptide or polypeptide complex $P_2$-$L_2$-$A_2$-$A_1$-$L_1$-$P_1$—$H_1$ (Formula Ia) has an increased $EC_0$ in an IFNγ release T-cell activation assay that is at least 400×higher than the $EC_{50}$ in an IFNγ release T-cell activation assay of a form of the polypeptide or polypeptide complex of Formula Ia that does not have $P_1$, $L_1$, $P_2$, or $L_2$. In some embodiments, the polypeptide or polypeptide complex $P_2$-$L_2$-$A_2$-$A_1$-$L_1$-$P_1$—$H_1$ (Formula Ia) has an increased $EC_0$ in an IFNγ release T-cell activation assay that is at least 500×higher than the $EC_{50}$ in an IFNγ release T-cell activation assay of a form of the polypeptide or polypeptide complex of Formula Ia that does not have $P_1$, $L_1$, $P_2$, or $L_2$. In some embodiments, the polypeptide or polypeptide complex $P_2$-$L_2$-$A_2$-$A_1$-$L_1$-$P_1$—$H_1$ (Formula Ia) has an increased $EC_{50}$ in an IFNγ release T-cell activation assay that is at least 600×higher than the $EC_{50}$ in an IFNγ release T-cell activation assay of a form of the polypeptide or polypeptide complex of Formula Ia that does not have $P_1$, $L_1$, $P_2$, or $L_2$. In some embodiments, the polypeptide or polypeptide complex $P_2$-$L_2$-$A_2$-$A_1$-$L_1$-$P_1$—$H_1$ (Formula Ia) has an increased $EC_{50}$ in an IFNγ release T-cell activation assay that is at least 700×higher than the $EC_{50}$ in an IFNγ release T-cell activation assay of a form of the polypeptide or polypeptide complex of Formula Ia that does not $P_1$, $L_1$, $P_2$, or $L_2$. In some embodiments, the polypeptide or polypeptide complex $P_2$-$L_2$-$A_2$-$A_1$-$L_1$-$P_1$—$H_1$(Formula Ia) has an increased $EC_{50}$ in an IFNγ release T-cell activation assay that is at least 800×higher than the $EC_{50}$ in an IFNγ release T-cell activation assay of a form of the polypeptide or polypeptide complex of Formula Ia that does not have $P_1$, $L_1$, $P_2$, or $L_2$. In some embodiments, the polypeptide or polypeptide complex $P_2$-$L_2$-$A_2$-$A_1$-$L_1$-$P_1$—$H_1$ (Formula Ia) has an increased $EC_{50}$ in an IFNγ release T-cell activation assay that is at least 900×higher than the $EC_{50}$ in an IFNγ release T-cell activation assay of a form of the polypeptide or polypeptide complex of Formula Ia that does not have $P_1$, $L_1$, $P_2$, or $L_2$.

In some embodiments, the polypeptide or polypeptide complex $P_2$-$L_2$-$A_2$-$A_1$-$L_1$-$P_1$—$H_1$ (Formula Ia) has an increased $EC_{50}$ in an IFNγ release T-cell activation assay that is at least 1000× higher than the $EC_{50}$ in an IFNγ release T-cell activation assay of a form of the polypeptide or polypeptide complex of Formula Ia that does not have $P_1$, $L_1$, $P_2$, or $L_2$. In some embodiments, the polypeptide or polypeptide complex $P_2$-$L_2$-$A_2$-$A_1$-$L_1$-$P_1$—$H_1$ (Formula Ia) has an increased $EC_{50}$ in an IFNγ release T-cell activation assay that is at least 10,000×higher than the $EC_{50}$ in an IFNγ release T-cell activation assay of a form of the polypeptide or polypeptide complex of Formula Ia that does not have $P_1$, $L_1$, $P_2$, or $L_2$.

In some embodiments, the polypeptide or polypeptide complex $P_2$-$L_2$-$A_2$-$A_1$-$L_1$-$P_1$—$H_1$(Formula Ia) has an increased $EC_{50}$ in a T-cell cytolysis assay as compared to the $EC_{50}$ in a T-cell cytolysis assay of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-$L_1$-$P_1$—$H_1$ (Formula Ia) has an increased $EC_{50}$ in a T-cell cytolysis assay that is at least 10× higher than the $EC_{50}$ in a T-cell cytolysis assay of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-$L_1$-$P_1$—$H_1$ (Formula Ia) has an increased $EC_{50}$ in a T-cell cytolysis assay that is at least 50×higher than the $EC_{50}$ in a T-cell cytolysis assay of the polypeptide or polypeptide complex of Formula Ta in which $L_1$ and $L_2$ have been cleaved by the tumor specific proteases. In some embodiments, the polypeptide or polypeptide complex $P_2$-$L_2$-$A_2$-$A_1$-$L_1$-$P_1$—$H_1$ (Formula Ia) has an increased $EC_{50}$ in a T-cell cytolysis assay that is at least 75×higher than the $EC_{50}$ in a T-cell cytolysis assay of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-$L_1$-$P_1$—$H_1$ (Formula Ia) has an increased $EC_{50}$ in a T-cell cytolysis assay that is at least 100× higher than the $EC_{50}$ in a T-cell cytolysis assay of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-$L_1$-$P_1$—$H_1$ (Formula Ia) has an increased $EC_{50}$ in a T-cell cytolysis assay that is at least 200×higher than the $EC_{50}$ in a T-cell cytolysis assay of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-$L_1$-$P_1$—$H_1$ (Formula Ia) has an increased $EC_{50}$ in a T-cell cytolysis assay that is at least 300×higher than the $EC_{50}$ in a T-cell cytolysis assay of the polypeptide or polypeptide complex of Formula Ta in which $L_1$ and $L_2$ have been cleaved by the tumor specific proteases. In some embodiments, the polypeptide or polypeptide complex $P_2$-$L_2$-$A_2$-$A_1$-$L_1$-$P_1$—$H_1$ (Formula Ia) has an increased $EC_{50}$ in a T-cell cytolysis assay that is at least 400×higher than the $EC_{50}$ in a T-cell cytolysis assay of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-$L_1$-$P_1$—$H_1$ (Formula Ia) has an increased $EC_{50}$ in a T-cell cytolysis assay that is at least 500×higher than the $EC_{50}$ in a T-cell cytolysis assay of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-$L_1$-$P_1$—$H_1$ (Formula Ia) has an increased $EC_{50}$ in a T-cell cytolysis assay that is at least 600×higher than the $EC_{50}$ in a T-cell cytolysis assay of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-$L_1$-$P_1$—$H_1$ (Formula Ia) has an increased $EC_{50}$ in a T-cell cytolysis assay that is at least 700×higher than the $EC_{50}$ in a T-cell cytolysis assay of the polypeptide or polypeptide complex of Formula Ta in which $L_1$ and $L_2$ have been cleaved by the tumor specific proteases. In some embodiments, the polypeptide or polypeptide complex $P_2$-$L_2$-$A_2$-$A_1$-$L_1$-$P_1$—$H_1$ (Formula Ia) has an increased $EC_{50}$ in a T-cell cytolysis assay that is at least 800×higher than the $EC_{50}$ in a T-cell cytolysis assay of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-$L_1$-$P_1$—$H_1$ (Formula Ia) has an increased $EC_{50}$ in a T-cell cytolysis assay that is at least 900×higher than the $EC_{50}$ in a T-cell cytolysis assay of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-$L_1$-$P_1$—$H_1$ (Formula Ia) has an increased $EC_{50}$ in a T-cell cytolysis assay that is at least 1000×higher than the $EC_{50}$ in a T-cell cytolysis assay of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-$L_1$-$P_1$—$H_1$ (Formula Ia) has an increased $EC_{50}$ in a T-cell cytolysis assay that is at least 10,000×higher than the $EC_{50}$ in a T-cell cytolysis assay of the polypeptide or polypeptide complex of Formula Ia in which $L_1$ and $L_2$ have been cleaved by the tumor specific proteases.

In some embodiments, the polypeptide or polypeptide complex $P_2$-$L_2$-$A_2$-$A_1$-$L_1$-$P_1$—$H_1$(Formula Ia) has an increased $EC_{50}$ in a T-cell cytolysis assay as compared to the $EC_{50}$ in a T-cell cytolysis assay of an isolated polypeptide or polypeptide complex that does not have $P_1$, $L_1$, $P_2$, or $L_2$. In some embodiments, the polypeptide or polypeptide complex $P_2$-$L_2$-$A_2$-$A_1$-$L_1$-$P_1$—$H_1$ (Formula Ia) has an increased $EC_{50}$ in a T-cell cytolysis assay that is at least 10× higher than the $EC_{50}$ in a T-cell cytolysis assay of a form of the polypeptide or polypeptide complex of Formula Ia that does not have $P_1$, $L_1$, $P_2$, or $L_2$. In some embodiments, the polypeptide or polypeptide complex $P_2$-$L_2$-$A_2$-$A_1$-$L_1$-$P_1$—$H_1$ (Formula Ia) has an increased $EC_{50}$ in a T-cell cytolysis assay that is at least 50×higher than the $EC_{50}$ in a T-cell cytolysis assay of a form of the polypeptide or polypeptide complex of Formula Ia that does not have $P_1$, $L_1$, $P_2$, or $L_2$. In some embodiments, the polypeptide or polypeptide complex $P_2$-$L_2$-$A_2$-$A_1$-$L_1$-$P_1$—$H_1$ (Formula Ia) has an increased $EC_{50}$ in a T-cell cytolysis assay that is at least 75×higher than the $EC_{50}$ in a T-cell cytolysis assay of a form of the polypeptide or polypeptide complex of Formula Ia that does not have $P_1$, $L_1$, $P_2$, or $L_2$. In some embodiments, the polypeptide or polypeptide complex $P_2$-$L_2$-$A_2$-$A_1$-$L_1$-$P_1$—$H_1$ (Formula Ia) has an increased $EC_{50}$ in a T-cell cytolysis assay that is at least 100×higher than the $EC_{50}$ in a T-cell cytolysis assay of an isolated polypeptide or polypeptide complex that does not have $P_1$, $L_1$, $P_2$, or $L_2$. In some embodiments, the polypeptide or polypeptide complex $P_2$-$L_2$-$A_2$-$A_1$-$L_1$-$P_1$—$H_1$ (Formula Ia) has an increased $EC_{50}$ in a T-cell cytolysis assay that is at least 200×higher than the $EC_{50}$ in a T-cell cytolysis assay of an isolated polypeptide or polypeptide complex that does not have $P_1$, $L_1$, $P_2$, or $L_2$. In some embodiments, the polypeptide or polypeptide complex $P_2$-$L_2$-$A_2$-$A_1$-$L_1$-$P_1$—$H_1$ (Formula Ia) has an increased $EC_{50}$ in a T-cell cytolysis assay that is at least 300×higher than the $EC_{50}$ in a T-cell cytolysis assay of an isolated polypeptide or polypeptide complex that does not have $P_1$, $L_1$, $P_2$, or $L_2$. In some embodiments, the polypeptide or polypeptide complex $P_2$-$L_2$-$A_2$-$A_1$-$L_1$-$P_1$—$H_1$ (Formula Ia) has an increased $EC_{50}$ in a T-cell cytolysis assay that is at least 400×higher than the $EC_{50}$ in a T-cell cytolysis assay of an isolated polypeptide or polypeptide complex that does not have $P_1$, $L_1$, $P_2$, or $L_2$. In some embodiments, the polypeptide or polypeptide complex $P_2$-$L_2$-$A_2$-$A_1$-$L_1$-$P_1$—$H_1$ (Formula Ia) has an increased $EC_{50}$ in a T-cell cytolysis assay that is at least 500×higher than the $EC_{50}$ in a T-cell cytolysis assay of an isolated polypeptide or polypeptide complex that does not have $P_1$, $L_1$, $P_2$, or $L_2$. In some embodiments, the polypeptide or polypeptide complex $P_2$-$L_2$-$A_2$-$A_1$-$L_1$-$P_1$—$H_1$ (Formula Ia) has an increased $EC_{50}$ in a T-cell cytolysis assay that is at least 600×higher than the $EC_{50}$ in a T-cell cytolysis assay of an isolated polypeptide or polypeptide complex that does not have $P_1$, $L_1$, $P_2$, or $L_2$. In some embodiments, the polypeptide or polypeptide complex $P_2$-$L_2$-$A_2$-$A_1$-$L_1$-$P_1$—$H_1$ (Formula Ia) has an increased $EC_{50}$ in a T-cell cytolysis assay that is at least 700×higher than the $EC_{50}$ in a T-cell cytolysis assay of an isolated polypeptide or polypeptide complex that does not have $P_1$, $L_1$, $P_2$, or $L_2$. In some embodiments, the polypeptide or polypeptide complex $P_2$-$L_2$-$A_2$-$A_1$-$L_1$-$P_1$—$H_1$ (Formula Ia) has an increased $EC_{50}$ in a T-cell cytolysis assay that is at least 800×higher than the $EC_{50}$ in a T-cell cytolysis assay of an isolated polypeptide or polypeptide complex that does not have $P_1$, $L_1$, $P_2$, or $L_2$. In some embodiments, the polypeptide or polypeptide complex $P_2$-$L_2$-$A_2$-$A_1$-$L_1$-$P_1$—$H_1$ (Formula Ia) has an increased $EC_{50}$ in a T-cell cytolysis assay that is at least 900×higher than the $EC_{50}$ in a T-cell cytolysis assay of an isolated polypeptide or polypeptide complex that does not have $P_1$, $L_1$, $P_2$, or $L_2$. In some embodiments, the polypeptide or polypeptide complex $P_2$-$L_2$-$A_2$-$A_1$-$L_1$-$P_1$—$H_1$ (Formula Ia) has an increased $EC_{50}$ in a T-cell cytolysis assay that is at least 1000× higher than the $EC_{50}$ in a T-cell cytolysis assay of an isolated polypeptide or polypeptide complex that does not have $P_1$, $L_1$, $P_2$, or $L_2$. In some embodiments, the polypeptide or polypeptide complex $P_2$-$L_2$-$A_2$-$A_1$-$L_1$-$P_1$—$H_1$ (Formula Ia) has an increased $EC_{50}$ in a T-cell cytolysis assay that is at least 10,000× higher than the $EC_{50}$ in a T-cell cytolysis assay of an isolated polypeptide or polypeptide complex that does not have $P_1$, $L_1$, $P_2$, or $L_2$.

In some embodiments, the polypeptide or polypeptide complex $P_2$-$L_2$-$A_2$-$A_1$-$L_1$-$P_1$—$H_1$(Formula Ia) has an increased $EC_{50}$ in a T-cell cytolysis assay as compared to the $EC_{50}$ in a T-cell cytolysis assay of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-$L_1$-$P_1$—$H_1$ (Formula Ia) has an increased $EC_{50}$ in a T-cell cytolysis assay that is at least 10× higher than the $EC_{50}$ in a T-cell cytolysis assay of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-$L_1$-$P_1$—$H_1$ (Formula Ia) has an increased $EC_{50}$ in a T-cell cytolysis assay that is at least 50×higher than the $EC_{50}$ in a T-cell cytolysis assay of the polypeptide or polypeptide complex of Formula Ta in which $L_1$ and $L_2$ have been cleaved by the tumor specific proteases. In some embodiments, the polypeptide or polypeptide complex $P_2$-$L_2$-$A_2$-$A_1$-$L_1$-$P_1$—$H_1$ (Formula Ia) has an increased $EC_{50}$ in a T-cell cytolysis assay that is at least 75×higher than the $EC_{50}$ in a T-cell cytolysis assay of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-$L_1$-$P_1$—$H_1$ (Formula Ia) has an increased $EC_{50}$ in a T-cell cytolysis assay that is at least 100×higher than the $EC_{50}$ in a T-cell cytolysis assay of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-$L_1$-$P_1$—$H_1$ (Formula Ia) has an increased $EC_{50}$ in a T-cell cytolysis assay that is at least 200×higher than the $EC_{50}$ in a T-cell cytolysis assay of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-$L_1$-$P_1$—$H_1$ (Formula Ia) has an increased $EC_{50}$ in a T-cell cytolysis assay that is at least 300×higher than the $EC_{50}$ in a T-cell cytolysis assay of the polypeptide or polypeptide complex of Formula Ta in which $L_1$ and $L_2$ have been cleaved by the tumor specific proteases. In some embodiments, the polypeptide or polypeptide complex $P_2$-$L_2$-$A_2$-$A_1$-$L_1$-$P_1$—$H_1$ (Formula Ia) has an increased $EC_{50}$ in a T-cell cytolysis assay that is at least 400×higher than the $EC_{50}$ in a T-cell cytolysis assay of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-$L_1$-$P_1$—$H_1$ (Formula Ia) has an increased $EC_{50}$ in a T-cell cytolysis assay that is at least 500×higher than the $EC_{50}$ in a T-cell cytolysis assay of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-$L_1$-$P_1$—$H_1$ (Formula Ia) has an increased $EC_{50}$ in a T-cell cytolysis assay that is at least 600×higher than the $EC_{50}$ in a T-cell cytolysis assay of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-$L_1$-$P_1$—$H_1$ (Formula Ia) has an increased $EC_{50}$ in a T-cell cytolysis assay that is at least 700×higher than the $EC_{50}$ in a T-cell cytolysis assay of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-$L_1$-$P_1$—$H_1$ (Formula Ia) has an increased $EC_{50}$ in a T-cell cytolysis assay that is at least 800×higher than the $EC_{50}$ in a T-cell cytolysis assay of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-$L_1$-$P_1$—$H_1$ (Formula Ia) has an increased $EC_{50}$ in a T-cell cytolysis assay that is at least 900×higher than the $EC_{50}$ in a T-cell cytolysis assay of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-$L_1$-$P_1$—$H_1$ (Formula Ia) has an increased $EC_{50}$ in a T-cell cytolysis assay that is at least 1000×higher than the $EC_{50}$ in a T-cell cytolysis assay of the polypeptide or polypeptide complex of Formula Ia in which $L_1$ and $L_2$ have been cleaved by the tumor specific proteases. In some embodiments, the polypeptide or polypeptide complex $P_2$-$L_2$-$A_2$-$A_1$-$L_1$-$P_1$—$H_1$ (Formula Ia) has an increased $EC_{50}$ in a T-cell cytolysis assay that is at least 10,000×higher than the $EC_{50}$ in a T-cell cytolysis assay of the polypeptide or polypeptide complex of Formula Ia in which L₁ and L₂ have been cleaved by the tumor specific proteases.

Second Antigen Recognizing Molecule (A₂)

In some embodiments, A₂ comprises an antibody or antibody fragment. In some embodiments, the antibody or antibody fragment thereof comprises a single chain variable fragment, a single domain antibody, a Fab, or a Fab'. In some embodiments, the antibody or antibody fragment thereof comprises a single chain variable fragment (scFv), a heavy chain variable domain (VH domain), a light chain variable domain (VL domain), or a variable domain (VHH) of a camelid derived single domain antibody. In some embodiments, the antibody or antibody fragment thereof is humanized or human. In some embodiments, A₂ is the Fab or Fab'. In some embodiments, the Fab or Fab' comprises (a) a Fab light chain polypeptide and (b) a Fab heavy chain polypeptide. In some embodiments, the antibody or antibody fragment thereof comprises a PSMA binding domain.

In some embodiments, the antigen binding fragment (Fab) or Fab' that binds to PSMA comprises a Fab light chain polypeptide chain and a Fab heavy chain polypeptide. In some embodiments, the Fab light chain polypeptide comprises a Fab light chain variable domain. In some embodiments, the Fab heavy chain polypeptide comprises a Fab heavy chain variable domain. In some embodiments, the Fab heavy chain variable domain comprises at least one, two, or three complementarity determining regions (CDR)s disclosed in Table 2 or a sequence substantially identical thereto (e.g., a sequence that has at least 90%, 95%, 96%, 97%, 98%, or 99% sequence identity). In some embodiments, the Fab light chain variable domain comprises at least one, two, or three complementarity determining regions (CDR)s disclosed in Table 2 or a sequence substantially identical thereto (e.g., a sequence that has at least 90%, 95%, 96%, 97%, 98%, or 99% sequence identity).

In some embodiments, the Fab heavy chain variable domain comprises at least one, two, or three complementarity determining regions (CDR)s disclosed in Table 2 or a sequence substantially identical thereto (e.g., a sequence that has at least 90%, 95%, 96%, 97%, 98%, or 99% sequence identity); and the Fab light chain variable domain comprises at least one, two, or three complementarity determining regions (CDR)s disclosed in Table 2 or a sequence substantially identical thereto (e.g., a sequence that has at least 90%, 95%, 96%, 97%, 98%, or 99% sequence identity).

TABLE 2 anti-PSMA amino acid sequences
(CDRs as determined by IMGT numbering system)

| Construct Description | Amino Acid Sequence (N to C) | SEQ ID NO: |
|---|---|---|
| PSMA: HC: CDR1 | GFAFSRYG | 8 |
| PSMA: HC: CDR2 | IWYDGSNK | 9 |
| PSMA: HC: CDR3 | ARGGDFLYYYYYGMDV | 10 |
| PSMA: LC: CDR1 | QGISNY | 11 |
| PSMA: LC: CDR2 | EA | 12 |
| PSMA: LC: CDR3 | QNYNSAPFT | 13 |
| 006 PSMA Fab LC | DIQMTQSPSSLSASVGDRVTITCR ASQGISNYLAWYQQKTGKVPKF LIYEASTLQSGVPSRFSGGGSGTD FTLTISSLQPEDVATYYCQNYNSA | 14 |

TABLE 2-continued anti-PSMA amino acid sequences
(CDRs as determined by IMGT numbering system)

| Construct Description | Amino Acid Sequence (N to C) | SEQ ID NO: |
|---|---|---|
| | PFTFGPGTKVDIKRTVAAPSVFIFP PSDEQLKSGTASVVCLLNNFYPRE AKVQWKVDNALQSGNSQESVTE QDSKDSTYSLSSTLTLSKADYEKH KVYACEVTHQGLSSPVTKSFNRG EC | |
| 006 PSMA Fab HC | QVQLVESGGGVVQPGRSLRLSCA ASGFAFSRYGMHWVRQAPGKGL EWVAVIWYDGSNKYYADSVKG RFTISRDNSKNTQYLQMNSLRAE DTAVYYCARGGDFLYYYYYGM DVWGQGTTVTVSSASTKGPSVFP LAPSSKSTSGGTAALGCLVKDYFP EPVTVSWNSGALTSGVHTFPAVL QSSGLYSLSSVVTVPSSSLGTQTYI CNVNHKPSNTKVDKKVEPKSC | 15 |

In some embodiments, the Fab comprises complementarity determining regions (CDRs): HC-CDR1, HC-CDR2, and HC-CDR3, wherein the HC-CDR1, the HC-CDR2, and the HC-CDR3 of the Fab comprise: HC-CDR1: SEQ ID NO: 8, HC-CDR2: SEQ ID NO: 9, and HC-CDR3: SEQ ID NO: 10; and the Fab comprises CDRs: LC-CDR1, LC-CDR2, and LC-CDR3, wherein the LC-CDR1, the LC-CDR2, and the LC-CDR3 of the Fab comprise LC-CDR1: SEQ ID NO: 11, LC-CDR2: SEQ ID NO: 12, and LC-CDR3: SEQ ID NO: 13. In some embodiments, the Fab comprises complementarity determining regions (CDRs): HC-CDR1, HC-CDR2, and HC-CDR3, wherein the HC-CDR1, the HC-CDR2, and the HC-CDR3 of the Fab comprise: HC-CDR1: SEQ ID NO: 8, HC-CDR2: SEQ ID NO: 9, and HC-CDR3: SEQ ID NO: 10 and wherein the CDRs comprise from 0-2 amino acid modifications in at least one of the HC-CDR1, HC-CDR2, or HC-CDR3; and the Fab comprises CDRs: LC-CDR1, LC-CDR2, and LC-CDR3, wherein the LC-CDR1, the LC-CDR2, and the LC-CDR3 of the Fab comprise LC-CDR1: SEQ ID NO: 11, LC-CDR2: SEQ ID NO:12, and LC-CDR3: SEQ ID NO: 13 and wherein the CDRs comprise from 0-2 amino acid modifications in at least one of the LC-CDR1, LC-CDR2, or LC-CDR3.

In some embodiments, A₂ comprises complementarity determining regions (CDRs): HC-CDR1, HC-CDR2, and HC-CDR3, wherein the HC-CDR1, the HC-CDR2, and the HC-CDR3 of A₂ comprise: HC-CDR1: SEQ ID NO: 8, HC-CDR2: SEQ ID NO: 9, and HC-CDR3: SEQ ID NO: 10; and A₂ comprises CDRs: LC-CDR1, LC-CDR2, and LC-CDR3, wherein the LC-CDR1, the LC-CDR2, and the LC-CDR3 of A₂ comprise LC-CDR1: SEQ ID NO: 11, LC-CDR2: SEQ ID NO:12, and LC-CDR3: SEQ ID NO: 13. In some embodiments, A₂ comprises complementarity determining regions (CDRs): HC-CDR1, HC-CDR2, and HC-CDR3, wherein the HC-CDR1, the HC-CDR2, and the HC-CDR3 of A₂ comprise: HC-CDR1: SEQ ID NO: 8, HC-CDR2: SEQ ID NO: 9, and HC-CDR3: SEQ ID NO: 10 and wherein the CDRs comprise from 0-2 amino acid modifications in at least one of the HC-CDR1, HC-CDR2, or HC-CDR3; and A₂ comprises CDRs: LC-CDR1, LC-CDR2, and LC-CDR3, wherein the LC-CDR1, the LC-CDR2, and the LC-CDR3 of A₂ comprise LC-CDR1: SEQ ID NO: 11, LC-CDR2: SEQ ID NO:12, and LC-CDR3: SEQ ID NO: 13 and wherein the CDRs comprise from 0-2 amino acid modifications in at least one of the LC-CDR1, LC-CDR2, or LC-CDR3.

In some embodiments, the Fab light chain polypeptide comprises an amino acid sequence according to SEQ ID NO: 14. In some embodiments, the Fab light chain polypeptide comprises an amino acid sequence that has at least 80% sequence identity according to SEQ ID NO: 14. In some embodiments, the Fab light chain polypeptide comprises an amino acid sequence that has at least 85% sequence identity according to SEQ ID NO: 14. In some embodiments, the Fab light chain polypeptide comprises an amino acid sequence that has at least 90% sequence identity according to SEQ ID NO: 14. In some embodiments, the Fab light chain polypeptide comprises an amino acid sequence that has at least 95% sequence identity according to SEQ ID NO: 14. In some embodiments, the Fab light chain polypeptide comprises an amino acid sequence that has at least 99% sequence identity according to SEQ ID NO: 14.

In some embodiments, the Fab heavy chain polypeptide comprises an amino acid sequence according to SEQ ID NO: 15. In some embodiments, the Fab heavy chain polypeptide comprises an amino acid sequence that has at least 80% sequence identity according to SEQ ID NO: 15. In some embodiments, the Fab heavy chain polypeptide comprises an amino acid sequence that has at least 85% sequence identity according to SEQ ID NO: 15. In some embodiments, the Fab heavy chain polypeptide comprises an amino acid sequence that has at least 90% sequence identity according to SEQ ID NO: 15. In some embodiments, the Fab heavy chain polypeptide comprises an amino acid sequence that has at least 95% sequence identity according to SEQ ID NO: 15. In some embodiments, the Fab heavy chain polypeptide comprises an amino acid sequence that has at least 99% sequence identity according to SEQ ID NO: 15.

In some embodiments, the Fab light chain polypeptide of $A_2$ is bound to a C-terminus of the single chain variable fragment (scFv) of $A_1$. In some embodiments, the Fab heavy chain polypeptide of $A_2$ is bound to a C-terminus of the single chain variable fragment (scFv) $A_1$. In some embodiments, the Fab light chain polypeptide of $A_2$ is bound to a N-terminus of the single chain variable fragment (scFv) of $A_1$. In some embodiments, the Fab heavy chain polypeptide of $A_2$ is bound to a N-terminus of the single chain variable fragment (scFv) $A_1$. In some embodiments, the Fab heavy chain polypeptide of $A_2$ is bound to the scFv heavy chain polypeptide of $A_1$. In some embodiments, the Fab light chain polypeptide of $A_2$ is bound to the scFv heavy chain polypeptide of $A_1$. In some embodiments, the Fab heavy chain polypeptide of $A_2$ is bound to the scFv light chain polypeptide of A1. In some embodiments, the Fab light chain polypeptide of $A_2$ is bound to the scFv light chain polypeptide of $A_1$.

In some embodiments, $A_2$ further comprises $P_2$ and $L_2$, wherein $P_2$ comprises a peptide that binds to $A_2$; and $L_2$ comprises a linking moiety that connects $A_2$ to $P_2$ and is a substrate for a tumor specific protease. In some embodiments, the Fab heavy chain polypeptide of $A_2$ is bound to the scFv heavy chain polypeptide of $A_1$ and $L_2$ is bound to the Fab light chain polypeptide of $A_2$. In some embodiments, the Fab light chain polypeptide of $A_2$ is bound to the scFv heavy chain polypeptide of $A_1$ and $L_2$ is bound to the Fab heavy chain polypeptide of $A_2$. In some embodiments, the Fab heavy chain polypeptide of $A_2$ is bound to the scFv light chain polypeptide of $A_1$ and $L_2$ is bound to the Fab light chain polypeptide of $A_2$. In some embodiments, the Fab light chain polypeptide of $A_2$ is bound to the scFv light chain polypeptide of $A_1$ and $L_2$ is bound to the Fab heavy chain polypeptide of $A_2$.

In some embodiments, the Fab heavy chain polypeptide of $A_2$ is bound to the scFv heavy chain polypeptide of $A_1$ and $L_2$ is bound to the Fab light chain polypeptide of $A_2$. In some embodiments, the Fab light chain polypeptide of $A_2$ is bound to the scFv heavy chain polypeptide of $A_1$ and $L_2$ is bound to the Fab heavy chain polypeptide of $A_2$. In some embodiments, the Fab heavy chain polypeptide of $A_2$ is bound to the scFv light chain polypeptide of $A_1$ and $L_2$ is bound to the Fab light chain polypeptide of $A_2$. In some embodiments, the Fab light chain polypeptide of $A_2$ is bound to the scFv light chain polypeptide of $A_1$ and $L_2$ is bound to the Fab heavy chain polypeptide of $A_2$.

Peptide ($P_1$ and $P_2$ and $P_1$)

In some embodiments, $P_1$, $P_2$, or $P_{1a}$ comprises a sequence as disclosed in Table 3 or a sequence substantially identical thereto (e.g., a sequence that has 0, 1, or 2 amino acid modifications).

TABLE 3

| $P_1$ and $P_2$ and $P_{1a}$ Sequences | | |
|---|---|---|
| Construct Description | Amino Acid Sequence (N to C) | SEQ ID NO: |
| SP34.185 scFv mask | GGGSQCLGPEWEVCPY | 16 |
| SP34.185 scFv mask | GGVYCGPEFDESVGCM | 17 |
| SP34.185 scFv mask Peptide-A | GSQCLGPEWEVCPY | 18 |
| SP34.185 scFv mask Peptide-B | VYCGPEFDESVGCM | 19 |
| SP34.194 scFv mask Peptide-AM | YLWGCEWNCAGITT | 78 |

In some embodiments, $P_1$ impairs binding of $A_1$ to a first target antigen. In some embodiments, $P_1$ impairs binding of $A_1$ to the effector cell antigen. In some embodiments, $P_1$ is bound to $A_1$ through ionic interactions, electrostatic interactions, hydrophobic interactions, Pi-stacking interactions, and H-bonding interactions, or a combination thereof. In some embodiments, $P_1$ is bound to $A_1$ at or near an antigen binding site. In some embodiments, $P_1$ becomes unbound from $A_1$ when $L_1$ is cleaved by the tumor specific protease thereby exposing $A_1$ to the effector cell antigen. In some embodiments, the protease comprises a matrix metalloprotease (MMP) or a serine protease. In some embodiments, the matrix metalloprotease comprises MMP2, MMP7, MMP9, MMP13, or MMP14. In some embodiments, the serine protease comprises matriptase (MTSP1), urokinase, or hepsin. In some embodiments, $P_1$ has less than 70% sequence identity to the effector cell antigen. In some embodiments, $P_1$ has less than 75% sequence identity to the effector cell antigen. In some embodiments, $P_1$ has less than 80% sequence identity to the effector cell antigen. In some embodiments, $P_1$ has less than 85% sequence identity to the effector cell antigen. In some embodiments, $P_1$ has less than 90% sequence identity to the effector cell antigen. In some embodiments, $P_1$ has less than 95% sequence identity to the effector cell antigen. In some embodiments, $P_1$ has less than 98% sequence identity to the effector cell antigen. In some embodiments, $P_1$ has less than 99% sequence identity to the effector cell antigen. In some embodiments, $P_1$ comprises a de novo amino acid sequence that shares less than 10% sequence identity to the effector cell antigen. In some embodiments, $P_1$ comprises an amino acid sequence according to any one of SEQ ID NOs: 16-19. In some embodiments, $P_1$ comprises the amino acid sequence of SEQ ID NO: 16. In some embodiments, $P_1$ comprises the amino acid sequence of SEQ ID NO: 17. In some embodiments, $P_1$ comprises the amino acid sequence of SEQ ID NO: 18. In some embodiments, $P_1$ comprises the amino acid sequence of SEQ ID NO: 19. In some embodiments, $P_1$ comprises the amino acid sequence of SEQ ID NO: 78.

In some embodiments, $P_1$ comprises an amino acid sequence according to $Z_1$-$Z_2$—C— $Z_4$—P—$Z_6$-$Z_7$—$Z_8$—$Z_9$-$Z_{10}$-$Z_{11}$-$Z_{12}$—C—$Z_{14}$ and $Z_1$ is selected from D, Y, F, I, N, V, H, L, A, T, S, and P; $Z_2$ is selected from D, Y, L, F, I, N, A, V, H, T, and S; $Z_4$ is selected from G and W; $Z_6$ is selected from E, D, V, and P; $Z_7$ is selected from W, L, F, V, G, M, I, and Y; $Z_8$ is selected from E, D, P, and Q; $Z_9$ is selected from E, D, Y, V, F, W, P, L, and Q; $Z_{10}$ is selected from S, D, Y, T, I, F, V, N, A, P, L, and H; $Z_{11}$ is selected from I, Y, F, V, L, T, N, S, D, A, and H; $Z_{12}$ is selected from F, D, Y, L, I, V, A, N, T, P, S, and H; $Z_{14}$ is selected from D, Y, N, F, I, P, V, A, T, H, L and S. In some embodiments, $Z_1$ is selected from D, Y, F, I, and N; $Z_2$ is selected from D, Y, L, F, I, and N; $Z_4$ is selected from G and W; $Z_6$ is selected from E and D; $Z_7$ is selected from W, L, F, and V; $Z_8$ is selected from E and D; $Z_9$ is selected from E, D, Y, and V; $Z_{10}$ is selected from S, D, Y, T, and I; $Z_{11}$ is selected from I, Y, F, V, L, and T; $Z_{12}$ is selected from F, D, Y, L, I, V, A, and W; $Z_{14}$ is selected from D, Y, N, F, I, and P. In some embodiments, $Z_1$ is selected from D, Y, and F; $Z_2$ is selected from D, Y, L, and F; $Z_4$ is selected from G and W; $Z_6$ is selected from E and D; $Z_7$ is selected from W, L, and F; $Z_8$ is selected from E and D; $Z_9$ is selected from E and D; $Z_{10}$ is selected from S, D, and Y; Zn is selected from I, Y, and F; $Z_{12}$ is selected from F, D, Y, and L; and $Z_{14}$ is selected from D, Y, and N.

In some embodiments, $P_1$ comprises an amino acid sequence according to $U_1$-$U_2$—C-$U_4$—P—$U_6$-$U_7$-$U_8$-$U_9$-$U_{10}$-$U_{11}$-$U_{12}$—C—$U_{14}$ and $U_1$ is selected from D, Y, F, I, N, V, H, L, A, T, S, and P; $U_2$ is selected from D, Y, L, F, I, N, A, V, H, T, and S; $U_4$ is selected from G and W; $U_6$ is selected from E, D, V, and P; $U_7$ is selected from W, L, F, V, G, M, I, and Y; $U_8$ is selected from E, D, P, and Q; $U_9$ is selected from E, D, Y, V, F, W, P, L, and Q; $U_{10}$ is selected from S, D, Y, T, I, F, V, N, A, P, L, and H; $U_{11}$ is selected from I, Y, F, V, L, T, N, S, D, A, and H; $U_{12}$ is selected from F, D, Y, L, I, V, A, N, T, P, S, G, and H; and $U_{14}$ is selected from D, Y, N, F, I, P, V, A, T, H, L, M, and S. In some embodiments, $U_1$ is selected from D, Y, F, I, V, and N; $U_2$ is selected from D, Y, L, F, I, and N; $U_4$ is selected from G and W; $U_6$ is selected from E and D; $U_7$ is selected from W, L, F, G, and V; $U_8$ is selected from E and D; $U_9$ is selected from E, D, Y, and V; $U_{10}$ is selected from S, D, Y, T, and I; $U_{11}$ is selected from I, Y, F, V, L, and T; $U_{12}$ is selected from F, D, Y, L, I, V, A, G, and N; and $U_{14}$ is selected from D, Y, N, F, I, M, and P. In some embodiments, $U_1$ is selected from D, Y, V, and F; $U_2$ is selected from D, Y, L, and F; $U_4$ is selected from G and W; $U_6$ is selected from E and D; $U_7$ is selected from W, L, G, and F; $U_8$ is selected from E and D; $U_9$ is selected from E and D; $U_{10}$ is selected from S, D, T, and Y; $U_{11}$ is selected from I, Y, V, L, and F; $U_{12}$ is selected from F, D, Y, G, A, and L; and $U_{14}$ is selected from D, Y, M, and N.

In some embodiments, $P_1$ comprises the amino acid sequences according to any one of SEQ ID NOs: 79-105. In some embodiments, $P_1$ comprises an amino acid sequences according to any of the sequences of Table 20. In some embodiments, $P_1$ comprises the amino acid sequences according to any one of SEQ ID NOs: 106-117.

In some embodiments, $P_1$ comprises the amino acid sequence according to SEQ ID NO: 18 or a peptide sequence that has 1, 2, or 3, amino acid substitutions, additions, or deletions relative to the amino acid sequence of SEQ ID NO: 18.

In some embodiments, $P_1$ comprises the amino acid sequence according to SEQ ID NO: 19 or a peptide sequence that has 1, 2, or 3, amino acid substitutions, additions, or deletions relative to the amino acid sequence of SEQ ID NO: 19.

In some embodiments, $P_1$ comprises the amino acid sequence according to SEQ ID NO: 116 or a peptide sequence that has 1, 2, or 3, amino acid substitutions, additions, or deletions relative to the amino acid sequence of SEQ ID NO: 116.

In some embodiments, $P_1$ comprises the amino acid sequence according to SEQ ID NO: 18.

In some embodiments, $P_1$ comprises the amino acid sequence according to SEQ ID NO: 19.

In some embodiments, $P_1$ comprises the amino acid sequence according to SEQ ID NO: 116.

In some embodiments, $P_2$ impairs binding of $A_2$ to the second target antigen. In some embodiments, wherein $P_2$ impairs binding of $A_2$ to PSMA. In some embodiments, $P_2$ is bound to $A_2$ through ionic interactions, electrostatic interactions, hydrophobic interactions, Pi-stacking interactions, and H-bonding interactions, or a combination thereof. In some embodiments, $P_2$ is bound to $A_2$ at or near an antigen binding site. In some embodiments, $P_2$ becomes unbound from $A_2$ when $L_2$ is cleaved by the tumor specific protease thereby exposing $A_2$ to the PSMA. In some embodiments, the protease comprises a matrix metalloprotease (MMP) or a serine protease. In some embodiments, the matrix metalloprotease comprises MMP2, MMP7, MMP9, MMP13, or MMP14. In some embodiments, the serine protease comprises matriptase (MTSP1), urokinase, or hepsin. In some embodiments, $P_2$ has less than 70% sequence identity to the PSMA. In some embodiments, $P_2$ has less than 75% sequence identity to the PSMA. In some embodiments, $P_2$ has less than 80% sequence identity to the PSMA. In some embodiments, $P_2$ has less than 85% sequence identity to the PSMA. In some embodiments, $P_2$ has less than 90% sequence identity to the PSMA. In some embodiments, $P_2$ has less than 95% sequence identity to the PSMA. In some embodiments, $P_2$ has less than 98% sequence identity to the PSMA. In some embodiments, $P_2$ has less than 99% sequence identity to the PSMA. In some embodiments, $P_2$ comprises a de novo amino acid sequence that shares less than 10% sequence identity to the PSMA.

In some embodiments, $P_{1a}$ when $L_{1a}$ is uncleaved impairs binding of the antigen recognizing molecule to the target antigen. In some embodiments, the antigen recognizing molecule comprises an antibody or antibody fragment. In some embodiments, the target antigen is an anti-CD3 effector cell antigen. In some embodiments, the target antigen is prostate-specific membrane antigen (PSMA). In some embodiments, $P_{1a}$ has less than 70% sequence identity to the target antigen. In some embodiments, $P_{1a}$ has less than 75% sequence identity to the target antigen. In some embodiments, $P_{1a}$ has less than 80% sequence identity to the target antigen. In some embodiments, $P_{1a}$ has less than 85% sequence identity to the target antigen. In some embodiments, $P_{1a}$ has less than 90% sequence identity to the target antigen. In some embodiments, $P_{1a}$ has less than 95% sequence identity to the target antigen. In some embodiments, $P_{1a}$ has less than 98% sequence identity to the target antigen. In some embodiments, $P_{1a}$ has less than 99% sequence identity to the target antigen. In some embodiments, $P_{1a}$ comprises a de novo amino acid sequence that shares less than 10% sequence identity to the second target antigen.

In some embodiments, $P_{1a}$ comprises an amino acid sequence according to $Z_1$-$Z_2$—C—$Z_4$—P—$Z_6$-$Z_7$—$Z_8$—$Z_9$-$Z_{10}$—$Z_{11}$—$Z_{12}$—C—$Z_{14}$ and $Z_1$ is selected from D, Y, F, I, N, V, H, L, A, T, S, and P; $Z_2$ is selected from D, Y, L, F, I, N, A, V, H, T, and S; $Z_4$ is selected from G and W; $Z_6$ is selected from E, D, V, and P; $Z_7$ is selected from W, L, F, V, G, M, I, and Y; Zs is selected from E, D, P, and Q; $Z_9$ is selected from E, D, Y, V, F, W, P, L, and Q; $Z_{10}$ is selected from S, D, Y, T, I, F, V, N, A, P, L, and H; Zn is selected from I, Y, F, V, L, T, N, S, D, A, and H; $Z_{12}$ is selected from F, D, Y, L, I, V, A, N, T, P, S, and H; and $Z_{14}$ is selected from D, Y, N, F, I, P, V, A, T, H, L and S. In some embodiments, $Z_1$ is selected from D, Y, F, I, and N; $Z_2$ is selected from D, Y, L, F, I, and N; $Z_4$ is selected from G and W; $Z_6$ is selected from E and D; $Z_7$ is selected from W, L, F, and V; Zs is selected from E and D; $Z_9$ is selected from E, D, Y, and V; $Z_{10}$ is selected from S, D, Y, T, and I; $Z_n$ is selected from I, Y, F, V, L, and T; $Z_{12}$ is selected from F, D, Y, L, I, V, A, and N; and $Z_{14}$ is selected from D, Y, N, F, I, and P. In some embodiments, $Z_1$ is selected from D, Y, and F; $Z_2$ is selected from D, Y, L, and F; $Z_4$ is selected from G and W; $Z_6$ is selected from E and D; $Z_7$ is selected from W, L, and F; $Z_8$ is selected from E and D; $Z_9$ is selected from E and D; $Z_{10}$ is selected from S, D, and Y; Zn is selected from I, Y, and F; Zu is selected from F, D, Y, and L; and $Z_{14}$ is selected from D, Y, and N.

In some embodiments, $P_{1a}$ comprises an amino acid sequence according to $U_1$-$U_2$—C—$U_4$—P—$U_6$-$U_7$—$U_8$—$U_9$-$U_{10}$—$U_{11}$—$U_{12}$—C—$U_{14}$ and $U_1$ is selected from D, Y, F, I, N, V, H, L, A, T, S, and P; $U_2$ is selected from D, Y, L, F, I, N, A, V, H, T, and S; $U_4$ is selected from G and W; $U_6$ is selected from E, D, V, and P; $U_7$ is selected from W, L, F, V, G, M, I, and Y; $U_8$ is selected from E, D, P, and Q; $U_9$ is selected from E, D, Y, V, F, W, P, L, and Q; $U_{10}$ is selected from S, D, Y, T, I, F, V, N, A, P, L, and H; $U_{11}$ is selected from I, Y, F, V, L, T, N, S, D, A, and H; $U_{12}$ is selected from F, D, Y, L, I, V, A, N, T, P, S, G, and H; and $U_{14}$ is selected from D, Y, N, F, I, P, V, A, T, H, L, M, and S. In some embodiments, $U_1$ is selected from D, Y, F, I, V, and N; $U_2$ is selected from D, Y, L, F, I, and N; $U_4$ is selected from G and W; $U_6$ is selected from E and D; $U_7$ is selected from W, L, F, G, and V; $U_8$ is selected from E and D; $U_9$ is selected from E, D, Y, and V; $U_{10}$ is selected from S, D, Y, T, and I; $U_{11}$ is selected from I, Y, F, V, L, and T; $U_{12}$ is selected from F, D, Y, L, I, V, A, G, and N; and $U_{14}$ is selected from D, Y, N, F, I, M, and P. In some embodiments, $U_1$ is selected from D, Y, V, and F; $U_2$ is selected from D, Y, L, and F; $U_4$ is selected from G and W; $U_6$ is selected from E and D; $U_7$ is selected from W, L, G, and F; $U_8$ is selected from E and D; $U_9$ is selected from E and D; $U_{10}$ is selected from S, D, T, and Y; Un is selected from I, Y, V, L, and F; $U_{12}$ is selected from F, D, Y, G, A, and L; and $U_{14}$ is selected from D, Y, M, and N.

In some embodiments, $P_{1a}$ comprises the amino acid sequences according to any one of SEQ ID NOs: 79-105.

In some embodiments, $P_{1a}$ comprises an amino acid sequences according to any of the sequences of Table 20.

In some embodiments, $P_{1a}$ comprises the amino acid sequences according to any one of SEQ ID NOs: 106-117.

In some embodiments, $P_{1a}$ comprises the amino acid sequence according to SEQ ID NO: 18 or a peptide sequence that has 1, 2, or 3, amino acid substitutions, additions, or deletions relative to the amino acid sequence of SEQ ID NO: 18.

In some embodiments, $P_{1a}$ comprises the amino acid sequence according to SEQ ID NO: 19 or a peptide sequence that has 1, 2, or 3, amino acid substitutions, additions, or deletions relative to the amino acid sequence of SEQ ID NO: 19.

In some embodiments, $P_{1a}$ comprises the amino acid sequence according to SEQ ID NO: 116 or a peptide sequence that has 1, 2, or 3, amino acid substitutions, additions, or deletions relative to the amino acid sequence of SEQ ID NO: 116.

In some embodiments, $P_{1a}$ comprises the amino acid sequence according to SEQ ID NO: 18.

In some embodiments, $P_{1a}$ comprises the amino acid sequence according to SEQ ID NO: 19.

In some embodiments, $P_{1a}$ comprises the amino acid sequence according to SEQ ID NO: 116.

In some embodiments, $P_1$, $P_2$, or $P_{1a}$ comprises a peptide sequence of at least 5 amino acids in length. In some embodiments, $P_1$, $P_2$, or $P_{1a}$ comprises a peptide sequence of at least 6 amino acids in length. In some embodiments, $P_1$, $P_2$, or $P_{1a}$ comprises a peptide sequence of at least 10 amino acids in length. In some embodiments, $P_1$, $P_2$, or $P_{1a}$ comprises a peptide sequence of at least 10 amino acids in length and no more than 20 amino acids in length. In some embodiments, $P_1$, $P_2$, or $P_{1a}$ comprises a peptide sequence of at least 16 amino acids in length. In some embodiments, $P_1$, $P_2$, or $P_{1a}$ comprises a peptide sequence of no more than 40 amino acids in length. In some embodiments, $P_1$, $P_2$, or $P_{1a}$ comprises at least two cysteine amino acid residues. In some embodiments, $P_1$, $P_2$, or $P_{1a}$ comprises a cyclic peptide or a linear peptide. In some embodiments, $P_1$, $P_2$, or $P_{1a}$ comprises a cyclic peptide. In some embodiments, $P_1$, $P_2$, or $P_{1a}$ comprises a linear peptide.

In some embodiments, $P_1$, $P_2$, or $P_{1a}$ or $P_1$, $P_2$, and $P_{1a}$ comprise a modified amino acid or non-natural amino acid, or a modified non-natural amino acid, or a combination thereof. In some embodiments, the modified amino acid or a modified non-natural amino acid comprises a post-translational modification. In some embodiments $P_1$, $P_2$, or $P_{1a}$ or $P_1$, $P_2$, and $P_{1a}$ comprise a modification including, but not limited to acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. Modifications are made anywhere to $P_1$, $P_2$, or $P_{1a}$ or $P_1$, $P_2$, and $P_{1a}$ including the peptide backbone, the amino acid side chains, and the terminus.

In some embodiments, $P_1$, $P_2$, or $P_{1a}$ does not comprise albumin or an albumin fragment. In some embodiments, $P_1$, $P_2$, or $P_{1a}$ does not comprise an albumin binding domain.
Linking Moiety ($L_1$, $L_2$, $L_3$, and $L_1$)

In some embodiments, $L_1$, $L_2$, $L_3$, or $L_{1a}$ is a peptide sequence having at least 5 to no more than 50 amino acids. In some embodiments $L_1$, $L_2$, $L_3$, or $L_{1a}$ is a peptide sequence having at least 10 to no more than 30 amino acids. In some embodiments, $L_1$, $L_2$, $L_3$, or $L_{1a}$ is a peptide sequence having at least 10 amino acids. In some embodiments, $L_1$, $L_2$, $L_3$, or $L_{1a}$ is a peptide sequence having at least 18 amino acids. In some embodiments, $L_1$, $L_2$, $L_3$, or $L_{1a}$ is a peptide sequence having at least 26 amino acids. In some embodiments, $L_1$, $L_2$, $L_3$, or $L_{1a}$ has a formula comprising $(G_2S)_n$, wherein n is an integer from 1 to 3 (SEQ ID NO: 118). In some embodiments, $L_1$, $L_2$, $L_3$, or L1a has a formula comprising $(G_2S)_n$, wherein n is an integer of at least 1. In some embodiments, $L_1$, $L_2$, $L_3$, or $L_{1a}$ has a formula selected from the group consisting of $(G_2S)_n$, $(GS)_n$, $(GSGGS)_n$(SEQ ID NO: 50), $(GGGS)_n$(SEQ ID NO: 51), $(GGGGS)_n$(SEQ ID NO: 52), and $(GSSGGS)_n$(SEQ ID NO: 53), wherein n is an integer of at least 1. In some embodiments, the tumor specific protease is selected from the group consisting of metalloprotease, serine protease, cysteine protease, threonine protease, and aspartic protease. In some embodiments $L_1$, $L_2$, $L_3$, or $L_{1a}$ comprises a urokinase cleavable amino acid sequence, a matriptase cleavable amino acid sequence, a legumain cleavable amino acid sequence, or a matrix metalloprotease cleavable amino acid sequence. In some embodiments, the matrix metalloprotease comprises MMP2, MMP7, MMP9, MMP13, or MMP14. In some embodiments, the serine protease comprises matriptase (MTSP1), urokinase, or hepsin.

In some embodiments, $L_1$, $L_2$, $L_3$, or $L_{1a}$ comprises a sequence as disclosed in Table 4 or a sequence substantially identical thereto (e.g., a sequence that has 0, 1, or 2 amino acid modifications).

In some embodiments, $L_1$, comprises the sequence of Linker-25 (SEQ ID NO: 45). In some embodiments, $L_1$, comprises the sequence of Linker-26 (SEQ ID NO: 46). In some embodiments, $L_1$, comprises the sequence of (Linker-27 (SEQ ID NO: 47). In some embodiments, L, comprises the sequence of Linker-28 (SEQ ID NO: 48).

In some embodiments, $L_2$, comprises the sequence of Linker-25 (SEQ ID NO: 45). In some embodiments, $L_2$, comprises the sequence of Linker-26 (SEQ ID NO: 46). In some embodiments, $L_2$, comprises the sequence of Linker-27 (SEQ ID NO: 47). In some embodiments, $L_2$, comprises the sequence of Linker-28 (SEQ ID NO: 48).

TABLE 4

$L_1$, $L_2$, $L_3$, and $L_{1a}$ Sequences

| Construct Description | Amino Acid Sequence (N to C) | SEQ ID NO: |
|---|---|---|
| Linker 1 | GGGGSGGGGSGGGGS | 20 |
| Linker 2 | GGGGS | 21 |
| Linker 3 | GGGGSGGGS | 22 |
| Cleavable linker | GGGGSGGGLSGRSDAGSPLGLAG SGGGS | 23 |
| Linker 4 | GGGGSLSGRSDNHGSSGT | 24 |
| Linker 5 | GGGGSSGGSGGGSGLSGRSDNHGS SGT | 25 |
| Linker 6 | ASGRSDNH | 26 |
| Linker 7 | LAGRSDNH | 27 |
| Linker 8 | ISSGLASGRSDNH | 28 |
| Linker 9 | ISSGLLAGRSDNH | 29 |
| Linker 10 | LSGRSDNH | 30 |
| Linker 11 | ISSGLLSGRSDNP | 31 |

TABLE 4-continued $L_1$, $L_2$, $L_3$, and $L_{1a}$ Sequences

| Construct Description | Amino Acid Sequence (N to C) | SEQ ID NO: |
|---|---|---|
| Linker 12 | ISSGLLSGRSDNH | 32 |
| Linker 13 | LSGRSDNHSPLGLAGS | 33 |
| Linker 14 | SPLGLAGSLSGRSDNH | 34 |
| Linker 15 | SPLGLSGRSDNH | 35 |
| Linker 16 | LAGRSDNHSPLGLAGS | 36 |
| Linker 17 | LSGRSDNHVPLSLKMG | 37 |
| Linker 18 | LSGRSDNHVPLSLSMG | 38 |
| Linker 19 | GSSGGSGGSGGSGISSGLLSGRSD NHGSSGT | 39 |
| Linker 20 | GSSGGSGGSGGISSGLLSGRSDNH GGGS | 40 |
| Linker 21 | ASGRSDNH | 41 |
| Linker 22 | LAGRSDNH | 42 |
| Linker 23 | ISSGLASGRSDNH | 43 |
| Linker 24 | LSGRSDAG | 44 |
| Linker 25 | ISSGLLSGRSDAG | 45 |
| Linker 26 | AAGLLAPPGGLSGRSDAG | 46 |
| Linker 27 | SPLGLSGRSDAG | 47 |
| Linker 28 | LSGRSDAGSPLGLAG | 48 |
| Non-cleavable linker | GGGGSGGGSGGGGSGGASSGAG GSGGGS | 49 |

In some embodiments, $L_1$ is bound to a N-terminus of $A_1$. In some embodiments, $L_1$ is bound to a C-terminus of $A_1$. In some embodiments, $L_2$ is bound to a N-terminus of $A_2$. In some embodiments, $L_2$ is bound to a C-terminus of $A_2$. In some embodiments, $P_1$ becomes unbound from $A_1$ when $L_1$ is cleaved by the tumor specific protease thereby exposing $A_1$ to the effector cell antigen. In some embodiments, $P_2$ becomes unbound from $A_2$ when $L_2$ is cleaved by the tumor specific protease thereby exposing $A_2$ to PSMA.

In some embodiments, $L_1$, $L_2$, $L_3$, or $L_{1a}$ comprise a modified amino acid or non-natural amino acid, or a modified non-natural amino acid, or a combination thereof. In some embodiments, the modified amino acid or a modified non-natural amino acid comprises a post-translational modification. In some embodiments, $L_1$, $L_2$, $L_3$, or $L_{1a}$ comprise a modification including, but not limited, to acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Modifications are made anywhere to $L_1$, $L_2$, $L_3$, or $L_{1a}$ including the peptide backbone, or the amino acid side chains.

In some embodiments, the cleavable linker is cleavable by a protease. In some embodiments, the protease is present in higher levels in a disease-state microenvironment relative to levels in healthy tissue or a microenvironment that is not the disease-state microenvironment. In some embodiments, the protease comprises a tumor specific protease. In some embodiments, the protease comprises a matrix metalloprotease (MMP) or a serine protease. In some embodiments, the matrix metalloprotease comprises MMP2, MMP7, MMP9, MMP13, or MMP14. In some embodiments, the matrix metalloprotease is selected from the group consisting of connects $H_{1a}$ to $P_{1a}$. In some embodiments, the half-life extending molecule ($H_1$ or $H_{1a}$) does not have binding affinity to antigen recognizing molecule. In some embodiments, the half-life extending molecule ($H_1$ or $H_{1a}$) does not have binding affinity to the effector cell antigen. In some embodiments, the half-life extending molecule ($H_1$ or $H_{1a}$) does not shield antigen recognizing molecule from the effector cell antigen. In some embodiments, the half-life extending molecule ($H_1$ or $H_{1a}$) is not directly linked to antigen recognizing molecule.

In some embodiments, $H_1$ or $H_{1a}$ comprises a sequence as disclosed in Table 5 or a sequence substantially identical thereto (e.g., a sequence that has at least 90%, 95%, 96%, 97%, 98%, or 99% sequence identity).

TABLE 5

| $H_1$ and $H_{1a}$ Sequences | | |
|---|---|---|
| Construct Description | Amino Acid Sequence (N to C) | SEQ ID NO: |
| Anti-Albumin: CDR-H1 | GSTFYTAV | 54 |
| Anti-Albumin: CDR-H2 | IRWTALTT | 55 |
| Anti-Albumin: CDR-H3 | AARGTLGLFTTADSYDY | 56 |
| Anti-albumin | EVQLVESGGGLVQPGGSLRLSCAASGSTF YTAVMGWVRQAPGKGLEWVAAIRWTA LTTSYADSVKGRFTISRDGAKTTLYLQM NSLRPEDTAVYYCAARGTLGLFTTADSY DYWGQGTLVTVSS | 57 |
| 10G Anti-Albumin: CDR-H1 | GFTFSKFG | 58 |
| 10G Anti-Albumin: CDR-H2 | ISGSGRDT | 59 |
| 10G Anti-Albumin: CDR-H3 | TIGGSLSV | 60 |
| 10G Anti-albumin | EVQLVESGGGLVQPGNSLRLSCAASGFT FSKFGMSWVRQAPGKGLEWVSSISGSGR DTLYADSVKGRFTISRDNAKTTLYLQMN SLRPEDTAVYYCTIGGSLSVSSQGTLVTV SS | 61 |

MMP2, MMP7, MMP9, MMP13, and MMP14. In some embodiments, the matrix metalloprotease comprises MMP2. In some embodiments, the matrix metalloprotease comprises MMP7. In some embodiments, the matrix metalloprotease comprises MMP9. In some embodiments, the matrix metalloprotease comprises MMP13. In some embodiments, the matrix metalloprotease comprises MMP14. In some embodiments, the serine protease comprises matriptase (MTSP1), urokinase, or hepsin. In some embodiments, the serine protease is selected from the group consisting of matriptase (MTSP1), urokinase, and hepsin. In some embodiments, the serine protease comprises matriptase (MTSP1). In some embodiments, the serine protease comprises urokinase. In some embodiments, the serine protease comprises hepsin. In some embodiments, the cleavable linker is cleaved by a variety of proteases. In some embodiments, the cleavable linker is cleaved by at least 1, 2, 3, 4, 5, 6, 7, 8, 9, 10, 15, 20, or more than 20 different proteases. Half-Life Extending Molecule ($H_1$ and $H_{1a}$)

In some embodiments, $H_1$ does not block $A_1$ binding to the effector cell antigen. In some embodiments, $H_1$ comprises a linking moiety ($L_3$) that connects $H_1$ to $P_1$. In some embodiments, $H_{1a}$ does not block the first antigen recognizing molecule binding to the effector cell antigen. In some embodiments, $H_{1a}$ comprises a linking moiety ($L_3$) that In some embodiments, $H_1$ or $H_{1a}$ comprise an amino acid sequence that has repetitive sequence motifs. In some embodiments, $H_1$ or $H_{1a}$ comprises an amino acid sequence that has highly ordered secondary structure. "Highly ordered secondary structure," as used in this context, means that at least about 50%, or about 70%, or about 80%, or about 90%, of amino acid residues of $H_1$ or $H_{1a}$ contribute to secondary structure, as measured or determined by means, including, but not limited to, spectrophotometry (e.g. by circular dichroism spectroscopy in the "far-UV" spectral region (190-250 nm), and computer programs or algorithms, such as the Chou-Fasman algorithm and the Garnier-Osguthorpe-Robson ("GOR") algorithm.

In some embodiments, $H_1$ or $H_{1a}$ comprises a polymer. In some embodiments, the polymer is polyethylene glycol (PEG). In some embodiments, $H_1$ or $H_{1a}$ comprises albumin. In some embodiments, $H_1$ or $H_{1a}$ comprises an Fc domain. In some embodiments, the albumin is serum albumin. In some embodiments, the albumin is human serum albumin. In some embodiments, $H_1$ or $H_{1a}$ comprises a polypeptide, a ligand, or a small molecule. In some embodiments, the polypeptide, the ligand or the small molecule binds serum protein or a fragment thereof, a circulating immunoglobulin or a fragment thereof, or CD35/CR1. In some embodiments, the serum protein comprises a thyroxine-binding protein, a transthyretin, a 1-acid glycoprotein, a transferrin, transferrin receptor or a transferrin-binding portion thereof, a fibrinogen, or an albumin. In some embodiments, the circulating immunoglobulin molecule comprises IgG1, IgG2, IgG3, IgG4, sIgA, IgM or IgD. In some embodiments, the serum protein is albumin. In some embodiments, the polypeptide is an antibody. In some embodiments, the antibody comprises a single domain antibody, a single chain variable fragment or a Fab. In some embodiments, the single domain antibody comprises a single domain antibody that binds to albumin. In some embodiments, the single domain antibody is a human or humanized antibody. In some embodiments, the single domain antibody is selected from the group consisting of 645gH1gL1, 645dsgH5gL4, 23-13-A01-sc02, A10m3 or a fragment thereof, DOM7r-31, DOM7h-11-15, Alb-1, Alb-8, Alb-23, 10G, 10E and SA21. In some embodiments, the single domain antibody comprises complementarity determining regions (CDRs): HC-CDR1, HC-CDR2, and HC-CDR3, wherein the HC-CDR1, the HC-CDR2, and the HC-CDR3 of the single domain antibody comprise: HC-CDR1: SEQ ID NO: 54, HC-CDR2: SEQ ID NO: 55, and HC-CDR3: SEQ ID NO: 56. In some embodiments, the single domain antibody comprises complementarity determining regions (CDRs): HC-CDR1, HC-CDR2, and HC-CDR3, wherein the HC-CDR1, the HC-CDR2, and the HC-CDR3 of the single domain antibody comprise: HC-CDR1: SEQ ID NO: 54, HC-CDR2: SEQ ID NO: 55, and HC-CDR3: SEQ ID NO: 56; and wherein the CDRs comprise from 0-2 amino acid modifications in at least one of the HC-CDR1, HC-CDR2, or HC-CDR3. In some embodiments, the single domain antibody comprises complementarity determining regions (CDRs): HC-CDR1, HC-CDR2, and HC-CDR3, wherein the HC-CDR1, the HC-CDR2, and the HC-CDR3 of the single domain antibody comprise: HC-CDR1: SEQ ID NO: 58, HC-CDR2: SEQ ID NO: 59, and HC-CDR3: SEQ ID NO: 60. In some embodiments, the single domain antibody comprises complementarity determining regions (CDRs): HC-CDR1, HC-CDR2, and HC-CDR3, wherein the HC-CDR1, the HC-CDR2, and the HC-CDR3 of the single domain antibody comprise: HC-CDR1: SEQ ID NO: 58, HC-CDR2: SEQ ID NO: 59, and HC-CDR3: SEQ ID NO: 60; and wherein the CDRs comprise from 0-2 amino acid modifications in at least one of the HC-CDR1, HC-CDR2, or HC-CDR3.

In some embodiments, $H_1$ comprises an amino acid sequence according to SEQ ID NO: 57. In some embodiments, $H_1$ comprises an amino acid sequence that has at least 80% sequence identity to SEQ ID NO: 57. In some embodiments, $H_1$ comprises an amino acid sequence that has at least 85% sequence identity to SEQ ID NO: 57. In some embodiments, $H_1$ comprises an amino acid sequence that has at least 90% sequence identity to SEQ ID NO: 57. In some embodiments, $H_1$ comprises an amino acid sequence that has at least 95% sequence identity to SEQ ID NO: 57. In some embodiments, $H_1$ comprises an amino acid sequence that has at least 99% sequence identity to SEQ ID NO: 57.

In some embodiments, $H_{1a}$ comprises an amino acid sequence according to SEQ ID NO: 57. In some embodiments, $H_{1a}$ comprises an amino acid sequence that has at least 80% sequence identity to SEQ ID NO: 57. In some embodiments, $H_{1a}$ comprises an amino acid sequence that has at least 85% sequence identity to SEQ ID NO: 57. In some embodiments, $H_{1a}$ comprises an amino acid sequence that has at least 90% sequence identity to SEQ ID NO: 57. In some embodiments, $H_{1a}$ comprises an amino acid sequence that has at least 95% sequence identity to SEQ ID NO: 57. In some embodiments, $H_{1a}$ comprises an amino acid sequence that has at least 99% sequence identity to SEQ ID NO: 57.

In some embodiments, $H_1$ comprises an amino acid sequence according to SEQ ID NO: 61. In some embodiments, $H_1$ comprises an amino acid sequence that has at least 80% sequence identity to SEQ ID NO: 61. In some embodiments, $H_1$ comprises an amino acid sequence that has at least 85% sequence identity to SEQ ID NO: 61. In some embodiments, $H_1$ comprises an amino acid sequence that has at least 90% sequence identity to SEQ ID NO: 61. In some embodiments, $H_1$ comprises an amino acid sequence that has at least 95% sequence identity to SEQ ID NO: 61. In some embodiments, $H_1$ comprises an amino acid sequence that has at least 99% sequence identity to SEQ ID NO: 61.

In some embodiments, $H_{1a}$ comprises an amino acid sequence according to SEQ ID NO: 61. In some embodiments, $H_{1a}$ comprises an amino acid sequence that has at least 80% sequence identity to SEQ ID NO: 61. In some embodiments, $H_{1a}$ comprises an amino acid sequence that has at least 85% sequence identity to SEQ ID NO: 61. In some embodiments, $H_{1a}$ comprises an amino acid sequence that has at least 90% sequence identity to SEQ ID NO: 61. In some embodiments, $H_{1a}$ comprises an amino acid sequence that has at least 95% sequence identity to SEQ ID NO: 61. In some embodiments, $H_{1a}$ comprises an amino acid sequence that has at least 99% sequence identity to SEQ ID NO: 61.

In some embodiments, $H_1$ or $H_{1a}$ or $H_1$ and $H_{1a}$ comprise a modified amino acid or non-natural amino acid, or a modified non-natural amino acid, or a combination thereof. In some embodiments, the modified amino acid or a modified non-natural amino acid comprises a post-translational modification. In some embodiments $H_1$ or $H_{1a}$ or $H_1$ and $H_{1a}$ comprise a modification including, but not limited to acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. Modifications are made anywhere to $H_1$ or $H_{1a}$ or $H_1$ and $H_{1a}$ including the peptide backbone, the amino acid side chains, and the terminus.

In some embodiments, $H_1$ comprises a linking moiety ($L_3$) that connects $H_1$ to $P_1$. In some embodiments, $L_3$ is a peptide sequence having at least 5 to no more than 50 amino acids. In some embodiments, $L_3$ is a peptide sequence having at least 10 to no more than 30 amino acids. In some embodiments, $L_3$ is a peptide sequence having at least 10 amino acids. In some embodiments, $L_3$ is a peptide sequence having at least 18 amino acids. In some embodiments, $L_3$ is a peptide sequence having at least 26 amino acids. In some embodiments, $L_3$ has a formula selected from the group consisting of $(G_2S)_n$, $(GS)_n$, $(GSGGS)_n$(SEQ ID NO: 50), $(GGGS)_n$(SEQ ID NO: 51), $(GGGGS)_n$(SEQ ID NO: 52), and $(GSSGGS)_n$(SEQ ID NO: 53), wherein n is an integer of at least 1. In some embodiments, $L_3$ comprises an amino acid sequence according to SEQ ID NO: 22.

In some embodiments, $H_{1a}$ comprises a linking moiety ($L_{1a}$) that connects $H_{1a}$ to $P_{1a}$. In some embodiments, $L_{1a}$ is a peptide sequence having at least 5 to no more than 50 amino acids. In some embodiments, $L_{1a}$ is a peptide sequence having at least 10 to no more than 30 amino acids. In some embodiments, Lia is a peptide sequence having at least 10 amino acids. In some embodiments, Lia is a peptide sequence having at least 18 amino acids. In some embodiments, Lia is a peptide sequence having at least 26 amino acids. In some embodiments, $L_{1a}$ has a formula selected from the group consisting of $(G_2S)_n$, $(GS)_n$, $(GSGGGS)_n$(SEQ ID NO: 50), $(GGGS)_n$(SEQ ID NO: 51), $(GGGGS)_n$(SEQ ID NO: 52), and $(GSSGGS)_n$(SEQ ID NO: 53), wherein n is an integer of at least 1. In some embodiments, $L_{1a}$ comprises an amino acid sequence according to SEQ ID NO: 22.

Antibodies that Bind to PSMA and CD3

In some embodiments, the polypeptide or polypeptide complex comprises an amino acid sequence disclosed in Table 6 or a sequence substantially identical thereto (e.g., a sequence that has at least 90%, 95%, 96%, 97%, 98%, or 99% sequence identity). In some embodiments, the polypeptide or polypeptide complex comprises an amino acid sequence with at least 95% sequence identity to any one of SEQ ID NOs: 62-77. In some embodiments, the polypeptide or polypeptide complex comprises an amino acid sequence with at least 95% sequence identity to SEQ ID NO: 72. In some embodiments, the polypeptide or polypeptide complex comprises an amino acid sequence with at least 95% sequence identity to SEQ ID NO: 73.

TABLE 6

Polypeptide complex sequences

| Construct Description | Amino Acid Sequence (N to C) | SEQ ID NO: |
|---|---|---|
| PC1: LC: 006 PSMA Fab LC | DIQMTQSPSSLSASVGDRVTITCRASQGISNYLAWYQ QKTGKVPKFLIYEASTLQSGVPSRFSGGGSGTDFTLTIS SLQPEDVATYYCQNYNSAPFTFGPGTKVDIKRTVAAP SVFIFPPSDEQLKSGTASVVCLLNNFYPREAKVQWKV DNALQSGNSQESVTEQDSKDSTYSLSSTLTLSKADYE KHKVYACEVTHQGLSSPVTKSFNRGEC | 62 |
| PC1: HC: SP34.185 scFv Linker 2 006 PSMA Fab HC | EVQLVESGGGLVQPGGSLKLSCAASGFTFNKYAMN WVRQAPGKGLEWVARIRSKYNNYATYYADSVKDRF TISRDDSKNTAYLQMNNLKTEDTAVYYCVRHGNFGN SYISYWAYWGQGTLVTVSSGGGGSGGGGSGGGGSQT VVTQEPSLTVSPGGTVTLTCGSSTGAVTSGNYPNWV QQKPGQAPRGLIGGTKFLAPGTPARFSGSLLGGKAAL TLSGVQPEDEAEYYCVLWYSNRWVFGGGTKLTVLG GGGSQVQLVESGGGVVQPGRSLRLSCAASGFAFSRY GMHWVRQAPGKGLEWVAVIWYDGSNKYYADSVKG RFTISRDNSKNTQYLQMNSLRAEDTAVYYCARGGDF LYYYYYGMDVWGQGTTVTVSSASTKGPSVFPLAPSS KSTSGGTAALGCLVKDYFPEPVTVSWNSGALTSGVHT FPAVLQSSGLYSLSSVVTVPSSSLGTQTYICNVNHKPS NTKVDKKVEPKSC | 63 |
| PC: 2: LC SP34.185 scFv Linker 2 006 PSMA Fab LC | EVQLVESGGGLVQPGGSLKLSCAASGFTFNKYAMN WVRQAPGKGLEWVARIRSKYNNYATYYADSVKDRF TISRDDSKNTAYLQMNNLKTEDTAVYYCVRHGNFGN SYISYWAYWGQGTLVTVSSGGGGSGGGGSGGGGSQT VVTQEPSLTVSPGGTVTLTCGSSTGAVTSGNYPNWV QQKPGQAPRGLIGGTKFLAPGTPARFSGSLLGGKAAL TLSGVQPEDEAEYYCVLWYSNRWVFGGGTKLTVLG GGGSDIQMTQSPSSLSASVGDRVTITCRASQGISNYLA WYQQKTGKVPKFLIYEASTLQSGVPSRFSGGGSGTDF TLTISSLQPEDVATYYCQNYNSAPFTFGPGTKVDIKRT VAAPSVFIFPPSDEQLKSGTASVVCLLNNFYPREAKVQ WKVDNALQSGNSQESVTEQDSKDSTYSLSSTLTLSKA DYEKHKVYACEVTHQGLSSPVTKSFNRGEC | 64 |
| PC2: HC 006 PSMA Fab HC | QVQLVESGGGVVQPGRSLRLSCAASGFAFSRYGMH WVRQAPGKGLEWVAVIWYDGSNKYYADSVKGRFTI SRDNSKNTQYLQMNSLRAEDTAVYYCARGGDFLYY YYYGMDVWGQGTTVTVSSASTKGPSVFPLAPSSKSTS GGTAALGCLVKDYFPEPVTVSWNSGALTSGVHTFPA VLQSSGLYSLSSVVTVPSSSLGTQTYICNVNHKPSNTK VDKKVEPKSC | 65 |
| PC3: LC 006 PSMA Fab LC | DIQMTQSPSSLSASVGDRVTITCRASQGISNYLAWYQ QKTGKVPKFLIYEASTLQSGVPSRFSGGGSGTDFTLTIS SLQPEDVATYYCQNYNSAPFTFGPGTKVDIKRTVAAP SVFIFPPSDEQLKSGTASVVCLLNNFYPREAKVQWKV DNALQSGNSQESVTEQDSKDSTYSLSSTLTLSKADYE KHKVYACEVTHQGLSSPVTKSFNRGEC | 66 |
| PC3: HC Anti-albumin (SEQ ID NO: 57) + Linker 3 + SP34.185 scFv mask (SEQ ID NO: | EVQLVESGGGLVQPGGSLRLSCAASGSTFYTAVMGW VRQAPGKGLEWVAAIRWTALTTSYADSVKGRFTISR DGAKTTLYLQMNSLRPEDTAVYYCAARGTLGLFTT ADSYDYWGQGTLVTVSSGGGGSGGGSGGGSQCLGPE WEVCPYGGGGSGGGLSGRSDAGSPLGLAGSGGGSEV | 67 |

TABLE 6-continued

Polypeptide complex sequences

| Construct Description | Amino Acid Sequence (N to C) | SEQ ID NO: |
|---|---|---|
| 16) + cleavable linker + SP34.185 scFv (VH-linker 1-VL) + Linker 2 + 006 PSMA Fab HC | QLVESGGGLVQPGGSLKLSCAASGFTFNKYAMNWV RQAPGKGLEWVARIRSKYNNYATYYADSVKDRFTIS RDDSKNTAYLQMNNLKTEDTAVYYCVRHGNFGNSY ISYWAYWGQGTLVTVSSGGGGSGGGGSGGGGSQTV VTQEPSLTVSPGGTVTLTCGSSTGAVTSGNYPNWVQ QKPGQAPRGLIGGTKFLAPGTPARFSGSLLGGKAALT LSGVQPEDEAEYYCVLWYSNRWVFGGGTKLTVLGG GGSQVQLVESGGGVVQPGRSLRLSCAASGFAFSRYG MHWVRQAPGKGLEWVAVIWYDGSNKYYADSVKGR FTISRDNSKNTQYLQMNSLRAEDTAVYYCARGGDFL YYYYYGMDVWGQGTTVTVSSASTKGPSVFPLAPSSK STSGGTAALGCLVKDYFPEPVTVSWNSGALTSGVHTF PAVLQSSGLYSLSSVVTVPSSSLGTQTYICNVNHKPSN TKVDKKVEPKSC | |
| PC4: LC Anti-albumin (SEQ ID NO: 57) + Linker 3 + SP34.185 scFv mask (SEQ ID NO: 16) + cleavable linker + SP34.185 scFv (VH-linker 1-VL) + Linker 2 + 006 PSMA Fab LC | EVQLVESGGGLVQPGGSLRLSCAASGSTFYTAVMGW VRQAPGKGLEWVAAIRWTALTTSYADSVKGRFTISR DGAKTTLYLQMNSLRPEDTAVYYCAARGTLGLFTT ADSYDYWGQGTLVTVSSGGGGSGGGGSGGGGSQCLGPE WEVCPYGGGGSGGGGLSGRSDAGSPLGLAGSGGGSEV QLVESGGGLVQPGGSLKLSCAASGFTFNKYAMNWV RQAPGKGLEWVARIRSKYNNYATYYADSVKDRFTIS RDDSKNTAYLQMNNLKTEDTAVYYCVRHGNFGNSY ISYWAYWGQGTLVTVSSGGGGSGGGGSGGGGSQTV VTQEPSLTVSPGGTVTLTCGSSTGAVTSGNYPNWVQ QKPGQAPRGLIGGTKFLAPGTPARFSGSLLGGKAALT LSGVQPEDEAEYYCVLWYSNRWVFGGGTKLTVLGG GGSDIQMTQSPSSLSASVGDRVTITCRASQGISNYLAW YQQKTGKVPKFLIYEASTLQSGVPSRFSGGGSGTDFTL TISSLQPEDVATYYCQNYNSAPFTFGPGTKVDIKRTV AAPSVFIFPPSDEQLKSGTASVVCLLNNFYPREAKVQ WKVDNALQSGNSQESVTEQDSKDSTYSLSSTLTLSKA DYEKHKVYACEVTHQGLSSPVTKSFNRGEC | 68 |
| PC4: HC 006 PSMA Fab HC | QVQLVESGGGVVQPGRSLRLSCAASGFAFSRYGMH WVRQAPGKGLEWVAVIWYDGSNKYYADSVKGRFTI SRDNSKNTQYLQMNSLRAEDTAVYYCARGGDFLYY YYYGMDVWGQGTTVTVSSASTKGPSVFPLAPSSKSTS GGTAALGCLVKDYFPEPVTVSWNSGALTSGVHTFPA VLQSSGLYSLSSVVTVPSSSLGTQTYICNVNHKPSNTK VDKKVEPKSC | 69 |
| PC5: LC 006 PSMA Fab LC | DIQMTQSPSSLSASVGDRVTITCRASQGISNYLAWYQ QKTGKVPKFLIYEASTLQSGVPSRFSGGGSGTDFTLTIS SLQPEDVATYYCQNYNSAPFTFGPGTKVDIKRTVAAP SVFIFPPSDEQLKSGTASVVCLLNNFYPREAKVQWKV DNALQSGNSQESVTEQDSKDSTYSLSSTLTLSKADYE KHKVYACEVTHQGLSSPVTKSFNRGEC | 70 |
| PC5: HC Anti-albumin (SEQ ID NO: 57) + Linker 3 + SP34.185 scFv mask (SEQ ID NO: 17) + cleavable linker + SP34.185 scFv (VH-linker 1-VL) + Linker 2 + 006 PSMA Fab HC | EVQLVESGGGLVQPGGSLRLSCAASGSTFYTAVMGW VRQAPGKGLEWVAAIRWTALTTSYADSVKGRFTISR DGAKTTLYLQMNSLRPEDTAVYYCAARGTLGLFTT ADSYDYWGQGTLVTVSSGGGGSGGGGSGGGVYCGPEFD ESVGCMGGGGSGGGGLSGRSDAGSPLGLAGSGGGSEV QLVESGGGLVQPGGSLKLSCAASGFTFNKYAMNWV RQAPGKGLEWVARIRSKYNNYATYYADSVKDRFTIS RDDSKNTAYLQMNNLKTEDTAVYYCVRHGNFGNSY ISYWAYWGQGTLVTVSSGGGGSGGGGSGGGGSQTV VTQEPSLTVSPGGTVTLTCGSSTGAVTSGNYPNWVQ QKPGQAPRGLIGGTKFLAPGTPARFSGSLLGGKAALT LSGVQPEDEAEYYCVLWYSNRWVFGGGTKLTVLGG GGSQVQLVESGGGVVQPGRSLRLSCAASGFAFSRYG MHWVRQAPGKGLEWVAVIWYDGSNKYYADSVKGR FTISRDNSKNTQYLQMNSLRAEDTAVYYCARGGDFL YYYYYGMDVWGQGTTVTVSSASTKGPSVFPLAPSSK STSGGTAALGCLVKDYFPEPVTVSWNSGALTSGVHTF PAVLQSSGLYSLSSVVTVPSSSLGTQTYICNVNHKPSN TKVDKKVEPKSC | 71 |
| PC6: LC Anti-albumin (SEQ ID NO: 57) + Linker 3 + SP34.185 scFv mask (SEQ ID NO: 17) + cleavable | EVQLVESGGGLVQPGGSLRLSCAASGSTFYTAVMGW VRQAPGKGLEWVAAIRWTALTTSYADSVKGRFTISR DGAKTTLYLQMNSLRPEDTAVYYCAARGTLGLFTT ADSYDYWGQGTLVTVSSGGGGSGGGGSGGGVYCGPEFD ESVGCMGGGGSGGGGLSGRSDAGSPLGLAGSGGGSEV QLVESGGGLVQPGGSLKLSCAASGFTFNKYAMNWV | 72 |

TABLE 6-continued

| Polypeptide complex sequences | | |
|---|---|---|
| Construct Description | Amino Acid Sequence (N to C) | SEQ ID NO: |
| linker + SP34.185 scFv (VH-linker 1-VL) + Linker 2 + 006 PSMA Fab LC | RQAPGKGLEWVARIRSKYNNYATYYADSVKDRFTIS RDDSKNTAYLQMNNLKTEDTAVYYCVRHGNFGNSY ISYWAYWGQGTLVTVSSGGGGSGGGGSGGGGSQTV VTQEPSLTVSPGGTVTLTCGSSTGAVTSGNYPNWVQ QKPGQAPRGLIGGTKFLAPGTPARFSGSLLGGKAALT LSGVQPEDEAEYYCVLWYSNRWVFGGGTKLTVLGG GGSDIQMTQSPSSLSASVGDRVTITCRASQGISNYLAW YQQKTGKVPKFLIYEASTLQSGVPSRFSGGGSGTDFTL TISSLQPEDVATYYCQNYNSAPFTFGPGTKVDIKRTV AAPSVFIFPPSDEQLKSGTASVVCLLNNFYPREAKVQ WKVDNALQSGNSQESVTEQDSKDSTYSLSSTLTLSKA DYEKHKVYACEVTHQGLSSPVTKSFNRGEC | |
| PC6: HC 006 PSMA Fab HC | QVQLVESGGGVVQPGRSLRLSCAASGFAFSRYGMH WVRQAPGKGLEWVAVIWYDGSNKYYADSVKGRFTI SRDNSKNTQYLQMNSLRAEDTAVYYCARGGDFLYY YYYGMDVWGQGTTVTVSSASTKGPSVFPLAPSSKSTS GGTAALGCLVKDYFPEPVTVSWNSGALTSGVHTFPA VLQSSGLYSLSSVVTVPSSSLGTQTYICNVNHKPSNTK VDKKVEPKSC | 73 |
| PC7: LC | EVQLVESGGGLVQPGNSLRLSCAASGFTFSKFGMSW VRQAPGKGLEWVSSISGSGRDTLYADSVKGRFTISRD NAKTTLYLQMNSLRPEDTAVYYCTIGGSLSVSSQGTL VTVSSGGGGSGGGGSGGVYCGPEFDESVGCMGGGGSG GGLSGRSDAGSPLGLAGSGGGSEVQLVESGGGLVQPG GSLKLSCAASGFTFNKYAMNWVRQAPGKGLEWVAR IRSKYNNYATYYADSVKDRFTISRDDSKNTAYLQMN NLKTEDTAVYYCVRHGNFGNSYISYWAYWGQGTLV TVSSGGGGSGGGGSGGGGSQTVVTQEPSLTVSPGGTV TLTCGSSTGAVTSGNYPNWVQQKPGQAPRGLIGGTK FLAPGTPARFSGSLLGGKAALTLSGVQPEDEAEYYCV LWYSNRWVFGGGTKLTVLGGGGSDIQMTQSPSSLSA SVGDRVTITCRASQGISNYLAWYQQKTGKVPKFLIYE ASTLQSGVPSRFSGGGSGTDFTLTISSLQPEDVATYYC QNYNSAPFT**FGPGTKVDIKRTVAAPSVFIFPPSDEQLK SGTASVVCLLNNFYPREAKVQWKVDNALQSGNSQES VTEQDSKDSTYSLSSTLTLSKADYEKHKVYACEVTHQ GLSSPVTKSFNRGEC | 74 |
| PC7: HC | QVQLVESGGGVVQPGRSLRLSCAASGFAFSRYGMH WVRQAPGKGLEWVAVIWYDGSNKYYADSVKGRFTI SRDNSKNTQYLQMNSLRAEDTAVYYCARGGDFLYY YYYGMDVWGQGTTVTVSSASTKGPSVFPLAPSSKSTS GGTAALGCLVKDYFPEPVTVSWNSGALTSGVHTFPA VLQSSGLYSLSSVVTVPSSSLGTQTYICNVNHKPSNTK VDKKVEPKSC | 75 |
| PC8: LC | EVQLVESGGGLVQPGNSLRLSCAASGFTFSKFGMSW VRQAPGKGLEWVSSISGSGRDTLYADSVKGRFTISRD NAKTTLYLQMNSLRPEDTAVYYCTIGGSLSVSSQGTL VTVSSGGGGSGGGGSGGVYCGPEFDESVGCMGGGGSG GGSGGGGSGGASSGAGGSGGGSEVQLVESGGGLVQP GGSLKLSCAASGFTFNKYAMNWVRQAPGKGLEWVA RIRSKYNNYATYYADSVKDRFTISRDDSKNTAYLQM NNLKTEDTAVYYCVRHGNFGNSYISYWAYWGQGTL VTVSSGGGGSGGGGSGGGGSQTVVTQEPSLTVSPGGT VTLTCGSSTGAVTSGNYPNWVQQKPGQAPRGLIGGT KFLAPGTPARFSGSLLGGKAALTLSGVQPEDEAEYYC VLWYSNRWVFGGGTKLTVLGGGGSDIQMTQSPSSLS ASVGDRVTITCRASQGISNYLAWYQQKTGKVPKFLIY EASTLQSGVPSRFSGGGSGTDFTLTISSLQPEDVATYY CQNYNSAPFTFGPGTKVDIKRTVAAPSVFIFPPSDEQL KSGTASVVCLLNNFYPREAKVQWKVDNALQSGNSQE SVTEQDSKDSTYSLSSTLTLSKADYEKHKVYACEVTH QGLSSPVTKSFNRGEC | 76 |
| PC8: HC | QVQLVESGGGVVQPGRSLRLSCAASGFAFSRYGMH WVRQAPGKGLEWVAVIWYDGSNKYYADSVKGRFTI SRDNSKNTQYLQMNSLRAEDTAVYYCARGGDFLYY YYYGMDVWGQGTTVTVSSASTKGPSVFPLAPSSKSTS GGTAALGCLVKDYFPEPVTVSWNSGALTSGVHTFPA VLQSSGLYSLSSVVTVPSSSLGTQTYICNVNHKPSNTK VDKKVEPKSC | 77 |

In some embodiments, the polypeptide or polypeptide complex comprises amino acid sequences according to SEQ ID NO: 62 and SEQ ID NO: 63. In some embodiments, the polypeptide or polypeptide complex comprises amino acid sequences with at least 90% sequence identity to SEQ ID NO: 62 and SEQ ID NO: 63. In some embodiments, the polypeptide or polypeptide complex comprises amino acid sequences with at least 95% sequence identity to SEQ ID NO: 62 and SEQ ID NO: 63. In some embodiments, the polypeptide or polypeptide complex comprises amino acid sequences with at least 99% sequence identity to SEQ ID NO: 62 and SEQ ID NO: 63.

In some embodiments, the polypeptide or polypeptide complex comprises amino acid sequences according to SEQ ID NO: 64 and SEQ ID NO: 65. In some embodiments, the polypeptide or polypeptide complex comprises amino acid sequences with at least 90% sequence identity to SEQ ID NO: 64 and SEQ ID NO: 65. In some embodiments, the polypeptide or polypeptide complex comprises amino acid sequences with at least 95% sequence identity to SEQ ID NO: 64 and SEQ ID NO: 65. In some embodiments, the polypeptide or polypeptide complex comprises amino acid sequences with at least 99% sequence identity to SEQ ID NO: 64 and SEQ ID NO: 65.

In some embodiments, the polypeptide or polypeptide complex comprises amino acid sequences according to SEQ ID NO: 66 and SEQ ID NO: 67. In some embodiments, the polypeptide or polypeptide complex comprises amino acid sequences with at least 90% sequence identity to SEQ ID NO: 66 and SEQ ID NO: 67. In some embodiments, the polypeptide or polypeptide complex comprises amino acid sequences with at least 95% sequence identity to SEQ ID NO: 66 and SEQ ID NO: 67. In some embodiments, the polypeptide or polypeptide complex comprises amino acid sequences with at least 99% sequence identity to SEQ ID NO: 66 and SEQ ID NO: 67.

In some embodiments, the polypeptide or polypeptide complex comprises amino acid sequences according to SEQ ID NO: 68 and SEQ ID NO: 69. In some embodiments, the polypeptide or polypeptide complex comprises amino acid sequences with at least 90% sequence identity to SEQ ID NO: 68 and SEQ ID NO: 69. In some embodiments, the polypeptide or polypeptide complex comprises amino acid sequences with at least 95% sequence identity to SEQ ID NO: 68 and SEQ ID NO: 69. In some embodiments, the polypeptide or polypeptide complex comprises amino acid sequences with at least 99% sequence identity to SEQ ID NO: 68 and SEQ ID NO: 69.

In some embodiments, the polypeptide or polypeptide complex comprises amino acid sequences according to SEQ ID NO: 70 and SEQ ID NO: 71. In some embodiments, the polypeptide or polypeptide complex comprises amino acid sequences with at least 90% sequence identity to SEQ ID NO: 70 and SEQ ID NO: 71. In some embodiments, the polypeptide or polypeptide complex comprises amino acid sequences with at least 95% sequence identity to SEQ ID NO: 70 and SEQ ID NO: 71. In some embodiments, the polypeptide or polypeptide complex comprises amino acid sequences with at least 99% sequence identity to SEQ ID NO: 70 and SEQ ID NO: 71.

In some embodiments, the polypeptide or polypeptide complex comprises amino acid sequences according to SEQ ID NO: 72 and SEQ ID NO: 73. In some embodiments, the polypeptide or polypeptide complex comprises amino acid sequences with at least 90% sequence identity to SEQ ID NO: 72 and SEQ ID NO: 73. In some embodiments, the polypeptide or polypeptide complex comprises amino acid sequences with at least 95% sequence identity to SEQ ID NO: 72 and SEQ ID NO: 73. In some embodiments, the polypeptide or polypeptide complex comprises amino acid sequences with at least 99% sequence identity to SEQ ID NO: 72 and SEQ ID NO: 73.

In some embodiments, the polypeptide or polypeptide complex comprises amino acid sequences according to SEQ ID NO: 74 and SEQ ID NO: 75. In some embodiments, the polypeptide or polypeptide complex comprises amino acid sequences with at least 90% sequence identity to SEQ ID NO: 74 and SEQ ID NO: 75. In some embodiments, the polypeptide or polypeptide complex comprises amino acid sequences with at least 95% sequence identity to SEQ ID NO: 74 and SEQ ID NO: 75. In some embodiments, the polypeptide or polypeptide complex comprises amino acid sequences with at least 99% sequence identity to SEQ ID NO: 74 and SEQ ID NO: 75.

In some embodiments, the polypeptide or polypeptide complex comprises amino acid sequences according to SEQ ID NO: 76 and SEQ ID NO: 77. In some embodiments, the polypeptide or polypeptide complex comprises amino acid sequences with at least 90% sequence identity to SEQ ID NO: 76 and SEQ ID NO: 77. In some embodiments, the polypeptide or polypeptide complex comprises amino acid sequences with at least 95% sequence identity to SEQ ID NO: 76 and SEQ ID NO: 77. In some embodiments, the polypeptide or polypeptide complex comprises amino acid sequences with at least 99% sequence identity to SEQ ID NO: 76 and SEQ ID NO: 77.

Polypeptides or polypeptide complexes, in some embodiments, comprise a sequence set forth in Table 6. In some embodiments, the sequence comprises at least or about 70%, 80%, 85%, 90%, 91%, 92%, 93%, 94%, 95%, 96%, 97%, 98%, 99%, or 100% sequence identity to any one of SEQ ID NOs: 62-77. In some instances, the sequence comprises at least or about 95% homology to any one of SEQ ID NOs: 62-77. In some instances, the sequence comprises at least or about 97% homology to any one of SEQ ID NOs: 62-77. In some instances, the sequence comprises at least or about 99% homology to any one of SEQ ID NOs: 62-77. In some instances, the sequence comprises at least or about 100% homology to any one of SEQ ID NOs: 62-77. In some instances, the sequence comprises at least a portion having at least or about 10, 20, 30, 40, 50, 60, 70, 80, 90, 100, 110, 120, 130, 140, 150, 160, 170, 180, 190, 200, 210, or more than 210 amino acids of any one of SEQ ID NOs: 62, 65, 66, 69, 70, 73, 75, or 77. In some instances, the sequence comprises at least a portion having at least or about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, or more than 450 amino acids of any one of SEQ ID NOs: 63 or 64. In some instances, the sequence comprises at least a portion having at least or about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, or more than 640 amino acids of any one of SEQ ID NOs: 67, 68, 71, 72, 74, or 76.

As used herein, the term "percent (%) amino acid sequence identity" with respect to a sequence is defined as the percentage of amino acid residues in a candidate sequence that are identical with the amino acid residues in the specific sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as EMBOSS MATCHER, EMBOSS WATER, EMBOSS STRETCHER, EMBOSS NEEDLE, EMBOSS LALIGN, BLAST, BLAST-2, ALIGN or Megalign (DNASTAR) software. Those skilled in the art can determine appropriate parameters for measuring alignment, including any algorithms needed to achieve maximal alignment over the full length of the sequences being compared. In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y, where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

Figure 1A:
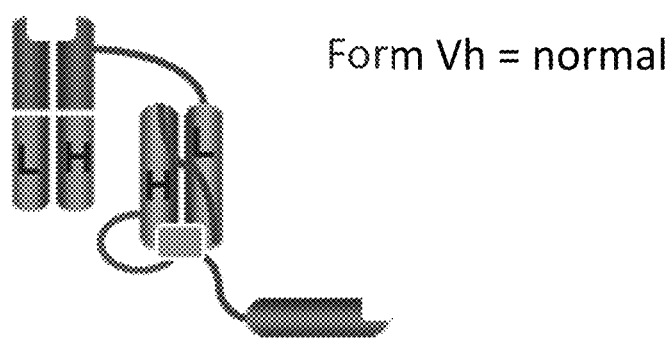
FIGS. 1A-1R illustrate polypeptide complexes of this disclosure in a normal orientation (FIG. 1A), flipped orientation (FIG. 1B), and in several structural arrangements (FIGS. 1C-1R).
Figure 1B:
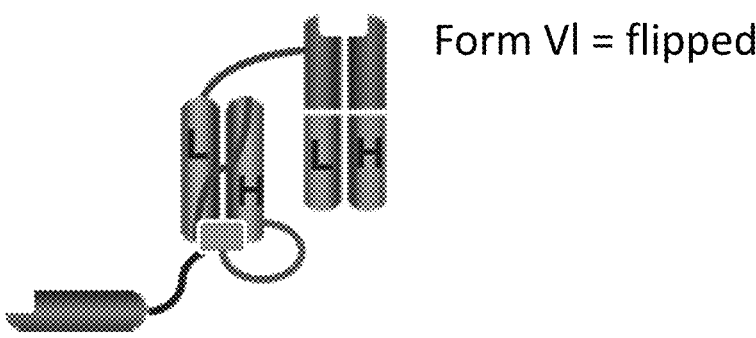
Figure 1C:
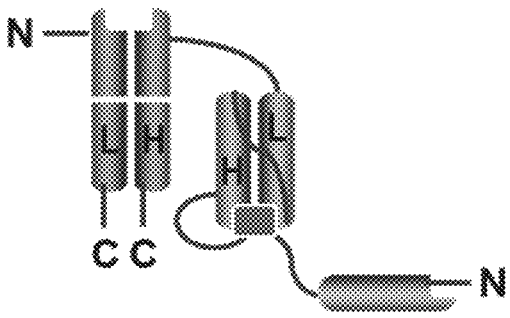

Disclosed herein, in some embodiments, are isolated polypeptides or polypeptide complexes comprising a structural arrangement according to the configuration shown in FIG. 1C, wherein the polypeptide complex comprises a single chain variable fragment (scFv) comprising a light chain variable domain and a heavy chain variable domain, wherein the scFv further comprises a peptide that impairs binding of the scFv to an effector cell antigen and the peptide is linked to the heavy chain variable domain of the scFv with a linking moiety that is a substrate for a tumor specific protease, and the peptide further comprises a half-life extending molecule; and a Fab or a Fab' that binds to prostate-specific membrane antigen (PSMA), wherein the Fab or Fab' comprises a Fab light chain polypeptide chain and a Fab heavy chain polypeptide chain, and wherein the Fab heavy chain polypeptide chain is linked to a C terminus of the light chain variable domain of the scFv.

Figure 1D:
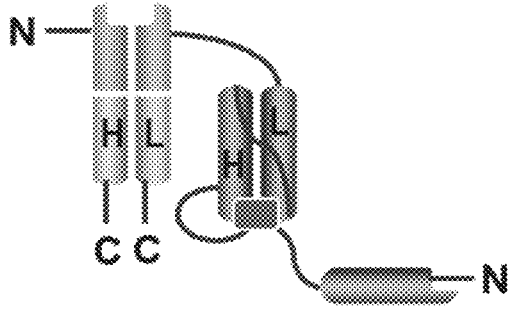

Disclosed herein, in some embodiments, are isolated polypeptides or polypeptide complexes comprising a structural arrangement according to the configuration shown in FIG. 1D, wherein the polypeptide complex comprises a single chain variable fragment (scFv) comprising a light chain variable domain and a heavy chain variable domain, wherein the scFv further comprises a peptide that impairs binding of the scFv to an effector cell antigen and the peptide is linked to a N-terminus of the heavy chain variable domain of the scFv with a linking moiety that is a substrate for a tumor specific protease, and the peptide further comprises a half-life extending molecule; and a Fab or Fab' that binds to prostate-specific membrane antigen (PSMA), wherein the Fab or Fab' comprises a Fab light chain polypeptide and a Fab heavy chain polypeptide, wherein the Fab light chain polypeptide is linked to a C terminus of the light chain variable domain of the scFv.

Figure 1E:
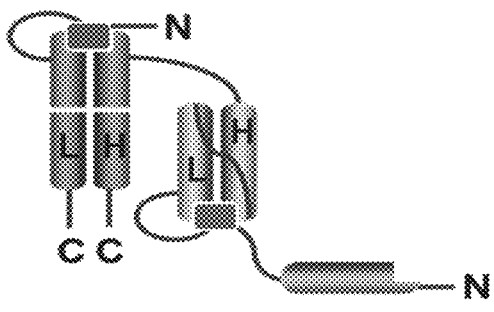

Disclosed herein, in some embodiments, are isolated polypeptides or polypeptide complexes comprising a structural arrangement according to the configuration shown in FIG. 1E, wherein the polypeptide or polypeptide complex comprises a single chain variable fragment (scFv) comprising a light chain variable domain and a heavy chain variable domain, wherein the scFv is linked to a peptide ($P_1$) that impairs binding of the scFv to an effector cell antigen and $P_1$ is linked to a N-terminus of the light chain variable domain of the scFv with a linking moiety ($L_1$) that is a substrate for a tumor specific protease, and $P_1$ is further linked to a half-life extending molecule; and a Fab that binds to prostate-specific membrane antigen (PSMA), wherein the Fab comprises a Fab light chain polypeptide and a Fab heavy chain polypeptide, wherein the Fab heavy chain polypeptide is linked to a C terminus of the heavy chain variable domain of the scFv, and wherein the Fab is linked to $P_2$ and $L_2$, wherein $P_2$ comprises a peptide that impairs binding of the Fab to PSMA; and $L_2$ comprises a linking moiety that connects the Fab light chain polypeptide to $P_2$ and is a substrate for a tumor specific protease.

Figure 1F:
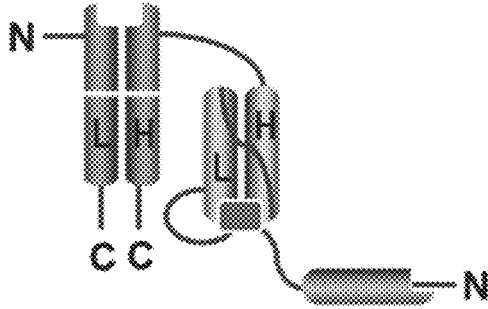

Disclosed herein, in some embodiments, are isolated polypeptides or polypeptide complexes comprising a structural arrangement according to the configuration shown in FIG. 1F, wherein the polypeptide or polypeptide complex comprises a single chain variable fragment (scFv) comprising a light chain variable domain and a heavy chain variable domain, wherein the scFv is linked to a peptide that impairs binding of the scFv to an effector cell antigen and the peptide is linked to the light chain variable domain of the scFv with a linking moiety that is a substrate for a tumor specific protease, and the peptide is further linked to a half-life extending molecule; and a Fab that binds to prostate-specific membrane antigen (PSMA), wherein the Fab comprises a Fab light chain polypeptide chain and a Fab heavy chain polypeptide chain, and wherein the Fab heavy chain polypeptide chain is linked to a C terminus of the heavy chain variable domain of the scFv.

Figure 1G:
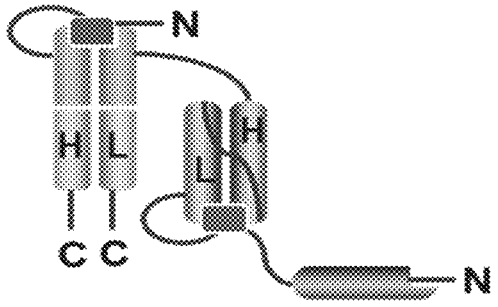

Disclosed herein, in some embodiments, are isolated polypeptides or polypeptide complexes comprising a structural arrangement according to the configuration shown in FIG. 1G, wherein the polypeptide or polypeptide complex comprises a single chain variable fragment (scFv) comprising a light chain variable domain and a heavy chain variable domain, wherein the scFv is linked to a peptide ($P_1$) that impairs binding of the scFv to an effector cell antigen and $P_1$ is linked to a N-terminus of the light chain variable domain of the scFv with a linking moiety that is a substrate for a tumor specific protease, and $P_1$ is further linked to a half-life extending molecule; and a Fab that binds to prostate-specific membrane antigen (PSMA), wherein the Fab comprises a Fab light chain polypeptide and a Fab heavy chain polypeptide, wherein the Fab light chain polypeptide is linked to a C terminus of the heavy chain variable domain of the scFv, and wherein the Fab is linked to $P_2$ and $L_2$, wherein $P_2$ comprises a peptide that impairs binding to PSMA; and $L_2$ comprises a linking moiety that connects the Fab heavy chain polypeptide to $P_2$ and is a substrate for a tumor specific protease.

Figure 1H:
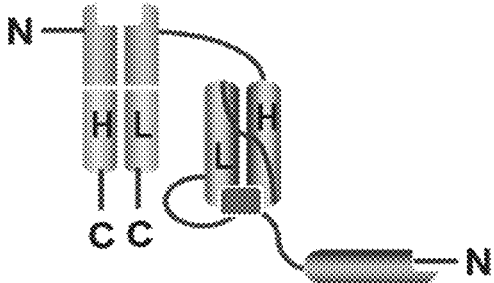

Disclosed herein, in some embodiments, are isolated polypeptides or polypeptide complexes comprising a structural arrangement according to the configuration shown in FIG. 1H, wherein the polypeptide or polypeptide complex comprises a single chain variable fragment (scFv) comprising a light chain variable domain and a heavy chain variable domain, wherein the scFv is further linked to a peptide that impairs binding of the scFv to an effector cell antigen and the peptide is linked to a N-terminus of the light chain variable domain of the scFv with a linking moiety that is a substrate for a tumor specific protease, and the peptide is further linked to a half-life extending molecule; and a Fab that binds to prostate-specific membrane antigen (PSMA), wherein the Fab comprises a Fab light chain polypeptide and a Fab heavy chain polypeptide, wherein the Fab light chain polypeptide is linked to a C terminus of the heavy chain variable domain of the scFv.

Figure 1I:
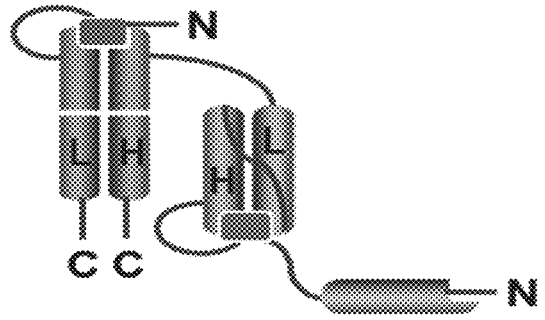

Disclosed herein, in some embodiments, are isolated polypeptides or polypeptide complexes comprising a structural arrangement according to the configuration shown in FIG. 1I, wherein the polypeptide or polypeptide complex comprises a single chain variable fragment (scFv) comprising a light chain variable domain and a heavy chain variable domain, wherein the scFv is linked to a peptide $(P_1)$ that impairs binding of the scFv to an effector cell antigen and $P_1$ is linked to a N-terminus of the heavy chain variable domain of the scFv with a linking moiety $(L_1)$ that is a substrate for a tumor specific protease, and $P_1$ is further linked to a half-life extending molecule; and a Fab that binds to prostate-specific membrane antigen (PSMA), wherein the Fab comprises a Fab light chain polypeptide and a Fab heavy chain polypeptide, wherein the Fab heavy chain polypeptide is linked to a C terminus of the light chain variable domain of the scFv, and wherein the Fab is linked to $P_2$ and $L_2$, wherein $P_2$ comprises a peptide that impairs binding to PSMA; and $L_2$ comprises a linking moiety that connects the Fab light chain polypeptide to $P_2$ and is a substrate for a tumor specific protease.

Figure 1J:
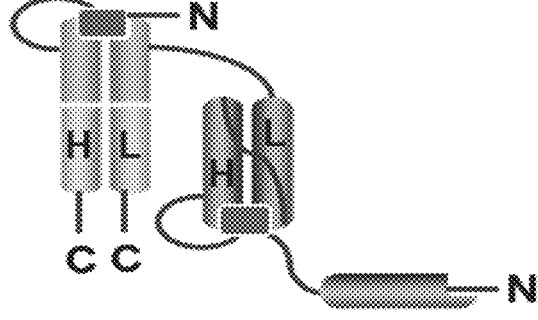

Disclosed herein, in some embodiments, are isolated polypeptides or polypeptide complexes comprising a structural arrangement according to the configuration shown in FIG. 1J, wherein the polypeptide or polypeptide complex comprises a single chain variable fragment (scFv) comprising a light chain variable domain and a heavy chain variable domain, wherein the scFv is linked to a peptide $(P_1)$ that impairs binding of the scFv to an effector cell antigen and $P_1$ is linked to a N-terminus of the heavy chain variable domain of the scFv with a linking moiety $(L_1)$ that is a substrate for a tumor specific protease, and $P_1$ is further linked to a half-life extending molecule; and a Fab that binds to prostate-specific membrane antigen (PSMA), wherein the Fab comprises a Fab light chain polypeptide and a Fab heavy chain polypeptide, wherein the Fab light chain polypeptide is linked to a C terminus of the light chain variable domain of the scFv, and wherein the Fab is linked to $P_2$ and $L_2$, wherein $P_2$ comprises a peptide that impairs binding to PSMA; and $L_2$ comprises a linking moiety that connects the Fab heavy chain polypeptide to $P_2$ and is a substrate for a tumor specific protease.

Figure 1K:
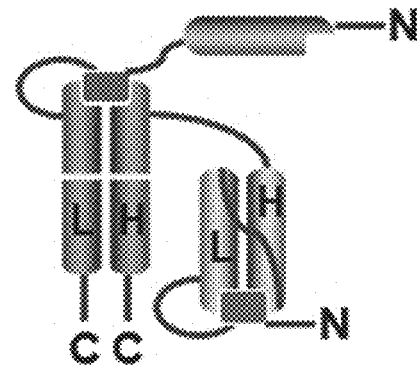

Disclosed herein, in some embodiments, are isolated polypeptides or polypeptide complexes comprising a structural arrangement according to the configuration shown in FIG. 1K, wherein the polypeptide or polypeptide complex comprises a Fab that binds to prostate-specific membrane antigen (PSMA), the Fab comprising a Fab light chain polypeptide and a Fab heavy chain polypeptide, wherein the Fab is linked to a peptide $(P_1)$ that impairs binding of the Fab to PSMA and $P_1$ is linked to a N terminus of the Fab light chain polypeptide with a linking moiety $(L_1)$ that is a substrate for a tumor specific protease, and the $P_1$ is further linked to a half-life extending molecule; and a single chain variable fragment (scFv) that binds to an effector cell antigen, the scFv comprising a light chain variable domain and a heavy chain variable domain, wherein the heavy chain variable domain of the scFv is linked to an N terminus of the Fab heavy chain polypeptide, wherein the scFv is linked to $P_2$ and $L_2$, wherein $P_2$ comprises a peptide that impairs binding of the scFv to the effector cell antigen, and $L_2$ comprises a linking moiety that connects the light chain variable domain of the scFv to $P_2$ and is a substrate for a tumor specific protease.

Figure 1L:
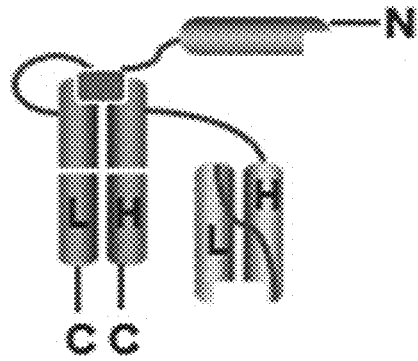

Disclosed herein, in some embodiments, are isolated polypeptides or polypeptide complexes comprising a structural arrangement according to the configuration shown in FIG. 1L, wherein the polypeptide or polypeptide complex comprises a Fab that binds to prostate-specific membrane antigen (PSMA), the Fab comprising a Fab light chain polypeptide and a Fab heavy chain polypeptide, wherein the Fab is linked to a peptide that impairs binding of the Fab to PSMA and the peptide is linked to a N terminus of the Fab light chain polypeptide with a linking moiety that is a substrate for a tumor specific protease, and the peptide is further linked to half-life extending molecule; and a single chain variable fragment (scFv) that binds to an effector cell antigen, the scFv comprising a light chain variable domain and a heavy chain variable domain, wherein the heavy chain variable domain of the scFv is linked to an N terminus of the Fab heavy chain polypeptide.

Figure 1M:
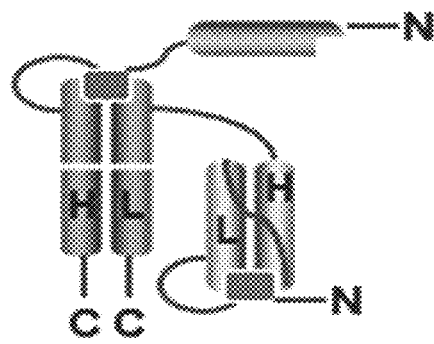

Disclosed herein, in some embodiments, are isolated polypeptides or polypeptide complexes comprising a structural arrangement according to the configuration shown in FIG. 1M, wherein the polypeptide or polypeptide complex comprises a Fab that binds to prostate-specific membrane antigen (PSMA), the Fab comprising a Fab light chain polypeptide and a Fab heavy chain polypeptide, wherein the Fab is linked to a peptide $(P_1)$ that impairs binding of the Fab to PSMA and $P_1$ is linked to a N terminus of the Fab heavy chain polypeptide with a linking moiety $(L_1)$ that is a substrate for a tumor specific protease, and $P_1$ is further linked to a half-life extending molecule; and a single chain variable fragment (scFv) that binds to an effector cell antigen, the scFv comprising a light chain variable domain and a heavy chain variable domain, wherein the heavy chain variable domain of the scFv is linked to an N terminus of the Fab light chain polypeptide, wherein the scFv further is linked to $P_2$ and $L_2$, wherein $P_2$ comprises a peptide that impairs binding of the scFv to the effector cell antigen, and $L_2$ comprises a linking moiety that connects the light chain variable domain of the scFv to $P_2$ and is a substrate for a tumor specific protease.

Figure 1N:
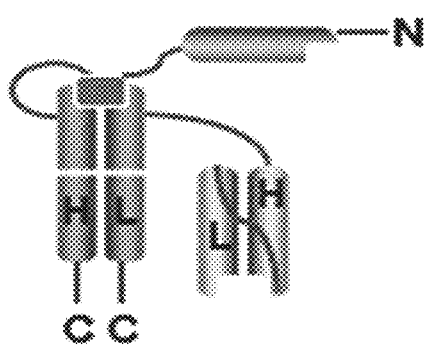

Disclosed herein, in some embodiments, are isolated polypeptides or polypeptide complexes comprising a structural arrangement according to the configuration shown in FIG. 1N, wherein the polypeptide or polypeptide complex comprises a Fab that binds to prostate-specific membrane antigen (PSMA), the Fab comprising a Fab light chain polypeptide and a Fab heavy chain polypeptide, wherein the Fab is linked to a peptide that impairs binding of the Fab to PSMA and the peptide is linked to a N terminus of the Fab heavy chain polypeptide with a linking moiety that is a substrate for a tumor specific protease, and the peptide is further linked to a half-life extending molecule; and a single chain variable fragment (scFv) that binds to an effector cell antigen, the scFv comprising a light chain variable domain and a heavy chain variable domain, wherein the heavy chain variable domain of the scFv is linked to an N terminus of the Fab light chain polypeptide.

Figure 1O:
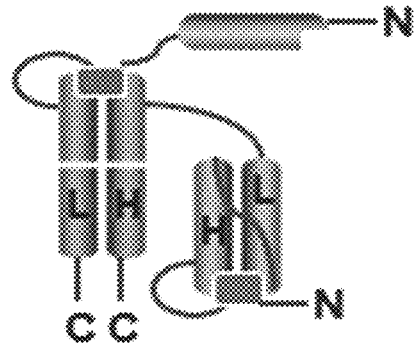

Disclosed herein, in some embodiments, are isolated polypeptides or polypeptide complexes comprising a structural arrangement according to the configuration shown in FIG. 1O, wherein the polypeptide or polypeptide complex comprises a Fab that binds to prostate-specific membrane antigen (PSMA), the Fab comprising a Fab light chain polypeptide and a Fab heavy chain polypeptide, wherein the Fab is linked to a peptide (P$_1$) that impairs binding of the Fab to PSMA and P$_1$ is linked to a N terminus of the Fab light chain polypeptide with a linking moiety (L$_1$) that is a substrate for a tumor specific protease, and P$_1$ is further linked to a half-life extending molecule; and a single chain variable fragment (scFv) that binds to an effector cell antigen, the scFv comprising a light chain variable domain and a heavy chain variable domain, wherein the light chain variable domain of the scFv is linked to an N terminus of the Fab heavy chain polypeptide, wherein the scFv is linked to P$_2$ and L$_2$, wherein P$_2$ comprises a peptide that impairs binding of the scFv to the effector cell antigen, and L$_2$ comprises a linking moiety that connects the heavy chain variable domain of the scFv to P$_2$ and is a substrate for a tumor specific protease.

Figure 1P:
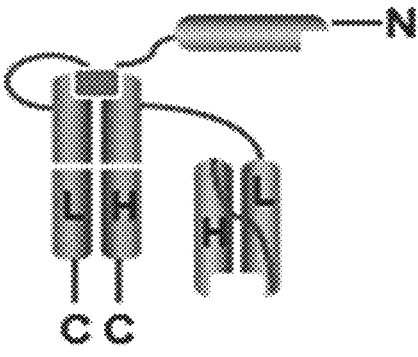

Disclosed herein, in some embodiments, are isolated polypeptides or polypeptide complexes comprising a structural arrangement according to the configuration shown in FIG. 1P, wherein the polypeptide or polypeptide complex comprises a Fab that binds to prostate-specific membrane antigen (PSMA), the Fab comprising a Fab light chain polypeptide and a Fab heavy chain polypeptide, wherein the Fab is linked to a peptide that impairs binding of the Fab to PSMA and the peptide is linked to a N terminus of the Fab light chain polypeptide with a linking moiety that is a substrate for a tumor specific protease, and the peptide is further linked to a half-life extending molecule; and a single chain variable fragment (scFv) that binds to an effector cell antigen, the scFv comprising a light chain variable domain and a heavy chain variable domain, wherein the light chain variable domain of the scFv is linked to an N terminus of the Fab heavy chain polypeptide.

Figure 1Q:
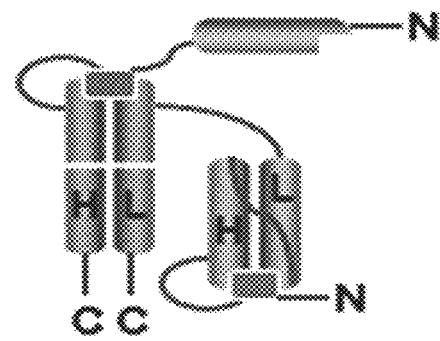

Disclosed herein, in some embodiments, are isolated polypeptides or polypeptide complexes comprising a structural arrangement according to the configuration shown in FIG. 1Q, wherein the polypeptide or polypeptide complex comprises a Fab that binds to prostate-specific membrane antigen (PSMA), the Fab comprising a Fab light chain polypeptide and a Fab heavy chain polypeptide, wherein the Fab is linked to a (P$_1$) that impairs binding of the Fab to PSMA and P$_1$ is linked to a N terminus of the Fab heavy chain polypeptide with a linking moiety (L$_1$) that is a substrate for a tumor specific protease, and P$_1$ is further linked to a half-life extending molecule; and a single chain variable fragment (scFv) that binds to an effector cell antigen, the scFv comprising a light chain variable domain and a heavy chain variable domain, wherein the light chain variable domain of the scFv is linked to an N terminus of the Fab light chain polypeptide, wherein the scFv is linked to P$_2$ and L$_2$, wherein P$_2$ comprises a peptide that impairs binding of the scFv to the effector cell antigen, and L$_2$ comprises a linking moiety that connects the heavy chain variable domain of the scFv to P$_2$ and is a substrate for a tumor specific protease.

Figure 1R:
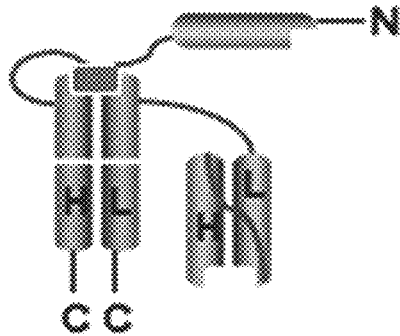

Disclosed herein, in some embodiments, are isolated polypeptides or polypeptide complexes comprising a structural arrangement according to the configuration shown in FIG. 1R, wherein the polypeptide or polypeptide complex comprises a Fab that binds to prostate-specific membrane antigen (PSMA), the Fab comprising a Fab light chain polypeptide and a Fab heavy chain polypeptide, wherein the Fab is linked to a peptide that impairs binding of the Fab to PSMA and the peptide is linked to a N terminus of the Fab heavy chain polypeptide with a linking moiety that is a substrate for a tumor specific protease, and the peptide is further linked to a half-life extending molecule; and a single chain variable fragment (scFv) that binds to an effector cell antigen, the scFv comprising a light chain variable domain and a heavy chain variable domain, wherein the light chain variable domain of the scFv is linked to an N terminus of the Fab light chain polypeptide.

Polynucleotides Encoding Polypeptides or Polypeptide Complexes

Disclosed herein, in some embodiments, are isolated recombinant nucleic acid molecules encoding polypeptides or polypeptide complexes as disclosed herein. In some embodiments, the polypeptides or polypeptide complexes comprise an antibody or an antibody fragment. In some embodiments, the polypeptides or polypeptide complexes comprise a Fab and a single chain variable fragment (scFv).

Disclosed herein, in some embodiments, are isolated recombinant nucleic acid molecules encoding polypeptides or polypeptide complexes according to Formula I:

$$A_2\text{-}A_1\text{-}L_1\text{-}P_1—H_1 \quad \text{(Formula I)}$$

wherein: A$_1$ comprises a first antigen recognizing molecule that binds to an effector cell antigen; P$_1$ comprises a peptide that binds to A$_1$; L$_1$ comprises a linking moiety that connects A$_1$ to P$_1$ and is a substrate for a tumor specific protease; H$_1$ comprises a half-life extending molecule; and A$_2$ comprises a second antigen recognizing molecule that binds to prostate-specific membrane antigen (PSMA).

Disclosed herein, in some embodiments, are isolated recombinant nucleic acid molecules encoding polypeptides or polypeptide complexes according to Formula I:

$$A_2\text{-}A_1\text{-}L_1\text{-}P_1—H_1 \quad \text{(Formula I)}$$

wherein: A$_1$ is a first antigen recognizing molecule that binds to an effector cell antigen; P$_1$ is a peptide that binds to A$_1$; L$_1$ is a linking moiety that connects A$_1$ to P$_1$ and is a substrate for a tumor specific protease; H$_1$ is a half-life extending molecule; and A$_2$ is a second antigen recognizing molecule that binds to prostate-specific membrane antigen (PSMA).

Disclosed herein, in some embodiments, are isolated recombinant nucleic acid molecules encoding polypeptides or polypeptide complexes comprising Formula I:

$$A_2\text{-}A_1\text{-}L_1\text{-}P_1—H_1 \quad \text{(Formula I)}$$

wherein: A$_1$ comprises a first antigen recognizing molecule that binds to an effector cell antigen; P$_1$ comprises a peptide that binds to A$_1$; L$_1$ comprises a linking moiety that connects A$_1$ to P$_1$ and is a substrate for a tumor specific protease; H$_1$ comprises a half-life extending molecule; and A$_2$ comprises a second antigen recognizing molecule that binds to prostate-specific membrane antigen (PSMA).

Disclosed herein, in some embodiments, are isolated recombinant nucleic acid molecules encoding polypeptides or polypeptide complexes comprising Formula I:

$$A_2\text{-}A_1\text{-}L_1\text{-}P_1—H_1 \quad \text{(Formula I)}$$

wherein: A$_1$ is a first antigen recognizing molecule that binds to an effector cell antigen; P$_1$ is a peptide that binds to A$_1$; L$_1$ is a linking moiety that connects A$_1$ to P$_1$ and is a substrate for a tumor specific protease; H$_1$ is a half-life extending molecule; and A$_2$ is a second antigen recognizing molecule that binds to prostate-specific membrane antigen (PSMA).

Disclosed herein, in some embodiments, are isolated recombinant nucleic acid molecules encoding polypeptides or polypeptide complexes according to Formula Ia:

$$P_2\text{-}L_2\text{-}A_2\text{-}A_1\text{-}L_1\text{-}P_1—H_1 \quad \text{(Formula Ia).}$$

Disclosed herein, in some embodiments, are isolated recombinant nucleic acid molecules encoding polypeptides or polypeptide complexes according to Formula I:

$$L_{1a}\text{-}P_{1a}\text{—}H_{1a} \qquad \text{(Formula II)}$$

wherein: $L_{1a}$ comprises a tumor specific protease-cleaved linking moiety that when uncleaved connects $P_{1a}$ to a first antigen recognizing molecule that binds to an effector cell antigen and the first antigen recognizing molecule is connected to a second antigen recognizing molecule that binds to prostate-specific membrane antigen (PSMA); $P_{1a}$ comprises a peptide that binds to the first antigen recognizing molecule when $L_{1a}$ is uncleaved; and $H_{1a}$ comprises a half-life extending molecule.

Disclosed herein, in some embodiments, are isolated recombinant nucleic acid molecules encoding polypeptides or polypeptide complexes comprising Formula II:

$$L_{1a}\text{-}P_{1a}\text{—}H_{1a} \qquad \text{(Formula II)}$$

wherein: $L_{1a}$ comprises a tumor specific protease-cleaved linking moiety that when uncleaved connects $P_{1a}$ to a first antigen recognizing molecule that binds to an effector cell antigen and the first antigen recognizing molecule is connected to a second antigen recognizing molecule that binds to prostate-specific membrane antigen (PSMA); $P_{1a}$ comprises a peptide that binds to the first antigen recognizing molecule when $L_{1a}$ is uncleaved; and $H_{1a}$ comprises a half-life extending molecule.

Disclosed herein, in some embodiments, are isolated recombinant nucleic acid molecules encoding polypeptides or polypeptide complexes according to Formula II:

$$L_{1a}\text{-}P_{1a}\text{—}H_{1a} \qquad \text{(Formula II)}$$

wherein: $L_{1a}$ is a tumor specific protease-cleaved linking moiety that when uncleaved connects $P_{1a}$ to a first antigen recognizing molecule that binds to an effector cell antigen and the first antigen recognizing molecule is connected to a second antigen recognizing molecule that binds to prostate-specific membrane antigen (PSMA); $P_{1a}$ is a peptide that binds to the first antigen recognizing molecule when $L_{1a}$ is uncleaved; and $H_{1a}$ is a half-life extending molecule.

Disclosed herein, in some embodiments, are isolated recombinant nucleic acid molecules encoding polypeptides or polypeptide complexes comprising Formula II:

$$L_{1a}\text{-}P_{1a}\text{—}H_{1a} \qquad \text{(Formula II)}$$

wherein: $L_{1a}$ is a tumor specific protease-cleaved linking moiety that when uncleaved connects $P_{1a}$ to a first antigen recognizing molecule that binds to an effector cell antigen and the first antigen recognizing molecule is connected to a second antigen recognizing molecule that binds to prostate-specific membrane antigen (PSMA); $P_{1a}$ is a peptide that binds to the first antigen recognizing molecule when $L_{1a}$ is uncleaved; and $H_{1a}$ is a half-life extending molecule.

Disclosed herein, in some embodiments, are isolated nucleic acid molecules encoding polypeptides or polypeptide complexes comprising a structural arrangement according to the configuration shown in FIG. 1C, wherein the polypeptide complex comprises a single chain variable fragment (scFv) comprising a light chain variable domain and a heavy chain variable domain, wherein the scFv further comprises a peptide that impairs binding of the scFv to an effector cell antigen and the peptide is linked to the heavy chain variable domain of the scFv with a linking moiety that is a substrate for a tumor specific protease, and the peptide further comprises a half-life extending molecule; and a Fab or a Fab' that binds to prostate-specific membrane antigen (PSMA), wherein the Fab or Fab' comprises a Fab light chain polypeptide chain and a Fab heavy chain polypeptide chain, and wherein the Fab heavy chain polypeptide chain is linked to a C terminus of the light chain variable domain of the scFv.

Disclosed herein, in some embodiments, are isolated nucleic acid molecules encoding polypeptides or polypeptide complexes comprising a structural arrangement according to the configuration shown in FIG. 1D, wherein the polypeptide complex comprises a single chain variable fragment (scFv) comprising a light chain variable domain and a heavy chain variable domain, wherein the scFv further comprises a peptide that impairs binding of the scFv to an effector cell antigen and the peptide is linked to a N-terminus of the heavy chain variable domain of the scFv with a linking moiety that is a substrate for a tumor specific protease, and the peptide further comprises a half-life extending molecule; and a Fab or Fab' that binds to prostate-specific membrane antigen (PSMA), wherein the Fab or Fab' comprises a Fab light chain polypeptide and a Fab heavy chain polypeptide, wherein the Fab light chain polypeptide is linked to a C terminus of the light chain variable domain of the scFv.

Pharmaceutical Compositions

Disclosed herein, in some embodiments, are pharmaceutical compositions comprising: (a) the polypeptides or polypeptide complexes as disclosed herein; and (b) a pharmaceutically acceptable excipient.

In some embodiments, the pharmaceutical composition comprises (a) polypeptides or polypeptide complexes according to Formula I:

$$A_2\text{-}A_1\text{-}L_1\text{-}P_1\text{—}H_1 \qquad \text{(Formula I)}$$

wherein: $A_1$ comprises a first antigen recognizing molecule that binds to an effector cell antigen; $P_1$ comprises a peptide that binds to $A_1$; $L_1$ comprises a linking moiety that connects $A_1$ to $P_1$ and is a substrate for a tumor specific protease; $H_1$ comprises a half-life extending molecule; and $A_2$ comprises a second antigen recognizing molecule that binds to prostate-specific membrane antigen (PSMA); and (b) a pharmaceutically acceptable excipient.

In some embodiments, the pharmaceutical composition comprises (a) polypeptides or polypeptide complexes according to Formula I:

$$A_2\text{-}A_1\text{-}L_1\text{-}P_1\text{—}H_1 \qquad \text{(Formula I)}$$

wherein: $A_1$ is a first antigen recognizing molecule that binds to an effector cell antigen; $P_1$ is a peptide that binds to $A_1$; $L_1$ is a linking moiety that connects $A_1$ to $P_1$ and is a substrate for a tumor specific protease; $H_1$ is a half-life extending molecule; and $A_2$ is a second antigen recognizing molecule that binds to prostate-specific membrane antigen (PSMA); and (b) a pharmaceutically acceptable excipient.

In some embodiments, the pharmaceutical composition comprises (a) polypeptides or polypeptide complexes comprising Formula I:

$$A_2\text{-}A_1\text{-}L_1\text{-}P_1\text{—}H_1 \qquad \text{(Formula I)}$$

wherein: $A_1$ comprises a first antigen recognizing molecule that binds to an effector cell antigen; $P_1$ comprises a peptide that binds to $A_1$; $L_1$ comprises a linking moiety that connects $A_1$ to $P_1$ and is a substrate for a tumor specific protease; $H_1$ comprises a half-life extending molecule; and $A_2$ comprises a second antigen recognizing molecule that binds to prostate-specific membrane antigen (PSMA); and (b) a pharmaceutically acceptable excipient.

In some embodiments, the pharmaceutical composition comprises (a) polypeptides or polypeptide complexes comprising Formula I:

$$A_2\text{-}A_1\text{-}L_1\text{-}P_1\text{—}H_1 \qquad \text{(Formula I)}$$

wherein: $A_1$ is a first antigen recognizing molecule that binds to an effector cell antigen; $P_1$ is a peptide that binds to $A_1$; $L_1$ is a linking moiety that connects $A_1$ to $P_1$ and is a substrate for a tumor specific protease; $H_1$ is a half-life extending molecule; and $A_2$ is a second antigen recognizing molecule that binds to prostate-specific membrane antigen (PSMA); and (b) a pharmaceutically acceptable excipient.

In some embodiments, the pharmaceutical composition comprises (a) polypeptides or polypeptide complexes according to Formula Ia:

$$P_2\text{-}L_2\text{-}A_2\text{-}A_1\text{-}L_1\text{-}P_1\text{—}H_1 \qquad \text{(Formula Ia)};$$

and (b) a pharmaceutically acceptable excipient.

In some embodiments, the pharmaceutical composition comprises (a) polypeptides or polypeptide complexes according to Formula II:

$$L_{1a}\text{-}P_{1a}\text{—}H_{1a} \qquad \text{(Formula II)}$$

wherein: $L_{1a}$ comprises a tumor specific protease-cleaved linking moiety that when uncleaved connects $P_{1a}$ to a first antigen recognizing molecule that binds to an effector cell antigen and the first antigen recognizing molecule is connected to a second antigen recognizing molecule that binds to prostate-specific membrane antigen (PSMA); $P_{1a}$ comprises a peptide that binds to the first antigen recognizing molecule when $L_{1a}$ is uncleaved; and $H_{1a}$ comprises a half-life extending molecule; and (b) a pharmaceutically acceptable excipient.

In some embodiments, the pharmaceutical composition comprises (a) polypeptides or polypeptide complexes comprising Formula II:

$$L_{1a}\text{-}P_{1a}\text{—}H_{1a} \qquad \text{(Formula II)}$$

wherein: $L_{1a}$ comprises a tumor specific protease-cleaved linking moiety that when uncleaved connects $P_{1a}$ to a first antigen recognizing molecule that binds to an effector cell antigen and the first antigen recognizing molecule is connected to a second antigen recognizing molecule that binds to prostate-specific membrane antigen (PSMA); $P_{1a}$ comprises a peptide that binds to the first antigen recognizing molecule when $L_{1a}$ is uncleaved; and $H_{1a}$ comprises a half-life extending molecule; and (b) a pharmaceutically acceptable excipient.

In some embodiments, the pharmaceutical composition comprises (a) polypeptides or polypeptide complexes according to Formula II:

$$L_{1a}\text{-}P_{1a}\text{—}H_{1a} \qquad \text{(Formula II)}$$

wherein: $L_{1a}$ is a tumor specific protease-cleaved linking moiety that when uncleaved connects $P_{1a}$ to a first antigen recognizing molecule that binds to an effector cell antigen and the first antigen recognizing molecule is connected to a second antigen recognizing molecule that binds to prostate-specific membrane antigen (PSMA); $P_{1a}$ is a peptide that binds to the first antigen recognizing molecule when $L_{1a}$ is uncleaved; and $H_{1a}$ is a half-life extending molecule; and (b) a pharmaceutically acceptable excipient.

In some embodiments, the pharmaceutical composition comprises (a) polypeptides or polypeptide complexes comprising Formula II:

$$L_{1a}\text{-}P_{1a}\text{—}H_{1a} \qquad \text{(Formula II)}$$

wherein: $L_{1a}$ is a tumor specific protease-cleaved linking moiety that when uncleaved connects $P_{1a}$ to a first antigen recognizing molecule that binds to an effector cell antigen and the first antigen recognizing molecule is connected to a second antigen recognizing molecule that binds to prostate-specific membrane antigen (PSMA); $P_{1a}$ is a peptide that binds to the first antigen recognizing molecule when $L_{1a}$ is uncleaved; and $H_{1a}$ is a half-life extending molecule; and (b) a pharmaceutically acceptable excipient.

Disclosed herein, in some embodiments, the pharmaceutical composition comprises (a) polypeptides or polypeptide complexes comprising a structural arrangement according to the configuration shown in FIG. 1C, wherein the polypeptide complex comprises a single chain variable fragment (scFv) comprising a light chain variable domain and a heavy chain variable domain, wherein the scFv further comprises a peptide that impairs binding of the scFv to an effector cell antigen and the peptide is linked to the heavy chain variable domain of the scFv with a linking moiety that is a substrate for a tumor specific protease, and the peptide further comprises a half-life extending molecule; and a Fab or a Fab' that binds to prostate-specific membrane antigen (PSMA), wherein the Fab or Fab' comprises a Fab light chain polypeptide chain and a Fab heavy chain polypeptide chain, and wherein the Fab heavy chain polypeptide chain is linked to a C terminus of the light chain variable domain of the scFv; and (b) a pharmaceutically acceptable excipient. Disclosed herein, in some embodiments, the pharmaceutical composition comprises (a) polypeptides or polypeptide complexes comprising a structural arrangement according to the configuration shown in FIG. 1D.

wherein the polypeptide complex comprises a single chain variable fragment (scFv) comprising a light chain variable domain and a heavy chain variable domain, wherein the scFv further comprises a peptide that impairs binding of the scFv to an effector cell antigen and the peptide is linked to a N-terminus of the heavy chain variable domain of the scFv with a linking moiety that is a substrate for a tumor specific protease, and the peptide further comprises a half-life extending molecule; and a Fab or Fab' that binds to prostate-specific membrane antigen (PSMA), wherein the Fab or Fab' comprises a Fab light chain polypeptide and a Fab heavy chain polypeptide, wherein the Fab light chain polypeptide is linked to a C terminus of the light chain variable domain of the scFv; and (b) a pharmaceutically acceptable excipient.

In some embodiments, the polypeptide or polypeptide complex further comprises a detectable label, a therapeutic agent, or a pharmacokinetic modifying moiety. In some embodiments, the detectable label comprises a fluorescent label, a radiolabel, an enzyme, a nucleic acid probe, or a contrast agent.

For administration to a subject, the polypeptide or polypeptide complex as disclosed herein, may be provided in a pharmaceutical composition together with one or more pharmaceutically acceptable carriers or excipients. The term "pharmaceutically acceptable carrier" includes, but is not limited to, any carrier that does not interfere with the effectiveness of the biological activity of the ingredients and that is not toxic to the patient to whom it is administered. Examples of suitable pharmaceutical carriers are well known in the art and include phosphate buffered saline solutions, water, emulsions, such as oil/water emulsions, various types of wetting agents, sterile solutions etc. Such carriers can be formulated by conventional methods and can be administered to the subject at a suitable dose. Preferably, the compositions are sterile. These compositions may also contain adjuvants such as preservative, emulsifying agents and dispersing agents. Prevention of the action of microorganisms may be ensured by the inclusion of various antibacterial and antifungal agents.

The pharmaceutical composition may be in any suitable form, (depending upon the desired method of administration). It may be provided in unit dosage form, may be provided in a sealed container and may be provided as part of a kit. Such a kit may include instructions for use. It may include a plurality of said unit dosage forms.

The pharmaceutical composition may be adapted for administration by any appropriate route, including a parenteral (e.g., subcutaneous, intramuscular, or intravenous) route. Such compositions may be prepared by any method known in the art of pharmacy, for example by mixing the active ingredient with the carrier(s) or excipient(s) under sterile conditions.

Dosages of the substances of the present disclosure can vary between wide limits, depending upon the disease or disorder to be treated, the age and condition of the individual to be treated, etc. and a physician will ultimately determine appropriate dosages to be used.

Methods of Treatment

In some embodiments, are methods of treating cancer in a subject need in need thereof comprising administering to the subject an isolated polypeptide or polypeptide complex as described herein. In some embodiments, the cancer has cells that express PSMA. In some instances, the cancer is a solid tumor cancer. In some embodiments, the cancer is lung, breast (e.g. HER2+; ER/PR+; TNBC), cervical, ovarian, colorectal, pancreatic or gastric.

In some embodiments, are methods of treating prostate cancer in a subject need in need thereof comprising administering to the subject an isolated polypeptide or polypeptide complex as described herein. In some embodiments, are methods of treating metastatic castrate-resistant prostate cancer (mCRPC) in a subject need in need thereof comprising administering to the subject an isolated polypeptide or polypeptide complex as described herein.

Described herein, in some embodiments, are isolated polypeptides or polypeptide complexes, wherein the polypeptides or polypeptide complexes comprise a long half-life. In some instances, the half-life of the polypeptides or polypeptide complexes is at least or about 12 hours, 24 hours 36 hours, 48 hours, 60 hours, 72 hours, 84 hours, 96 hours, 100 hours, 108 hours, 119 hours, 120 hours, 140 hours, 160 hours, 180 hours, 200 hours, or more than 200 hours. In some instances, the half-life of the polypeptides or polypeptide complexes is in a range of about 12 hours to about 300 hours, about 20 hours to about 280 hours, about 40 hours to about 240 hours, about 60 hours to about 200 hours, or about 80 hours to about 140 hours.

Described herein, in some embodiments, are polypeptide or polypeptide complexes administered as once weekly. In some embodiments, the polypeptide or polypeptide complexes are administered once weekly by intravenous, intramuscular, intralesional, topical, subcutaneous, infusion, or oral. In some embodiments, the polypeptide or polypeptide complexes are administered once weekly by bolus injection. In some embodiments, the polypeptide or polypeptide complexes are administered once weekly by continuous infusion. In some embodiments, the polypeptide or polypeptide complex is administered to the subject once a week as a continuous infusion over a period of no more than 60 minutes. In some embodiments, the polypeptide or polypeptide complex is administered to the subject once a week as a continuous intravenous infusion over a period of no more than 30 minutes. In some embodiments, the polypeptide or polypeptide complex is administered to the subject once a week as a continuous intravenous infusion over a period of at least 10 minutes.

In some embodiments, the polypeptide or polypeptide complex is administered to the subject once a week and the polypeptide or polypeptide complex has a half-life of at least 30 hours. In some embodiments, the polypeptide or polypeptide complex is administered to the subject once a week and the polypeptide or polypeptide complex has a half-life of at least 50 hours. In some embodiments, the polypeptide or polypeptide complex is administered to the subject once a week and the polypeptide or polypeptide complex has a half-life of at least 60 hours. In some embodiments, the polypeptide or polypeptide complex is administered to the subject once a week and the polypeptide or polypeptide complex has a half-life of at least 70 hours. In some embodiments, the polypeptide or polypeptide complex is administered to the subject once a week and the polypeptide or polypeptide complex has a half-life of at least 80 hours. In some embodiments, the polypeptide or polypeptide complex is administered to the subject once a week and the polypeptide or polypeptide complex has a half-life of at least 90 hours. In some embodiments, the polypeptide or polypeptide complex is administered to the subject once a week and the polypeptide or polypeptide complex has a half-life of at least 100 hours. In some embodiments, the polypeptide or polypeptide complex is administered to the subject once a week and the polypeptide or polypeptide complex has a half-life of at least 110 hours. In some embodiments, the polypeptide or polypeptide complex is administered to the subject once a week and the polypeptide or polypeptide complex has a half-life of at least 115 hours. In some embodiments, the polypeptide or polypeptide complex is administered to the subject once a week and the polypeptide or polypeptide complex has a half-life of at least 119 hours.

Production of Antibodies that Bind to PSMA and CD3

In some embodiments, polypeptides described herein (e.g., antibodies and its binding fragments) are produced using any method known in the art to be useful for the synthesis of polypeptides (e.g., antibodies), in particular, by chemical synthesis or by recombinant expression, and are preferably produced by recombinant expression techniques.

In some instances, an antibody or its binding fragment thereof is expressed recombinantly, and the nucleic acid encoding the antibody or its binding fragment is assembled from chemically synthesized oligonucleotides (e.g., as described in Kutmeier et al., 1994, BioTechniques 17:242), which involves the synthesis of overlapping oligonucleotides containing portions of the sequence encoding the antibody, annealing and ligation of those oligonucleotides, and then amplification of the ligated oligonucleotides by PCR.

Alternatively, a nucleic acid molecule encoding an antibody is optionally generated from a suitable source (e.g., an antibody cDNA library, or cDNA library generated from any tissue or cells expressing the immunoglobulin) by PCR amplification using synthetic primers hybridizable to the 3' and 5' ends of the sequence or by cloning using an oligonucleotide probe specific for the particular gene sequence.

In some instances, an antibody or its binding fragment is optionally generated by immunizing an animal, such as a mouse, to generate polyclonal antibodies or, more preferably, by generating monoclonal antibodies, e.g., as described by Kohler and Milstein (1975, Nature 256:495-497) or, as described by Kozbor et al. (1983, Immunology Today 4:72) or Cole et al. (1985 in Monoclonal Antibodies and Cancer Therapy, Alan R. Liss, Inc., pp. 77-96). Alternatively, a clone encoding at least the Fab portion of the antibody is optionally obtained by screening Fab expression libraries (e.g., as described in Huse et al., 1989, Science 246:1275-1281) for clones of Fab fragments that bind the specific antigen or by screening antibody libraries (See, e.g., Clackson et al., 1991, Nature 352:624; Hane et al., 1997 Proc. Natl. Acad. Sci. USA 94:4937).

In some embodiments, techniques developed for the production of "chimeric antibodies" (Morrison et al., 1984, Proc. Natl. Acad. Sci. 81:851-855; Neuberger et al., 1984, Nature 312:604-608; Takeda et al., 1985, Nature 314:452-454) by splicing genes from a mouse antibody molecule of appropriate antigen specificity together with genes from a human antibody molecule of appropriate biological activity are used. A chimeric antibody is a molecule in which different portions are derived from different animal species, such as those having a variable region derived from a murine monoclonal antibody and a human immunoglobulin constant region.

In some embodiments, techniques described for the production of single chain antibodies (U.S. Pat. No. 4,694,778; Bird, 1988, Science 242:423-42; Huston et al., 1988, Proc. Natl. Acad. Sci. USA 85:5879-5883; and Ward et al., 1989, Nature 334:544-54) are adapted to produce single chain antibodies. Single chain antibodies are formed by linking the heavy and light chain fragments of the Fv region via an amino acid bridge, resulting in a single chain polypeptide. Techniques for the assembly of functional Fv fragments in *E. coli* are also optionally used (Skerra et al., 1988, Science 242:1038-1041).

In some embodiments, an expression vector comprising the nucleotide sequence of an antibody or the nucleotide sequence of an antibody is transferred to a host cell by conventional techniques (e.g., electroporation, liposomal transfection, and calcium phosphate precipitation), and the transfected cells are then cultured by conventional techniques to produce the antibody. In specific embodiments, the expression of the antibody is regulated by a constitutive, an inducible or a tissue, specific promoter.

In some embodiments, a variety of host-expression vector systems is utilized to express an antibody, or its binding fragment described herein. Such host-expression systems represent vehicles by which the coding sequences of the antibody is produced and subsequently purified, but also represent cells that are, when transformed or transfected with the appropriate nucleotide coding sequences, express an antibody or its binding fragment in situ. These include, but are not limited to, microorganisms such as bacteria (e.g., *E. coli* and *B. subtilis*) transformed with recombinant bacteriophage DNA, plasmid DNA or cosmid DNA expression vectors containing an antibody or its binding fragment coding sequences; yeast (e.g., *Saccharomyces Pichia*) transformed with recombinant yeast expression vectors containing an antibody or its binding fragment coding sequences; insect cell systems infected with recombinant virus expression vectors (e.g., baculovirus) containing an antibody or its binding fragment coding sequences; plant cell systems infected with recombinant virus expression vectors (e.g., cauliflower mosaic virus (CaMV) and tobacco mosaic virus (TMV)) or transformed with recombinant plasmid expression vectors (e.g., Ti plasmid) containing an antibody or its binding fragment coding sequences; or mammalian cell systems (e.g., COS, CHO, BH, 293, 293T, 3T3 cells) harboring recombinant expression constructs containing promoters derived from the genome of mammalian cells (e.g., metallothionein promoter) or from mammalian viruses (e.g. the adenovirus late promoter; the vaccinia virus 7.5K promoter).

For long-term, high-yield production of recombinant proteins, stable expression is preferred. In some instances, cell lines that stably express an antibody are optionally engineered. Rather than using expression vectors that contain viral origins of replication, host cells are transformed with DNA controlled by appropriate expression control elements (e.g., promoter, enhancer, sequences, transcription terminators, polyadenylation sites, etc.), and a selectable marker. Following the introduction of the foreign DNA, engineered cells are then allowed to grow for 1-2 days in an enriched media, and then are switched to a selective media. The selectable marker in the recombinant plasmid confers resistance to the selection and allows cells to stably integrate the plasmid into their chromosomes and grow to form foci that in turn are cloned and expanded into cell lines. This method can advantageously be used to engineer cell lines which express the antibody or its binding fragments.

In some instances, a number of selection systems are used, including but not limited to the herpes simplex virus thymidine kinase (Wigler et al., 1977, Cell 11:223), hypoxanthine-guanine phosphoribosyltransferase (Szybalska & Szybalski, 192, Proc. Natl. Acad. Sci. USA 48:202), and adenine phosphoribosyltransferase (Lowy et al., 1980, Cell 22:817) genes are employed in tk-, hgprt- or aprt-cells, respectively. Also, antimetabolite resistance are used as the basis of selection for the following genes: dhfr, which confers resistance to methotrexate (Wigler et al., 1980, Proc. Natl. Acad. Sci. USA 77:357; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Clinical Pharmacy 12:488-505; Wu and Wu, 1991, Biotherapy 3:87-95; Tolstoshev, 1993, Ann. Rev. Pharmacol. Toxicol. 32:573-596; Mulligan, 1993, Science 260:926-932; and Morgan and Anderson, 1993, Ann. Rev. Biochem. 62:191-217; May 1993, TIB TECH 11(5):155-215) and hygro, which confers resistance to hygromycin (Santerre et al., 1984, Gene 30:147). Methods commonly known in the art of recombinant DNA technology which can be used are described in Ausubel et al. (eds., 1993, Current Protocols in Molecular Biology, John Wiley & Sons, NY; Kriegler, 1990, Gene Transfer and Expression, A Laboratory Manual, Stockton Press, NY; and in Chapters 12 and 13, Dracopoli et al. (eds), 1994, Current Protocols in Human Genetics, John Wiley & Sons, NY.; Colberre-Garapin et al., 1981, J. Mol. Biol. 150:1).

In some instances, the expression levels of an antibody are increased by vector amplification (for a review, see Bebbington and Hentschel, the use of vectors based on gene amplification for the expression of cloned genes in mammalian cells in DNA cloning, Vol. 3. (Academic Press, New York, 1987)). When a marker in the vector system expressing an antibody is amplifiable, an increase in the level of inhibitor present in the culture of the host cell will increase the number of copies of the marker gene. Since the amplified region is associated with the nucleotide sequence of the antibody, production of the antibody will also increase (Crouse et al., 1983, Mol. Cell Biol. 3:257).

In some instances, any method known in the art for purification of an antibody is used, for example, by chromatography (e.g., ion exchange, affinity, particularly by affinity for the specific antigen after Protein A, and sizing column chromatography), centrifugation, differential solubility, or by any other standard technique for the purification of proteins.

Expression Vectors

In some embodiments, vectors include any suitable vector derived from either a eukaryotic or prokaryotic sources. In some cases, vectors are obtained from bacteria (e.g. *E. coli*), insects, yeast (e.g. *Pichia pastoris*), algae, or mammalian sources. Exemplary bacterial vectors include pACYC177, pASK75, pBAD vector series, pBADM vector series, pET vector series, pETM vector series, pGEX vector series, pHAT, pHAT2, pMal-c2, pMal-p2, pQE vector series, pRSET A, pRSET B, pRSET C, pTrcHis2 series, pZA31-Luc, pZE21-MCS-1, pFLAG ATS, pFLAG CTS, pFLAG MAC, pFLAG Shift-12c, pTAC-MAT-1, pFLAG CTC, or pTAC-MAT-2.

Exemplary insect vectors include pFastBacl, pFastBac DUAL, pFastBac ET, pFastBac HTa, pFastBac HTb, pFast-Bac HTc, pFastBac M30a, pFastBact M30b, pFastBac, M30c, pVL1392, pVL1393, pVL1393 M10, pVL1393 M11, pVL1393 M12, FLAG vectors such as pPolh-FLAG1 or pPolh-MAT 2, or MAT vectors such as pPolh-MAT1, or pPolh-MAT2.

In some cases, yeast vectors include Gateway® pDEST™ 14 vector, Gateway® pDEST™ 15 vector, Gateway® pDEST™ 17 vector, Gateway® pDEST™ 24 vector, Gateway® pYES-DEST52 vector, pBAD-DEST49 Gateway® destination vector, pAO815 *Pichia* vector, pFLD1 Pichi *pastoris* vector, pGAPZA,B, & C *Pichia pastoris* vector, pPIC3.5K *Pichia* vector, pPIC6 A, B, & C *Pichia* vector, pPIC9K *Pichia* vector, pTEF1/Zeo, pYES2 yeast vector, pYES2/CT yeast vector, pYES2/NT A, B, & C yeast vector, or pYES3/CT yeast vector.

Exemplary algae vectors include pChlamy-4 vector or MCS vector.

Examples of mammalian vectors include transient expression vectors or stable expression vectors. Mammalian transient expression vectors may include pRK5, p3xFLAG-CMV 8, pFLAG-Myc-CMV 19, pFLAG-Myc-CMV 23, pFLAG-CMV 2, pFLAG-CMV 6a,b,c, pFLAG-CMV 5.1, pFLAG-CMV 5a,b,c, p3xFLAG-CMV 7.1, pFLAG-CMV 20, p3xFLAG-Myc-CMV 24, pCMV-FLAG-MAT1, pCMV-FLAG-MAT2, pBICEP-CMV 3, or pBICEP-CMV 4. Mammalian stable expression vector may include pFLAG-CMV 3, p3xFLAG-CMV 9, p3xFLAG-CMV 13, pFLAG-Myc-CMV 21, p3xFLAG-Myc-CMV 25, pFLAG-CMV 4, p3xFLAG-CMV 10, p3xFLAG-CMV 14, pFLAG-Myc-CMV 22, p3xFLAG-Myc-CMV 26, pBICEP-CMV 1, or pBICEP-CMV 2.

In some instances, a cell-free system is a mixture of cytoplasmic and/or nuclear components from a cell and is used for in vitro nucleic acid synthesis. In some cases, a cell-free system utilizes either prokaryotic cell components or eukaryotic cell components. Sometimes, a nucleic acid synthesis is obtained in a cell-free system based on for example *Drosophila* cell, *Xenopus* egg, or HeLa cells. Exemplary cell-free systems include, but are not limited to, *E. coli* S30 Extract system, *E. coli* T7 S30 system, or PURExpress®.

Host Cells

In some embodiments, a host cell includes any suitable cell such as a naturally derived cell or a genetically modified cell. In some instances, a host cell is a production host cell. In some instances, a host cell is a eukaryotic cell. In other instances, a host cell is a prokaryotic cell. In some cases, a eukaryotic cell includes fungi (e.g., yeast cells), animal cell or plant cell. In some cases, a prokaryotic cell is a bacterial cell. Examples of bacterial cells include gram-positive bacteria or gram-negative bacteria. Sometimes the gram-negative bacteria is anaerobic, rod-shaped, or both.

In some instances, gram-positive bacteria include Actinobacteria, Firmicutes or Tenericutes. In some cases, gram-negative bacteria include Aquificae, Deinococcus-*Thermus*, Fibrobacteres-Chlorobi/Bacteroidetes (FCB group), Fusobacteria, Gemmatimonadetes, Nitrospirae, Planctomycetes-Verrucomicrobia/Chlamydiae (PVC group), Proteobacteria, Spirochaetes or Synergistetes. Other bacteria can be Acidobacteria, Chloroflexi, Chrysiogenetes, Cyanobacteria, Deferribacteres, Dictyoglomi, Thermodesulfobacteria or Thermotogae. A bacterial cell can be *Escherichia coli, Clostridium botulinum*, or *Coli* bacilli.

Exemplary prokaryotic host cells include, but are not limited to, BL21, Mach1™, DH10B™, TOP10, DH5α, DH10Bac™, OmniMax™, MegaX™, DH12S™, INV110, TOP10F', INVαF, TOP10/P3, ccdB Survival, PIR1, PIR2, Stbl2™, Stbl3™, or Stbl4™.

In some instances, animal cells include a cell from a vertebrate or from an invertebrate. In some cases, an animal cell includes a cell from a marine invertebrate, fish, insects, amphibian, reptile, or mammal. In some cases, a fungus cell includes a yeast cell, such as brewer's yeast, baker's yeast, or wine yeast.

Fungi include ascomycetes such as yeast, mold, filamentous fungi, basidiomycetes, or zygomycetes. In some instances, yeast includes Ascomycota or Basidiomycota. In some cases, Ascomycota includes Saccharomycotina (true yeasts, e.g. *Saccharomyces cerevisiae* (baker's yeast)) or Taphrinomycotina (e.g. Schizosaccharomycetes (fission yeasts)). In some cases, Basidiomycota includes Agaricomycotina (e.g. Tremellomycetes) or Pucciniomycotina (e.g. Microbotryomycetes).

Exemplary yeast or filamentous fungi include, for example, the genus: *Saccharomyces, Schizosaccharomyces, Candida, Pichia, Hansenula, Kluyveromyces, Zygosaccharomyces, Yarrowia, Trichosporon, Rhodosporidi, Aspergillus, Fusarium*, or *Trichoderma*. Exemplary yeast or filamentous fungi include, for example, the species: *Saccharomyces cerevisiae, Schizosaccharomyces pombe, Candida utilis, Candida boidini, Candida albicans, Candida tropicalis, Candida stellatoidea, Candida glabrata, Candida krusei, Candida parapsilosis, Candida guilliermondii, Candida viswanathii, Candida lusitaniae, Rhodotorula mucilaginosa, Pichia metanolica, Pichia angusta, Pichia pastoris, Pichia anomala, Hansenula polymorpha, Kluyveromyces lactis, Zygosaccharomyces rouxii, Yarrowia lipolytica, Trichosporon pullulans*, Rhodosporidium toru-*Aspergillus niger, Aspergillus nidulans, Aspergillus awamori, Aspergillus oryzae, Trichoderma reesei, Yarrowia lipolytica, Brettanomyces bruxellensis, Candida stellata, Schizosaccharomyces pombe, Torulaspora delbrueckii, Zygosaccharomyces bailii, Cryptococcus neoformans, Cryptococcus gattii*, or *Saccharomyces boulardii*.

Exemplary yeast host cells include, but are not limited to, *Pichia pastoris* yeast strains such as GS115, KM71H, SMD1168, SMD1168H, and X-33; and *Saccharomyces cerevisiae* yeast strain such as INVSc1.

In some instances, additional animal cells include cells obtained from a mollusk, arthropod, annelid or sponge. In some cases, an additional animal cell is a mammalian cell, e.g., from a primate, ape, equine, bovine, porcine, canine, feline or rodent. In some cases, a rodent includes mouse, rat, hamster, gerbil, hamster, chinchilla, fancy rat, or guinea pig.

Exemplary mammalian host cells include, but are not limited to, 293A cell line, 293FT cell line, 293F cells, 293

H cells, CHO DG44 cells, CHO—S cells, CHO-K1 cells, FUT8 KO CHOKI, Expi293FTM cells, Flp-In™ T-REx™ 293 cell line, Flp-In™-293 cell line, Flp-In™-3T3 cell line, Flp-In™—BHK cell line, Flp-In™—CHO cell line, Flp-In™—CV-1 cell line, Flp-In™-Jurkat cell line, FreeStyle™ 293-F cells, FreeStyle™ CHO—S cells, GripTite™ 293 MSR cell line, GS-CHO cell line, HepaRG™ cells, T-REx™ Jurkat cell line, Per.C6 cells, T-REx™-293 cell line, T-REx™—CHO cell line, and T-REx™—HeLa cell line.

In some instances, a mammalian host cell is a stable cell line, or a cell line that has incorporated a genetic material of interest into its own genome and has the capability to express the product of the genetic material after many generations of cell division. In some cases, a mammalian host cell is a transient cell line, or a cell line that has not incorporated a genetic material of interest into its own genome and does not have the capability to express the product of the genetic material after many generations of cell division.

Exemplary insect host cells include, but are not limited to, *Drosophila* S2 cells, Sf9 cells, Sf21 cells, High Five™ cells, and expresSF+® cells.

In some instances, plant cells include a cell from algae. Exemplary insect cell lines include, but are not limited to, strains from *Chlamydomonas reinhardtii* 137c, or Synechoccus *elongatus* PPC 7942.

Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper that is pierceable by a hypodermic injection needle). At least one active agent in the composition is a bispecific antibody comprising a first antigen-binding site that specifically binds to CD3 and a second antigen-binding site that specifically binds to PSMA as defined herein before.

The label or package insert indicates that the composition is used for treating the condition of choice. Moreover, the article of manufacture may comprise (a) a first container with a composition contained therein, wherein the composition comprises the bispecific antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition.

Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Certain Definitions

The terminology used herein is for the purpose of describing particular cases only and is not intended to be limiting.

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

The term "antibody" is used in the broadest sense and covers fully assembled antibodies, antibody fragments that can bind antigen, for example, Fab, F(ab')2, Fv, single chain antibodies (scFv), diabodies, antibody chimeras, hybrid antibodies, bispecific antibodies, and the like.

The term "complementarity determining region" or "CDR" is a segment of the variable region of an antibody that is complementary in structure to the epitope to which the antibody binds and is more variable than the rest of the variable region. Accordingly, a CDR is sometimes referred to as hypervariable region. A variable region comprises three CDRs. CDR peptides can be obtained by constructing genes encoding the CDR of an antibody of interest. Such genes are prepared, for example, by using the polymerase chain reaction to synthesize the variable region from RNA of antibody-producing cells. See, for example, Larrick et al., *Methods: A Companion to Methods in Enzymology* 2: 106 (1991); Courtenay-Luck, "Genetic Manipulation of Monoclonal Antibodies," in *Monoclonal Antibodies: Production, Engineering and Clinical Application*, Ritter et al. (eds.), pages 166-179 (Cambridge University Press 1995); and Ward et al., "Genetic Manipulation and Expression of Antibodies," in *Monoclonal Antibodies: Principles and Applications*, Birch et al., (eds.), pages 137-185 (Wiley-Liss, Inc. 1995).

The term "Fab" refers to a protein that contains the constant domain of the light chain and the first constant domain (CH1) of the heavy chain. Fab fragments differ from Fab' fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. Fab' fragments are produced by reducing the F(ab')2 fragment's heavy chain disulfide bridge. Other chemical couplings of antibody fragments are also known.

A "single-chain variable fragment (scFv)" is a fusion protein of the variable regions of the heavy (VH) and light chains (VL) of an antibody, connected with a short linker peptide of ten to about 25 amino acids. The linker is usually rich in glycine for flexibility, as well as serine or threonine for solubility, and can either connect the N-terminus of the VH with the C-terminus of the VL, or vice versa. This protein retains the specificity of the original antibody, despite removal of the constant regions and the introduction of the linker. scFv antibodies are, e.g. described in Houston, J. S., Methods in Enzymol. 203 (1991) 46-96). In addition, antibody fragments comprise single chain polypeptides having the characteristics of a VH domain, namely being able to assemble together with a VL domain, or of a VL domain, namely being able to assemble together with a VH domain to a functional antigen binding site and thereby providing the antigen binding property of full length antibodies.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

EMBODIMENTS

Embodiment 1 comprises an isolated polypeptide or polypeptide complex according to Formula I: $A_2$-$A_1$-$L_1$-$P_1$—$H_1$ wherein:$A_1$ comprises a first antigen recognizing molecule that binds to an effector cell antigen; $P_1$ comprises a peptide that binds to $A_1$; $L_1$ comprises a linking moiety that connects $A_1$ to $P_1$ and is a substrate for a tumor specific protease; $H_1$ comprises a half-life extending molecule; and $A_2$ comprises a second antigen recognizing molecule that binds to prostate-specific membrane antigen (PSMA).

Embodiment 2 comprises an isolated polypeptide or polypeptide complex of embodiment 1, wherein the first antigen recognizing molecule comprises an antibody or antibody fragment.

Embodiment 3 comprises an isolated polypeptide or polypeptide complex of embodiment 1, wherein first antigen recognizing molecule comprises an antibody or antibody fragment that is human or humanized.

Embodiment 4 comprises an isolated polypeptide or polypeptide complex of any one of embodiments 1-3, wherein $L_1$ is bound to N-terminus of the first antigen recognizing molecule.

Embodiment 5 comprises an isolated polypeptide or polypeptide complex of any one of embodiments 1-3, wherein $A_2$ is bound to C-terminus of the first antigen recognizing molecule.

Embodiment 6 comprises an isolated polypeptide or polypeptide complex of any one of embodiments 1-3, wherein $L_1$ is bound to C-terminus of the first antigen recognizing molecule.

Embodiment 7 comprises an isolated polypeptide or polypeptide complex of any one of embodiments 1-3, wherein $A_2$ is bound to N-terminus of the first antigen recognizing molecule.

Embodiment 8 comprises an isolated polypeptide or polypeptide complex of any one of embodiments 2-7, wherein the antibody or antibody fragment comprises a single chain variable fragment, a single domain antibody, or a Fab fragment.

Embodiment 9 comprises an isolated polypeptide or polypeptide complex of embodiment 8, wherein $A_1$ is the single chain variable fragment (scFv).

Embodiment 10 comprises an isolated polypeptide or polypeptide complex of embodiment 9, wherein the scFv comprises a scFv heavy chain polypeptide and a scFv light chain polypeptide.

Embodiment 11 comprises an isolated polypeptide or polypeptide complex of embodiment 8, wherein $A_1$ is the single domain antibody, Embodiment 12 comprises an isolated polypeptide or polypeptide complex of embodiment 8, wherein the antibody or antibody fragment comprises a single chain variable fragment (scFv), a heavy chain variable domain (VH domain), a light chain variable domain (VL domain), or a variable domain (VHH) of a camelid derived single domain antibody.

Embodiment 13 comprises an isolated polypeptide or polypeptide complex of any one of embodiments 1-12, wherein $A_1$ comprises an anti-CD3e single chain variable fragment.

Embodiment 14 comprises an isolated polypeptide or polypeptide complex of any one of embodiments 1-12, wherein $A_1$ comprises an anti-CD3e single chain variable fragment that has a $K_D$ binding of 1 µM or less to CD3 on CD3 expressing cells.

Embodiment 15 comprises an isolated polypeptide or polypeptide complex of any one of embodiments 1-14, wherein the effector cell antigen comprises CD3.

Embodiment 16 comprises an isolated polypeptide or polypeptide complex of embodiment 1, wherein $A_1$ comprises a variable light chain and variable heavy chain each of which is capable of specifically binding to human CD3.

Embodiment 17 comprises an isolated polypeptide or polypeptide complex of embodiment 1, wherein $A_1$ comprises complementary determining regions (CDRs) selected from the group consisting of muromonab-CD3 (OKT3), otelixizumab (TRX4), teplizumab (MGA031), visilizumab (Nuvion), SP34, X35, VIT3, BMA030 (BW264/56), CLB-T3/3, CRIS7, YTH12.5, F111-409, CLB-T3.4.2, TR-66, WT32, SPv-T3b, 11D8, XIII-141, XIII-46, XIII-87, 12F6, T3/RW2-8C8, T3/RW2-4B6, OKT3D, M-T301, SMC2, F101.01, UCHT-1, WT-31, 15865, 15865v12, 15865v16, and 15865v19.

Embodiment 18 comprises an isolated polypeptide or polypeptide complex of embodiment 1, wherein the polypeptide or polypeptide complex of Formula I binds to an effector cell when $L_1$ is cleaved by the tumor specific protease.

Embodiment 19 comprises an isolated polypeptide or polypeptide complex of embodiment 1, wherein the polypeptide or polypeptide complex of Formula I binds to an effector cell when $L_1$ is cleaved by the tumor specific protease and $A_1$ binds to the effector cell.

Embodiment 20 comprises an isolated polypeptide or polypeptide complex of embodiment 19, wherein the effector cell is a T cell.

Embodiment 21 comprises an isolated polypeptide or polypeptide complex of embodiment 1, wherein $A_1$ binds to a polypeptide that is part of a TCR-CD3 complex on the effector cell.

Embodiment 22 comprises an isolated polypeptide or polypeptide complex of embodiment 21, wherein the polypeptide that is part of the TCR-CD3 complex is human CD3E.

Embodiment 23 comprises an isolated polypeptide or polypeptide complex of embodiment 1, wherein the effector cell antigen comprises CD3, wherein the scFv comprises complementarity determining regions (CDRs): HC-CDR1, HC-CDR2, and HC-CDR3, wherein the HC-CDR1, the HC-CDR2, and the HC-CDR3 of the scFv comprise: HC-CDR1: SEQ ID NO: 1, HC-CDR2: SEQ ID NO: 2, and HC-CDR3: SEQ ID NO: 3; and the scFv comprises CDRs: LC-CDR1, LC-CDR2, and LC-CDR3, wherein the LC-CDR1, the LC-CDR2, and the LC-CDR3 of the scFv comprise: LC-CDR1: SEQ ID NO: 4, LC-CDR2: SEQ ID NO:5, and LC-CDR3: SEQ ID NO: 6.

Embodiment 24 comprises an isolated polypeptide or polypeptide complex of embodiment 1, wherein the effector cell antigen comprises CD3, and the scFv comprises an amino acid sequence according to SEQ ID NO: 7.

Embodiment 25 comprises an isolated polypeptide or polypeptide complex of any one of embodiments 1-24, wherein second antigen recognizing molecule comprises an antibody or antibody fragment.

Embodiment 26 comprises an isolated polypeptide or polypeptide complex of embodiment 25, wherein the antibody or antibody fragment thereof comprises a single chain variable fragment, a single domain antibody, or a Fab.

Embodiment 27 comprises an isolated polypeptide or polypeptide complex of embodiment 25, wherein the antibody or antibody fragment thereof comprises a single chain variable fragment (scFv), a heavy chain variable domain (VH domain), a light chain variable domain (VL domain), a variable domain (VHH) of a camelid derived single domain antibody.

Embodiment 28 comprises an isolated polypeptide or polypeptide complex of embodiment 25, wherein the antibody or antibody fragment thereof is humanized or human.

Embodiment 29 comprises an isolated polypeptide or polypeptide complex of embodiment 26, wherein $A_2$ is the Fab.

Embodiment 30 comprises an isolated polypeptide or polypeptide complex of embodiment 29, wherein the Fab comprises (a) a Fab light chain polypeptide and (b) a Fab heavy chain polypeptide.

Embodiment 31 comprises an isolated polypeptide or polypeptide complex of embodiment 29, wherein the Fab comprises complementarity determining regions (CDRs): HC-CDR1, HC-CDR2, and HC-CDR3, wherein the HC-CDR1, the HC-CDR2, and the HC-CDR3 of the Fab comprise: HC-CDR1: SEQ ID NO: 8, HC-CDR2: SEQ ID NO: 9, and HC-CDR3: SEQ ID NO: 10; and the Fab comprises CDRs: LC-CDR1, LC-CDR2, and LC-CDR3, wherein the LC-CDR1, the LC-CDR2, and the LC-CDR3 of the Fab comprise: LC-CDR1: SEQ ID NO: 11, LC-CDR2: SEQ ID NO:12, and LC-CDR3: SEQ ID NO: 13.

Embodiment 32 comprises an isolated polypeptide or polypeptide complex of embodiment 30, wherein the Fab light chain polypeptide comprises an amino acid sequence according to SEQ ID NO: 14.

Embodiment 33 comprises an isolated polypeptide or polypeptide complex of embodiment 30, wherein Fab heavy chain polypeptide comprises an amino acid sequence according to SEQ ID NO: 15.

Embodiment 34 comprises an isolated polypeptide or polypeptide complex of embodiment 30, wherein the Fab light chain polypeptide of $A_2$ is bound to a C-terminus of the single chain variable fragment (scFv) of $A_1$.

Embodiment 35 comprises an isolated polypeptide or polypeptide complex of embodiment 30, wherein the Fab heavy chain polypeptide of $A_2$ is bound to a C-terminus of the single chain variable fragment (scFv) $A_1$.

Embodiment 36 comprises an isolated polypeptide or polypeptide complex of embodiment 30, wherein the Fab light chain polypeptide of $A_2$ is bound to a N-terminus of the single chain variable fragment (scFv) of $A_1$.

Embodiment 37 comprises an isolated polypeptide or polypeptide complex of embodiment 30, wherein the Fab heavy chain polypeptide of $A_2$ is bound to a N-terminus of the single chain variable fragment (scFv) $A_1$.

Embodiment 38 comprises a polypeptide or polypeptide complex of embodiment 30, wherein the Fab heavy chain polypeptide of $A_2$ is bound to the scFv heavy chain polypeptide of $A_1$.

Embodiment 39 comprises a polypeptide or polypeptide complex of embodiment 30, wherein the Fab light chain polypeptide of $A_2$ is bound to the scFv heavy chain polypeptide of $A_1$.

Embodiment 40 comprises a polypeptide or polypeptide complex of embodiment 30, wherein the Fab heavy chain polypeptide of $A_2$ is bound to the scFv light chain polypeptide of $A_1$.

Embodiment 41 comprises a polypeptide or polypeptide complex of embodiment 30, wherein the Fab light chain polypeptide of $A_2$ is bound to the scFv light chain polypeptide of $A_1$.

Embodiment 42 comprises a polypeptide or polypeptide complex of any one of embodiments 1-41, wherein $A_2$ further comprises $P_2$ and $L_2$, wherein $P_2$ comprises a peptide that binds to $A_2$; and $L_2$ comprises a linking moiety that connects $A_2$ to $P_2$ and is a substrate for a tumor specific protease.

Embodiment 43 comprises a polypeptide or polypeptide complex of embodiment 42, wherein the polypeptide or polypeptide complex is according to Formula Ia: $P_2$-$L_2$-$A_2$-$A_1$-$L_1$-$P_1$—$H_1$.

Embodiment 44 comprises a polypeptide or polypeptide complex of embodiment 43, wherein the Fab heavy chain polypeptide of $A_2$ is bound to the scFv heavy chain polypeptide of $A_1$ and $L_2$ is bound to the Fab light chain polypeptide of $A_2$.

Embodiment 45 comprises a polypeptide or polypeptide complex of embodiment 43, wherein the Fab light chain polypeptide of $A_2$ is bound to the scFv heavy chain polypeptide of $A_1$ and $L_2$ is bound to the Fab heavy chain polypeptide of $A_2$.

Embodiment 46 comprises a polypeptide or polypeptide complex of embodiment 43, wherein the Fab heavy chain polypeptide of $A_2$ is bound to the scFv light chain polypeptide of $A_1$ and $L_2$ is bound to the Fab light chain polypeptide of $A_2$.

Embodiment 47 comprises a polypeptide or polypeptide complex of embodiment 43, wherein the Fab light chain polypeptide of $A_2$ is bound to the scFv light chain polypeptide of $A_1$ and $L_2$ is bound to the Fab heavy chain polypeptide of $A_2$.

Embodiment 48 comprises a polypeptide or polypeptide complex of any one of embodiments 1-47, wherein $P_1$ impairs binding of $A_1$ to the effector cell antigen.

Embodiment 49 comprises a polypeptide or polypeptide complex of any one of embodiments 1-48, wherein $P_1$ is bound to $A_1$ through ionic interactions, electrostatic interactions, hydrophobic interactions, Pi-stacking interactions, or H-bonding interactions, or a combination thereof.

Embodiment 50 comprises a polypeptide or polypeptide complex of any one of embodiments 1-48, wherein $P_1$ has less than 70% sequence homology to the effector cell antigen.

Embodiment 51 comprises a polypeptide or polypeptide complex of any one of embodiments 1-50, wherein $P_2$ impairs binding of $A_2$ to PSMA.

Embodiment 52 comprises a polypeptide or polypeptide complex of any one of embodiments 1-50, wherein $P_2$ is bound to $A_2$ through ionic interactions, electrostatic interactions, hydrophobic interactions, Pi-stacking interactions, or H-bonding interactions, or a combination thereof.

Embodiment 53 comprises a polypeptide or polypeptide complex of any one of embodiments 1-50, wherein $P_2$ is bound to $A_2$ at or near an antigen binding site.

Embodiment 54 comprises a polypeptide or polypeptide complex of any one of embodiments 1-50, wherein $P_2$ has less than 70% sequence homology to PSMA.

Embodiment 55 comprises a polypeptide or polypeptide complex of any one of embodiments 1-54, wherein $P_1$ or $P_2$ comprises a peptide sequence of at least 10 amino acids in length.

Embodiment 56 comprises a polypeptide or polypeptide complex of any one of embodiments 1-54, wherein $P_1$ or $P_2$ comprises a peptide sequence of at least 10 amino acids in length and no more than 20 amino acids in length.

Embodiment 57 comprises a polypeptide or polypeptide complex of any one of embodiments 1-54, wherein $P_1$ or $P_2$ comprises a peptide sequence of at least 16 amino acids in length.

Embodiment 58 comprises a polypeptide or polypeptide complex of any one of embodiments 1-54, wherein $P_1$ or $P_2$ comprises a peptide sequence of no more than 40 amino acids in length.

Embodiment 59 comprises an isolated polypeptide or polypeptide complex of any one of embodiments 1-54, wherein $P_1$ or $P_2$ comprises at least two cysteine amino acid residues.

Embodiment 60 comprises an isolated polypeptide or polypeptide complex of any one of embodiments 1-54, wherein $P_1$ or $P_2$ comprises a cyclic peptide or a linear peptide.

Embodiment 61 comprises an isolated polypeptide or polypeptide complex of any one of embodiments 1-54, wherein $P_1$ or $P_2$ comprises a cyclic peptide.

Embodiment 62 comprises an isolated polypeptide or polypeptide complex of any one of embodiments 1-54, wherein $P_1$ or $P_2$ comprises a linear peptide Embodiment 63 comprises an isolated polypeptide or polypeptide complex of any one of embodiments 1-54, wherein $P_1$ comprises at least two cysteine amino acid residues.

Embodiment 64 comprises a polypeptide or polypeptide complex of any one of embodiments 1-54, wherein $P_1$ comprises an amino acid sequence according to any one of SEQ ID NOs: 16-19 or 78.

Embodiment 65 comprises an isolated polypeptide or polypeptide complex of any one of embodiments 1-64, wherein $L_1$ is bound to N-terminus of $A_1$.

Embodiment 66 comprises an isolated polypeptide or polypeptide complex of any one of embodiments 1-64, wherein $L_1$ is bound to C-terminus of $A_1$.

Embodiment 67 comprises an isolated polypeptide or polypeptide complex of any one of embodiments 1-66, wherein $L_2$ is bound to N-terminus of $A_2$.

Embodiment 68 comprises an isolated polypeptide or polypeptide complex of any one of embodiments 1-66, wherein $L_2$ is bound to C-terminus of $A_2$.

Embodiment 69 comprises an isolated polypeptide or polypeptide complex of any one of embodiments 1-68, wherein $L_1$ or $L_2$ is a peptide sequence having at least 5 to no more than 50 amino acids.

Embodiment 70 comprises an isolated polypeptide or polypeptide complex of any one of embodiments 1-68, wherein $L_1$ or $L_2$ is a peptide sequence having at least 10 to no more than 30 amino acids.

Embodiment 71 comprises an isolated polypeptide or polypeptide complex of any one of embodiments 1-68, wherein $L_1$ or $L_2$ is a peptide sequence having at least 10 amino acids.

Embodiment 72 comprises an isolated polypeptide or polypeptide complex of any one of embodiments 1-68, wherein $L_1$ or $L_2$ is a peptide sequence having at least 18 amino acids.

Embodiment 73 comprises an isolated polypeptide or polypeptide complex of any one of embodiments 1-68, wherein $L_1$ or $L_2$ is a peptide sequence having at least 26 amino acids.

Embodiment 74 comprises an isolated polypeptide or polypeptide complex of any one of embodiments 1-68, wherein $L_1$ or $L_2$ has a formula comprising $(G_2S)_n$, wherein n is an integer from 1 to 3 (SEQ ID NO: 118).

Embodiment 75 comprises an isolated polypeptide or polypeptide complex of any one of embodiments 1-68, wherein $L_1$ has a formula selected from the group consisting of $(G_2S)_n$, $(GS)_n$, $(GSGGS)_n$(SEQ ID NO: 50), $(GGGS)_n$(SEQ ID NO: 51), $(GGGGS)_n$(SEQ ID NO: 52), and $(GSSGGS)_n$(SEQ ID NO: 53), wherein n is an integer of at least 1.

Embodiment 76 comprises an isolated polypeptide or polypeptide complex of any one of embodiments 1-68, wherein $P_1$ becomes unbound from $A_1$ when $L_1$ is cleaved by the tumor specific protease thereby exposing $A_1$ to the effector cell antigen.

Embodiment 77 comprises an isolated polypeptide or polypeptide complex of any one of embodiments 1-68, wherein $P_2$ becomes unbound from $A_2$ when $L_2$ is cleaved by the tumor specific protease thereby exposing $A_2$ to PSMA.

Embodiment 78 comprises an isolated polypeptide or polypeptide complex of any one of embodiments 1-68, wherein the tumor specific protease is selected from the group consisting of a matrix metalloprotease (MMP), serine protease, cysteine protease, threonine protease, and aspartic protease.

Embodiment 79 comprises an isolated polypeptide or polypeptide complex of embodiment 78, wherein the matrix metalloprotease comprises MMP2, MMP7, MMP9, MMP13, or MMP14.

Embodiment 80 comprises an isolated polypeptide or polypeptide complex of embodiment 78, wherein the serine protease comprises matriptase (MTSP1), urokinase, or hepsin.

Embodiment 81 comprises an isolated polypeptide or polypeptide complex of any one of embodiments 1-68, wherein $L_1$ or $L_2$ comprises a urokinase cleavable amino acid sequence, a matriptase cleavable amino acid sequence, matrix metalloprotease cleavable amino acid sequence, or a legumain cleavable amino acid sequence.

Embodiment 82 comprises an isolated polypeptide or polypeptide complex of any one of embodiments 1-68, wherein $L_1$ or $L_2$ comprises an amino acid sequence according to SEQ ID NO: 23.

Embodiment 83 comprises an isolated polypeptide or polypeptide complex of any one of embodiments 1-68, wherein $L_1$ or $L_2$ comprises an amino acid sequence according to any one of SEQ ID NOs: 20-49.

Embodiment 84 comprises an isolated polypeptide or polypeptide complex of any one of embodiments 1-68, wherein $L_1$ or $L_2$ comprises an amino acid sequence of Linker 25 (ISSGLLSGRSDAG) (SEQ ID NO: 45), Linker 26 (AAGLLAPPGGLSGRSDAG) (SEQ ID NO: 46), Linker 27 (SPLGLSGRSDAG) (SEQ ID NO: 47), or Linker 28 (LSGRSDAGSPLGLAG) (SEQ ID NO: 48), or an amino acid sequence that has 1, 2, or 3 amino acid substitutions, additions, or deletions relative to the amino acid sequence of Linker 25, Linker 26, Linker 27, or Linker 28.

Embodiment 85 comprises an isolated polypeptide or polypeptide complex of any one of embodiments 1-83, wherein $H_1$ comprises a polymer.

Embodiment 86 comprises an isolated polypeptide or polypeptide complex of any one of embodiments 1-83, wherein the polymer is polyethylene glycol (PEG).

Embodiment 87 comprises an isolated polypeptide or polypeptide complex of any one of embodiments 1-83, wherein $H_1$ comprises albumin.

Embodiment 88 comprises an isolated polypeptide or polypeptide complex of any one of embodiments 1-83, wherein $H_1$ comprises an Fc domain.

Embodiment 89 comprises an isolated polypeptide or polypeptide complex of embodiment 87, wherein the albumin is serum albumin.

Embodiment 90 comprises an isolated polypeptide or polypeptide complex of embodiment 87, wherein the albumin is human serum albumin.

Embodiment 91 comprises an isolated polypeptide or polypeptide complex of any one of embodiments 1-83, wherein $H_1$ comprises a polypeptide, a ligand, or a small molecule.

Embodiment 92 comprises an isolated polypeptide or polypeptide complex of embodiment 91, wherein the polypeptide, the ligand or the small molecule binds serum protein or a fragment thereof, a circulating immunoglobulin or a fragment thereof, or CD35/CR1.

Embodiment 93 comprises an isolated polypeptide or polypeptide complex of embodiment 88, wherein the serum protein comprises a thyroxine-binding protein, a transthyretin, a 1-acid glycoprotein, a transferrin, transferrin receptor or a transferrin-binding portion thereof, a fibrinogen, or an albumin.

Embodiment 94 comprises an isolated polypeptide or polypeptide complex of embodiment 88, wherein the circulating immunoglobulin molecule comprises IgG1, IgG2, IgG3, IgG4, sIgA, IgM or IgD.

Embodiment 95 comprises an isolated polypeptide or polypeptide complex of embodiment 92, wherein the serum protein is albumin.

Embodiment 96 comprises an isolated polypeptide or polypeptide complex of embodiment 91, wherein the polypeptide is an antibody.

Embodiment 97 comprises an isolated polypeptide or polypeptide complex of embodiment 96, wherein the antibody comprises a single domain antibody, a single chain variable fragment, or a Fab.

Embodiment 98 comprises an isolated polypeptide or polypeptide complex of embodiment 97, wherein the single domain antibody comprises a single domain antibody that binds to albumin.

Embodiment 99 comprises an isolated polypeptide or polypeptide complex of embodiment 97, wherein the single domain antibody is a human or humanized antibody.

Embodiment 100 comprises an isolated polypeptide or polypeptide complex of embodiment 97, wherein the single domain antibody is 645gH1gL1.

Embodiment 101 comprises an isolated polypeptide or polypeptide complex of embodiment 97, wherein the single domain antibody is 645dsgH5gL4.

Embodiment 102 comprises an isolated polypeptide or polypeptide complex of embodiment 97, wherein the single domain antibody is 23-13-A01-sc02.

Embodiment 103 comprises an isolated polypeptide or polypeptide complex of embodiment 97, wherein the single domain antibody is A10m3 or a fragment thereof.

Embodiment 104 comprises an isolated polypeptide or polypeptide complex of embodiment 97, wherein the single domain antibody is DOM7r-31.

Embodiment 105 comprises an isolated polypeptide or polypeptide complex of embodiment 97, wherein the single domain antibody is DOM7h-11-15.

Embodiment 106 comprises an isolated polypeptide or polypeptide complex of embodiment 97, wherein the single domain antibody is Alb-1, Alb-8, or Alb-23.

Embodiment 107 comprises an isolated polypeptide or polypeptide complex of embodiment 97, wherein the single domain antibody is 10E.

Embodiment 108 comprises an isolated polypeptide or polypeptide complex of embodiment 97, wherein the single domain antibody comprises complementarity determining regions (CDRs): HC-CDR1, HC-CDR2, and HC-CDR3, wherein the HC-CDR1, the HC-CDR2, and the HC-CDR3 of the single domain antibody comprise: HC-CDR1: SEQ ID NO: 54, HC-CDR2: SEQ ID NO: 55, and HC-CDR3: SEQ ID NO: 56.

Embodiment 109 comprises an isolated polypeptide or polypeptide complex of embodiment 97, wherein the single domain antibody comprises complementarity determining regions (CDRs): HC-CDR1, HC-CDR2, and HC-CDR3, wherein the HC-CDR1, the HC-CDR2, and the HC-CDR3 of the single domain antibody comprise: HC-CDR1: SEQ ID NO: 58, HC-CDR2: SEQ ID NO: 59, and HC-CDR3: SEQ ID NO: 60.

Embodiment 110 comprises an isolated polypeptide or polypeptide complex of embodiment 97, wherein the single domain antibody is SA21.

Embodiment 111 comprises an isolated polypeptide or polypeptide complex of any one of embodiments 1-110, wherein the polypeptide or polypeptide complex comprises a modified amino acid, a non-natural amino acid, a modified non-natural amino acid, or a combination thereof.

Embodiment 112 comprises an isolated polypeptide or polypeptide complex of embodiment 111, wherein the modified amino acid or modified non-natural amino acid comprises a post-translational modification.

Embodiment 113 comprises an isolated polypeptide or polypeptide complex of any one of embodiments 1-112, wherein $H_1$ comprises a linking moiety ($L_3$) that connects $H_1$ to $P_1$.

Embodiment 114 comprises an isolated polypeptide or polypeptide complex of embodiment 113, wherein $L_3$ is a peptide sequence having at least 5 to no more than 50 amino acids.

Embodiment 115 comprises an isolated polypeptide or polypeptide complex of embodiment 113, wherein $L_3$ is a peptide sequence having at least 10 to no more than 30 amino acids.

Embodiment 116 comprises an isolated polypeptide or polypeptide complex of embodiment 113, wherein $L_3$ is a peptide sequence having at least 10 amino acids.

Embodiment 117 comprises an isolated polypeptide or polypeptide complex of embodiment 113, wherein $L_3$ is a peptide sequence having at least 18 amino acids.

Embodiment 118 comprises an isolated polypeptide or polypeptide complex of embodiment 113, wherein $L_3$ is a peptide sequence having at least 26 amino acids.

Embodiment 119 comprises an isolated polypeptide or polypeptide complex of embodiment 113, wherein $L_3$ has a formula selected from the group consisting of $(G_2S)_n$, $(GS)_n$, $(GSGGS)_n$(SEQ ID NO: 50), $(GGGS)_n$(SEQ ID NO: 51), $(GGGGS)_n$(SEQ ID NO: 52), and $(GSSGGS)_n$(SEQ ID NO: 53), wherein n is an integer of at least 1.

Embodiment 120 comprises an isolated polypeptide or polypeptide complex of embodiment 113, wherein $L_3$ comprises an amino acid sequence according to SEQ ID NO: 22.

Embodiment 121 comprises an isolated polypeptide or polypeptide complex of embodiment 1, wherein the polypeptide or polypeptide complex comprises an amino acid sequence with at least 95% sequence identity to SEQ ID NOs: 62-77.

Embodiment 122 comprises an isolated polypeptide or polypeptide complex of embodiment 1, wherein the polypeptide or polypeptide complex comprises an amino acid sequence with at least 95% sequence identity to SEQ ID NO: 72.

Embodiment 123 comprises an isolated polypeptide or polypeptide complex of embodiment 1, wherein the polypeptide or polypeptide complex comprises an amino acid sequence with at least 95% sequence identity to SEQ ID NO: 73.

Embodiment 124 comprises an isolated polypeptide or polypeptide complex of embodiment 1, wherein the polypeptide or polypeptide complex comprises an amino acid sequence with at least 95% sequence identity to SEQ ID NO: 62 and SEQ ID NO: 63.

Embodiment 125 comprises an isolated polypeptide or polypeptide complex of embodiment 1, wherein the polypeptide or polypeptide complex comprises an amino acid sequence with at least 95% sequence identity to SEQ ID NO: 64 and SEQ ID NO: 65.

Embodiment 126 comprises an isolated polypeptide or polypeptide complex of embodiment 1, wherein the polypeptide or polypeptide complex comprises an amino acid sequence with at least 95% sequence identity to SEQ ID NO: 66 and SEQ ID NO: 67.

Embodiment 127 comprises an isolated polypeptide or polypeptide complex of embodiment 1, wherein the polypeptide or polypeptide complex comprises an amino acid sequence with at least 95% sequence identity to SEQ ID NO: 68 and SEQ ID NO: 69.

Embodiment 128 comprises an isolated polypeptide or polypeptide complex of embodiment 1, wherein the polypeptide or polypeptide complex comprises an amino acid sequence with at least 95% sequence identity to SEQ ID NO: 70 and SEQ ID NO: 71.

Embodiment 129 comprises an isolated polypeptide or polypeptide complex of embodiment 1, wherein the polypeptide or polypeptide complex comprises an amino acid sequence with at least 95% sequence identity to SEQ ID NO: 72 and SEQ ID NO: 73.

Embodiment 130 comprises an isolated polypeptide or polypeptide complex of embodiment 1, wherein the polypeptide or polypeptide complex comprises an amino acid sequence with at least 95% sequence identity to SEQ ID NO: 74 and SEQ ID NO: 75.

Embodiment 131 comprises an isolated polypeptide or polypeptide complex of embodiment 1, wherein the polypeptide or polypeptide complex comprises an amino acid sequence with at least 95% sequence identity to SEQ ID NO: 76 and SEQ ID NO: 77.

Embodiment 132 comprises a pharmaceutical composition comprising: (a) the polypeptide or polypeptide complex of any one of embodiments 1-131; and (b) a pharmaceutically acceptable excipient.

Embodiment 133 comprises an isolated recombinant nucleic acid molecule encoding the polypeptide or polypeptide complex of any one of embodiments 1-131.

Embodiment 134 comprises an isolated polypeptide or polypeptide complex according to Formula II: $L_{1a}$-$P_{1a}$—$H_{1a}$ wherein: $L_{1a}$ comprises a tumor specific protease-cleaved linking moiety that when uncleaved connects $P_{1a}$ to a first antigen recognizing molecule that binds to an effector cell antigen and the first antigen recognizing molecule is connected to a second antigen recognizing molecule that binds to PSMA; $P_{1a}$ comprises a peptide that binds to the first antigen recognizing molecule when $L_{1a}$ is uncleaved; and $H_{1a}$ comprises a half-life extending molecule.

Embodiment 135 comprises an isolated polypeptide or polypeptide complex of embodiment 134, wherein $P_{1a}$ when $L_{1a}$ is uncleaved impairs binding of the first antigen recognizing molecule to the effector cell antigen.

Embodiment 136 comprises an isolated polypeptide or polypeptide complex of embodiment 134, wherein the first antigen recognizing molecule comprises an antibody or antibody fragment.

Embodiment 137 comprises an isolated polypeptide or polypeptide complex of embodiment 134, wherein the effector cell antigen is an anti-CD3 effector cell antigen.

Embodiment 138 comprises an isolated polypeptide or polypeptide complex of embodiment 134, wherein $P_{1a}$ has less than 70% sequence homology to the effector cell antigen.

Embodiment 139 comprises an isolated polypeptide or polypeptide complex of embodiment 134, wherein $P_{1a}$ comprises a peptide sequence of at least 10 amino acids in length.

Embodiment 140 comprises an isolated polypeptide or polypeptide complex of embodiment 134, wherein $P_{1a}$ comprises a peptide sequence of at least 10 amino acids in length and no more than 20 amino acids in length.

Embodiment 141 comprises an isolated polypeptide or polypeptide complex of embodiment 134, wherein $P_{1a}$ comprises a peptide sequence of at least 16 amino acids in length.

Embodiment 142 comprises an isolated polypeptide or polypeptide complex of embodiment 134, wherein $P_{1a}$ comprises a peptide sequence of no more than 40 amino acids in length.

Embodiment 143 comprises an isolated polypeptide or polypeptide complex of embodiment 134, wherein $P_{1a}$ comprises at least two cysteine amino acid residues.

Embodiment 144 comprises an isolated polypeptide or polypeptide complex of embodiment 134, wherein $P_{1a}$ comprises a cyclic peptide or a linear peptide.

Embodiment 145 comprises an isolated polypeptide or polypeptide complex of embodiment 134, wherein $P_{1a}$ comprises a cyclic peptide.

Embodiment 146 comprises an isolated polypeptide or polypeptide complex of embodiment 134, wherein $P_{1a}$ comprises a linear peptide.

Embodiment 147 comprises an isolated polypeptide or polypeptide complex of embodiment 134, wherein $P_{1a}$ comprises an amino acid sequence selected from the group consisting of any one of SEQ ID NOs: 16-19.

Embodiment 148 comprises an isolated polypeptide or polypeptide complex of any one of embodiments 132-145, wherein Ha comprises a polymer.

Embodiment 149 comprises an isolated polypeptide or polypeptide complex of embodiment 148, wherein the polymer is polyethylene glycol (PEG).

Embodiment 150 comprises an isolated polypeptide or polypeptide complex of any one of embodiments 134-147, wherein Ha comprises albumin.

Embodiment 151 comprises an isolated polypeptide or polypeptide complex of any one of embodiments 134-147, wherein Ha comprises an Fc domain.

Embodiment 152 comprises an isolated polypeptide or polypeptide complex of embodiment 150, wherein the albumin is serum albumin.

Embodiment 153 comprises an isolated polypeptide or polypeptide complex of embodiment 152, wherein the albumin is human serum albumin.

Embodiment 154 comprises an isolated polypeptide or polypeptide complex of any one of embodiments 134-147, wherein $H_{1a}$ comprises a polypeptide, a ligand, or a small molecule.

Embodiment 155 comprises an isolated polypeptide or polypeptide complex of embodiment 154, wherein the polypeptide, the ligand or the small molecule binds a serum protein or a fragment thereof, a circulating immunoglobulin or a fragment thereof, or CD35/CR1.

Embodiment 156 comprises an isolated polypeptide or polypeptide complex of embodiment 155, wherein the serum protein comprises a thyroxine-binding protein, a transthyretin, a 1-acid glycoprotein, a transferrin, transferrin receptor or a transferrin-binding portion thereof, a fibrinogen, or an albumin.

Embodiment 157 comprises an isolated polypeptide or polypeptide complex of embodiment 155, wherein the circulating immunoglobulin molecule comprises IgG1, IgG2, IgG3, IgG4, sIgA, IgM or IgD.

Embodiment 158 comprises an isolated polypeptide or polypeptide complex of embodiment 153, wherein the serum protein is albumin.

Embodiment 159 comprises an isolated polypeptide or polypeptide complex of embodiment 154, wherein the polypeptide is an antibody.

Embodiment 160 comprises an isolated polypeptide or polypeptide complex of embodiment 159, wherein the antibody comprises a single domain antibody, a single chain variable fragment or a Fab.

Embodiment 161 comprises an isolated polypeptide or polypeptide complex of embodiment 159, wherein the antibody comprises a single domain antibody that binds to albumin.

Embodiment 162 comprises an isolated polypeptide or polypeptide complex of embodiment 159, wherein the antibody is a human or humanized antibody.

Embodiment 163 comprises an isolated polypeptide or polypeptide complex of embodiment 160, wherein the single domain antibody is 645gH1gL1.

Embodiment 164 comprises an isolated polypeptide or polypeptide complex of embodiment 160, wherein the single domain antibody is 645dsgH5gL4.

Embodiment 165 comprises an isolated polypeptide or polypeptide complex of embodiment 160, wherein the single domain antibody is 23-13-A01-sc02.

Embodiment 166 comprises an isolated polypeptide or polypeptide complex of embodiment 160, wherein the single domain antibody is A10m3 or a fragment thereof.

Embodiment 167 comprises an isolated polypeptide or polypeptide complex of embodiment 160, wherein the single domain antibody is DOM7r-31.

Embodiment 168 comprises an isolated polypeptide or polypeptide complex of embodiment 160, wherein the single domain antibody is DOM7h-11-15.

Embodiment 169 comprises an isolated polypeptide or polypeptide complex of embodiment 160, wherein the single domain antibody is Alb-1, Alb-8, or Alb-23.

Embodiment 170 comprises an isolated polypeptide or polypeptide complex of embodiment 160, wherein the single domain antibody is 10E.

Embodiment 171 comprises an isolated polypeptide or polypeptide complex of embodiment 160, wherein the single domain antibody comprises complementarity determining regions (CDRs): HC-CDR1, HC-CDR2, and HC-CDR3, wherein the HC-CDR1, the HC-CDR2, and the HC-CDR3 of the single domain antibody comprise: HC-CDR1: SEQ ID NO: 54, HC-CDR2: SEQ ID NO: 55, and HC-CDR3: SEQ ID NO: 56.

Embodiment 172 comprises an isolated polypeptide or polypeptide complex of embodiment 158, wherein the single domain antibody comprises complementarity determining regions (CDRs): HC-CDR1, HC-CDR2, and HC-CDR3, wherein the HC-CDR1, the HC-CDR2, and the HC-CDR3 of the single domain antibody comprise: HC-CDR1: SEQ ID NO: 58, HC-CDR2: SEQ ID NO: 59, and HC-CDR3: SEQ ID NO: 60.

Embodiment 173 comprises an isolated polypeptide or polypeptide complex of embodiment 160, wherein the single domain antibody is SA21.

Embodiment 174 comprises an isolated polypeptide or polypeptide complex of any one of embodiments 134-173, wherein $H_{1a}$ comprises a linking moiety ($L_{1a}$) that connects $H_{1a}$ to $P_{1a}$.

Embodiment 175 comprises an isolated polypeptide or polypeptide complex of embodiment 174, wherein Lia is a peptide sequence having at least 5 to no more than 50 amino acids.

Embodiment 176 comprises an isolated polypeptide or polypeptide complex of embodiment 174, wherein Lia is a peptide sequence having at least 10 to no more than 30 amino acids.

Embodiment 177 comprises an isolated polypeptide or polypeptide complex of embodiment 174, wherein $L_{1a}$ is a peptide sequence having at least 10 amino acids.

Embodiment 178 comprises an isolated polypeptide or polypeptide complex of embodiment 174, wherein Lia is a peptide sequence having at least 18 amino acids.

Embodiment 179 comprises an isolated polypeptide or polypeptide complex of embodiment 174, wherein $L_{1a}$ is a peptide sequence having at least 26 amino acids.

Embodiment 180 comprises an isolated polypeptide or polypeptide complex of embodiment 174, wherein $L_{1a}$ has a formula selected from the group consisting of $(G_2S)_n$, $(GS)_n$, $(GSGGS)_n$(SEQ ID NO: 50), $(GGGS)_n$(SEQ ID NO: 51), $(GGGGS)_n$(SEQ ID NO: 52), and $(GSSGGS)_n$(SEQ ID NO: 53), wherein n is an integer of at least 1.

Embodiment 181 comprises an isolated polypeptide or polypeptide complex of embodiment 174, wherein $L_{1a}$ comprises an amino acid sequence according to SEQ ID NO: 23.

Embodiment 182 comprises an isolated polypeptide or polypeptide complex of any one of embodiments 134-181, wherein $P_{1a}$ comprises an amino acid sequence according to $Z_1$-$Z_2$—C—$Z_4$—P—$Z_6$-$Z_7$-Zs-$Z_9$-$Z_{10}$—$Z_{11}$—$Z_{12}$—C—$Z_{14}$ and $Z_1$ is selected from D, Y, F, I, N, V, H, L, A, T, S, and P; $Z_2$ is selected from D, Y, L, F, I, N, A, V, H, T, and S; $Z_4$ is selected from G and W; $Z_6$ is selected from E, D, V, and P; $Z_7$ is selected from W, L, F, V, G, M, I, and Y; Zs is selected from E, D, P, and Q; $Z_9$ is selected from E, D, Y, V, F, W, P, L, and Q; $Z_{10}$ is selected from S, D, Y, T, I, F, V, N, A, P, L, and H; Zn is selected from I, Y, F, V, L, T, N, S, D, A, and H; $Z_{12}$ is selected from F, D, Y, L, I, V, A, N, T, P, S, and H; and $Z_{14}$ is selected from D, Y, N, F, I, P, V, A, T, H, L and S.

Embodiment 183 comprises an isolated polypeptide or polypeptide complex of embodiment 182, wherein $Z_1$ is selected from D, Y, F, I, and N; $Z_2$ is selected from D, Y, L, F, I, and N; $Z_4$ is selected from G and W; $Z_6$ is selected from E and D; $Z_7$ is selected from W, L, F, and V; Zs is selected from E and D; $Z_9$ is selected from E, D, Y, and V; $Z_{10}$ is selected from S, D, Y, T, and I; Zn is selected from I, Y, F, V, L, and T; $Z_{12}$ is selected from F, D, Y, L, I, V, A, and N; and $Z_{14}$ is selected from D, Y, N, F, I, and P;

Embodiment 184 comprises an isolated polypeptide or polypeptide complex of any one of embodiments 182-183, wherein $Z_1$ is selected from D, Y, and F; $Z_2$ is selected from D, Y, L, and F; $Z_4$ is selected from G and W; $Z_6$ is selected from E and D; $Z_7$ is selected from W, L, and F; $Z_8$ is selected from E and D; $Z_9$ is selected from E and D; $Z_{10}$ is selected from S, D, and Y; Zu is selected from I, Y, and F; $Z_{12}$ is selected from F, D, Y, and L; and $Z_{14}$ is selected from D, Y, and N.

Embodiment 185 comprises an isolated polypeptide or polypeptide complex of any one of embodiments 134-181, wherein $P_{1a}$ comprises an amino acid sequence according to $U_1$-$U_2$—C—$U_4$—P—$U_6$-$U_7$—$U_8$—$U_9$-$U_{10}$—$U_{11}$—$U_{12}$—C—$U_{14}$ and $U_1$ is selected from D, Y, F, I, N, V, H, L, A, T, S, and P; $U_2$ is selected from D, Y, L, F, I, N, A, V, H, T, and S; $U_4$ is selected from G and W; $U_6$ is selected from E, D, V, and P; $U_7$ is selected from W, L, F, V, G, M, I, and Y; $U_8$ is selected from E, D, P, and Q; $U_9$ is selected from E, D, Y, V, F, W, P, L, and Q; $U_{10}$ is selected from S, D, Y, T, I, F, V, N, A, P, L, and H; $U_{11}$ is selected from I, Y, F, V, L, T, N, S, D, A, and H; $U_{12}$ is selected from F, D, Y, L, I, V, A, N, T, P, S, G, and H; and $U_{14}$ is selected from D, Y, N, F, I, P, V, A, T, H, L, M, and S.

Embodiment 186 comprises an isolated polypeptide or polypeptide complex of embodiment 185, wherein $U_1$ is selected from D, Y, F, I, V, and N; $U_2$ is selected from D, Y, L, F, I, and N; $U_4$ is selected from G and W; $U_6$ is selected from E and D; $U_7$ is selected from W, L, F, G, and V; $U_8$ is selected from E and D; $U_9$ is selected from E, D, Y, and V; $U_{10}$ is selected from S, D, Y, T, and I; $U_{11}$ is selected from I, Y, F, V, L, and T; $U_{12}$ is selected from F, D, Y, L, I, V, A, G, and N; and $U_{14}$ is selected from D, Y, N, F, I, M, and P.

Embodiment 187 comprises an isolated polypeptide or polypeptide complex of embodiment 186, wherein $U_1$ is selected from D, Y, V, and F; $U_2$ is selected from D, Y, L, and F; $U_4$ is selected from G and W; $U_6$ is selected from E and D; $U_7$ is selected from W, L, G, and F; $U_8$ is selected from E and D; $U_9$ is selected from E and D; $U_{10}$ is selected from S, D, T, and Y; Un is selected from I, Y, V, L, and F; $U_{12}$ is selected from F, D, Y, G, A, and L; and $U_{14}$ is selected from D, Y, M, and N.

Embodiment 188 comprises an isolated polypeptide or polypeptide complex of any one of embodiments 134-181 and 70-88, wherein $P_{1a}$ comprises the amino acid sequences according to SEQ ID NOs: 79-105.

Embodiment 189 comprises an isolated polypeptide or polypeptide complex of any one of embodiments 134-181 and 70-88, wherein $P_{1a}$ comprises an amino acid sequences according to any of the sequences of Table 20.

Embodiment 190 comprises an isolated polypeptide or polypeptide complex of any one of embodiments 134-181, or 189, wherein $P_{1a}$ comprises the amino acid sequences according to any one of SEQ ID NOs: 106-117.

Embodiment 191 comprises an isolated polypeptide or polypeptide complex of any one of embodiments 134-181, wherein $P_{1a}$ comprises the amino acid sequence according to SEQ ID NO: 18 or a peptide sequence that has 1, 2, or 3, amino acid substitutions, additions, or deletions relative to the amino acid sequence of SEQ ID NO: 18.

Embodiment 192 comprises an isolated polypeptide or polypeptide complex of any one of embodiments 134-187, wherein $P_{1a}$ comprises the amino acid sequence according to SEQ ID NO: 19 or a peptide sequence that has 1, 2, or 3, amino acid substitutions, additions, or deletions relative to the amino acid sequence of SEQ ID NO: 19.

Embodiment 193 comprises an isolated polypeptide or polypeptide complex of any one of embodiments 134-187, wherein $P_{1a}$ comprises the amino acid sequence according to SEQ ID NO: 116 or a peptide sequence that has 1, 2, or 3, amino acid substitutions, additions, or deletions relative to the amino acid sequence of SEQ ID NO: 116.

Embodiment 194 comprises an isolated polypeptide or polypeptide complex of embodiment 191, wherein $P_{1a}$ comprises the amino acid sequence according to SEQ ID NO: 18.

Embodiment 195 comprises an isolated polypeptide or polypeptide complex of embodiment 192, wherein $P_{1a}$ comprises the amino acid sequence according to SEQ ID NO: 19.

Embodiment 196 comprises an isolated polypeptide or polypeptide complex of embodiment 193, wherein $P_{1a}$ comprises the amino acid sequence according to SEQ ID NO: 116.

Embodiment 197 comprises a polypeptide complex comprising a structural arrangement according to the configuration shown in FIG. 1C, wherein the polypeptide complex comprises a single chain variable fragment (scFv) comprising a light chain variable domain and a heavy chain variable domain, wherein the scFv further comprises a peptide that impairs binding of the scFv to an effector cell antigen and the peptide is linked to the heavy chain variable domain of the scFv with a linking moiety that is a substrate for a tumor specific protease, and the peptide further comprises a half-life extending molecule; and a Fab or a Fab' that binds to prostate-specific membrane antigen (PSMA), wherein the Fab or Fab' comprises a Fab light chain polypeptide chain and a Fab heavy chain polypeptide chain, and wherein the Fab heavy chain polypeptide chain is linked to a C terminus of the light chain variable domain of the scFv.

Embodiment 198 comprises a polypeptide complex comprising a structural arrangement according to the configuration shown in FIG. 1D, wherein the polypeptide complex comprises a single chain variable fragment (scFv) comprising a light chain variable domain and a heavy chain variable domain, wherein the scFv further comprises a peptide that impairs binding of the scFv to an effector cell antigen and the peptide is linked to a N-terminus of the heavy chain variable domain of the scFv with a linking moiety that is a substrate for a tumor specific protease, and the peptide further comprises a half-life extending molecule; and a Fab or Fab' that binds to prostate-specific membrane antigen (PSMA), wherein the Fab or Fab' comprises a Fab light chain polypeptide and a Fab heavy chain polypeptide, wherein the Fab light chain polypeptide is linked to a C terminus of the light chain variable domain of the scFv.

Embodiment 199 comprises an isolated polypeptide or polypeptide complex of any one of embodiments 1-133, wherein $P_1$ comprises an amino acid sequence according to $Z_1$-$Z_2$—C—$Z_4$—P—$Z_6$-$Z_7$—$Z_8$—$Z_9$-$Z_{10}$—$Z_{11}$—$Z_{12}$—C—$Z_{14}$ and $Z_1$ is selected from D, Y, F, I, N, V, H, L, A, T, S, and P; $Z_2$ is selected from D, Y, L, F, I, N, A, V, H, T, and S; $Z_4$ is selected from G and W; $Z_6$ is selected from E, D, V, and P; $Z_7$ is selected from W, L, F, V, G, M, I, and Y; $Z_8$ is selected from E, D, P, and Q; $Z_9$ is selected from E, D, Y, V, F, W, P, L, and Q; $Z_{10}$ is selected from S, D, Y, T, I, F, V, N, A, P, L, and H; Zn is selected from I, Y, F, V, L, T, N, S, D, A, and H; $Z_{12}$ is selected from F, D, Y, L, I, V, A, N, T, P, S, and H; and $Z_{14}$ is selected from D, Y, N, F, I, P, V, A, T, H, L and S.

Embodiment 200 comprises an isolated polypeptide or polypeptide complex of embodiment 199, wherein $Z_1$ is selected from D, Y, F, I, and N; $Z_2$ is selected from D, Y, L, F, I, and N; $Z_4$ is selected from G and W; $Z_6$ is selected from E and D; $Z_7$ is selected from W, L, F, and V; Zs is selected from E and D; $Z_9$ is selected from E, D, Y, and V; $Z_{10}$ is selected from S, D, Y, T, and I; Zn is selected from I, Y, F, V, L, and T; $Z_{12}$ is selected from F, D, Y, L, I, V, A, and N; and $Z_{14}$ is selected from D, Y, N, F, I, and P.

Embodiment 201 comprises an isolated polypeptide or polypeptide complex of any one of embodiments 199-200, wherein $Z_1$ is selected from D, Y, and F; $Z_2$ is selected from D, Y, L, and F; $Z_4$ is selected from G and W; $Z_6$ is selected from E and D; $Z_7$ is selected from W, L, and F; $Z_8$ is selected from E and D; $Z_9$ is selected from E and D; $Z_{10}$ is selected from S, D, and Y; Zu is selected from I, Y, and F; $Z_{12}$ is selected from F, D, Y, and L; and $Z_{14}$ is selected from D, Y, and N.

Embodiment 202 comprises an isolated polypeptide or polypeptide complex of any one of embodiments 1-133, wherein $P_1$ comprises an amino acid sequence according to $U_1$-$U_2$—C—$U_4$—P—$U_6$-$U_7$—$U_8$—$U_9$-$U_{10}$—$U_{11}$—$U_{12}$—C—$U_{14}$ and $U_1$ is selected from D, Y, F, I, N, V, H, L, A, T, S, and P; $U_2$ is selected from D, Y, L, F, I, N, A, V, H, T, and S; $U_4$ is selected from G and W; $U_6$ is selected from E, D, V, and P; $U_7$ is selected from W, L, F, V, G, M, I, and Y; $U_8$ is selected from E, D, Y, V, F, W, P, L, and Q; $U_{10}$ is selected from S, D, Y, T, I, F, V, N, A, P, L, and H; Un is selected from I, Y, F, V, L, T, N, S, D, A, and H; $U_{12}$ is selected from F, D, Y, L, I, V, A, N, T, P, S, G, and H; and $U_{14}$ is selected from D, Y, N, F, I, P, V, A, T, H, L, M, and S.

Embodiment 203 comprises an isolated polypeptide or polypeptide complex of embodiment 202, wherein $U_1$ is selected from D, Y, F, I, V, and N; $U_2$ is selected from D, Y, L, F, I, and N; $U_4$ is selected from G and W; $U_6$ is selected from E and D; $U_7$ is selected from W, L, F, G, and V; $U_8$ is selected from E and D; $U_9$ is selected from E, D, Y, and V; $U_{10}$ is selected from S, D, Y, T, and I; Un is selected from I, Y, F, V, L, and T; $U_{12}$ is selected from F, D, Y, L, I, V, A, G, and N; and $U_{14}$ is selected from D, Y, N, F, I, M, and P.

Embodiment 204 comprises an isolated polypeptide or polypeptide complex of embodiment 203, wherein $U_1$ is selected from D, Y, V, and F; $U_2$ is selected from D, Y, L, and F; $U_4$ is selected from G and W; $U_6$ is selected from E and D; $U_7$ is selected from W, L, G, and F; $U_8$ is selected from E and D; $U_9$ is selected from E and D; $U_{10}$ is selected from S, D, T, and Y; Un is selected from I, Y, V, L, and F; $U_{12}$ is selected from F, D, Y, G, A, and L; and $U_{14}$ is selected from D, Y, M, and N.

Embodiment 205 comprises an isolated polypeptide or polypeptide complex of any one of embodiments 1-133 and 200-204, wherein $P_1$ comprises the amino acid sequences according to any one of SEQ ID NOs: 79-105.

Embodiment 206 comprises an isolated polypeptide or polypeptide complex of any one of embodiments 1-133 and 200-204, wherein $P_1$ comprises an amino acid sequences according to any of the sequences of Table 20.

Embodiment 207 comprises an isolated polypeptide or polypeptide complex of any one of embodiments 1-133, or 206, wherein $P_1$ comprises the amino acid sequences according to SEQ ID NOs: 106-117.

Embodiment 208 comprises an isolated polypeptide or polypeptide complex of any one of embodiments 1-133, wherein $P_1$ comprises the amino acid sequence according to SEQ ID NO: 18 or a peptide sequence that has 1, 2, or 3, amino acid substitutions, additions, or deletions relative to the amino acid sequence of SEQ ID NO: 18.

Embodiment 209 comprises an isolated polypeptide or polypeptide complex of any one of embodiments 1-133, 200-204, wherein $P_1$ comprises the amino acid sequence according to SEQ ID NO: 19 or a peptide sequence that has 1, 2, or 3, amino acid substitutions, additions, or deletions relative to the amino acid sequence of SEQ ID NO: 19.

Embodiment 210 comprises an isolated polypeptide or polypeptide complex of any one of embodiments 1-133, 200-204, wherein $P_1$ comprises the amino acid sequence according to SEQ ID NO: 116 or a peptide sequence that has 1, 2, or 3, amino acid substitutions, additions, or deletions relative to the amino acid sequence of SEQ ID NO: 116.

Embodiment 211 comprises an isolated polypeptide or polypeptide complex of embodiment 208, wherein $P_1$ comprises the amino acid sequence according to SEQ ID NO: 18.

Embodiment 212 comprises an isolated polypeptide or polypeptide complex of embodiment 209, wherein $P_1$ comprises the amino acid sequence according to SEQ ID NO: 19.

Embodiment 213 comprises an isolated polypeptide or polypeptide complex of embodiment 210, wherein $P_1$ comprises the amino acid sequence according to SEQ ID NO: 116.

Embodiment 214 comprises a pharmaceutical composition comprising: (a) the polypeptide or polypeptide complex of any of embodiments 1-213; and (b) a pharmaceutically acceptable excipient.

Embodiment 215 comprises an isolated recombinant nucleic acid molecule encoding the polypeptide or polypeptide complex of any of embodiments 1-213.

Embodiment 216 comprises a method of treating lung cancer comprising administering to a subject in need thereof an isolated polypeptide or polypeptide complex according to Embodiments 1-213.

Embodiment 217 comprises a method of treating breast cancer comprising administering to a subject in need thereof an isolated polypeptide or polypeptide complex according to Embodiments 1-213.

Embodiment 218 comprises a method of treating cervical cancer comprising administering to a subject in need thereof an isolated polypeptide or polypeptide complex according to Embodiments 1-213.

Embodiment 219 comprises a method of treating ovarian cancer comprising administering to a subject in need thereof an isolated polypeptide or polypeptide complex according to Embodiments 1-213.

Embodiment 220 comprises a method of treating pancreatic cancer comprising administering to a subject in need thereof an isolated polypeptide or polypeptide complex according to Embodiments 1-213.

Embodiment 221 comprises a method of treating colorectal cancer comprising administering to a subject in need thereof an isolated polypeptide or polypeptide complex according to Embodiments 1-213.

Embodiment 222 comprises a method of treating gastric cancer comprising administering to a subject in need thereof an isolated polypeptide or polypeptide complex according to Embodiments 1-213.

Embodiment 223 comprises a method of treating pancreatic cancer comprising administering to a subject in need thereof an isolated polypeptide or polypeptide complex according to Embodiments 1-213.

Embodiment 224 comprises a method of treating metastatic castrate-resistant prostate cancer comprising administering to a subject in need thereof an isolated polypeptide or polypeptide complex according to Embodiments 1-213.

EXAMPLES

Example 1: PSMA Polypeptide Complex Binding

The PSMA-CD3 polypeptide complexes of Table 7 were evaluated for PSMA and CD3ε binding.

TABLE 7

| Polypeptide complexes | | | | | | |
|---|---|---|---|---|---|---|
| Polypeptide complex | Form | Fab Mask | CD3 | CD3 Mask | Cleavable linker | sdA |
| PC1 | Vh | | | | | |
| PC3 | Vh | — | SEQ ID NO. 7 | SEQ ID NO. 16 | LSGRSD AGSPLG LAG (SEQ ID NO: 48) | SEQ ID NO. 57 |

TABLE 7-continued

| Polypeptide complexes | | | | | | |
|---|---|---|---|---|---|---|
| Polypeptide complex | Form | Fab Mask | CD3 | CD3 Mask | Cleavable linker | sdA |
| PC5 | Vh | — | SEQ ID NO. 7 | SEQ ID NO. 17 | LSGRSD AGSPLG LAG (SEQ ID NO: 48) | SEQ ID NO. 57 |
| PC2 | Vl | | | | | |
| PC4 | Vl | — | SEQ ID NO. 7 | SEQ ID NO. 16 | LSGRSD AGSPLG LAG (SEQ ID NO: 48) | SEQ ID NO. 57 |
| PC6 | Vl | — | SEQ ID NO. 7 | SEQ ID NO. 17 | LSGRSD AGSPLG LAG (SEQ ID NO: 48) | SEQ ID NO. 57 |

The polypeptide complex molecules of Table 7 were evaluated for their ability to bind PSMA as well as CD3 in a standard enzyme linked immunosorbent assay (ELISA) format. Polypeptide complex binding of PSMA or CD3 were measured before and after protease treatment. Briefly, biotinylated antigen was captured on neutravidin coated plates. Polypeptide complex molecules were treated with active matriptase (MTSP1) where indicated. Polypeptide complex molecules diluted in buffer were then added to the antigen coated plates. Bound polypeptide complex was detected using a standard horse radish peroxidase conjugate secondary antibody. The concentration of polypeptide complex required to achieve 50% maximal signal (EC50) was calculated in Graphpad Prism.

Figure 2A:
FIG. 2A illustrates titration data for PSMA binding for several polypeptide complexes of this disclosure.
Figure 2B:
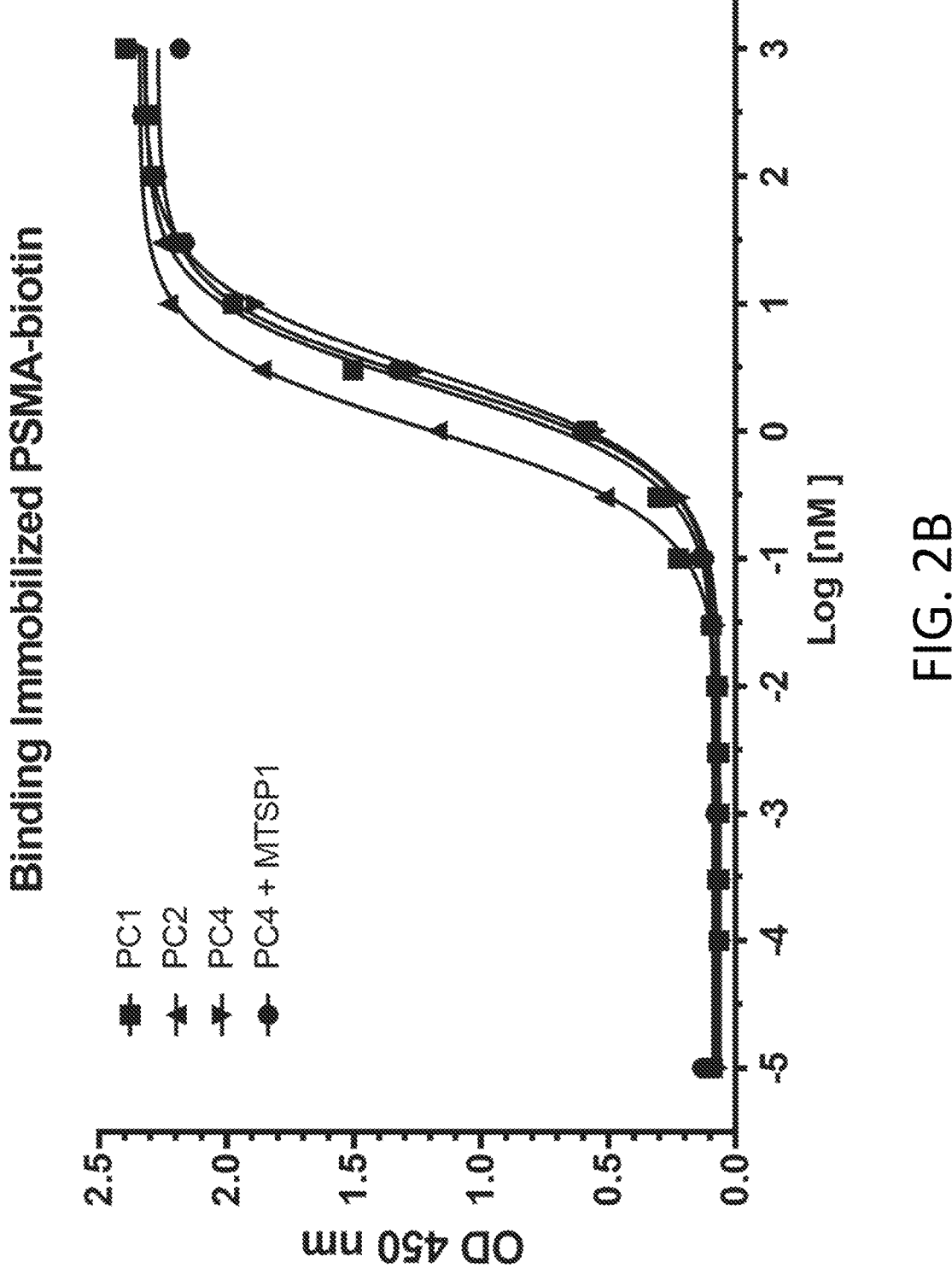
FIG. 2B illustrates titration data for PSMA binding for several polypeptide complexes of this disclosure.
Figure 2C:
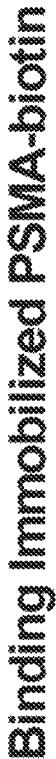
FIG. 2C illustrates titration data for PSMA binding for several polypeptide complexes of this disclosure.
Figure 3A:
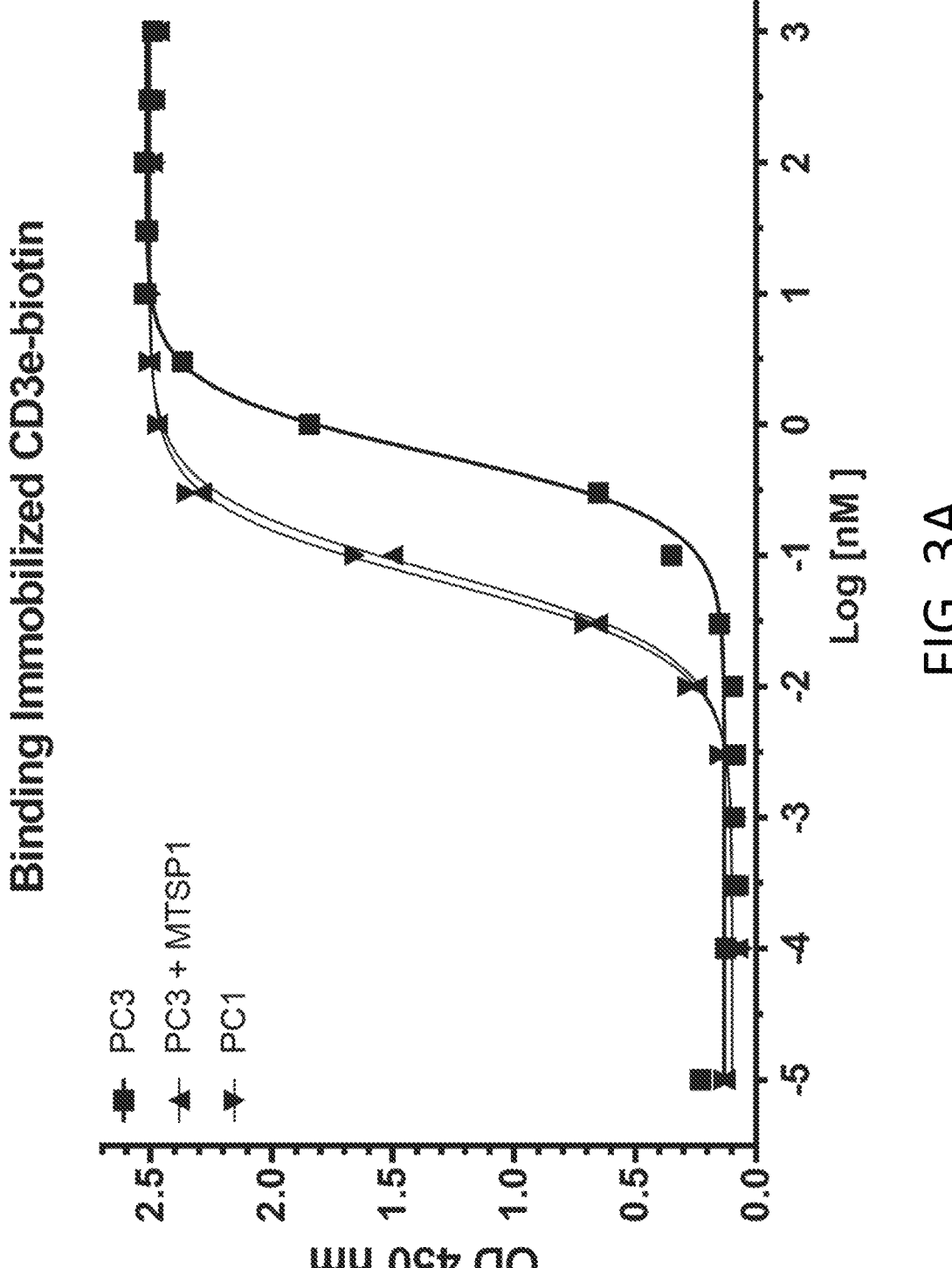
FIG. 3A illustrates titration data for CD3ε binding for several polypeptide complexes of this disclosure.
Figure 3B:
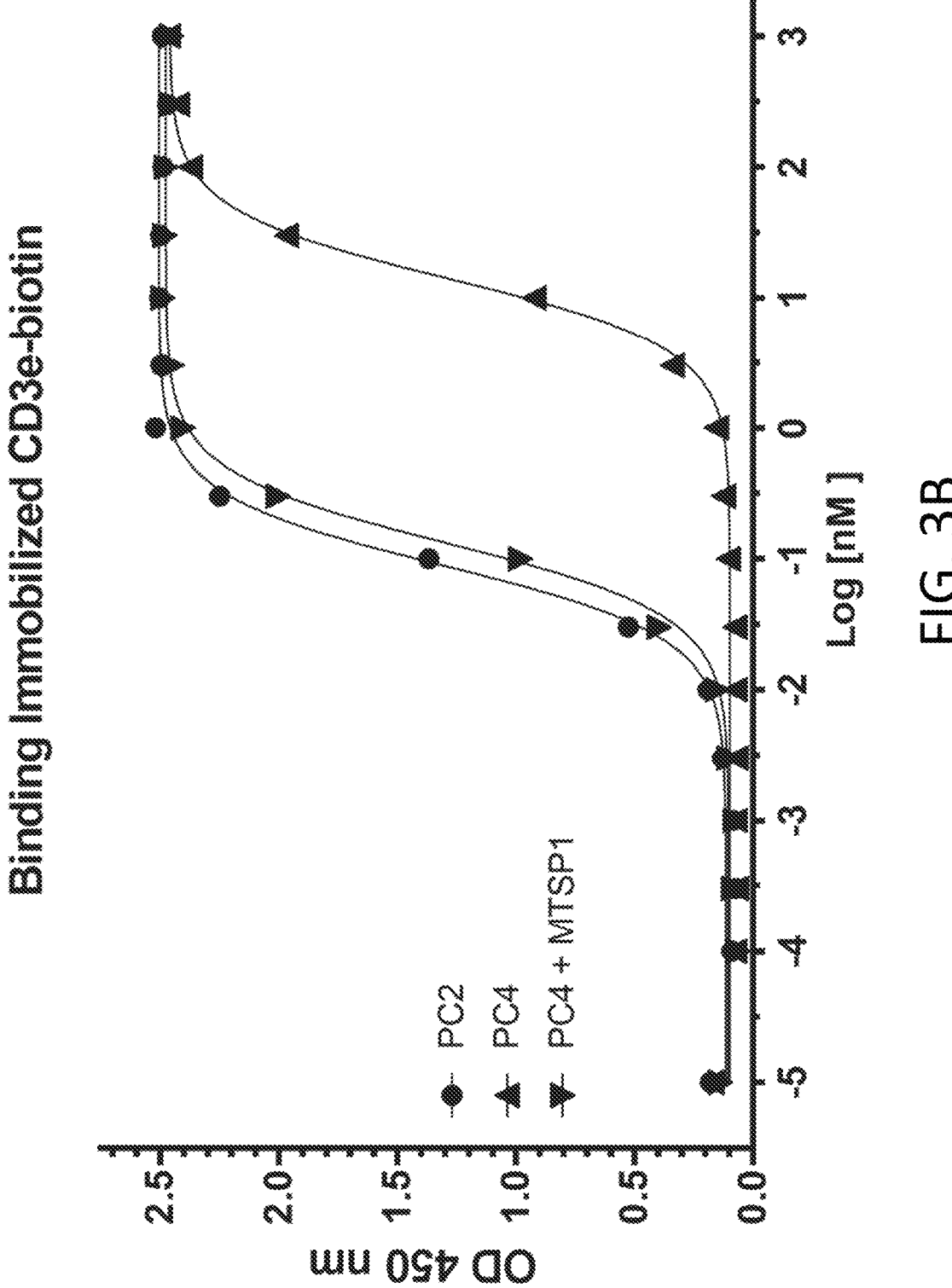
FIG. 3B illustrates titration data for CD3ε binding for several polypeptide complexes of this disclosure.
Figure 3C:
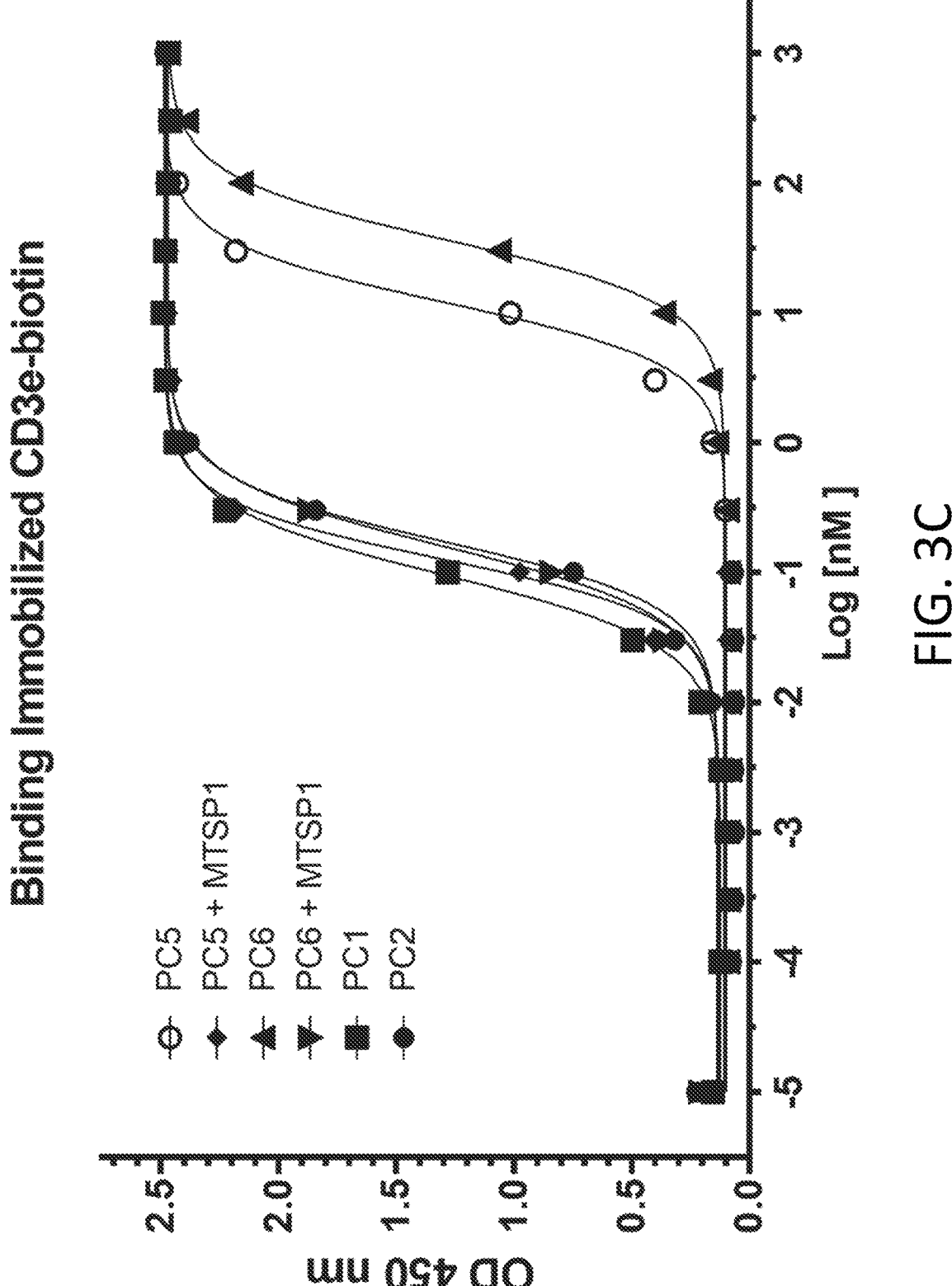
FIG. 3C illustrates titration data for CD3ε binding for several polypeptide complexes of this disclosure.

FIGS. 2A, 2B and 2C show representative PSMA binding ELISAs. This data is summarized in Table 8. FIGS. 3A, 3B and 3C show representative CD3 binding ELISAs. This data is summarized in Table 9. The masked polypeptide complex of PC3 has an EC50 about 8 fold higher than the protease treated PC3. The masked polypeptide complex of PC5 has an EC50 about 95 fold higher than the protease treated PC3. The masked polypeptide complexes of PC4 and PC6 had EC50s about 100 fold and about 230 fold higher than the respective protease treated polypeptide complexes.

TABLE 8

| PSMA binding | | |
|---|---|---|
| EC50 nM | Masked | Cleaved |
| PC1 | — | 2.68 |
| PC3 | 1.78 | 5.73 |
| PC5 | 5.67 | 5.65 |
| PC2 | — | 1.93 |
| PC4 | 2.88 | 2.40 |
| PC6 | 2.70 | 2.89 |

TABLE 9

| CD3 binding | | | |
|---|---|---|---|
| EC50 nM | Masked | Cleaved | Fold shift |
| PC1 | — | 0.08 | |
| PC3 | 0.5923 | 0.07384 | 8x |
| PC5 | 12.05 | 0.1266 | 95.2x |

TABLE 9-continued

| CD3 binding | | | |
|---|---|---|---|
| EC50 nM | Masked | Cleaved | Fold shift |
| PC2 | — | 0.10 | — |
| PC4 | 13.96 | 0.1313 | 106.3x |
| PC6 | 36.49 | 0.1593 | 229.1x |

Example 2: Polypeptide Complex Mediated Tumor Cytotoxicity and T Cell Activation Polypeptide complexes were evaluated in a functional in vitro tumor cell killing assay using the PSMA positive tumor cell lines 22Rv1 and LNCaP. Tumor cell killing was measured using a real time cell analyzer from Acea Biosciences that relies on sensor impedance measurements (cell index) that increased as tumor cells adhere, spread, and expand on the surface of the sensor. Likewise, as the tumor cells were killed the impedance decreased. 25,000 tumor cells were added per well and allowed to adhere overnight. The following day polypeptide complexes titrated in human serum supplemented medium along with 75,000 CD8+ T cells were added to the wells. Cell index measurements were taken every 10 minutes for an additional 96 hours. The cell index times number of hours (tumor cell growth kinetics) was then plotted versus concentration of polypeptide complex where the concentration required to reduce the tumor growth 50% (IC50) was calculated using Graphpad Prism.

Figure 4:
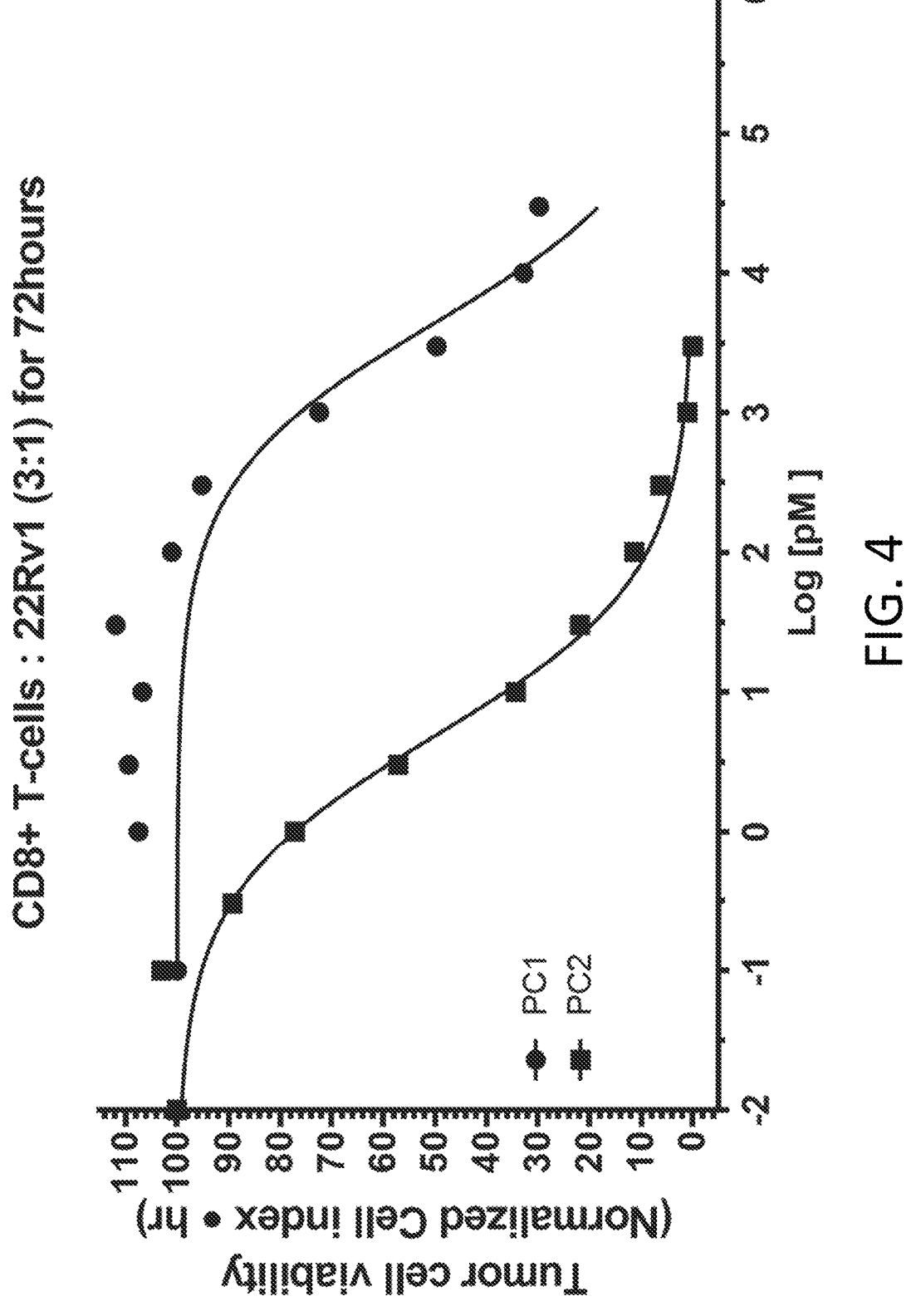
FIG. 4 illustrates cell viability data for 22Rv1 tumor cells treated with PC1 or PC2.
Figure 5A:
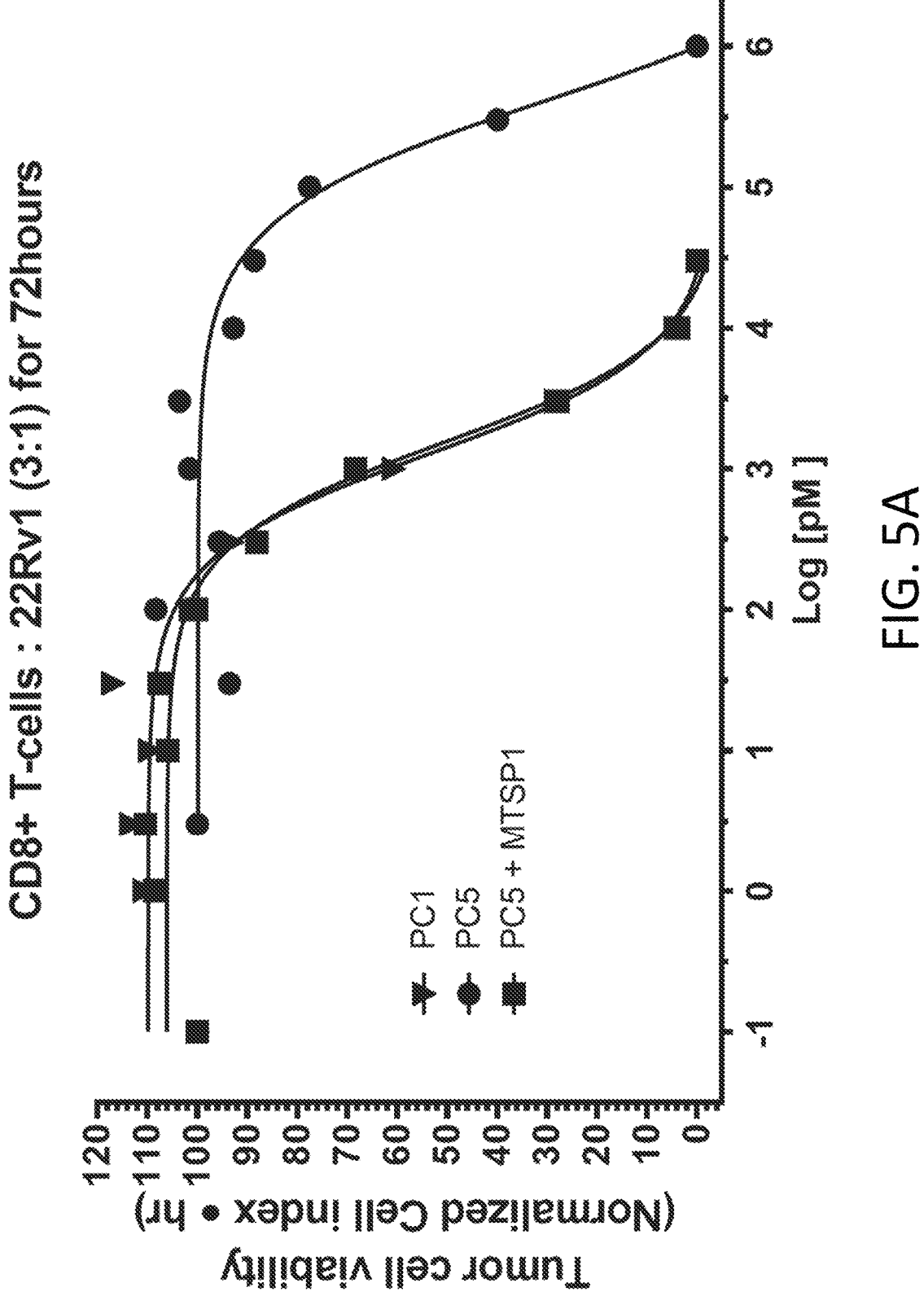
FIG. 5A illustrates cell viability data for 22Rv1 tumor cells treated with PC1, PC5 or MTSP1 treated PC5.
Figure 5B:
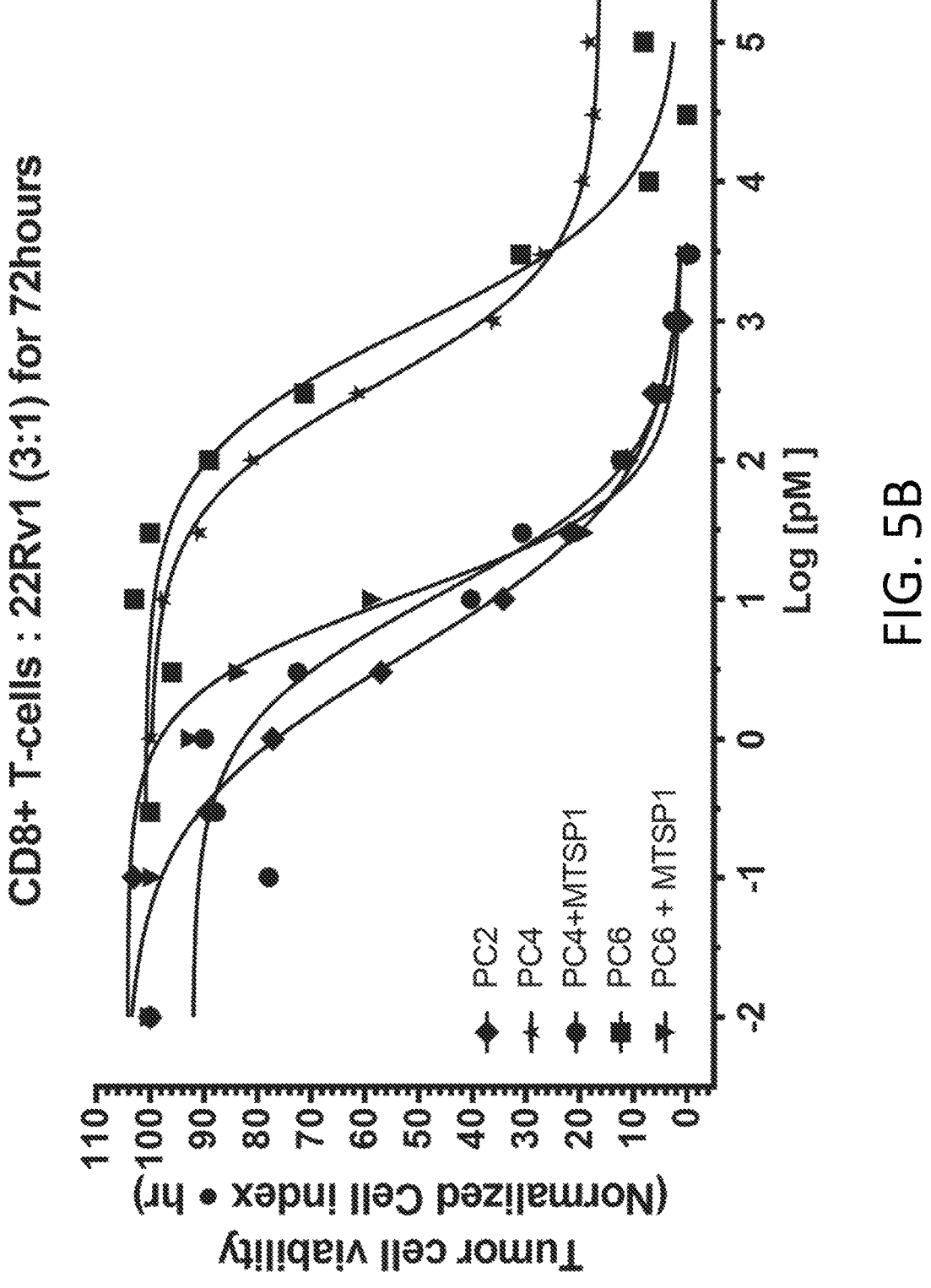
FIG. 5B illustrates cell viability data for 22Rv1 tumor cells treated with PC2, or PC4 or PC6 with and without MTSP1 treatment.

The 22Rv1 tumor cell line has a PSMA density of about 3000 copies per cell. FIG. 4 shows representative viability data for 22Rv1 treated with PC1 or PC2. This data is summarized in Table 10, and shows that PC2 is about 1000 times more potent than PC1. FIGS. 5A and 5B, and Tables 11 and 12, show viability data for 22Rv1 cells treated with masked or cleaved polypeptide complexes. The masked polypeptide complex of PC5 has an IC50 greater than 50 fold higher than the unmasked polypeptide complex of PC1, protease treatment reduced the IC50 to less than the IC50 of PC1. Similarly, the masked polypeptide complexes of PC4 and PC6 had IC50s about 150 and 200 fold higher than PC2 respectively, and protease treatment rescues both to about 1.7 and 2.5 fold higher than PC2.

Figure 6:
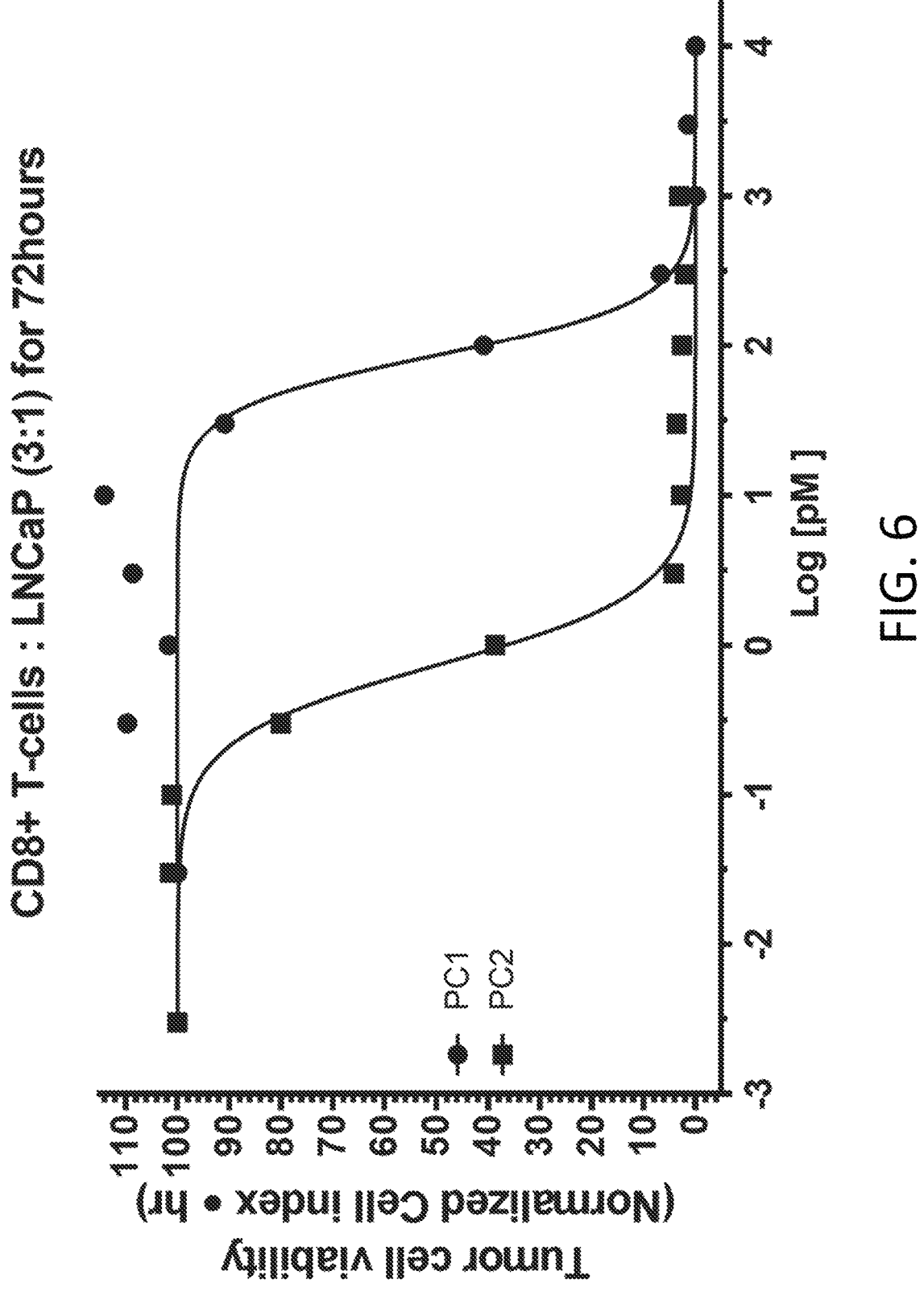
FIG. 6 illustrates cell viability data for LNCaP tumor cells treated with PC1 or PC2.
Figure 7:
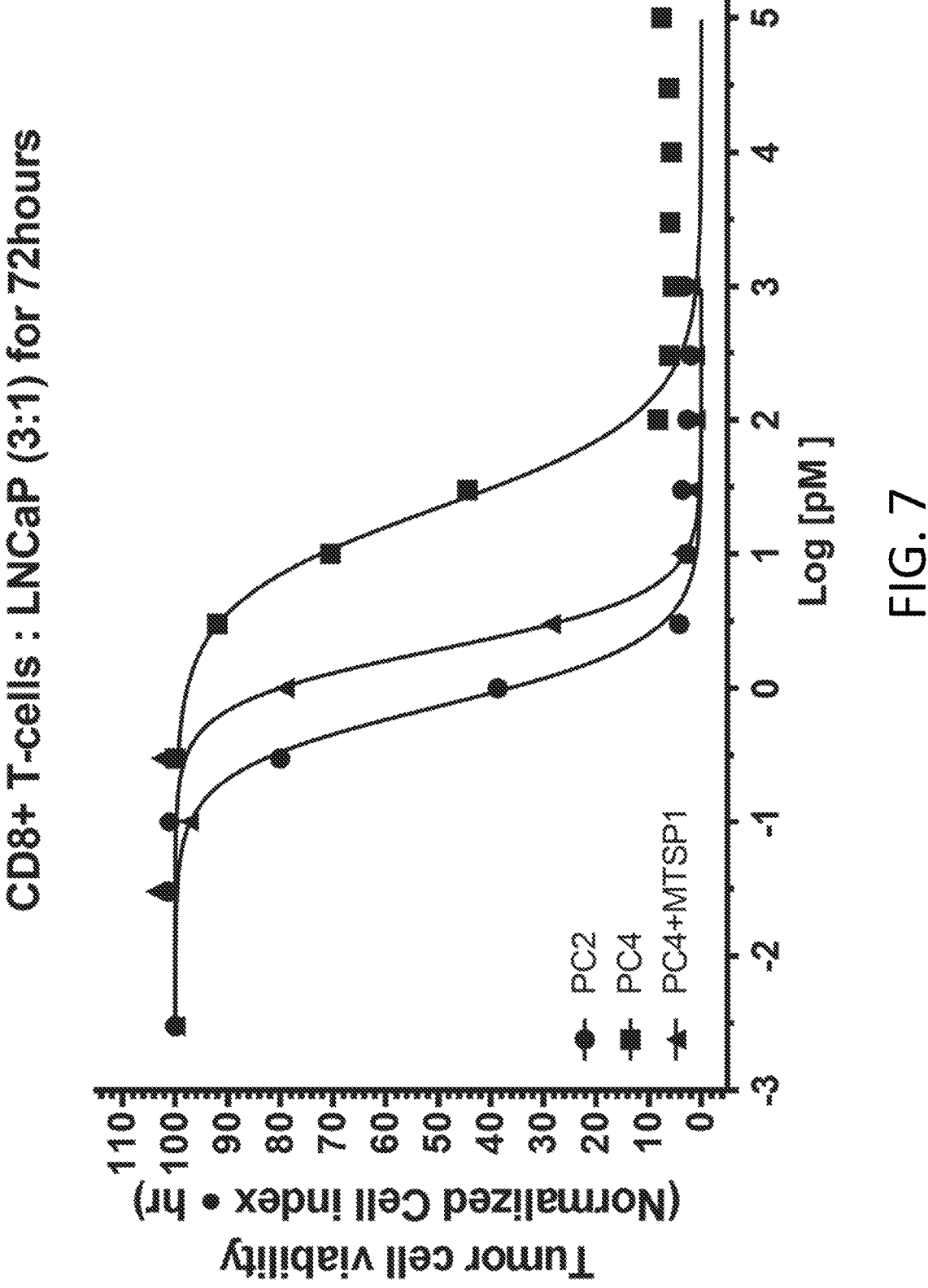
FIG. 7 illustrates cell viability data for LNCaP tumor cells treated with PC2, PC4 or MTSP1 treated PC4.

The LNCaP tumor cell line has a PSMA density of about 350,000 copies per cell. FIG. 6 shows representative viability data for LNCaP. This data is summarized in Table 13 and shows that PC2 is about 100 times more potent than PC1. FIG. 7, and Table 14 show viability data for LNCaP cells treated with masked or cleaved polypeptide complexes. The masked polypeptide complex of PC4 has an IC50 about 30 fold higher than the unmasked polypeptide complex of PC2, protease treatment rescues the IC50 to about 2.5 fold higher than the unmasked polypeptide complex.

TABLE 10

| 22Rv1 cell viability | | |
|---|---|---|
| 22Rv1 IC50 pM | PC1.01 | PC2.01 |
| 72 hr | 4409 | 4.831 |

TABLE 11

| 22Rv1 cell viability | | | |
|---|---|---|---|
| 22Rv1 72 hr | PC1 | PC5 | PC5+ MTSP1 |
| IC50 pM | 3,916 | 212810 | 1591 |
| Fold shift | 1x | 54.3x | 0.4x |

TABLE 12

| 22Rv1 cell viability | | | | | |
|---|---|---|---|---|---|
| 22Rv1 72 hr | PC2 | PC4 | PC4+ MTSP1 | PC6 | PC6+ MTSP1 |
| IC50 pM | 4.831 | 757.3 | 8.169 | 984.9 | 12.03 |
| Fold shift | 1x | 156.8x | 1.7x | 203.9x | 2.5x |

TABLE 13

| LNCaP cell viability | | |
|---|---|---|
| LNCaP IC50 pM | PC1 | PC2 |
| 72 hr | 85.97 | 0.73 |

TABLE 14

| LNCaP cell viability | | |
|---|---|---|
| LNCaP IC50 pM | PC2 | PC4+ MTSP1 | PC4 |
| 72 hr | 0.73 (1x) | 1.94 (2.65x) | 22.1 (30.2x) |

Example 3: Polypeptide Complex Mediated Tumor Cell Killing

Figure 8A:
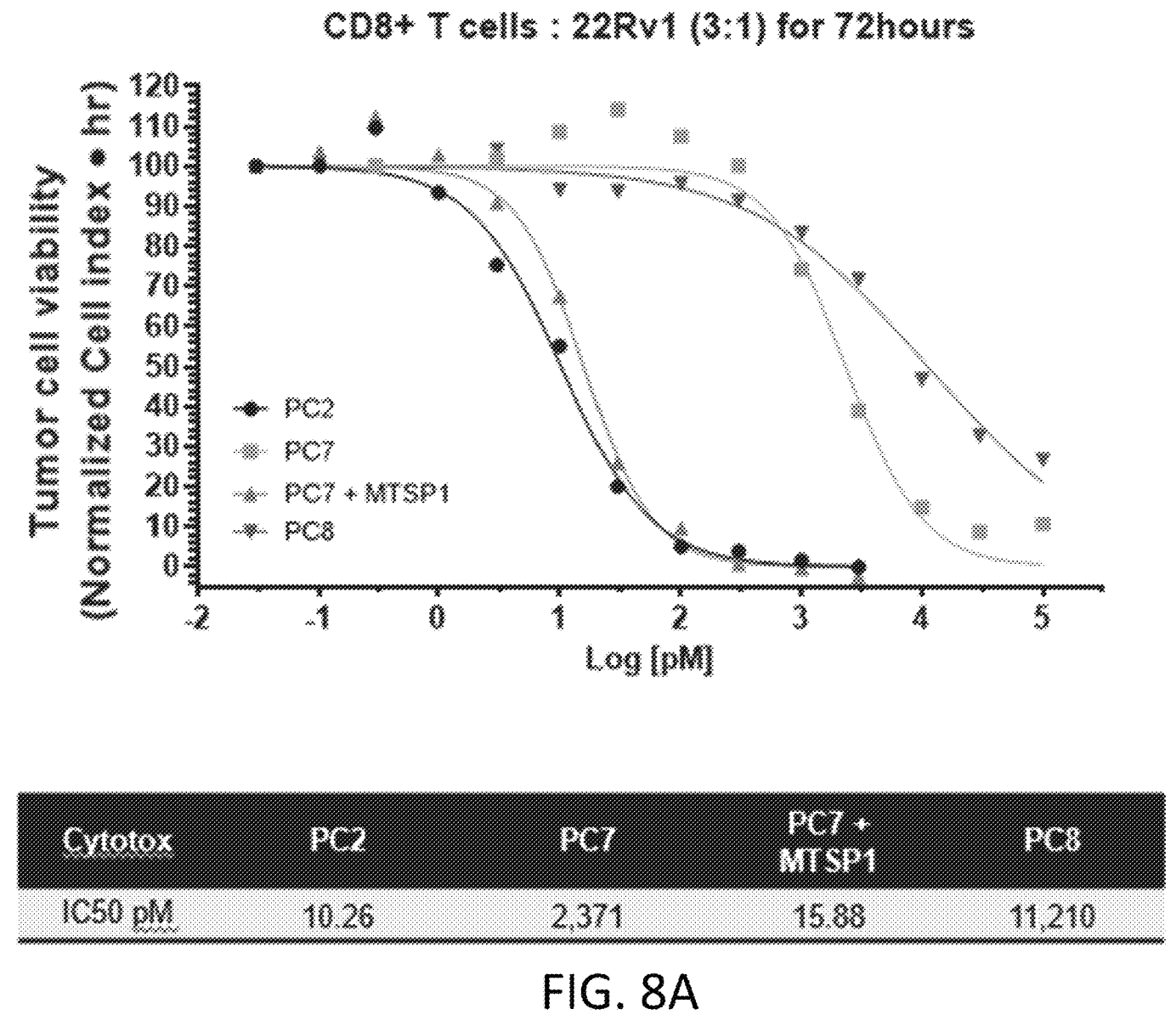
Figure 8B:
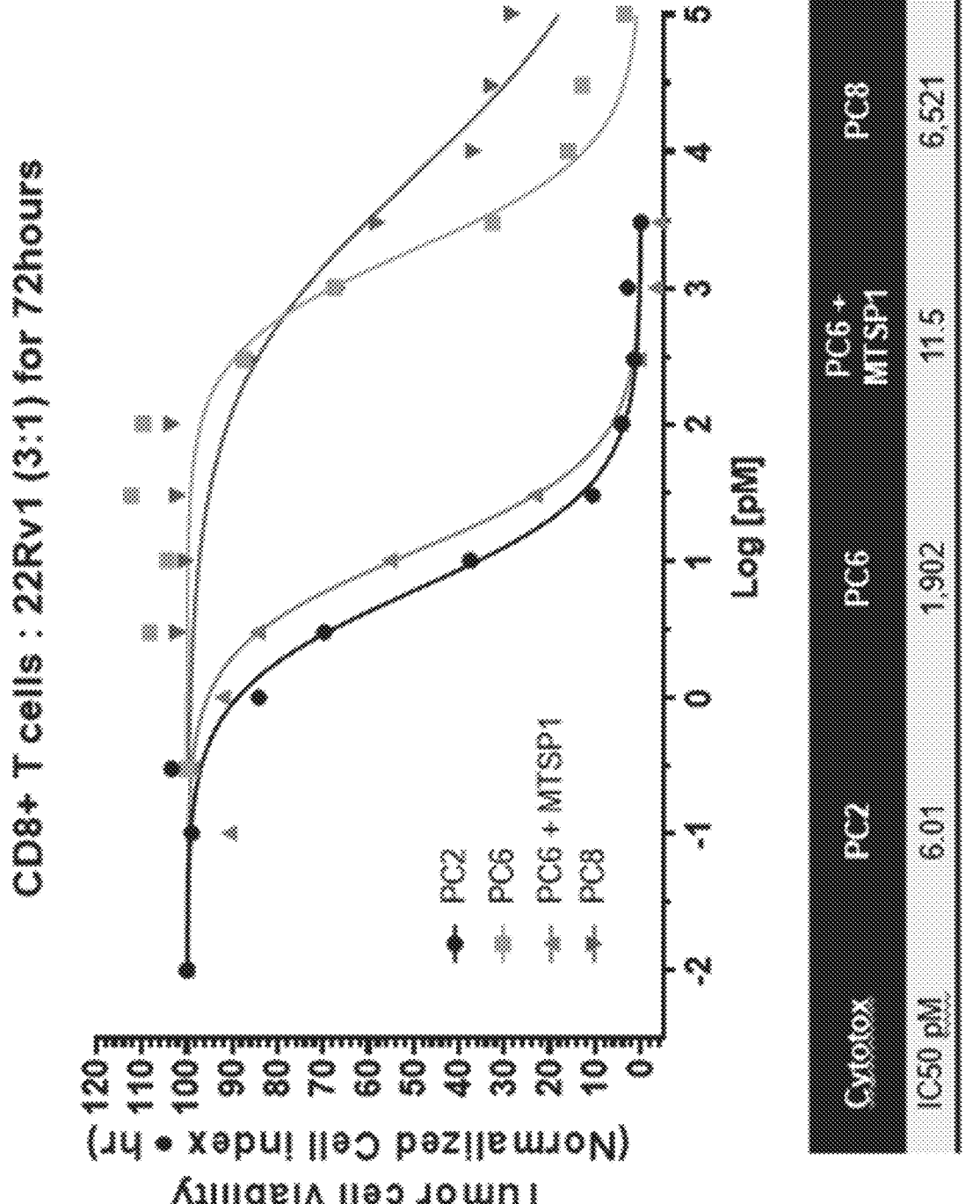

Polypeptide complexes were evaluated in a functional in vitro tumor cell killing assay using the PSMA positive tumor cell lines 22Rv1. Tumor cell killing was measured using an xCelligence real time cell analyzer from Agilent that relies on sensor impedance measurements (cell index) that increased as tumor cells adhere, spread, and expand on the surface of the sensor. Likewise, as the tumor cells were killed the impedance decreased. 10,000 tumor cells were added per well and allowed to adhere overnight on a 96 well E-Plate. The following day polypeptide complexes titrated in human serum supplemented medium along with 30,000 CD8+ T cells were added to the wells. Cell index measurements were taken every 10 minutes for an additional 72 hours. The cell index times number of hours (tumor cell growth kinetics) was then plotted versus concentration of polypeptide complex where the concentration required to reduce the tumor growth 50% (IC50) was calculated using Graphpad Prism software. Data is seen in FIGS. 8A-8B.

Example 4: Polypeptide Complex Pharmacokinetics in Cynomolgus Monkey

Figure 9A:
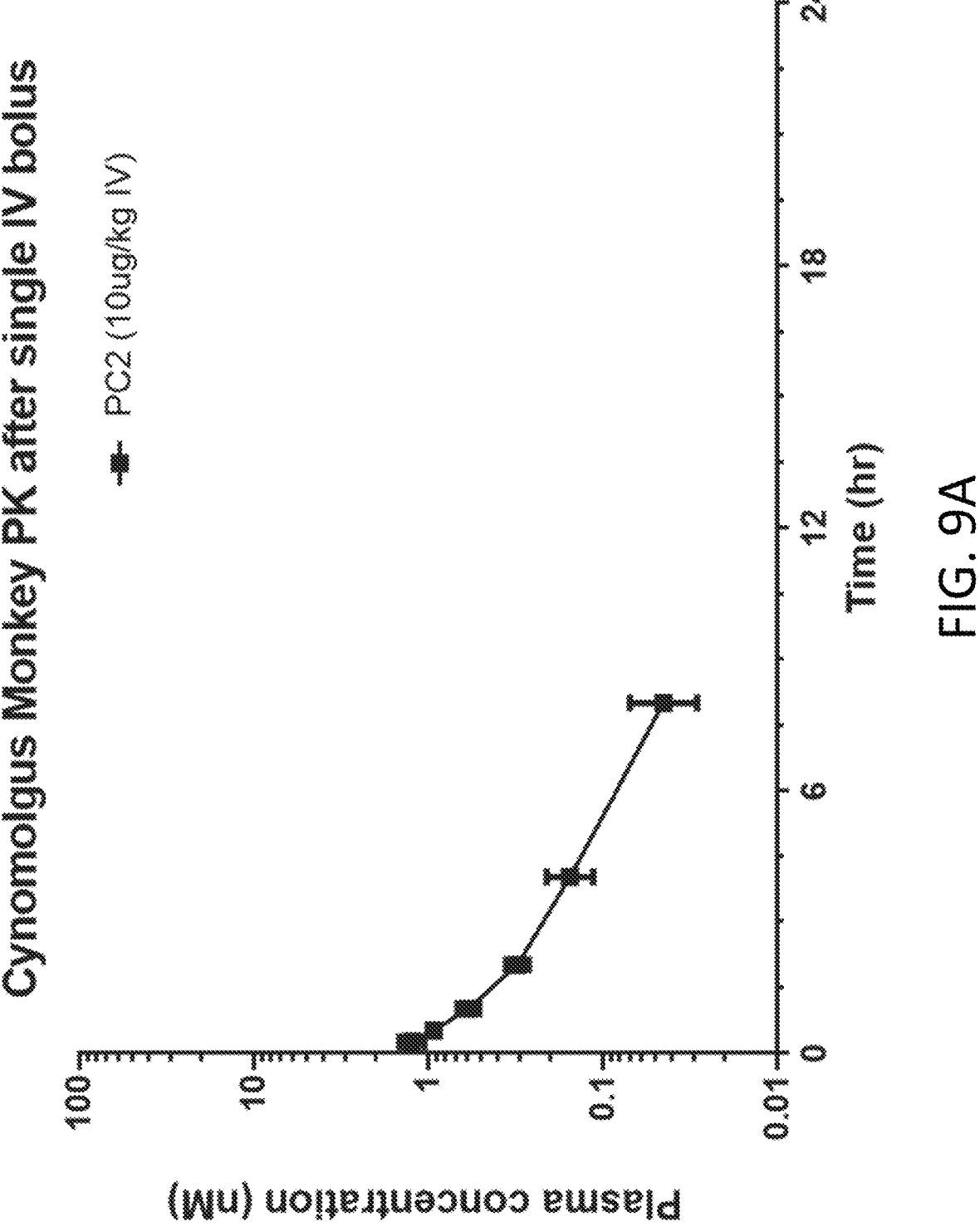
FIG. 9A illustrates polypeptide (PSMA TCEs) pharmacokinetics in cynomolgus monkeys after a single IV bolus injection.
Figure 9B:
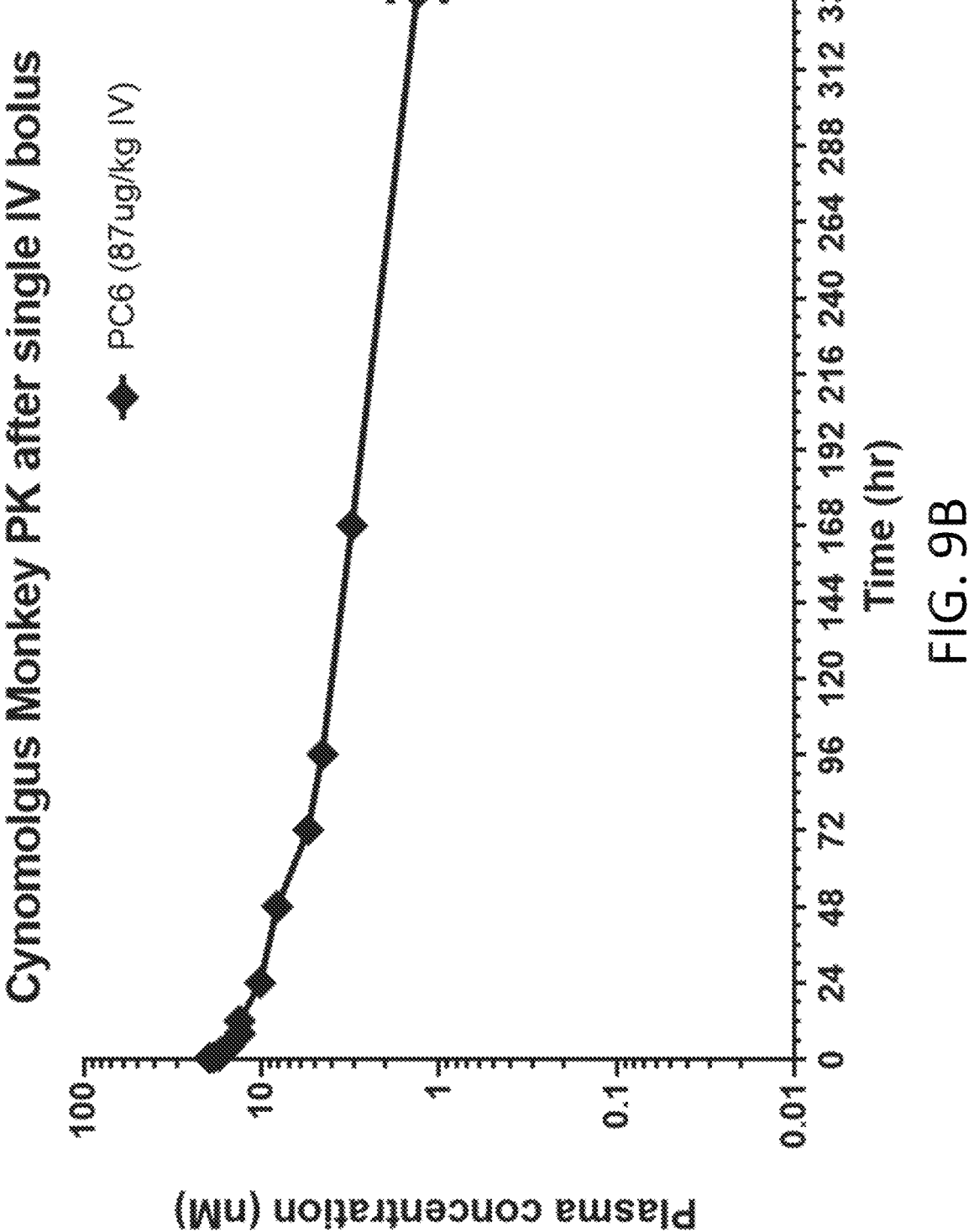
FIG. 9B illustrates polypeptide (PSMA TRACTrs) pharmacokinetics in cynomolgus monkeys after a single IV bolus injection.

Pharmacokinetics and exploratory safety of polypeptide molecules were evaluated in cynomolgus monkeys. Briefly, cynomolgus monkeys of approximately 3 kg bodyweight were administered polypeptides as an IV bolus and observed daily for signs of adverse events. No in-life adverse events were observed. After dosing, blood was collected in K2 EDTA tubes at specific timepoints and processed to plasma. Plasma was stored frozen until analysis. Concentration of polypeptide molecules in plasma was measured via standard ELISA techniques relative to a reference standard diluted in control cyno plasma. Plasma concentration curves were fit to a standard two phase exponential equation representing distribution and elimination phases. Fitting of pharmacokinetics enabled the calculation of Cmax, half-life, volume of distribution, clearance, and 7 day area under the curve (AUC) shown in Table 15 for PSMA TCE polypeptide complexes and Table 16 for PSMA TRACTr polypeptide complexes. Data is seen in FIGS. 9A-9B. Measured pharmacokinetics in cyno support once weekly dosing in humans.

TABLE 15

| PSMA TCE | | |
| --- | --- | --- |
| | PC2 10 ug/kg | Units |
| $C_{MAX}$ | 1.69 | nM |
| $t_{1/2}$ | 2.17 | hr |
| Vd | 0.23 | L |
| VSS | 0.67 | L |
| CL | 24.49 | mL/hr/kg |
| BW | 3.00 | kg |
| 7 day AUC | 141 | nM · min |

TABLE 16

| PSMA TRACTr | | |
| --- | --- | --- |
| | PC6 87 ug/kg | Units |
| $C_{MAX}$ | 17.90 | nM |
| $t_{1/2}$ | 118.99 | hr |
| Vd | 0.18 | L |
| VSS | 0.35 | L |
| CL | 0.34 | mL/hr/kg |
| BW | 3.00 | kg |
| 7 day AUC | 63,731 | nM · min |

Example 5: Polypeptide Complexes in Cynomolgus Cytokine Release

Figure 10A:
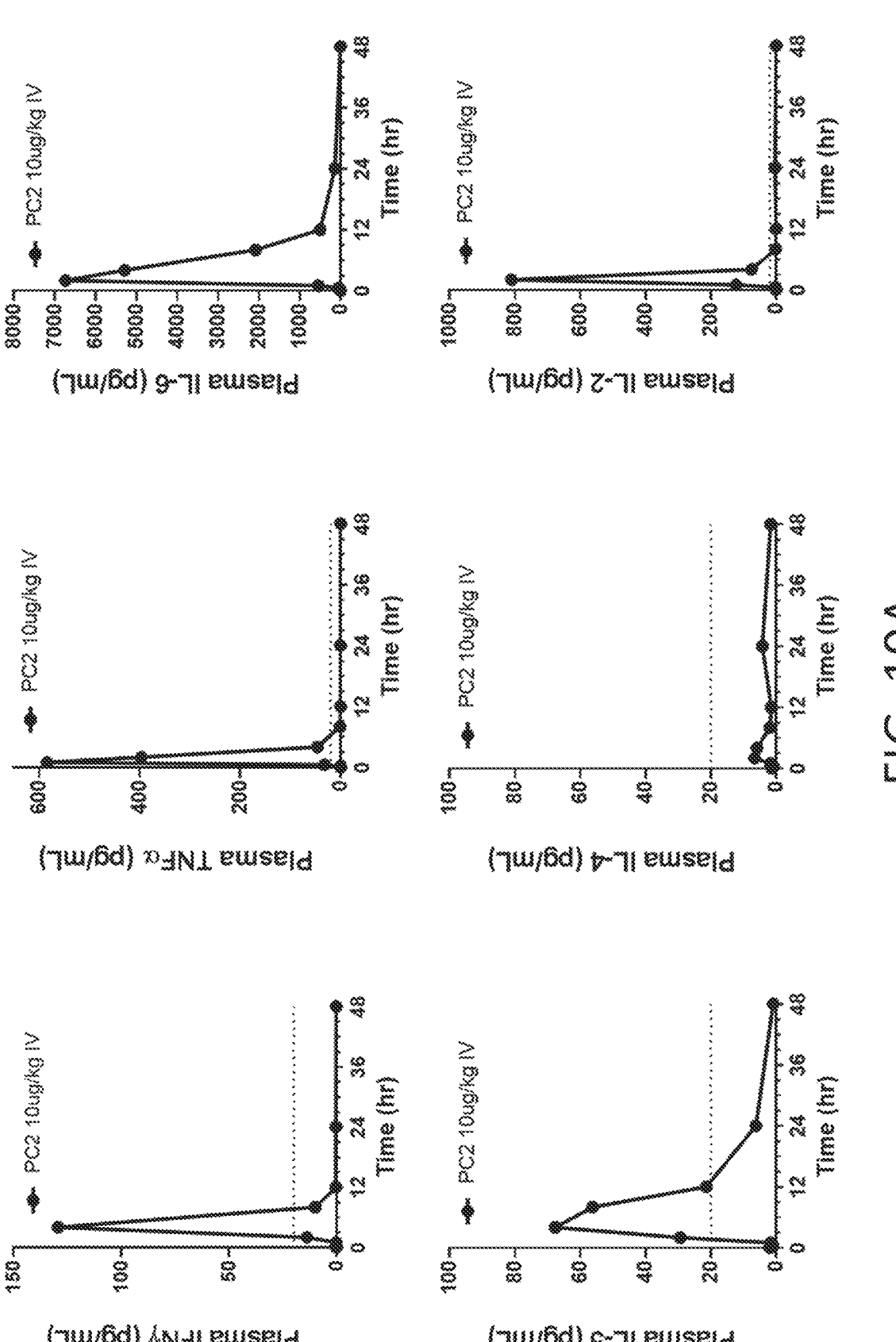
FIG. 10A illustrates cytokine release in cynomolgus monkeys after single IV bolus of PSMA TCE.
Figure 10B:
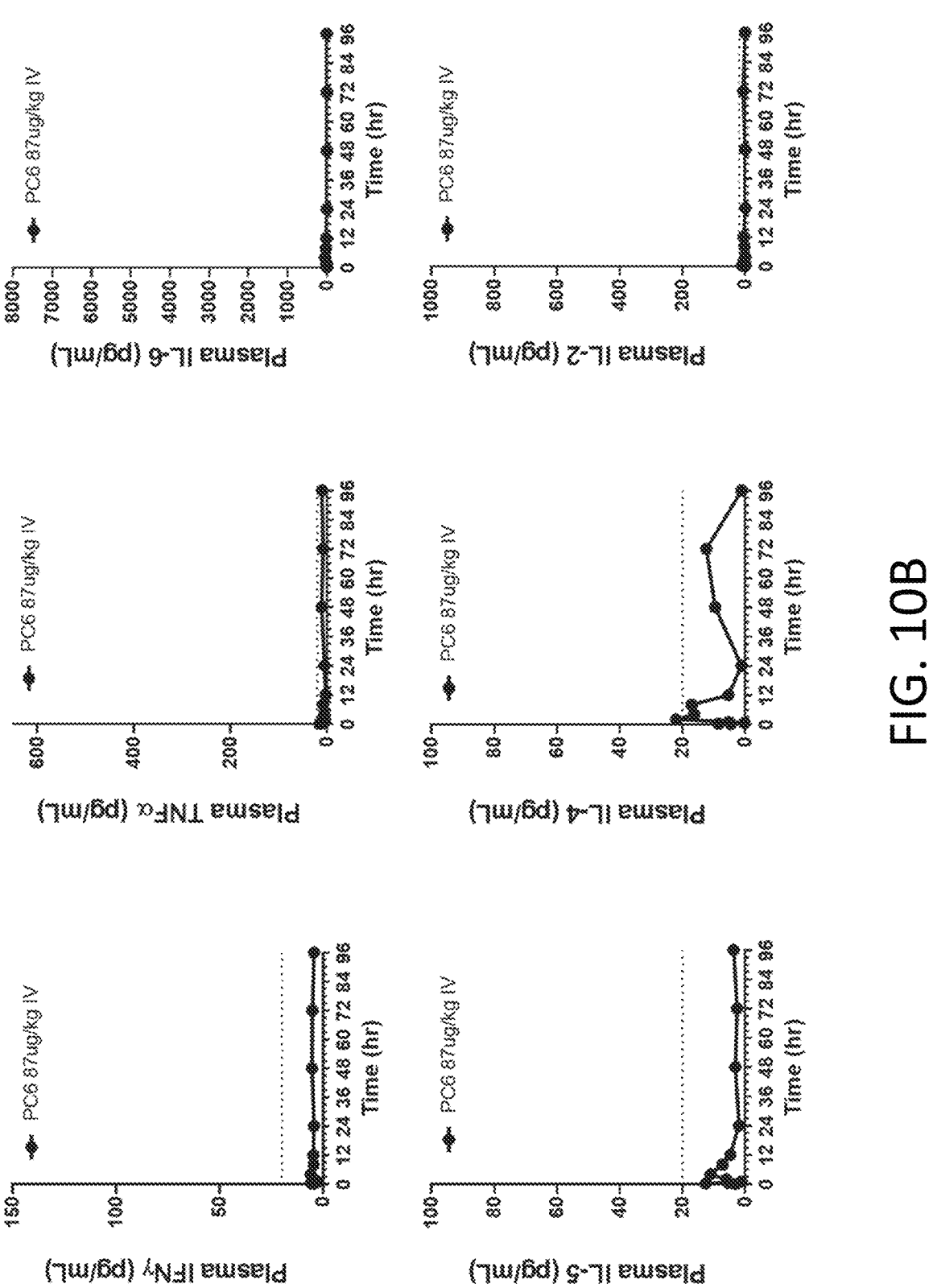
FIG. 10B illustrates cytokine release in cynomolgus monkeys after single IV bolus of PSMA polypeptide TRACTr complex.
Figure 10C:
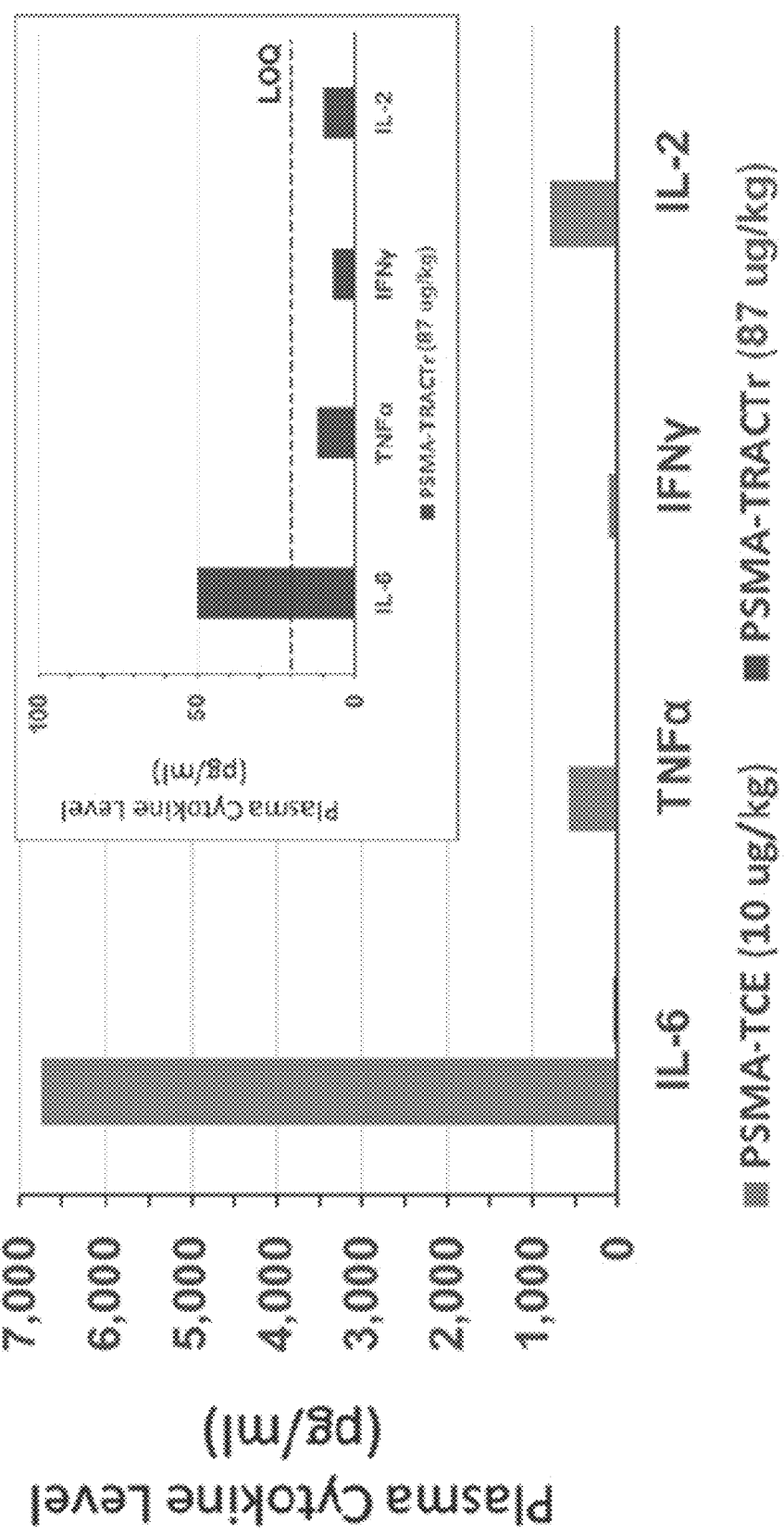
FIG. 10C illustrates cytokine release in cynomolgus monkeys using PSMA TCE versus PSMA TRACTRs.

Cytokine release after polypeptide molecule administration by IV bolus was evaluated in cynomolgus monkeys. Briefly, cynomolgus monkeys of approximately 3 kg bodyweight were administered polypeptides as an IV bolus and observed daily for signs of adverse events. No in-life adverse events were observed. After dosing, blood was collected in K2 EDTA tubes at specific timepoints and processed to plasma. Plasma was stored frozen until analysis. Plasma samples were analyzed for cytokines using a non-human primate cytometric Th1/Th2 bead array kit from BD biosciences following the manufacturer's instructions. Interferon gamma, tumor necrosis factor alpha, interleukin 6, interleukin 5, interleukin 4, and interleukin 2 levels in plasma were calculated relative to reference standards provided with the bead array kit. Data is seen in FIGS. 10A-10C.

Example 6: Polypeptide Complexes in Cynomolgus Toxicity

Figure 11A:
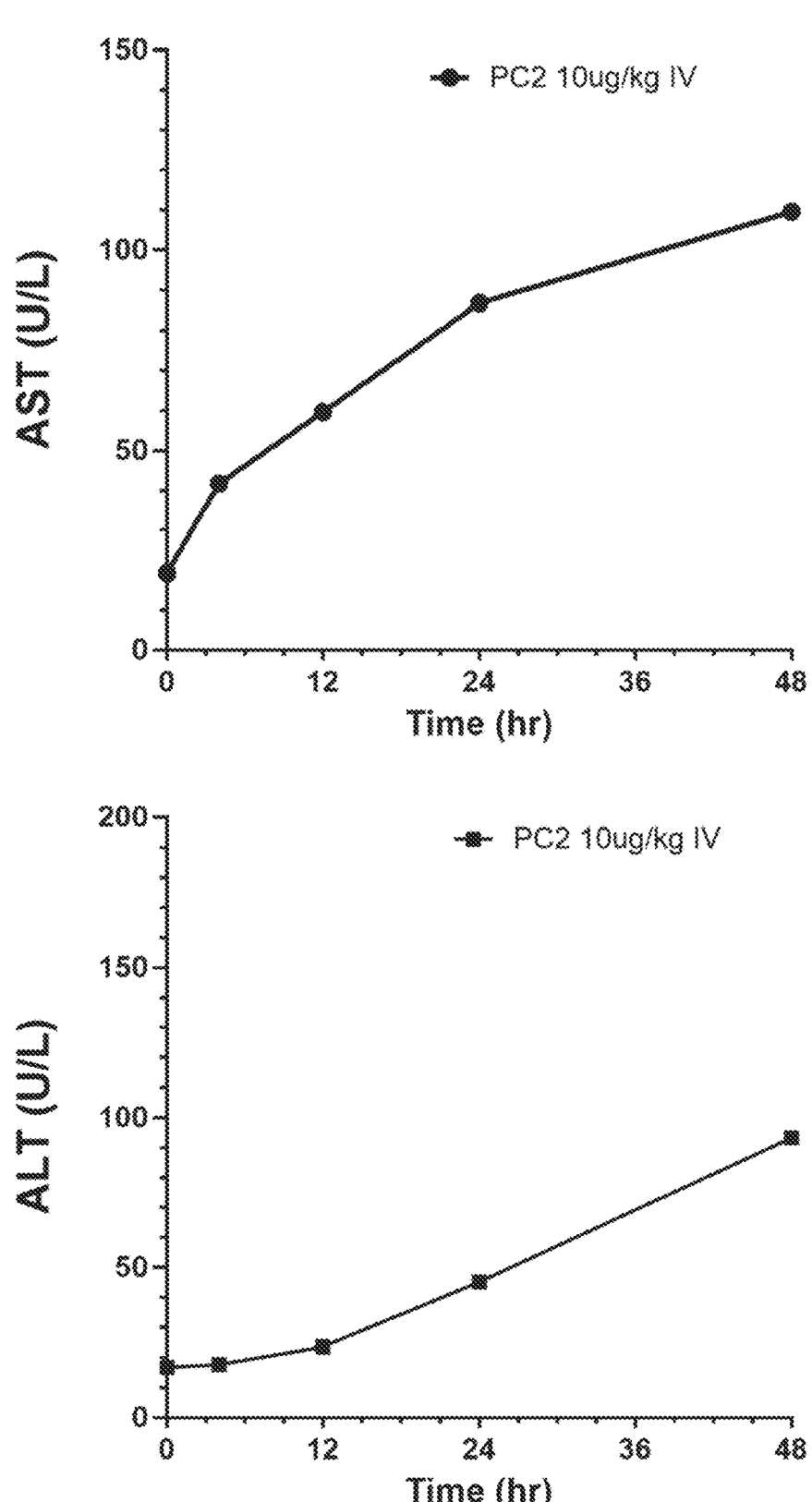
FIG. 11A illustrates serum liver enzymes in cynomolgus monkeys after single IV bolus of PSMA TCE.
Figure 11B:
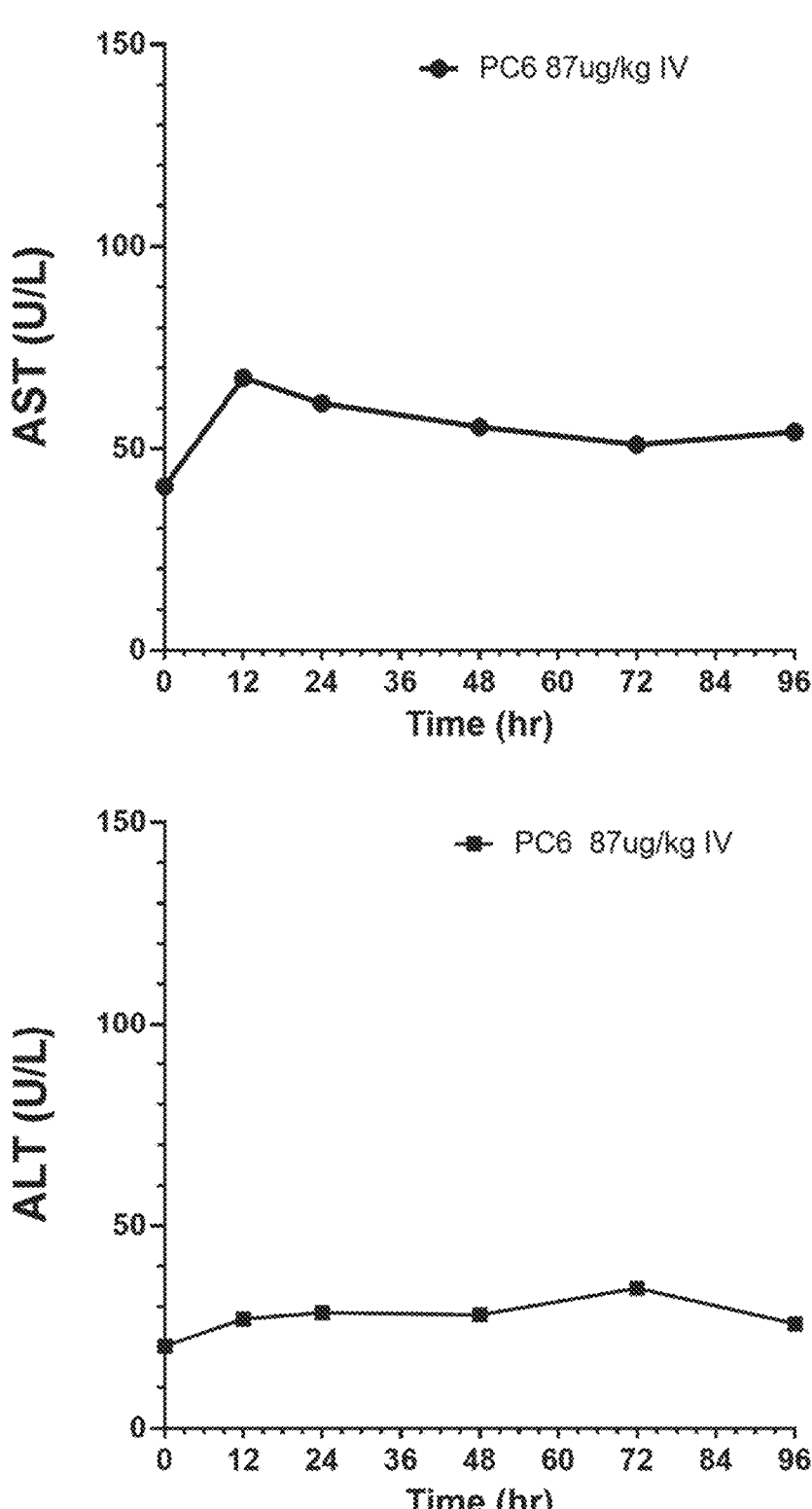
FIG. 11B illustrates serum liver enzymes in cynomolgus monkeys after single IV bolus of PSMA polypeptide TRACTr complex.

Systemic liver enzymes after polypeptide molecule administration by IV bolus was evaluated in cynomolgus monkeys. Briefly, cynomolgus monkeys of approximately 3 kg bodyweight were administered polypeptides as an IV bolus and observed daily for signs of adverse events. No in-life adverse events were observed. After dosing, blood was collected in K2 EDTA tubes at specific timepoints and processed to plasma. Plasma was stored frozen until analysis. Plasma samples were analyzed for the presence of liver enzymes aspartate transaminase (AST) and alanine aminotransferase (ALT) as signs of potential liver toxicity. AST and ALT levels remained within the normal ranges for all timepoints tested after dosing suggesting a lack of liver toxicity. AST and ALT were quantified following the instructions provided in a commercially available kit from Millipore. AST and ALT levels were calculated according to manufacturer's instructions relative to a positive control reference standard. Data is seen in FIGS. 11A-11B.

Example 7: Optimized Phage Library Construction—CD3 scFv Peptides

Sequence activity relationships (SAR) were established for Peptide-A and Peptide-B by mutating each individual residue within the peptide to alanine and measuring binding and inhibition against SP34.185 scFv. Peptide residues whose alanine mutations significantly weakened binding and inhibition can be considered critical residues where mutations were not tolerated. Peptide residues whose alanine mutations performed similarly to the non-mutated sequence can be considered non-critical sites where mutations were indeed tolerated. Using the peptide SAR, DNA oligo libraries were constructed where codons encoding critical residues within each peptide sequence were minimally mutated and codons encoding non-critical residues were heavily mutated. The resulting oligos were cloned into bacteriophage vectors used to display the SAR guided peptides via fusion to the pIII filament of the bacteriophage. The relevant vectors were then used to produce the phage optimization libraries via amplification in bacteria using standard techniques in the field.

Peptides were evaluated for their ability to bind SP34.185 scFv by standard enzyme linked immunosorbent assays (ELISAs). Briefly, biotinylated peptides were captured on neutravidin coated plates, quenched with biocytin followed by a washing step. SP34.185 scFv was then titrated onto the peptide captured plates. Plates were then washed and bound SP34.185 scFv was detected using a secondary horse radish peroxidase antibody conjugate. After washing again, plates were developed using standard ELISA techniques and stopped using acid. The concentration of SP34.185 scFv required to achieve 50% maximal signal or EC50 was calculated using Graphpad prism. Data is shown in FIGS. 12A-12F and summarized in Tables 17A-17D. Peptide Sequences of CD3 Ala Scan Peptides for Peptide A and Peptide-B are shown in Table 19.

TABLE 17A

Figure 12A:
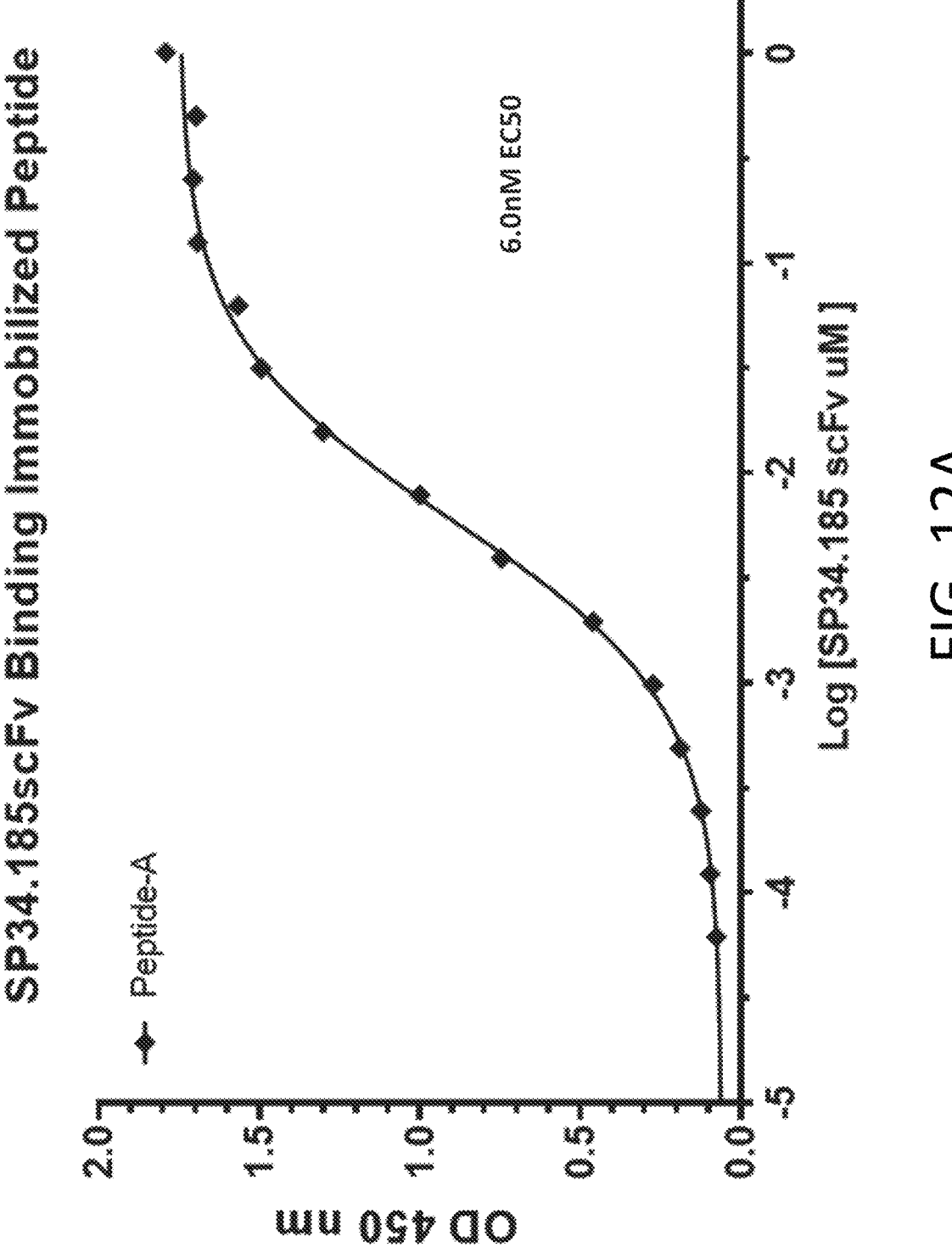
Figure 12B:
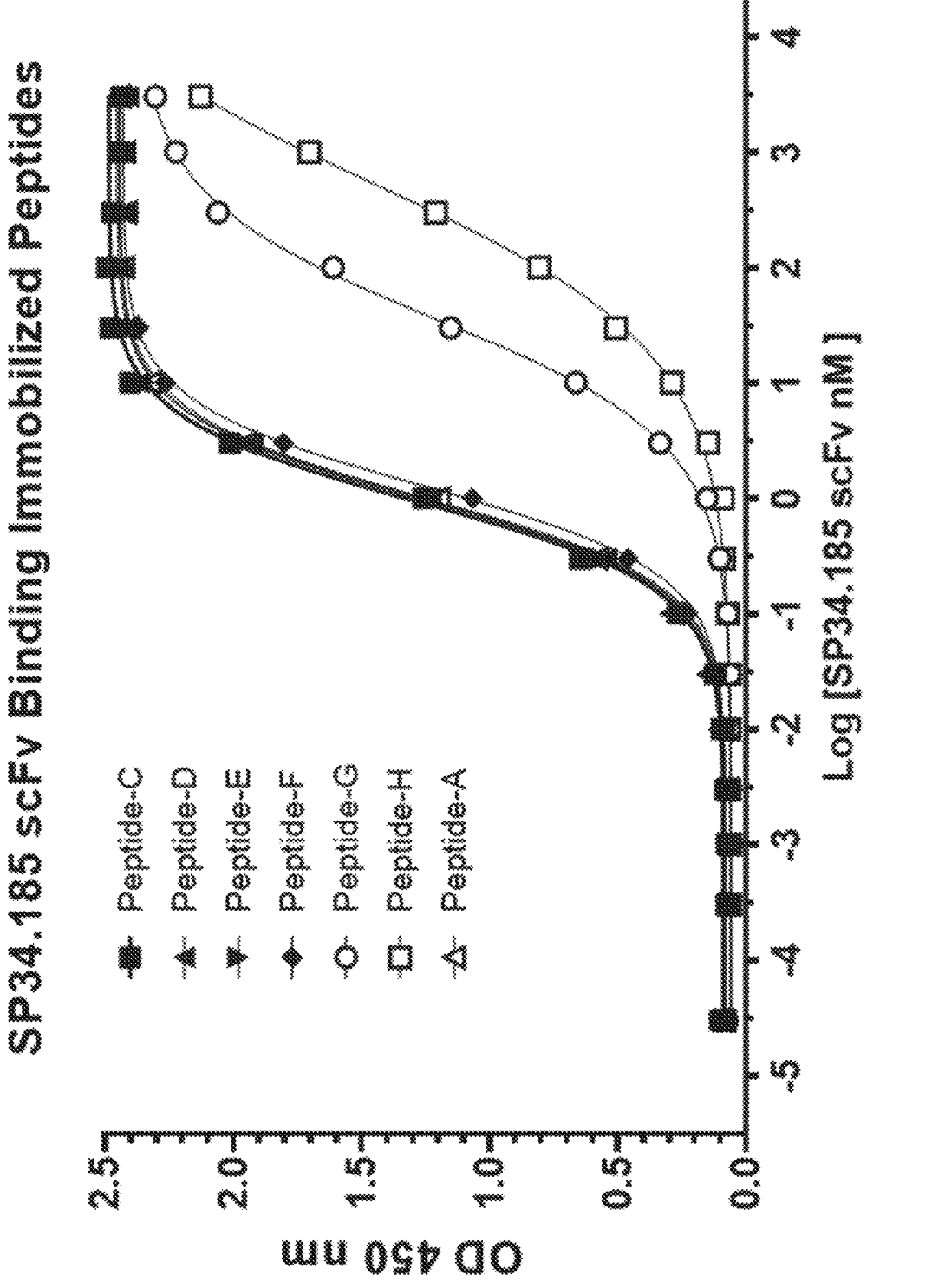

| ELISA | Peptide-A | Peptide-C | Peptide-D | Peptide-E | Peptide-F | Peptide-G | Peptide-H |
|---|---|---|---|---|---|---|---|
| | | | Summary of FIG. 12B | | | | |
| EC50 nM | 1.013 | 0.9429 | 1.018 | 0.9738 | 1.27 | 47.5 | 346.2 |

TABLE 17B

Figure 12C:
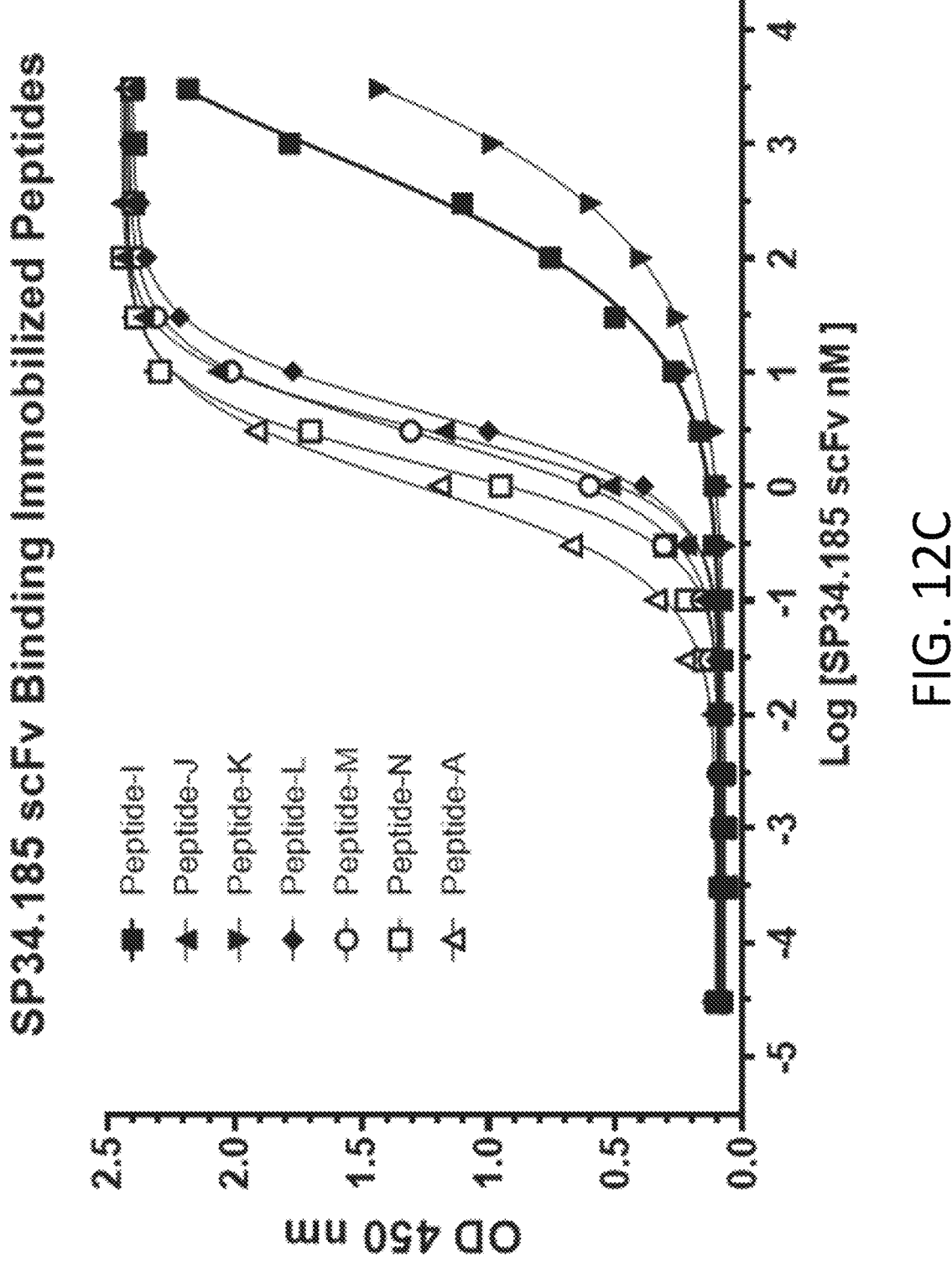
Figure 12D:
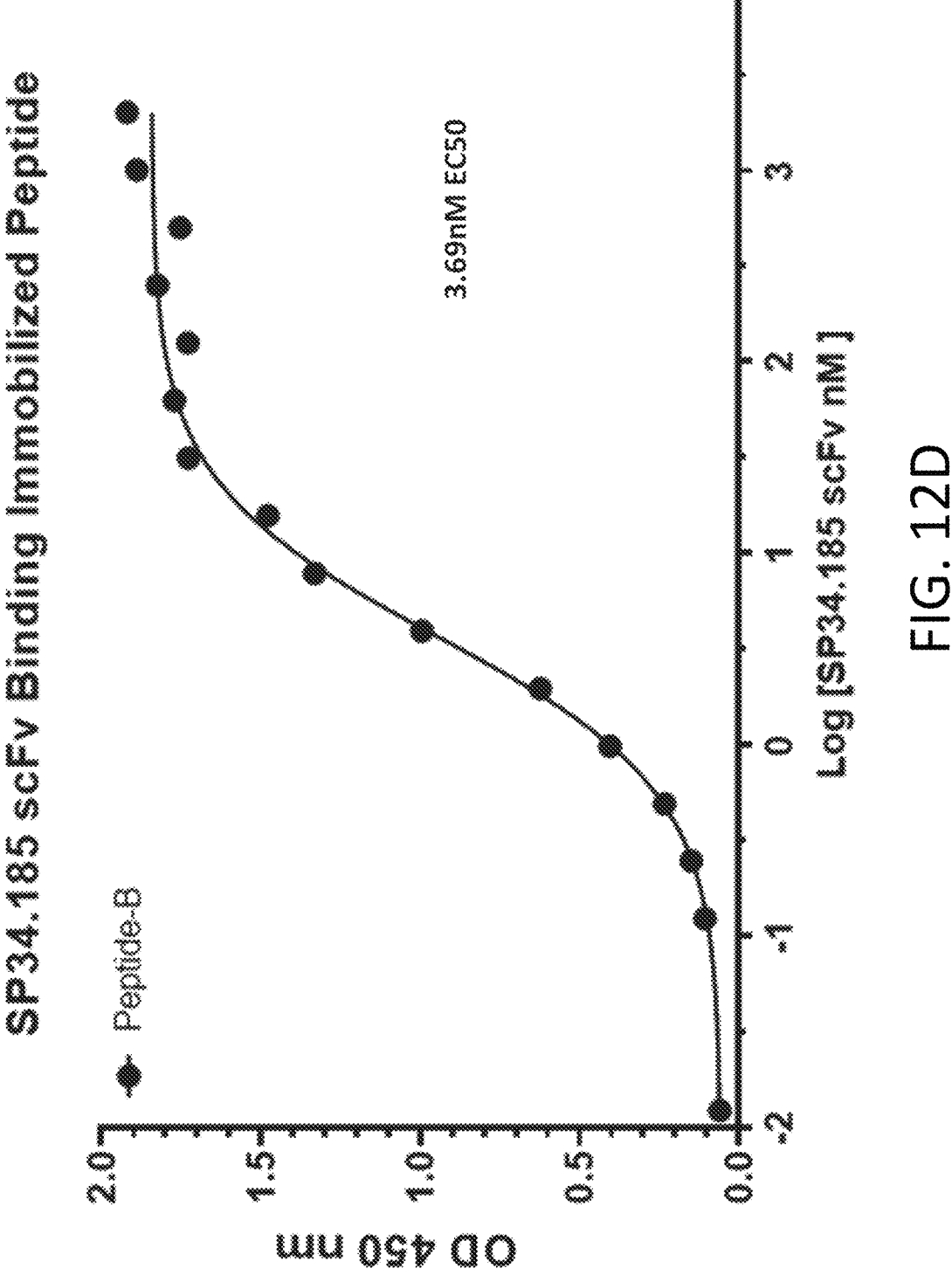

| ELISA | Peptide-A | Peptide-I | Peptide-J | Peptide-K | Peptide-L | Peptide-M | Peptide-N |
|---|---|---|---|---|---|---|---|
| | | | Summary of FIG. 12C | | | | |
| EC50 nM | 0.986 | 310.8 | 3.134 | 1,960 | 4.363 | 2.76 | 1.546 |

TABLE 17C

Figure 12E:
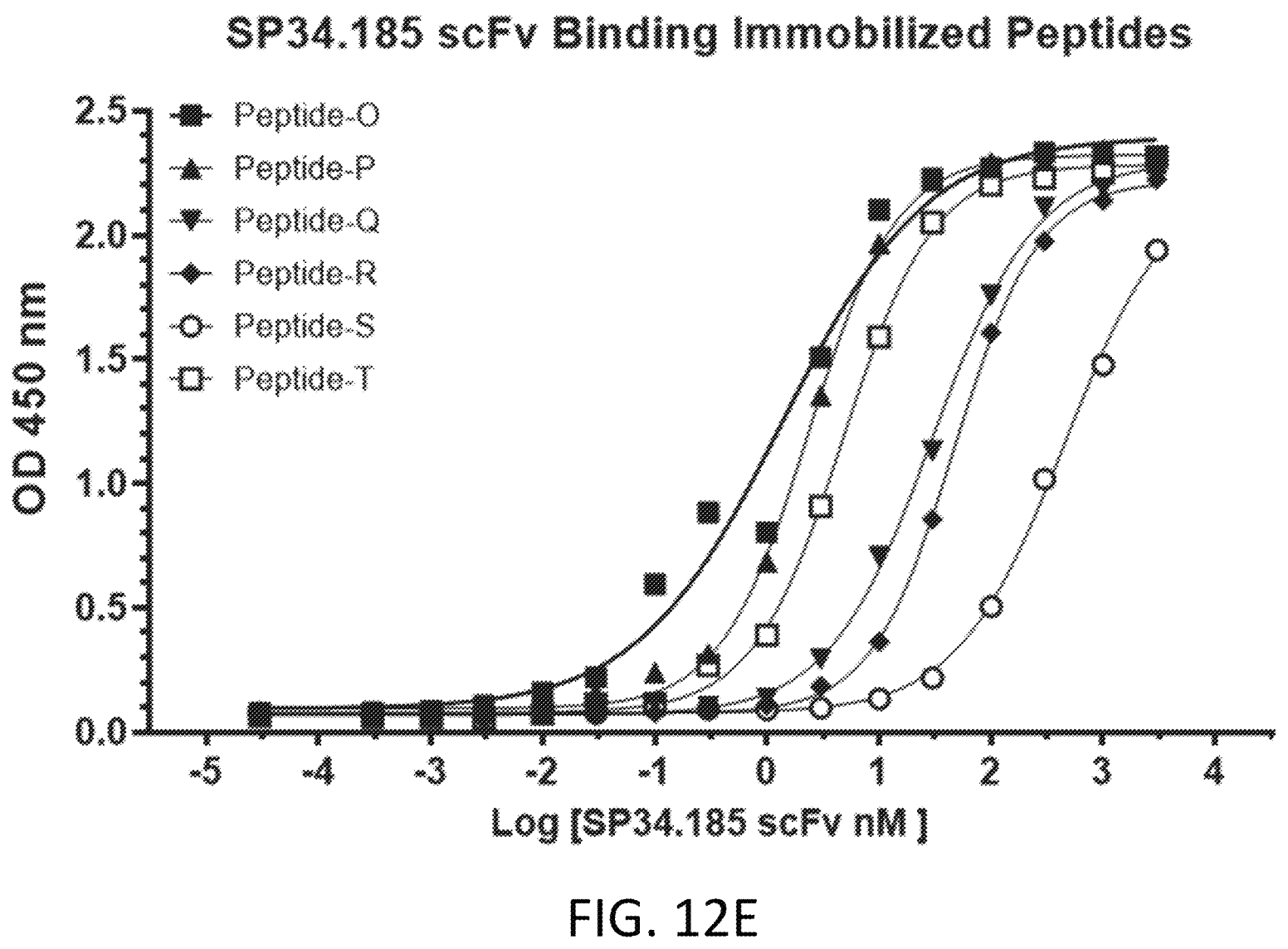

| ELISA | Peptide-O | Peptide-P | Peptide-Q | Peptide-R | Peptide-S | Peptide-T |
|---|---|---|---|---|---|---|
| | | | Summary of FIG. 12E | | | |
| EC50 nM | 1.356 | 2.359 | 30.04 | 47.50 | 457.1 | 4.762 |

TABLE 17D

Figure 12F:
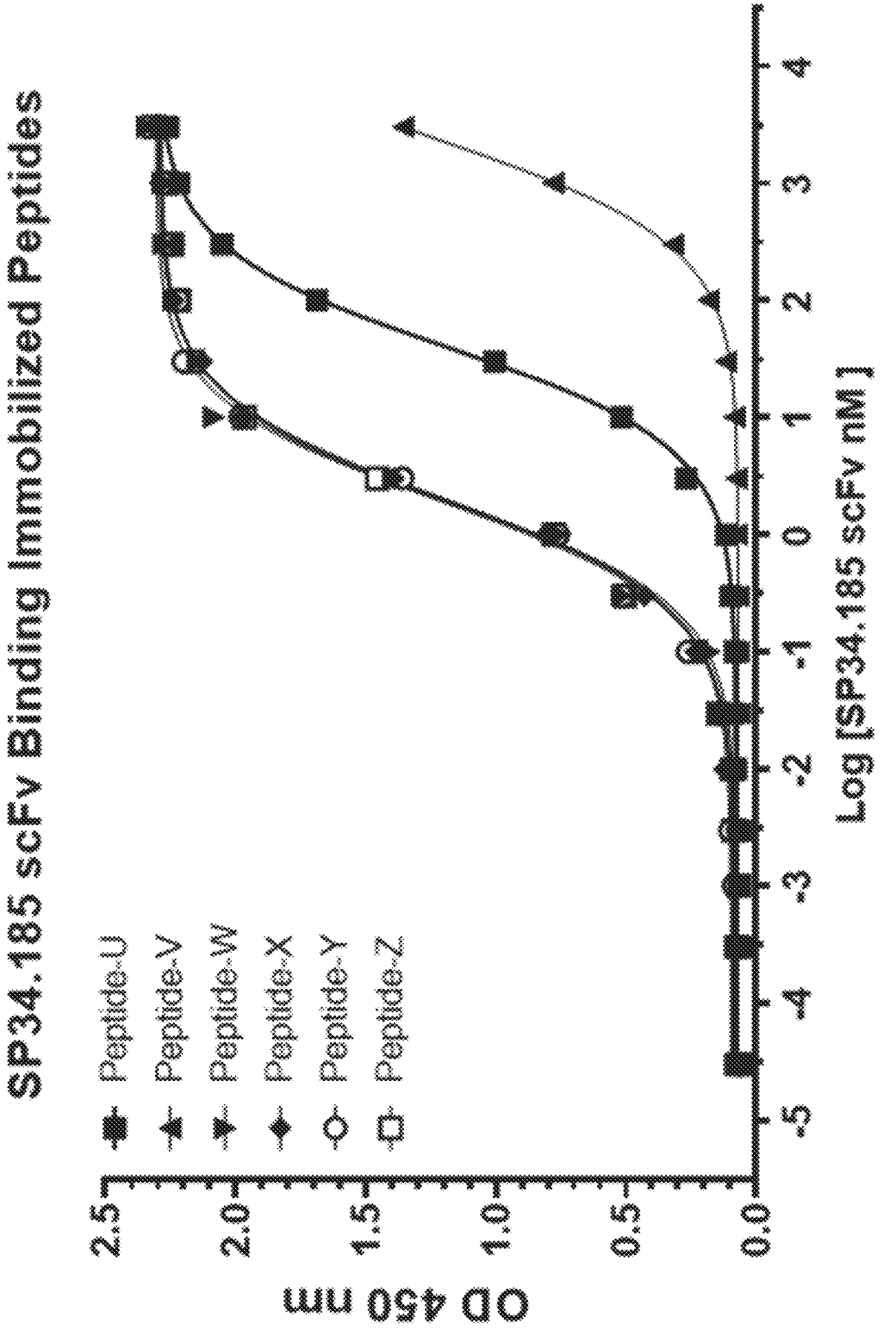

| ELISA | Peptide-U | Peptide-V | Peptide-W | Peptide-X | Peptide-Y | Peptide-Z |
|---|---|---|---|---|---|---|
| | | | Summary of FIG. 12F | | | |
| EC50 nM | 39.90 | 2168 | 1.916 | 1.948 | 2.012 | 1.833 |

Peptides were evaluated for their ability to inhibit SP34.185 scFv from binding CD3e by standard enzyme linked immunosorbent assays (ELISAs). Briefly, a fixed concentration of SP34.185 scFv was incubated with varying concentrations of peptides in solution. SP34.185scFv and peptide solutions were incubated for 1 hr prior to addition to CD3 coated plates. Binding was allowed to proceed for 30 min prior to washing. After washing, bound SP34.185 scFv using a secondary horse radish peroxidase antibody conjugate. After washing again, plates were developed using standard ELISA techniques and stopped using acid. The concentration of peptide required to inhibit 50% of the SP34.185 scFv CD3 binding signal (IC50) was calculated using Graphpad prism. Data is shown in FIGS. 13A-13F and summarized in Tables 18A-18D.

TABLE 18A

Figure 13A:
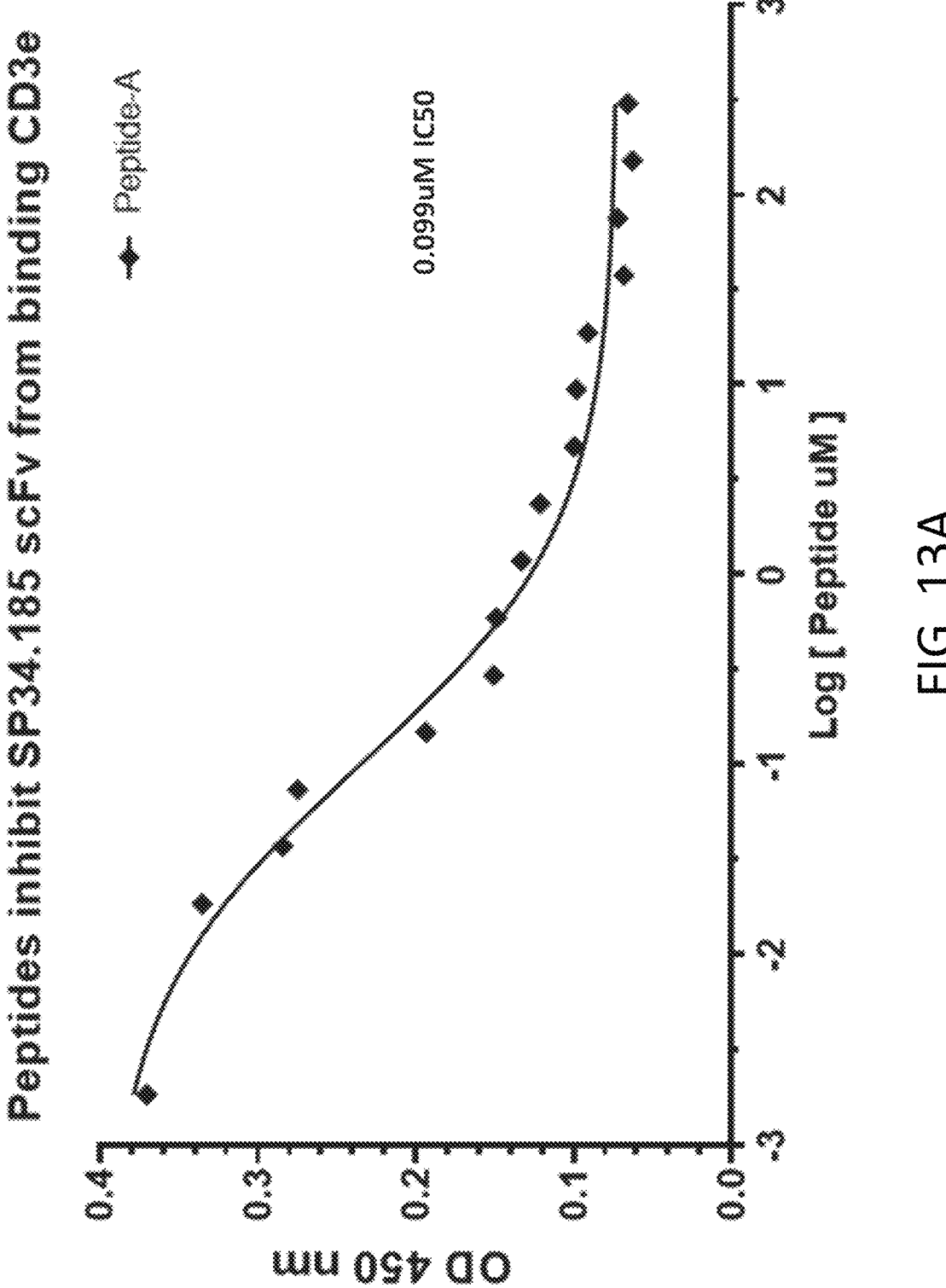
FIGS. 13A-13F illustrate inhibition of anti-CD3 scFv binding to CD3 by alanine scanning peptides of anti-CD3 scFv Peptide-A and Peptide-B as measured by ELISA.
Figure 13B:
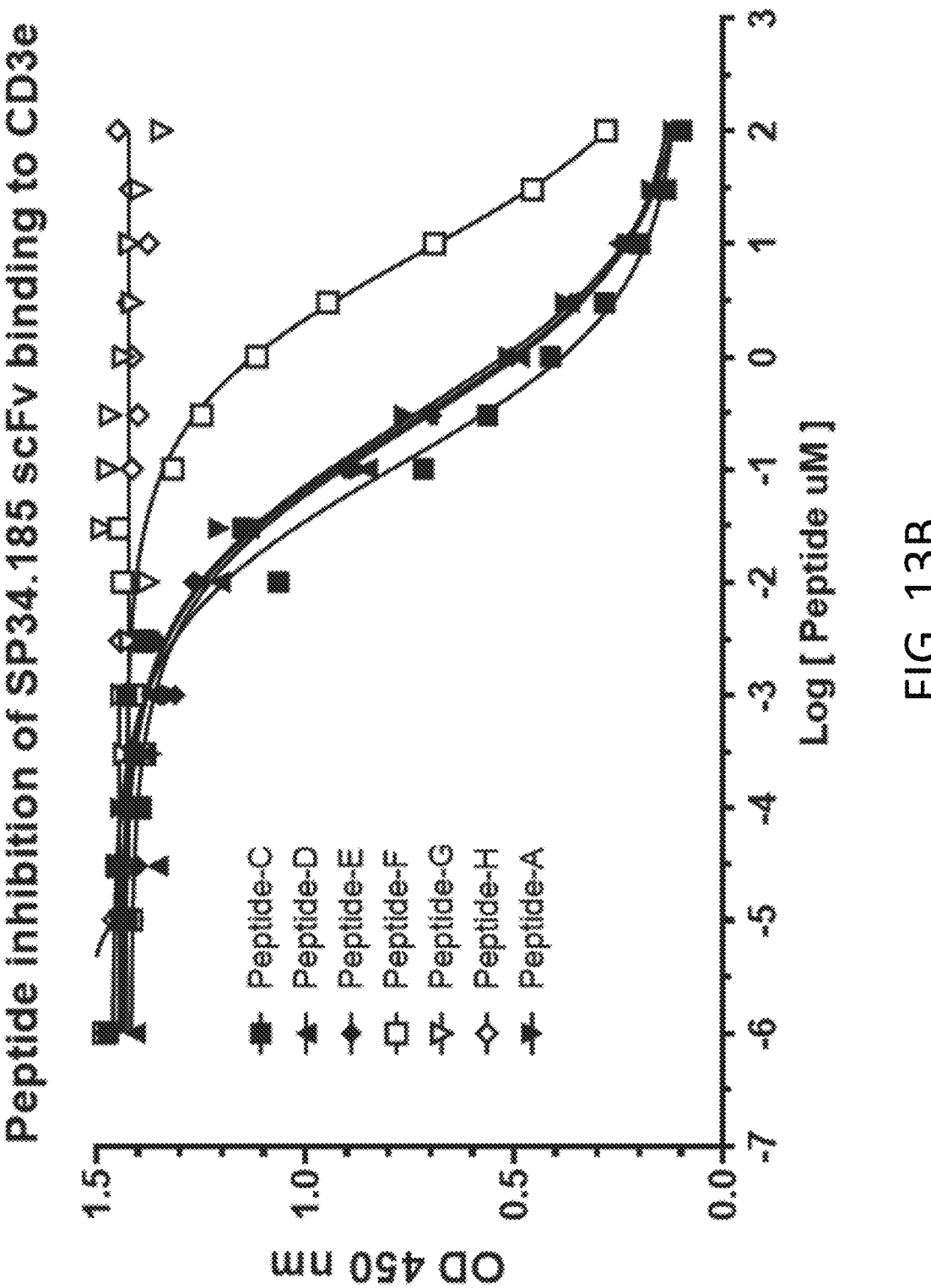

| ELISA | Peptide-A | Peptide-C | Peptide-D | Peptide-E | Peptide-F | Peptide-G | Peptide-H |
|---|---|---|---|---|---|---|---|
| | | | Summary of FIG. 13B | | | | |
| IC50 uM | 0.1926 | 0.1025 | 0.2318 | 0.1905 | 5.484 | >100 | >100 |

TABLE 18B

Figure 13C:
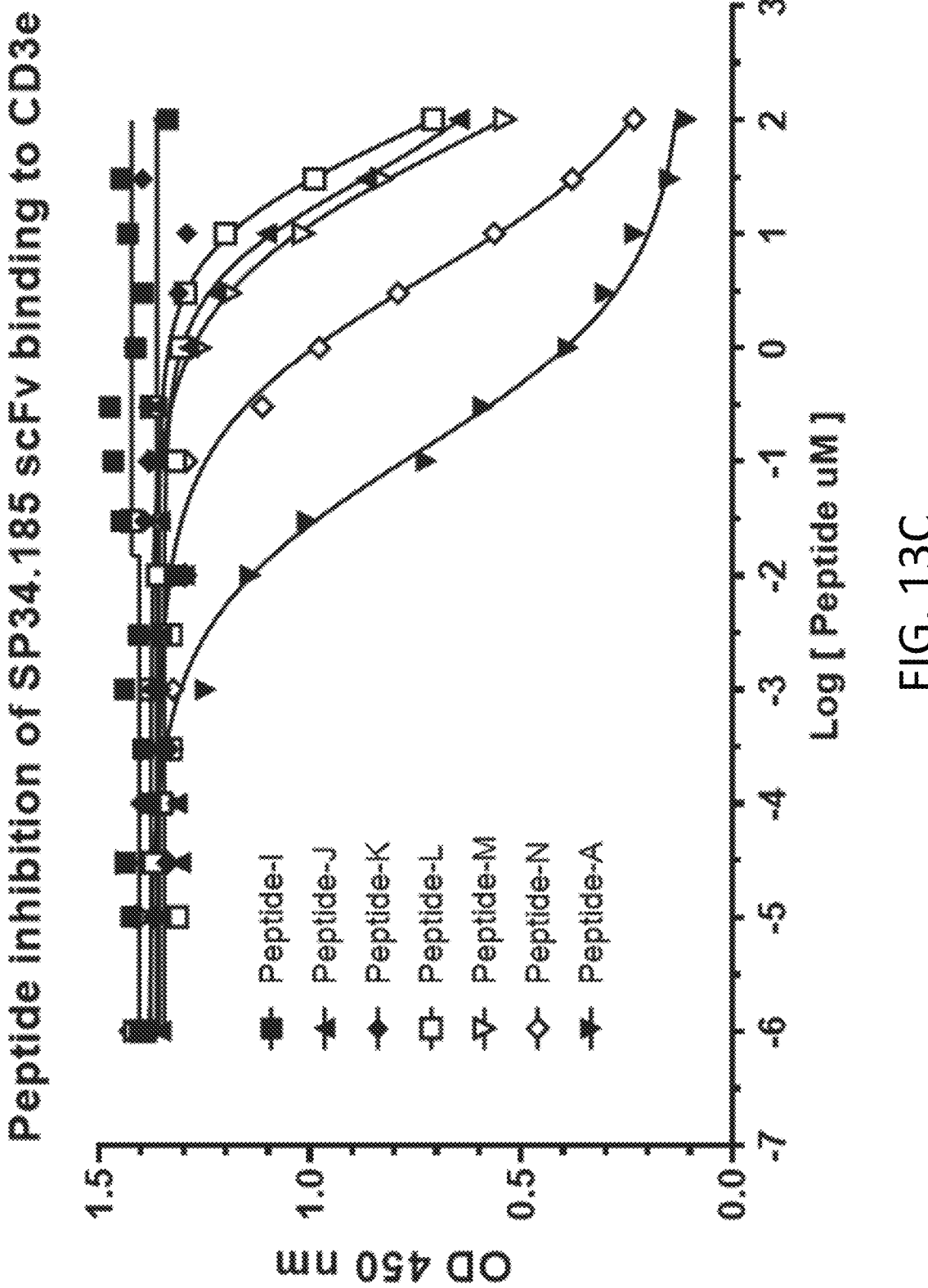
Figure 13D:
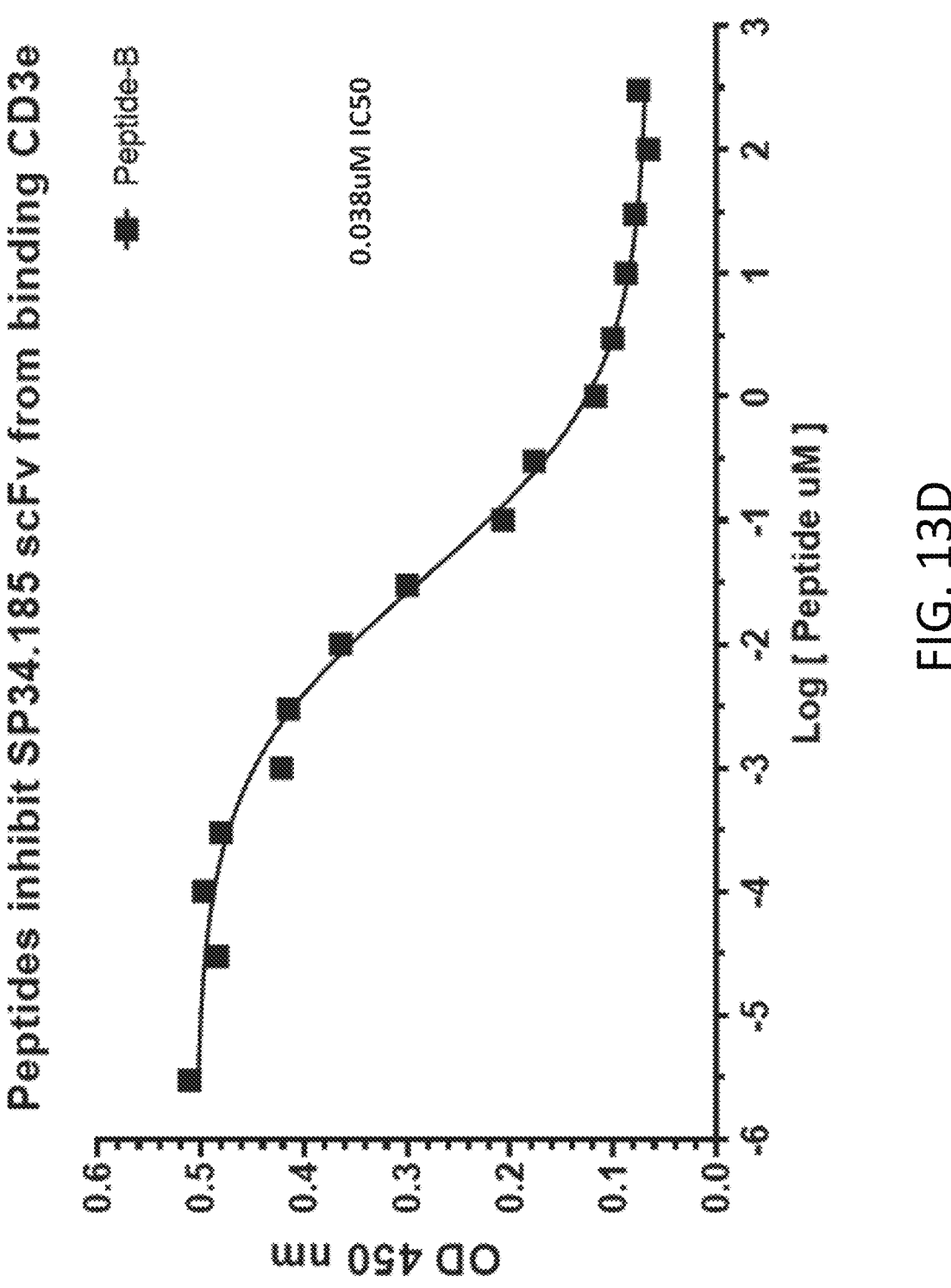

| ELISA | Peptide-A | Peptide-I | Peptide-10 | Peptide-K | Peptide-L | Peptide-M | Peptide-N |
|---|---|---|---|---|---|---|---|
| | | | Summary of FIG. 13C | | | | |
| IC50 uM | 0.1138 | >100 | 63.18 | >100 | 86.78 | 36.66 | 3.009 |

TABLE 18C

Figure 13E:
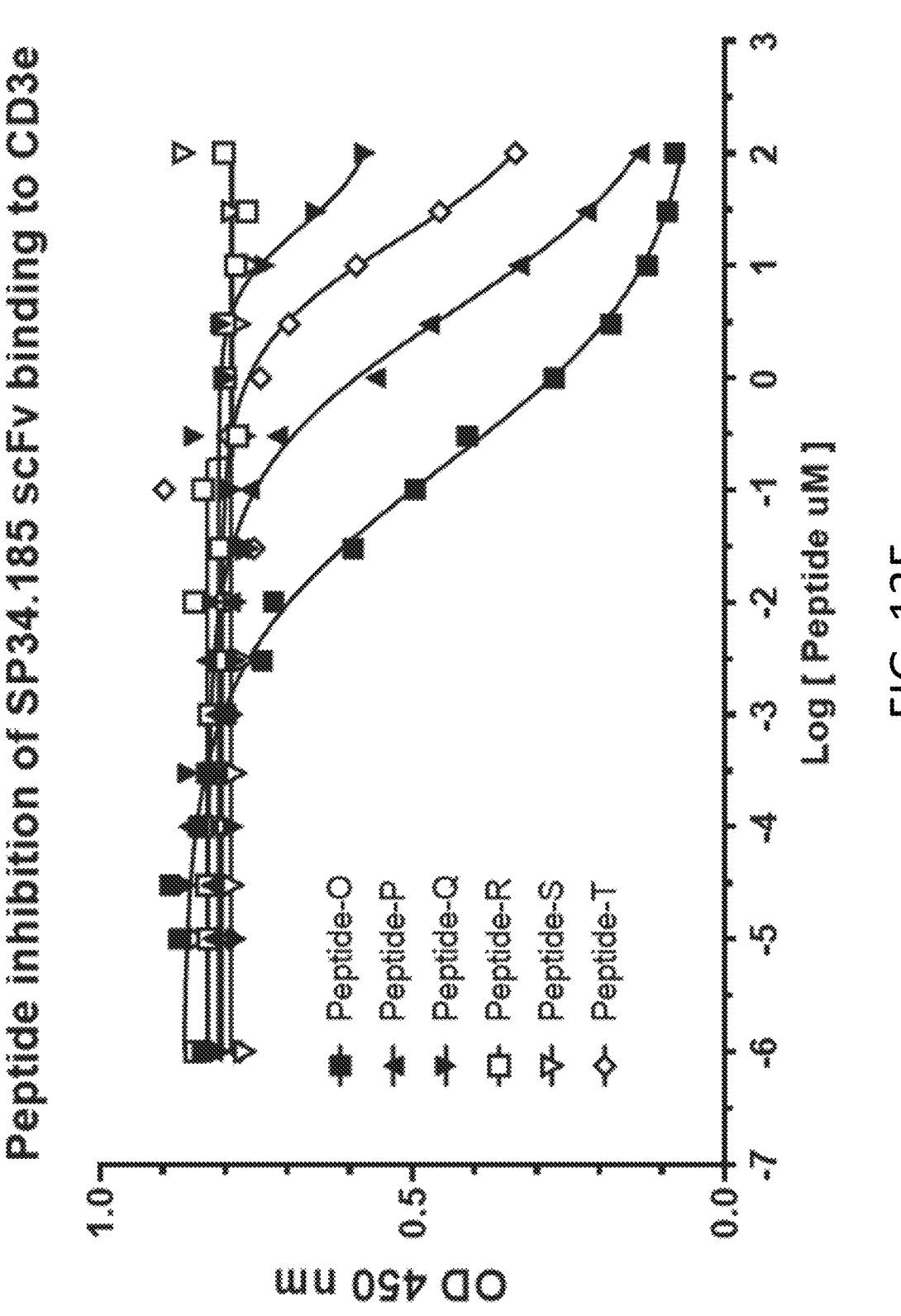

| | | | Summary of FIG. 13E | | | |
|---|---|---|---|---|---|
| ELISA | Peptide-O | Peptide-P | Peptide-Q | Peptide-R | Peptide-S | Peptide-T |
| IC50 uM | 0.1473 | 3.333 | >100 | >100 | >100 | 41.46 |

TABLE 18D

Figure 13F:
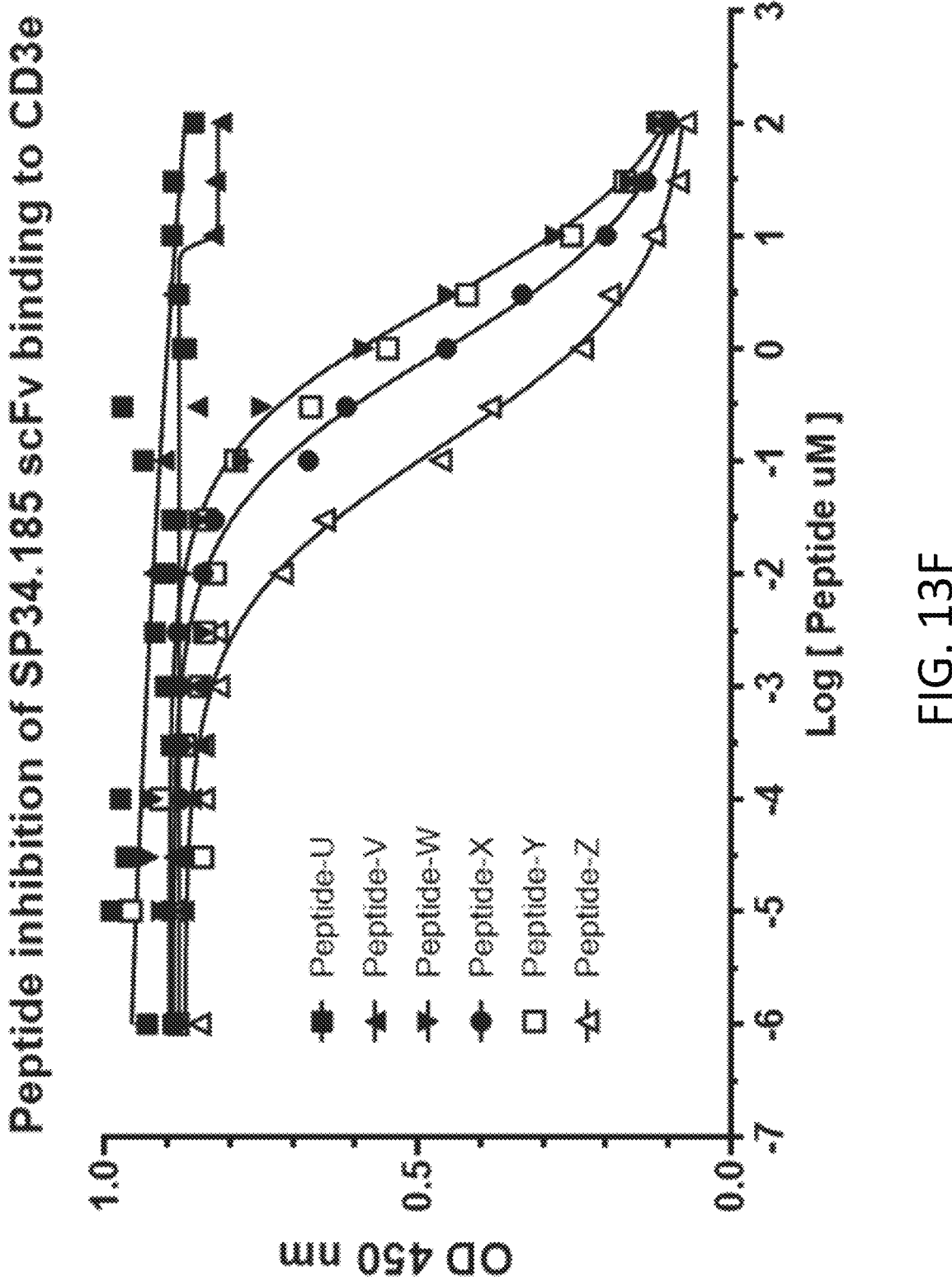

| | | | Summary of FIG. 13F | | |
|---|---|---|---|---|---|
| ELISA | Peptide-U | Peptide-V | Peptide-W | Peptide-X | Peptide-Y | Peptide-Z |
| IC50 uM | >100 | >100 | 1.912 | 0.6992 | 1.456 | 0.1180 |

TABLE 19

CD3 Ala Scan Sequences -
Peptide A and Peptide-B

| Peptide-ID | anti-CD3 Panned target | Sequence | SEQ ID NO: |
|---|---|---|---|
| Peptide-A | SP34.185 | GSQCLGPEWEVCPY | 79 |
| Peptide-C | SP34.185 | ASQCLGPEWEVCPY | 80 |
| Peptide-D | SP34.185 | GAQCLGPEWEVCPY | 81 |
| Peptide-E | SP34.185 | GSACLGPEWEVCPY | 82 |
| Peptide-F | SP34.185 | GSQCAGPEWEVCPY | 83 |
| Peptide-G | SP34.185 | GSQCLAPEWEVCPY | 84 |
| Peptide-H | SP34.185 | GSQCLGAEWEVCPY | 85 |
| Peptide-I | SP34.185 | GSQCLGPAWEVCPY | 86 |
| Peptide-J | SP34.185 | GSQCLGPEAEVCPY | 87 |
| Peptide-K | SP34.185 | GSQCLGPEWAVCPY | 88 |
| Peptide-L | SP34.185 | GSQCLGPEWEACPY | 89 |
| Peptide-M | SP34.185 | GSQCLGPEWEVCAY | 90 |
| Peptide-N | SP34.185 | GSQCLGPEWEVCPA | 91 |
| Peptide-A | SP34.185 | GSQCLGPEWEVCPY | 92 |
| Peptide-B | SP34.185 | VYCGPEFDESVGCM | 93 |
| Peptide-O | SP34.185 | AYCGPEFDESVGCM | 94 |
| Peptide-P | SP34.185 | VACGPEFDESVGCM | 95 |
| Peptide-Q | SP34.185 | VYCAPEFDESVGCM | 96 |
| Peptide-R | SP34.185 | VYCGAEFDESVGCM | 97 |
| Peptide-S | SP34.185 | VYCGPAFDESVGCM | 98 |
| Peptide-T | SP34.185 | VYCGPEADESVGCM | 99 |
| Peptide-U | SP34.185 | VYCGPEFAESVGCM | 100 |
| Peptide-V | SP34.185 | VYCGPEFDASVGCM | 101 |
| Peptide-W | SP34.185 | VYCGPEFDEAVGCM | 102 |
| Peptide-X | SP34.185 | VYCGPEFDESAGCM | 103 |

TABLE 19-continued

CD3 Ala Scan Sequences -
Peptide A and Peptide-B

| Peptide-ID | anti-CD3 Panned target | Sequence | SEQ ID NO: |
|---|---|---|---|
| Peptide-Y | SP34.185 | VYCGPEFDESVACM | 104 |
| Peptide-Z | SP34.185 | VYCGPEFDESVGCA | 105 |

Example 8: Panning of the Optimized Phage Library Construction—CD3 scFv Peptides Once the phage optimization libraries were completed, phage libraries were bio-panned using SP34.185 scFv loaded beads. Multiple rounds of panning were performed where bacteriophage was allowed to bind to SP34.185 scFv loaded beads, washed, eluted, and amplified. Additional selective pressure was included during each round of panning using a fixed concentration of CD3, Peptide-A, or Peptide-B. After panning, phage infected bacteria were plated out and colonies picked into 96 well blocks. Clonal phage was then amplified and separated from bacterial cells via centrifugation. Phage containing supernatants were tested in binding ELISAs against SP34.185 scFv coated plates in the presence or absence of saturating concentration of CD3. Phage able to bind SP34.185 scFv were selected for sequence analysis if the binding signal was reduced in the presence of CD3.

Example 9: Panning ELISAs—CD3 scFv Peptides

Clonal phages were harvested as crude supernatants and screened via standard enzyme linked immunsorbent assays (ELISAs). Briefly, biotinylated SP34.185 scFv was captured on neutravidin coated plates. Prior to the addition of clonal phage, wells were incubated with blocking buffer and CD3 or blocking buffer alone. Without washing or aspirating, clonal phage supernatants were then added to the wells and incubated for a short time. Wells were then washed followed by detection of bound phage using a horse radish peroxidase conjugated anti-M13 antibody. Clonal phage of interest was then sent for sequence analysis.

Phage panning results of CD3 scFv Peptide-A library sequences are shown in Table 20. The sequences of those peptides selected for synthesis are shown in Table 21, and further evaluated for binding to anti-CD3 scFv (FIGS. 14A-14B) and inhibition of anti-CD3 scFv binding to CD3 (FIGS. 15A-15B). The consensus sequence shown in FIG.

16 was calculated from all the sequences shown in Table 20 and was generated using WebLogo 3.7.4.

TABLE 20

Clonal Phage Peptide Sequences from the Peptide-B Optimization Library Panning (-)
indicates same amino acid as in CD3 scFv Peptide-B corresponding position (e.g. Phage-1 position).

| Phage ID | Amino acid position sequence | | | | | | | | | | | | | | Phage binding ELISA | | | SEQ ID NO: |
| | 1 | 2 | 3 | 4 | 5 | 6 | 7 | 8 | 9 | 10 | 11 | 12 | 13 | 14 | Backgroud signal | SP34.185 scFv signal | SP34.185 scFv signal in presence of CD3 | |
|---|---|---|---|---|---|---|---|---|---|---|---|---|---|---|---|---|---|---|
| Phage-1/ Peptide B | V | Y | C | G | P | E | F | D | E | S | V | G | C | M | 0.06 | 2.79 | 0.09 | 19 |
| Phage-2 | D | D | — | W | — | D | W | E | F | D | F | A | — | A | 0.08 | 2.75 | 0.09 | 106 |
| Phage-3 | Y | I | — | — | L | D | — | P | D | F | L | Y | — | D | 0.08 | 2.88 | 0.10 | 107 |
| Phage-4 | F | D | — | W | — | D | W | E | — | Y | F | V | — | D | 0.08 | 2.79 | 0.09 | 108 |
| Phage-5 | Y | I | — | W | — | D | W | E | — | Y | F | D | — | D | 0.08 | 2.74 | 0.09 | 109 |
| Phage-6 | N | I | — | W | — | D | W | E | D | D | Y | F | — | F | 0.09 | 2.54 | 0.09 | 110 |
| Phage-7 | N | F | — | W | — | D | W | E | Y | I | Y | P | — | I | 0.07 | 2.77 | 0.09 | 111 |
| Phage-8 | — | D | — | W | — | D | W | E | — | D | F | L | — | I | 0.08 | 2.54 | 0.08 | 112 |
| Phage-9 | H | A | — | W | — | D | W | E | — | Y | F | P | — | N | 0.08 | 2.85 | 0.09 | 113 |
| Phage-10 | Y | D | — | — | — | D | V | — | — | — | Y | V | — | V | 0.09 | 2.63 | 0.10 | 114 |
| Phage-11 | I | D | — | W | — | D | W | E | D | D | T | F | — | Y | 0.09 | 2.73 | 0.08 | 115 |
| Phage-12 | Y | L | — | — | — | D | G | — | — | T | L | A | — | Y | 0.08 | 2.66 | 0.15 | 116 |
| Phage-13 | — | D | — | — | — | D | G | — | — | — | I | L | — | Y | 0.11 | 2.13 | 0.08 | 117 |
| Phage-14 | F | I | — | W | — | D | W | E | — | D | Y | F | — | A | 0.07 | 2.44 | 0.09 | 119 |
| Phage-15 | G | D | — | W | — | D | W | E | W | D | F | Y | — | D | 0.07 | 2.71 | 0.07 | 120 |
| Phage-16 | Y | L | — | W | — | D | W | E | Y | I | D | L | — | D | 0.12 | 2.67 | 0.08 | 121 |
| Phage-17 | S | F | — | W | — | D | W | E | — | Y | F | D | — | D | 0.10 | 2.60 | 0.07 | 122 |
| Phage-18 | D | D | — | W | — | D | W | E | — | Y | A | S | — | D | 0.09 | 2.57 | 0.07 | 123 |
| Phage-19 | N | L | — | W | — | D | W | E | Y | P | F | F | — | D | 0.09 | 2.52 | 0.09 | 124 |
| Phage-20 | F | D | — | W | — | D | W | E | — | — | F | V | — | D | 0.08 | 2.34 | 0.09 | 125 |
| Phage-21 | D | I | — | — | — | D | G | — | — | T | I | I | — | D | 0.13 | 2.30 | 0.10 | 126 |
| Phage-22 | D | D | — | W | — | D | W | E | Y | Y | A | V | — | D | 0.09 | 2.28 | 0.09 | 127 |
| Phage-23 | Y | D | — | W | — | D | W | E | — | Y | S | N | — | D | 0.10 | 2.17 | 0.08 | 128 |
| Phage-24 | I | N | — | W | — | D | W | E | D | Y | F | F | — | D | 0.07 | 2.16 | 0.07 | 129 |
| Phage-25 | N | I | — | W | — | D | W | E | D | D | T | F | — | F | 0.06 | 2.87 | 0.07 | 130 |
| Phage-26 | N | I | — | W | — | D | W | E | P | N | S | F | — | F | 0.09 | 2.87 | 0.08 | 131 |
| Phage-27 | Y | D | — | — | — | — | M | — | — | — | I | D | — | F | 0.09 | 2.39 | 0.08 | 132 |
| Phage-28 | D | F | — | W | — | D | W | E | F | P | F | I | — | H | 0.11 | 2.73 | 0.12 | 133 |
| Phage-29 | D | F | — | — | — | — | M | — | — | — | I | T | — | I | 0.07 | 2.36 | 0.08 | 134 |
| Phage-30 | Y | D | — | — | — | — | — | — | — | — | T | V | — | I | 0.10 | 2.32 | 0.08 | 135 |
| Phage-31 | H | D | — | W | — | D | W | E | W | D | I | F | — | I | 0.07 | 2.26 | 0.08 | 136 |
| Phage-32 | H | A | — | W | — | D | W | E | — | Y | N | P | — | N | 0.11 | 2.71 | 0.11 | 137 |
| Phage-33 | D | V | — | W | — | D | W | E | W | D | F | F | — | N | 0.08 | 2.65 | 0.08 | 138 |
| Phage-34 | N | I | — | W | — | D | W | E | Y | Y | I | P | — | N | 0.10 | 2.57 | 0.08 | 139 |
| Phage-35 | I | I | — | W | — | D | W | E | F | I | D | Y | — | N | 0.08 | 2.10 | 0.07 | 140 |
| Phage-36 | S | L | — | W | — | D | W | E | Y | D | I | A | — | P | 0.07 | 2.53 | 0.08 | 141 |
| Phage-37 | D | L | — | — | — | — | — | — | — | — | I | F | — | P | 0.08 | 2.49 | 0.09 | 142 |
| Phage-38 | T | N | — | W | — | D | W | E | W | V | L | P | — | P | 0.14 | 2.47 | 0.10 | 143 |
| Phage-39 | I | E | — | W | — | D | W | E | P | N | Y | F | — | P | 0.13 | 2.29 | 0.09 | 144 |
| Phage-40 | I | F | — | W | — | D | W | E | D | Y | — | D | — | P | 0.07 | 2.28 | 0.07 | 145 |
| Phage-41 | I | D | — | W | — | D | W | E | Y | D | F | F | — | P | 0.07 | 2.26 | 0.08 | 146 |
| Phage-42 | L | F | — | W | — | D | W | E | D | — | F | F | — | P | 0.18 | 2.11 | 0.13 | 147 |
| Phage-43 | — | D | — | W | — | D | W | E | D | Y | A | D | — | T | 0.11 | 2.20 | 0.10 | 148 |
| Phage-44 | — | T | — | W | — | D | W | E | Q | Y | F | P | — | V | 0.11 | 2.34 | 0.09 | 149 |
| Phage-45 | I | E | — | W | — | D | W | E | P | I | Y | P | — | Y | 0.09 | 2.85 | 0.09 | 150 |
| Phage-46 | I | T | — | W | — | D | W | E | V | Y | F | P | — | Y | 0.07 | 2.55 | 0.08 | 151 |
| Phage-47 | I | D | — | W | — | D | W | E | Y | I | H | P | — | Y | 0.06 | 2.51 | 0.09 | 152 |
| Phage-48 | I | D | — | W | — | D | W | E | Y | I | N | P | — | Y | 0.12 | 2.50 | 0.12 | 153 |
| Phage-49 | A | D | — | W | — | D | W | E | — | A | F | P | — | Y | 0.09 | 2.44 | 0.09 | 154 |
| Phage-50 | I | D | — | W | — | D | W | E | Y | I | Y | P | — | Y | 0.09 | 2.31 | 0.07 | 155 |
| Phage-51 | N | I | — | W | — | D | W | E | D | D | N | F | — | F | 0.09 | 2.08 | 0.09 | 156 |
| Phage-52 | Y | D | — | W | — | D | W | E | Y | V | D | A | — | Y | 0.09 | 2.06 | 0.09 | 157 |
| Phage-53 | F | — | — | — | — | D | G | — | — | — | Y | V | — | D | 0.09 | 2.03 | 0.11 | 158 |
| Phage-54 | D | T | — | W | — | D | W | E | Y | I | N | I | — | S | 0.11 | 2.02 | 0.11 | 159 |
| Phage-55 | F | V | — | W | — | D | W | E | D | F | N | F | — | D | 0.07 | 2.01 | 0.08 | 160 |
| Phage-56 | F | A | — | W | — | D | W | E | Y | — | A | — | D | | 0.07 | 2.01 | 0.09 | 161 |
| Phage-57 | D | N | — | W | — | D | W | E | Y | D | F | F | — | V | 0.08 | 1.99 | 0.09 | 162 |
| Phage-58 | Y | D | — | W | — | D | W | E | — | Y | N | D | — | A | 0.09 | 1.96 | 0.11 | 163 |
| Phage-59 | D | D | — | — | — | D | G | — | — | T | I | I | — | V | 0.07 | 1.91 | 0.09 | 164 |
| Phage-60 | F | P | — | W | — | D | W | E | — | Y | A | J | — | D | 0.10 | 1.89 | 0.10 | 165 |
| Phage-61 | P | D | — | — | — | D | G | V | — | V | L | F | — | T | 0.12 | 1.86 | 0.07 | 166 |
| Phage-62 | D | N | — | W | — | D | W | E | Y | D | Y | F | — | V | 0.07 | 1.83 | 0.07 | 167 |
| Phage-63 | I | F | — | W | — | D | W | E | — | F | Y | D | — | Y | 0.12 | 1.82 | 0.08 | 168 |
| Phage-64 | A | D | — | W | — | D | W | E | — | Y | F | P | — | N | 0.08 | 1.82 | 0.08 | 169 |
| Phage-65 | H | T | — | W | — | D | W | E | D | D | I | F | — | N | 0.12 | 1.81 | 0.10 | 170 |

TABLE 20-continued

Clonal Phage Peptide Sequences from the Peptide-B Optimization Library Panning (-)
indicates same amino acid as in CD3 scFv Peptide-B corresponding position (e.g. Phage-1 position).

| Phage | Amino acid position sequence | | | | | | | | | | | | | | Background signal | SP34.185 scFv signal | SP34.185 scFv signal in presence of CD3 | SEQ ID NO: |
|---|---|---|---|---|---|---|---|---|---|---|---|---|---|---|---|---|---|---|
| ID | 1 | 2 | 3 | 4 | 5 | 6 | 7 | 8 | 9 | 10 | 11 | 12 | 13 | 14 | | | | |
| Phage-66 | F | A | — | W | — | D | W | E | — | A | F | L | — | L | 0.09 | 1.80 | 0.09 | 171 |
| Phage-67 | Y | D | — | — | — | — | L | — | — | — | I | A | — | D | 0.08 | 1.77 | 0.08 | 172 |
| Phage-68 | N | S | — | W | — | D | W | E | Y | D | I | I | — | D | 0.08 | 1.77 | 0.10 | 173 |
| Phage-69 | F | A | — | W | — | D | W | E | — | V | A | P | — | Y | 0.07 | 1.75 | 0.07 | 174 |
| Phage-70 | L | D | — | — | — | D | G | — | — | T | L | T | — | Y | 0.10 | 1.75 | 0.12 | 175 |
| Phage-71 | — | L | — | W | — | D | W | E | — | F | Y | D | — | P | 0.07 | 1.74 | 0.09 | 176 |
| Phage-72 | H | A | — | W | — | V | W | E | — | Y | F | P | — | N | 0.07 | 1.72 | 0.08 | 177 |
| Phage-73 | N | E | — | W | — | N | G | E | P | T | F | P | — | T | 0.08 | 1.71 | 0.07 | 178 |
| Phage-74 | L | T | — | — | — | D | G | — | — | T | L | Y | — | D | 0.08 | 1.70 | 0.07 | 179 |
| Phage-75 | Y | D | — | — | — | — | Y | — | — | — | — | D | — | I | 0.13 | 1.67 | 0.09 | 180 |
| Phage-76 | I | E | — | W | — | D | W | E | P | N | S | F | — | D | 0.09 | 1.66 | 0.08 | 181 |
| Phage-77 | Y | D | — | — | — | — | L | — | — | — | I | H | — | Y | 0.12 | 1.66 | 0.09 | 182 |
| Phage-78 | I | — | — | — | — | — | — | — | — | — | T | I | — | N | 0.08 | 1.63 | 0.08 | 183 |
| Phage-79 | I | — | — | — | — | — | V | E | — | A | Y | L | — | Y | 0.09 | 1.62 | 0.10 | 184 |
| Phage-80 | F | D | — | — | — | D | G | — | — | T | — | Y | — | D | 0.09 | 1.61 | 0.08 | 185 |
| Phage-81 | I | D | — | — | — | D | G | — | — | T | I | S | — | Y | 0.08 | 1.57 | 0.11 | 186 |
| Phage-82 | N | I | — | — | — | — | — | — | — | — | S | T | — | L | 0.10 | 1.55 | 0.11 | 187 |
| Phage-83 | Y | D | — | — | — | D | G | — | — | — | Y | F | — | D | 0.08 | 1.53 | 0.08 | 188 |
| Phage-84 | N | F | — | W | — | D | W | E | Y | F | N | D | — | N | 0.09 | 1.53 | 0.09 | 189 |
| Phage-85 | — | L | — | W | — | D | W | E | A | F | F | D | — | D | 0.07 | 1.47 | 0.07 | 190 |
| Phage-86 | I | — | — | — | — | — | W | E | W | P | — | A | — | N | 0.16 | 1.47 | 0.10 | 191 |
| Phage-87 | — | F | — | W | — | D | W | E | D | N | F | F | — | N | 0.08 | 1.46 | 0.10 | 192 |
| Phage-88 | — | V | — | W | — | D | W | E | T | F | F | P | — | D | 0.08 | 1.46 | 0.08 | 193 |
| Phage-89 | D | N | — | — | — | D | G | — | — | T | Y | I | — | N | 0.10 | 1.45 | 0.09 | 194 |
| Phage-90 | D | N | — | W | — | D | W | E | Y | N | F | F | — | V | 0.07 | 1.45 | 0.08 | 195 |
| Phage-91 | F | — | — | — | — | — | V | E | — | D | Y | L | — | I | 0.10 | 1.43 | 0.10 | 196 |
| Phage-92 | D | N | — | W | — | D | W | E | Y | D | I | F | — | V | 0.07 | 1.43 | 0.07 | 197 |
| Phage-93 | T | D | — | — | — | — | — | — | — | — | I | A | — | P | 0.08 | 1.42 | 0.08 | 198 |
| Phage-94 | Y | F | — | — | — | — | V | E | — | Y | T | L | — | F | 0.10 | 1.42 | 0.10 | 199 |
| Phage-95 | F | — | — | — | — | — | — | — | — | — | A | P | — | N | 0.06 | 1.37 | 0.08 | 200 |
| Phage-96 | F | D | — | — | — | — | V | E | — | Y | F | Y | — | A | 0.11 | 1.36 | 0.08 | 201 |
| Phage-97 | D | F | — | W | — | D | W | E | D | F | F | F | — | A | 0.18 | 1.35 | 0.12 | 202 |
| Phage-98 | F | F | — | — | — | D | G | — | — | T | L | S | — | N | 0.08 | 1.35 | 0.09 | 203 |
| Phage-99 | F | I | — | — | — | — | — | — | — | — | — | A | — | L | 0.14 | 1.35 | 0.09 | 204 |
| Phage-100 | Y | D | — | — | — | — | — | — | — | A | I | — | — | Y | 0.09 | 1.32 | 0.10 | 205 |
| Phage-101 | Y | I | — | W | — | D | W | E | — | Y | L | Y | — | P | 0.10 | 1.32 | 0.15 | 206 |
| Phage-102 | F | D | — | W | — | D | W | E | — | P | T | T | — | H | 0.08 | 1.31 | 0.08 | 207 |
| Phage-103 | Y | D | — | W | — | D | W | E | D | F | P | I | — | D | 0.14 | 1.31 | 0.10 | 208 |
| Phage-104 | — | V | — | W | — | D | W | E | Y | I | D | D | — | S | 0.08 | 1.30 | 0.07 | 209 |
| Phage-105 | I | N | — | W | — | D | W | E | V | I | S | F | — | D | 0.12 | 1.30 | 0.08 | 210 |
| Phage-106 | L | S | — | W | — | D | W | E | — | V | T | P | — | L | 0.10 | 1.29 | 0.10 | 211 |
| Phage-107 | F | A | — | W | — | D | W | E | — | V | D | I | — | Y | 0.09 | 1.28 | 0.08 | 212 |
| Phage-108 | Y | D | — | — | — | — | M | — | — | — | I | V | — | D | 0.10 | 1.25 | 0.08 | 213 |
| Phage-109 | Y | D | — | W | — | D | W | E | V | F | I | V | — | D | 0.06 | 1.25 | 0.07 | 214 |
| Phage-110 | D | N | — | W | — | D | W | E | H | N | F | F | — | V | 0.10 | 1.25 | 0.08 | 215 |
| Phage-111 | Y | D | — | — | — | D | G | — | — | — | I | Y | — | P | 0.07 | 1.23 | 0.08 | 216 |
| Phage-112 | Y | D | — | — | — | — | — | E | F | P | Y | Y | — | F | 0.12 | 1.23 | 0.12 | 217 |
| Phage-113 | A | D | — | — | — | — | Y | — | — | — | — | P | — | V | 0.11 | 1.22 | 0.09 | 218 |
| Phage-114 | F | L | — | — | — | — | V | E | — | V | H | Y | — | S | 0.08 | 1.22 | 0.10 | 219 |
| Phage-115 | T | D | — | W | — | D | W | E | Y | I | T | S | — | S | 0.08 | 1.22 | 0.08 | 220 |

TABLE 20-continued

Clonal Phage Peptide Sequences from the Peptide-B Optimization Library Panning (-)
indicates same amino acid as in CD3 scFv Peptide-B corresponding position (e.g. Phage-1 position).

| Phage ID | \multicolumn Amino acid position sequence 1 | 2 | 3 | 4 | 5 | 6 | 7 | 8 | 9 | 10 | 11 | 12 | 13 | 14 | Background signal | SP34.185 scFv signal | SP34.185 scFv signal in presence of CD3 | SEQ ID NO: |
|---|---|---|---|---|---|---|---|---|---|---|---|---|---|---|---|---|---|---|
| Phage-116 | A | F | — | — | — | — | L | — | — | — | I | T | — | D | 0.09 | 1.21 | 0.09 | 221 |
| Phage-117 | N | D | — | W | — | D | W | E | — | Y | F | S | — | Y | 0.09 | 1.19 | 0.09 | 222 |
| Phage-118 | F | D | — | — | — | — | W | E | I | V | T | D | — | Y | 0.08 | 1.19 | 0.09 | 223 |
| Phage-119 | N | L | — | — | — | — | M | — | — | — | I | I | — | P | 0.13 | 1.19 | 0.11 | 224 |
| Phage-120 | D | L | — | — | — | — | M | — | — | — | I | Y | — | D | 0.10 | 1.19 | 0.14 | 225 |
| Phage-121 | F | D | — | — | — | D | G | V | — | D | Y | I | — | D | 0.09 | 1.18 | 0.09 | 226 |
| Phage-122 | Y | A | — | W | — | D | W | E | — | D | F | A | — | Y | 0.11 | 1.18 | 0.08 | 227 |
| Phage-123 | H | D | — | — | — | — | M | — | — | — | I | V | — | V | 0.10 | 1.17 | 0.10 | 228 |
| Phage-124 | — | F | — | — | — | — | — | E | F | I | F | L | — | A | 0.07 | 1.17 | 0.08 | 229 |
| Phage-125 | Y | D | — | — | — | — | L | I | — | — | I | L | — | D | 0.08 | 1.16 | 0.09 | 230 |
| Phage-126 | S | V | — | W | — | D | W | E | — | F | Y | S | — | D | 0.11 | 1.16 | 0.10 | 231 |
| Phage-127 | P | — | — | — | — | D | G | — | — | T | A | I | — | T | 0.13 | 1.16 | 0.10 | 232 |
| Phage-128 | D | D | — | — | — | — | L | E | W | Y | Y | P | — | Y | 0.09 | 1.16 | 0.08 | 233 |
| Phage-129 | F | I | — | — | — | — | — | — | — | — | L | P | — | N | 0.08 | 1.14 | 0.09 | 234 |
| Phage-130 | I | D | — | — | — | — | — | — | — | — | L | P | — | D | 0.11 | 1.14 | 0.33 | 235 |
| Phage-131 | F | L | — | — | — | — | — | E | — | D | A | P | — | Y | 0.08 | 1.13 | 0.08 | 236 |
| Phage-132 | I | F | — | — | — | D | G | — | — | T | H | I | — | H | 0.10 | 1.13 | 0.07 | 237 |
| Phage-133 | — | F | — | W | — | D | W | E | Y | I | D | F | — | N | 0.10 | 1.11 | 0.21 | 238 |
| Phage-134 | I | F | — | — | — | — | Y | — | — | — | L | H | — | I | 0.12 | 1.11 | 0.11 | 239 |
| Phage-135 | H | L | — | W | — | D | W | E | W | Y | — | D | — | P | 0.08 | 1.11 | 0.10 | 240 |
| Phage-136 | F | I | — | — | — | — | M | — | — | — | I | A | — | N | 0.08 | 1.11 | 0.09 | 241 |
| Phage-137 | I | F | — | — | — | — | V | E | M | I | F | L | — | N | 0.09 | 1.10 | 0.08 | 242 |
| Phage-138 | Y | D | — | — | — | — | W | E | F | P | — | D | — | I | 0.11 | 1.09 | 0.11 | 243 |
| Phage-139 | N | L | — | — | — | — | — | — | — | — | I | T | — | F | 0.10 | 1.09 | 0.08 | 244 |
| Phage-140 | F | — | — | — | — | — | V | E | D | F | Y | F | — | Y | 0.08 | 1.09 | 0.08 | 245 |
| Phage-141 | D | — | — | — | — | — | — | — | — | — | L | I | — | N | 0.11 | 1.07 | 0.11 | 246 |
| Phage-142 | D | — | — | — | — | — | — | — | — | — | L | P | — | D | 0.08 | 1.07 | 0.08 | 247 |
| Phage-143 | A | I | — | — | — | — | L | — | — | — | I | A | — | P | 0.09 | 1.07 | 0.09 | 248 |
| Phage-144 | — | I | — | — | — | — | V | E | D | Y | N | L | — | Y | 0.08 | 1.07 | 0.09 | 249 |
| Phage-145 | H | T | — | W | — | D | W | E | D | Y | T | V | — | P | 0.10 | 1.06 | 0.09 | 250 |
| Phage-146 | S | D | — | W | — | D | W | E | Y | F | Y | D | — | N | 0.10 | 1.06 | 0.08 | 251 |
| Phage-147 | — | F | — | — | — | D | G | — | — | T | — | H | — | D | 0.09 | 1.05 | 0.08 | 252 |
| Phage-148 | D | — | — | — | — | — | Y | — | — | — | — | H | — | I | 0.09 | 1.05 | 0.08 | 253 |

TABLE 20-continued

Clonal Phage Peptide Sequences from the Peptide-B Optimization Library Panning (-)
indicates same amino acid as in CD3 scFv Peptide-B corresponding position (e.g. Phage-1 position).

| Phage ID | \multicolumn{14}{c}{Amino acid position sequence} | | | | | | | | | | | | | Background signal | SP34.185 scFv signal | SP34.185 scFv signal in presence of CD3 | SEQ ID NO: |
|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | | | | |
| Phage-149 | A | D | — | — | — | D | G | — | — | — | — | I | I | — | H | 0.07 | 1.05 | 0.08 | 254 |
| Phage-150 | F | — | — | — | — | — | L | — | — | — | — | L | T | — | V | 0.10 | 1.05 | 0.08 | 255 |
| Phage-151 | I | L | — | — | — | — | V | E | — | D | Y | Y | — | Y | 0.11 | 1.04 | 0.09 | 256 |
| Phage-152 | H | L | — | W | — | D | W | E | — | Y | H | S | — | D | 0.09 | 1.04 | 0.09 | 257 |
| Phage-153 | I | F | — | W | — | D | W | E | D | Y | N | F | — | T | 0.08 | 1.04 | 0.11 | 258 |
| Phage-154 | I | V | — | — | — | D | G | — | — | T | L | I | — | H | 0.12 | 1.04 | 0.11 | 259 |
| Phage-155 | A | D | — | W | — | D | W | E | W | D | Y | T | — | D | 0.12 | 1.03 | 0.11 | 260 |
| Phage-156 | I | T | — | — | — | — | — | — | — | — | T | T | — | N | 0.20 | 1.02 | 0.21 | 261 |
| Phage-157 | Y | H | — | W | — | D | W | E | — | Y | T | S | — | D | 0.20 | 1.02 | 0.09 | 262 |
| Phage-158 | N | — | — | — | — | — | V | E | — | Y | A | L | — | T | 0.11 | 1.01 | 0.10 | 263 |
| Phage-159 | F | I | — | — | — | — | M | — | — | — | I | H | — | D | 0.15 | 1.00 | 0.19 | 264 |
| Phage-160 | D | N | — | W | — | D | W | E | — | F | A | V | — | P | 0.14 | 1.00 | 0.10 | 265 |
| Phage-161 | Y | D | — | — | — | — | L | — | — | T | — | V | — | D | 0.10 | 1.00 | 0.09 | 266 |
| Phage-162 | Y | D | — | — | — | — | — | — | — | — | I | A | — | Y | 0.08 | 0.99 | 0.08 | 267 |
| Phage-163 | I | D | — | W | — | D | W | E | Y | T | — | H | — | D | 0.07 | 0.97 | 0.09 | 268 |
| Phage-164 | D | D | — | — | — | — | L | — | — | — | I | I | — | I | 0.09 | 0.96 | 0.09 | 269 |
| Phage-165 | — | — | — | — | — | — | Y | — | — | — | S | F | — | F | 0.09 | 0.91 | 0.08 | 270 |
| Phage-166 | F | N | — | W | — | D | W | E | D | P | Y | F | — | V | 0.09 | 0.86 | 0.07 | 271 |
| Phage-167 | Y | D | — | — | — | — | Y | — | — | — | S | Y | — | S | 0.08 | 0.82 | 0.07 | 272 |
| Phage-168 | — | A | — | W | — | D | W | E | Y | T | D | S | — | F | 0.13 | 0.79 | 0.09 | 273 |
| Phage-169 | T | D | — | — | — | — | — | — | — | — | — | A | — | Y | 0.10 | 0.77 | 0.09 | 274 |
| Phage-170 | T | D | — | W | — | D | W | E | F | Y | A | D | — | D | 0.07 | 0.75 | 0.08 | 275 |
| Phage-171 | Y | D | — | — | — | — | L | — | — | — | — | I | — | H | 0.09 | 0.69 | 0.09 | 276 |
| Phage-172 | S | D | — | — | — | D | G | — | — | — | I | I | — | T | 0.07 | 0.69 | 0.07 | 277 |
| Phage-173 | Y | — | — | — | — | — | — | — | — | — | I | D | — | D | 0.08 | 0.67 | 0.09 | 278 |
| Phage-174 | F | F | — | — | — | — | I | — | — | — | I | A | — | V | 0.08 | 0.62 | 0.09 | 279 |
| Phage-175 | D | — | — | — | — | — | — | — | — | — | T | F | — | D | 0.16 | 0.60 | 0.10 | 280 |
| Phage-176 | Y | D | — | — | — | — | W | E | W | P | I | D | — | V | 0.10 | 0.59 | 0.10 | 281 |
| Phage-177 | F | — | — | — | — | — | T | E | L | F | S | F | — | Y | 0.13 | 0.59 | 0.11 | 282 |
| Phage-178 | Y | — | — | — | — | — | V | — | — | — | I | T | — | P | 0.15 | 0.42 | 0.11 | 283 |
| Phage-179 | I | L | — | — | — | — | — | — | — | — | I | N | — | N | 0.09 | 0.37 | 0.25 | 284 |
| Phage-180 | — | V | — | — | — | A | M | G | Q | H | Y | L | — | D | 0.08 | 0.09 | 0.08 | 285 |
| Phage-181 | — | V | — | — | T | K | M | G | — | H | Y | L | — | S | 0.08 | 0.08 | 0.08 | 286 |

TABLE 20-continued

Clonal Phage Peptide Sequences from the Peptide-B Optimization Library Panning (-)
indicates same amino acid as in CD3 scFv Peptide-B corresponding position (e.g. Phage-1 position).

| Phage ID | \multicolumn{14}{c}{Amino acid position sequence} | | | | | | | | | | | | | | Background signal | SP34.185 scFv signal | SP34.185 scFv signal in presence of CD3 | SEQ ID NO: |
|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | | | | |
| Phage-182 | Y | D | — | W | — | D | W | E | Y | V | Y | A | — | Y | 0.08 | 0.98 | 0.08 | 287 |
| Phage-183 | D | L | — | — | — | — | L | — | — | — | — | N | — | D | 0.09 | 0.98 | 0.08 | 288 |
| Phage-184 | Y | — | — | — | — | — | — | — | — | — | T | V | — | Y | 0.14 | 0.97 | 0.16 | 289 |
| Phage-185 | L | D | — | W | — | D | W | E | W | P | Y | S | — | N | 0.08 | 0.96 | 0.09 | 290 |
| Phage-186 | F | I | — | W | — | D | W | E | D | D | F | F | — | Y | 0.08 | 0.96 | 0.09 | 291 |
| Phage-187 | D | L | — | — | — | — | V | E | W | Y | F | F | — | N | 0.11 | 0.95 | 0.10 | 292 |
| Phage-188 | Y | D | — | — | — | — | L | — | — | — | I | V | — | F | 0.07 | 0.94 | 0.08 | 293 |
| Phage-189 | L | N | — | W | — | V | W | E | D | D | — | F | — | Y | 0.09 | 0.92 | 0.09 | 294 |
| Phage-190 | F | N | — | W | — | D | W | E | D | P | N | F | — | V | 0.09 | 0.91 | 0.09 | 295 |
| Phage-191 | — | I | — | W | — | D | W | E | D | D | Y | F | — | P | 0.10 | 0.91 | 0.13 | 296 |
| Phage-192 | F | L | — | — | — | — | — | — | — | — | S | V | — | Y | 0.10 | 0.91 | 0.08 | 297 |
| Phage-193 | Y | D | — | — | — | — | L | — | — | — | I | F | — | Y | 0.10 | 0.91 | 0.09 | 298 |
| Phage-194 | H | L | — | — | — | D | G | — | — | — | F | T | — | F | 0.11 | 0.90 | 0.10 | 299 |
| Phage-195 | Y | F | — | — | — | — | M | — | — | — | L | Y | — | I | 0.08 | 0.90 | 0.08 | 300 |
| Phage-196 | Y | — | — | — | — | — | V | E | — | Y | A | N | — | Y | 0.07 | 0.90 | 0.07 | 301 |
| Phage-197 | N | T | — | — | — | — | — | — | — | — | T | A | — | Y | 0.16 | 0.90 | 0.58 | 302 |
| Phage-198 | I | D | — | W | — | D | W | E | — | A | F | N | — | Y | 0.09 | 0.90 | 0.08 | 303 |
| Phage-199 | A | — | — | — | — | — | L | E | — | F | F | L | — | T | 0.09 | 0.89 | 0.08 | 304 |
| Phage-200 | I | — | — | — | — | — | V | E | — | V | H | H | — | Y | 0.08 | 0.89 | 0.08 | 305 |
| Phage-201 | F | F | — | — | — | — | — | — | — | — | — | A | — | D | 0.10 | 0.89 | 0.11 | 306 |
| Phage-202 | Y | D | — | — | — | — | L | — | — | T | I | I | — | A | 0.08 | 0.89 | 0.08 | 307 |
| Phage-203 | I | L | — | — | — | — | W | E | Y | P | L | D | — | S | 0.09 | 0.89 | 0.10 | 308 |
| Phage-204 | F | I | — | — | — | — | — | — | — | — | T | T | — | N | 0.09 | 0.88 | 0.10 | 309 |
| Phage-205 | F | — | — | — | — | — | L | — | — | — | — | S | — | D | 0.17 | 0.88 | 0.15 | 310 |
| Phage-206 | H | L | — | — | — | — | L | — | — | — | — | T | — | F | 0.10 | 0.87 | 0.10 | 311 |
| Phage-207 | L | I | — | — | — | — | V | E | D | Y | S | L | — | H | 0.09 | 0.87 | 0.09 | 312 |
| Phage-208 | Y | F | — | — | — | — | M | — | — | — | — | Y | — | D | 0.08 | 0.87 | 0.08 | 313 |
| Phage-209 | H | — | — | — | — | — | M | — | — | — | I | Y | — | I | 0.13 | 0.87 | 0.09 | 314 |
| Phage-210 | F | D | — | — | — | — | L | — | — | — | I | N | — | D | 0.08 | 0.87 | 0.09 | 315 |
| Phage-211 | Y | — | — | — | — | — | V | E | — | Y | T | Y | — | T | 0.07 | 0.87 | 0.08 | 316 |
| Phage-212 | L | A | — | W | — | V | R | E | — | I | N | A | — | I | 0.08 | 0.85 | 0.07 | 317 |
| Phage-213 | I | D | — | W | — | D | W | E | D | I | T | F | — | D | 0.08 | 0.85 | 0.08 | 318 |
| Phage-214 | T | V | — | — | — | — | L | — | — | — | I | T | — | P | 0.11 | 0.85 | 0.15 | 319 |

TABLE 20-continued

Clonal Phage Peptide Sequences from the Peptide-B Optimization Library Panning (-)
indicates same amino acid as in CD3 scFv Peptide-B corresponding position (e.g. Phage-1 position).

| Phage | Amino acid position sequence | | | | | | | | | | | | | | Background | SP34.185 scFv | SP34.185 scFv signal in presence | SEQ ID |
|---|---|---|---|---|---|---|---|---|---|---|---|---|---|---|---|---|---|---|
| ID | 1 | 2 | 3 | 4 | 5 | 6 | 7 | 8 | 9 | 10 | 11 | 12 | 13 | 14 | signal | signal | of CD3 | NO: |
| Phage-215 | F | — | — | — | — | — | — | E | L | P | A | D | — | D | 0.08 | 0.85 | 0.09 | 320 |
| Phage-216 | F | D | — | — | — | — | — | — | — | — | N | P | — | F | 0.10 | 0.85 | 0.09 | 321 |
| Phage-217 | D | A | — | W | — | D | W | E | — | Y | S | S | — | D | 0.10 | 0.83 | 0.10 | 322 |
| Phage-218 | D | H | — | W | — | D | W | E | P | N | Y | F | — | V | 0.08 | 0.83 | 0.09 | 323 |
| Phage-219 | D | — | — | W | — | D | W | E | I | N | Y | I | — | F | 0.09 | 0.83 | 0.10 | 324 |
| Phage-220 | I | — | — | W | — | D | W | E | Y | V | Y | A | — | N | 0.10 | 0.82 | 0.09 | 325 |
| Phage-221 | D | F | — | — | — | — | V | E | — | D | Y | L | — | D | 0.07 | 0.82 | 0.08 | 326 |
| Phage-222 | H | D | — | — | — | D | G | R | — | D | Y | D | — | A | 0.11 | 0.82 | 0.09 | 327 |
| Phage-223 | L | A | — | W | — | D | W | E | D | D | Y | F | — | V | 0.08 | 0.82 | 0.09 | 328 |
| Phage-224 | D | I | — | W | — | D | W | E | D | Y | L | P | — | V | 0.10 | 0.82 | 0.10 | 329 |
| Phage-225 | I | L | — | — | — | — | I | E | V | Y | A | L | — | P | 0.08 | 0.81 | 0.10 | 330 |
| Phage-226 | I | F | — | — | — | — | W | E | F | — | — | L | — | N | 0.10 | 0.81 | 0.11 | 331 |
| Phage-227 | T | — | — | — | — | — | V | E | D | F | S | L | — | V | 0.07 | 0.80 | 0.08 | 332 |
| Phage-228 | F | I | — | — | — | — | W | E | F | V | D | A | — | F | 0.11 | 0.80 | 0.09 | 333 |
| Phage-229 | F | A | — | W | — | D | W | E | — | D | S | P | — | D | 0.06 | 0.80 | 0.07 | 334 |
| Phage-230 | I | L | — | — | — | — | V | E | — | L | I | F | — | P | 0.12 | 0.80 | 0.08 | 335 |
| Phage-231 | F | — | — | — | — | — | V | E | — | Y | I | Y | — | Y | 0.08 | 0.80 | 0.08 | 336 |
| Phage-232 | D | S | — | — | — | — | L | — | — | — | I | I | — | D | 0.10 | 0.79 | 0.09 | 337 |
| Phage-233 | F | L | — | — | — | D | G | — | — | T | S | V | — | D | 0.11 | 0.79 | 0.08 | 338 |
| Phage-234 | F | N | — | W | — | N | G | E | P | T | Y | F | — | V | 0.11 | 0.79 | 0.08 | 339 |
| Phage-235 | L | A | — | W | — | V | W | E | Y | P | — | T | — | I | 0.09 | 0.78 | 0.09 | 340 |
| Phage-236 | D | — | — | — | — | — | V | E | — | D | — | Y | — | Y | 0.09 | 0.78 | 0.09 | 341 |
| Phage-237 | I | T | — | W | — | D | W | E | — | Y | A | N | — | T | 0.08 | 0.77 | 0.07 | 342 |
| Phage-238 | F | F | — | — | — | D | G | — | — | T | Y | S | — | I | 0.15 | 0.77 | 0.13 | 343 |
| Phage-239 | T | D | — | W | — | D | W | E | Y | A | T | S | — | D | 0.09 | 0.76 | 0.09 | 344 |
| Phage-240 | F | N | — | — | — | D | G | Y | — | D | Y | L | — | D | 0.10 | 0.76 | 0.11 | 345 |
| Phage-241 | Y | D | — | W | — | D | W | E | V | D | F | H | — | P | 0.11 | 0.76 | 0.08 | 346 |
| Phage-242 | N | I | — | W | — | D | W | E | D | D | S | F | — | F | 0.08 | 0.76 | 0.08 | 347 |
| Phage-243 | A | T | — | — | — | — | — | — | — | — | I | — | — | S | 0.13 | 0.75 | 0.09 | 348 |
| Phage-244 | S | — | — | — | — | — | — | — | — | — | T | F | — | D | 0.10 | 0.74 | 0.09 | 349 |
| Phage-245 | P | I | — | — | — | — | Y | — | — | — | D | V | — | A | 0.08 | 0.74 | 0.08 | 350 |
| Phage-246 | Y | — | — | — | — | D | G | — | — | Y | N | S | — | T | 0.11 | 0.74 | 0.11 | 351 |
| Phage-247 | — | D | — | W | — | D | W | E | V | F | I | A | — | D | 0.11 | 0.74 | 0.10 | 352 |

TABLE 20-continued

Clonal Phage Peptide Sequences from the Peptide-B Optimization Library Panning (-)
indicates same amino acid as in CD3 scFv Peptide-B corresponding position (e.g. Phage-1 position).

| Phage ID | \multicolumn Amino acid position sequence | | | | | | | | | | | | | | Backgroud signal | SP34.185 scFv signal | SP34.185 scFv signal in presence of CD3 | SEQ ID NO: |
|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | signal | signal | of CD3 | NO: |
| Phage-248 | D | L | — | — | — | — | V | E | — | V | N | L | — | L | 0.12 | 0.74 | 0.10 | 353 |
| Phage-249 | F | D | — | — | — | — | M | — | — | — | T | T | — | F | 0.09 | 0.74 | 0.09 | 354 |
| Phage-250 | N | F | — | W | — | D | W | E | P | I | Y | F | — | T | 0.13 | 0.74 | 0.14 | 355 |
| Phage-251 | — | D | — | — | — | D | G | — | — | — | F | F | — | L | 0.08 | 0.73 | 0.08 | 356 |
| Phage-252 | — | D | — | — | — | D | G | — | — | T | A | F | — | I | 0.10 | 0.73 | 0.09 | 357 |
| Phage-253 | N | I | — | — | — | — | M | — | — | — | L | V | — | I | 0.10 | 0.73 | 0.09 | 358 |
| Phage-254 | I | I | — | — | — | — | — | — | — | — | F | F | — | F | 0.08 | 0.73 | 0.09 | 359 |
| Phage-255 | N | F | — | — | — | — | Y | — | — | — | I | S | — | I | 0.10 | 0.73 | 0.38 | 360 |
| Phage-256 | H | L | — | — | — | — | I | E | — | A | D | I | — | N | 0.11 | 0.73 | 0.51 | 361 |
| Phage-257 | D | — | — | — | — | — | V | E | — | D | Y | L | — | D | 0.08 | 0.72 | 0.09 | 362 |
| Phage-258 | D | — | — | — | — | — | L | — | — | — | I | N | — | D | 0.11 | 0.72 | 0.10 | 363 |
| Phage-259 | F | — | — | — | — | — | L | — | — | — | L | F | — | V | 0.09 | 0.72 | 0.08 | 364 |
| Phage-260 | P | D | — | — | — | — | W | E | F | Y | — | T | — | N | 0.12 | 0.72 | 0.08 | 365 |
| Phage-261 | F | D | — | — | — | — | — | E | Y | I | Y | A | — | T | 0.09 | 0.72 | 0.08 | 366 |
| Phage-262 | D | — | — | — | — | — | — | — | — | — | S | I | — | N | 0.12 | 0.72 | 0.11 | 367 |
| Phage-263 | D | F | — | — | — | — | V | E | — | Y | I | F | — | F | 0.08 | 0.72 | 0.07 | 368 |
| Phage-264 | P | V | — | W | — | D | W | E | Y | V | S | S | — | D | 0.08 | 0.71 | 0.08 | 369 |
| Phage-265 | Y | I | — | — | — | — | R | — | — | — | N | L | — | L | 0.09 | 0.71 | 0.09 | 370 |
| Phage-266 | Y | D | — | — | — | — | L | — | — | — | I | V | — | D | 0.11 | 0.71 | 0.11 | 371 |
| Phage-267 | H | D | — | W | — | D | W | E | D | F | Y | F | — | V | 0.09 | 0.71 | 0.08 | 372 |
| Phage-268 | H | — | — | — | — | — | Y | — | — | — | I | D | — | Y | 0.12 | 0.71 | 0.10 | 373 |
| Phage-269 | L | F | — | — | — | — | M | P | — | D | I | F | — | N | 0.08 | 0.71 | 0.08 | 374 |
| Phage-270 | H | D | — | — | — | — | L | E | F | H | Y | A | — | Y | 0.10 | 0.71 | 0.12 | 375 |
| Phage-271 | D | F | — | — | — | — | L | — | — | — | I | N | — | F | 0.08 | 0.70 | 0.08 | 376 |
| Phage-272 | Y | F | — | — | — | — | L | — | — | — | I | A | — | N | 0.10 | 0.70 | 0.10 | 377 |
| Phage-273 | T | D | — | W | — | D | W | E | D | D | I | I | — | D | 0.10 | 0.70 | 0.08 | 378 |
| Phage-274 | Y | D | — | — | — | — | L | — | — | — | I | Y | — | F | 0.09 | 0.70 | 0.08 | 379 |
| Phage-275 | Y | — | — | W | — | D | W | W | — | Y | — | T | — | D | 0.10 | 0.70 | 0.11 | 380 |
| Phage-276 | P | I | — | — | — | — | L | E | — | — | Y | L | — | N | 0.13 | 0.69 | 0.52 | 381 |
| Phage-277 | F | D | — | — | — | — | — | — | — | — | I | V | — | Y | 0.12 | 0.69 | 0.11 | 382 |
| Phage-278 | — | L | — | — | — | D | G | I | — | F | F | D | — | P | 0.09 | 0.68 | 0.07 | 383 |
| Phage-279 | A | — | — | — | — | — | Y | — | — | — | L | T | — | V | 0.07 | 0.68 | 0.07 | 384 |
| Phage-280 | D | F | — | — | — | — | L | — | — | — | I | I | — | A | 0.14 | 0.68 | 0.14 | 385 |

TABLE 20-continued

Clonal Phage Peptide Sequences from the Peptide-B Optimization Library Panning (-)
indicates same amino acid as in CD3 scFv Peptide-B corresponding position (e.g. Phage-1 position).

| Phage ID | | | | | | | Amino acid position sequence | | | | | | | | Background signal | SP34.185 scFv signal | SP34.185 scFv signal in presence of CD3 | SEQ ID NO: |
|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | | | | |
| Phage-281 | Y | D | — | — | — | — | — | — | — | — | L | D | — | N | 0.08 | 0.68 | 0.08 | 386 |
| Phage-282 | A | I | — | — | — | — | — | — | — | — | — | A | — | D | 0.14 | 0.67 | 0.08 | 387 |
| Phage-283 | L | L | — | — | — | D | G | V | — | D | F | F | — | D | 0.10 | 0.67 | 0.10 | 388 |
| Phage-284 | N | F | — | — | — | — | L | P | — | D | I | F | — | F | 0.12 | 0.66 | 0.13 | 389 |
| Phage-285 | F | — | — | — | — | — | V | E | — | V | S | L | — | N | 0.08 | 0.66 | 0.08 | 390 |
| Phage-286 | Y | D | — | — | — | D | G | Y | — | A | F | Y | — | H | 0.12 | 0.66 | 0.10 | 391 |
| Phage-287 | N | F | — | — | — | — | I | E | F | D | Y | L | — | D | 0.08 | 0.65 | 0.08 | 392 |
| Phage-288 | D | — | — | — | — | D | G | V | — | D | F | I | — | N | 0.06 | 0.65 | 0.08 | 393 |
| Phage-289 | T | D | — | W | — | D | W | E | Y | I | Y | S | — | S | 0.08 | 0.65 | 0.07 | 394 |
| Phage-290 | F | — | — | — | — | — | — | E | — | I | T | N | — | I | 0.14 | 0.65 | 0.11 | 395 |
| Phage-291 | F | D | — | W | — | D | W | E | — | — | F | F | — | H | 0.07 | 0.64 | 0.08 | 396 |
| Phage-292 | D | F | — | — | — | D | G | — | — | — | — | F | — | P | 0.08 | 0.63 | 0.08 | 397 |
| Phage-293 | H | N | — | — | — | — | L | — | — | — | L | V | — | D | 0.13 | 0.63 | 0.09 | 398 |
| Phage-294 | I | — | — | — | — | D | G | A | — | D | Y | T | — | D | 0.07 | 0.63 | 0.07 | 399 |
| Phage-295 | F | D | — | — | — | — | — | E | F | P | — | I | — | F | 0.08 | 0.62 | 0.08 | 400 |
| Phage-296 | Y | N | — | — | — | — | L | — | — | — | — | T | — | D | 0.09 | 0.62 | 0.08 | 401 |
| Phage-297 | F | D | — | — | — | — | L | — | — | — | I | H | — | A | 0.07 | 0.62 | 0.08 | 402 |
| Phage-298 | D | I | — | — | — | — | V | E | — | Y | F | L | — | F | 0.15 | 0.61 | 0.10 | 403 |
| Phage-299 | F | D | — | — | — | — | V | — | — | — | L | T | — | F | 0.10 | 0.61 | 0.09 | 404 |
| Phage-300 | F | D | — | — | — | — | I | E | — | F | H | L | — | F | 0.08 | 0.61 | 0.08 | 405 |
| Phage-301 | A | — | — | — | — | — | L | — | — | — | I | I | — | D | 0.12 | 0.61 | 0.10 | 406 |
| Phage-302 | Y | N | — | — | — | — | L | — | — | — | I | T | — | N | 0.09 | 0.61 | 0.10 | 407 |
| Phage-303 | F | D | — | W | — | D | W | E | — | P | — | D | — | L | 0.08 | 0.61 | 0.07 | 408 |
| Phage-304 | D | V | — | — | — | — | L | — | — | — | — | L | — | P | 0.08 | 0.60 | 0.08 | 409 |
| Phage-305 | N | — | — | — | — | — | L | — | — | — | L | P | — | P | 0.09 | 0.60 | 0.08 | 410 |
| Phage-306 | Y | — | — | W | — | D | W | E | Y | D | I | F | — | S | 0.08 | 0.60 | 0.10 | 411 |
| Phage-307 | D | D | — | — | — | — | — | — | — | — | T | Y | — | N | 0.08 | 0.60 | 0.09 | 412 |
| Phage-308 | F | — | — | — | — | — | — | E | — | V | F | H | — | Y | 0.09 | 0.60 | 0.09 | 413 |
| Phage-309 | T | D | — | W | — | D | W | E | — | Y | F | L | — | D | 0.07 | 0.60 | 0.09 | 414 |
| Phage-310 | — | — | — | — | — | — | W | E | — | — | Y | L | — | P | 0.09 | 0.60 | 0.09 | 415 |
| Phage-311 | D | D | — | — | — | N | G | Y | A | T | F | I | — | Y | 0.06 | 0.59 | 0.08 | 416 |
| Phage-312 | F | L | — | — | — | — | I | E | D | D | T | H | — | Y | 0.16 | 0.59 | 0.38 | 417 |
| Phage-313 | F | A | — | W | — | D | W | E | — | T | I | P | — | H | 0.08 | 0.59 | 0.08 | 418 |

TABLE 20-continued

Clonal Phage Peptide Sequences from the Peptide-B Optimization Library Panning (-)
indicates same amino acid as in CD3 scFv Peptide-B corresponding position (e.g. Phage-1 position).

| Phage ID | 1 | 2 | 3 | 4 | 5 | 6 | 7 | 8 | 9 | 10 | 11 | 12 | 13 | 14 | Background signal | SP34.185 scFv signal | SP34.185 scFv signal in presence of CD3 | SEQ ID NO: |
|---|---|---|---|---|---|---|---|---|---|---|---|---|---|---|---|---|---|---|
| Phage-314 | — | L | — | — | — | — | — | — | — | — | Y | N | — | Y | 0.10 | 0.58 | 0.08 | 419 |
| Phage-315 | Y | D | — | — | — | — | — | — | — | — | I | S | — | I | 0.09 | 0.58 | 0.09 | 420 |
| Phage-316 | Y | D | — | — | — | — | — | — | — | — | — | N | — | Y | 0.12 | 0.57 | 0.10 | 421 |
| Phage-317 | A | I | — | W | — | D | W | E | — | F | — | D | — | Y | 0.10 | 0.57 | 0.09 | 422 |
| Phage-318 | L | T | — | W | — | V | R | E | — | I | F | A | — | D | 0.07 | 0.57 | 0.08 | 423 |
| Phage-319 | — | L | — | — | — | — | — | — | — | — | Y | Y | — | N | 0.09 | 0.57 | 0.09 | 424 |
| Phage-320 | N | V | — | — | — | — | Y | — | — | — | A | P | — | N | 0.07 | 0.56 | 0.08 | 425 |
| Phage-321 | H | D | — | — | — | — | — | — | — | — | I | S | — | V | 0.11 | 0.55 | 0.09 | 426 |
| Phage-322 | F | D | — | — | — | — | L | — | — | T | — | D | — | N | 0.12 | 0.55 | 0.41 | 427 |
| Phage-323 | Y | F | — | — | — | — | V | E | — | H | F | Y | — | Y | 0.09 | 0.55 | 0.08 | 428 |
| Phage-324 | D | — | — | — | — | — | L | — | — | — | I | I | — | H | 0.09 | 0.54 | 0.09 | 429 |
| Phage-325 | D | D | — | — | — | — | V | P | — | D | I | T | — | Y | 0.11 | 0.54 | 0.08 | 430 |
| Phage-326 | D | N | — | — | — | — | L | — | — | — | — | V | — | D | 0.10 | 0.54 | 0.08 | 431 |
| Phage-327 | — | H | — | W | — | D | W | E | P | N | Y | V | — | D | 0.10 | 0.54 | 0.08 | 432 |
| Phage-328 | D | — | — | — | — | — | L | — | — | — | L | F | — | L | 0.09 | 0.53 | 0.09 | 433 |
| Phage-329 | D | D | — | — | — | — | L | — | — | — | — | V | — | A | 0.08 | 0.53 | 0.11 | 434 |
| Phage-330 | A | A | — | — | — | — | L | — | — | — | I | V | — | D | 0.13 | 0.53 | 0.09 | 435 |
| Phage-331 | D | F | — | — | — | — | — | E | — | I | N | N | — | F | 0.14 | 0.52 | 0.48 | 436 |
| Phage-332 | Y | — | — | — | — | — | — | — | — | — | N | A | — | Y | 0.08 | 0.52 | 0.07 | 437 |
| Phage-333 | — | L | — | — | — | — | — | — | — | — | N | S | — | Y | 0.10 | 0.52 | 0.11 | 438 |
| Phage-334 | Y | D | — | — | — | — | — | — | — | I | T | D | — | D | 0.09 | 0.52 | 0.09 | 439 |
| Phage-335 | D | S | — | — | — | — | — | E | F | Y | Y | V | — | F | 0.11 | 0.52 | 0.14 | 440 |
| Phage-336 | Y | I | — | — | — | — | L | — | — | — | L | I | — | H | 0.10 | 0.52 | 0.08 | 441 |
| Phage-337 | F | D | — | — | — | — | V | E | — | D | Y | F | — | Y | 0.11 | 0.52 | 0.10 | 442 |
| Phage-338 | F | D | — | — | — | — | Y | — | — | — | L | Y | — | F | 0.08 | 0.52 | 0.07 | 443 |
| Phage-339 | — | L | — | — | — | D | G | — | — | Y | S | F | — | H | 0.10 | 0.51 | 0.10 | 444 |
| Phage-340 | I | P | — | — | — | — | M | — | — | — | — | V | — | N | 0.12 | 0.51 | 0.09 | 445 |
| Phage-341 | I | I | — | — | — | D | G | Y | — | D | F | T | — | D | 0.12 | 0.51 | 0.09 | 446 |
| Phage-342 | I | F | — | — | — | — | L | — | — | — | I | I | — | Y | 0.11 | 0.51 | 0.08 | 447 |
| Phage-343 | — | D | — | — | — | — | — | — | — | — | Y | D | — | Y | 0.18 | 0.51 | 0.18 | 448 |
| Phage-344 | L | S | — | — | — | — | M | — | — | — | L | Y | — | D | 0.12 | 0.51 | 0.08 | 449 |
| Phage-345 | Y | D | — | W | — | D | W | E | Y | N | I | D | — | H | 0.08 | 0.51 | 0.09 | 450 |
| Phage-346 | N | H | — | — | — | D | G | — | — | T | I | V | — | F | 0.09 | 0.51 | 0.08 | 451 |

TABLE 20-continued

Clonal Phage Peptide Sequences from the Peptide-B Optimization Library Panning (-)
indicates same amino acid as in CD3 scFv Peptide-B corresponding position (e.g. Phage-1 position).

| Phage ID | Amino acid position sequence | | | | | | | | | | | | | | Background signal | SP34.185 scFv signal | SP34.185 scFv signal in presence of CD3 | SEQ ID NO: |
|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | | | | |
| Phage-347 | N | F | — | — | — | — | L | — | — | — | I | P | — | H | 0.11 | 0.50 | 0.12 | 452 |
| Phage-348 | F | H | — | — | — | — | I | E | — | Y | A | L | — | D | 0.08 | 0.50 | 0.09 | 453 |
| Phage-349 | — | — | — | — | — | — | V | E | D | Y | N | L | — | Y | 0.07 | 0.50 | 0.08 | 454 |
| Phage-350 | — | — | — | — | — | D | G | — | — | L | A | N | — | Y | 0.09 | 0.50 | 0.08 | 455 |
| Phage-351 | L | I | — | — | — | V | I | A | — | D | L | P | — | N | 0.17 | 0.50 | 0.26 | 456 |
| Phage-352 | D | I | — | — | — | — | I | P | — | D | — | S | — | D | 0.10 | 0.50 | 0.08 | 457 |
| Phage-353 | I | — | — | — | — | — | W | E | — | A | D | Y | — | D | 0.11 | 0.50 | 0.45 | 458 |
| Phage-354 | I | D | — | W | — | D | W | E | D | D | S | I | — | Y | 0.10 | 0.50 | 0.10 | 459 |
| Phage-355 | — | L | — | — | — | — | V | E | D | F | T | L | — | D | 0.09 | 0.50 | 0.11 | 460 |
| Phage-356 | L | — | — | — | — | V | I | E | — | I | Y | Y | — | Y | 0.09 | 0.49 | 0.09 | 461 |
| Phage-357 | F | F | — | — | — | — | — | E | V | H | S | D | — | N | 0.14 | 0.49 | 0.38 | 462 |
| Phage-358 | N | D | — | — | — | — | V | E | L | V | S | D | — | N | 0.10 | 0.49 | 0.08 | 463 |
| Phage-359 | D | L | — | — | — | — | L | — | — | — | T | V | — | D | 0.09 | 0.49 | 0.08 | 464 |
| Phage-360 | I | P | — | — | — | — | V | E | D | Y | N | L | — | N | 0.08 | 0.49 | 0.08 | 465 |
| Phage-361 | Y | — | — | — | — | — | L | E | W | P | — | V | — | N | 0.10 | 0.49 | 0.10 | 466 |
| Phage-362 | Y | D | — | — | — | — | L | — | — | — | — | I | — | N | 0.08 | 0.49 | 0.10 | 467 |
| Phage-363 | — | — | — | — | — | D | G | — | — | — | F | D | — | A | 0.08 | 0.49 | 0.08 | 468 |
| Phage-364 | N | D | — | — | — | — | W | E | D | T | Y | F | — | L | 0.08 | 0.49 | 0.10 | 469 |
| Phage-365 | P | — | — | — | — | — | M | E | — | L | S | N | — | S | 0.13 | 0.48 | 0.16 | 470 |
| Phage-366 | D | D | — | — | — | — | — | E | V | I | S | D | — | Y | 0.15 | 0.48 | 0.10 | 471 |
| Phage-367 | D | L | — | — | — | — | — | P | — | D | — | P | — | D | 0.08 | 0.48 | 0.08 | 472 |
| Phage-368 | I | — | — | — | — | — | — | — | — | — | F | V | — | Y | 0.11 | 0.48 | 0.10 | 473 |
| Phage-369 | A | — | — | — | — | — | Y | E | V | F | A | D | — | N | 0.10 | 0.48 | 0.11 | 474 |
| Phage-370 | I | D | — | — | — | — | Y | — | — | — | — | D | — | L | 0.09 | 0.48 | 0.09 | 475 |
| Phage-371 | H | I | — | W | — | D | W | E | — | F | H | D | — | N | 0.07 | 0.48 | 0.08 | 476 |
| Phage-372 | Y | D | — | — | — | — | L | — | — | T | I | T | — | L | 0.08 | 0.48 | 0.08 | 477 |
| Phage-373 | Y | L | — | — | — | — | L | — | — | T | I | L | — | N | 0.09 | 0.48 | 0.08 | 478 |
| Phage-374 | F | F | — | — | — | — | — | E | — | A | F | L | — | F | 0.10 | 0.48 | 0.14 | 479 |
| Phage-375 | I | L | — | — | — | — | L | — | — | — | F | T | — | A | 0.07 | 0.47 | 0.08 | 480 |
| Phage-376 | F | H | — | — | — | — | V | E | L | Y | T | D | — | N | 0.09 | 0.47 | 0.08 | 481 |
| Phage-377 | N | L | — | — | — | — | V | E | — | Y | N | F | — | Y | 0.08 | 0.47 | 0.08 | 482 |
| Phage-378 | F | D | — | — | — | — | V | E | — | T | Y | Y | — | F | 0.21 | 0.47 | 0.09 | 483 |
| Phage-379 | — | F | — | — | — | — | — | E | — | D | H | Y | — | Y | 0.12 | 0.47 | 0.37 | 484 |

TABLE 20-continued

Clonal Phage Peptide Sequences from the Peptide-B Optimization Library Panning (-)
indicates same amino acid as in CD3 scFv Peptide-B corresponding position (e.g. Phage-1 position).

| Phage | Amino acid position sequence | | | | | | | | | | | | | | Phage binding ELISA | | | SEQ ID |
| | | | | | | | | | | | | | | | Backgroud | SP34.185 scFv | SP34.185 scFv signal in presence | |
| ID | 1 | 2 | 3 | 4 | 5 | 6 | 7 | 8 | 9 | 10 | 11 | 12 | 13 | 14 | signal | signal | of CD3 | NO: |
|---|---|---|---|---|---|---|---|---|---|---|---|---|---|---|---|---|---|---|
| Phage-380 | A | I | — | — | — | — | W | E | V | V | A | D | — | N | 0.11 | 0.47 | 0.11 | 485 |
| Phage-381 | F | I | — | W | — | D | W | E | — | D | N | Y | — | N | 0.12 | 0.47 | 0.25 | 486 |
| Phage-382 | I | — | — | — | — | — | — | — | — | — | F | I | — | D | 0.08 | 0.47 | 0.10 | 487 |
| Phage-383 | N | L | — | — | — | — | V | E | D | V | Y | D | — | H | 0.12 | 0.47 | 0.43 | 488 |
| Phage-384 | H | — | — | — | — | — | V | E | — | Y | H | N | — | N | 0.09 | 0.47 | 0.09 | 489 |
| Phage-385 | D | I | — | — | — | — | Y | — | — | — | Y | S | — | T | 0.09 | 0.47 | 0.09 | 490 |
| Phage-386 | D | — | — | — | — | V | L | — | — | T | L | I | — | A | 0.13 | 0.46 | 0.10 | 491 |
| Phage-387 | I | A | — | — | — | — | M | P | — | D | I | D | — | Y | 0.12 | 0.46 | 0.09 | 492 |
| Phage-388 | I | D | — | — | — | — | L | — | — | — | I | F | — | D | 0.10 | 0.46 | 0.10 | 493 |
| Phage-389 | Y | F | — | — | — | D | V | E | — | D | F | A | — | D | 0.11 | 0.46 | 0.11 | 494 |
| Phage-390 | Y | N | — | — | — | — | W | E | Y | A | I | L | — | D | 0.12 | 0.46 | 0.34 | 495 |
| Phage-391 | I | — | — | — | — | — | V | E | D | Y | I | V | — | N | 0.14 | 0.46 | 0.22 | 496 |
| Phage-392 | Y | D | — | — | — | — | I | — | — | — | T | P | — | A | 0.07 | 0.46 | 0.07 | 497 |
| Phage-393 | D | T | — | W | — | D | W | E | H | I | Y | A | — | D | 0.09 | 0.46 | 0.09 | 498 |
| Phage-394 | D | I | — | — | — | — | M | — | — | — | — | T | — | N | 0.13 | 0.45 | 0.12 | 499 |
| Phage-395 | Y | D | — | W | — | D | W | E | R | Y | F | P | — | I | 0.10 | 0.45 | 0.09 | 500 |
| Phage-396 | H | L | — | — | — | — | L | — | — | — | — | A | — | S | 0.13 | 0.45 | 0.11 | 501 |
| Phage-397 | Y | D | — | — | — | D | G | — | — | T | T | I | — | A | 0.09 | 0.45 | 0.09 | 502 |
| Phage-398 | Y | — | — | — | — | — | Y | E | D | V | L | D | — | F | 0.07 | 0.45 | 0.08 | 503 |
| Phage-399 | D | F | — | — | — | — | M | — | — | T | I | S | — | D | 0.14 | 0.45 | 0.10 | 504 |
| Phage-400 | I | L | — | — | — | — | L | — | — | — | L | V | — | D | 0.08 | 0.44 | 0.07 | 505 |
| Phage-401 | L | I | — | — | — | — | W | E | V | I | T | N | — | D | 0.12 | 0.44 | 0.40 | 506 |
| Phage-402 | Y | D | — | — | — | — | — | — | — | Y | F | — | — | P | 0.09 | 0.44 | 0.09 | 507 |
| Phage-403 | A | L | — | — | — | — | V | E | V | Y | D | V | — | V | 0.08 | 0.44 | 0.08 | 508 |
| Phage-404 | Y | H | — | W | — | D | W | E | D | V | N | F | — | Y | 0.10 | 0.44 | 0.09 | 509 |
| Phage-405 | F | L | — | — | — | M | G | G | L | T | F | Y | — | Y | 0.09 | 0.44 | 0.08 | 510 |
| Phage-406 | I | I | — | — | — | — | — | — | — | Y | — | — | — | F | 0.09 | 0.43 | 0.19 | 511 |
| Phage-407 | F | F | — | — | — | — | M | — | — | — | — | H | — | F | 0.11 | 0.43 | 0.09 | 512 |
| Phage-408 | A | F | — | — | — | — | — | — | — | — | L | F | — | A | 0.09 | 0.43 | 0.09 | 513 |
| Phage-409 | N | — | — | — | — | D | G | — | — | T | N | I | — | D | 0.08 | 0.43 | 0.08 | 514 |
| Phage-410 | Y | L | — | — | — | — | W | E | W | V | H | N | — | L | 0.13 | 0.43 | 0.09 | 515 |
| Phage-411 | A | T | — | — | — | D | G | — | — | — | H | I | — | A | 0.08 | 0.43 | 0.09 | 516 |
| Phage-412 | — | — | — | — | — | — | V | E | V | L | D | Y | — | D | 0.07 | 0.42 | 0.08 | 517 |
| Phage-413 | I | H | — | — | — | — | W | E | F | Y | T | D | — | D | 0.08 | 0.42 | 0.08 | 518 |

TABLE 20-continued

Clonal Phage Peptide Sequences from the Peptide-B Optimization Library Panning (-)
indicates same amino acid as in CD3 scFv Peptide-B corresponding position (e.g. Phage-1 position).

| Phage ID | \| | 1 | 2 | 3 | 4 | 5 | 6 | 7 | 8 | 9 | 10 | 11 | 12 | 13 | 14 | \| | Background signal | SP34.185 scFv signal | SP34.185 scFv signal in presence of CD3 | SEQ ID NO: |
|---|---|---|---|---|---|---|---|---|---|---|---|---|---|---|---|---|---|---|---|---|
| Phage-414 | | D | D | — | — | — | — | L | — | — | T | — | A | — | D | | 0.13 | 0.42 | 0.32 | 519 |
| Phage-415 | | Y | L | — | — | — | — | — | — | — | — | I | D | — | N | | 0.11 | 0.42 | 0.17 | 520 |
| Phage-416 | | L | L | — | — | — | — | V | E | D | V | F | A | — | Y | | 0.09 | 0.42 | 0.09 | 521 |
| Phage-417 | | Y | D | — | — | — | — | L | — | — | — | L | T | — | D | | 0.08 | 0.42 | 0.08 | 522 |
| Phage-418 | | F | D | — | — | — | — | L | — | — | T | — | N | — | Y | | 0.09 | 0.41 | 0.09 | 523 |
| Phage-419 | | F | A | — | W | — | D | W | E | — | I | N | D | — | H | | 0.08 | 0.41 | 0.09 | 524 |
| Phage-420 | | Y | — | — | — | — | — | Y | E | — | D | I | Y | — | N | | 0.09 | 0.41 | 0.09 | 525 |
| Phage-421 | | N | V | — | — | — | — | V | E | D | Y | T | F | — | Y | | 0.09 | 0.40 | 0.08 | 526 |
| Phage-422 | | A | — | — | — | — | — | L | E | — | Y | D | F | — | T | | 0.12 | 0.40 | 0.08 | 527 |
| Phage-423 | | F | D | — | — | — | — | I | — | — | — | T | I | — | T | | 0.08 | 0.40 | 0.09 | 528 |
| Phage-424 | | N | L | — | — | — | — | L | — | — | T | L | V | — | A | | 0.10 | 0.40 | 0.09 | 529 |
| Phage-425 | | Y | S | — | W | — | D | W | E | — | Y | L | A | — | N | | 0.08 | 0.40 | 0.08 | 530 |
| Phage-426 | | G | I | — | — | — | — | V | E | D | Y | N | Y | — | D | | 0.09 | 0.40 | 0.10 | 531 |
| Phage-427 | | F | F | — | — | — | — | L | — | — | — | — | N | — | H | | 0.07 | 0.40 | 0.07 | 532 |
| Phage-428 | | Y | — | — | — | — | — | Y | E | — | D | F | Y | — | F | | 0.11 | 0.40 | 0.09 | 533 |
| Phage-429 | | L | — | — | — | — | — | Y | — | — | — | T | D | — | Y | | 0.11 | 0.40 | 0.10 | 534 |
| Phage-430 | | D | — | — | — | — | — | V | E | — | D | F | L | — | Y | | 0.10 | 0.40 | 0.08 | 535 |
| Phage-431 | | T | L | — | — | — | — | V | E | L | Y | I | F | — | D | | 0.08 | 0.40 | 0.09 | 536 |
| Phage-432 | | F | — | — | — | — | — | — | E | Q | I | A | D | — | Y | | 0.11 | 0.40 | 0.09 | 537 |
| Phage-433 | | D | D | — | — | — | — | V | E | — | Y | H | L | — | D | | 0.11 | 0.40 | 0.18 | 538 |
| Phage-434 | | D | — | — | — | — | — | L | E | D | V | T | L | — | H | | 0.13 | 0.39 | 0.09 | 539 |
| Phage-435 | | — | L | — | — | — | — | V | E | D | V | N | L | — | Y | | 0.09 | 0.39 | 0.08 | 540 |
| Phage-436 | | D | T | — | — | — | — | L | — | — | T | I | D | — | Y | | 0.09 | 0.39 | 0.09 | 541 |
| Phage-437 | | T | — | — | — | — | — | V | E | — | D | I | N | — | Y | | 0.08 | 0.39 | 0.08 | 542 |
| Phage-438 | | I | V | — | W | — | D | W | E | — | Y | P | N | — | D | | 0.08 | 0.39 | 0.08 | 543 |
| Phage-439 | | S | D | — | — | — | — | L | — | — | — | I | I | — | T | | 0.11 | 0.39 | 0.10 | 544 |
| Phage-440 | | Y | D | — | — | — | — | L | P | — | D | Y | D | — | N | | 0.15 | 0.39 | 0.10 | 545 |
| Phage-441 | | N | L | — | W | — | D | W | E | — | Y | Y | A | — | D | | 0.12 | 0.39 | 0.17 | 546 |
| Phage-442 | | D | D | — | — | — | — | L | — | — | — | L | P | — | H | | 0.10 | 0.39 | 0.08 | 547 |
| Phage-443 | | S | L | — | — | — | D | G | Q | — | D | Y | T | — | F | | 0.08 | 0.39 | 0.08 | 548 |
| Phage-444 | | L | I | — | W | — | D | W | E | — | Y | N | F | — | T | | 0.13 | 0.39 | 0.11 | 549 |
| Phage-445 | | F | H | — | — | — | D | G | — | — | T | — | P | — | I | | 0.08 | 0.39 | 0.08 | 550 |
| Phage-446 | | F | D | — | — | — | — | W | E | W | I | Y | D | — | F | | 0.08 | 0.38 | 0.08 | 551 |
| Phage-447 | | I | — | — | — | — | — | W | I | I | — | L | D | — | D | | 0.08 | 0.38 | 0.09 | 552 |

TABLE 20-continued

Clonal Phage Peptide Sequences from the Peptide-B Optimization Library Panning (-)
indicates same amino acid as in CD3 scFv Peptide-B corresponding position (e.g. Phage-1 position).

| Phage | Amino acid position sequence | | | | | | | | | | | | | | Background | SP34.185 scFv | SP34.185 scFv signal in presence | SEQ ID |
|---|---|---|---|---|---|---|---|---|---|---|---|---|---|---|---|---|---|---|
| ID | 1 | 2 | 3 | 4 | 5 | 6 | 7 | 8 | 9 | 10 | 11 | 12 | 13 | 14 | signal | signal | of CD3 | NO: |
| Phage-448 | L | I | — | — | — | — | I | — | — | — | A | S | — | N | 0.10 | 0.38 | 0.11 | 553 |
| Phage-449 | T | S | — | W | V | D | W | E | — | F | S | D | — | I | 0.11 | 0.38 | 0.34 | 554 |
| Phage-450 | Y | — | — | — | — | — | V | E | — | D | Y | V | — | D | 0.10 | 0.38 | 0.08 | 555 |
| Phage-451 | D | D | — | — | — | — | Q | E | F | T | Y | A | — | T | 0.09 | 0.38 | 0.08 | 556 |
| Phage-452 | A | D | — | W | — | D | W | E | — | Y | A | D | — | Y | 0.11 | 0.38 | 0.10 | 557 |
| Phage-453 | Y | — | — | — | — | — | — | — | — | — | I | H | — | I | 0.08 | 0.38 | 0.07 | 558 |
| Phage-454 | S | E | — | W | — | D | W | E | P | F | F | D | — | N | 0.08 | 0.37 | 0.09 | 559 |
| Phage-455 | Y | H | — | — | — | — | M | — | — | — | L | I | — | T | 0.07 | 0.37 | 0.07 | 560 |
| Phage-456 | S | D | — | W | — | D | W | E | D | A | Y | F | — | I | 0.09 | 0.37 | 0.07 | 561 |
| Phage-457 | — | D | — | — | — | — | V | E | — | Y | Y | H | — | D | 0.08 | 0.37 | 0.08 | 562 |
| Phage-458 | D | N | — | — | — | — | Y | — | — | — | I | A | — | N | 0.10 | 0.37 | 0.10 | 563 |
| Phage-459 | L | — | — | — | — | V | — | E | F | Y | D | Y | — | Y | 0.08 | 0.37 | 0.10 | 564 |
| Phage-460 | Y | T | — | — | — | — | M | — | — | — | — | T | — | I | 0.09 | 0.37 | 0.08 | 565 |
| Phage-461 | N | F | — | W | — | D | W | E | V | N | S | F | — | D | 0.09 | 0.37 | 0.08 | 566 |
| Phage-462 | N | A | — | W | — | D | W | E | Y | I | D | F | — | N | 0.12 | 0.36 | 0.09 | 567 |
| Phage-463 | Y | N | — | — | — | — | M | — | — | — | I | F | — | S | 0.09 | 0.36 | 0.07 | 568 |
| Phage-464 | L | D | — | — | — | — | L | — | — | — | I | T | — | Y | 0.08 | 0.36 | 0.09 | 569 |
| Phage-465 | H | — | — | — | — | — | — | — | — | — | I | N | — | D | 0.11 | 0.36 | 0.08 | 570 |
| Phage-466 | I | I | — | — | — | — | L | P | — | D | Y | V | — | T | 0.08 | 0.36 | 0.08 | 571 |
| Phage-467 | D | I | — | — | — | — | — | — | — | — | I | D | — | S | 0.08 | 0.36 | 0.08 | 572 |
| Phage-468 | P | — | — | — | — | — | — | — | — | — | — | L | — | F | 0.10 | 0.36 | 0.09 | 573 |
| Phage-469 | — | F | — | — | — | — | — | — | — | — | — | D | — | Y | 0.07 | 0.36 | 0.08 | 574 |
| Phage-470 | Y | D | — | W | — | D | W | E | — | A | L | P | — | A | 0.08 | 0.36 | 0.08 | 575 |
| Phage-471 | D | D | — | W | — | D | W | E | D | Y | — | F | — | F | 0.10 | 0.36 | 0.10 | 576 |
| Phage-472 | H | F | — | — | — | — | W | E | L | F | S | D | — | Y | 0.11 | 0.36 | 0.11 | 577 |
| Phage-473 | I | T | — | W | — | D | W | E | V | N | F | P | — | Y | 0.07 | 0.35 | 0.07 | 578 |
| Phage-474 | P | D | — | — | — | — | L | — | — | — | I | T | — | N | 0.20 | 0.35 | 0.16 | 579 |
| Phage-475 | N | L | — | W | — | D | W | E | A | F | F | P | — | Y | 0.08 | 0.35 | 0.07 | 580 |
| Phage-476 | F | — | — | — | — | — | — | E | Y | I | R | D | — | Y | 0.08 | 0.35 | 0.07 | 581 |
| Phage-477 | F | F | — | — | — | — | — | — | — | — | I | I | — | D | 0.09 | 0.35 | 0.10 | 582 |
| Phage-478 | — | L | — | — | — | K | G | G | P | T | Y | N | — | S | 0.08 | 0.35 | 0.10 | 583 |
| Phage-479 | L | A | — | W | — | V | W | E | — | P | G | H | — | D | 0.11 | 0.35 | 0.10 | 584 |
| Phage-480 | D | — | — | — | — | — | V | E | D | V | N | D | — | Y | 0.07 | 0.35 | 0.08 | 585 |
| Phage-481 | D | — | — | — | — | — | — | E | — | A | H | Y | — | N | 0.08 | 0.35 | 0.07 | 586 |

TABLE 20-continued

Clonal Phage Peptide Sequences from the Peptide-B Optimization Library Panning (-)
indicates same amino acid as in CD3 scFv Peptide-B corresponding position (e.g. Phage-1 position).

| Phage ID | \multicolumn amino acid position sequence 1 | 2 | 3 | 4 | 5 | 6 | 7 | 8 | 9 | 10 | 11 | 12 | 13 | 14 | Background signal | SP34.185 scFv signal | SP34.185 scFv signal in presence of CD3 | SEQ ID NO: |
|---|---|---|---|---|---|---|---|---|---|---|---|---|---|---|---|---|---|---|
| Phage-482 | — | L | — | — | — | — | L | — | — | T | L | T | — | I | 0.08 | 0.35 | 0.07 | 587 |
| Phage-483 | Y | — | — | — | — | — | I | E | D | Y | N | L | — | N | 0.10 | 0.34 | 0.09 | 588 |
| Phage-484 | Y | I | — | — | — | — | V | E | — | Y | Y | N | — | F | 0.13 | 0.34 | 0.14 | 589 |
| Phage-485 | D | I | — | — | — | — | L | — | — | — | I | F | — | F | 0.08 | 0.34 | 0.09 | 590 |
| Phage-486 | D | I | — | — | — | — | V | E | — | D | Y | L | — | Y | 0.07 | 0.34 | 0.08 | 591 |
| Phage-487 | T | L | — | — | — | — | — | E | — | D | A | P | — | I | 0.10 | 0.34 | 0.08 | 592 |
| Phage-488 | N | — | — | W | — | D | W | E | Y | I | N | S | — | V | 0.14 | 0.34 | 0.09 | 593 |
| Phage-489 | N | D | — | — | — | — | V | E | — | Y | Y | Y | — | T | 0.07 | 0.34 | 0.09 | 594 |
| Phage-490 | I | T | — | — | — | — | M | — | — | — | I | D | — | N | 0.08 | 0.34 | 0.08 | 595 |
| Phage-491 | Y | — | — | — | — | — | M | A | — | D | L | I | — | D | 0.10 | 0.34 | 0.29 | 596 |
| Phage-492 | I | D | — | — | — | — | L | — | — | — | I | V | — | T | 0.11 | 0.33 | 0.09 | 597 |
| Phage-493 | H | T | — | W | — | D | W | E | W | D | — | Y | — | D | 0.08 | 0.33 | 0.07 | 598 |
| Phage-494 | I | H | — | — | — | — | W | E | L | I | D | D | — | L | 0.08 | 0.33 | 0.10 | 599 |
| Phage-495 | Y | T | — | — | — | — | L | — | — | — | T | T | — | T | 0.08 | 0.33 | 0.08 | 600 |
| Phage-496 | F | H | — | — | — | — | V | E | — | T | — | Y | — | F | 0.11 | 0.33 | 0.09 | 601 |
| Phage-497 | D | — | — | — | — | — | L | — | — | — | L | I | — | N | 0.07 | 0.33 | 0.08 | 602 |
| Phage-498 | I | — | — | — | — | — | — | — | — | — | D | Y | — | I | 0.08 | 0.33 | 0.10 | 603 |
| Phage-499 | D | L | — | — | — | — | I | E | — | D | L | V | — | T | 0.09 | 0.33 | 0.09 | 604 |
| Phage-500 | N | I | — | — | — | — | L | Q | — | D | I | V | — | P | 0.09 | 0.33 | 0.09 | 605 |
| Phage-501 | N | N | — | — | — | — | M | — | — | — | I | T | — | Y | 0.08 | 0.33 | 0.08 | 606 |
| Phage-502 | H | T | — | — | — | — | L | — | — | — | I | V | — | V | 0.08 | 0.33 | 0.08 | 607 |
| Phage-503 | Y | — | — | — | — | — | I | E | D | I | L | V | — | T | 0.12 | 0.33 | 0.23 | 608 |
| Phage-504 | N | T | — | — | — | — | — | E | F | V | H | L | — | P | 0.07 | 0.33 | 0.11 | 609 |
| Phage-505 | D | I | — | — | — | — | M | — | — | — | T | V | — | D | 0.10 | 0.33 | 0.09 | 610 |
| Phage-506 | A | I | — | — | — | — | V | E | I | V | N | Y | — | Y | 0.09 | 0.32 | 0.07 | 611 |
| Phage-507 | H | L | — | — | — | — | V | E | D | P | T | A | — | V | 0.10 | 0.32 | 0.28 | 612 |
| Phage-508 | A | D | — | — | — | — | L | — | — | — | I | S | — | T | 0.10 | 0.32 | 0.09 | 613 |
| Phage-509 | F | D | — | — | — | — | L | — | — | — | — | I | — | D | 0.07 | 0.32 | 0.09 | 614 |
| Phage-510 | D | V | — | — | — | — | — | — | — | — | I | D | — | N | 0.10 | 0.32 | 0.08 | 615 |
| Phage-511 | Y | L | — | — | — | — | V | E | — | I | S | I | — | F | 0.08 | 0.32 | 0.07 | 616 |
| Phage-512 | S | A | — | — | — | — | — | — | — | — | L | H | — | V | 0.10 | 0.31 | 0.30 | 617 |
| Phage-513 | H | L | — | W | — | D | W | E | — | D | S | A | — | N | 0.08 | 0.31 | 0.08 | 618 |
| Phage-514 | H | T | — | W | — | D | W | E | Y | D | Y | D | — | F | 0.10 | 0.31 | 0.08 | 619 |
| Phage-515 | Y | D | — | — | — | — | W | E | — | V | A | L | — | N | 0.10 | 0.31 | 0.10 | 620 |

TABLE 20-continued

Clonal Phage Peptide Sequences from the Peptide-B Optimization Library Panning (-)
indicates same amino acid as in CD3 scFv Peptide-B corresponding position (e.g. Phage-1 position).

| Phage ID | \multicolumn{14}{c}{Amino acid position sequence} | | | | | | | | | | | | | Background signal | SP34.185 scFv signal | SP34.185 scFv signal in presence of CD3 | SEQ ID NO: |
|---|---|---|---|---|---|---|---|---|---|---|---|---|---|---|---|---|---|---|
|  | 1 | 2 | 3 | 4 | 5 | 6 | 7 | 8 | 9 | 10 | 11 | 12 | 13 | 14 |  |  |  |  |
| Phage-516 | T | L | — | — | — | — | I | E | — | Y | I | V | — | Y | 0.09 | 0.31 | 0.23 | 621 |
| Phage-517 | S | — | — | — | — | — | — | — | — | — | I | F | — | T | 0.09 | 0.31 | 0.09 | 622 |
| Phage-518 | D | I | — | — | — | — | — | — | — | — | L | H | — | Y | 0.08 | 0.31 | 0.08 | 623 |
| Phage-519 | L | F | — | — | — | — | — | E | — | A | Y | L | — | I | 0.08 | 0.31 | 0.08 | 624 |
| Phage-520 | I | F | — | — | — | — | I | E | — | D | F | V | — | T | 0.10 | 0.31 | 0.10 | 625 |
| Phage-521 | D | D | — | — | — | — | W | E | Y | Y | — | A | — | V | 0.08 | 0.31 | 0.08 | 626 |
| Phage-522 | D | D | — | — | — | — | L | — | — | T | T | I | — | Y | 0.10 | 0.31 | 0.09 | 627 |
| Phage-523 | A | S | — | — | — | — | L | — | — | — | T | A | — | D | 0.10 | 0.31 | 0.09 | 628 |
| Phage-524 | Y | L | — | — | — | — | V | E | D | Y | D | Y | — | Y | 0.08 | 0.31 | 0.09 | 629 |
| Phage-525 | D | L | — | — | — | — | W | E | — | T | I | F | — | A | 0.12 | 0.30 | 0.09 | 630 |
| Phage-526 | D | F | — | — | — | D | G | E | — | F | Y | I | — | P | 0.12 | 0.30 | 0.11 | 631 |
| Phage-527 | — | — | — | — | — | — | V | E | — | N | I | L | — | H | 0.15 | 0.30 | 0.17 | 632 |
| Phage-528 | D | — | — | — | — | — | V | E | — | N | Y | F | — | F | 0.12 | 0.30 | 0.21 | 633 |
| Phage-529 | N | D | — | W | — | D | W | Y | — | F | L | S | — | D | 0.10 | 0.30 | 0.10 | 634 |
| Phage-530 | R | D | — | W | — | D | W | E | V | P | Y | F | — | D | 0.08 | 0.30 | 0.09 | 635 |
| Phage-531 | N | L | — | — | — | — | V | E | — | A | — | Y | — | Y | 0.10 | 0.30 | 0.13 | 636 |
| Phage-532 | F | D | — | W | — | D | G | E | L | N | Y | L | — | T | 0.23 | 0.30 | 0.08 | 637 |
| Phage-533 | Y | — | — | — | — | — | V | E | D | V | N | L | — | I | 0.18 | 0.30 | 0.10 | 638 |
| Phage-534 | D | N | — | — | — | — | Y | — | — | — | I | T | — | L | 0.11 | 0.29 | 0.09 | 639 |
| Phage-535 | L | N | — | W | — | D | W | E | — | D | Y | S | — | N | 0.09 | 0.29 | 0.09 | 640 |
| Phage-536 | P | T | — | — | — | — | V | E | — | L | L | S | — | N | 0.12 | 0.29 | 0.26 | 641 |
| Phage-537 | D | H | — | — | — | — | V | E | L | I | F | Y | — | H | 0.11 | 0.29 | 0.08 | 642 |
| Phage-538 | F | H | — | — | — | — | L | — | — | — | I | F | — | Y | 0.08 | 0.29 | 0.08 | 643 |
| Phage-539 | F | D | — | — | — | — | L | E | — | T | — | V | — | P | 0.16 | 0.29 | 0.16 | 644 |
| Phage-540 | D | F | — | — | — | — | L | — | — | — | L | P | — | A | 0.08 | 0.29 | 0.08 | 645 |
| Phage-541 | D | S | — | — | — | — | L | — | — | — | I | Y | — | D | 0.09 | 0.29 | 0.09 | 646 |
| Phage-542 | A | D | — | W | — | D | W | E | — | F | L | L | — | F | 0.12 | 0.29 | 0.10 | 647 |
| Phage-543 | I | L | — | — | — | — | V | E | — | L | D | F | — | N | 0.10 | 0.28 | 0.08 | 648 |
| Phage-544 | F | F | — | — | — | — | — | E | — | I | F | L | — | Y | 0.09 | 0.28 | 0.07 | 649 |
| Phage-545 | Y | N | — | — | — | D | G | — | — | — | Y | D | — | H | 0.07 | 0.28 | 0.07 | 650 |
| Phage-546 | D | N | — | — | — | — | L | — | — | T | I | T | — | F | 0.11 | 0.28 | 0.11 | 651 |
| Phage-547 | H | N | — | — | — | D | G | — | — | A | F | I | — | N | 0.09 | 0.28 | 0.23 | 652 |
| Phage-548 | D | — | — | — | — | — | V | E | — | D | L | V | — | P | 0.10 | 0.28 | 0.23 | 653 |

TABLE 20-continued

Clonal Phage Peptide Sequences from the Peptide-B Optimization Library Panning (-)
indicates same amino acid as in CD3 scFv Peptide-B corresponding position (e.g. Phage-1 position).

| Phage ID | \multicolumn{14}{c}{Amino acid position sequence} | | | | | | | | | | | | | Backgroud signal | SP34.185 scFv signal | SP34.185 scFv signal in presence of CD3 | SEQ ID NO: |
|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | | | | |
| Phage-549 | D | — | — | — | — | — | L | — | — | — | — | L | N | — | F | 0.08 | 0.28 | 0.07 | 654 |
| Phage-550 | D | — | — | — | — | — | — | Q | — | D | F | H | — | H | 0.11 | 0.28 | 0.27 | 655 |
| Phage-551 | Y | D | — | — | — | — | W | E | F | T | D | D | — | I | 0.10 | 0.28 | 0.18 | 656 |
| Phage-552 | D | I | — | — | — | — | Y | E | — | D | I | I | — | Y | 0.14 | 0.28 | 0.19 | 657 |
| Phage-553 | F | D | — | — | — | — | L | — | — | T | — | P | — | P | 0.11 | 0.28 | 0.08 | 658 |
| Phage-554 | N | — | — | — | — | — | L | — | — | T | S | V | — | D | 0.09 | 0.28 | 0.26 | 659 |
| Phage-555 | Y | — | — | — | — | — | W | E | F | — | F | D | — | D | 0.17 | 0.28 | 0.11 | 660 |
| Phage-556 | Y | A | — | — | — | — | L | — | — | — | — | T | — | D | 0.09 | 0.28 | 0.08 | 661 |
| Phage-557 | F | L | — | — | — | — | V | E | Q | D | Y | F | — | V | 0.08 | 0.28 | 0.10 | 662 |
| Phage-558 | D | N | — | — | — | — | — | — | — | — | — | R | — | D | 0.09 | 0.27 | 0.26 | 663 |
| Phage-559 | N | D | — | — | — | D | G | I | — | T | — | D | — | Y | 0.10 | 0.27 | 0.24 | 664 |
| Phage-560 | Y | F | — | — | — | — | V | E | D | Y | N | D | — | F | 0.08 | 0.27 | 0.09 | 665 |
| Phage-561 | N | L | — | — | — | — | — | — | — | — | I | F | — | Y | 0.10 | 0.27 | 0.07 | 666 |
| Phage-562 | I | D | — | W | — | D | W | E | — | Y | I | P | — | T | 0.10 | 0.27 | 0.08 | 667 |
| Phage-563 | I | — | — | — | — | D | G | — | — | — | F | I | — | A | 0.07 | 0.27 | 0.08 | 668 |
| Phage-564 | D | — | — | — | — | — | — | — | — | — | — | V | — | Y | 0.08 | 0.27 | 0.07 | 669 |
| Phage-565 | — | F | — | — | — | — | W | E | D | I | T | D | — | D | 0.13 | 0.27 | 0.09 | 670 |
| Phage-566 | L | D | — | — | — | — | V | — | — | T | F | T | — | H | 0.08 | 0.26 | 0.08 | 671 |
| Phage-567 | D | D | — | — | — | — | Y | — | — | — | F | A | — | H | 0.13 | 0.26 | 0.10 | 672 |
| Phage-568 | I | — | — | — | — | — | Y | Q | — | D | L | P | — | N | 0.12 | 0.26 | 0.11 | 673 |
| Phage-569 | L | D | — | — | — | — | V | E | — | Y | N | Y | — | V | 0.09 | 0.26 | 0.08 | 674 |
| Phage-570 | Y | V | — | — | — | — | — | — | — | — | S | A | — | N | 0.14 | 0.26 | 0.08 | 675 |
| Phage-571 | T | P | — | — | — | — | L | E | — | A | I | — | — | Y | 0.10 | 0.26 | 0.10 | 676 |
| Phage-572 | Y | F | — | — | — | — | — | — | — | — | A | D | — | N | 0.08 | 0.26 | 0.08 | 677 |
| Phage-573 | D | D | — | — | — | — | — | E | — | D | I | I | — | D | 0.12 | 0.26 | 0.25 | 678 |
| Phage-574 | L | — | — | — | — | V | V | E | — | L | N | H | — | N | 0.08 | 0.26 | 0.09 | 679 |
| Phage-575 | — | I | — | — | — | D | G | E | — | L | I | A | — | A | 0.09 | 0.26 | 0.27 | 680 |
| Phage-576 | F | A | — | W | — | D | W | Q | — | T | Y | V | — | N | 0.09 | 0.25 | 0.08 | 681 |
| Phage-577 | Y | I | — | — | — | — | V | E | F | L | F | F | — | N | 0.08 | 0.25 | 0.08 | 682 |
| Phage-578 | T | Q | — | — | — | K | G | E | P | T | Y | H | — | Y | 0.12 | 0.25 | 0.12 | 683 |
| Phage-579 | N | — | — | — | — | — | V | E | — | Y | H | N | — | D | 0.10 | 0.25 | 0.17 | 684 |
| Phage-580 | — | — | — | — | — | — | W | E | F | F | S | D | — | A | 0.08 | 0.25 | 0.07 | 685 |
| Phage-581 | F | — | — | — | — | — | L | E | — | — | F | F | — | Y | 0.10 | 0.25 | 0.22 | 686 |

TABLE 20-continued

Clonal Phage Peptide Sequences from the Peptide-B Optimization Library Panning (-)
indicates same amino acid as in CD3 scFv Peptide-B corresponding position (e.g. Phage-1 position).

| Phage | Amino acid position sequence | | | | | | | | | | | | | | Backgroud signal | SP34.185 scFv signal | SP34.185 scFv signal in presence of CD3 | SEQ ID NO: |
|---|---|---|---|---|---|---|---|---|---|---|---|---|---|---|---|---|---|---|
| ID | 1 | 2 | 3 | 4 | 5 | 6 | 7 | 8 | 9 | 10 | 11 | 12 | 13 | 14 | | | | |
| Phage-582 | D | — | — | — | — | — | I | E | — | N | F | Y | — | Y | 0.13 | 0.25 | 0.09 | 687 |
| Phage-583 | Y | A | — | — | — | — | V | E | — | Y | — | Y | — | A | 0.08 | 0.25 | 0.09 | 688 |
| Phage-584 | — | D | — | — | — | — | — | L | — | — | — | I | — | D | 0.08 | 0.25 | 0.07 | 689 |
| Phage-585 | N | D | — | — | — | — | M | — | — | — | — | I | A | — | Y | 0.07 | 0.25 | 0.07 | 690 |
| Phage-586 | — | — | — | — | — | — | — | — | — | Y | L | A | — | A | 0.09 | 0.25 | 0.21 | 691 |
| Phage-587 | — | I | — | — | — | — | — | — | — | — | A | N | — | D | 0.08 | 0.25 | 0.09 | 692 |
| Phage-588 | L | T | — | W | — | D | W | E | — | D | F | F | — | N | 0.07 | 0.24 | 0.07 | 693 |
| Phage-589 | F | — | — | — | — | — | Q | E | — | I | N | Y | — | Y | 0.10 | 0.24 | 0.23 | 694 |
| Phage-590 | T | — | — | — | — | — | L | E | — | F | F | L | — | Y | 0.13 | 0.24 | 0.08 | 695 |
| Phage-591 | P | D | — | — | — | — | L | — | — | — | — | A | — | H | 0.12 | 0.24 | 0.09 | 696 |
| Phage-592 | N | D | — | — | — | — | — | E | — | I | I | F | — | V | 0.09 | 0.24 | 0.24 | 697 |
| Phage-593 | Y | I | — | — | — | — | — | — | — | — | F | Y | — | N | 0.25 | 0.24 | 0.08 | 698 |
| Phage-594 | H | A | — | — | — | — | L | — | — | — | L | L | — | N | 0.20 | 0.24 | 0.07 | 699 |
| Phage-595 | Y | — | — | — | — | — | W | E | — | A | — | L | — | A | 0.09 | 0.24 | 0.21 | 700 |
| Phage-596 | A | F | — | — | — | — | V | E | — | Y | D | L | — | N | 0.10 | 0.24 | 0.16 | 701 |
| Phage-597 | Y | N | — | — | — | — | — | — | — | — | — | A | — | S | 0.15 | 0.23 | 0.09 | 702 |
| Phage-598 | Y | L | — | — | — | — | V | E | D | A | T | L | — | A | 0.08 | 0.23 | 0.09 | 703 |
| Phage-599 | A | V | — | — | — | — | — | — | — | — | — | N | — | D | 0.08 | 0.23 | 0.08 | 704 |
| Phage-600 | N | — | — | — | — | — | W | E | V | Y | S | L | — | P | 0.13 | 0.23 | 0.08 | 705 |
| Phage-601 | D | F | — | — | — | — | V | E | — | D | T | Y | — | H | 0.07 | 0.23 | 0.07 | 706 |
| Phage-602 | I | S | — | — | — | — | Y | E | W | D | Y | A | — | N | 0.08 | 0.23 | 0.10 | 707 |
| Phage-603 | — | N | — | — | — | — | L | — | — | — | I | I | — | Y | 0.08 | 0.23 | 0.08 | 708 |
| Phage-604 | Y | D | — | — | — | — | — | — | — | T | A | P | — | Y | 0.07 | 0.23 | 0.08 | 709 |
| Phage-605 | Y | L | — | — | — | — | — | E | — | N | F | L | — | T | 0.09 | 0.23 | 0.22 | 710 |
| Phage-606 | F | D | — | — | — | — | V | — | — | — | — | D | — | A | 0.08 | 0.22 | 0.09 | 711 |
| Phage-607 | Y | D | — | — | — | — | Q | E | — | I | S | F | — | N | 0.09 | 0.22 | 0.09 | 712 |
| Phage-608 | I | D | — | — | — | — | T | E | L | Y | D | D | — | F | 0.09 | 0.22 | 0.09 | 713 |
| Phage-609 | T | F | — | — | — | — | L | — | — | — | — | Y | — | Y | 0.08 | 0.22 | 0.07 | 714 |
| Phage-610 | F | F | — | — | — | — | I | — | — | — | N | A | — | V | 0.09 | 0.22 | 0.07 | 715 |
| Phage-611 | Y | H | — | W | — | D | W | E | P | I | Y | I | — | I | 0.12 | 0.22 | 0.10 | 716 |
| Phage-612 | A | I | — | — | — | — | Y | E | — | D | H | Y | — | Y | 0.08 | 0.22 | 0.08 | 717 |
| Phage-613 | P | L | — | — | — | D | G | F | — | N | Y | N | — | F | 0.12 | 0.22 | 0.08 | 718 |
| Phage-614 | F | P | — | W | — | D | W | E | W | D | N | N | — | H | 0.09 | 0.22 | 0.09 | 719 |

TABLE 20-continued

Clonal Phage Peptide Sequences from the Peptide-B Optimization Library Panning (-)
indicates same amino acid as in CD3 scFv Peptide-B corresponding position (e.g. Phage-1 position).

| Phage ID | Amino acid position sequence | | | | | | | | | | | | | | Background signal | SP34.185 scFv signal | SP34.185 scFv signal in presence of CD3 | SEQ ID NO: |
|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | | | | |
| Phage-615 | — | D | — | — | — | D | G | — | — | L | A | A | — | H | 0.10 | 0.22 | 0.11 | 720 |
| Phage-616 | — | D | — | W | — | D | W | E | — | Y | Y | S | — | D | 0.08 | 0.22 | 0.07 | 721 |
| Phage-617 | — | — | — | — | — | — | Y | — | — | — | Y | D | — | T | 0.07 | 0.21 | 0.10 | 722 |
| Phage-618 | N | L | — | — | — | — | W | E | N | F | A | D | — | F | 0.08 | 0.21 | 0.08 | 723 |
| Phage-619 | Y | L | — | — | — | — | L | E | V | F | F | V | — | D | 0.12 | 0.21 | 0.10 | 724 |
| Phage-620 | I | F | — | — | — | — | L | E | D | Y | S | I | — | F | 0.09 | 0.21 | 0.08 | 725 |
| Phage-621 | D | — | — | — | — | — | L | E | Q | Y | D | L | — | F | 0.09 | 0.21 | 0.08 | 726 |
| Phage-622 | L | L | — | — | — | V | N | E | D | P | L | D | — | Y | 0.11 | 0.21 | 0.13 | 727 |
| Phage-623 | I | D | — | — | — | — | — | — | — | — | — | F | — | Y | 0.08 | 0.21 | 0.08 | 728 |
| Phage-624 | I | I | — | — | — | — | V | E | — | I | D | I | — | S | 0.08 | 0.21 | 0.08 | 729 |
| Phage-625 | I | A | — | W | — | D | W | E | D | Y | S | S | — | P | 0.08 | 0.21 | 0.11 | 730 |
| Phage-626 | Y | — | — | — | — | — | V | E | D | I | N | D | — | I | 0.09 | 0.21 | 0.07 | 731 |
| Phage-627 | N | I | — | — | — | — | M | — | — | — | I | D | — | I | 0.08 | 0.21 | 0.07 | 732 |
| Phage-628 | F | D | — | W | — | D | W | E | — | L | — | S | — | Y | 0.07 | 0.21 | 0.08 | 733 |
| Phage-629 | Y | F | — | — | — | — | W | E | D | H | F | F | — | D | 0.09 | 0.21 | 0.19 | 734 |
| Phage-630 | T | — | — | — | — | — | — | E | — | D | S | Y | — | D | 0.12 | 0.20 | 0.09 | 735 |
| Phage-631 | N | L | — | — | — | — | V | E | L | I | D | I | — | S | 0.11 | 0.20 | 0.09 | 736 |
| Phage-632 | D | N | — | — | — | — | W | E | — | V | Y | L | — | N | 0.08 | 0.20 | 0.08 | 737 |
| Phage-633 | F | L | — | — | — | — | — | — | — | — | D | L | — | F | 0.08 | 0.20 | 0.09 | 738 |
| Phage-634 | H | I | — | — | — | — | Q | — | — | — | I | — | — | T | 0.09 | 0.20 | 0.19 | 739 |
| Phage-635 | F | D | — | W | — | D | W | E | D | N | S | Y | — | D | 0.10 | 0.20 | 0.09 | 740 |
| Phage-636 | T | A | — | — | — | — | W | E | F | D | F | N | — | D | 0.08 | 0.20 | 0.07 | 741 |
| Phage-637 | H | H | — | W | — | D | W | E | D | Y | S | T | — | P | 0.10 | 0.20 | 0.11 | 742 |
| Phage-638 | Y | — | — | — | — | — | — | — | — | — | — | N | — | F | 0.07 | 0.20 | 0.08 | 743 |
| Phage-639 | L | H | — | W | — | D | W | E | — | I | D | I | — | D | 0.08 | 0.20 | 0.09 | 744 |
| Phage-640 | D | I | — | — | — | D | G | Q | — | D | F | V | — | S | 0.08 | 0.20 | 0.09 | 745 |
| Phage-641 | D | V | — | W | — | D | W | E | V | N | Y | F | — | D | 0.09 | 0.20 | 0.07 | 746 |
| Phage-642 | — | N | — | — | — | — | M | — | — | — | I | D | — | A | 0.12 | 0.20 | 0.10 | 747 |
| Phage-643 | D | N | — | — | — | — | — | — | — | A | T | V | — | N | 0.11 | 0.19 | 0.19 | 748 |
| Phage-644 | D | L | — | — | — | — | — | E | — | V | H | N | — | N | 0.08 | 0.19 | 0.08 | 749 |
| Phage-645 | — | N | — | — | — | — | — | — | — | — | S | Y | — | F | 0.13 | 0.19 | 0.09 | 750 |
| Phage-646 | N | I | — | W | — | D | W | E | — | D | N | F | — | S | 0.08 | 0.19 | 0.08 | 751 |
| Phage-647 | F | V | — | — | — | — | W | E | V | Y | D | D | — | D | 0.08 | 0.19 | 0.08 | 752 |

TABLE 20-continued

Clonal Phage Peptide Sequences from the Peptide-B Optimization Library Panning (-)
indicates same amino acid as in CD3 scFv Peptide-B corresponding position (e.g. Phage-1 position).

| Phage ID | Amino acid position sequence | | | | | | | | | | | | | | Phage binding ELISA | | | SEQ ID NO: |
|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | Background signal | SP34.185 scFv signal | SP34.185 scFv signal in presence of CD3 | |
| Phage-648 | A | — | — | — | — | — | L | E | V | V | H | L | — | V | 0.10 | 0.19 | 0.17 | 753 |
| Phage-649 | P | F | — | — | — | — | M | — | — | T | I | D | — | Y | 0.07 | 0.19 | 0.09 | 754 |
| Phage-650 | L | L | — | — | — | V | M | E | D | V | F | A | — | Y | 0.08 | 0.19 | 0.08 | 755 |
| Phage-651 | D | L | — | — | — | — | — | — | — | — | T | N | — | Y | 0.07 | 0.19 | 0.08 | 756 |
| Phage-652 | H | D | — | — | — | — | M | E | — | Y | Y | L | — | P | 0.10 | 0.18 | 0.10 | 757 |
| Phage-653 | T | D | — | — | — | — | Y | — | — | — | I | I | — | P | 0.08 | 0.18 | 0.09 | 758 |
| Phage-654 | — | L | — | W | — | D | W | E | D | Y | A | D | — | N | 0.09 | 0.18 | 0.08 | 759 |
| Phage-655 | N | D | — | — | — | — | L | — | — | — | L | T | — | D | 0.07 | 0.18 | 0.09 | 760 |
| Phage-656 | I | — | — | — | — | — | L | — | — | — | I | A | — | Y | 0.11 | 0.18 | 0.08 | 761 |
| Phage-657 | N | — | — | — | — | — | V | E | — | F | N | F | — | H | 0.11 | 0.18 | 0.14 | 762 |
| Phage-658 | D | V | — | — | — | — | I | E | — | Y | S | F | — | I | 0.08 | 0.18 | 0.09 | 763 |
| Phage-659 | D | L | — | — | — | — | V | E | — | I | T | D | — | A | 0.10 | 0.18 | 0.12 | 764 |
| Phage-660 | H | D | — | — | — | — | — | — | — | — | — | F | — | I | 0.12 | 0.18 | 0.12 | 765 |
| Phage-661 | P | L | — | — | — | V | L | E | — | D | I | Y | — | Y | 0.10 | 0.18 | 0.13 | 766 |
| Phage-662 | D | L | — | — | — | — | — | E | D | I | I | D | — | N | 0.10 | 0.18 | 0.11 | 767 |
| Phage-663 | D | — | — | — | — | — | V | E | V | P | S | N | — | N | 0.10 | 0.18 | 0.18 | 768 |
| Phage-664 | I | I | — | — | — | — | L | — | — | — | T | A | — | D | 0.10 | 0.18 | 0.09 | 769 |
| Phage-665 | D | H | — | — | — | — | — | — | — | — | — | N | — | D | 0.10 | 0.18 | 0.14 | 770 |
| Phage-666 | F | D | — | — | — | — | — | — | — | — | L | Y | — | S | 0.07 | 0.18 | 0.07 | 771 |
| Phage-667 | F | A | — | W | — | D | W | E | — | V | Y | I | — | Y | 0.08 | 0.18 | 0.08 | 772 |
| Phage-668 | L | — | — | — | — | — | — | — | — | — | L | D | — | S | 0.08 | 0.18 | 0.09 | 773 |
| Phage-669 | D | L | — | — | — | — | L | E | — | A | F | L | — | A | 0.09 | 0.18 | 0.08 | 774 |
| Phage-670 | F | A | — | — | — | — | L | — | — | T | L | T | — | L | 0.10 | 0.18 | 0.08 | 775 |
| Phage-671 | F | D | — | — | — | — | V | E | — | I | S | N | — | D | 0.17 | 0.18 | 0.10 | 776 |
| Phage-672 | — | H | — | — | — | — | L | E | Y | P | F | D | — | N | 0.09 | 0.17 | 0.16 | 777 |
| Phage-673 | A | — | — | — | — | — | — | E | — | H | T | T | — | N | 0.10 | 0.17 | 0.15 | 778 |
| Phage-674 | L | — | — | — | — | V | S | E | W | F | T | F | — | I | 0.08 | 0.17 | 0.08 | 779 |
| Phage-675 | D | — | — | — | — | — | L | — | — | — | Y | D | — | N | 0.10 | 0.17 | 0.09 | 780 |
| Phage-676 | F | — | — | — | — | — | W | E | — | F | D | V | — | I | 0.13 | 0.17 | 0.15 | 781 |
| Phage-677 | F | T | — | — | — | — | V | E | — | Y | D | H | — | I | 0.08 | 0.17 | 0.09 | 782 |
| Phage-678 | Y | N | — | — | — | — | — | — | — | — | — | T | — | F | 0.12 | 0.17 | 0.11 | 783 |
| Phage-679 | A | V | — | — | — | — | N | — | — | — | N | S | — | A | 0.08 | 0.17 | 0.08 | 784 |
| Phage-680 | I | — | — | W | — | D | W | E | V | P | N | D | — | A | 0.10 | 0.17 | 0.09 | 785 |

TABLE 20-continued

Clonal Phage Peptide Sequences from the Peptide-B Optimization Library Panning (-)
indicates same amino acid as in CD3 scFv Peptide-B corresponding position (e.g. Phage-1 position).

| Phage ID | \multicolumn{14}{Amino acid position sequence} | | | | | | | | | | | | | | Background signal | SP34.185 scFv signal | SP34.185 scFv signal in presence of CD3 | SEQ ID NO: |
|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | signal | signal | of CD3 | NO: |
| Phage-681 | Y | F | — | — | — | — | — | E | — | F | F | H | — | Y | 0.12 | 0.17 | 0.12 | 786 |
| Phage-682 | Y | V | — | — | — | D | G | — | — | — | S | F | — | D | 0.12 | 0.17 | 0.12 | 787 |
| Phage-683 | I | S | — | — | — | — | V | E | — | F | F | Y | — | Y | 0.10 | 0.17 | 0.08 | 788 |
| Phage-684 | L | I | — | — | — | V | — | E | — | D | — | Y | — | D | 0.17 | 0.17 | 0.15 | 789 |
| Phage-685 | — | — | — | — | — | — | V | E | D | H | N | Y | — | A | 0.14 | 0.17 | 0.16 | 790 |
| Phage-686 | L | D | — | — | — | — | — | E | F | V | Y | I | — | A | 0.08 | 0.17 | 0.10 | 791 |
| Phage-687 | Y | D | — | — | — | — | — | E | — | D | L | P | — | I | 0.17 | 0.17 | 0.11 | 792 |
| Phage-688 | D | V | — | — | — | — | V | E | — | D | Y | Y | — | D | 0.10 | 0.17 | 0.14 | 793 |
| Phage-689 | N | D | — | W | — | D | W | E | Y | D | N | V | — | V | 0.08 | 0.17 | 0.10 | 794 |
| Phage-690 | D | L | — | — | — | — | — | E | V | A | N | D | — | N | 0.10 | 0.16 | 0.16 | 795 |
| Phage-691 | H | D | — | — | — | — | L | — | — | — | I | S | — | N | 0.09 | 0.16 | 0.07 | 796 |
| Phage-692 | L | D | — | W | — | D | W | E | — | T | T | H | — | D | 0.08 | 0.16 | 0.08 | 797 |
| Phage-693 | I | I | — | — | — | — | V | E | — | D | D | Y | — | L | 0.09 | 0.16 | 0.09 | 798 |
| Phage-694 | Y | — | — | W | — | D | W | E | — | V | I | I | — | D | 0.09 | 0.16 | 0.09 | 799 |
| Phage-695 | F | D | — | — | — | — | I | — | — | Y | T | N | — | N | 0.12 | 0.16 | 0.09 | 800 |
| Phage-696 | I | T | — | — | — | — | L | — | — | T | I | N | — | D | 0.08 | 0.16 | 0.11 | 801 |
| Phage-697 | D | S | — | — | — | — | V | E | — | D | I | Y | — | I | 0.07 | 0.16 | 0.08 | 802 |
| Phage-698 | Y | L | — | — | — | — | — | — | — | — | G | N | — | H | 0.07 | 0.16 | 0.08 | 803 |
| Phage-699 | D | N | — | — | — | — | L | P | — | D | Y | F | — | D | 0.08 | 0.16 | 0.10 | 804 |
| Phage-700 | — | L | — | — | — | — | — | E | — | V | S | N | — | N | 0.11 | 0.16 | 0.08 | 805 |
| Phage-701 | — | D | — | W | — | D | W | E | — | D | I | V | — | D | 0.10 | 0.16 | 0.09 | 806 |
| Phage-702 | — | — | — | W | — | D | W | E | D | N | F | P | — | Y | 0.07 | 0.16 | 0.07 | 807 |
| Phage-703 | D | — | — | — | — | — | V | E | — | H | F | N | — | H | 0.08 | 0.16 | 0.08 | 808 |
| Phage-704 | A | D | — | — | — | — | I | E | — | D | A | Y | — | Y | 0.12 | 0.16 | 0.09 | 809 |
| Phage-705 | I | L | — | W | — | D | W | E | D | A | T | F | — | Y | 0.09 | 0.16 | 0.07 | 810 |
| Phage-706 | I | H | — | W | — | D | W | E | D | F | N | I | — | P | 0.09 | 0.16 | 0.08 | 811 |
| Phage-707 | T | I | — | — | — | — | V | E | D | Y | N | D | — | I | 0.07 | 0.16 | 0.07 | 812 |
| Phage-708 | D | D | — | — | — | — | L | — | — | — | — | A | — | I | 0.08 | 0.16 | 0.08 | 813 |
| Phage-709 | D | D | — | W | — | D | W | E | D | H | I | F | — | F | 0.13 | 0.16 | 0.08 | 814 |
| Phage-710 | — | N | — | — | — | — | V | E | — | I | I | F | — | D | 0.12 | 0.15 | 0.12 | 815 |
| Phage-711 | I | F | — | W | — | D | W | E | D | D | T | V | — | I | 0.08 | 0.15 | 0.09 | 816 |
| Phage-712 | I | I | — | — | — | — | — | E | — | I | S | D | — | L | 0.12 | 0.15 | 0.15 | 817 |
| Phage-713 | F | D | — | — | — | — | V | E | — | Y | N | D | — | D | 0.11 | 0.15 | 0.09 | 818 |

TABLE 20-continued

Clonal Phage Peptide Sequences from the Peptide-B Optimization Library Panning (-)
indicates same amino acid as in CD3 scFv Peptide-B corresponding position (e.g. Phage-1 position).

| Phage ID | \multicolumn{14}{c}{Amino acid position sequence} | | | | | | | | | | | | | Background signal | SP34.185 scFv signal | SP34.185 scFv signal in presence of CD3 | SEQ ID NO: |
|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | | | | |
| Phage-714 | N | D | — | — | — | — | L | — | — | T | L | Y | — | I | 0.08 | 0.15 | 0.10 | 819 |
| Phage-715 | A | I | — | — | — | — | L | E | — | D | I | S | — | N | 0.12 | 0.15 | 0.17 | 820 |
| Phage-716 | H | L | — | — | — | — | — | — | — | — | T | N | — | Y | 0.07 | 0.15 | 0.07 | 821 |
| Phage-717 | S | — | — | — | — | — | L | — | — | — | — | A | — | I | 0.10 | 0.15 | 0.11 | 822 |
| Phage-718 | L | — | — | — | — | — | — | E | Q | L | A | D | — | T | 0.08 | 0.15 | 0.08 | 823 |
| Phage-719 | I | D | — | — | — | — | L | — | — | — | I | A | — | N | 0.07 | 0.15 | 0.08 | 824 |
| Phage-720 | F | D | — | — | — | D | G | Q | — | D | L | V | — | N | 0.10 | 0.15 | 0.08 | 825 |
| Phage-721 | N | L | — | — | — | — | — | E | — | F | F | D | — | Y | 0.09 | 0.15 | 0.15 | 826 |
| Phage-722 | S | I | — | — | — | — | L | Q | — | D | I | V | — | P | 0.09 | 0.14 | 0.14 | 827 |
| Phage-723 | N | P | — | — | — | — | Y | — | — | — | A | H | — | D | 0.08 | 0.14 | 0.08 | 828 |
| Phage-724 | Y | D | — | — | — | — | L | — | — | Y | Y | N | — | N | 0.12 | 0.14 | 0.11 | 829 |
| Phage-725 | — | D | — | — | — | — | L | — | — | T | I | F | — | D | 0.07 | 0.14 | 0.08 | 830 |
| Phage-726 | D | N | — | — | — | — | L | — | — | — | — | T | — | T | 0.09 | 0.14 | 0.10 | 831 |
| Phage-727 | — | D | — | — | — | — | L | — | — | — | S | Y | — | D | 0.10 | 0.14 | 0.13 | 832 |
| Phage-728 | Y | — | — | — | — | — | — | E | F | I | D | F | — | F | 0.07 | 0.14 | 0.07 | 833 |
| Phage-729 | Y | D | — | W | — | D | W | E | V | I | T | Y | — | N | 0.08 | 0.14 | 0.09 | 834 |
| Phage-730 | F | D | — | — | — | — | I | E | — | D | F | F | — | V | 0.06 | 0.14 | 0.07 | 835 |
| Phage-731 | I | F | — | W | — | D | W | — | D | I | N | F | — | D | 0.10 | 0.14 | 0.14 | 836 |
| Phage-732 | N | F | — | — | — | — | L | P | — | D | I | T | — | Y | 0.37 | 0.14 | 0.09 | 837 |
| Phage-733 | S | L | — | — | — | — | — | E | — | Y | Y | H | — | L | 0.09 | 0.14 | 0.07 | 838 |
| Phage-734 | A | S | — | — | — | — | L | — | — | — | L | D | — | L | 0.12 | 0.14 | 0.13 | 839 |
| Phage-735 | S | F | — | — | — | — | R | E | W | D | L | A | — | Y | 0.09 | 0.14 | 0.08 | 840 |
| Phage-736 | H | L | — | — | — | — | — | E | D | V | L | D | — | I | 0.08 | 0.14 | 0.12 | 841 |
| Phage-737 | L | D | — | — | — | D | G | — | — | F | Y | Y | — | L | 0.20 | 0.14 | 0.09 | 842 |
| Phage-738 | D | N | — | W | — | D | W | E | — | D | I | A | — | T | 0.16 | 0.14 | 0.11 | 843 |
| Phage-739 | S | D | — | — | — | — | L | — | — | T | I | H | — | I | 0.09 | 0.14 | 0.08 | 844 |
| Phage-740 | N | S | — | — | — | D | G | — | — | — | — | D | — | L | 0.08 | 0.14 | 0.08 | 845 |
| Phage-741 | D | L | — | — | — | — | L | — | — | — | T | L | — | I | 0.07 | 0.14 | 0.08 | 846 |
| Phage-742 | F | D | — | — | — | — | S | — | — | — | F | N | — | Y | 0.09 | 0.14 | 0.11 | 847 |
| Phage-743 | D | L | — | — | — | — | — | E | — | D | D | I | — | Y | 0.12 | 0.14 | 0.13 | 848 |
| Phage-744 | H | A | — | — | — | — | — | E | — | D | T | Y | — | F | 0.10 | 0.14 | 0.14 | 849 |
| Phage-745 | S | D | — | — | — | — | L | — | — | — | — | A | — | I | 0.11 | 0.14 | 0.08 | 850 |
| Phage-746 | I | V | — | — | — | — | L | P | — | D | Y | N | — | Y | 0.09 | 0.13 | 0.11 | 851 |
| Phage-747 | D | L | — | — | — | — | — | — | — | — | F | I | — | F | 0.09 | 0.13 | 0.08 | 852 |

TABLE 20-continued

Clonal Phage Peptide Sequences from the Peptide-B Optimization Library Panning (-)
indicates same amino acid as in CD3 scFv Peptide-B corresponding position (e.g. Phage-1 position).

| Phage ID | \multicolumn Amino acid position sequence | | | | | | | | | | | | | | Backgroud signal | SP34.185 scFv signal | SP34.185 scFv signal in presence of CD3 | SEQ ID NO: |
|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | | | | |
| Phage-748 | Y | D | — | — | — | — | — | — | — | T | L | T | — | N | 0.13 | 0.13 | 0.08 | 853 |
| Phage-749 | Y | D | — | — | — | — | V | E | — | I | — | N | — | D | 0.11 | 0.13 | 0.12 | 854 |
| Phage-750 | — | F | — | — | — | — | I | E | D | D | H | V | — | I | 0.07 | 0.13 | 0.07 | 855 |
| Phage-751 | F | I | — | — | — | — | W | E | D | D | Y | A | — | S | 0.12 | 0.13 | 0.12 | 856 |
| Phage-752 | N | F | — | — | — | — | — | — | — | — | — | — | — | N | 0.10 | 0.13 | 0.09 | 857 |
| Phage-753 | N | L | — | — | — | — | V | E | — | I | L | I | — | D | 0.07 | 0.13 | 0.07 | 858 |
| Phage-754 | D | S | — | — | — | — | V | E | — | Y | D | L | — | N | 0.11 | 0.13 | 0.08 | 859 |
| Phage-755 | T | L | — | — | — | — | — | E | — | I | T | D | — | N | 0.09 | 0.13 | 0.08 | 860 |
| Phage-756 | T | V | — | — | — | K | M | E | M | N | S | T | — | D | 0.09 | 0.13 | 0.09 | 861 |
| Phage-757 | — | H | — | W | — | D | W | E | D | A | — | S | — | N | 0.10 | 0.12 | 0.11 | 862 |
| Phage-758 | D | L | — | — | — | D | G | N | — | L | D | F | — | F | 0.08 | 0.12 | 0.08 | 863 |
| Phage-759 | D | L | — | — | — | D | G | E | — | H | Y | Y | — | D | 0.09 | 0.12 | 0.07 | 864 |
| Phage-760 | F | N | — | — | — | — | V | E | — | I | L | L | — | T | 0.11 | 0.12 | 0.12 | 865 |
| Phage-761 | H | — | — | — | — | — | V | E | N | I | N | D | — | I | 0.09 | 0.12 | 0.07 | 866 |
| Phage-762 | I | D | — | — | — | — | L | — | — | — | — | I | — | D | 0.09 | 0.12 | 0.08 | 867 |
| Phage-763 | I | F | — | — | — | — | I | E | Q | P | A | L | — | Y | 0.08 | 0.12 | 0.09 | 868 |
| Phage-764 | Y | D | — | — | — | — | — | Q | — | D | L | V | — | P | 0.10 | 0.12 | 0.08 | 869 |
| Phage-765 | H | A | — | W | — | D | W | E | — | P | N | Y | — | D | 0.13 | 0.12 | 0.09 | 870 |
| Phage-766 | N | V | — | W | — | D | W | E | — | D | Y | N | — | Y | 0.11 | 0.12 | 0.10 | 871 |
| Phage-767 | S | F | — | — | Q | — | L | G | D | N | Y | D | — | I | 0.09 | 0.12 | 0.12 | 872 |
| Phage-768 | D | D | — | — | — | — | L | — | — | T | T | V | — | Y | 0.08 | 0.12 | 0.09 | 873 |
| Phage-769 | N | F | — | — | — | — | W | E | V | A | T | L | — | L | 0.09 | 0.12 | 0.14 | 874 |
| Phage-770 | D | L | — | — | — | — | V | E | — | D | T | Y | — | N | 0.09 | 0.11 | 0.07 | 875 |
| Phage-771 | A | L | — | — | — | — | V | E | Q | V | D | L | — | T | 0.08 | 0.11 | 0.08 | 876 |
| Phage-772 | D | D | — | — | — | — | L | — | — | — | — | N | — | N | 0.08 | 0.11 | 0.08 | 877 |
| Phage-773 | I | F | — | — | — | — | — | E | Q | I | I | Y | — | D | 0.09 | 0.11 | 0.11 | 878 |
| Phage-774 | S | D | — | W | — | D | W | E | — | V | Y | Y | — | S | 0.09 | 0.11 | 0.10 | 879 |
| Phage-775 | F | F | — | — | — | D | G | — | — | V | A | I | — | D | 0.09 | 0.11 | 0.07 | 880 |
| Phage-776 | D | D | — | W | — | D | W | E | D | D | — | Y | — | Y | 0.11 | 0.11 | 0.07 | 881 |
| Phage-777 | Y | D | — | — | — | — | — | — | — | T | — | V | — | P | 0.08 | 0.11 | 0.08 | 882 |
| Phage-778 | S | — | — | — | — | — | L | — | — | — | — | N | — | V | 0.10 | 0.11 | 0.08 | 883 |
| Phage-779 | A | F | — | V | S | F | Q | Q | S | L | P | H | — | D | 0.09 | 0.11 | 0.10 | 884 |
| Phage-780 | — | N | — | — | — | — | V | E | — | Y | F | V | — | F | 0.09 | 0.11 | 0.09 | 885 |
| Phage-781 | T | N | — | W | — | D | W | E | — | D | F | A | — | V | 0.07 | 0.11 | 0.08 | 886 |

TABLE 20-continued

Clonal Phage Peptide Sequences from the Peptide-B Optimization Library Panning (-)
indicates same amino acid as in CD3 scFv Peptide-B corresponding position (e.g. Phage-1 position).

| Phage ID | \multicolumn{14}{c}{Amino acid position sequence} | | | | | | | | | | | | | | Background signal | SP34.185 scFv signal | SP34.185 scFv signal in presence of CD3 | SEQ ID NO: |
|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | | | | |
| Phage-782 | D | D | — | — | — | — | — | E | — | I | I | L | — | F | 0.08 | 0.10 | 0.08 | 887 |
| Phage-783 | N | S | — | — | — | — | L | E | D | Y | H | L | — | P | 0.08 | 0.10 | 0.10 | 888 |
| Phage-784 | I | H | — | — | — | D | S | — | G | F | D | F | — | D | 0.09 | 0.10 | 0.08 | 889 |
| Phage-785 | F | D | — | — | — | — | L | E | — | D | H | L | — | F | 0.08 | 0.10 | 0.08 | 890 |
| Phage-786 | T | V | — | W | — | D | — | E | — | Y | A | D | — | D | 0.10 | 0.10 | 0.08 | 891 |
| Phage-787 | Y | F | — | W | — | D | W | E | — | A | A | D | — | L | 0.09 | 0.10 | 0.09 | 892 |
| Phage-788 | — | S | — | — | — | — | — | — | — | — | — | D | — | I | 0.08 | 0.10 | 0.07 | 893 |
| Phage-789 | A | V | — | — | — | — | L | P | — | D | I | V | — | Y | 0.08 | 0.10 | 0.08 | 894 |
| Phage-790 | — | L | — | — | — | — | V | E | — | Y | H | L | — | A | 0.08 | 0.10 | 0.30 | 895 |
| Phage-791 | S | L | — | W | — | D | W | E | — | V | D | N | — | F | 0.12 | 0.10 | 0.11 | 896 |
| Phage-792 | T | I | — | — | — | D | G | Q | — | D | Y | N | — | H | 0.07 | 0.10 | 0.07 | 897 |
| Phage-793 | F | L | — | — | — | — | G | E | P | T | Y | L | — | T | 0.12 | 0.10 | 0.09 | 898 |
| Phage-794 | D | D | — | W | L | — | Q | H | D | I | Y | V | — | A | 0.10 | 0.10 | 0.08 | 899 |
| Phage-795 | I | F | — | — | — | — | V | E | — | V | A | F | — | F | 0.07 | 0.10 | 0.08 | 900 |
| Phage-796 | A | L | — | — | — | — | V | E | D | D | Y | D | — | L | 0.09 | 0.10 | 0.09 | 901 |
| Phage-797 | D | D | — | — | — | — | I | E | L | Y | L | T | — | A | 0.08 | 0.10 | 0.08 | 902 |
| Phage-798 | T | D | — | W | — | D | W | E | D | D | S | I | — | D | 0.07 | 0.10 | 0.07 | 903 |
| Phage-799 | S | I | — | — | — | — | L | E | — | I | F | L | — | N | 0.08 | 0.10 | 0.08 | 904 |
| Phage-800 | N | D | — | — | — | — | L | E | — | D | I | L | — | F | 0.07 | 0.10 | 0.09 | 905 |
| Phage-801 | D | D | — | — | — | — | L | — | — | T | Y | S | — | Y | 0.09 | 0.09 | 0.08 | 906 |
| Phage-802 | F | V | — | — | — | — | W | E | — | I | D | L | — | I | 0.10 | 0.09 | 0.09 | 907 |
| Phage-803 | Y | D | — | — | — | — | L | — | — | — | L | S | — | P | 0.07 | 0.09 | 0.07 | 908 |
| Phage-804 | N | L | — | — | — | — | L | — | — | — | I | I | — | P | 0.08 | 0.09 | 0.08 | 909 |
| Phage-805 | I | D | — | W | — | D | W | E | — | F | N | N | — | F | 0.08 | 0.09 | 0.09 | 910 |
| Phage-806 | A | — | — | — | — | — | L | E | — | H | D | Y | — | Y | 0.08 | 0.09 | 0.09 | 911 |
| Phage-807 | D | D | — | S | — | Q | — | — | Q | I | D | L | — | D | 0.14 | 0.09 | 0.09 | 912 |
| Phage-808 | S | — | — | — | — | — | S | — | — | — | I | Y | — | Y | 0.08 | 0.09 | 0.07 | 913 |
| Phage-809 | S | L | — | — | — | — | — | Q | — | D | A | P | — | N | 0.07 | 0.09 | 0.07 | 914 |
| Phage-810 | D | A | — | — | — | — | L | — | — | T | T | H | — | D | 0.09 | 0.09 | 0.08 | 915 |
| Phage-811 | N | D | — | — | — | — | V | E | — | V | A | D | — | F | 0.07 | 0.09 | 0.08 | 916 |
| Phage-812 | Y | I | — | — | — | — | — | E | Q | D | Y | F | — | F | 0.08 | 0.09 | 0.08 | 917 |
| Phage-813 | T | D | — | — | — | D | G | — | — | T | N | Y | — | F | 0.11 | 0.09 | 0.08 | 918 |
| Phage-814 | Y | D | — | — | — | — | V | — | — | — | — | L | — | P | 0.08 | 0.09 | 0.08 | 919 |
| Phage-815 | I | D | — | — | — | — | — | — | — | — | A | Y | — | T | 0.08 | 0.09 | 0.08 | 920 |

TABLE 20-continued

Clonal Phage Peptide Sequences from the Peptide-B Optimization Library Panning (-)
indicates same amino acid as in CD3 scFv Peptide-B corresponding position (e.g. Phage-1 position).

| Phage ID | Amino acid position sequence 1 | 2 | 3 | 4 | 5 | 6 | 7 | 8 | 9 | 10 | 11 | 12 | 13 | 14 | Background signal | SP34.185 scFv signal | SP34.185 scFv signal in presence of CD3 | SEQ ID NO: |
|---|---|---|---|---|---|---|---|---|---|---|---|---|---|---|---|---|---|---|
| Phage-816 | F | D | — | — | — | — | — | E | — | F | F | H | — | Y | 0.09 | 0.09 | 0.09 | 921 |
| Phage-817 | F | P | — | — | — | — | I | E | — | Y | D | Y | — | V | 0.09 | 0.09 | 0.08 | 922 |
| Phage-818 | A | D | — | — | — | I | — | E | S | I | D | I | — | V | 0.09 | 0.09 | 0.07 | 923 |
| Phage-819 | I | S | — | — | — | D | L | W | P | T | D | I | — | T | 0.10 | 0.09 | 0.10 | 924 |
| Phage-820 | D | D | — | — | — | D | G | — | — | V | H | T | — | N | 0.09 | 0.09 | 0.07 | 925 |
| Phage-821 | I | D | — | W | — | D | W | E | G | — | F | A | — | N | 0.09 | 0.09 | 0.08 | 926 |
| Phage-822 | L | N | — | — | — | D | G | — | — | T | F | Y | — | D | 0.08 | 0.08 | 0.07 | 927 |
| Phage-823 | I | H | — | — | — | — | L | G | A | Y | I | S | — | S | 0.08 | 0.08 | 0.09 | 928 |
| Phage-824 | T | I | — | W | — | D | W | E | — | D | Y | F | — | Y | 0.08 | 0.08 | 0.08 | 929 |
| Phage-825 | H | S | — | L | A | Q | — | — | Q | D | L | V | — | I | 0.07 | 0.08 | 0.07 | 930 |
| Phage-826 | N | N | — | A | S | D | L | S | — | D | N | S | — | I | 0.07 | 0.08 | 0.08 | 931 |
| Phage-827 | — | N | — | W | — | D | W | E | — | D | — | A | — | N | 0.09 | 0.08 | 0.07 | 932 |
| Phage-828 | — | — | — | — | — | — | L | — | — | — | F | Y | — | F | 0.08 | 0.08 | 0.07 | 933 |
| Phage-829 | L | F | — | — | T | V | L | — | — | F | F | D | — | D | 0.07 | 0.08 | 0.07 | 934 |
| Phage-830 | F | D | — | — | — | — | L | — | — | — | — | S | — | A | 0.08 | 0.08 | 0.07 | 935 |
| Phage-831 | Y | — | — | — | — | — | V | E | — | N | — | Y | — | I | 0.07 | 0.08 | 0.08 | 936 |
| Phage-832 | D | — | — | — | — | — | L | — | D | — | T | I | — | H | 0.12 | 0.08 | 0.10 | 937 |
| Phage-833 | — | F | — | — | — | Q | W | A | — | A | N | A | — | F | 0.09 | 0.08 | 0.07 | 938 |
| Phage-834 | F | T | — | — | — | — | Y | — | — | — | I | T | — | P | 0.09 | 0.08 | 0.09 | 939 |
| Phage-835 | L | N | — | — | — | V | N | — | — | — | S | V | — | I | 0.07 | 0.08 | 0.08 | 940 |
| Phage-836 | A | I | — | W | — | D | W | E | — | F | S | D | — | H | 0.07 | 0.08 | 0.07 | 941 |
| Phage-837 | Y | — | — | — | V | D | L | G | A | N | — | Y | — | Y | 0.10 | 0.08 | 0.09 | 942 |
| Phage-838 | H | — | — | — | — | — | V | E | — | D | Y | H | — | D | 0.07 | 0.08 | 0.07 | 943 |
| Phage-839 | N | D | — | — | S | L | Q | Y | D | I | P | T | — | V | 0.08 | 0.08 | 0.07 | 944 |
| Phage-840 | Y | V | — | R | — | Q | L | — | V | Y | H | Y | — | N | 0.15 | 0.08 | 0.07 | 945 |
| Phage-841 | H | D | — | — | — | D | G | — | — | — | I | I | — | S | 0.08 | 0.08 | 0.07 | 946 |
| Phage-842 | F | D | — | — | — | — | L | — | — | T | I | I | — | P | 0.08 | 0.08 | 0.08 | 947 |
| Phage-843 | — | D | — | — | S | D | R | G | — | N | A | A | — | H | 0.07 | 0.08 | 0.07 | 948 |
| Phage-844 | N | I | — | L | A | Q | — | N | — | D | P | T | — | N | 0.07 | 0.08 | 0.08 | 949 |
| Phage-845 | T | N | — | — | S | K | S | Q | V | — | D | H | — | I | 0.10 | 0.08 | 0.09 | 950 |
| Phage-846 | N | H | — | H | — | Q | — | W | — | L | T | N | — | N | 0.09 | 0.07 | 0.07 | 951 |
| Phage-847 | L | L | — | H | — | Q | G | — | L | Y | H | L | — | H | 0.09 | 0.07 | 0.08 | 952 |
| Phage-848 | T | N | — | D | S | K | L | E | G | D | D | N | — | F | 0.09 | 0.07 | 0.07 | 953 |
| Phage-849 | N | D | — | — | — | — | M | — | — | — | L | L | — | D | 0.08 | 0.07 | 0.07 | 954 |

TABLE 20-continued

Clonal Phage Peptide Sequences from the Peptide-B Optimization Library Panning (-)
indicates same amino acid as in CD3 scFv Peptide-B corresponding position (e.g. Phage-1 position).

| Phage ID | Amino acid position sequence 1 | 2 | 3 | 4 | 5 | 6 | 7 | 8 | 9 | 10 | 11 | 12 | 13 | 14 | Background signal | SP34.185 scFv signal | SP34.185 scFv signal in presence of CD3 | SEQ ID NO: |
|---|---|---|---|---|---|---|---|---|---|---|---|---|---|---|---|---|---|---|
| Phage-850 | F | H | — | — | — | — | V | — | — | — | I | N | — | N | 0.07 | 0.07 | 0.07 | 955 |
| Phage-851 | D | F | — | — | — | D | G | — | — | T | Y | V | — | S | 0.07 | 0.07 | 0.08 | 956 |
| Phage-852 | — | S | — | — | — | Q | — | — | — | N | N | T | — | N | 0.07 | 0.07 | 0.08 | 957 |
| Phage-853 | — | — | — | H | L | — | S | E | Q | F | D | I | — | T | 0.08 | 0.07 | 0.08 | 958 |
| Phage-854 | D | D | — | — | — | — | W | E | F | V | F | F | — | D | 0.08 | 0.07 | 0.08 | 959 |
| Phage-855 | Y | N | — | E | Q | Q | Q | — | — | D | P | S | — | I | 0.07 | 0.07 | 0.07 | 960 |
| Phage-856 | N | T | — | — | T | — | Q | H | — | F | N | — | — | L | 0.08 | 0.07 | 0.08 | 961 |
| Phage-857 | H | P | — | Q | — | G | — | E | — | V | D | Y | — | V | 0.08 | 0.07 | 0.08 | 962 |
| Phage-858 | — | A | — | S | R | Q | L | G | — | D | A | Y | — | N | 0.07 | 0.07 | 0.07 | 963 |
| Phage-859 | D | I | — | — | A | Q | E | V | H | V | Y | T | — | P | 0.07 | 0.07 | 0.07 | 964 |
| Phage-860 | F | F | — | E | G | N | L | — | A | Y | L | L | — | L | 0.08 | 0.07 | 0.08 | 965 |
| Phage-861 | Y | — | — | — | — | D | G | E | — | N | I | V | — | D | 0.07 | 0.07 | 0.07 | 966 |

TABLE 21

Sequences of those peptides
selected for synthesis
(CD3 scFv Peptide-B Optimization)

| Peptide-ID | Sequence | SEQ ID NO: |
|---|---|---|
| Peptide-AA | DDCWPDWEFDFACA | 106 |
| Peptide-AB | YICGLDFPDFLYCD | 107 |
| Peptide-AC | FDCWPDWEEYFVCD | 108 |
| Peptide-AD | YICWPDWEEYFDCD | 109 |
| Peptide-AE | NICWPDWEDDYFCF | 110 |
| Peptide-AF | NFCWPDWEYIYPCI | 111 |
| Peptide-AG | VDCWPDWEEDFLCI | 112 |
| Peptide-AH | HACWPDWEEYFPCN | 113 |
| Peptide-AI | YDCGPDVDESYVCV | 114 |
| Peptide-AJ | IDCWPDWEDDTFCY | 115 |

TABLE 21-continued

Sequences of those peptides
selected for synthesis
(CD3 scFv Peptide-B Optimization)

| Peptide-ID | Sequence | SEQ ID NO: |
|---|---|---|
| Peptide-AK | YLCGPDGDETLACY | 116 |
| Peptide-AL | VDCGPDGDESILCY | 117 |

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. A method of treating prostate cancer in a subject, the method comprising administering to the subject a therapeutically effective amount of a polypeptide or polypeptide complex according to Formula I:

$$A_2\text{-}A_1\text{-}L_1\text{-}P_1\text{—}H_1 \qquad \text{(Formula I)}$$

wherein: $A_1$ comprises a first antigen recognizing molecule that binds to an effector cell antigen, wherein $A_1$ comprises an anti-CD3 binding molecule comprising complementarity determining regions (CDRs): HC-CDR1, HC-CDR2, and HC-CDR3, wherein the HC-CDR1, the HC-CDR2, and the HC-CDR3 of $A_1$ comprise: HC-CDR1: SEQ ID NO: 1, HC-CDR2: SEQ ID NO: 2, and HC-CDR3: SEQ ID NO: 3; and $A_1$ comprises CDRs: LC-CDR1, LC-CDR2, and LC-CDR3, wherein the LC-CDR1, the LC-CDR2, and the LC-CDR3 of $A_1$ comprise LC-CDR1: SEQ ID NO: 4, LC-CDR2: SEQ ID NO: 5, and LC-CDR3: SEQ ID NO: 6;

$P_1$ comprises a peptide that binds to $A_1$, wherein Pi comprises an amino acid sequence according to $U_1\text{-}U_2\text{—}C\text{—}U_4\text{—}P\text{—}U_6\text{-}U_7\text{—}U_8\text{—}U_9\text{-}U_{10}\text{—}U_{11}\text{—}U_{12}\text{—}C\text{—}U_{14}$ and $U_1$ is selected from D, Y, F, I, N, V, H, L, A, T, S, and P; $U_2$ is selected from D, Y, L, F, I, N, A, V, H, T, and S; $U_4$ is selected from G and W; $U_6$ is selected from E, D, V, and P; $U_7$ is selected from W, L, F, V, G, M, I, and Y; $U_8$ is selected from E, D, P, and Q; U$_9$ is selected from E, D, Y, V, F, W, P, L, and Q; U$_{10}$
is selected from S, D, Y, T, I, F, V, N, A, P, L, and H;
U$_{11}$ is selected from I, Y, F, V, L, T, N, S, D, A, and H;
U$_{12}$ is selected from F, D, Y, L, I, V, A, N, T, P, S, G,
and H; and U$_{14}$ is selected from D, Y, N, F, I, P, V, A,
T, H, L, M, and S;

L$_1$ comprises a linking moiety that connects A$_1$ to P$_1$ and
is a substrate for a tumor specific protease;

H$_1$ comprises a half-life extending molecule; and

A$_2$ comprises a second antigen recognizing molecule that
binds to prostate-specific membrane antigen (PSMA).

2. The method of claim 1, wherein the prostate cancer is
metastatic castration-resistant prostate cancer (mCRPC).

3. The method of claim 1, wherein the administering
comprises administering on a weekly basis.

4. The method of claim 1, wherein the administering
comprises administering intravenously, intramuscularly,
intralesionally, topically, subcutaneously, or orally.

5. The method of claim 1, wherein the administering
comprises administering by continuous infusion or bolus
injection.

6. The method of claim 1, wherein the administering
comprises administering on a weekly basis through continu-
ous intravenous infusion.

7. The method of claim 1, wherein A$_2$ comprises comple-
mentarity determining regions (CDRs): HC-CDR1, HC-
CDR2, and HC-CDR3, wherein the HC-CDR1, the HC-
CDR2, and the HC-CDR3 comprise: HC-CDR1: SEQ ID
NO: 8, HC-CDR2: SEQ ID NO: 9, and HC-CDR3: SEQ ID
NO: 10; and A$_2$ comprises CDRs: LC-CDR1, LC-CDR2,
and LC-CDR3, wherein the LC-CDR1, the LC-CDR2, and
the LC-CDR3 of A$_2$ comprise LC-CDR1: SEQ ID NO: 11,
LC-CDR2: SEQ ID NO: 12, and LC-CDR3: SEQ ID NO:
13.

8. The method of claim 1, wherein the effector cell antigen
comprises cluster of differentiation 3 (CD3).

9. The method of claim 1, wherein A$_1$ comprises an
antibody format selected from single chain variable frag-
ment and a Fab or Fab' fragment.

10. The method of claim 1, wherein A$_2$ comprises an
antibody format selected from single chain variable frag-
ment, a single domain antibody, and a Fab or Fab' fragment.

11. The method of claim 1, wherein A$_1$ comprises an
antibody format of a single chain variable fragment (scFv),
and A$_2$ comprises an antibody format of a Fab or Fab'.

12. The method of claim 1, wherein Pi becomes unbound
from A$_1$ when L$_1$ is cleaved by the tumor specific protease
thereby exposing A$_1$ to the effector cell antigen.

13. The method of claim 1, wherein the tumor specific
protease is selected from the group consisting of a matrix
metalloprotease (MMP), serine protease, cysteine protease,
threonine protease, and aspartic protease.

14. The method of claim 13, wherein the matrix metal-
loprotease comprises MMP2, MMP7, MMP9, MMP13, or
MMP14.

15. The method of claim 13, wherein the serine protease
comprises matriptase (MTSP1), urokinase, or hepsin.

16. The method of claim 1, wherein L$_1$ comprises a
urokinase cleavable amino acid sequence, a matriptase
cleavable amino acid sequence, a matrix metalloprotease
cleavable amino acid sequence, or a legumain cleavable
amino acid sequence.

396

17. The method of claim 1, wherein L$_1$ comprises an
amino acid sequence according to SEQ ID NO: 23.

18. The method of claim 1, wherein L$_1$ comprises an
amino acid sequence according to any one of SEQ ID NOs:
20-49.

19. The method of claim 1, wherein L$_1$ comprises an
amino acid sequence of Linker 25 (ISSGLLSGRSDAG)
(SEQ ID NO: 45), Linker 26 (AAGLLAPPGGLSGRS-
DAG) (SEQ ID NO: 46), Linker 27 (SPLGLSGRSDAG)
(SEQ ID NO: 47), or Linker 28 (LSGRSDAGSPLGLAG)
(SEQ ID NO: 48), or an amino acid sequence that has 1, 2,
or 3 amino acid substitutions, additions, or deletions relative
to the amino acid sequences of Linker 25, Linker 26, Linker
27, or Linker 28.

20. The method of claim 1, wherein H$_1$ comprises serum
albumin.

21. The method of claim 20, wherein the albumin is
human serum albumin.

22. The method of claim 1, wherein H$_1$ comprises a single
domain antibody.

23. The method of claim 1, wherein H$_1$ comprises comple-
mentarity determining regions (CDRs): HC-CDR1, HC-
CDR2, and HC-CDR3, wherein the HC-CDR1, the HC-
CDR2, and the HC-CDR3 of H$_1$ comprise: HC-CDR1: SEQ
ID NO: 54, HC-CDR2: SEQ ID NO: 55, and HC-CDR3:
SEQ ID NO: 56.

24. The method of claim 1, wherein H$_1$ comprises comple-
mentarity determining regions (CDRs): HC-CDR1, HC-
CDR2, and HC-CDR3, wherein the HC-CDR1, the HC-
CDR2, and the HC-CDR3 of H$_1$ comprise: HC-CDR1: SEQ
ID NO: 58, HC-CDR2: SEQ ID NO: 59, and HC-CDR3:
SEQ ID NO: 60.

25. The method of claim 1, wherein U$_1$ is selected from
D, Y, F, I, V, and N; U$_2$ is selected from D, Y, L, F, I, and N;
U$_4$ is selected from G and W; U$_6$ is selected from E and D;
U$_7$ is selected from W, L, F, G, and V; U$_8$ is selected from
E and D; U$_9$ is selected from E, D, Y, and V; U$_{10}$ is selected
from S, D, Y, T, and I; U$_{11}$ is selected from I, Y, F, V, L, and
T; U$_{12}$ is selected from F, D, Y, L, I, V, A, G, and N; and U$_{14}$
is selected from D, Y, N, F, I, M, and P.

26. The method of claim 25, wherein U$_1$ is selected from
D, Y, V, and F; U$_2$ is selected from D, Y, L, and F; U$_4$ is
selected from G and W; U$_6$ is selected from E and D; U$_7$ is
selected from W, L, G, and F; U$_8$ is selected from E and D;
U$_9$ is selected from E and D; U$_{10}$ is selected from S, D, T,
and Y; U$_{11}$ is selected from I, Y, V, L, and F; U$_{12}$ is selected
from F, D, Y, G, A, and L; U$_{14}$ is selected from D, Y, M, and
N.

27. The method of claim 1, wherein P$_1$ comprises the
amino acid sequences according to any one of SEQ ID NOs:
93-95 and 102-105.

28. The method of claim 1, wherein P$_1$ comprises the
amino acid sequences according to any one of SEQ ID NOs:
106 and 108-117.

29. The method of claim 1, wherein P$_1$ comprises the
amino acid sequence according to SEQ ID NO: 19.

30. The method of claim 1, wherein P$_1$ comprises the
amino acid sequence according to SEQ ID NO: 116.

31. The method of claim 1, wherein the polypeptide or
polypeptide complex comprises the amino acid sequences
according to SEQ ID NO: 72 and SEQ ID NO: 73.

* * * * *